(12) United States Patent
Thanos et al.

(10) Patent No.: US 12,012,600 B2
(45) Date of Patent: *Jun. 18, 2024

(54) ENGINEERED IMMUNOSTIMULATORY BACTERIAL STRAINS AND USES THEREOF

(71) Applicant: ACTYM THERAPEUTICS, INC., Berkeley, CA (US)

(72) Inventors: Christopher D. Thanos, Tiburon, CA (US); Laura Hix Glickman, Oakland, CA (US)

(73) Assignee: Actym Therapeutics, Inc., Berkeley, CA (US)

( * ) Notice: Subject to any disclaimer, the term of this patent is extended or adjusted under 35 U.S.C. 154(b) by 1 day.

This patent is subject to a terminal disclaimer.

(21) Appl. No.: 17/560,080

(22) Filed: Dec. 22, 2021

(65) Prior Publication Data

US 2022/0112501 A1 Apr. 14, 2022

Related U.S. Application Data

(62) Division of application No. 16/554,478, filed on Aug. 28, 2019, now Pat. No. 11,242,528.

(60) Provisional application No. 62/723,999, filed on Aug. 28, 2018.

(51) Int. Cl.
| | | |
|---|---|---|
| C07H 21/04 | (2006.01) | |
| A61K 35/74 | (2015.01) | |
| A61K 35/768 | (2015.01) | |
| A61K 47/68 | (2017.01) | |
| A61P 35/00 | (2006.01) | |
| A61P 35/04 | (2006.01) | |
| C07K 16/40 | (2006.01) | |
| C12N 7/00 | (2006.01) | |
| C12N 15/113 | (2010.01) | |

(52) U.S. Cl.
CPC .......... *C12N 15/1137* (2013.01); *A61K 35/74* (2013.01); *A61K 35/768* (2013.01); *A61K 47/6873* (2017.08); *A61P 35/00* (2018.01); *A61P 35/04* (2018.01); *C07K 16/40* (2013.01); *C12N 7/00* (2013.01); *C07K 2317/76* (2013.01); *C12N 2310/122* (2013.01); *C12N 2310/14* (2013.01); *C12N 2310/531* (2013.01); *C12N 2710/16633* (2013.01); *C12N 2710/24133* (2013.01); *C12N 2720/12033* (2013.01); *C12N 2760/18433* (2013.01)

(58) Field of Classification Search
None
See application file for complete search history.

(56) References Cited

U.S. PATENT DOCUMENTS

| | | | |
|---|---|---|---|
| 3,536,809 A | 10/1970 | Applezweig | 424/28 |
| 3,598,123 A | 8/1971 | Zaffaroni | 128/268 |
| 3,630,200 A | 12/1971 | Higuchi | 128/260 |
| 3,710,795 A | 1/1973 | Higuchi et al. | 128/260 |
| 3,845,770 A | 11/1974 | Theeuwes et al. | 128/260 |
| 3,847,770 A | 11/1974 | Radlowe et al. | 204/159.23 |
| 3,916,899 A | 11/1975 | Theeuwes et al. | 128/260 |
| 3,936,354 A | 2/1976 | LaPointe et al. | 195/79 |
| 4,008,719 A | 2/1977 | Theeuwes et al. | 128/260 |
| 4,044,126 A | 8/1977 | Cook et al. | 424/243 |
| 4,364,923 A | 12/1982 | Cook et al. | 424/46 |
| 4,414,209 A | 11/1983 | Cook et al. | 424/243 |
| 4,687,660 A | 8/1987 | Baker et al. | 424/465 |
| 4,769,027 A | 9/1988 | Baker et al. | 424/493 |
| 5,033,252 A | 7/1991 | Carter | 53/425 |
| 5,052,558 A | 10/1991 | Carter | 206/439 |
| 5,059,595 A | 10/1991 | Le Grazie | 424/468 |
| 5,073,543 A | 12/1991 | Marshall et al. | 514/21 |
| 5,120,548 A | 6/1992 | McClelland et al. | 424/473 |
| 5,323,907 A | 6/1994 | Kalvelage | 206/531 |
| 5,354,556 A | 10/1994 | Sparks et al. | 424/419 |
| 5,591,767 A | 1/1997 | Mohr et al. | 514/413 |
| 5,639,476 A | 6/1997 | Oshlack et al. | 424/468 |

(Continued)

FOREIGN PATENT DOCUMENTS

| | | |
|---|---|---|
| AU | 2005316458 | 6/2006 |
| CA | 2591565 | 6/2006 |

(Continued)

OTHER PUBLICATIONS

Bruna Prati: (Expression of genes from DNA damage repair pathways in cells infected by human papillomavirus (HPV), Aug. 14, 2014, pp. 1-82).*

Letter/Written Disclosure of the Information Disclosure Statement for the above-referenced application, filed herewith on Mar. 8, 2022, 2 pages.

(Continued)

*Primary Examiner* — Kimberly Chong

(74) *Attorney, Agent, or Firm* — Womble Bond Dickinson (US) LLP; Stephanie Seidman

(57) ABSTRACT

Provided are immunostimulatory bacteria and oncolytic viruses, and pharmaceutical compositions containing the bacteria and/or viruses, that act as three prime repair exonuclease 1 (TREX1) antagonists. The bacteria and viruses are for treating tumors that are human papillomavirus (HPV) positive or that have a high tumor mutational burden (TMB). The immunostimulatory bacteria and oncolytic viruses encode therapeutic products such RNAi, such as shRNA and microRNA, that mediate gene disruption and/or inhibit expression of TREX1, or that inhibit TREX1. The bacteria contain additional modifications to enhance their anti-tumor activity. The bacteria and viruses are used for treatment of tumors in which TREX1 expression correlates with the presence of the tumor or properties of the tumor, such that inhibition of TREX1 advantageously treats the tumor.

32 Claims, 58 Drawing Sheets

Specification includes a Sequence Listing.

(56) References Cited

U.S. PATENT DOCUMENTS

| | | | |
|---|---|---|---|
| 5,674,533 A | 10/1997 | Santus et al. | 424/493 |
| 5,716,613 A | 2/1998 | Guber et al. | 424/93.2 |
| 5,716,826 A | 2/1998 | Gruber et al. | 435/320.1 |
| 5,733,566 A | 3/1998 | Lewis | 424/426 |
| 5,851,529 A | 12/1998 | Guber et al. | 424/188.1 |
| 5,997,881 A | 12/1999 | Powell et al. | 424/234.1 |
| 6,024,961 A | 2/2000 | Curtiss, III et al. | 424/200.1 |
| 6,080,849 A | 6/2000 | Bermudes et al. | 536/23.7 |
| 6,190,657 B1 | 2/2001 | Pawelek et al. | 424/93.1 |
| 6,383,496 B1 | 5/2002 | Curtiss, III et al. | 424/200.1 |
| 6,428,968 B1 | 8/2002 | Molnar-Kimber et al. | 435/7.23 |
| 6,447,784 B1 | 9/2002 | Bermudes et al. | 424/235.1 |
| 6,475,482 B1 | 11/2002 | Bermudes et al. | 424/93.4 |
| 6,548,287 B1 | 4/2003 | Powell et al. | 435/69.1 |
| 6,632,670 B1 | 10/2003 | Wadsworth et al. | 435/455 |
| 6,635,472 B1 | 10/2003 | Lauermann | 435/320.1 |
| 6,639,139 B2 | 10/2003 | Muller | 84/483.1 |
| 6,653,103 B2 | 11/2003 | Petersen et al. | 435/69.1 |
| 6,689,871 B1 | 2/2004 | Wolfe et al. | 530/412 |
| 6,723,316 B2 | 4/2004 | Laquerre et al. | 424/93.2 |
| 6,863,894 B2 | 3/2005 | Bermudes et al. | 424/235 |
| 6,897,045 B2 | 5/2005 | Engelhardt et al. | 435/69.6 |
| 6,923,972 B2 | 8/2005 | Bermudes et al. | 424/235.1 |
| 6,962,696 B1 | 11/2005 | Bermudes et al. | 424/93.4 |
| 7,001,765 B2 | 2/2006 | Maas et al. | 435/320.1 |
| 7,033,826 B2 | 4/2006 | Perricaudet et al. | 435/320.1 |
| 7,083,794 B2 | 8/2006 | Curtiss, III et al. | 424/200.1 |
| 7,115,269 B2 | 10/2006 | Darji et al. | 424/200.1 |
| 7,153,510 B1 | 12/2006 | Rose | 424/199.1 |
| 7,172,893 B2 | 2/2007 | Rabinowitz et al. | 435/235.1 |
| 7,195,757 B2 | 3/2007 | Curtiss, III et al. | 424/93.48 |
| 7,238,526 B2 | 7/2007 | Wilson et al. | 435/382 |
| 7,241,447 B1 | 7/2007 | Engelhardt et al. | 424/193.1 |
| 7,344,710 B2 | 3/2008 | Dang et al. | 424/93.1 |
| 7,390,646 B2 | 6/2008 | Andino-Pavlovsky et al. | 435/252.33 |
| 7,452,531 B2 | 11/2008 | Bermudes et al. | 424/93.4 |
| 7,514,089 B2 | 4/2009 | Bermudes et al. | 369/30.31 |
| 7,537,924 B2 | 5/2009 | Coffin | 435/235.1 |
| 7,550,296 B2 | 6/2009 | Hermiston et al. | 435/473 |
| 7,588,767 B2 | 9/2009 | Szalay et al. | 424/199.1 |
| 7,662,627 B2 | 2/2010 | Johnson, Jr. | 435/367 |
| 7,731,952 B2 | 6/2010 | Mohr et al. | 424/93.2 |
| 7,731,974 B2 | 6/2010 | Bell et al. | 424/199.1 |
| 7,732,417 B2 | 6/2010 | Beach et al. | 514/44 |
| 7,811,814 B2 | 10/2010 | Bohn et al. | 435/320.1 |
| 7,892,740 B2 | 2/2011 | Weichselbaum et al. | 435/6 |
| 7,897,146 B2 | 3/2011 | Brown et al. | 424/93.1 |
| 7,906,111 B2 | 3/2011 | Wilson et al. | 424/93.2 |
| 7,927,585 B2 | 4/2011 | Snyder | 424/93.2 |
| 7,943,374 B2 | 5/2011 | Hildinger | 435/320.1 |
| 7,968,340 B2 | 6/2011 | Hallek et al. | 435/440 |
| 7,998,461 B2 | 8/2011 | Forbes et al. | 424/9.2 |
| 8,007,780 B2 | 8/2011 | Arbetman et al. | 424/93.2 |
| 8,052,968 B2 | 11/2011 | Chen et al. | 424/93.21 |
| 8,093,025 B2 | 1/2012 | Loessner et al. | 435/69.5 |
| 8,202,846 B2 | 6/2012 | Hannon et al. | 514/44 |
| 8,221,739 B2 | 7/2012 | Leonard et al. | 424/93.2 |
| 8,232,259 B2 | 7/2012 | Klinman et al. | 514/44 |
| 8,241,844 B2 | 8/2012 | Bulla, Jr. et al. | 435/5 |
| 8,383,599 B2 | 2/2013 | Hannon et al. | 514/44 |
| 8,426,375 B2 | 4/2013 | Kandimalla et al. | 514/44 |
| 8,426,675 B2 | 4/2013 | Dickins et al. | 800/14 |
| 8,440,207 B2 | 5/2013 | Bermudes et al. | 424/200.1 |
| 8,580,757 B2 | 11/2013 | Federov et al. | 514/44 A |
| 8,647,618 B2 | 2/2014 | Leonard et al. | 424/93.48 |
| 8,679,473 B2 | 3/2014 | Fensterle et al. | 424/93.1 |
| 8,822,194 B2 | 9/2014 | Zhao et al. | 435/252.3 |
| 8,829,254 B2 | 9/2014 | Nair et al. | 570/155 |
| 9,181,546 B2 | 11/2015 | Li et al. | 424/93.1 |
| 9,242,000 B2 | 1/2016 | Cheresh et al. | 514/44 R |
| 9,265,804 B2 | 2/2016 | Newman et al. | 424/93.48 |
| 9,315,815 B2 | 4/2016 | Bermudes et al. | 435/252.3 |
| 9,320,787 B2 | 4/2016 | Gunn | 424/257.1 |
| 9,453,227 B2 | 9/2016 | Diamond et al. | 424/258.1 |
| 9,511,129 B2 | 12/2016 | Hanson et al. | 435/821 |
| 9,616,114 B1 | 4/2017 | Bermudes et al. | 424/258.1 |
| 9,624,494 B2 | 4/2017 | Hannon et al. | 514/44 A |
| 9,790,504 B2 | 10/2017 | Khodarev et al. | 514/44 A |
| 10,052,371 B2 | 8/2018 | Newman | 424/93.48 |
| 10,087,451 B2 | 10/2018 | Bermudes et al. | 424/258.1 |
| 10,100,314 B2 | 10/2018 | Diamond et al. | 424/258.1 |
| 10,195,259 B2 | 2/2019 | Newman et al. | 530/388.4 |
| 10,286,051 B1 | 5/2019 | Bermudes et al. | 424/258.1 |
| 10,421,971 B2 | 9/2019 | Deng et al. | 514/44 R |
| 10,449,237 B1 | 10/2019 | Bermudes | 424/258.1 |
| 10,626,403 B2 | 4/2020 | Bermudes et al. | 424/258.1 |
| 11,045,504 B2 | 6/2021 | Newman | 530/388.4 |
| 11,103,538 B2 | 8/2021 | Forbes et al. | 424/93.2 |
| 11,141,492 B2 | 10/2021 | Diamond et al. | 424/93.48 |
| 11,471,494 B2 | 10/2022 | Falb et al. | 424/93.4 |
| 2003/0031683 A1 | 2/2003 | Curtiss, III et al. | 424/200.1 |
| 2003/0109026 A1 | 6/2003 | Bermudes et al. | 435/252.3 |
| 2003/0170276 A1 | 9/2003 | Bermudes et al. | 424/258.1 |
| 2003/0175297 A1 | 9/2003 | Urashima | 424/200.1 |
| 2004/0009604 A1 | 1/2004 | Zhang et al. | 435/456 |
| 2004/0120962 A1 | 6/2004 | Curtiss, III et al. | 424/184.1 |
| 2004/0229338 A1 | 11/2004 | King | 435/252.3 |
| 2004/0234455 A1 | 11/2004 | Szalay | 424/9.6 |
| 2005/0220818 A1 | 10/2005 | Lorence | 424/214.1 |
| 2005/0255088 A1 | 11/2005 | Bermudes et al. | 424/93.2 |
| 2005/0260601 A1 | 11/2005 | Whitt et al. | 435/6 |
| 2006/0039894 A1 | 2/2006 | Mohr et al. | 424/93.6 |
| 2006/0051380 A1 | 3/2006 | Schulick et al. | 424/277.1 |
| 2007/0098743 A1 | 5/2007 | Bell et al. | 424/224.1 |
| 2007/0110720 A1 | 5/2007 | Brown et al. | 424/93.2 |
| 2007/0298012 A1 | 12/2007 | King et al. | 424/93.2 |
| 2008/0091375 A1 | 4/2008 | Brunell | 702/107 |
| 2008/0112928 A1 | 5/2008 | Loessner et al. | 424/69.5 |
| 2009/0010889 A1 | 1/2009 | Brown et al. | 424/93.2 |
| 2009/0111762 A1 | 4/2009 | Roth et al. | 514/44 |
| 2009/0123426 A1 | 5/2009 | Li et al. | 424/93.1 |
| 2009/0208534 A1 | 8/2009 | Xu et al. | 424/258.1 |
| 2009/0215147 A1 | 8/2009 | Zhang et al. | 435/235.1 |
| 2009/0220459 A1 | 9/2009 | Fensterle et al. | 424/93.2 |
| 2009/0274728 A1 | 11/2009 | Brown et al. | 424/231.1 |
| 2009/0285860 A1 | 11/2009 | Martuza et al. | 424/277.1 |
| 2010/0092515 A1 | 4/2010 | Conner et al. | 424/231.1 |
| 2010/0113567 A1 | 5/2010 | Barber | 514/44 R |
| 2010/0172877 A1 | 7/2010 | van den Pol et al. | 424/93.6 |
| 2010/0178684 A1 | 7/2010 | Woo et al. | 435/235.1 |
| 2011/0158948 A1 | 6/2011 | Brown et al. | 424/93.2 |
| 2011/0177032 A1 | 7/2011 | Martuza et al. | 424/93.2 |
| 2011/0212530 A1 | 9/2011 | Baltimore et al. | 435/455 |
| 2011/0293527 A1 | 12/2011 | Chen et al. | 424/9.3 |
| 2012/0009153 A1 | 1/2012 | Guo et al. | 424/93.2 |
| 2012/0093773 A1 | 4/2012 | Li et al. | 424/93.1 |
| 2012/0142080 A1 | 6/2012 | Bermudes | 424/200.1 |
| 2012/0294929 A1 | 11/2012 | Roth et al. | 424/450 |
| 2013/0142786 A1 | 6/2013 | Liu et al. | 424/133.1 |
| 2013/0150258 A1 | 6/2013 | Weichselbaum et al. | 435/6 |
| 2014/0127284 A1 | 5/2014 | Cheresh et al. | 424/450 |
| 2014/0178341 A1 | 6/2014 | Zhao et al. | 424/93.2 |
| 2014/0186401 A1 | 7/2014 | Diamond et al. | 424/258.1 |
| 2014/0212396 A1 | 7/2014 | Newman | 424/93.48 |
| 2014/0220661 A1 | 8/2014 | Bermudes | 435/252.3 |
| 2014/0242095 A1 | 8/2014 | Wang et al. | 424/174.1 |
| 2015/0071873 A1 | 3/2015 | Biot et al. | 424/85.1 |
| 2015/0147315 A1 | 5/2015 | Wei | 435/7.32 |
| 2015/0224151 A1 | 8/2015 | Julian Gomez et al. | 424/93.4 |
| 2016/0184456 A1 | 6/2016 | Diamond et al. | 424/93.48 |
| 2016/0199422 A1 | 7/2016 | Newman | 424/93.48 |
| 2016/0222387 A1 | 8/2016 | Khodarev et al. | 514/44 A |
| 2016/0222393 A1 | 8/2016 | Bermudes | 424/258.1 |
| 2016/0228523 A1 | 8/2016 | Newman | 530/388.4 |
| 2016/0333355 A1 | 11/2016 | Deng et al. | 514/44 R |
| 2016/0369213 A1 | 12/2016 | Li et al. | 424/93.1 |
| 2017/0020931 A1 | 1/2017 | Zhou et al. | 424/144.1 |
| 2017/0081671 A1 | 3/2017 | Diamond et al. | 424/258.1 |
| 2017/0298362 A1 | 10/2017 | Khodarev et al. | 514/44 A |
| 2017/0333490 A1 | 11/2017 | Forbes et al. | 424/93.2 |
| 2018/0104320 A1 | 4/2018 | Gravekamp | 424/236.1 |
| 2018/0311343 A1 | 11/2018 | Huang et al. | 514/44 R |
| 2019/0017050 A1 | 1/2019 | Thanos et al. | 424/258.1 |

(56) References Cited

U.S. PATENT DOCUMENTS

| | | | |
|---|---|---|---|
| 2019/0017057 A1 | 1/2019 | Bermudes | 424/258.1 |
| 2019/0071679 A1 | 3/2019 | Khodarev et al. | 514/44 A |
| 2019/0153452 A1 | 5/2019 | Diamond et al. | 424/258.1 |
| 2019/0160115 A1 | 5/2019 | Falb et al. | 424/93.2 |
| 2019/0307869 A1 | 10/2019 | Newman | 530/388.4 |
| 2019/0336544 A1 | 11/2019 | Falb et al. | 424/93.4 |
| 2020/0261572 A1 | 8/2020 | Huang et al. | 514/44 R |
| 2022/0047649 A1 | 2/2022 | Newman | 424/277.1 |
| 2022/0241432 A1 | 8/2022 | Diamond et al. | 424/93.48 |
| 2023/0226122 A1 | 7/2023 | Falb et al. | 424/93.4 |

FOREIGN PATENT DOCUMENTS

| | | |
|---|---|---|
| CN | 103468626 B | 5/2016 |
| EP | 1520175 | 11/2007 |
| EP | 1606411 | 12/2008 |
| EP | 2270136 | 1/2011 |
| EP | 1385466 | 3/2011 |
| EP | 2 941 258 B1 | 9/2019 |
| WO | WO 1998/048026 | 10/1998 |
| WO | WO 1999/013053 | 3/1999 |
| WO | WO 1999/025387 | 5/1999 |
| WO | WO 2001/025399 | 4/2001 |
| WO | WO 2003/096812 | 11/2003 |
| WO | WO 2005/116233 | 12/2005 |
| WO | WO 2006/066048 | 6/2006 |
| WO | WO 2007/130604 | 11/2007 |
| WO | WO 2008/039408 | 4/2008 |
| WO | WO 2008/091375 | 7/2008 |
| WO | WO 2009/006450 | 1/2009 |
| WO | WO 2009/095436 | 8/2009 |
| WO | WO 2010/057009 | 5/2010 |
| WO | WO 2011/100489 | 8/2011 |
| WO | WO 2012/149364 | 11/2012 |
| WO | WO 2013/163893 | 11/2013 |
| WO | WO 2014/107365 | 7/2014 |
| WO | WO 2014/189996 | 11/2014 |
| WO | WO 2015/002969 | 1/2015 |
| WO | WO 2015/032165 | 3/2015 |
| WO | WO 2015/108595 | 7/2015 |
| WO | WO 2015/134722 | 9/2015 |
| WO | WO 2015/142875 | 9/2015 |
| WO | WO 2015/191861 | 12/2015 |
| WO | WO 2016/025582 | 2/2016 |
| WO | WO 2017/005773 | 1/2017 |
| WO | WO 2017/210649 | 12/2017 |
| WO | WO 2018/045058 | 3/2018 |
| WO | WO 2018/197621 | 11/2018 |
| WO | WO 2019/014398 | 1/2019 |

OTHER PUBLICATIONS

Ablasser et al., "Cell intrinsic immunity spreads to bystander cells via the intercellular transfer of cGAMP," Nature 503(7477):530-534 (2013).
Ablasser et al., "TREX1 Deficiency Triggers Cell-Autonomous Immunity in a cGAS-Dependent Manner," J. Immunol. 192:5993-5997 (2014).
Agbor, T.A. and B.A. McCormick, "*Salmonella* Effectors: Important players modulating host cell function during infection," Cell Microbiol. 13(12):1858-1869 (2011).
Ahn et al., "Intrinsic Self-DNA Triggers Inflammatory Disease Dependent on STING," J. Immunol. 193(9):4634-4642 (2014).
Ahn et al., "Extrinsic Phagocyte-Dependent STING Signaling Dictates the Immunogenicity of Dying Cells," Cancer Cell 33(5):862-873 (2018).
Akira et al., "Toll-like receptors: critical proteins linking innate and acquired immunity," Nat. Immunol. 2(8):675-80 (2001).
Alshangiti et al., "Antiangiogenic therapies in non-small-cell lung cancer," Curr. Oncol. 25(Suppl 1):S45-S58 (2018).

Anassi, E. and U. A. Ndefo, "Sipuleucel-T (Provenge) Injection the First Immunotherapy Agent (Vaccine) for Hormone-Refractory Prostate Cancer," P&T 36(4):197-202 (2011).
Angelakopoulos, H. and E.L. Hohmann, "Pilot Study of phoP/phoQ-Deleted *Salmonella enterica* Serovar Typhimurium Expressing *Helicobacter pylori* Urease in Adult Volunteers," Infection and Immunity 68(4):2135-2141 (2000).
Angelova et al., "The Oncolytic Virotherapy Era in Cancer Management: Prospects of Applying H-1 Parvovirus to Treat Blood and Solid Cancers," Front. Oncol. 7:93 (2017), 8 pages.
Angelova et al., "Tumor selectivity of oncolytic parvoviruses: from in vitro and animal models to cancer patients," Frontiers in Bioengineering and Biotechnology 3:55 (2015), 14 pages.
Ansel, H.C., "Introduction to Pharmaceutical Dosage Forms," Fourth Edition, p. 126 (1985).
Antonioli et al., "Immunity, inflammation and cancer: a leading role for adenosine," Nat. Rev. Cancer 13(12):842-857 (2013).
Anwar et al., "Modulation of Biofilm-Formation in *Salmonella enterica* Serovar Typhimurium by the Periplasmic DsbA/DsbB Oxidoreductase System Requires the GGDEF-EAL Domain Protein STM3615," PLoS One 9(8):e106095 (2014), 12 pages.
Aref et al., "Measles to the Rescue: A Review of Oncolytic Measles Virus," Viruses 8:294 (2016), 16 pages.
Arpaia et al., "TLR signaling is required for virulence of an intracellular pathogen," Cell 144(5):675-688 (2011).
Auyeung et al., "Beyond secondary structure: primary-sequence determinants license pri-miRNA hairpins for processing," Cell 152(4):844-858 (2013).
Baban et al., "Bacteria as vectors for gene therapy of cancer," Bioengineered Bugs 1(6):385-394 (2010).
Baguley, B.C., "Antivascular therapy of cancer: DMXAA," Lancet Oncol. 4(3):141-148 (2003).
Barber, G.N., "Cytoplasmic DNA innate immune pathways," Immunol. Rev. 243(1):99-108 (2011).
Barber, G.N., "STING: infection, inflammation and cancer," Nat. Rev. Immunol. 15(12):760-770 (2015).
Baroudy et al., "Incompletely base-paired flip-flop terminal loops link the two DNA strands of the vaccinia virus genome into one uninterrupted polynucleotide chain," Cell 28(2):315-324 (1982).
Bastin et al., "Capitalizing on Cancer Specific Replication: Oncolytic Viruses as a Versatile Platform for the Enhancement of Cancer Immunotherapy Strategies," Biomedicines 4(3), 21 (2016), 19 pages.
Bermudes et al., "Tumour-Selective *Salmonella*-Based Cancer Therapy," Biotechnology and Genetic Engineering Reviews 18(1):219-233 (2001).
Bermudes et al., "Tumor-Targeted *Salmonella* Highly Selective Delivery Vectors," Cancer Gene Therapy: Past Achievements and Future Challenges, ed. Habib, Kluwer Academic/Plenum Publishers, New York, Chp. 6, pp. 57-63 (2000).
Bermudes et al., "Live bacteria as anticancer agents and tumor-selective protein delivery vectors," Curr. Opin. Drug Discov. Devel. 5(2):194-199 (2002).
Bethune, M.T. and A.V. Joglekar, "Personalized T-cell mediated cancer immunotherapy: progress and challenges," Curr. Opin. Biotech. 48:142-152 (2017).
Bian et al., "Cd47-Sirpα interaction and IL-10 constrain inflammation-induced macrophage phagocytosis of healthy self-cells," Proc. Natl. Acad. Sci. USA 113(37):E5434-E5443 (2016).
Binder et al., "Antigen-Specific Bacterial Vaccine Combined with Anti-PD-L1 Rescues Dysfunctional Endogenous T Cells to Reject Long-Established Cancer," Cancer Immunol. Res. 1(2):123-133 (2013).
Bishnoi et al., "Oncotargeting by Vesicular Stomatitis Virus (VSV): Advances in Cancer Therapy," Viruses 10(2):90 (2018), 20 pages.
Blache et al., "Systemic Delivery of *Salmonella typhimurium* Transformed with IDO shRNA Enhances Intratumoral Vector Colonization and Suppresses Tumor Growth," Cancer Res. 72(24):6447-6456 (2012).
Boden et al., "Enhanced gene silencing of HIV-1 specific siRNA using microRNA designed hairpins," Nucleic Acids Research 32(3):1154-1158 (2004).
Bradley et al., "Applications of coxsackievirus A21 in oncology," Oncolytic Virotheraphy 3:47-55 (2014).

(56) References Cited

OTHER PUBLICATIONS

Broadway et al., "Complete genome sequence of *Salmonella enterica* serovar Typhimurium VNP20009, a strain engineered for tumor targeting," Journal of Biotechnology 192:177-178 (2014).
Broadway et al., "Rescuing chemotaxis of the anticancer agent *Salmonella enterica* serovar Typhimurium VNP20009," Journal of Biotechnology 211:117-120 (2015).
Broder, C.C. and P.L. Earl, "Recombinant vaccinia viruses. Design, generation, and isolation," Mol. Biotechnol. 13(3):223-245 (1999).
Broz, P. and Monack, D. M., "Molecular Mechanisms of Inflammasome Activation during Microbial Infections," Immunol. Rev. 243(1):174-190 (2011).
Bucarey et al., "The *Salmonella enterica* Serovar Typhi tsx Gene, Encoding a Nucleoside-Specific Porin, Is Essential for Prototrophic Growth in the Absence of Nucleosides," Infection and Immunity 73(10):6210-6219 (2005).
Buchbinder, E. and F.S. Hodi, "Cytotoxic T lymphocyte antigen-4 and immune checkpoint blockade," J. Clin. Invest. 125(9):3377-3383 (2015).
Burdette et al., "STING is a direct innate immune sensor of cyclic-di-GMP," Nature 478(7370):515-518 (2011).
Burke, M.J., "Oncolytic Seneca Valley Virus: past perspectives and future directions," Oncolytic Virotherapy 5:81-89 (2016).
Burke et al., "Phase I Trial of Seneca Valley Virus (NTX-010) in Children with Relapsed/Refractory Solid Tumors: A Report of the Children's Oncology Group," Pediatr. Blood Cancer 62(5):743-750 (2015).
Camacho et al., "Engineering *Salmonella* as intracellular factory for effective killing of tumour cells," Sci. Rep. 6(30591):1-12 (2016).
Carrillo, H. and D. Lipman, "The multiple sequence alignment problem in biology," Siam J. Applied Math 48(5):1073-1082 (1988).
Carroll, V.A. and M. Ashcroft, "Targeting the molecular basis for tumour hypoxia," Expert Rev. Mol. Med. 7(6):1-16 (2005).
Caskey et al., "Synthetic double-stranded RNA induces innate immune responses similar to a live viral vaccine in humans," J. Exp. Med. 208(12):2357-2366 (2011).
Chang et al., "Creating an miR30-Based shRNA Vector," Cold Spring Harb. Protoc. doi:10.1101/pdb.prot075853, pp. 631-635 (2013).
Chatfield et al., "Use of the nirB promoter to direct the stable expression of heterologous antigens in *Salmonella* oral vaccine strains: development of a single-dose oral tetanus vaccine," Biotechnology 10(8):888-892 (1992).
Chen, L. and X. Han, "Anti-PD-1/PD-L1 therapy of human cancer: past, present and future." J. Clin. Invest. 125(9):3384-3391 (2015).
Cheng et al., "Genetic Modification of Oncolytic Newcastle Disease Virus for Cancer Therapy," J. Virol. 90(1):5343-5352 (2016).
Chi et al., "Anti-tumor Activity of Toll-Like Receptor 7 Agonists," Frontiers in Pharmacology 8:304 (2017), 10 pages.
Chiu et al., "RNA polymerase III detects cytosolic DNA and induces type-I interferons through the RIG-I pathway," Cell 138(3):576-591 (2009).
Choi et al., "Polymeric oncolytic adenovirus for cancer gene therapy," J. Control. Release 219:181-191 (2015).
Chorobik et al., "*Salmonella* and cancer: from pathogens to therapeutics," Acta Biochimica Polonica 60(3):285-297 (2013).
Chung et al., "Polycistronic RNA polymerase II expression vectors for RNA interference based on BIC/miR-155," Nucleic Acids Res. 34(7):e53 (2006), 14 pages.
Civril et al., "Structural mechanism of cytosolic DNA sensing by cGAS," Nature 498(7454):332-337 (2013).
Clairmont et al., "Biodistribution and Genetic Stability of the Novel Antitumor Agent VNP20009, a Genetically Modified Strain of *Salmonella typhimurium*," Journal of Infectious Diseases 181:1996-2002 (2000).
Clevers H. and R. Nusse, "Wnt/β-Catenin Signaling and Disease," Cell 149:1192-1205 (2012).
Copier, J. and A. Dalgleish, "Whole-cell vaccines: A failure or a success waiting to happen?" Curr. Opin. Mol. Ther. 12(1):14-20 (2010) [abstract only].

Corrales et al., "Direct activation of STING in the tumor microenvironment leads to potent and systemic tumor regression and immunity," Cell Rep. 11(7):1018-1030 (2015).
Crull et al., "Biofilm formation by *Salmonella enterica* serovar Typhimurium colonizing solid tumours," Cellular Microbiology 13(8):1223-1233 (2011).
Dang et al., "Combination bacteriolytic therapy for the treatment of experimental tumors," Proc. Natl. Acad. Sci. USA 98(26):15155-15160 (2001).
Datsenko, K.A. and B.L. Wanner, "One-step inactivation of chromosomal genes in *Escherichia coli* K-12 using PCR products," PNAS 97(12):6640-6645 (2000).
Dean et al., "Sequence requirements for plasmid nuclear import," Exp. Cell Res. 253(2):713-722 (1999).
Del Solar et al., "Replication and Control of Circular Bacterial Plasmids," Microbiology and Molecular Biology Reviews 62(2):434-464 (1998).
Deng et al., "A New VISTA on combination therapy for negative checkpoint regulator blockade," Journal for ImmunoTherapy of Cancer 4:86 (2016), 7 pages.
Diamond et al., "Type I interferon is selectively required by dendritic cells for immune rejection of tumors," J. Exp. Med. 208(10):1989-2003 (2011).
Dinarello, C.A., "Proinflammatory and Anti-inflammatory Cytokines as Mediators in the Pathogenesis of Septic Shock," Chest 112(6 Suppl):321S-329S (1997).
Diner et al., "The innate immune DNA sensor cGAS produces a non-canonical cyclic-di-nucleotide that activates human STING," Cell Rep. 3(5):1355-1361 (2013).
DiPetrillo et al., "Safety and immunogenicity of phoP/phoQ-deleted *Salmonella typhi* expressing *Helicobacter pylori* urease in adult volunteers," Vaccine 18(5-6):449-459 (2000).
Di Domenico et al., "Biofilm Producing *Salmonella typhi*: Chronic Colonization and Development of Gallbladder Cancer," Int. J. Mol. Sci. 18:1887 (2017), 14 pages.
Dold et al., "Application of interferon modulators to overcome partial resistance of human ovarian cancers to VSV-GP oncolytic viral therapy," Molecular Therapy—Oncolytics 3:16021 (2016), 11 pages.
Drees et al., "Vasculature Disruption Enhances Bacterial Targeting of Autochthonous Tumors," Journal of Cancer 6(9):843-848 (2015).
Drees et al., "Attenuated *Salmonella enterica* Typhimurium Reduces Tumor Burden in an Autochthonous Breast Cancer Model," Anticancer Research 35:843-850 (2015).
Dreher et al., "Genetic background of attenuated *Salmonella typhimurium* has profound influence on infection and cytokine patterns in human dendritic cells," J. Leukoc. Biol. 69:583-589 (2001).
Durfee et al., "The complete genome sequence of *Escherichia coli* DH10B: insights into the biology of a laboratory workhorse," J. Bacteriol. 190(7):2597-2606 (2008).
Edwards et al., "DNA Damage Repair Genes Controlling Human Papillomavirus (HPV) Episome Levels under Conditions of Stability and Extreme Instability," PLoS One 8(10):e75406 (2013), 16 pages.
Eissa et al., "Genomic Signature of the Natural Oncolytic Herpes Simplex Virus HF10 and Its Therapeutic Role in Preclinical and Clinical Trials," Front. Oncol. 7:149 (2017), 12 pages.
Esebanmen, G.E. and W.H.R. Langridge, "The role of TGF-beta signaling in dendritic cell tolerance," Immunol. Res. 65(5):987-994 (2017).
Faulds-Pain et al., "Flagellin Redundancy in *Caulobacter crescentus* and its Implications for Flagellar Filament Assembly," Journal of Bacteriology 193(11):2695-2707 (2011).
Felgner et al., "aroA-Deficient *Salmonella enterica* Serovar Typhimurium Is More Than a Metabolically Attenuated Mutant," mBio 7(5):e01220-16 (2016).
Felgner et al., "Optimizing *Salmonella enterica* serovar Typhimurium for bacteria-mediated tumor therapy," Gut Microbes 7(2):171-177 (2016).

(56) References Cited

OTHER PUBLICATIONS

Felgner et al., "Engineered *Salmonella enterica* serovar Typhimurium overcomes limitations of anti-bacterial immunity in bacteria-mediated tumor therapy," Oncoimmunology 7(2):e1382791 (2018), 12 pages.
Felgner et al., "Tumor-targeting bacteria-based cancer therapies for increased specificity and improved outcome," Microbial Biotechnology 10(5):1074-1078 (2017).
Fellmann et al., "An optimized microRNA backbone for effective single-copy RNAi," Cell Rep. 5(6):1704-1713 (2013).
Felt, S.A. and V.Z. Grdzelishvili, "Recent advances in vesicular stomatitis virus-based oncolytic virotherapy: a 5-year update," Journal of General Virology 98:2895-2911 (2017).
Fields et al., "Mutants of *Salmonella typhimurium* that cannot survive within the macrophage are avirulent," Proc. Natl. Acad. Sci. USA 83:5189-5193 (1986).
Fink, S.L. and B.T. Cookson, "Pyroptosis and host cell death responses during *Salmonella* infection," Cellular Microbiology 9(11):2562-2570 (2007).
Fisher C., "Recent Insights into the Control of Human Papillomavirus (HPV) Genome Stability, Loss, and Degradation," J. Clin. Med. 4(2):204-230 (2015).
Frahm et al., "Efficiency of Conditionally Attenuated *Salmonella enterica* Serovar Typhimurium in Bacterium-Mediated Tumor Therapy," mBio 6(2):e00254-15 (2015), 11 pages.
Freeman et al., "Phase I/II Trial of Intravenous NDV-HUJ Oncolytic Virus in Recurrent Glioblastoma Multiforme," Mol. Ther. 13(1):221-228 (2006).
Fu et al., "Effective Treatment of Pancreatic Cancer Xenografts with a Conditionally Replicating Virus Derived from Type 2 Herpes Simplex Virus," Clin. Cancer Res. 12(10):3152-3157 (2006).
Fuertes et al., "Host type I IFN signals are required for antitumor CD8+ T cell responses through CD8α+ dendritic cells," J. Exp. Med. 208(10):2005-2016 (2011).
Fujita et al., "The Clinical Relevance of the miR-197/CKS1B/STAT3-mediated PD-L1 Network in Chemoresistant Non-small-cell Lung Cancer," Mol. Ther. 23(4):717-727 (2015).
Gajewski et al., "Molecular profiling to identify relevant immune resistance mechanisms in the tumor microenvironment," Curr. Opin. Immunol. 23(2):286-292 (2011).
Galan, J. E. and R. Curtiss, III., "Virulence and vaccine potential of phoP mutants of *Salmonella typhimurium*," Microb. Pathog. 6(6):433-443 (1989).
Galan, J. E. and H. Wolf-Watz, "Protein delivery into eukaryotic cells by type III secretion machines," Nature 444:567-573 (2006).
Galan et al., "Cloning and characterization of the asd gene of *Salmonella typhimurium*: use in stable maintenance of recombinant plasmids in *Salmonella* vaccine strains," Gene 94(1):29-35 (1990).
Gao et al., "Overexpression of PD-L1 Significantly Associates with Tumor Aggressiveness and Postoperative Recurrence in Human Hepatocellular Carcinoma," Clin. Cancer Res. 15(3):971-979 (2009).
Gao et al., "Integrative Analysis of Complex Cancer Genomics and Clinical Profiles Using the cBioPortal," Sci. Signal. 6(269):p. 11 (2013), 34 pages.
Gao et al., "VISTA is an inhibitory immune checkpoint that is increased after ipilimumab therapy in patients with prostate cancer," Nat. Med. 23(5):551-555 (2017).
Gardlik et al., "Gene therapy for cancer: bacteria-mediated anti-angiogenesis therapy," Gene Therapy 18:425-431 (2011).
Geiss et al., "Preclinical Testing of an Oncolytic Parvovirus: Standard Protoparvovirus H-1PV Efficiently Induces Osteosarcoma Cell Lysis in Vitro," Viruses 9:301 (2017), 18 pages.
Geletneky et al., "Oncolytic H-1 Parvovirus Shows Safety and Signs of Immunogenic Activity in a First Phase I/IIa Glioblastoma Trial," Mol. Ther. 25(12):2620-2634 (2017).
Gibney et al., "Predictive biomarkers for checkpoint inhibitor-based immunotherapy," Lancet Oncol. 17(12):e542-e551 (2016).
Ginting et al., "Proinflammatory response induced by Newcastle disease virus in tumor and normal cells," Oncolytic Virotherapy 6:21-30 (2017).

Gong et al., "Clinical development of reovirus for cancer therapy: An oncolytic virus with immune-mediated antitumor activity," World J. Methodol. 6(1):25-42 (2016).
Goodman et al., "Tumor Mutational Burden as an Independent Predictor of Response to Immunotherapy in Diverse Cancers," Mol. Cancer Ther. 16(11):2598-2608 (2017).
Gray et al., "Cutting Edge: cGAS Is Required for Lethal Autoimmune Disease in the Trex1-Deficient Mouse Model of Aicardi-Goutieres Syndrome," J. Immunol. 195(5):1939-1943 (2015).
Grenga et al., "PD-L1 and MHC-I expression in 19 human tumor cell lines and modulation by interferon-gamma treatment," J. Immuno Therapy of Cancer 2(Suppl 3):p. 102 (2014).
Gribskov, M. and R.R. Burgess, "Sigma factors from *E. coli, B. subtilis*, phage SP01, and phage T4 are homologous proteins," Nucleic Acids Res. 14(16):6745-6763 (1986).
Groisman et al., "*Salmonella typhimurium* phoP virulence gene is a transcriptional regulator," Proc. Natl. Acad. Sci. USA 86:7077-7081 (1989).
Guo et al., "Targeting tumor gene by shRNA-expressing *Salmonella*-mediated RNAi," Gene Therapy 18:95-105 (2011).
Hagar et al., "WildCARDs: Inflammatory caspases directly detect LPS," Cell Research 25:149-150 (2015).
Haque, S. and Morris, J.C., "Transforming growth factor-β: A therapeutic target for cancer," Human Vaccines & Immunotherapeutics 13(8):1741-1750 (2017).
Hasan et al., "Trex1 regulates lysosomal biogenesis and interferon-independent activation of antiviral genes," Nature Immunology 14(1):61-71 (2013).
Hasan, M. and N. Yan, "Safeguard against DNA sensing: the role of TREX1 in HIV-1 infection and autoimmune diseases," Front. Microbiol. 5:193 (2014), 6 pages.
Heimann, D.M. and S.A. Rosenberg, "Continuous Intravenous Administration of Live Genetically Modified *Salmonella typhimurium* in Patients With Metastatic Melanoma," J. Immunother. 26(2):179-180 (2003).
Heo et al., "Sequential Therapy With JX-594, A Targeted Oncolytic Poxvirus, Followed by Sorafenib in Hepatocellular Carcinoma: Preclinical and Clinical Demonstration of Combination Efficacy," Mol. Ther. 19(6):1170-1179 (2011).
Hervas-Stubbs et al., "Conventional but not plasmacytoid dendritic cells foster the systemic virus-induced type I IFN response needed for efficient CD8 T cell priming," J. Immunol. 193(3):1151-1161 (2014).
Hodi et al., "Improved Survival with Ipilimumab in Patients with Metastatic Melanoma," N. Engl. J. Med. 363(8):711-723 (2010).
Hohmann et al., "phoP/phoQ-Deleted *Salmonella typhi* (Ty800) Is a Safe and Immunogenic Single-Dose Typhoid Fever Vaccine in Volunteers," J. Infect. Dis. 173:1408-1414 (1996).
Hossain et al., "Leukemia cell-targeted STAT3 silencing and TLR9 triggering generate systemic antitumor immunity," Blood 123(1):15-25 (2014).
Hu et al., "Differential outcome of TRIF-mediated signaling in TLR4 and TLR3 induced DC maturation," Proc. Natl. Acad. Sci. USA 112(45):13994-13999 (2015).
Huang, X., "A Time-Efficient, Linear-Space Local Similarity Algorithm," Adv. Appl. Math. 12:337-357 (1991).
Huang et al., "Targeting CD47: the achievements and concerns of current studies on cancer immunotherapy," J. Thorac. Dis. 9(2):E168-E174 (2017).
Husseiny, M.I. and M. Hensel, "Rapid method for the construction of *Salmonella enterica* Serovar Typhimurium vaccine carrier strains," Infect. Immun. 73(3):1598-1605 (2005).
Hutzen et al., "Advances in the design and development of oncolytic measles viruses," Oncolytic Virotherapy 4:109-118 (2015).
Irandoust et al., "Engagement of SIRPα Inhibits Growth and Induces Programmed Cell Death in Acute Myeloid Leukemia Cells," PLoS One 8(1):e52143 (2013), 13 pages.
Ireton, R.C. and M. Gale, Jr., "RIG-I Like Receptors in Antiviral Immunity and Therapeutic Applications," Viruses 3:906-919 (2011).
IUPAC-IUB Commission on Biochemical Nomenclature, "A One-Letter Notation for Amino Acid Sequences: Tentative Rules," The Journal of Biological Chemistry 243(13):3557-3559 (1968).

(56) References Cited

OTHER PUBLICATIONS

IUPAC-IUB Commission on Biochemical Nomenclature, "Symbols for Amino-Acid Derivatives and Peptides: Recommendations (1971)," Biochem. 11(9):1726-1732 (1972).
Iwasaki, A. and R. Medzhitov, "Regulation of adaptive immunity by the innate immune system," Science 327(5963):291-295 (2010).
Jackson et al., "Driving CAR T-cells forward," Nat. Rev. Clin. Oncol. 13(6):370-383 (2016).
Jacobson et al., "Cap-dependent translational control of oncolytic measles virus infection in malignant mesothelioma," Oncotarget 8(38):63096-63109 (2017).
Jiang et al., "Oncolytic adenovirus research evolution: from cell-cycle checkpoints to immune checkpoints," Curr. Opin. Virol. 13:33-39 (2015).
Kahn, M., "Can we safely target the WNT pathway?" Nat. Rev. Drug Discov. 13(7):513-532 (2014).
Kakarla, S. and S. Gottschalk, "CAR T cells for solid tumors: armed and ready to go?" Cancer J. 20(2):151-155 (2014).
Kang et al., "Preventative and therapeutic effects of auxotrophic *Edwardsiella tarda* mutant harboring CpG 1668 motif-enriched plasmids against scuticociliatosis in olive flounder (*Paralichthys olivaceus*)," Experimental Parasitology 144:34-38 (2014).
Kasinskas, R.W. and N.S. Forbes, "*Salmonella typhimurium* lacking ribose chemoreceptors localize in tumor quiescence and induce apoptosis," Cancer Res. 67(7):3201-3209 (2007).
Kawaguchi et al., "High-efficacy targeting of colon-cancer liver metastasis with *Salmonella typhimurium* A1-R via intra-portal-vein injection in orthotopic nude-mouse models," Oncotarget 8(12):19065-19073 (2017).
Kawai, T. and S. Akira, "Pathogen recognition with Toll-like receptors," Curr. Opin. Immunol. 17(4):338-344 (2005).
Kelly et al., "Novel Oncolytic Agent GLV-1h68 Is Effective Against Malignant Pleural Mesothelioma," Hum. Gene Ther. 19:774-782 (2008).
Kemp et al., "Exploring Reovirus Plasticity for Improving Its Use as Oncolytic Virus," Viruses 8, 4 (2016), 16 pages.
Khan et al., "A lethal role for lipid A in *Salmonella* infections," Mol. Microbiol. 29(2):571-579 (1998).
Kim et al., "Inhibition of vascular endothelial growth factor-induced angiogenesis suppresses tumour growth in vivo," Nature 362(6423):841-844 (1993).
Kim et al., "Overview analysis of adjuvant therapies for melanoma—a special reference to results from vaccinia melanoma oncolysate adjuvant therapy trials," Surgical Oncol. 10(1-2):53-59 (2001).
Kimpel et al., "The Oncolytic Virus VSV-GP Is Effective against Malignant Melanoma," Viruses 10, 108 (2018), 16 pages.
Kimura et al., "Selective Localization and Growth of *Bifidobacterium bifidum* in Mouse Tumors following Intravenous Administration," Cancer Res. 40:2061-2068 (1980).
Kocijancic et al., "Local application of bacteria improves safety of *Salmonella*-mediated tumor therapy and retains advantages of systemic infection," Oncotarget 8(30):49988-50001 (2017).
Kohlhapp, F.J. and H.L. Kaufman, "Molecular Pathways: Mechanism of Action for Talimogene Laherparepvec, a New Oncolytic Virus Immunotherapy," Clin. Cancer Res. 22(5):1048-1054 (2016).
Kong et al., "Turning self-destructing *Salmonella* into a universal DNA vaccine delivery platform," PNAS 109(47):19414-19419 (2012).
Kong et al., "Palmitoylation State Impacts Induction of Innate and Acquired Immunity by the *Salmonella enterica* Serovar Typhimurium msbB Mutant," Infection and Immunity 79(12):5027-5038 (2011).
Koopman et al., "Inhibition of *Salmonella enterica* Biofilm Formation Using Small-Molecule Adenosine Mimetics," Antimicrobial Agents and Chemotherapy 59(1):76-84 (2015).
Kzhyshkowska et al., "Stabilin-1, a homeostatic scavenger receptor with multiple functions," J. Cell Mol. Med. 10(3):635-649 (2006).
Lam et al., "Safety and Clinical Usage of Newcastle Disease Virus in Cancer Therapy," Journal of Biomedicine and Biotechnology, Article ID: 718710 (2011), 14 pages.

Lan et al., "Dnase2a deficiency uncovers lysosomal clearance of damaged nuclear DNA via autophagy," Cell Rep. 9(1):180-192 (2014).
Laurie et al., "A Phase 1 Clinical Study of Intravenous Administration of PV701, an Oncolytic Virus, Using Two-Step Desensitization," Clin. Cancer Res. 12(8):2555-2562 (2006).
Le et al., "A Live-attenuated Listeria Vaccine (ANZ-100) and a Live-attenuated Listeria Vaccine Expressing Mesothelin (CRS-207) for Advanced Cancers: Phase 1 Studies of Safety and Immune Induction," Clin. Cancer Res. 18(3):858-868 (2012).
Le et al., "Safety and Survival With GVAX Pancreas Prime and *Listeria monocytogenes*-Expressing Mesothelin (CRS-207) Boost Vaccines for Metastatic Pancreatic Cancer," J. Clin. Oncol. 33(12):1325-1333 (2015).
Lee et al., "B7-H1 (Programmed Cell Death Ligand 1) Is Required for the Development of Multifunctional Th1 Cells and Immunity to Primary, but Not Secondary, *Salmonella* Infection," J. Immunol. 185:2442-2449 (2010).
Lee et al., "Comparative Evaluation of the Acute Toxic Effects in Monkeys, Pigs and Mice of a Genetically Engineered *Salmonella* Strain (VNP20009) Being Developed as an Antitumor Agent," Int. J. Toxicol. 19:19-25 (2000).
Lee et al., "MHC class-I-restricted CD8 T cells play a protective role during primary *Salmonella* infection," Immunol. Lett. 148(2):138-143 (2012).
Lee et al., "The *C. elegans* heterochronic gene lin-4 encodes small RNAs with antisense complementarity to lin-14," Cell 75(5):843-854 (1993).
LeMercier et al., "VISTA regulates the development of protective anti-tumor immunity," Cancer Res. 74(7):1933-1944 (2014).
Leschner et al., "Tumor Invasion of *Salmonella enterica* Serovar Typhimurium Is Accompanied by Strong Hemorrhage Promoted by TNF-α," PLoS One 4(8):e6692 (2009), 11 pages.
Leventhal et al., "LB-131/28—Activation of innate and adaptive immunity via combinatorial immunotherapy using Synthetic Biotic™ Medicines," Abstract presented at the American Association for Cancer Research (AACR) meeting from Apr. 14-18, 2018, Chicago, IL, 2 pages.
Li et al., "Coadministration of a Herpes Simplex Virus-2-Based Oncolytic Virus and Cyclophosphamide Produces a Synergistic Antitumor Effect and Enhances Tumor-Specific Immune Responses," Cancer Res. 67:7850-7855 (2007).
Li et al., "Increased Susceptibility to *Salmonella* Infection in Signal Regulatory Protein α-Deficient Mice," J. Immunol. 189(5):2537-2544 (2012).
Li, Y. and K.V. Kowdley, "MicroRNAs in Common Human Diseases," Genomics Proteomics Bioinformatics 10:246-253 (2012).
Lightfield et al., "Critical role of Naip5 in inflammasome activation by a conserved C-terminal domain of flagellin," Nat. Immunol. 9(10):1171-1178 (2008).
Lin et al., "Oncolytic Vaccinia Virotherapy of Anaplastic Thyroid Cancer in Vivo," J. Clin. Endocrinol. Metab. 93:4403-4407 (2008).
Lin et al., "Treatment of anaplastic thyroid carcinoma in vitro with a mutant vaccinia virus," Surgery 142(6):976-983 (2007).
Lindahl et al., "Biochemical properties of mammalian TREX1 and its association with DNA replication and inherited inflammatory disease," Biochem. Soc. Trans. 37(Pt 3):535-538 (2009).
Liu et al., "Blockage of autophagy pathway enhances *Salmonella* tumor-targeting," Oncotarget 7(16):22873-22882 (2016).
Liu et al., "NF-κB signaling in inflammation," Signal Transduction and Targeted Therapy 2:e17023 (2017), 9 pages.
Liu et al., "Inhibition of HIV-1 by multiple siRNAs expressed from a single microRNA polycistron," Nucleic Acids Res. 36(9):2811-2824 (2008).
Liu et al., "Immune-checkpoint proteins VISTA and PD-1 nonredundantly regulate murine T-cell responses," Proc. Natl. Acad. Sci. USA 112(21):6682-6687 (2015).
Liu et al., "Pre-Clinical Development of a Humanized Anti-CD47 Antibody with Anti-Cancer Therapeutic Potential," PLoS ONE 10(9):e0137345 (2015), 23 pages.
Liu et al., "CD47 Blockade Triggers T cell-mediated Destruction of Immunogenic Tumors," Nat. Med. 21(10):1209-1215 (2015).

(56) References Cited

OTHER PUBLICATIONS

Liu et al., "Outer membrane vesicles from flagellin-deficient *Salmonella enterica* serovar Typhimurium induce cross-reactive immunity and provide cross-protection against heterologous *Salmonella* challenge," Scientific Reports 6:34776 (2016), 13 pages.
Liu et al., "The Targeted Oncolytic Poxvirus JX-594 Demonstrates Antitumoral, Antivascular, and Anti-HBV Activities in Patients with Hepatocellular Carcinoma," Mol. Ther. 16(9):1637-1642 (2008).
Lo et al., "T cell responses to Gram-negative intracellular bacterial pathogens: a role for CD8+ T cells in immunity to *Salmonella* infection and the involvement of MHC class Ib molecules," J. Immunol. 162(9):5398-5406 (1999).
Loeffler et al., "Attenuated *Salmonella* engineered to produce human cytokine LIGHT inhibit tumor growth," PNAS 104(31):12879-12883 (2007).
Loeffler et al., "IL-18-producing *Salmonella* inhibit tumor growth," Cancer Gene Ther. 15(12):787-794 (2008).
Loeffler et al., "Inhibition of Tumor Growth Using *Salmonella* Expressing Fas Ligand," J. Natl. Cancer Inst. 100:1113-1116 (2008).
Low et al., "Construction of VNP20009: A Novel, Genetically Stable Antibiotic-Sensitive Strain of Tumor-Targeting *Salmonella* for Parenteral Administration in Humans," Methods in Molecular Medicine, vol. 90, Suicide Gene Therapy: Methods and Reviews (Chp. 3), pp. 47-59 (2003).
Low et al., "Lipid A mutant *Salmonella* with suppressed virulence and TNFα induction retain tumor-targeting in vivo," Nature Biotechnology 17:37-41 (1999).
Lundberg et al., "Growth phase-regulated induction of *Salmonella*-induced macrophage apoptosis correlates with transient expression of SPI-1 genes," J. Bacteriol. 181(11):3433-3437 (1999).
Luo et al., "Antitumor Effect of VNP20009, an Attenuated *Salmonella*, in Murine Tumor Models," Oncology Research 12:501-508 (2002).
Machine-generated English language translation of Chinese Patent No. CN 103468626 B, 35 pages.
Mackenzie et al., "Ribonuclease H2 mutations induce as cGAS/STING-dependent innate immune response," EMBO J. 35(8):831-844 (2016).
Mahoney et al., "Combination cancer immunotherapy and new immunomodulatory targets," Nat. Rev. Drug Discov. 14(8):561-584 (2015).
Makinen et al., "Stable RNA interference: comparison of U6 and H1 promoters in endothelial cells and in mouse brain," J. Gene Med. 8:433-441 (2006).
Manuel et al., "*Salmonella*-Based Therapy Targeting Indoleamine 2,3-Dioxygenase Coupled with Enzymatic Depletion of Tumor Hyaluronan Induces Complete Regression of Aggressive Pancreatic Tumors," Cancer Immunol. Res. 3(9):1096-1107 (2015).
Manuel et al., "Enhancement of Cancer Vaccine Therapy by Systemic Delivery of a Tumor-Targeting *Salmonella*-Based STAT3 shRNA Suppresses the Growth of Established Melanoma Tumors," Cancer Res. 71(12):4183-4191 (2011).
Manuel, E.R. and D.J. Diamond, "A road less traveled paved by IDO silencing," Oncolmmunology 2(3):e23322 (2013), 3 pages.
Matveeva et al., "Oncolysis by paramyxoviruses: preclinical and clinical studies," Molecular Therapy—Oncolytics 2, 150017 (2015), 14 pages.
Mazur, D.J. and F.W. Perrino, "Excision of 3' Termini by the Trex1 and TREX2 3' → 5' Exonucleases," J. Biol. Chem. 276(20):17022-17029 (2001).
Mazurek et al., "Assessment of the total cfDNA and HPV16/18 detection in plasma samples of head and neck squamous cell carcinoma patients," Oral Oncol. 54:36-41 (2016).
McBride et al., "Artificial miRNAs mitigate shRNA-mediated toxicity in the brain: Implications for the therapeutic development of RNAi," Proc. Natl. Acad. Sci. USA 105(15):5868-5873 (2008).
McBride, A.A., "Oncogenic Human Papillomaviruses," Phil. Trans. R. Soc. B 372:20160273 (2017), 9 pages.

McCart et al., "Systemic Cancer Therapy with a Tumor-selective Vaccinia Virus Mutant Lacking Thymidine Kinase and Vaccinia Growth Factor Genes," Cancer Res. 61:8751-8757 (2001).
McCracken et al., "Molecular Pathways: Activating T Cells After Cancer Cell Phagocytosis from Blockade of CD47 "Don't Eat Me" Signals," Clin. Cancer Res. 21(16):3597-3601 (2015).
McKelvey et al., "Cell-specific expression of TLR9 isoforms in inflammation," J. Autoimmun. 36(1):76-86 (2011).
Methner et al., "*Salmonella* Enteritidis with double deletion in phoP fliC—A potential live *Salmonella* vaccine candidate with novel characteristics for use in chickens," Vaccine 29:3248-3253 (2011).
Miles et al., "Anthrax toxin receptor 1 is the cellular receptor for Seneca Valley virus," J. Clin. Invest. 127(8):2957-2967 (2017).
Miller et al., "A two-component regulatory system (phoP phoQ) controls *Salmonella typhimurium* virulence," Proc. Natl. Acad. Sci. USA 86:5054-5058 (1989).
Moehler et al., "Oncolytic virotherapy as emerging immunotherapeutic modality: potential of parvovirus H-1," Frontiers in Oncology 4:92 (2014), 10 pages.
Moore et al., "Short Hairpin RNA (shRNA): Design, Delivery and Assessment of Gene Knockdown," Methods Mol. Biol. 629:141-158 (2010).
Morita et al., "Gene-Targeted Mice Lacking the Trex1 (DNase III) 3'→5' DNA Exonuclease Develop Inflammatory Myocarditis," Mol. Cell. Biol. 24(15):6719-6727 (2004).
Moss, B., "Poxvirus vectors: cytoplasmic expression of transferred genes," Curr. Opin. Genet. Dev. 3(1):86-90 (1993).
Msaouel et al., "Oncolytic Measles Virus Strains as Novel Anticancer Agents," Expert Opin. Biol. Ther. 13(4):483-502 (2013).
Mui et al., "Viral Oncology: Molecular Biology and Pathogenesis," J. Clin. Med. 6, 111 (2017), 58 pages.
Muik et al., "Re-engineering Vesicular Stomatitis Virus to Abrogate Neurotoxicity, Circumvent Humoral Immunity, and Enhance Oncolytic Potency," Cancer Res. 74(13):3567-3578 (2014).
Murakami et al., "Tumor-targeting *Salmonella typhimurium* A1-R regresses an osteosarcoma in a patient-derived xenograft model resistant to a molecular-targeting drug," Oncotarget 8(5):8035-8042 (2017).
Murata et al., "The CD47-SIRPα signalling system: its physiological roles and therapeutic application," J. Biochem. 155(6):335-344 (2014).
Needleman, S.B. and C.D. Wunsch, "A General Method Applicable to the Search for Similarities in the Amino Acid Sequence of Two Proteins," J. Mol. Biol. 48:443-453 (1970).
Nemunaitis et al., "Pilot trial of genetically modified, attenuated *Salmonella* expressing the *E. coli* cytosine deaminase gene in refractory cancer patients," Cancer Gene Therapy 10:737-744 (2003).
Nie et al., "Regulation of U6 Promoter Activity by Transcriptional Interference in Viral Vector-Based RNAi," Genomics Proteomics Bioinformatics 8(3):170-179 (2010).
Ohlson et al., "Structure and function of SifA indicate that interactions with SKIP, SseJ, and RhoA family GTPases induce endosomal tubulation," Cell Host Microbe. 4(5):434-446 (2008).
Olsen et al., "The role of flagella and chemotaxis genes in host pathogen interaction of the host adapted *Salmonella enterica* serovar Dublin compared to the broad host range serovar S. Typhimurium," BMC Microbiology 13:67 (2013), 11 pages.
O'Rourke et al., "A single dose of peripherally infused EGFRvIII-directed CAR T cells mediates antigen loss and induces adaptive resistance in patients with recurrent glioblastoma," Sci. Transl. Med. 9(399):eaaa0984 (2017), 30 pages.
Osterberg et al., "Decrease of VEGF-A in myeloid cells attenuates glioma progression and prolongs survival in an experimental glioma model," Neuro-Oncology 18(7):939-949 (2016).
Owen et al., "*Salmonella* Suppresses the TRIF-Dependent Type I Interferon Response in Macrophages," mBio 7(1):e02051-15 (2016), 15 pages.
Palani et al., "Monocyte Stabilin-1 Suppresses the Activation of Th1 Lymphocytes," J. Immunol. 196(1):115-123 (2016).
Pandey et al., "Microbial Sensing by Toll-Like Receptors and Intracellular Nucleic Acid Sensors," Cold Spring Harb. Perspect. Biol. 7:a016246 (2015), 18 pages.

(56) References Cited

OTHER PUBLICATIONS

Park et al., "Analysis of virulence and growth of a purine auxotrophic mutant of *Xanthomonas oryzae* pathovar *oryzae*," FEMS Microbiol. Lett. 276(1):55-59 (2007).
Park et al., "Use of a targeted oncolytic poxvirus, JX-594, in patients with refractory primary or metastatic liver cancer: a phase I trial," Lancet Oncol. 9(6):533-542 (2008).
Pasquinelli et al., "Conservation of the sequence and temporal expression of let-7 heterochronic regulatory RNA," Nature 408(6808):86-89 (2000).
Patyar et al., "Bacteria in cancer therapy: a novel experimental strategy," J. Biomed. Sci. 17:21 (2010), 9 pages.
Pawelek et al., "Bacteria as tumour-targeting vectors," Lancet Oncol. 4:548-556 (2003).
Pawelek et al., "Tumor-targeted *Salmonella* as a Novel Anticancer Vector," Cancer Research 57:4537-4544 (1997).
Pebernard, S. and R.D. Iggo, "Determinants of interferon-stimulated gene induction by RNAi vectors," Differentiation 72(2-3):103-111 (2004).
Pereira-Lopes et al., "The exonuclease Trex1 restrains macrophage proinflammatory activation," J. Immunol. 191:6128-6135 (2013).
Peschke et al., "Loss of Trex1 in Dendritic Cells Is Sufficient to Trigger Systemic Autoimmunity," J. Immunol. 197(6):2157-2166 (2016).
Phan et al., "Cancer regression and autoimmunity induced by cytotoxic T lymphocyte-associated antigen 4 blockade in patients with metastatic melanoma," PNAS 100(14):8372-8377 (2003).
Prati et al., "Three Prime Repair Exonuclease 1 (TREX1) Expression Correlates with Cervical Cancer Cells Growth in vitro and Disease Progression in vivo," Scientific Reports 9:351 (2019), 14 pages.
Prati, B., "Expressao de genes de vias de reparo de dano ao DNA em celulas infectadas por papilomavirus humano (HPV)." M.Sc. Thesis, Aug. 14, 2014, pp. 1-82, Sao Paulo, Brazil. Retrieved on Jan. 14, 2020, from: <URL:teses.usp.br/teses/disponiveis/42/42132/tde-12082014-175455/publico/BrunaPrati_Mestrado.pdf, 83 pages [In Portuguese with English Abstract].
Prati, B., "Expressao de genes de vias de reparo de dano ao DNA em celulas infectadas por papilomavirus humano (HPV)." M.Sc. Thesis, Aug. 14, 2014, pp. 1-82, Sao Paulo, Brazil. Retrieved on Jan. 14, 2020, from: <URL:teses.usp.br/teses/disponiveis/42/42132/tde-12082014-175455/publico/BrunaPrati_Mestrado.pdf, 83 pages [Machine-generated English language translation].
Pulliero et al., "Inhibition of neuroblastoma cell growth by TREX1-mutated human lymphocytes," Oncology Reports 27:1689-1694 (2012).
Qian et al., "Seneca Valley Virus Suppresses Host Type I Interferon Production by Targeting Adaptor Proteins MAVS, TRIF, and TANK for Cleavage," J. Virol. 91(16):e00823-17 (2017), 17 pages.
Qin et al., "Cervical Cancer Neoantigen Landscape and Immune Activity is Associated with Human Papillomavirus Master Regulators," Front. Immunol. 8:689 (2017), 8 pages.
Rabe, B., "Aicardi-Goutieres syndrome: clues from the RNase H2 knock-out mouse," J. Mol. Med. (Berl) 91(11):1235-1240 (2013).
Raetz, C.R.H. and C. Whitfield, "Lipopolysaccharide endotoxins," Annu. Rev. Biochem. 71:635-700 (2002).
Rantakari et al., "Stabilin-1 expression defines a subset of macrophages that mediate tissue homeostasis and prevent fibrosis in chronic liver injury," Proc. Natl. Acad. Sci. USA 113(33):9298-9303 (2016).
Ribas, A., "Releasing the Brakes on Cancer Immunotherapy," N. Engl. J. Med. 373(16):1490-1492 (2015).
Rosenberg et al., "Antitumor Effects in Mice of the Intravenous Injection of Attenuated *Salmonella typhimurium*," Journal of Immunotherapy 25(3):218-225 (2002).
Rosenberg et al., "Cancer immunotherapy: moving beyond current vaccines," Nat. Med. 10(9):909-915 (2004).
Re: Rosenberg et al. (2004) Nat. Med. 10(9):909-915, Correspondence to the Editor by Mocellin et al., p. 1278, Correspondence to the Editor by Timmerman et al., p. 1279, and Reply by Rosenberg et al., in Nat. Med. 10(12):1278-1280 (2004).

Ruegg et al., "Evidence for the involvement of endothelial cell integrin $\alpha V\beta 3$ in the disruption of the tumor vasculature induced by TNF and IFN-$\gamma$," Nature Med. 4(4):408-414 (1998).
Ruella, M. and M.V. Maus, "Catch me if you can: Leukemia Escape after CD19-Directed T Cell Immunotherapies," Comput. Struct. Biotechnol. J. 14:357-362 (2016).
Sadelain, M., "CAR therapy: the CD19 paradigm," J. Clin. Invest. 125(9):3392-3400 (2015).
Schadendorf et al., "Pooled Analysis of Long-Term Survival Data From Phase II and Phase III Trials of Ipilimumab in Unresectable or Metastatic Melanoma," J. Clin. Oncol. 33(17):1889-1894 (2015).
Scheiermann, J. and D.M. Klinman, "Clinical evaluation of CpG oligonucleotides as adjuvants for vaccines targeting infectious diseases and cancer," Vaccine 32(48):6377-6389 (2014).
Schmitt et al., "Absence of All Components of the Flagellar Export and Synthesis Machinery Differentially Alters Virulence of *Salmonella enterica* Serovar Typhimurium in Models of Typhoid Fever, Survival in Macrophages, Tissue Culture Invasiveness, and Calf Enterocolitis," Infection and Immunity 69(9):5619-5625 (2001).
Schwartz, R.M. and M.O. Dayhoff, "Matrices for detecting distant relationships," in: Atlas of Protein Sequence and Structure, National Biomedical Research Foundation, pp. 353-358 (1978).
Seiwert et al., "Integrative and Comparative Genomic Analysis of HPV-Positive and HPV-Negative Head and Neck Squamous Cell Carcinomas," Clin. Cancer Res. 21(3):632-641 (2015).
Sharma et al., "Novel cancer immunotherapy agents with survival benefit: recent successes and next steps," Nat. Rev. Cancer 11(11):805-812 (2011).
Sharma et al., "Primary, Adaptive, and Acquired Resistance to Cancer Immunotherapy," Cell 168:707-723 (2017).
Shaw, A.R. and M. Suzuki, "Recent advances in oncolytic adenovirus therapies for cancer," Curr. Opin. Virol. 21:9-15 (2016).
Shi et al., "Combined prokaryotic-eukaryotic delivery and expression of therapeutic factors through a primed autocatalytic positive-feedback loop," Journal of Controlled Release 222:130-140 (2016).
Sirard et al., "Live attenuated *Salmonella*: a paradigm of mucosal vaccines," Immunol. Rev. 171:5-26 (1999).
Smith, T.F. and M.S. Waterman, "Comparison of Biosequences," Adv. Appl. Math. 2:482-489 (1981).
Sokolowski et al., "Oncolytic virotherapy using herpes simplex virus: how far have we come?" Oncolytic Virotherapy 4:207-219 (2015).
Sorenson et al., "Safety and immunogenicity of *Salmonella typhimurium* expressing C-terminal truncated human IL-2 in a murine model," Biologics: Targets & Therapy 4:61-73 (2010).
Spranger et al., "Melanoma-intrinsic $\beta$-catenin signalling prevents anti-tumour immunity," Nature 523(7559):231-235 (2015).
Stagg, J. and M.J. Smyth, "Extracellular adenosine triphosphate and adenosine in cancer," Oncogene 29:5346-5358 (2010).
Starks et al., "Listeria monocytogenes as a Vaccine Vector: Virulence Attenuation or Existing Antivector Immunity Does Not Diminish Therapeutic Efficacy," J. Immunol. 173:420-427 (2004).
Stetson et al., "Trex1 prevents cell-intrinsic initiation of autoimmunity," Cell 134(4):587-598 (2008).
Stritzker et al., "Enterobacterial tumor colonization in mice depends on bacterial metabolism and macrophages but is independent of chemotaxis and motility," Int. J. Med. Microbiol. 300:449-456 (2010).
Sun et al., "Cyclic GMP-AMP Synthase is a Cytosolic DNA Sensor that Activates the Type-I Interferon Pathway," Science 339(6121):786-791 (2013).
Swift, L.H. and R.M. Golsteyn, "Genotoxic Anti-Cancer Agents and Their Relationship to DNA Damage, Mitosis, and Checkpoint Adaptation in Proliferating Cancer Cells," Int. J. Mol. Sci. 15(3):3403-3431 (2014).
Tai et al., "Targeting the WNT Signaling Pathway in Cancer Therapeutics," The Oncologist 20:1189-1198 (2015).
Tayeb et al., "Therapeutic potential of oncolytic Newcastle disease virus: a critical review," Oncolytic Virotherapy 4:49-62 (2015).
Timiryasova, T.M., "Construction of Recombinant Vaccinia Viruses Using PUV-Inactivated Virus as a Helper," BioTechniques 31(3):534-540 (2001).

(56) References Cited

OTHER PUBLICATIONS

Tjuvajev et al., "*Salmonella*-based tumor-targeted cancer therapy: tumor amplified protein expression therapy (TAPET™) for diagnostic imaging," J. Control Release 74(1-3):313-315 (2001).
Tome et al., "Primer Dosing of *S. typhimuium* A1-R Potentiates Tumor-Targeting and Efficacy in Immunocompetent Mice," Anticancer Research 33:97-102 (2013).
Toley, B.J. and N.S. Forbes, "Motility is Critical for Effective Distribution and Accumulation of Bacteria in Tumor Tissue," Integr Biol (Camb) 4(2):165-176 (2012).
Tomicic et al., "Human three prime exonuclease TREX1 is induced by genotoxic stress and involved in protection of glioma and melanoma cells to anticancer drugs," Biochimica et Biophysica Acta 1833:1832-1843 (2013).
Tominaga, A. and Kutsukake, K., "Expressed and cryptic flagellin genes in the H44 and H55 type strains of *Escherichia coli*," Genes Genet. Syst. 82:1-8 (2007).
Topalian et al., "Safety, Activity, and Immune Correlates of Anti-PD-1 Antibody in Cancer," N. Engl. J. Med. 366(26):2443-2454 (2012).
Torres et al., "Bacteria in cancer therapy: beyond immunostimulation," J. Cancer Metastasis Treat. 4:4 (2018), 25 pages.
Toso et al., "Phase I Study of the Intravenous Administration of Attenuated *Salmonella typhimurium* to Patients With Metastatic Melanoma," Journal of Clinical Oncology 20(1):142-152 (2002).
Traktman, P., "Chapter 27, Poxvirus DNA Replication," in: DNA Replication in Eukaryotic Cells, Cold Spring Harbor Laboratory Press, pp. 775-798 (1996).
Travis, M.A. and D. Sheppard, "TGF-β activation and function in immunity," Annu. Rev. Immunol. 32:51-82 (2014).
Tukel et al., "CsgA is a pathogen-associated molecular pattern of *Salmonella enterica* serotype Typhimurium that is recognized by Toll-like receptor 2," Mol. Microbiol. 58(1):289-304 (2005).
Tyle, P., "Iontophoretic Devices for Drug Delivery," Pharmaceutical Research 3(6):318-326 (1986).
Uusi-Kerttula et al., "Oncolytic Adenovirus: Strategies and Insights for Vector Design and Immuno-Oncolytic Applications," Viruses 7:6009-6042 (2015).
Vanpouille-Box et al., "DNA exonuclease Trex1 regulates radiotherapy-induced tumor immunogenicity," Nat. Comm. 8:15618 (2017), 15 pages.
Vaupel, P. and A. Mayer, "Hypoxia-Driven Adenosine Accumulation: A Crucial Microenvironmental Factor Promoting Tumor Progression," in: Oxygen Transport to Tissue XXXVII, Advances in Experimental Medicine and Biology 876, C. E. Elwell et al. (eds.), Springer Science + Business Media, New York, Chp. 22, pp. 177-183 (2016).
Veinalde et al., "Oncolytic measles virus encoding interleukin-12 mediates potent antitumor effects through T cell activation," Oncoimmunology 6(4):e1285992 (2017), 12 pages.
Wang et al., "TREX1 acts in degrading damaged DNA from drug-treated tumor cells," DNA Repair (Amst) 8(10):1179-1189 (2009).
Wang, R.F. and S.R. Kushner, "Construction of versatile low-copy-number vectors for cloning, sequencing and gene expression in *Escherichia coli*" Gene 100:195-199 (1991).
Wang et al., "VISTA, a novel mouse Ig superfamily ligand that negatively regulates T cell responses," J. Exp. Med. 208(3):577-592 (2011).
Wang et al., "IL-10 Contributes to the Suppressive Function of Tumor Associated Myeloid Cells and Enhances Myeloid Cell Accumulation in Tumors," Scand. J. Immunol. 75(3):273-281 (2012).
Wang et al., "New technologies in developing recombinant attenuated *Salmonella* vaccine vectors," Microbial Pathogenesis 58:17-28 (2013).
Wang et al., "Detection of somatic mutations and HPV in the saliva and plasma of patients with head and neck squamous cell carcinomas," Sci. Transl. Med. 7(293):293ra104 (2015), 8 pages.
Watanabe et al., "Quantitative evaluation of first, second, and third generation hairpin systems reveals the limit of mammalian vector-based RNAi," RNA Biology 13(1):25-33 (2016).
Watson et al., "Molecular Biology of the Gene," $4^{th}$ Edition, The Benjamin/Cummings Publ. Co., Inc, p. 224 (1987), 25 pages.
Weiskopf et al., "CD47-blocking immunotherapies stimulate macrophage-mediated destruction of small-cell lung cancer," J. Clin. Invest. 126(7):2610-2620 (2016).
Wheeler et al., "TREX1 Knockdown Induces an Interferon Response to HIV that Delays Viral Infection in Humanized Mice," Cell Reports 15:1715-1727 (2016).
Wilson et al., "MicroRNA regulation of endothelial TREX1 reprograms the tumour microenvironment," Nat Comm. 7:13597 (2016), 10 pages.
Wu et al., "Cyclic-GMP-AMP Is an Endogenous Second Messenger in Innate Immune Signaling by Cytosolic DNA," Science 339(6121):826-830 (2013).
Xia et al., "An enhanced U6 promoter for synthesis of short hairpin RNA," Nucleic Acids Res. 31(17):e100 (2003).
Xie et al., "MiR-140 Expression Regulates Cell Proliferation and Targets PD-L1 in NSCLC," Cell Physiol. Biochem. 46(2):654-663 (2018).
Xu et al., "Effective Cancer Vaccine Platform Based on Attenuated *Salmonella* and Type III Secretion System," Cancer Res. 74(21):6260-6270 (2014).
Yamamoto et al., "Recent advances in genetic modification of adenovirus vectors for cancer treatment," Cancer Sci. 108:831-837 (2017).
Yan et al., "The cytosolic exonuclease TREX1 inhibits the innate immune response to HIV-1," Nat. Immunol. 11(11):1005-1013 (2010).
Yanagita et al., "Anti-SIRPα antibodies as a potential new tool for cancer immunotherapy," JCI Insight 2(1):e89140 (2017).
Yang et al., "Trex1 Exonuclease Degrades ssDNA to Prevent Chronic Checkpoint Activation and Autoimmune Disease," Cell 131:873-886 (2007).
Yasutake et al., "Comparison of antitumor activity of *Lactobacillus casei* with other bacterial immunopotentiators," Med. Microbiol. Immunol. 173(3):113-125 (1984).
Yee, C., "Adoptive T Cell Therapy for Cancer: Boutique Therapy or Treatment Modality?" Clin. Cancer Res. 19(17):4550-4552 (2013).
Yee et al., "MicroRNA-155 induction via TNF-α and IFN-γ suppresses expression of programmed death ligand-1 (PD-L1) in human primary cells," J. Biol. Chem. 292(50):20683-20693 (2017).
Yin et al., "Modulation of the Intratumoral Immune Landscape by Oncolytic Herpes Simplex Virus Virotherapy," Front. Oncol. 7:136 (2017), 7 pages.
Ylä-Pelto et al., "Therapeutic Use of Native and Recombinant Enteroviruses," Viruses 8:57 (2016), 15 pages.
Yokoda et al., "Oncolytic Adenoviruses in Gastrointestinal Cancers," Biomedicines 6:33 (2018), 13 pages.
Yoon et al., "Application of genetically engineered *Salmonella typhimurium* for interferon-gamma-induced therapy against melanoma," European Journal of Cancer 70:48-61 (2017).
Yoon et al., "Suppression of Inflammation by Recombinant *Salmonella typhimurium* Harboring CCL22 MicroRNA," DNA and Cell Biology 31(3):289-296 (2012).
Yu et al., "Explicit hypoxia targeting with tumor suppression by creating an "obligate" anaerobic *Salmonella typhimurium* strain," Scientific Reports 2:436 (2012), 10 pages.
Yu et al., "Oncolytic vaccinia therapy of squamous cell carcinoma," Mol. Cancer 8:45 (2009), 9 pages.
Yu et al., "Regression of human pancreatic tumor xenografts in mice after a single systemic injection of recombinant vaccinia virus GLV-1h68," Mol. Cancer Ther. 8(1):141-151 (2009).
Yu et al., "Visualization of tumors and metastases in live animals with bacteria and vaccinia virus encoding light-emitting proteins," Nat. Biotech. 22(3):313-320 (2004).
Zakikhany et al., "Unphosphorylated CsgD controls biofilm formation in *Salmonella enterica* serovar Typhimurium," Molecular Microbiology 77(3):771-786 (2010).
Zeng et al., "Flagellin is the Major Proinflammatory Determinant of Enteropathogenic *Salmonella*," J. Immunol. 171:3668-3674 (2003).

(56) References Cited

OTHER PUBLICATIONS

Zhang et al., "Eradication of Solid Human Breast Tumors in Nude Mice with an Intravenously Injected Light-Emitting Oncolytic Vaccinia Virus," Cancer Res. 67(20):10038-10046 (2007).
Zhang et al., "Intratumoral Delivery and Suppression of Prostate Tumor Growth by Attenuated *Salmonella enterica* serovar *typhimurium* Carrying Plasmid-Based Small Interfering RNAs," Cancer Res. 67(12):5859-5864 (2007).
Zhang et al., "shRNA-armed conditionally replicative adenoviruses: a promising approach for cancer therapy," Oncotarget 7(20):29824-29834 (2016).
Zhao et al., "Efficacy against lung metastasis with a tumor-targeting mutant of *Salmonella typhimurium* in immunocompetent mice," Cell Cycle 11(1):187-193 (2012).
Zhao et al., "Strategic Combinations: The Future of Oncolytic Virotherapy with Reovirus," Mol. Cancer Ther. 15(5):767-773 (2016).
Zhao et al., "Targeted Therapy with a *Salmonella typhimurium* Leucine-Arginine Auxotroph Cures Orthotopic Human Breast Tumors in Nude Mice," Cancer Res. 66(15):7647-7652 (2006).
Zhao et al., "Tumor-targeting bacterial therapy with amino acid auxotrophs of GFP-expressing *Salmonella typhimurium*," PNAS 102(3):755-760 (2005).
Zheng et al., "Two-step enhanced cancer immunotherapy with engineered *Salmonella typhimurium* secreting heterologous flagellin," Sci. Transl. Med. 9:eaak9537 (2017), 11 pages.
Zheng et al., "Targeted Cancer Therapy Using Engineered *Salmonella typhimurium*," Chonnam Med. J. 52:173-184 (2016).
Zheng et al., "Tumor Amplified Protein Expression Therapy: *Salmonella* as a Tumor-Selective Protein Delivery Vector," Oncol. Res. 12:127-135 (2000).
Zhu et al., "Current landscape and future directions of biomarkers for predicting responses to immune checkpoint inhibitors," Cancer Management and Research 10:2475-2488 (2018).
Zielinski et al., "Dissecting the human immunologic memory for pathogens," Immunol. Rev. 240:40-51 (2011).
Zitvogel et al., "Type I interferons in anticancer immunity" Nature Reviews Immunology 15:405-414 (2015).
Zu, C. and J. Wang, "Tumor-colonizing bacteria: A potential tumor targeting therapy," Crit. Rev. Microbiol. 40(3):225-235 (2014).
Glickman et al., Actym Therapeutics Poster Presentation, entitled "STACT-TREX1: A Novel Tumor-Targeting Systemically-Delivered STING Pathway Agonist Demonstrates Robust Anti-Tumor Efficacy in Multiple Murine Cancer Models." Abstract # P235. Presented at the Society for Immunotherapy of Cancer (SITC) Annual Meeting, in Washington, D.C., on Nov. 9, 2018, 1 page.
Makarova et al., Actym Therapeutics Poster Presentation, entitled "STACT-TREX1: A Systemically-Administered STING Pathway Agonist Targets Tumor-Resident Myeloid Cells and Induces Adaptive Anti-Tumor Immunity in Multiple Preclinical Models," Abstract # 5016. Presented at the American Association for Cancer Research (AACR) Annual Meeting, in Atlanta, Ga., on Apr. 3, 2019, 1 page.
Glickman et al., Actym Therapeutics Poster Presentation, entitled "STACT: A Novel Therapeutic Platform that Delivers Immunomodulatory Payloads to Tumor-Resident Myeloid Cells After IV Dosing and Demonstrates Potent Anti-Tumor Efficacy in Preclinical Studies." Poster #P482. Presented at the Society for Immunotherapy of Cancer (SITC) Annual Meeting, in National Harbor, MD, on Nov. 9, 2019, 1 page.
Rae et al., Actym Therapeutics Poster Presentation, entitled "STACT: A novel Tumor-Targeting, Systemically-Administered Delivery Platform Capable of Targeting Intractable Pathways and Precise Immuno-Modulation of the Tumor Microenvironment." Abstract # 4782. Presented at the American Association for Cancer Research (AACR) Annual Meeting, in Atlanta, Ga., on Apr. 3, 2019, 1 page.
Christopher D. Thanos, Ph.D., Actym Therapeutics Presentation, entitled "A Novel Systemically Delivered STING Pathway Agonist Therapy Demonstrates Robust Anti-Tumor Efficacy in Multiple Murine Cancer Models." Presented at the 15th Annual PEGS Conference in Boston, MA, on Apr. 12, 2019, 35 pages.

Actym Therapeutics, Inc., "The next frontier in immuno-oncology," BioPharma Dealmakers, B22, Mar. 2019, 1 page.
Illumina Ventures Portfolio Company Spotlight, entitled, "Acytm Therapeutics: A New Path to Immunology." Published Aug. 2021 [online]; retrieved on Nov. 8, 2021, from: <URL:.illuminaventures.com/spotlight-actym-2021, 2 pages.
Invitation to Pay Additional Fees and Partial International Search, dated Oct. 17, 2018, in connection with International Patent Application No. PCT/US2018/041713, 25 pages.
Response to Invitation to Pay Additional Fees, submitted Nov. 15, 2018, in connection with International Patent Application No. PCT/US2018/041713, 13 pages.
International Search Report and Written Opinion, dated Jan. 3, 2019, in connection with International Patent Application No. PCT/US2018/041713, 34 pages.
Response, filed May 13, 2019, to International Search Report and Written Opinion, dated Jan. 3, 2019, in connection with International Patent Application No. PCT/US2018/041713, 55 pages.
Invitation to Restrict or Pay Additional Examination Fees, dated Jun. 7, 2019, in connection with International Patent Application No. PCT/US2018/041713, 9 pages.
Response, filed Jul. 5, 2019, to Invitation to Restrict or Pay Additional Examination Fees, dated Jun. 7, 2019, in connection with International Patent Application No. PCT/US2018/041713, 4 pages.
Written Opinion of the International Preliminary Examining Authority, dated Aug. 6, 2019, in connection with International Patent Application No. PCT/US2018/041713, 13 pages.
Replacement Claim Sets, filed Sep. 6, 2019, and Response, filed Sep. 5, 2019, to the Written Opinion of the International Preliminary Examining Authority, dated Aug. 6, 2019, in connection with International Patent Application No. PCT/US2018/041713, 61 pages.
International Preliminary Report on Patentability (Chapter II of the PCT), dated Oct. 14, 2019, in connection with International Patent Application No. PCT/US2018/041713, 17 pages.
Office Action, dated Mar. 11, 2020, in connection with U.S. Appl. No. 16/033,187, 16 pages.
Response, filed Apr. 10, 2020, to Office Action, dated Mar. 11, 2020, in connection with U.S. Appl. No. 16/033,187, 19 pages.
Final Office Action, dated Jul. 14, 2020, in connection with U.S. Appl. No. 16/033,187, 9 pages.
Request for Continued Examination (RCE) and Preliminary Amendment, filed Aug. 12, 2020, in response to the Final Office Action, dated Jul. 14, 2020, in connection with U.S. Appl. No. 16/033,187, 11 pages.
Office Action, dated Nov. 3, 2020, in connection with U.S. Appl. No. 16/033,187, 8 pages.
Response, filed Nov. 24, 2020, to Office Action, dated Nov. 3, 2020, in connection with U.S. Appl. No. 16/033,187, 11 pages.
Office Action, dated Mar. 11, 2021, in connection with U.S. Appl. No. 16/033,187, 10 pages.
Response, filed Apr. 7, 2021, to Office Action, dated Mar. 11, 2021, in connection with U.S. Appl. No. 16/033,187, 9 pages.
Office Action, dated Jan. 15, 2021, in connection with U.S. Appl. No. 16/554,478, 15 pages.
Response, filed Jul. 14, 2021, to Office Action, dated Jan. 15, 2021, in connection with U.S. Appl. No. 16/554,478, 51 pages.
Notice of Allowance, dated Sep. 27, 2021, in connection with U.S. Appl. No. 16/554,478, 7 pages.
Invitation to Pay Additional Fees and Partial International Search, dated Nov. 22, 2019, in connection with International Patent Application No. PCT/US2019/048659, 20 pages.
Response, filed Dec. 20, 2019, to Invitation to Pay Additional Fees and Partial International Search, dated Nov. 22, 2019, in connection with International Patent Application No. PCT/US2019/048659, 11 pages.
International Search Report and Written Opinion, dated Mar. 13, 2020, in connection with International Patent Application No. PCT/US2019/048659, 28 pages.
PCT Demand for International Preliminary Examination (Chapter II) (Demand under Article 31 of the PCT), filed Jun. 29, 2020, in response to the International Search Report and Written Opinion,

(56) References Cited

OTHER PUBLICATIONS dated Mar. 13, 2020, in connection with International Patent Application No. PCT/US2019/048659, 7 pages.
Invitation to Submit Amendments (PCT Rule 60.1 (g)), dated Jul. 15, 2020, in connection with International Patent Application No. PCT/US2019/048659, 1 page.
Response, filed Aug. 14, 2020, to Invitation to Submit Amendments (PCT Rule 60.1 (g)), dated Jul. 15, 2020, in connection with International Patent Application No. PCT/US2019/048659, 116 pages.
Written Opinion of the International Preliminary Examining Authority, dated Nov. 13, 2020, in connection with International Patent Application No. PCT/US2019/048659, 15 pages.
Response, filed Dec. 14, 2020, to the Written Opinion of the International Preliminary Examining Authority, dated Nov. 13, 2020, in connection with International Patent Application No. PCT/US2019/048659, 51 pages.
Supplementary Response, filed Dec. 31, 2020, to the Written Opinion of the International Preliminary Examining Authority, dated Nov. 13, 2020, and to the Notification Concerning Informal Communications with the Applicant, dated Dec. 22, 2020, in connection with International Patent Application No. PCT/US2019/048659, 16 pages.
International Preliminary Report on Patentability (Chapter II of the PCT), dated Jan. 22, 2021, in connection with International Patent Application No. PCT/US2019/048659, 14 pages.
Invitation to Pay Additional Fees and Partial International Search, dated Oct. 18, 2019, in connection with International Patent Application No. PCT/US2019/041489, 22 pages.
Response, filed Nov. 15, 2019, to Invitation to Pay Additional Fees and Partial International Search, dated Oct. 18, 2019, in connection with International Patent Application No. PCT/US2019/041489, 17 pages.
International Search Report and Written Opinion, dated Jan. 16, 2020, in connection with International Patent Application No. PCT/US2019/041489, 30 pages.
Demand for International Preliminary Examination (Chapter II) and Response under Article 34(2)(b) PCT, filed May 11, 2020, in response to the International Search Report and Written Opinion, dated Jan. 16, 2020, in connection with International Patent Application No. PCT/US2019/041489, 54 pages.
Written Opinion of the International Preliminary Examining Authority, dated May 27, 2020, in connection with International Patent Application No. PCT/US2019/041489, 11 pages.
Response, filed Jun. 29, 2020, to the Written Opinion of the International Preliminary Examining Authority, dated May 27, 2020, in connection with International Patent Application No. PCT/US2019/041489, 63 pages.
International Preliminary Report on Patentability (Chapter II of the PCT), dated Oct. 21, 2020, in connection with International Patent Application No. PCT/US2019/041489, 13 pages.
Response, filed Dec. 31, 2020, to the International Preliminary Report on Patentability (Chapter II of the PCT), dated Oct. 21, 2020, in connection with International Patent Application No. PCT/US2019/041489, 28 pages.
International Preliminary Report on Patentability (Chapter II of the PCT), dated Jan. 28, 2021, in connection with International Patent Application No. PCT/US2019/041489, 12 pages.
U.S. Appl. No. 16/520,155, filed Jul. 23, 2019, 2020-0215123, Jul. 9, 2020.
U.S. Appl. No. 16/824,500, filed Mar. 19, 2020, 2020-0270613, Aug. 27, 2020.
U.S. Appl. No. 17/037,455, filed Sep. 29, 2020, 2021-0030813, Feb. 4, 2021.
U.S. Appl. No. 17/320,200, filed May 13, 2021.
U.S. Appl. No. 17/483,523, filed Sep. 23, 2021, 2022-0017904, Jan. 20, 2022.
U.S. Appl. No. 17/569,290, filed Jan. 5, 2022.
U.S. Appl. No. 17/573,569, filed Jan. 11, 2022.
U.S. Appl. No. 17/590,700, filed Feb. 1, 2022.
Letter/Written Disclosure of the Information Disclosure Statement for the above-referenced application, filed herewith on Nov. 22, 2023, 2 pages.

* cited by examiner

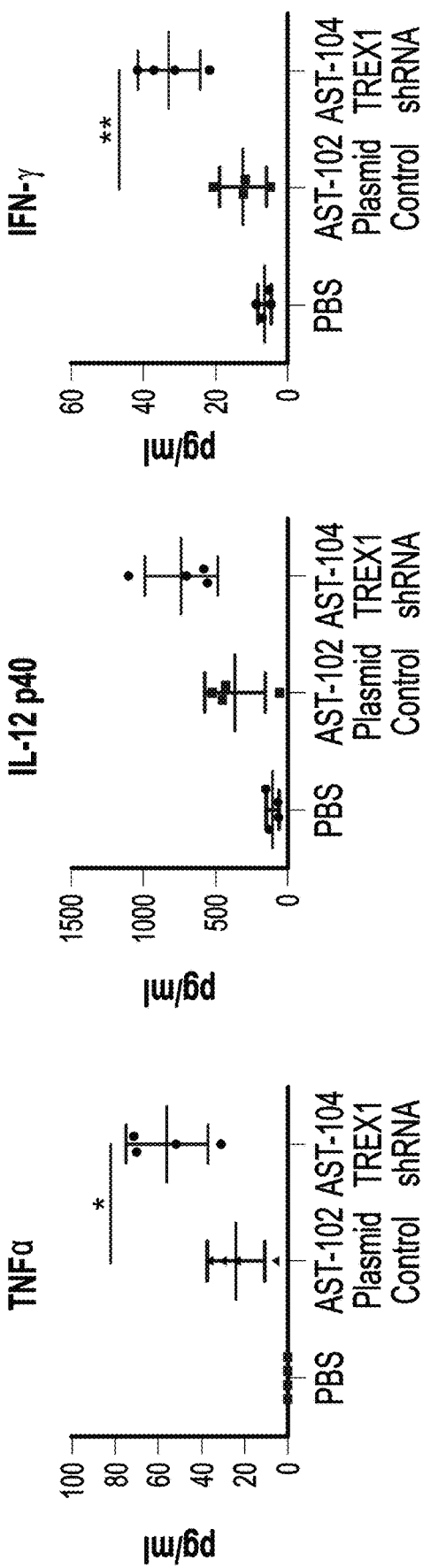
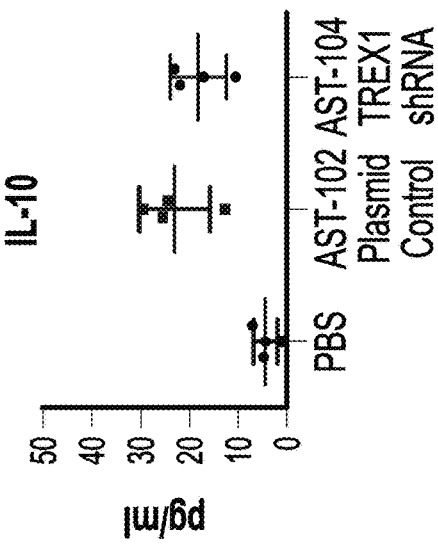
Figure 24A
Figure 24B

ENGINEERED IMMUNOSTIMULATORY BACTERIAL STRAINS AND USES THEREOF

RELATED APPLICATIONS

This application is a divisional of allowed U.S. patent application Ser. No. 16/554,478, filed on Aug. 28, 2019, to Applicant Actym Therapeutics, Inc., inventors Christopher D. Thanos, and Laura Hix Glickman, and entitled "ENGINEERED IMMUNOSTIMULATORY BACTERIAL STRAINS AND USES THEREOF," which claims the benefit of priority to U.S. Provisional Application Ser. No. 62/723,999, filed on Aug. 28, 2018, to Applicant Actym Therapeutics, Inc., inventors Christopher D. Thanos, and Laura Hix Glickman, and entitled "ENGINEERED IMMUNOSTIMULATORY BACTERIAL STRAINS AND USES THEREOF."

This application is related to International Patent Application No. PCT/US2019/048659, filed on Aug. 28, 2019, to Applicant Actym Therapeutics, Inc., inventors Christopher D. Thanos, and Laura Hix Glickman, and entitled "ENGINEERED IMMUNOSTIMULATORY BACTERIAL STRAINS AND USES THEREOF."

This application also is related to International Patent Application No. PCT/US2018/041713, filed on Jul. 11, 2018, and published as Publication No. WO 2019/014398 on Jan. 17, 2019, and is related to co-pending U.S. patent application Ser. No. 16/033,187, filed on Jul. 11, 2018, and published as U.S. Publication No. 2019/0017050 A1 on Jan. 17, 2019, each to Applicant Actym Therapeutics, Inc., inventors Christopher D. Thanos, Laura Hix Glickman, and Justin Skoble, and each entitled "ENGINEERED IMMUNOSTIMULATORY BACTERIAL STRAINS AND USES THEREOF."

This application also is related to International Patent Application No. PCT/US2019/041489, filed on Jul. 11, 2019, and is related to co-pending U.S. patent application Ser. No. 16/520,155, filed on Jul. 23, 2019, each to Applicant Actym Therapeutics, Inc., inventors Christopher D. Thanos, Laura Hix Glickman, Justin Skoble and Alexandre Charles Michel Iannello, and entitled "ENGINEERED IMMUNOSTIMULATORY BACTERIAL STRAINS AND USES THEREOF."

This application also is related to U.S. Provisional Application Ser. No. 62/828,990, filed on Apr. 3, 2019, to Applicant Actym Therapeutics, Inc., inventors Christopher D. Thanos, Laura Hix Glickman, Justin Skoble and Alexandre Charles Michel Iannello, and entitled "*SALMONELLA* STRAINS ENGINEERED TO COLONIZE TUMORS AND THE TUMOR MICROENVIRONMENT."

Immunostimulatory bacteria provided in each of these applications can be modified and/or used, as appropriate, as described in this application, and such bacteria are incorporated by reference herein. Where permitted, the subject matter of each of these applications is incorporated by reference in its entirety.

Incorporation by Reference of Sequence Listing Provided Electronically

An electronic version of the Sequence Listing is filed herewith, the contents of which are incorporated by reference in their entirety. The electronic file was created on Dec. 20, 2021, is 411 kilobytes in size, and is entitled 1702BSEQ001.txt.

BACKGROUND

The field of cancer immunotherapy has made great strides, as evidenced by clinical successes of anti-CTLA4, anti-PD-1 and anti-PD-L1 immune checkpoint antibodies (see, e.g., Buchbinder et al. (2015) *J. Clin. Invest.* 125:3377-3383; Hodi et al. (2015) *J. Clin. Invest.* 125:3392-4000; and Chen et al. (2015) *J. Clin. Invest.* 125:3384-3391). Tumors have evolved a profoundly immunosuppressive environment. They initiate multiple mechanisms to evade immune surveillance, reprogram anti-tumor immune cells to suppress immunity, and continually mutate resistance to the latest cancer therapies (see, e.g., Mahoney et al. (2015) *Nat. Rev. Drug Discov.* 14(8):561-584). Designing immunotherapies that overcome immune tolerance and escape, while limiting the autoimmune-related toxicities of current immunotherapies, challenges the field of immuno-oncology. Hence, additional and innovative immunotherapies and other therapies are needed.

SUMMARY

Provided are methods for treating a cancer by administering a three prime repair exonuclease 1 (TREX1) antagonist. The TREX1 antagonist is administered to subjects with a cancer that comprises a tumor that is human papillomavirus (HPV) positive or that has a high tumor mutational burden (TMB), where tumor mutational burden (TMB) in a tumor is the number of somatic mutations per megabase (Mb) of the genome of the tumor. Generally, a high TMB is 10 or is at least 10 mutations per Mb of the genome of the tumor. Any TREX1 antagonist can be administered to effect treatment of such tumors. The antagonists include immunostimulatory bacteria and oncolytic viruses that encode an inhibitor or antagonist of TREX1. The inhibitors or antagonists include antibodies, such as single chain antibodies, and RNAi that inhibit expression of TREX1.

Provided are methods for treating a cancer by administering an oncolytic virus or immunostimulatory bacterium. The virus or bacterium comprises a sequence of nucleotides encoding inhibitory RNA (RNAi) that inhibits, suppresses or disrupts expression of TREX1, or another therapeutic product that inhibits, suppresses or otherwise disrupts expression of TREX1. The cancer comprises a tumor that is HPV positive and/or has a high tumor mutational burden (TMB). Generally, a high TMB is 10 or is at least 10 mutations per Mb of the genome of the tumor.

Examples of tumors and cancers that have a high TMB include, but are not limited to, melanoma, colorectal cancers, and head and neck cancers. TMB and/or HPV can be tested in a tumor sample or body fluid sample, such as blood, plasma, cerebrospinal fluid (CSF), and urine, to identify subjects with cancers for treatment with the TREX1 antagonist.

The immunostimulatory bacteria are any that are described herein or in co-pending U.S. application Ser. No. 16/033,187, and/or International Patent Application No. PCT/US2018/041713. The oncolytic viruses are any oncolytic virus that encodes an RNAi that suppresses, inhibits, disrupts or otherwise silences or reduces the expression of TREX1, or that encodes an antibody that inhibits expression of TREX1.

Also provided are compositions for use for inhibiting TREX1 in tumors that are HPV positive or that have a high tumor mutational burden (TMB). The compositions comprise a TREX1 antagonist. Subjects for treatment can be identified by testing a tumor sample or body fluid sample for high TMB or HPV positivity or prior HPV infection. Any subject whose tumor has a high TMB, generally at least or at least about 10 mutations per megabase (Mb) of the tumor genome or the subject's genome, or is HPV positive, is treated with a TREX1 antagonist.

Provided are methods for identifying subjects for treatment with a TREX1 antagonist. The methods include obtaining a tumor sample or body fluid sample that comprises tumor cells or tissue, and determining the tumor mutational burden (TMB) or testing for human papillomavirus (HPV) or prior HPV infection. A subject whose tumor has a high TMB or positive HPV test is treated with a TREX1 antagonist. The sample can be a tumor biopsy or a body fluid in which metastases or tumor cells or tumor stem cells may be present. Body fluids include blood, tears, sweat, plasma, urine and CSF. Generally, a high TMB is at least 10 mutations per Mb of the genome of the tumor or the genome of the subject. If the subject sample tests positive for HPV or a high TMB, the subject is treated with a TREX1 antagonist. TREX1 antagonists include any immunostimulatory bacterium or oncolytic virus that encodes a therapeutic product, such as RNAi that suppresses, inhibits, disrupts or otherwise silences or reduces the expression of TREX1, including any described herein or in co-pending U.S. application Ser. No. 16/033,187, and/or International Patent Application No. PCT/US2018/041713. The therapeutic product encoded by the immunostimulatory bacteria can be a product that inhibits TREX1, such as an inhibitory antibody that specifically binds and inhibits TREX1.

The immunostimulatory bacteria contain a plasmid encoding the therapeutic product under control of a eukaryotic promoter, wherein the genome of the immunostimulatory bacterium is modified whereby the bacterium is flagellin$^-$ (fliC$^-$/fljB$^-$) and/or pagP$^-$, where the wild-type bacterium comprises flagella. The bacteria also can be auxotrophic for adenosine. The plasmid generally is a low to medium, generally low, copy number plasmid.

The genome of the immunostimulatory bacteria is modified so that the bacterium preferentially infects tumor-resident immune cells, and/or the genome of the immunostimulatory bacterium is modified so that it induces less cell death in tumor-resident immune cells (decreases pyroptosis), whereby the immunostimulatory bacterium accumulates in tumors or in the tumor microenvironment (TME) or in tumor-resident immune cells to thereby deliver the therapeutic product, in this instance, a product that is antagonistic to TREX1, such as RNAi, to reduce expression of TREX1, or an antibody or antigen-binding fragment thereof, to inhibit TREX1, to the tumor microenvironment.

Provided are immunostimulatory microorganisms that encode RNAi, including microRNA (miRNA), shRNA, and siRNA, that are designed to suppress, inhibit, disrupt or otherwise silence immune checkpoint genes and products, and other targets that play a role in pathways that are immunosuppressive, and pathways that are immunostimulatory, to improve the anti-tumor response. The microorganisms, which include immunostimulatory bacteria and oncolytic viruses, contain a sequence of nucleotides encoding RNA (RNAi) that inhibits, suppresses or disrupts expression of three prime repair exonuclease 1 (TREX1). Also provided are oncolytic viruses that encode RNAi designed to suppress, inhibit, disrupt or otherwise silence TREX1 expression. RNAi in all embodiments herein include microRNA, shRNA and siRNA, and any form of RNA or dsRNA that inhibits expression of a gene and/or translation of mRNA. The RNAi for use herein inhibits TREX1, and includes any described herein and in co-pending U.S. application Ser. No. 16/033,187, and/or International Patent Application No. PCT/US2018/041713.

These microorganisms are used in methods of treating tumors in which TREX1 expression is correlated with the tumors, such that its inhibition is therapeutic. These microorganisms are for use for treating virally driven cancers, such as cervical cancers, and for treating colorectal cancers, head and neck cancers, and reproductive system cancers, such as ovarian cancer. It is shown herein that TREX1 expression is correlated with virally driven cervical cancers, and head and neck cancers, and with mutational load in colorectal cancers. The immunostimulatory bacteria described throughout the disclosure that encode RNAi that suppresses, inhibits, disrupts or otherwise silences or reduces expression of TREX1, are used for the treatment of these cancers. Also provided are oncolytic viruses that encode RNAi, such as microRNA, shRNA, and siRNA, that suppresses, inhibits, disrupts or otherwise silences or reduces the expression of TREX1. The oncolytic viruses are for use for treating and in methods of treating these cancers.

Provided are bacteria modified to be immunostimulatory for anti-cancer therapy. Immunostimulatory bacteria, as provided herein, provide a multi-faceted approach to anti-tumor therapy. As provided herein, bacteria, such as species of *Salmonella*, can be fine-tuned to have potent anti-tumor activity. Bacteria provide a platform in which there are numerous avenues for eliciting anti-tumor immunostimulatory activity. The bacteria contain plasmids that encode anti-cancer therapeutics, such as RNA, including microRNA (miRNA), shRNA, and siRNA, that are designed to suppress, inhibit, disrupt or otherwise silence immune checkpoint genes and products, and other targets that play a role in pathways that are immunosuppressive and pathways that are immunostimulatory, and improve an anti-tumor response, such as Stimulator of Interferon Genes (STING) and cGAS. Bacteria by their nature stimulate the immune system; bacterial infection induces immune and inflammatory pathways and responses, some of which are desirable for anti-tumor treatment, and others, are undesirable. Modification of the bacteria by deleting or modifying genes and products that result in undesirable inflammatory response, and modifying or introducing genes that induce desirable immunostimulatory anti-tumor responses, can improve the anti-tumor activity of the bacteria. Bacteria also accumulate in tumor cells and tissues, and by replicating therein, can lyse cells. Bacteria migrate from the sites of administration and can accumulate in tumors and tumor cells to provide an abscopal effect. Herein, all of these properties of bacteria are exploited to produce demonstrably immunostimulatory bacteria with a plurality of anti-tumor activities and properties that can act synergistically.

Provided are compositions, uses thereof and methods that modulate immune responses for treatment of diseases, including for treatment of cancer. The compositions contain immunostimulatory bacteria provided herein. Methods of treatment and uses of the bacteria for treatment also are provided. The subjects for treatment include humans and other primates, pets, such as dogs and cats, and other animals, such as horses.

Provided are pharmaceutical compositions containing the immunostimulatory bacteria, and methods and uses thereof for treatment of diseases and disorders, particularly proliferative disorders, such as tumors, including solid tumors.

Also provided are methods of inhibiting the growth or reducing the volume of a solid tumor by administering the immunostimulatory bacteria or pharmaceutical compositions, or using the compositions for treatment. For example, provided are methods of administering or using a composition that contains, for a single dosage, an effective amount of an attenuated *Salmonella* species to a subject, such as a human patient, having a solid tumor cancer.

It is understood that all of the RNAi's and modifications of the bacteria and the plasmids described can be combined in any desired combination. Reference to immunostimulatory bacteria refers to bacteria that include RNAi against at least one target and that can have any or all of the modifications described herein.

Provided are immunostimulatory bacteria that contain a sequence of nucleotides encoding RNA (RNAi) that inhibits, suppresses or disrupts expression of an immune checkpoint or other target whose inhibition, suppression or disruption increases the anti-tumor immune response in a subject; the RNA is encoded on a plasmid in the bacterium; and the immunostimulatory bacterium is aspartate-semialdehyde dehydrogenase⁻ (asd⁻).

For purposes herein, RNAi includes all forms of double stranded RNA that can be used to silence expression of targeted nucleic acids. RNAi includes shRNA, siRNA and microRNA. Any of these forms can be interchanged in the embodiments disclosed and described herein. In general, the RNAi is encoded on a plasmid in the bacterium. The plasmids can include other heterologous nucleic acids that encode products of interest that modulate or add activities or products to the bacterium, or other such products that can modulate the immune system of a subject to be treated with the bacterium. Bacterial genes also can be added, deleted or disrupted. These genes can encode products for growth and replication of the bacteria, or products that also modulate the immune response of the host to the bacteria.

Also provided are immunostimulatory bacteria that contain a sequence of nucleotides encoding RNA (RNAi) that inhibits, suppresses or disrupts expression of three prime repair exonuclease 1 (TREX1), and that are auxotrophic for adenosine. Also provided are immunostimulatory bacteria that contain a sequence of nucleotides encoding RNA that inhibits, suppresses or disrupts expression of VISTA (the gene encoding V-domain Ig suppressor of T cell activation), and are auxotrophic for adenosine. Also provided are immunostimulatory bacteria that comprise a sequence of nucleotides encoding RNA (RNAi) that inhibits, suppresses, or disrupts expression of programmed death-ligand 1 (PD-L1).

Among these immunostimulatory bacteria are those of *Salmonella* species. These include *Salmonella* that contain nucleic acids that encodes an RNA (RNAi) that inhibits or suppresses, disrupts or silences expression of three prime repair exonuclease 1 (TREX1) and/or VISTA.

Also provided are immunostimulatory bacteria that contain a sequence of nucleotides encoding RNA that inhibits, suppresses or disrupts expression of three prime repair exonuclease 1 (TREX1), and a sequence of nucleotides encoding RNA that inhibits, suppresses or disrupts expression of PD-L1.

Also provided are immunostimulatory bacteria that contain a sequence of nucleotides encoding RNA that inhibits, suppresses or disrupts expression of VISTA, and a sequence of nucleotides encoding RNA that inhibits, suppresses or disrupts expression of PD-L1.

Provided are immunostimulatory bacteria, such as *S. typhimurium*, carrying plasmids encoding RNAi, such as miRNA or shRNA, that mediate gene disruption of one or more of TREX1, VISTA and PD-L1 and other such targets known to those of skill in the art and/or enumerated or exemplified herein. Bacterial species that carry such plasmids, include, but are not limited to, for example, strains of *Salmonella*, *Shigella*, *Listeria*, *E. coli*, and *Bifidobacteriae*. For example, species include *Shigella sonnei*, *Shigella flexneri*, *Shigella dysenteriae*, *Listeria monocytogenes*, *Salmonella typhi*, *Salmonella typhimurium*, *Salmonella gallinarum*, and *Salmonella enteritidis*.

Species include, for example, strains of *Salmonella*, *Shigella*, *E. coli*, Bifidobacteriae, *Rickettsia*, *Vibrio*, *Listeria*, *Klebsiella*, *Bordetella*, *Neisseria*, *Aeromonas*, *Francisella*, *Cholera*, *Corynebacterium*, *Citrobacter*, *Chlamydia*, *Haemophilus*, *Brucella*, *Mycobacterium*, *Mycoplasma*, *Legionella*, *Rhodococcus*, *Pseudomonas*, *Helicobacter*, *Bacillus*, and *Erysipelothrix*, or an attenuated strain thereof or modified strain thereof of any of the preceding list of bacterial strains.

Other suitable bacterial species include *Rickettsia*, *Klebsiella*, *Bordetella*, *Neisseria*, *Aeromonas*, *Francisella*, *Corynebacterium*, *Citrobacter*, *Chlamydia*, *Haemophilus*, *Brucella*, *Mycobacterium*, *Mycoplasma*, *Legionella*, *Rhodococcus*, *Pseudomonas*, *Helicobacter*, *Vibrio*, *Bacillus*, and *Erysipelothrix*. For example, *Rickettsia rickettsii*, *Rickettsia prowazekii*, *Rickettsia tsutsugamushi*, *Rickettsia mooseri*, *Rickettsia sibirica*, *Bordetella bronchiseptica*, *Neisseria meningitidis*, *Neisseria gonorrhoeae*, *Aeromonas eucrenophila*, *Aeromonas salmonicida*, *Francisella tularensis*, *Corynebacterium pseudotuberculosis*, *Citrobacter freundii*, *Chlamydia pneumoniae*, *Haemophilus somnus*, *Brucella abortus*, *Mycobacterium intracellulare*, *Legionella pneumophila*, *Rhodococcus equi*, *Pseudomonas aeruginosa*, *Helicobacter mustelae*, *Vibrio cholerae*, *Bacillus subtilis*, *Erysipelothrix rhusiopathiae*, *Yersinia enterocolitica*, *Rochalimaea quintana*, and *Agrobacterium tumefaciens*.

*Salmonella* is exemplified herein, and particularly, strains of *Salmonella typhimurium*, such as the strain designated YS1646 (ATCC #202165) or VNP20009. Other strains include, RE88, SL7207, χ8429, χ8431, and χ8468. The *Salmonella typhimurium* strains also include wild-type strains, such as the *Salmonella typhimurium* strain that is deposited as ATCC accession number 14028, or a *Salmonella typhimurium* strain having all of the identifying characteristics of the *Salmonella typhimurium* strain deposited as ATCC accession number 14028.

Exemplary of modified *Salmonella* strains provided herein are immunostimulatory bacterium strains AST-104, AST-105, AST-106, AST-108, AST-110, AST-112, AST-113, AST-115, AST-117, AST-118, AST-119, AST-120, AST-121, AST-122, and AST-123. Sequences thereof and descriptions are provided in the detailed description, examples and sequence listing. The immunostimulatory bacteria can be derived from attenuated strains of bacteria or they become attenuated by virtue of the modifications described herein, such as deletion of asd, whereby replication is limited in vivo.

Immunostimulatory bacteria that are auxotrophic for adenosine and target the TREX1 gene, such as by encoding a double-stranded RNA, such as an shRNA or miRNA that inhibits expression thereof, and optionally encode additional RNAs, such as miRNA or shRNA, that target and inhibit expression of other checkpoint inhibitors, are for use or in methods of treatment of cancers that are virally driven, such as HPV-driven, and/or that have a high TMB. Among these bacteria are immunostimulatory bacteria that are auxotrophic for adenosine. Methods of treatment and uses for treatment of tumors, including solid tumors and hematologic malignancies are provided. Among the methods and uses are those in which the immunostimulatory bacteria are auxotrophic for adenosine and the uses and treatments treat tumors that are cd73⁺ and/or cd73⁺/cd39⁺.

The RNAs are expressed under the control of promoters that are recognized by the eukaryotic host cell transcription machinery, such as RNA polymerase II (RNAPII) and RNA polymerase III (RNAPIII) promoters. RNAP III promoters generally are constitutively expressed in a eukaryotic host; RNAP II promoters can be regulated. The RNAs, such as miRNA and shRNA, are provided on plasmids stably expressed by the bacteria. Exemplary of such bacteria are Salmonella strains, generally attenuated strains, either attenuated by passage or other methods or by virtue of modifications described herein, such as adenosine auxotrophy. Exemplary of the bacteria are Salmonella strains. Exemplary of Salmonella strains are modified S. typhimurium strains that contain an asd mutation for antibiotic-free selection. These strains also can contain the asd mutation.

The promoters can be selected for the environment of the tumor cell, such as a promoter expressed in a tumor microenvironment (TME), such as a promoter expressed in hypoxic conditions, or in conditions where the pH is less than 7.

Provided are strains of bacteria that contain miRNA or shRNA against the TREX1 and VISTA gene. The TREX1 or VISTA gene can be under control of an RNAPIII promoter, such as the H1 promoter. TREX1 knockdown induces vascular disruption, which increases colonization, and also decreases immune suppression. The strains provided herein can include miRNA or shRNA that inhibits expression of other checkpoint inhibitors, including, but not limited to PD-L1. Strains that include a plurality of RNAs, such as miRNA or shRNAs, generally include different promoters for each RNA. For example, the bacterium can include a genetically modified S. typhimurium strain that contains miRNA or shRNA against the PD-L1 gene under control of the U6 promoter, and also contains miRNA or shRNA against TREX1 under control of the H1 promoter. Also provided are genetically modified S. typhimurium strains that contain miRNA or shRNA against the SIRP-α gene under control of the H1 promoter. The exemplary bacteria, such as S. typhimurium strains, can contain miRNA or shRNA against the β-catenin gene under control of an RNAPIII promoter, such as the H1 promoter and/or miRNA or shRNA against the VISTA gene under control of an RNAPIII promoter, such as the H1 promoter. Various combinations of adenosine auxotrophy, miRNA or shRNA against TREX1, and/or optionally against other immune checkpoint targets, such as RNA that inhibits, suppresses or disrupts PD-L1 or one or both of TREX1 and PD-1 or VISTA, can be included in the modified immunostimulatory bacteria.

Provided are immunostimulatory bacteria that are cyclic GMP-AMP synthase (cGAS) agonists. Exemplary of such bacteria is S. typhimurium that is one or both of a cGAS agonist and Stimulator of Interferon Genes (STING) agonist. These can be administered, for example, in uses and methods, such as radiotherapy and chemotherapy, in which cytosolic DNA is produced or accumulates. STING activates innate immunity in response to sensing nucleic acids in the cytosol. Downstream signaling is activated through binding of cyclic dinucleotides (CDNs), which are synthesized by bacteria or by host enzyme cGAS in response to binding to cytosolic dsDNA. Bacterial and host-produced CDNs have distinct phosphate bridge structures, which differentiates their capacity to activate STING. CDNs are synthesized by bacteria or by host enzyme cGAS in response to binding cytosolic dsDNA. IFN-β is the signature cytokine of activated STING.

The plasmids in any of the bacteria described and enumerated above and herein are plasmids that encode the therapeutic product, such RNAi and/or other heterologous nucleic acid. Plasmids can be present in many copies or fewer. This can be controlled by selection of elements, such as the origin of replication. Low, high and medium copy number plasmids and origins of replication are well known to those of skill in the art and can be selected. In embodiments of the immunostimulatory bacteria herein, the plasmid can be present in low to medium copy number, such as about 150 or 150 and fewer copies, to low copy number, which is less than about 25 or about 20 or 25 copies. Exemplary origins of replication are those derived from pBR322, p15A, pSC101, pMB1, colE1, colE2, pPS10, R6K, R1, RK2, and pUC.

The plasmids can include RNAi such that the RNA inhibits, suppresses or disrupts expression of an immune checkpoint or other target, and additionally their products. Among these are sequences of nucleic acids encoding listeriolysin O (LLO) protein lacking the signal sequence (cytoLLO), a CpG motif, a DNA nuclear targeting sequence (DTS), and a retinoic acid-inducible gene-I (RIG-I) binding element.

The immunostimulatory bacteria for use herein can be aspartate-semialdehyde dehydrogenase⁻ (asd⁻), which permits growth in diaminopimelic acid (DAP) supplemented medium, but limits replication in vivo when administered to subjects for treatment. Such bacteria will be self-limiting, which can be advantageous for treatment. The bacteria can be asd⁻ by virtue of disruption or deletion of all or a portion of the endogenous gene encoding aspartate-semialdehyde dehydrogenase (asd), whereby the endogenous asd is not expressed. In other embodiments, the gene encoding asd can be included on the plasmid for expression in vivo.

Any of the immunostimulatory bacteria can include nucleic acid, generally on the plasmid, that includes a CpG motif or a CpG island, wherein the motif is recognized by toll-like receptor 9 (TLR9). Nucleic acid encoding CpG motifs or islands are plentiful in prokaryotes, and, thus, the CpG motif can be included in or part of a bacterial gene that is encoded on the plasmid. The bacterial gene that encodes asd contains immunostimulatory CpGs.

The immunostimulatory bacteria provided can be auxotrophic for adenosine or for adenosine and adenine. Any of the bacteria herein can be rendered auxotrophic for adenosine, which advantageously can increase the anti-tumor activity, since adenosine accumulates in many tumors, and is immunosuppressive.

The immunostimulatory bacteria can be flagellin deficient, where the wild-type bacterium comprises flagella. They can be rendered flagellin deficient by disrupting or deleting all or a part of the gene or genes that encode the flagella. For example, provided are immunostimulatory bacteria that have deletions in the genes encoding one or both of flagellin subunits fliC and fljB, whereby the bacteria is flagella deficient.

The immunostimulatory bacteria can include a nucleic acid encoding cytoLLO, which is a listeriolysin O (LLO) protein lacking the periplasmic secretion signal sequence so that it accumulates in the cytoplasm. This mutation is advantageously combined with asd⁻ bacteria. LLO is a cholesterol-dependent pore forming hemolysin from Listeria monocytogenes that mediates phagosomal escape of bacteria. When the autolytic strain is introduced into tumor bearing hosts, such as humans, the bacteria are taken up by phagocytic immune cells and enter the vacuole. In this environment, the lack of DAP prevents bacterial replication, and results in autolysis of the bacteria in the vacuole. Lysis then releases the plasmid and the accumulated LLO forms pores in the cholesterol-containing vacuole membrane, and allows for delivery of the plasmid into the cytosol of the host cell.

The immunostimulatory bacteria can include a DNA nuclear targeting sequence (DTS), such as an SV40 DTS, encoded on the plasmid.

The immunostimulatory bacteria can have a deletion or modification in the gene encoding endonuclease-1 (endA), whereby endA activity is inhibited or eliminated. Exemplary of these are immunostimulatory bacteria that contain one or more of a CpG motif, an asd gene selectable marker for plasmid maintenance and a DNA nuclear targeting sequence.

The immunostimulatory bacteria can contain nucleic acids on the plasmid encoding two or more different RNA molecules that inhibit, suppress or disrupt expression of an immune checkpoint, or an RNA molecule that encodes an inhibitor of a metabolite that is immunosuppressive or is in an immunosuppressive pathway.

The nucleic acids encoding the RNAi, such as shRNA, miRNA or siRNA, can include a transcriptional terminator following the RNAi-encoding nucleic acid.

The RNAi encoded on the plasmid in the immunostimulatory bacteria can be short hairpin RNA (shRNA) or micro-RNA (miRNA).

The immunostimulatory bacteria include bacteria that are derived from or that are modified forms of strains of *Salmonella*, such as a *Salmonella typhimurium* strain, such as for example, an attenuated *Salmonella typhimurium* strain selected from among strains designated as AST-100, VNP20009, or strains YS1646 (ATCC #202165), RE88, SL7207, χ8429, χ8431, and χ8468. The immunostimulatory bacteria also can be derived from strains of wild-type *Salmonella typhimurium*, such as a *Salmonella typhimurium* strain that is or that has all of the identifying characteristics of the *Salmonella typhimurium* strain deposited under ATCC accession number 14028. The *Salmonella typhimurium* is modified so that it is a TREX1 antagonist, and also has other modifications that increase accumulation in tumors or the tumor microenvironment or in tumor-resident immune cells. The immunostimulatory bacteria can be flagellin⁻ (fliC⁻/fljB⁻). Therapeutic products, such as a product that inhibits, suppresses or disrupts expression of TREX1, such as RNAi, or an antibody or antigen-binding fragment thereof, such as single chain antibody, or a nanobody or other such binding protein, are encoded on a plasmid in the bacteria. The plasmid generally is a medium or low copy number plasmid.

Immunostimulatory bacteria where the plasmid comprises a sequence of nucleotides that encodes a therapeutic product, such as RNA that inhibits, suppresses or disrupts expression of at least two targets, and each RNA is expressed from a different promoter, are provided. Generally, at least one of the targets is TREX1. Exemplary bacteria are, where the targets for inhibition, suppression or disruption combinations are at least two that are selected from among TREX1 and PD-L1, TREX1 and PD-1, TREX1 and VISTA, TREX1 and SIRP-alpha, PD-L1 and TGF-beta isoform 1, PD-L1 and beta-catenin, PD-L1 and VISTA, TGF-beta isoform 1 and VISTA, SIRP-alpha and VISTA, and TREX1 and RNase H2.

Other combinations of RNAi, include RNAi that inhibits, suppresses or disrupts expression of one or a combination of TREX1 and any of PD-L1, VISTA, TGF-beta isoform 1, beta-catenin, SIRP-alpha, VEGF, RNase H2, DNase II, and CLEVER-1/Stabilin-1. Other combinations include those where the target for inhibition, suppression or disruption is a combination of at least two that are selected from among TREX1 and PD-L1, TREX1 and PD-1, TREX1 and VISTA, TREX1 and SIRP-alpha, PD-L1 and TGF-beta isoform 1, PD-L1 and beta-catenin, PD-L1 and VISTA, TGF-beta isoform 1 and VISTA, SIRP-alpha and VISTA, TREX1 and RNase H2, VISTA and RNase H2, VISTA and DNase II, or TREX1 and VEGF.

The immunostimulatory bacterium can also include nucleic acids encoding RNA that inhibits, suppresses or disrupts expression of another different immune checkpoint or target to be inhibited, suppressed or disrupted, selected from among any of CTLA-4, PD-L1 (B7-H1), PD-L2, PD-1, PD-2, IDOL IDO2, SIRPα, CD47, VISTA (B7-H5), VEGF, TGF-beta, LIGHT, HVEM, CD28, LAG3, TIM3, TIGIT, Galectin-9, CEACAM1, CD155, CD112, CD226, CD244 (2B4), B7-H2, B7-H3, ICOS, GITR, B7-H4, B7-H6, CD27, CD40, CD40 ligand (CD40L), CD48, CD70, CD80, CD86, CD137 (4-1BB), CD200, CD272 (BTLA), CD160, CD39, CD73, A2a receptor, A2b receptor, HHLA2, ILT-2, ILT-4, gp49B, PIR-B, HLA-G, ILT-2/4, OX40, OX40 ligand (OX-40L), KIR, TIM1, TIM4, STAT3, CLEVER-1, DNase II and RNase H2. Exemplary thereof are among human PD-L1 (SEQ ID NO:31), human beta-catenin (SEQ ID NO:32), human SIRPα (SEQ ID NO:33), human TREX1 (SEQ ID NO:34), human VISTA (SEQ ID NO:35), human TGF-beta isoform 1 (SEQ ID NO:193), and human VEGF (SEQ ID NO:194). RNAi can target or contain a sequence in the immune checkpoint nucleic acids set forth in any of SEQ ID NOs.: 1-30, 36-40, and 195-217.

The plasmids in any of the immunostimulatory bacteria herein also can encode a sequence of nucleotides that is an agonist of retinoic acid-inducible gene I (RIG-I), or a RIG-I binding element.

The immunostimulatory bacteria can include one or more of deletions in genes, such as one or more of purI⁻ (purM⁻), msbB⁻, purD⁻, flagellin⁻ (fliC⁻/fljB⁻), pagP⁻, adrA⁻, CsgD⁻ and hilA⁻. In particular, the immunostimulatory bacteria are flagellin⁻ (fliC⁻/fljB⁻). The immunostimulatory bacteria can be msbB⁻, or flagellin⁻ (fliC⁻/fljB⁻), or msbB⁻ and flagellin⁻ (fliC⁻/fljB⁻), or flagellin⁻ (fliC⁻/fljB⁻) and pagP⁻. For example, the immunostimulatory bacteria can contain a purI deletion, an msbB deletion, an asd deletion, and adrA deletion, and optionally a CsgD deletion. Exemplary of bacterial gene deletions/mutations are any of the following:

one or more of a mutation in a gene that alters the biosynthesis of lipopolysaccharide, selected from among one or more of rfaL, rfaG, rfaH, rfaD, rfaP, rFb, rfa, msbB, htrB, firA, pagL, pagP, lpxR, arnT, eptA, and lpxT; and/or one or more of a mutation that introduces a suicide gene and is selected from one or more of sacB, nuk, hok, gef, kil or phlA; and/or one or more of a mutation that introduces a bacterial lysis gene and is selected from one or both of hly and cly; and/or a mutation in one or more virulence factor(s) selected from among IsyA, pag, prg, iscA, virG, plc and act; and/or one or more mutations in a gene that modifies the stress response selected from among recA, htrA, htpR, hsp and groEL; and/or a mutation in min that disrupts the cell cycle; and/or one or more mutations in a gene that disrupts or inactivates regulatory functions selected from among cya, crp, phoP/phoQ, and ompR.

As described, the RNAi includes shRNA and miRNA. Exemplary of an miRNA backbone into which the RNA that encodes the target or complement thereof is inserted is one based on miR-16-2 (SEQ ID NO:248), or the miRNA backbone of SEQ ID NO:249. The immunostimulatory bacteria can include miR-103 (SEQ ID NO:252), where mature miR-103 comprises the sequence: 5'-AGCAG-CAUUGUACAGGGCUAUGA-3.'

The RNAi can be expressed under control of an RNA polymerase III or RNA polymerase II promoter. Generally, shRNA is expressed under control of an RNAP III promoter, and miRNA is expressed under control of an RNAP II promoter. Many RNAP III and II promoters are known and available to those of skill in the art. RNAP III promoters include, for example, U3, H1, U6, 7SK and 7SL, and RNAP II promoters include viral promoters, such as a cytomegalovirus (CMV) promoter, an SV40 promoter, and adenovirus promoters. Many viral promoters, particularly later promoters, are strong constitutive promoters.

The immunostimulatory bacterium can be a strain of *Salmonella, Shigella, E. coli*, Bifidobacteriae, *Rickettsia, Vibrio, Listeria, Klebsiella, Bordetella, Neisseria, Aeromonas, Francisella, Cholera, Corynebacterium, Citrobacter, Chlamydia, Haemophilus, Brucella, Mycobacterium, Mycoplasma, Legionella, Rhodococcus, Pseudomonas, Helicobacter, Bacillus*, and *Erysipelothrix*, or an attenuated strain thereof or modified strain thereof of any of the preceding list of bacterial strains.

Exemplary of the immunostimulatory bacteria are those where the plasmid contains one or more of sequence of nucleic acids encoding a listeriolysin O (LLO) protein lacking the signal sequence (cytoLLO), a CpG motif, a DNA nuclear targeting sequence (DTS), and a retinoic acid-inducible gene-I (RIG-I) binding element.

Where the plasmid contains two or more encoding RNAs that inhibit, suppress or disrupt expression, each is separated by at least about 75 nucleotides, or at least 75 nucleotides, up to about or at least 100, 150, 200, 250, 300, 350, 400, 450, 500, 550, 600, 700, 800, 900, 1000, 1100, 1200, 1300, 1400, 1500 nucleotides (or base pairs), up to about 1600 or 1600 nucleotides (or base pairs), or between 75-1500 or 1600 nucleotides (or base pairs).

Other exemplary immunostimulatory bacteria include those that are auxotrophic for adenosine, and comprise: a deletion in the gene(s) encoding the flagella; a deletion in endA; a plasmid that encodes CytoLLO; a nuclear localization sequence; and an asd plasmid complementation system; and encode RNA that inhibits, suppresses or disrupts expression of an immune checkpoint or other target whose inhibition, suppression or disruption increases the anti-tumor immune response in a subject.

The immunostimulatory bacterium can contain a plasmid encoding an shRNA encoded by the sequence of nucleotides set forth in any of SEQ ID NOs: 36-40 and 75-78, or an miRNA encoded by the sequence of nucleotides set forth in any of SEQ ID NOs: 214-217.

Any of the immunostimulatory bacteria are those that, when grown, are harvested at stationary phase. Methods of producing the immunostimulatory bacteria include those where they are cultured by standard methods, and harvested at stationary phase.

Compositions containing the immunostimulatory bacteria are provided. Such compositions contain the bacteria and a pharmaceutically acceptable excipient or vehicle. A single dose is therapeutically effective for treating a disease or disorder in which immune stimulation effects treatment. Exemplary of such stimulation is an immune response, that includes, but is not limited to, one or both of a specific immune response and non-specific immune response, both specific and non-specific responses, innate response, primary immune response, adaptive immunity, secondary immune response, memory immune response, immune cell activation, immune cell proliferation, immune cell differentiation, and cytokine expression.

Pharmaceutical compositions containing any of the immunostimulatory bacteria are provided, as are uses thereof for treatment of cancers, and methods of treatment of cancer. Methods and uses include treating a subject who has cancer, comprising administering an immunostimulatory bacterium or the pharmaceutical composition to a subject, such as a human. A method of treating a subject who has cancer, comprising administering an immunostimulatory bacterium is provided. The methods and uses include combination therapy in which a second anti-cancer agent or treatment is administered. The second anti-cancer agent is a chemotherapeutic agent that results in cytosolic DNA, or radiotherapy, or an anti-immune checkpoint inhibitor, such as an anti-PD-1, anti-PD-L1 or anti-CTLA4 antibody, or CAR-T cells or other therapeutic cells, such as stem cells, TIL cells and modified cells for cancer therapy.

As described herein, the immunostimulatory bacteria, such as the *Salmonella* strains, that encode RNAi, such as miRNA and shRNA, against TREX1 are complementary to therapies that are genotoxic or that target or harm DNA to result in cytosolic DNA.

Administration can be by any suitable route, such as parenteral, and include additional agents that can facilitate or enhance delivery. Administration can be oral or rectal or by aerosol into the lung, or intratumoral, intravenously, intramuscularly, or subcutaneously.

Cancers include solid tumors and hematologic malignancies, such as, but not limited to, cancer of the breast, heart, lung, small intestine, colon, spleen, kidney, bladder, uterus, head and neck, ovary, prostate, brain, pancreas, skin, bone, bone marrow, blood, thymus, uterus, testicles, cervix or liver.

The immunostimulatory bacteria can be formulated into compositions for administration, such as suspensions. They can be dried and stored as powders. Combinations of the immunostimulatory bacteria with others of the anti-cancer agents also are provided.

Also provided are shRNA and miRNA, such as the nucleic acid molecules comprising the sequence of nucleic acids set forth in any of SEQ ID NOS: 36-40 and 75-78. Plasmids containing such DNA also are provided. The immunostimulatory bacteria, such as *Salmonella* containing the plasmids, are provided.

Combination therapies for treatment of cancers and malignancies are provided. The immunostimulatory bacteria can be administered before, or concurrently with other cancer therapies, including radiotherapy, chemotherapies, particularly genotoxic chemotherapies that result in cytosolic DNA, and immunotherapies, such as anti-checkpoint inhibitor antibodies, including anti-PD-L1, anti-PD-1, anti-CTLA4, and other such immunotherapies.

Also provided are methods of treatment and uses for treating a subject who has a tumor that is cd73$^+$. The immunostimulatory bacterium for such treatment is auxotrophic for adenosine; and the subject has been or is identified as having a tumor that is cd73$^+$ by testing a tumor biopsy or other body tissue or fluid sample.

Methods of increasing colonization of an immunostimulatory bacterium in a subject are provided. These methods include administering the immunostimulatory bacterium to the subject, and inhibiting or suppressing expression of TREX1 and/or the activity of the encoded product of TREX1 in the subject.

Also provided are methods for identifying subjects for treatment with a TREX1 antagonist. The methods include obtaining a tumor sample or using a previously obtained tumor sample, such a biopsy or body fluid, and determining the tumor mutational burden (TMB) or testing for human papillomavirus (HPV) or prior HPV infection, wherein a subject whose tumor has a high TMB or positive HPV test is treated with a TREX1 antagonist. A high TMB is at least 10 mutations per Mb of the genome of the tumor; it can be higher, such as at least 20, 30, 40, 50, 60, 70, 80, 90 or 100 mutations per Mb. The TREX1 antagonist that can be used to treat such tumors can be an immunostimulatory bacterium or oncolytic virus that encodes RNAi that suppresses, inhibits, disrupts or otherwise silences or reduces expression of TREX1, or that encodes a therapeutic product that inhibits or otherwise interferes with TREX1. The immunostimulatory bacteria and oncolytic viruses include any described herein that are TREX1 antagonists by virtue of an encoded therapeutic product to reduce TREX1 activity or its expression. The subjects treated are those who have tumors with high TMB in a tumor sample or a tumor sample that is HPV positive. Tumor samples include, for example, a tumor biopsy or body fluid sample, such as a plasma sample.

The terms and expressions that are employed are used as terms of description and not of limitation, and there is no intention that, in the use of such terms and expressions, to exclude any equivalents of the features shown and described or portions thereof, but it is recognized that various modifications are contemplated.

BRIEF DESCRIPTION OF THE DRAWINGS

FIG. 2A depicts the results of qPCR analysis to determine the level of mRNA knockdown. FIG. 2B depicts the Western blot analysis of human PD-L1 shRNAs. Western blotting and densitometry were used to measure the level of PD-L1 protein expression.

FIG. 3A depicts results of qPCR analysis, used to determine the level of mRNA knockdown. FIG. 3B depicts results of Western blot analysis of the human TREX1 shRNAs. Western blotting and densitometry were used to measure the level of PD-L1 protein expression.

FIG. 4A depicts results of qPCR, used to determine the level of mRNA knockdown. FIG. 4B depicts the results of Western blot analysis of the human beta-catenin shRNAs. Western blotting and densitometry were used to measure the level of beta-catenin protein expression.

FIG. 5A depicts results of qPCR, used to determine the level of mRNA knockdown. FIG. 5B depicts the results of Western blot analysis of human SIRP-alpha shRNAs. Western blotting and densitometry were used to measure the level of SIRP-alpha protein expression.

FIG. 8A depicts results of qPCR, used to determine the level of mRNA knockdown. FIG. 8B depicts the results of Western blot analysis of human VISTA shRNAs. Western blotting and densitometry were used to measure the level of VISTA protein expression.

FIG. 9A depicts results of qPCR, used to determine the level of PD-L1 mRNA knockdown. FIG. 9B depicts results of qPCR, used to determine the level of TREX1 mRNA knockdown.

FIG. 10A depicts results of qPCR, used to determine the level of PD-L1 mRNA knockdown. FIG. 10B depicts results of qPCR, used to determine the level of SIRP-alpha mRNA knockdown.

FIG. 11A depicts results of qPCR, used to determine the level of PD-L1 mRNA knockdown. FIG. 11B depicts results of qPCR, used to determine the level of beta-catenin mRNA knockdown.

FIG. 12A depicts results of qPCR, used to determine the level of PD-L1 mRNA knockdown. FIG. 12B depicts results of qPCR, used to determine the level of VISTA mRNA knockdown.

FIG. 13A depicts results of qPCR, used to determine the level of PD-L1 mRNA knockdown. FIG. 13B depicts results of qPCR, used to determine the level of TREX1 mRNA knockdown.

FIG. 14A depicts results of qPCR, used to determine the level of PD-L1 mRNA knockdown. FIG. 14B depicts results of qPCR, used to determine the level of SIRP-alpha mRNA knockdown.

FIG. 15A depicts results of qPCR, used to determine the level of PDL1 mRNA knockdown. FIG. 15B depicts results of qPCR, used to determine the level of beta-catenin mRNA knockdown.

FIG. 16A depicts results of qPCR, used to determine the level of TREX1 mRNA knockdown. FIG. 16B depicts results of qPCR, used to determine the level of SIRP-alpha mRNA knockdown.

FIG. 17A depicts results of qPCR, used to determine the level of PD-L1 mRNA knockdown. FIG. 17B depicts results of qPCR, used to determine the level of beta-catenin mRNA knockdown.

FIG. 18A depicts results of qPCR, used to determine the level of TREX1 mRNA knockdown. FIG. 18B depicts results of qPCR, used to determine the level of VISTA mRNA knockdown.

FIG. 19A depicts results of qPCR, used to determine the level of PD-L1 mRNA knockdown. FIG. 19B depicts results of Western blot analysis; Western blotting and densitometry were used to measure the level of PD-L1 protein expression.

FIG. 21A depicts results of qPCR, used to determine the level of mouse TREX1 mRNA knockdown. FIG. 21B depicts results of Western blot analysis; Western blotting and densitometry were used to measure the level of mouse TREX1 protein expression.

FIG. 22A depicts results of qPCR, used to determine the level of mouse PD-L1 mRNA knockdown. FIG. 22B depicts results of Western blot analysis; Western blotting and densitometry were used to measure the level of mouse PD-L1 protein expression.

FIGS. 24A-24B depict the correlation of strain AST-104 mediated cytokine changes with STING signature. BALB/c were implanted with a single CT26 (2×10⁵ cells) subcutaneous flank tumor (n=8 per group). Mice with established tumors were IV injected with 5×10⁶ CFU of YS1646 strains containing either plasmid control (strain AST-102) or the TREX1 shRNA plasmid (AST-104), or PBS control. Mice were bled 6 hrs following the first dose and systemic serum cytokines tested on a Luminex 200 device (Luminex Corporation) and mouse cytometric bead array (BD bead array, FACS Fortessa, FCAP software, BD Biosciences). FIG. 24A depicts levels of pro-inflammatory cytokines. FIG. 24B depicts levels of immuno-suppressive cytokines. *p<0.05, **p<0.01, student's t-test.

FIG. 48A depicts the mean CFU per gram of tumor tissue, SD. FIG. 48B depicts the tumor to spleen colonization ratios.

FIG. 49A depicts the mean tumor growth of each group, ±SEM. *p<0.05, student's t-test. FIG. 49B depicts the levels of TNF-alpha and IL-6. Mice were bled 6 hrs following the first dose and systemic serum cytokines tested by Luminex (Luminex Corp.) and mouse cytometric bead array (FACS Fortessa, FCAP software, all BD Biosciences). **p<0.01, student's t-test.

DETAILED DESCRIPTION

Figure 1:
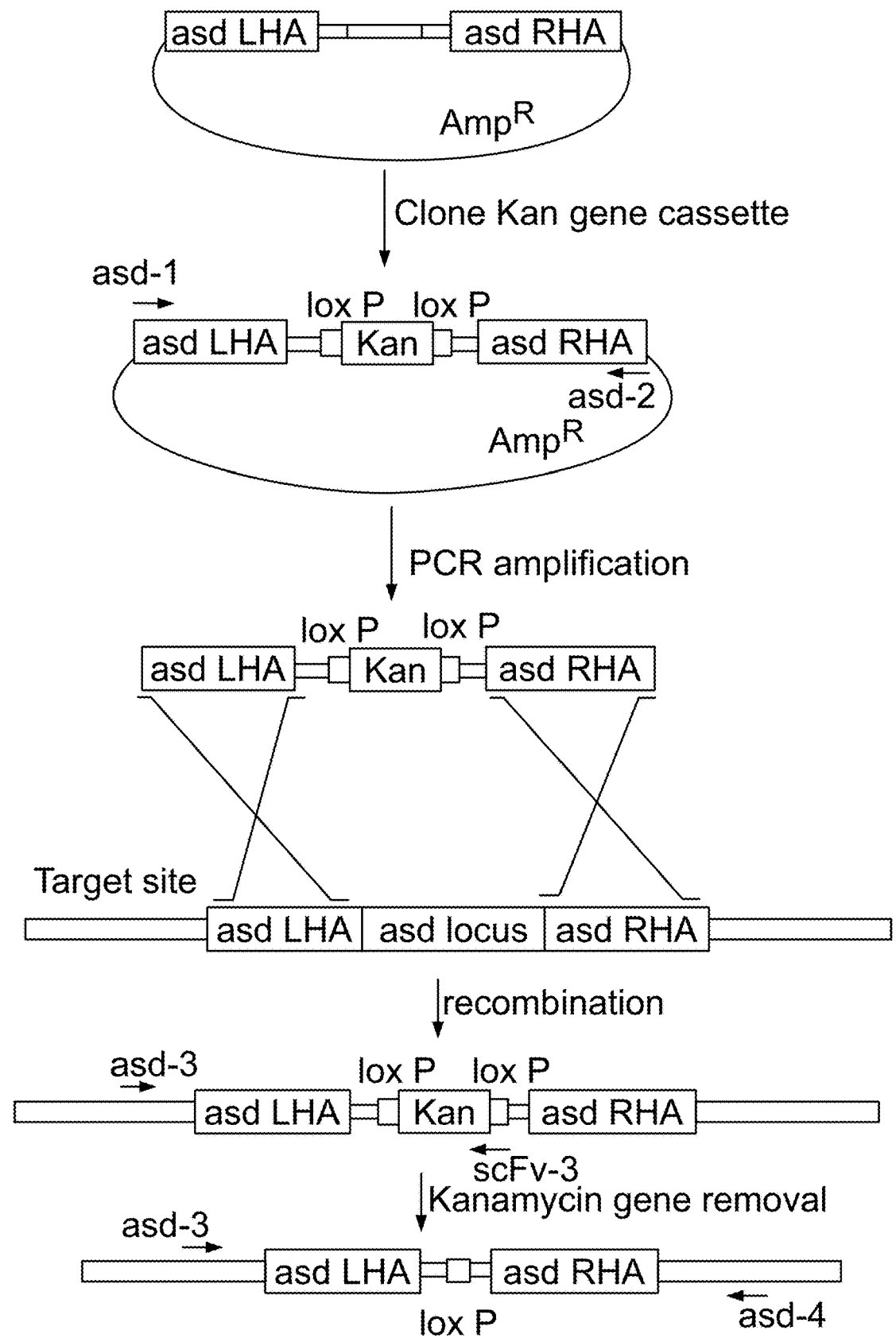
FIG. 1 depicts a schematic of the process used to delete the asd gene from strain YS1646. The asd gene from *S. typhimurium* strain YS1646 was deleted using lambda-derived Red recombination system as described in Datsenko and Wanner (*Proc. Natl. Acad. Sci. U.S.A.* 97:6640-6645 (2000)).

Outline
A. DEFINITIONS
B. OVERVIEW OF THE IMMUNOSTIMULATORY BACTERIA
C. CANCER IMMUNOTHERAPEUTICS
   1. Immunotherapies
   2. Adoptive Immunotherapies
   3. Cancer Vaccines and Oncolytic Viruses
D. ONCOLYTIC VIRUSES ENCODING RNAi AGAINST TREX1, USES OF AND METHODS OF TREATMENT OF TUMORS
E. BACTERIAL CANCER IMMUNOTHERAPY
   1. Bacterial Therapies
   2. Comparison of the Immune Responses to Bacteria and Viruses
   3. *Salmonella* Therapy
      a. Tumor-tropic Bacteria.
      b. *Salmonella enterica* serovar *typhimurium*
      c. Bacterial Attenuation
         i. msbB⁻ Mutants
         ii. purI⁻ Mutants
         iii. Combinations of Attenuating Mutations
         iv. VNP20009 and Other Attenuated *S. typhimurium* Strains
         v. Attenuated *S. typhimurium* Engineered To Deliver Macromolecules
   4. Enhancements of Immunostimulatory Bacteria to Increase Therapeutic Index
      a. asd Gene Deletion
      b. Adenosine Auxotrophy
      c. Flagellin Deficient Strains
      d. *Salmonella* Engineered to Escape the *Salmonella* Containing Vacuole (SCV)
      e. Deletions in *Salmonella* Genes Required for Biofilm Formation
      f. Deletions in Genes in the LPS Biosynthetic Pathway
      g. Deletions of SPI-1 Genes
      h. Endonuclease I (endA) Mutations To Increase Plasmid Delivery
      i. RIG-I Inhibition
      j. DNase II Inhibition
      k. RNase H2 Inhibition
      l. Stabilin-1/CLEVER-1 Inhibition
      m. Bacterial Culture Conditions
F. BACTERIAL ATTENUATION AND COLONIZATION
   1. Deletion of Flagellin (fliC
   2. Deletion of Genes in the LPS Biosynthetic Pathway
   3. Colonization G. CONSTRUCTING EXEMPLARY PLASMIDS
 1. Interfering RNAs (RNAi)
  a. shRNA
  b. microRNA
 2. Origin of Replication and Plasmid Copy Number
 3. CpG Motifs and CpG Islands
 4. Plasmid Maintenance/Selection Components
 5. RNA Polymerase Promoters
 6. DNA Nuclear Targeting Sequences
H. TUMOR TARGETING IMMUNOSTIMULATORY BACTERIA CONTAIN RNAI AGAINST EXEMPLARY IMMUNE TARGET GENES TO STIMULATE ANTI-TUMOR IMMUNITY
 1. TREX1
 2. PD-L1
 3. VISTA
 4. SIRPα
 5. β-catenin
 6. TGF-β
 7. VEGF
 8. Additional Exemplary Checkpoint Targets
I. COMBINATIONS OF RNAI/shRNAS TO MULTIPLE IMMUNE TARGETS WITHIN A SINGLE THERAPEUTIC MODALITY AND COMBINATION THERAPY
 1. TREX1 and Other Targets
 2. TREX1 and Radiotherapy
 3. TREX1 and Immunogenic Chemotherapy
 4. Combination Therapy with Anti-Checkpoint Antibodies
J. IDENTIFICATION AND TREATMENT OF TUMORS SUSCEPTIBLE TO TREATMENT WITH A TREX1 ANTAGONIST
 1. Tumor Mutational Burden (TMB)
 2. Virally Driven Tumors
 3. Oncoviruses
  a. Human Papillomavirus (HPV)
   Cervical Cancer
   Head and Neck Cancer (Oropharyngeal Cancer)
  b. Human Herpesvirus-8 (HHV-8)
  c. Hepatitis B Virus (HBV)
  d. Hepatitis C Virus (HCV)
  e. Merkel Cell Polyomavirus (MCPyV)
  f. Human T-Cell Lymphotropic Virus-1 (HTLV-1)
K. PHARMACEUTICAL PRODUCTION, COMPOSITIONS, AND FORMULATIONS
 1. Manufacturing
  a. Cell Bank Manufacturing
  b. Drug Substance Manufacturing
  c. Drug Product Manufacturing
 2. Compositions
 3. Formulations
  a. Liquids, Injectables, Emulsions
  b. Dried Thermostable Formulations
 4. Compositions for Other Routes of Administration
 5. Dosages and Administration
 6. Packaging and Articles of Manufacture
L. METHODS OF TREATMENT AND USES
 1. Cancers and Tumors
 2. Administration
 3. Monitoring
M. EXAMPLES

A. DEFINITIONS

Unless defined otherwise, all technical and scientific terms used herein have the same meaning as is commonly understood by one of skill in the art to which the invention(s) belong. All patents, patent applications, published applications and publications, GenBank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein, therapeutic bacteria are bacteria that effect therapy, such as cancer or anti-tumor therapy, when administered to a subject, such as a human.

As used herein, immunostimulatory bacteria are therapeutic bacteria that, when introduced into a subject, accumulate in immunoprivileged tissues and cells, such as tumors, and replicate and/or express products that are immunostimulatory or that result in immunostimulation. The immunostimulatory bacteria are attenuated in the host by virtue of reduced toxicity or pathogenicity and/or by virtue of encoded products that reduce toxicity or pathogenicity, as the immunostimulatory bacteria cannot replicate and/or express products, except primarily in immunoprivileged environments. Immunostimulatory bacteria provided herein are modified to encode a product or products or exhibit a trait or property that renders them immunostimulatory. Such products, properties and traits include, at least one of an shRNA that targets, disrupts or inhibits a checkpoint gene or gene encoding such inhibitor or a metabolite that is immunosuppressive or is in an immunosuppressive pathway. These include encoding an siRNA, such as an shRNA, that targets or inhibits TREX1 expression, a modification that renders the bacterium auxotrophic for adenosine, and/or an inhibitor or disruptor of an immune checkpoint gene or product thereof, such as an shRNA that disrupts or inhibits PD-L1.

As used herein, the strain designations VNP20009 (see, e.g., International PCT Application Publication No. WO 99/13053, see, also U.S. Pat. No. 6,863,894) and YS1646 and 41.2.9 are used interchangeably and each refer to the strain deposited with the American Type Culture Collection (ATCC) and assigned Accession No. 202165. VNP20009 is a modified attenuated strain of *Salmonella typhimurium*, which contains deletions in msbB and purI, and was generated from wild type strain ATCC 14028.

As used herein, the strain designations YS1456 and 8.7 are used interchangeably and each refer to the strain deposited with the American Type Culture Collection and assigned Accession No. 202164 (see, U.S. Pat. No. 6,863,894).

As used herein, an origin of replication is a sequence of DNA at which replication is initiated on a chromosome, plasmid or virus. For small DNA, including bacterial plasmids and small viruses, a single origin is sufficient. The origin of replication determines the vector copy number, which depends upon the selected origin of replication. For example, if the expression vector is derived from the low-copy-number plasmid pBR322, it is between about 25-50 copies/cell, and if derived from the high-copy-number plasmid pUC, it can be 150-200 copies/cell.

As used herein, medium copy number of a plasmid in cells is about or is 150 or less than 150, low copy number is 15-30, such as 20 or less than 20. Low to medium copy number is less than 150. High copy number is greater than 150 copies/cell.

As used herein, a "virus" refers to any of a large group of infectious entities that cannot grow or replicate without a host cell. Viruses typically contain a protein coat surrounding an RNA or DNA core of genetic material, but no semipermeable membrane, and are capable of growth and multiplication only in living cells. Viruses include, but are not limited to, poxviruses, herpesviruses, adenoviruses, adeno-associated viruses, lentiviruses, retroviruses, rhabdoviruses, papillomaviruses, vesicular stomatitis virus, measles virus, Newcastle disease virus, picornavirus, Sindbis virus, parvovirus, reovirus, coxsackievirus, influenza virus, mumps virus, poliovirus, Seneca Valley Virus, and semliki forest virus.

As used herein, oncolytic viruses refer to viruses that replicate selectively in tumor cells in tumorous subjects. Some oncolytic viruses can kill a tumor cell following infection of the tumor cell. For example, an oncolytic virus can cause death of the tumor cell by lysing the tumor cell or inducing cell death of the tumor cell. The oncolytic viruses provided herein encode RNAi that suppresses, inhibits, disrupts or otherwise silences or reduces expression of immune checkpoint genes and pathways. In particular, the oncolytic viruses encode RNAi that suppresses, inhibits, disrupts or otherwise silences or reduces expression of three prime repair exonuclease 1 (TREX1).

As used herein, a TREX1 antagonist is a product, such as a nucleic acid or a protein that inhibits, disrupts or otherwise silences or reduces expression of TREX1, or that inhibits the activity of TREX1, such as by specifically binding to TREX1 to thereby inhibit its activity. For purposes herein, reference to a TREX1 antagonist also refers to the vehicle, such as a bacterium or virus, that encodes the product.

As used herein, a CpG motif is a pattern of bases that include an unmethylated central CpG ("p" refers to the phosphodiester link between consecutive C and G nucleotides) surrounded by at least one base flanking (on the 3' and the 5' side of) the central CpG. A CpG oligodeoxynucleotide is an oligodeoxynucleotide that is at least about ten nucleotides in length and includes an unmethylated CpG. At least the C of the 5' CG 3' is unmethylated.

As used herein, a RIG-I binding sequence refers to a 5'triphosphate (5'ppp) structure directly, or that which is synthesized by RNA pol III from a poly(dA-dT) sequence, which by virtue of interaction with RIG-I can activate type I IFN via the RIG-I pathway. The RNA includes at least four A ribonucleotides (A-A-A-A); it can contain 4, 5, 6, 7, 8, 9, 10 or more. The RIG-I binding sequence is introduced into a plasmid in the bacterium for transcription into the polyA.

As used herein, a "modification" is in reference to modification of a sequence of amino acids of a polypeptide or a sequence of nucleotides in a nucleic acid molecule and includes deletions, insertions, and replacements of amino acids or nucleotides, respectively. Methods of modifying a polypeptide are routine to those of skill in the art, such as by using recombinant DNA methodologies.

As used herein, a modification to a bacterial genome or to a plasmid or gene includes deletions, replacements and insertions of nucleic acid.

As used herein, RNA interference (RNAi) is a biological process in which RNA molecules inhibit gene expression or translation, by neutralizing targeted mRNA molecules to inhibit translation and thereby expression of a targeted gene.

As used herein, RNA molecules that act via RNAi are referred to as inhibitory by virtue of their silencing of expression of a targeted gene. Silencing expression means that expression of the targeted gene is reduced or suppressed or inhibited.

As used herein, gene silencing via RNAi is said to inhibit, suppress, disrupt or silence expression of a targeted gene. A targeted gene contains sequences of nucleotides that correspond to the sequences in the inhibitory RNA, whereby the inhibitory RNA silences expression of mRNA.

As used herein, inhibiting, suppressing, disrupting or silencing a targeted gene refers to processes that alter expression, such as translation, of the targeted gene, whereby activity or expression of the product encoded by the targeted gene is reduced. Reduction, includes a complete knock-out or a partial knockout, whereby with reference to the immunostimulatory bacterium provided herein and administration herein, treatment is effected.

As used herein, small interfering RNAs (siRNAs) are small pieces of double-stranded (ds) RNA, usually about 21 nucleotides long, with 3' overhangs (2 nucleotides) at each end that can be used to "interfere" with the translation of proteins by binding to and promoting the degradation of messenger RNA (mRNA) at specific sequences. In doing so, siRNAs prevent the production of specific proteins based on the nucleotide sequences of their corresponding mRNAs. The process is called RNA interference (RNAi), and also is referred to as siRNA silencing or siRNA knockdown.

As used herein, a short-hairpin RNA or small-hairpin RNA (shRNA) is an artificial RNA molecule with a tight hairpin turn that can be used to silence target gene expression via RNA interference (RNAi). Expression of shRNA in cells is typically accomplished by delivery of plasmids or through viral or bacterial vectors.

As used herein, "tumor mutational burden (TMB)" refers to the number of somatic cell mutations in the tumor genome, which, for example, can be evaluated by assessing mutations per megabase using Next-Generation/Whole-Exome Sequencing. High tumor mutational burden (TMB) is more than 10 mutations per megabase (Mb), and low tumor mutational burden is less than 1 mutation/Mb (see, e.g., Bethune and Joglekar (2017) *Current Opinion in Biotechnology* 18:142-152). Tumors with high TMB, have neoantigens that form when somatic mutations result in the expression of epitopes. The epitopes are processed, presented by MHC molecules, and recognized by a specific subset of T-cells. The neoantigens are targets of endogenous immunity (Bethune and Joglekar (2017) *Current Opinion in Biotechnology* 18:142-152).

As used herein, a tumor microenvironment (TME) is the cellular environment in which the tumor exists, including surrounding blood vessels, immune cells, fibroblasts, bone marrow-derived inflammatory cells, lymphocytes, signaling molecules and the extracellular matrix (ECM). Conditions that exist include, but are not limited to, increased vascularization, hypoxia, low pH, increased lactate concentration, increased pyruvate concentration, increased interstitial fluid pressure and altered metabolites or metabolism, such as higher levels of adenosine, indicative of a tumor.

As used herein, human type I interferons (IFNs) are a subgroup of interferon proteins that regulate the activity of the immune system. All type I IFNs bind to a specific cell surface receptor complex, such as the IFN-$\alpha$ receptor. Type I interferons include IFN-$\alpha$ and IFN-$\beta$, among others. IFN-$\beta$ proteins are produced by fibroblasts, and have antiviral activity that is involved mainly in innate immune response. Two types of IFN-$\beta$ are IFN-$\beta$1 (IFNB1) and IFN-$\beta$3 (IFNB3).

As used herein, recitation that a nucleic acid or encoded RNA targets a gene means that it inhibits or suppresses or silences expression of the gene by any mechanism. Generally, such nucleic acid includes at least a portion complementary to the targeted gene, where the portion is sufficient to form a hybrid with the complementary portion.

As used herein, "deletion," when referring to a nucleic acid or polypeptide sequence, refers to the deletion of one or more nucleotides or amino acids compared to a sequence, such as a target polynucleotide or polypeptide or a native or wild-type sequence.

As used herein, "insertion," when referring to a nucleic acid or amino acid sequence, describes the inclusion of one or more additional nucleotides or amino acids, within a target, native, wild-type or other related sequence. Thus, a nucleic acid molecule that contains one or more insertions compared to a wild-type sequence, contains one or more additional nucleotides within the linear length of the sequence.

As used herein, "additions" to nucleic acid and amino acid sequences describe addition of nucleotides or amino acids onto either termini compared to another sequence.

As used herein, "substitution" or "replacement" refers to the replacing of one or more nucleotides or amino acids in a native, target, wild-type or other nucleic acid or polypeptide sequence with an alternative nucleotide or amino acid, without changing the length (as described in numbers of residues) of the molecule. Thus, one or more substitutions in a molecule does not change the number of amino acid residues or nucleotides of the molecule. Amino acid replacements compared to a particular polypeptide can be expressed in terms of the number of the amino acid residue along the length of the polypeptide sequence.

As used herein, "at a position corresponding to," or recitation that nucleotides or amino acid positions "correspond to" nucleotides or amino acid positions in a disclosed sequence, such as set forth in the Sequence Listing, refers to nucleotides or amino acid positions identified upon alignment with the disclosed sequence to maximize identity using a standard alignment algorithm, such as the GAP algorithm. By aligning the sequences, one skilled in the art can identify corresponding residues, for example, using conserved and identical amino acid residues as guides. In general, to identify corresponding positions, the sequences of amino acids are aligned so that the highest order match is obtained (see, e.g., *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; *Sequence Analysis Primer*, Gribskov, M. and Devereux, J., eds., M Stockton Press, New York, 1991; and Carrillo et al. (1988) *SIAM J Applied Math* 48:1073).

As used herein, alignment of a sequence refers to the use of homology to align two or more sequences of nucleotides or amino acids. Typically, two or more sequences that are related by 50% or more identity are aligned. An aligned set of sequences refers to 2 or more sequences that are aligned at corresponding positions and can include aligning sequences derived from RNAs, such as ESTs and other cDNAs, aligned with genomic DNA sequence. Related or variant polypeptides or nucleic acid molecules can be aligned by any method known to those of skill in the art. Such methods typically maximize matches, and include methods, such as using manual alignments and by using the numerous alignment programs available (e.g., BLASTP) and others known to those of skill in the art. By aligning the sequences of polypeptides or nucleic acids, one skilled in the art can identify analogous portions or positions, using conserved and identical amino acid residues as guides. Further, one skilled in the art also can employ conserved amino acid or nucleotide residues as guides to find corresponding amino acid or nucleotide residues between and among human and non-human sequences. Corresponding positions also can be based on structural alignments, for example by using computer simulated alignments of protein structure. In other instances, corresponding regions can be identified. One skilled in the art also can employ conserved amino acid residues as guides to find corresponding amino acid residues between and among human and non-human sequences.

As used herein, a "property" of a polypeptide, such as an antibody, refers to any property exhibited by a polypeptide, including, but not limited to, binding specificity, structural configuration or conformation, protein stability, resistance to proteolysis, conformational stability, thermal tolerance, and tolerance to pH conditions. Changes in properties can alter an "activity" of the polypeptide. For example, a change in the binding specificity of the antibody polypeptide can alter the ability to bind an antigen, and/or various binding activities, such as affinity or avidity, or in vivo activities of the polypeptide.

As used herein, an "activity" or a "functional activity" of a polypeptide, such as an antibody, refers to any activity exhibited by the polypeptide. Such activities can be empirically determined. Exemplary activities include, but are not limited to, ability to interact with a biomolecule, for example, through antigen-binding, DNA binding, ligand binding, or dimerization, or enzymatic activity, for example, kinase activity or proteolytic activity. For an antibody (including antibody fragments), activities include, but are not limited to, the ability to specifically bind a particular antigen, affinity of antigen-binding (e.g., high or low affinity), avidity of antigen-binding (e.g., high or low avidity), on-rate, off-rate, effector functions, such as the ability to promote antigen neutralization or clearance, virus neutralization, and in vivo activities, such as the ability to prevent infection or invasion of a pathogen, or to promote clearance, or to penetrate a particular tissue or fluid or cell in the body. Activity can be assessed in vitro or in vivo using recognized assays, such as ELISA, flow cytometry, surface plasmon resonance or equivalent assays to measure on- or off-rate, immunohistochemistry and immunofluorescence histology and microscopy, cell-based assays, flow cytometry and binding assays (e.g., panning assays).

As used herein, "bind," "bound" or grammatical variations thereof refers to the participation of a molecule in any attractive interaction with another molecule, resulting in a stable association in which the two molecules are in close proximity to one another. Binding includes, but is not limited to, non-covalent bonds, covalent bonds (such as reversible and irreversible covalent bonds), and includes interactions between molecules such as, but not limited to, proteins, nucleic acids, carbohydrates, lipids, and small molecules, such as chemical compounds including drugs.

As used herein, "antibody" refers to immunoglobulins and immunoglobulin fragments, whether natural or partially or wholly synthetically, such as recombinantly produced, including any fragment thereof containing at least a portion of the variable heavy chain and light region of the immunoglobulin molecule that is sufficient to form an antigen-binding site and, when assembled, to specifically bind an antigen. Hence, an antibody includes any protein having a binding domain that is homologous or substantially homologous to an immunoglobulin antigen-binding domain (antibody combining site). For example, an antibody refers to an antibody that contains two heavy chains (which can be denoted H and H') and two light chains (which can be denoted L and L'), where each heavy chain can be a full-length immunoglobulin heavy chain or a portion thereof sufficient to form an antigen-binding site (e.g., heavy chains include, but are not limited to, VH chains, VH-CH1 chains and VH-CH1-CH2-CH3 chains), and each light chain can be a full-length light chain or a portion thereof sufficient to form an antigen-binding site (e.g., light chains include, but are not limited to, VL chains and VL-CL chains). Each heavy chain (H and H') pairs with one light chain (L and L', respectively). Typically, antibodies minimally include all or at least a portion of the variable heavy (VH) chain and/or the variable light (VL) chain. The antibody also can include all or a portion of the constant region.

For purposes herein, the term antibody includes full-length antibodies and portions thereof including antibody fragments, such as anti-EGFR antibody fragments. Antibody fragments, include, but are not limited to, Fab fragments, Fab' fragments, F(ab')$_2$ fragments, Fv fragments, disulfide-linked Fvs (dsFv), Fd fragments, Fd' fragments, single-chain Fvs (scFv), single-chain Fabs (scFab), diabodies, anti-idio-typic (anti-Id) antibodies, or antigen-binding fragments of any of the above. Antibody also includes synthetic antibodies, recombinantly produced antibodies, multispecific antibodies (e.g., bispecific antibodies), human antibodies, non-human antibodies, humanized antibodies, chimeric antibodies, and intrabodies. Antibodies provided herein include members of any immunoglobulin class (e.g., IgG, IgM, IgD, IgE, IgA and IgY), any subclass (e.g., IgG1, IgG2, IgG3, IgG4, IgA1 and IgA2) or sub-subclass (e.g., IgG2a and IgG2b).

As used herein, "nucleic acid" refers to at least two linked nucleotides or nucleotide derivatives, including a deoxyribonucleic acid (DNA) and a ribonucleic acid (RNA), joined together, typically by phosphodiester linkages. Also included in the term "nucleic acid" are analogs of nucleic acids such as peptide nucleic acid (PNA), phosphorothioate DNA, and other such analogs and derivatives or combinations thereof. Nucleic acids also include DNA and RNA derivatives containing, for example, a nucleotide analog or a "backbone" bond other than a phosphodiester bond, for example, a phosphotriester bond, a phosphoramidate bond, a phosphorothioate bond, a thioester bond, or a peptide bond (peptide nucleic acid). The term also includes, as equivalents, derivatives, variants and analogs of either RNA or DNA made from nucleotide analogs, single (sense or antisense) and double-stranded nucleic acids. Deoxyribonucleotides include deoxyadenosine, deoxycytidine, deoxyguanosine and deoxythymidine. For RNA, the uracil base is uridine.

As used herein, an isolated nucleic acid molecule is one which is separated from other nucleic acid molecules which are present in the natural source of the nucleic acid molecule. An "isolated" nucleic acid molecule, such as a cDNA molecule, can be substantially free of other cellular material, or culture medium when produced by recombinant techniques, or substantially free of chemical precursors or other chemicals when chemically synthesized. Exemplary isolated nucleic acid molecules provided herein include isolated nucleic acid molecules encoding an antibody or antigen-binding fragments provided.

As used herein, "operably linked" with reference to nucleic acid sequences, regions, elements or domains means that the nucleic acid regions are functionally related to each other. For example, a nucleic acid encoding a leader peptide can be operably linked to a nucleic acid encoding a polypeptide, whereby the nucleic acids can be transcribed and translated to express a functional fusion protein, wherein the leader peptide effects secretion of the fusion polypeptide. In some instances, the nucleic acid encoding a first polypeptide (e.g., a leader peptide) is operably linked to a nucleic acid encoding a second polypeptide and the nucleic acids are transcribed as a single mRNA transcript, but translation of the mRNA transcript can result in one of two polypeptides being expressed. For example, an amber stop codon can be located between the nucleic acid encoding the first polypeptide and the nucleic acid encoding the second polypeptide, such that, when introduced into a partial amber suppressor cell, the resulting single mRNA transcript can be translated to produce either a fusion protein containing the first and second polypeptides, or can be translated to produce only the first polypeptide. In another example, a promoter can be operably linked to nucleic acid encoding a polypeptide, whereby the promoter regulates or mediates the transcription of the nucleic acid.

As used herein, "synthetic," with reference to, for example, a synthetic nucleic acid molecule or a synthetic gene or a synthetic peptide refers to a nucleic acid molecule or polypeptide molecule that is produced by recombinant methods and/or by chemical synthesis methods.

As used herein, the residues of naturally occurring α-amino acids are the residues of those 20 α-amino acids found in nature which are incorporated into protein by the specific recognition of the charged tRNA molecule with its cognate mRNA codon in humans.

As used herein, "polypeptide" refers to two or more amino acids covalently joined. The terms "polypeptide" and "protein" are used interchangeably herein.

As used herein, a "peptide" refers to a polypeptide that is from 2 to about or 40 amino acids in length.

As used herein, an "amino acid" is an organic compound containing an amino group and a carboxylic acid group. A polypeptide contains two or more amino acids. For purposes herein, amino acids contained in the antibodies provided include the twenty naturally-occurring amino acids (see Table below), non-natural amino acids, and amino acid analogs (e.g., amino acids wherein the α-carbon has a side chain). As used herein, the amino acids, which occur in the various amino acid sequences of polypeptides appearing herein, are identified according to their well-known, three-letter or one-letter abbreviations (see Table below). The nucleotides, which occur in the various nucleic acid molecules and fragments, are designated with the standard single-letter designations used routinely in the art.

As used herein, "amino acid residue" refers to an amino acid formed upon chemical digestion (hydrolysis) of a polypeptide at its peptide linkages. The amino acid residues described herein are generally in the "L" isomeric form. Residues in the "D" isomeric form can be substituted for any L-amino acid residue, as long as the desired functional property is retained by the polypeptide. NH$_2$ refers to the free amino group present at the amino terminus of a polypeptide. COOH refers to the free carboxy group present at the carboxyl terminus of a polypeptide. In keeping with standard polypeptide nomenclature described in *J. Biol. Chem.*, 243:3557-59 (1968) and adopted at 37 C.F.R. §§ 1.821-1.822, abbreviations for amino acid residues are shown in the following Table:

Table of Correspondence

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Proline |
| K | Lys | Lysine |
| H | His | Histidine |
| Q | Gln | Glutamine |
| E | Glu | Glutamic acid |
| Z | Glx | Glutamic Acid and/or Glutamine |
| W | Trp | Tryptophan |
| R | Arg | Arginine |
| D | Asp | Aspartic acid |
| N | Asn | Asparagine |
| B | Asx | Aspartic Acid and/or Asparagine |
| C | Cys | Cysteine |
| X | Xaa | Unknown or other |

All sequences of amino acid residues represented herein by a formula have a left to right orientation in the conventional direction of amino-terminus to carboxyl-terminus. The phrase "amino acid residue" is defined to include the amino acids listed in the above Table of Correspondence, modified, non-natural and unusual amino acids. A dash at the beginning or end of an amino acid residue sequence indicates a peptide bond to a further sequence of one or more amino acid residues or to an amino-terminal group such as NH$_2$ or to a carboxyl-terminal group such as COOH.

In a peptide or protein, suitable conservative substitutions of amino acids are known to those of skill in the art and generally can be made without altering a biological activity of a resulting molecule. Those of skill in the art recognize that, in general, single amino acid substitutions in non-essential regions of a polypeptide do not substantially alter biological activity (see, e.g., Watson et al., *Molecular Biology of the Gene,* 4th Edition, 1987, The Benjamin/Cummings Pub. Co., p. 224).

Such substitutions can be made in accordance with the exemplary substitutions set forth in the following Table:

Exemplary conservative amino acid substitutions

| Original residue | Exemplary Conservative substitution(s) |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |

-continued

Exemplary conservative amino acid substitutions

| Original residue | Exemplary Conservative substitution(s) |
|---|---|
| Thr (T) | Ser |
| Trp (W) | Tyr |
| Tyr (Y) | Trp; Phe |
| Val (V) | Ile; Leu |

Other substitutions also are permissible and can be determined empirically or in accord with other known conservative or non-conservative substitutions.

As used herein, "naturally occurring amino acids" refer to the 20 L-amino acids that occur in polypeptides.

As used herein, the term "non-natural amino acid" refers to an organic compound that has a structure similar to a natural amino acid but has been modified structurally to mimic the structure and reactivity of a natural amino acid. Non-naturally occurring amino acids thus include, for example, amino acids or analogs of amino acids other than the 20 naturally occurring amino acids and include, but are not limited to, the D-stereoisomers of amino acids. Exemplary non-natural amino acids are known to those of skill in the art, and include, but are not limited to, 2-Aminoadipic acid (Aad), 3-Aminoadipic acid (bAad), β-alanine/β-Amino-propionic acid (Bala), 2-Aminobutyric acid (Abu), 4-Aminobutyric acid/piperidinic acid (4Abu), 6-Aminocaproic acid (Acp), 2-Aminoheptanoic acid (Ahe), 2-Aminoisobutyric acid (Aib), 3-Aminoisobutyric acid (Baib), 2-Aminopimelic acid (Apm), 2,4-Diaminobutyric acid (Dbu), Desmosine (Des), 2,2'-Diaminopimelic acid (Dpm), 2,3-Diaminopropionic acid (Dpr), N-Ethylglycine (EtGly), N-Ethylasparagine (EtAsn), Hydroxylysine (Hyl), allo-Hydroxylysine (Ahyl), 3-Hydroxyproline (3Hyp), 4-Hydroxyproline (4Hyp), Isodesmosine (Ide), allo-Isoleucine (Aile), N-Methylglycine, sarcosine (MeGly), N-Methylisoleucine (MeIle), 6-N-Methyllysine (MeLys), N-Methylvaline (MeVal), Norvaline (Nva), Norleucine (Nle), and Ornithine (Orn).

As used herein, a DNA construct is a single or double stranded, linear or circular DNA molecule that contains segments of DNA combined and juxtaposed in a manner not found in nature. DNA constructs exist as a result of human manipulation, and include clones and other copies of manipulated molecules.

As used herein, a DNA segment is a portion of a larger DNA molecule having specified attributes. For example, a DNA segment encoding a specified polypeptide is a portion of a longer DNA molecule, such as a plasmid or plasmid fragment, which, when read from the 5' to 3' direction, encodes the sequence of amino acids of the specified polypeptide.

As used herein, the term polynucleotide means a single- or double-stranded polymer of deoxyribonucleotides or ribonucleotide bases read from the 5' to the 3' end. Polynucleotides include RNA and DNA, and can be isolated from natural sources, synthesized in vitro, or prepared from a combination of natural and synthetic molecules. The length of a polynucleotide molecule is given herein in terms of nucleotides (abbreviated "nt") or base pairs (abbreviated "bp"). The term nucleotides is used for single- and double-stranded molecules where the context permits. When the term is applied to double-stranded molecules it is used to denote overall length and will be understood to be equivalent to the term base pairs. It will be recognized by those skilled in the art that the two strands of a double-stranded polynucleotide can differ slightly in length and that the ends thereof can be staggered; thus all nucleotides within a double-stranded polynucleotide molecule cannot be paired. Such unpaired ends will, in general, not exceed 20 nucleotides in length.

As used herein, production by recombinant means by using recombinant DNA methods means the use of the well-known methods of molecular biology for expressing proteins encoded by cloned DNA.

As used herein, "expression" refers to the process by which polypeptides are produced by transcription and translation of polynucleotides. The level of expression of a polypeptide can be assessed using any method known in art, including, for example, methods of determining the amount of the polypeptide produced from the host cell. Such methods can include, but are not limited to, quantitation of the polypeptide in the cell lysate by ELISA, Coomassie blue staining following gel electrophoresis, Lowry protein assay and Bradford protein assay.

As used herein, a "host cell" is a cell that is used to receive, maintain, reproduce and/or amplify a vector. A host cell also can be used to express the polypeptide encoded by the vector. The nucleic acid contained in the vector is replicated when the host cell divides, thereby amplifying the nucleic acids.

As used herein, a "vector" is a replicable nucleic acid from which one or more heterologous proteins, can be expressed when the vector is transformed into an appropriate host cell. Reference to a vector includes those vectors into which a nucleic acid encoding a polypeptide or fragment thereof can be introduced, typically by restriction digest and ligation. Reference to a vector also includes those vectors that contain nucleic acid encoding a polypeptide, such as a modified anti-EGFR antibody. The vector is used to introduce the nucleic acid encoding the polypeptide into the host cell for amplification of the nucleic acid or for expression/display of the polypeptide encoded by the nucleic acid. The vectors typically remain episomal, but can be designed to effect integration of a gene or portion thereof into a chromosome of the genome. Also contemplated are vectors that are artificial chromosomes, such as yeast artificial chromosomes and mammalian artificial chromosomes. Selection and use of such vehicles are well-known to those of skill in the art. A vector also includes "virus vectors" or "viral vectors." Viral vectors are engineered viruses that are operatively linked to exogenous genes to transfer (as vehicles or shuttles) the exogenous genes into cells.

As used herein, an "expression vector" includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well-known to those of skill in the art and include those that are replicable in eukaryotic cells and/or prokaryotic cells and those that remain episomal or those which integrate into the host cell genome.

As used herein, "primary sequence" refers to the sequence of amino acid residues in a polypeptide or the sequence of nucleotides in a nucleic acid molecule.

As used herein, "sequence identity" refers to the number of identical or similar amino acids or nucleotide bases in a comparison between a test and a reference polypeptide or polynucleotide. Sequence identity can be determined by sequence alignment of nucleic acid or protein sequences to identify regions of similarity or identity. For purposes herein, sequence identity is generally determined by alignment to identify identical residues. The alignment can be local or global. Matches, mismatches and gaps can be identified between compared sequences. Gaps are null amino acids or nucleotides inserted between the residues of aligned sequences so that identical or similar characters are aligned. Generally, there can be internal and terminal gaps. When using gap penalties, sequence identity can be determined with no penalty for end gaps (e.g., terminal gaps are not penalized). Alternatively, sequence identity can be determined without taking into account gaps as the number of identical positions/length of the total aligned sequence×100.

As used herein, a "global alignment" is an alignment that aligns two sequences from beginning to end, aligning each letter in each sequence only once. An alignment is produced, regardless of whether or not there is similarity or identity between the sequences. For example, 50% sequence identity based on "global alignment" means that in an alignment of the full sequence of two compared sequences each of 100 nucleotides in length, 50% of the residues are the same. It is understood that global alignment also can be used in determining sequence identity even when the length of the aligned sequences is not the same. The differences in the terminal ends of the sequences will be taken into account in determining sequence identity, unless the "no penalty for end gaps" is selected. Generally, a global alignment is used on sequences that share significant similarity over most of their length. Exemplary algorithms for performing global alignment include the Needleman-Wunsch algorithm (Needleman et al. (1970) *J. Mol. Biol.* 48: 443). Exemplary programs for performing global alignment are publicly available and include the Global Sequence Alignment Tool available at the National Center for Biotechnology Information (NCBI) website (ncbi.nlm.nih.gov/), and the program available at deepc2.psi.iastate.edu/aat/align/align.html.

As used herein, a "local alignment" is an alignment that aligns two sequences, but only aligns those portions of the sequences that share similarity or identity. Hence, a local alignment determines if sub-segments of one sequence are present in another sequence. If there is no similarity, no alignment will be returned. Local alignment algorithms include BLAST or Smith-Waterman algorithm (*Adv. Appl. Math.* 2: 482 (1981)). For example, 50% sequence identity based on "local alignment" means that in an alignment of the full sequence of two compared sequences of any length, a region of similarity or identity of 100 nucleotides in length has 50% of the residues that are the same in the region of similarity or identity.

For purposes herein, sequence identity can be determined by standard alignment algorithm programs used with default gap penalties established by each supplier. Default parameters for the GAP program can include: (1) a unary comparison matrix (containing a value of 1 for identities and 0 for non-identities) and the weighted comparison matrix of Gribskov et al. (1986) *Nucl. Acids Res.* 14:6745, as described by Schwartz and Dayhoff, eds., *Atlas of Protein Sequence and Structure*, National Biomedical Research Foundation, pp. 353-358 (1979); (2) a penalty of 3.0 for each gap and an additional 0.10 penalty for each symbol in each gap; and (3) no penalty for end gaps. Whether any two nucleic acid molecules have nucleotide sequences or any two polypeptides have amino acid sequences that are at least 80%, 85%, 90%, 95%, 96%, 97%, 98% or 99% "identical," or other similar variations reciting a percent identity, can be determined using known computer algorithms based on local or global alignment (see e.g., wikipedia.org/wiki/Sequence_alignment_software, providing links to dozens of known and publicly available alignment databases and programs). Generally, for purposes herein sequence identity is determined using computer algorithms based on global alignment, such as the Needleman-Wunsch Global Sequence Alignment tool available from NCBI/BLAST (blast.ncbi.nlm.nih.gov/Blast.cgi?CMD=Web&Page_TYPE=BlastHome); LAlign (William Pearson implementing the Huang and Miller algorithm (*Adv. Appl. Math.* (1991) 12:337-357)); and the program from Xiaoqui Huang available at deepc2.psi.iastate.edu/aat/align/align.html. Typically, the full-length sequence of each of the compared polypeptides or nucleotides is aligned across the full-length of each sequence in a global alignment. Local alignment also can be used when the sequences being compared are substantially the same length.

Therefore, as used herein, the term "identity" represents a comparison or alignment between a test and a reference polypeptide or polynucleotide. In one non-limiting example, "at least 90% identical to" refers to percent identities from 90 to 100% relative to the reference polypeptide or polynucleotide. Identity at a level of 90% or more is indicative of the fact that, assuming for exemplification purposes a test and reference polypeptide or polynucleotide length of 100 amino acids or nucleotides are compared, no more than 10% (i.e., 10 out of 100) of amino acids or nucleotides in the test polypeptide or polynucleotide differ from those of the reference polypeptide. Similar comparisons can be made between a test and reference polynucleotides. Such differences can be represented as point mutations randomly distributed over the entire length of an amino acid sequence or they can be clustered in one or more locations of varying length up to the maximum allowable, e.g., 10/100 amino acid difference (approximately 90% identity). Differences also can be due to deletions or truncations of amino acid residues. Differences are defined as nucleic acid or amino acid substitutions, insertions or deletions. Depending on the length of the compared sequences, at the level of homologies or identities above about 85-90%, the result can be independent of the program and gap parameters set; such high levels of identity can be assessed readily, often without relying on software.

As used herein, "disease or disorder" refers to a pathological condition in an organism resulting from a cause or condition including, but not limited to, infections, acquired conditions, and genetic conditions, and that is characterized by identifiable symptoms.

As used herein, "treating" a subject with a disease or condition means that the subject's symptoms are partially or totally alleviated, or remain static following treatment.

As used herein, treatment refers to any effects that ameliorate symptoms of a disease or disorder. Treatment encompasses prophylaxis, therapy and/or cure. Treatment also encompasses any pharmaceutical use of any immunostimulatory bacterium or composition provided herein.

As used herein, prophylaxis refers to prevention of a potential disease and/or a prevention of worsening of symptoms or progression of a disease.

As used herein, "prevention" or prophylaxis, and grammatically equivalent forms thereof, refers to methods in which the risk or probability of developing a disease or condition is reduced.

As used herein, a "pharmaceutically effective agent" includes any therapeutic agent or bioactive agents, including, but not limited to, for example, anesthetics, vasoconstrictors, dispersing agents, and conventional therapeutic drugs, including small molecule drugs and therapeutic proteins.

As used herein, a "therapeutic effect" means an effect resulting from treatment of a subject that alters, typically improves or ameliorates, the symptoms of a disease or condition or that cures a disease or condition.

As used herein, a "therapeutically effective amount" or a "therapeutically effective dose" refers to the quantity of an agent, compound, material, or composition containing a compound that is at least sufficient to produce a therapeutic effect following administration to a subject. Hence, it is the quantity necessary for preventing, curing, ameliorating, arresting or partially arresting a symptom of a disease or disorder.

As used herein, "therapeutic efficacy" refers to the ability of an agent, compound, material, or composition containing a compound to produce a therapeutic effect in a subject to whom the agent, compound, material, or composition containing a compound has been administered.

As used herein, a "prophylactically effective amount" or a "prophylactically effective dose" refers to the quantity of an agent, compound, material, or composition containing a compound that when administered to a subject, will have the intended prophylactic effect, e.g., preventing or delaying the onset, or reoccurrence, of disease or symptoms, reducing the likelihood of the onset, or reoccurrence, of disease or symptoms, or reducing the incidence of viral infection. The full prophylactic effect does not necessarily occur by administration of one dose, and can occur only after administration of a series of doses. Thus, a prophylactically effective amount can be administered in one or more administrations.

As used herein, amelioration of the symptoms of a particular disease or disorder by a treatment, such as by administration of a pharmaceutical composition or other therapeutic, refers to any lessening, whether permanent or temporary, lasting or transient, of the symptoms that can be attributed to or associated with administration of the composition or therapeutic.

As used herein, an "anti-cancer agent" refers to any agent that is destructive or toxic to malignant cells and tissues. For example, anti-cancer agents include agents that kill cancer cells or otherwise inhibit or impair the growth of tumors or cancer cells. Exemplary anti-cancer agents are chemotherapeutic agents.

As used herein "therapeutic activity" refers to the in vivo activity of a therapeutic polypeptide. Generally, the therapeutic activity is the activity that is associated with treatment of a disease or condition.

As used herein, the term "subject" refers to an animal, including a mammal, such as a human being.

As used herein, a patient refers to a human subject.

As used herein, animal includes any animal, such as, but not limited to, primates including humans, gorillas and monkeys; rodents, such as mice and rats; fowl, such as chickens; ruminants, such as goats, cows, deer, sheep; pigs and other animals. Non-human animals exclude humans as the contemplated animal. The polypeptides provided herein are from any source, animal, plant, prokaryotic and fungal. Most polypeptides are of animal origin, including mammalian origin.

As used herein, a "composition" refers to any mixture. It can be a solution, suspension, liquid, powder, paste, aqueous, non-aqueous or any combination thereof.

As used herein, a "combination" refers to any association between or among two or more items. The combination can be two or more separate items, such as two compositions or two collections, a mixture thereof, such as a single mixture of the two or more items, or any variation thereof. The elements of a combination are generally functionally associated or related.

As used herein, combination therapy refers to administration of two or more different therapeutics. The different therapeutic agents can be provided and administered separately, sequentially, intermittently, or can be provided in a single composition.

As used herein, a kit is a packaged combination that optionally includes other elements, such as additional reagents and instructions for use of the combination or elements thereof, for a purpose including, but not limited to, activation, administration, diagnosis, and assessment of a biological activity or property.

As used herein, a "unit dose form" refers to physically discrete units suitable for human and animal subjects and packaged individually as is known in the art.

As used herein, a "single dosage formulation" refers to a formulation for direct administration.

As used herein, a multi-dose formulation refers to a formulation that contains multiple doses of a therapeutic agent and that can be directly administered to provide several single doses of the therapeutic agent. The doses can be administered over the course of minutes, hours, weeks, days or months. Multi-dose formulations can allow dose adjustment, dose-pooling and/or dose-splitting. Because multi-dose formulations are used over time, they generally contain one or more preservatives to prevent microbial growth.

As used herein, an "article of manufacture" is a product that is made and sold. As used throughout this application, the term is intended to encompass any of the compositions provided herein contained in articles of packaging.

As used herein, a "fluid" refers to any composition that can flow. Fluids thus encompass compositions that are in the form of semi-solids, pastes, solutions, aqueous mixtures, gels, lotions, creams and other such compositions.

As used herein, an isolated or purified polypeptide or protein (e.g., an isolated antibody or antigen-binding fragment thereof) or biologically-active portion thereof (e.g., an isolated antigen-binding fragment) is substantially free of cellular material or other contaminating proteins from the cell or tissue from which the protein is derived, or substantially free from chemical precursors or other chemicals when chemically synthesized. Preparations can be determined to be substantially free if they appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification does not detectably alter the physical and chemical properties, such as enzymatic and biological activities, of the substance. Methods for purification of the compounds to produce substantially chemically pure compounds are known to those of skill in the art. A substantially chemically pure compound, however, can be a mixture of stereoisomers. In such instances, further purification might increase the specific activity of the compound. As used herein, a "cellular extract" or "lysate" refers to a preparation or fraction which is made from a lysed or disrupted cell.

As used herein, a "control" refers to a sample that is substantially identical to the test sample, except that it is not treated with a test parameter, or, if it is a plasma sample, it can be from a normal volunteer not affected with the condition of interest. A control also can be an internal control.

As used herein, the singular forms "a," "an" and "the" include plural referents unless the context clearly dictates otherwise. Thus, for example, reference to a polypeptide, comprising "an immunoglobulin domain" includes polypeptides with one or a plurality of immunoglobulin domains.

As used herein, the term "or" is used to mean "and/or" unless explicitly indicated to refer to alternatives only or the alternatives are mutually exclusive.

As used herein, ranges and amounts can be expressed as "about" a particular value or range. About also includes the exact amount. Hence "about 5 amino acids" means "about 5 amino acids" and also "5 amino acids."

As used herein, "optional" or "optionally" means that the subsequently described event or circumstance does or does not occur and that the description includes instances where said event or circumstance occurs and instances where it does not. For example, an optionally variant portion means that the portion is variant or non-variant.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem*. (1972) 11(9): 1726-1732).

For clarity of disclosure, and not by way of limitation, the detailed description is divided into the subsections that follow.

B. OVERVIEW OF THE IMMUNOSTIMULATORY BACTERIA

Provided are modified bacteria, called immunostimulatory bacteria herein that accumulate and/or replicate in tumors and encode inhibitory RNAs, such as designed shRNAs and designed microRNAs, that target genes whose inhibition, suppression or silencing effects tumor therapy, upon expression of the RNAs in the treated subject. Strains of bacteria for modification are any suitable for therapeutic use. The modified immunostimulatory bacteria provided herein are for use and for methods for treating cancer. The bacteria are modified for such uses and methods.

The immunostimulatory bacteria provided herein are modified by deletion or modification of bacterial genes to attenuate their inflammatory responses, and are modified to enhance anti-tumor immune responses in hosts treated with the bacteria. For example, the plasmids encoding RNAi that inhibit checkpoint genes in the host are included in the bacteria, and the bacteria can be auxotrophic for adenosine. Attenuation of the inflammatory response to the bacteria can be effected by deletion of the msbB gene, which decreases TNF-alpha in the host, and/or knocking out flagellin genes. The bacteria are modified to stimulate host anti-tumor activity, for example, by adding plasmids encoding RNAi that target host immune checkpoints, and by adding nucleic acid with CpGs.

Bacterial strains can be attenuated strains or strains that are attenuated by standard methods or that, by virtue of the modifications provided herein, are attenuated in that their ability to colonize is limited primarily to immunoprivilaged tissues and organs, particularly immune and tumor cells, including solid tumors. Bacteria include, but are not limited to, for example, strains of *Salmonella, Shigella, Listeria, E. coli*, and *Bifidobacteriae*. For example, species include *Shigella sonnei, Shigella flexneri, Shigella dysenteriae, Listeria monocytogenes, Salmonella typhi, Salmonella typhimurium, Salmonella gallinarum*, and *Salmonella enteritidis*. Other suitable bacterial species include *Rickettsia, Klebsiella, Bordetella, Neisseria, Aeromonas, Francisella, Corynebacterium, Citrobacter, Chlamydia, Haemophilus, Brucella, Mycobacterium, Mycoplasma, Legionella, Rhodococcus, Pseudomonas, Helicobacter, Vibrio, Bacillus*, and *Erysipelothrix*. For example, *Rickettsia rickettsii, Rickettsia prowazekii, Rickettsia tsutsugamushi, Rickettsia mooseri, Rickettsia sibirica, Bordetella bronchiseptica, Neisseria meningitidis, Neisseria gonorrhoeae, Aeromonas eucrenophila, Aeromonas salmonicida, Francisella tularensis, Corynebacterium pseudotuberculosis, Citrobacter freundii, Chlamydia pneumoniae, Haemophilus somnus, Brucella abortus, Mycobacterium intracellulare, Legionella pneumophila, Rhodococcus equi, Pseudomonas aeruginosa, Helicobacter mustelae, Vibrio cholerae, Bacillus subtilis, Erysipelothrix rhusiopathiae, Yersinia enterocolitica, Rochalimaea quintana*, and *Agrobacterium tumefaciens*.

The bacteria accumulate by virtue of one or more properties, including, diffusion, migration and chemotaxis to immunoprivileged tissues or organs or environments, environments that provide nutrients or other molecules for which they are auxotrophic and/or environments that contain replicating cells that provide environments for entry and replication of bacteria. The immunostimulatory bacteria provided herein and species that effect such therapy include species of *Salmonella, Listeria*, and *E. coli*. The bacteria contain plasmids that encode one or more short hairpin (sh) RNA construct(s), or other RNAi modalities, whose expression inhibits or disrupts expression of targeted genes. The shRNA constructs are expressed under control of a eukaryotic promoter, such as an RNA polymerase (RNAP) II or III promoter. Typically, RNAPIII (also referred to as POLIII) promoters are constitutive, and RNAPII (also referred to as POLII) can be regulated. In some examples, the shRNAs target the gene TREX1, to inhibit its expression. In some embodiments, the plasmids encode a plurality of RNAi molecules, such as shRNAs or microRNAs, that inhibit two or more checkpoint genes, such as shRNAs for inhibiting PD-L1, VISTA, SIRPα, CTNNB1, TGF-beta, and/or VEGF and any others known to those of skill in the art. Where a plurality of shRNAs are encoded, expression of each is under control of different promoters.

Among the bacteria provided herein, are bacteria that are modified so that they are auxotrophic for adenosine. This can be achieved by modification or deletion of genes involved in purine synthesis, metabolism, or transport. For example, disruption of the tsx gene in *Salmonella* species, such as *Salmonella typhi*, results in adenosine auxotrophy. Adenosine is immunosuppressive and accumulates to high concentrations in tumors; auxotrophy for adenosine improves the anti-tumor activity of the bacteria because the bacteria selectively replicate in tissues rich in adenosine.

Also provided are bacteria that are modified so that they have a defective asd gene. These bacteria for use in vivo are modified to include carrying a functional asd gene on the introduced plasmid; this maintains selection for the plasmid so that an antibiotic-based plasmid maintenance/selection system is not needed. Also provided is the use of asd defective strains that do not contain a functional asd gene on a plasmid and are thus engineered to be autolytic in the host.

Also provided are bacteria that are modified so that they are incapable of producing flagella. This can be achieved by modifying the bacteria by means of deleting the genes that encode the flagellin subunits. The modified bacteria lacking flagellin are less inflammatory and therefore better tolerated and induce a more potent anti-tumor response.

Also provided are bacteria that are modified to produce listeriolysin 0, which improves plasmid delivery in phagocytic cells.

Also provided are bacteria modified to carry a low copy number, CpG-containing plasmid. The plasmid further can include other modifications, and RNAi.

The bacteria also can be modified to grow in a manner such that the bacteria, if a *Salmonella* species, expresses less of the toxic SPI-1 (*Salmonella* pathogenicity island-1) genes. In *Salmonella*, genes responsible for virulence, invasion, survival, and extra intestinal spread are located in *Salmonella* pathogenicity islands (SPIs).

The bacteria include plasmids that encode RNAi, such as shRNA or microRNA, that inhibits checkpoints, such as PD-L1 or TREX1 only, or TREX1 and one or more of a second immune checkpoint. The bacteria can be further modified for other desirable traits, including for selection of plasmid maintenance, particularly for selection without antibiotics, for preparation of the strains. The immunostimulatory bacteria optionally can encode therapeutic polypeptides, including anti-tumor therapeutic polypeptides and agents.

Exemplary of the immunostimulatory bacteria provided herein are species of *Salmonella*. Exemplary of bacteria for modification as described herein are engineered strains of *Salmonella typhimurium*, such as strain YS1646 (ATCC Catalog #202165; see, also International PCT Application Publication No. WO 99/13053, also referred to as VNP20009) that is engineered with plasmids to complement an asd gene knockout and antibiotic-free plasmid maintenance.

Modified immunostimulatory bacterial strains that are rendered auxotrophic for adenosine are provided herein as are pharmaceutical compositions containing such strains formulated for administration to a subject, such as a human, for use in methods of treating tumors and cancers.

The engineered immunostimulatory bacteria provided herein contain multiple synergistic modalities to induce immune re-activation of cold tumors and to promote tumor antigen-specific immune responses, while inhibiting immune checkpoint pathways that the tumor utilizes to subvert and evade durable anti-tumor immunity. Improved tumor targeting through adenosine auxotrophy and enhanced vascular disruption have improved potency, while localizing the inflammation to limit systemic cytokine exposure and the autoimmune toxicities observed with other immunotherapy modalities. Exemplary of the bacteria so-modified are *S. typhimurium* strains, including such modifications of the strain YS1646, particularly asd⁻ strains.

For example, as provided herein, are immunostimulatory bacteria that provide for shRNA-mediated gene disruption of PD-L1. It has been shown in mice that gene disruption of PD-L1 can improve tumor colonization. It has been shown, for example, that *S. typhimurium* infection in PD-L1 knockout mice, results in a 10-fold higher bacterial load than in wild-type mice (see, Lee et al. (2010) Immunol. 185:2442-2449). Hence, PD-L1 is protective against *S. typhimurium* infection. Provided herein are immunostimulatory bacteria, such as *S. typhimurium*, carrying plasmids capable of RNAi-mediated gene knockdown of TREX1, PD-L1, or of PD-L1 and TREX1. Such bacteria provide anti-tumor effects due to the combination of two independent pathways that lead to enhanced and sustained anti-tumor immune responses in a single therapy.

C. CANCER IMMUNOTHERAPEUTICS

The immunosuppressive milieu found within the tumor microenvironment (TME) is a driver of tumor initiation and progression. Cancers emerge after the immune system fails to control and contain tumors. Multiple tumor-specific mechanisms create tumor environments wherein the immune system is forced to tolerate tumors and their cells instead of eliminating them. The goal of cancer immunotherapy is to rescue the immune system's natural ability to eliminate tumors. Acute inflammation associated with microbial infection has been observationally linked with the spontaneous elimination of tumors for centuries.

1. Immunotherapies

Several clinical cancer immunotherapies have sought to perturb the balance of immune suppression towards anti-tumor immunity. Strategies to stimulate immunity through directly administering cytokines such as IL-2 and IFN-α have seen modest clinical responses in a minority of patients, while inducing serious systemic inflammation-related toxicities (Sharma et al. (2011) Nat Rev Cancer 11:805-812). The immune system has evolved several checks and balances to limit autoimmunity, such as upregulation of programmed cell death protein 1 (PD-1) on T cells and its binding to its cognate ligand, programmed death-ligand 1 (PD-L1), which is expressed on both antigen presenting cells (APCs) and tumor cells. The binding of PD-L1 to PD-1 interferes with $CD8^+$ T cell signaling pathways, impairing the proliferation and effector function of $CD8^+$ T cells, and inducing T cell tolerance. PD-1 and PD-L1 are two examples of numerous inhibitory "immune checkpoints," which function by downregulating immune responses. Other inhibitory immune checkpoints include cytotoxic T-lymphocyte-associated protein 4 (CTLA-4), signal regulatory protein α (SIRPα), V-domain Ig suppressor of T cell activation (VISTA), programmed death-ligand 2 (PD-L2), indoleamine 2,3-dioxygenase (IDO) 1 and 2, lymphocyte-activation gene 3 (LAG3), Galectin-9, T cell immunoreceptor with Ig and ITIM domains (TIGIT), T cell immunoglobulin and mucin-domain containing-3 (TIM-3, also known as hepatitis A virus cellular receptor 2 (HAVCR2)), herpesvirus entry mediator (HVEM), CD39, CD73, B7-H3 (also known as CD276), B7-H4, CD47, CD48, CD80 (B7-1), CD86 (B7-2), CD155, CD160, CD244 (2B4), B- and T-lymphocyte attenuator (BTLA, or CD272) and carcinoembryonic antigen-related cell adhesion molecule 1 (CEACAM1, or CD66a).

Antibodies designed to block immune checkpoints, such as anti-PD-1 (for example, pembrolizumab, nivolumab) and anti-PD-L1 (for example, atezolizumab, avelumab, durvalumab), have had durable success in preventing T cell anergy and breaking immune tolerance. Only a fraction of treated patients demonstrate clinical benefit, and those that do often present with autoimmune-related toxicities (see, e.g., Ribas (2015)N. Engl. J. Med. 373:1490-1492; Topalian et al. (2012) N. Engl. J. Med. 366: 2443-2454). This is further evidence for the need for therapies, provided herein, that are more effective and less toxic.

Another checkpoint blockade strategy inhibits the induction of CTLA-4 on T cells, which binds to and inhibits co-stimulatory receptors on APCs, such as CD80 or CD86, out-competing the co-stimulatory cluster differentiation 28 (CD28), which binds the same receptors, but with a lower affinity. This blocks the stimulatory signal from CD28, while the inhibitory signal from CTLA-4 is transmitted, preventing T cell activation (see, Phan et al. (2003) Proc. Natl. Acad Sci. U.S.A. 100:8372-8377). Anti-CTLA-4 therapy (for example, ipilimumab) have clinical success and durability in some patients, whilst exhibiting an even greater incidence of severe immune-related adverse events (see, e.g., Hodi et al. (2010) N. Engl. J. Med. 363:711-723; Schadendorf et al. (2015) J. Clin. Oncol. 33:1889-1894). It also has been shown that tumors develop resistance to anti-immune checkpoint antibodies, highlighting the need for more durable anticancer therapies, and provided herein.

2. Adoptive Immunotherapies

In seeking to reactivate a cold tumor to become more immunogenic, a class of immunotherapies known as adoptive cell therapy (ACT) encompasses a variety of strategies to harness immune cells and reprogram them to have anti-tumor activity (Zielinski et al. (2011) Immunol. Rev. 240: 40-51). Dendritic cell-based therapies introduce genetically engineered dendritic cells (DCs) with more immune-stimulatory properties. These therapies have not been successful because they fail to break immune tolerance to cancer (see, e.g., Rosenberg et al. (2004) Nat. Med. 10(12):1279). A method using whole irradiated tumor cells containing endogenous tumor antigens and granulocyte macrophage colony-stimulating factor (GM-CSF) to stimulate DC recruitment, known as GVAX, similarly failed in the clinic due to the lack of ability to break tumor tolerance (Copier et al. (2010) Curr. Opin. Mol. Ther. 12:14-20). A separate autologous cell-based therapy, Sipuleucel-T (Provenge), was FDA approved in 2010 for castration-resistant prostate cancer. It utilizes APCs retrieved from the patient and re-armed to express prostatic acid phosphatase (PAP) antigen to stimulate a T cell response, then re-introduced following lymphablation. Unfortunately, its broader adoption has been limited by low observed objective response rates and high costs, and its use is limited to only the early stages of prostate cancer (Anassi et al. (2011)P T 36(4):197-202). Similarly, autologous T cell therapies (ATCs) harvest a patient's own T cells and reactivate them ex vivo to overcome tumor tolerance, then reintroduce them to the patient following lymphablation. ATCs have had limited clinical success, and only in melanoma, while generating serious safety and feasibility issues that limit their utility (Yee et al. (2013) Clin. Cancer Res. 19(17):4550-4552).

Chimeric antigen receptor T cell (CAR-T) therapies are T cells harvested from patients that have been re-engineered to express a fusion protein between the T cell receptor and an antibody Ig variable extracellular domain. This confers upon them the antigen-recognition properties of antibodies with the cytolytic properties of activated T cells (Sadelain (2015) J. Clin. Invest. 125:3392-3400498). Success has been limited to B cell and hematopoietic malignancies, at the cost of deadly immune-related adverse events (Jackson et al. (2016) Nat. Rev. Clin. Oncol. 13:370-383). Tumors can also mutate to escape recognition by a target antigen, including CD19 (Ruella et al. (2016) Comput. Struct. Biotechnol. J. 14:357-362) and EGFRvIII (O'Rourke et al. (2017) Sci. Transl. Med. July 19; 9:399), thereby fostering immune escape. In addition, while CAR-T therapies are approved and are approved in the context of hematological malignancies, they face a significant hurdle for feasibility to treat solid tumors: overcoming the highly immunosuppressive nature of the solid tumor microenvironment. A number of additional modifications to existing CAR-T therapies will be required to potentially provide feasibility against solid tumors (Kakarla et al. (2014) *Cancer J.* March-April; 20(2):151-155). When the safety of CAR-Ts is significantly improved and their efficacy expanded to solid tumors, the feasibility and costs associated with these labor-intensive therapies will continue to limit their broader adoption.

3. Cancer Vaccines and Oncolytic Viruses

Cold tumors lack T cell and dendritic cell (DC) infiltration, and are non-T-cell-inflamed (Sharma et al. (2017) *Cell* 168(4):707-723). In seeking to reactivate a cold tumor to become more immunogenic, another class of immunotherapies harness microorganisms that can accumulate in tumors, either naturally or by virtue of engineering. These include viruses designed to stimulate the immune system to express tumor antigens, thereby activating and reprogramming the immune system to reject the tumor. Oncolytic viruses seek to preferentially replicate in dividing tumor cells over healthy tissue, whereupon subsequent tumor cell lysis leads to immunogenic tumor cell death and further viral dissemination. The oncolytic virus Talimogene laherparepvec (T-VEC), which uses a modified herpes simplex virus in combination with the DC-recruiting cytokine GM-CSF, is FDA approved for metastatic melanoma (Bastin et al. (2016) *Biomedicines* 4(3):21).

D. ONCOLYTIC VIRUSES ENCODING RNAi AGAINST TREX1, USES OF AND METHODS OF TREATMENT OF TUMORS

Oncolytic viruses are well known therapeutic viruses that preferentially accumulate and replicate in tumors, which can lead to tumor cell lysis and tumor regression. Oncolytic viruses effect treatment by colonizing or accumulating in tumor cells, including metastatic tumor cells such as circulating tumor cells, and replicating therein. For example, the oncolytic virus can be any naturally occurring or engineered recombinant virus such as, but not limited to, poxvirus, such as vaccinia virus, herpes simplex virus, adenovirus, adeno-associated virus, measles virus, reovirus, vesicular stomatitis virus (VSV), coxsackie virus, Semliki Forest Virus, Seneca Valley Virus, Newcastle Disease Virus, Sendai Virus, Dengue Virus, picornavirus, poliovirus, parvovirus, retrovirus, lentivirus, alphavirus, flavivirus, rhabdovirus, papillomavirus, influenza virus, mumps virus, gibbon ape leukemia virus, and Sindbis virus, among others. In many cases, tumor selectivity is an inherent property of the virus, such as vaccinia viruses and other oncolytic viruses.

Oncolytic viruses effect treatment by several mechanisms. Oncolytic viruses accumulate and replicate in tumors or tumor cells resulting in lysis. By virtue of the lysis tumor antigens are released, which can result in an immune response against the tumor. Oncolytic viruses are engineered to encode therapeutic products.

Numerous oncolytic viruses are known to those of skill in the art. Oncolytic viruses for use in the methods provided herein include, but are not limited to, those known to one of skill in the art and include, for example, vesicular stomatitis virus, see, e.g., U.S. Pat. Nos. 7,731,974, 7,153,510, 6,653,103 and U.S. Pat. Pub. Nos. 2010/0178684, 2010/0172877, 2010/0113567, 2007/0098743, 20050260601, 20050220818 and EP Patent Nos. 1385466, 1606411 and 1520175; herpes simplex virus, see, e.g., U.S. Pat. Nos. 7,897,146, 7,731,952, 7,550,296, 7,537,924, 6,723,316, 6,428,968 and U.S. Pat. Pub. Nos. 2011/0177032, 2011/0158948, 2010/0092515, 2009/0274728, 2009/0285860, 2009/0215147, 2009/0010889, 2007/0110720, 2006/0039894 and 20040009604; retroviruses, see, e.g., U.S. Pat. Nos. 6,689,871, 6,635,472, 6,639,139, 5,851,529, 5,716,826, 5,716,613 and U.S. Pat. Pub. No. 2011/0212530; and adeno-associated viruses, see, e.g., U.S. Pat. Nos. 8,007,780, 7,968,340, 7,943,374, 7,906,111, 7,927,585, 7,811,814, 7,662,627, 7,241,447, 7,238,526, 7,172,893, 7,033,826, 7,001,765, 6,897,045, and 6,632,670. Those of skill know how to growth, select, and modify oncolytic viruses for therapy.

The oncolytic viruses provided herein are modified to encode an RNAi, such as an shRNA or a microRNA. The microRNAs and shRNAs described herein for encoding in bacterial plasmids and bacteria can be encoded in oncolytic viruses. In particular, the oncolytic viruses encode RNAi, such as any of the shRNAs and microRNAs provided or described herein, to target and inhibit TREX1. The viruses are administered by any suitable methods, including, but not limited to, parenteral administration, such as intravenous, intratumoral and intraperitoneal administration. The viruses can be any known to those of skill in the art, and can encode additional therapeutic products. The viruses can be combined with other therapies suitable for the tumors, such as cis-platin for ovarian tumors, or gemcitabine for pancreatic tumors. As shown herein, TREX1 expression is enhanced in reproductive tumors, such as cervical cancers and ovarian tumors, and head and neck tumors, and colorectal cancers. TREX1 also is upregulated in virally driven tumors, such as tumors and cancers driven by human papillomavirus (HPV) and other viruses, such as Epstein-Barr virus (EBV), hepatitis B virus (HBV), human herpes virus-8 (HHV-8, also known as Kaposi sarcoma-associated herpesvirus), Merkel cell polyomavirus (MCPyV), hepatitis C virus (HCV) human T-cell lymphotropic virus-1 (HTLV-1), and other transforming viruses. Exemplary oncolytic viruses are those discussed below.

Adenovirus

Adenoviruses (Ads) are non-enveloped ds-DNA viruses with a linear genome that Human Ads are classified into 57 serotypes (Ad1-Ad57), based on cross-susceptibility, and 7 subgroups (A-G), based on virulence and tissue tropism. Adenovirus serotype 5 (Ad5) is the most commonly used adenovirus for oncolytic virotherapy. Infections in humans are mild and result in cold-like symptoms (Yokoda et al. (2018) *Biomedicines* 6, 33) and systemic administration results in liver tropism and can lead to hepatotoxicity (Yamamoto et al. (2017) *Cancer Sci.* 108:831-837), but Ads are considered safe for therapeutic purposes. Ads enter cells by attaching to the coxsackievirus and adenovirus receptor (CAR), followed by interaction between the $\alpha v \beta 3$ and $\alpha v \beta 5$ integrins on the cell surface and the Arg-Gly-Asp tripeptide motif (RGD) at the adenoviral penton base (Jiang et al. (2015) *Curr. Opin. Virol.* 13:33-39). CAR is expressed on the surfaces of most normal cells, but expression is highly variable across cancer cell types. On the other hand, RGD-related integrins are highly expressed by cancer cells, but are expressed at much lower levels in normal cells (Jiang et al. (2015)). As a result, Ads are often targeted to cancer cells via the RGD motif.

Ads are attractive as oncolytic viruses due to their high transduction efficiency in transformed cells, their lack of integration into the host genome/lack of insertional mutagenesis, their genomic stability, the ability to insert large therapeutic genes into their genomes, and their capacity for tumor selectivity via genetic manipulation, such as the substitution of viral promoters with cancer tissue-selective promoters (Yokoda et al. (2018) *Biomedicines* 6, 33; Choi et al. (2015) *J. Control. Release* 10(219):181-191).

Examples of oncolytic Ads with tumor-specific promoters include CV706 for prostate cancer treatment, with the adenovirus early region 1A (E1A) gene under control of the prostate specific antigen promoter, and OBP-301, which utilizes the telomerase reverse transcriptase (TERT) promoter for regulation of E1A gene expression (Yamamoto et al. (2017) *Cancer Sci.* 108:831-837). Another method for inducing tumor selectivity is the introduction of mutations in the E1 region of the Ad genome, where the missing genes are functionally complemented by genetic mutations commonly found in tumor cells, such as abnormalities in the retinoblastoma (Rb) pathway or p53 mutations (Yamamoto et al. (2017) *Cancer Sci.* 108:831-837). For example, the oncolytic Ads ONYX-015 and H101 have deletions in the E1B55K gene, which inactivates p53. These mutants cannot block the normal apoptotic defense pathway, resulting in tumor selectivity via the infection of neoplastic cells with defective p53 tumor suppressor pathways (Yamamoto et al. (2017) *Cancer Sci.* 108:831-837; Uusi-Kerttula et al. (2015) *Viruses* 7:6009-6042). E1AΔ24 is an oncolytic Ad that contains a 24-bp mutation in the E1A gene, disrupting the Rb-binding domain and promoting viral replication in cancer cells with Rb pathway mutations. ICOVIR-5 is an oncolytic Ad that combines E1A transcriptional control by the E2F promoter, the Δ24 mutation of E1A and an RGD-4C insertion into the adenoviral fiber (Yamamoto et al. (2017) *Cancer Sci.* 108:831-837; Uusi-Kerttula et al. (2015)). Delta-24-RGD, or DNX-2401, is an oncolytic Ad in which the Δ24 backbone is modified by insertion of the RGD motif, that demonstrated enhanced oncolytic effects in vitro and in vivo (Jiang et al. (2015)).

An alternative strategy for improving tumor selectivity involves overcoming the physical barrier in solid tumors by targeting the extracellular matrix (ECM). For example, an oncolytic Ad that expresses hyaluronidase, such as VCN-01, to facilitate delivery of encoded products and virus throughout a tumor Ads also have been engineered to express relaxin to disrupt the ECM (Yamamoto et al. (2017) *Cancer Sci.* 108:831-837; Shaw and Suzuki (2015) *Curr. Opin. Virol.* 21:9-15). Ads expressing suicide genes, such as cytosine deaminase (CD) and HSV-1 thymidine kinase (TK) have shown enhanced antitumor efficacy in vivo, as have Ads expressing immunostimulatory cytokines, such as ONCOS-102, which expresses GM-CSF (Yamamoto et al. (2017) *Cancer Sci.* 108:831-837; Shaw and Suzuki (2015) *Curr. Opin. Virol.* 21:9-15). A Δ24-based oncolytic Ad expressing an anti-CTLA4 antibody has shown promise in preclinical studies (Jiang et al. (2015)).

The adenovirus H101 (available under the trademark Oncorine®) was the first oncolytic Ad approved for clinical use in China in combination with chemotherapy, for treating patients with advanced nasopharyngeal cancer in 2005. Clinical trials have demonstrated the use of oncolytic adenoviruses for the treatment of a wide variety of cancers. For example, there have been and are clinical trials of oncolytic Ad5 encoding IL-12 in patients with metastatic pancreatic cancer (NCT03281382); an immunostimulatory Ad5 (LOAd703) expressing TMX-CD40L and 41BBL in patients with pancreatic adenocarcinoma, ovarian cancer, biliary carcinoma and colorectal cancer (NCT03225989); LOAd703 in combination with gemcitabine and nab-paclitaxel in patients with pancreatic cancer (NCT02705196); an oncolytic adenovirus encoding human PH20 hyaluronidase (VCN-01) in combination with gemcitabine and Abraxane® in patients with advanced solid tumors, including pancreatic adenocarcinoma (NCT02045602; NCT02045589); Telomelysin® (OBP-301), an oncolytic Ad with tumor selectivity, containing the human telomerase reverse transcriptase (hTERT) promoter, in patients with hepatocellular carcinoma (NCT02293850); an E1B gene deleted Ad5 in combination with transarterial chemoembolization (TACE) in patients with hepatocellular carcinoma (NCT01869088); CG0070, an oncolytic Ad that expresses GM-CSF and contains the cancer-specific E2F-1 promoter to drive expression of E1A, in patients with bladder cancer (NCT02365818; NCT01438112); Enadenotucirev (Colo-Ad1), an Ad11p/Ad3 chimeric Group B oncolytic virus, in patients with colon cancer, non-small cell lung cancer, bladder cancer and renal cell carcinoma (NCT02053220); and DNX-2401 (Ad5 E1AΔ24RGD) in combination with Temozolomide (NCT01956734), or in combination with IFNγ (NCT02197169) in patients with glioblastoma.

Herpes Simplex Virus

Herpes simplex virus (HSV) belongs to the family Herpesviridae and has a large linear double-stranded DNA genome, including many genes that are nonessential for viral replication, making it an ideal candidate for genetic manipulation. Other advantages include its ability to infect a broad range of cell types, its sensitivity to antivirals such as acyclovir and ganciclovir, and its lack of insertional mutagenesis (Sokolowski et al. (2015) *Oncolytic Virotherapy* 4:207-219; Yin et al. (2017) *Front. Oncol.* 7:136). There are two types of HSV, HSV type I (HSV-1) and type II (HSV-2), with the majority of oncolytic HSVs being derived from HSV-1. In humans, HSV-1 causes fever blister disease and infects epithelial cells, neurons, and immune cells by binding to nectins, glycoproteins, and the herpesvirus entry mediator (HVEM) on the cell surface (Kohlhapp and Kaufman (2016) *Clin. Cancer Res.* 22(5):1048-1054).

Many different oncolytic HSV-1 viruses have been generated to date. For example, HSV-1 has been engineered to express the anti-HER-2 antibody trastuzumab, targeting tumors that overexpress HER-2, such as breast and ovarian cancers, gastric carcinomas and glioblastomas. The gene encoding trastuzumab was inserted into two regions within the HSV-1 gD glycoprotein gene, generating two oncolytic HSVs, R-LM113 and R-LM249. R-LM113 and R-LM249 demonstrated preclinical activity against human breast and ovarian cancers, and against a murine model of HER2+ glioblastoma. Another oncolytic HSV-1, dlsptk HSV-1, contains a deletion in the unique long 23 (UL23) gene, which encodes the viral homologue of thymidine kinase (TK), while the hrR3 HSV-1 mutant contains a LacZ insertion mutation of the large subunit of ribonucleotide reductase (RR), also known as ICP6, encoded by the gene UL39. As a result, dlsptk and hrR3 HSV-1 mutants can only replicate in cancer cells that overexpress TK and RR, respectively (Sokolowski et al. (2015) *Oncolytic Virotherapy* 4:207-219).

HF10 is a spontaneously mutated oncolytic HSV-1 that lacks the genes encoding UL43, UL49.5, UL55, UL56 and latency-associated transcripts, and overexpresses UL53 and UL54. HF10 has shown promising results in preclinical studies and demonstrated high tumor selectivity, high viral replication, potent antitumor activity and a favorable safety profile (Eissa et al. (2017) *Front. Oncol.* 7:149). Clinical trials investigating HF10 include: a phase I study in patients with refractory head and neck cancer, squamous cell carcinoma of the skin, carcinoma of the breast and malignant melanoma (NCT01017185) and a Phase I study of HF10 in combination with chemotherapy (gemcitabine, Nab-paclitaxel, TS-1) in patients with unresectable pancreatic cancer (NCT03252808). HF10 also has been combined with the anti-CTLA-4 antibody ipilimumab, resulting in improved therapeutic efficacy in patients with stage IIIb, IIIc or IV unresectable or metastatic melanoma (NCT03153085). A phase II clinical study is investigating the combination of HF10 with the anti-PD-1 antibody Nivolumab in patients with resectable stage IIIb, IIIc and IV melanoma (NCT03259425) and in combination with ipilimumab in patients with unresectable or metastatic melanoma (NCT02272855). Paclitaxel and HF10 combination therapy resulted in superior survival rates in peritoneal colorectal cancer models compared with either treatment alone, while combination treatment with HF10 and erlotinib resulted in improved activity against pancreatic xenografts in vitro and in vivo than either HF10 or erlotinib alone (Eissa et al. (2017) Front. Oncol. 7:149).

Talimogene laherparepvec (Imlygic®, T-VEC), previously known as OncoVEXGM-CSF, is an FDA-approved oncolytic herpes simplex virus for the treatment of advanced melanoma, that was generated from the JS1 strain of HSV-1 and genetically engineered to express granulocyte macrophage stimulating factor (GM-CSF; Aref et al. (2016) Viruses 8:294). In T-VEC, GM-CSF expression enhances the antitumor cytotoxic immune response, while deletion of both copies of the infected cell protein 34.5 (ICP34.5) gene suppresses replication in normal tissues, and deletion of the ICP47 gene increases expression of MHC class I molecules, allowing for antigen presentation on infected cells (Eissa et al. (2017)). T-VEC exhibits tumor selectivity by binding to nectins on the surface of cancer cells and preferentially replicates in tumor cells by exploiting disrupted oncogenic and antiviral signaling pathways, particularly the protein kinase R (PKR) and type I IFN pathways. In normal cells, PKR is activated by viral infection, which then phosphorylates the eukaryotic initiation factor-2A protein (eIF-2A), inactivating it and in turn, inhibiting cellular protein synthesis, blocking cell proliferation and preventing viral replication. Wild-type HSV escapes the antiviral response due to expression of the ICP34.5 protein, which activates a phosphatase that dephosphorylates eIF-2A, restoring protein synthesis in the infected cells. Thus, deletion of ICP34.5 precludes viral replication of T-VEC in normal cells. The PKR-eIF-2A pathway in cancer cells, however, is disrupted, permitting continuous cell growth and uninhibited viral replication (Kohlhapp and Kaufman (2016) Clin. Cancer Res. 22(5):1048-1054; Yin et al. (2017) Front. Oncol. 7:136). The expression of GM-CSF improves the immunogenicity of T-VEC by causing dendritic cell accumulation, promoting antigen-presentation and priming T-cell responses (Kohlhapp and Kaufman (2016) Clin. Cancer Res. 22(5):1048-1054).

T-VEC has shown preferential replication in a variety of different cancer cell lines, including breast cancer, colorectal adenocarcinoma, melanoma, prostate cancer, and glioblastoma. Clinical trials include, for example, those investigating T-VEC in pancreatic cancer (NCT03086642, NCT00402025), recurrent breast cancer (NCT02658812), advanced non-CNS tumors in children (NCT02756845), non-melanoma skin cancer (NCT03458117), non-muscle invasive bladder transitional cell carcinoma (NCT03430687), and malignant melanoma (NCT03064763), as well as T-VEC in combination with atezolizumab in patients with metastatic triple negative breast cancer and metastatic colorectal cancer with liver metastases (NCT03256344), in combination with paclitaxel in patients with triple negative breast cancer (NCT02779855), in combination with nivolumab in patients with refractory lymphomas or advanced/refractory non-melanoma skin cancers (NCT02978625), in combination with cisplatin and radiotherapy in patients with advanced head and neck cancer (NCT01161498), and in combination with pembrolizumab in patients with liver tumors (NCT02509507), carcinoma of the head and neck (NCT02626000), sarcoma (NCT03069378) and melanoma (NCT02965716, NCT02263508).

In addition to GM-CSF, numerous other immune stimulating genes have been inserted into oncolytic HSVs, including those encoding IL-12, IL-15, IL-18, TNFα, IFNα/β and fms-like tyrosine kinase 3 ligand, resulting in increased therapeutic efficacy (Sokolowski et al. (2015); Yin et al. (2017)).

Another oncolytic HSV-1, R3616 contains deletions in both copies of the RL1 (also known as γ134.5) gene, which encodes ICP34.5, targeting cancer cells with disrupted PKR pathways. NV1020 (or R7020) is an HSV-1 mutant that contains deletions in the UL55, UL56, ICP4, RL1 and RL2 genes, resulting in reduced neurovirulence and cancer selectivity. NV1020 displayed promising results in murine models of head and neck squamous cell carcinoma, epidermoid carcinoma and prostrate adenocarcinoma (Sokolowski et al. (2015)). Additionally, clinical trials have investigated the safety and efficacy of NV1020 in colorectal cancer metastatic to the liver (NCT00149396 and NCT00012155).

G207 (or MGH-1) is another HSV-1 mutant with an RL1 (γ134.5) deletion and a LacZ inactivating insertion in the UL39 neurovirulence gene. Clinical studies utilizing G207 include the investigation of G207 administration alone or with a single radiation dose in children with progressive or recurrent supratentorial brain tumors (NCT02457845), the investigation of the safety and efficacy of G207 in patients with recurrent brain cancer (glioma, astrocytoma, glioblastoma) (NCT00028158), and the investigation of the effects of G207 administration followed by radiation therapy in patients with malignant glioma (NCT00157703).

G207 was used to generate G47Δ, which contains a further deletion in the gene encoding ICP47. Other HSV-1 derived oncolytic viruses include HSV1716, which contains deletions in RL1, but has an intact UL39 gene and replicates selectively in actively dividing cells, and the KM100 mutant, which has insertions in the UL48 and RL2 genes, resulting in a loss of expression of immediate early viral genes and cancer cell selectivity (Sokolowski et al. (2015); Yin et al. (2017) Front. Oncol. 7:136).

Oncolytic viruses also have been derived from HSV-2. For example, FusOn-H2 is an HSV-2 oncolytic virus with a deletion of the N-terminal region of the ICP10 gene that encodes a serine/threonine protein kinase (PK) domain. This PK is responsible for phosphorylating GTPase-activating protein Ras-FAP, which activates the Ras/MEK/MAPK mitogenic pathway and induces and stabilizes c-Fos, which is required for efficient HSV-2 replication. Normal cells usually have an inactivated Ras signaling pathway. Thus, FusOn-H2 exhibits tumor selectivity by replicating only in tumor cells with activated Ras signaling pathways (Fu et al. (2006) Clin. Cancer Res. 12(10):3152-3157). FusOn-H2 has demonstrated activity against pancreatic cancer xenografts (Fu et al. (2006) Clin. Cancer Res. 12(10):3152-3157), against Lewis lung carcinoma xenografts in combination with cyclophosphamide, and against syngeneic murine mammary tumors and neuroblastoma (Li et al. (2007) Cancer Res. 67:7850-7855).

Poxvirus—Vaccinia Virus

Vaccinia viruses are exemplary of poxviruses. Examples of vaccinia viruses include, but are not limited to, Lister (also known as Elstree), New York City Board of Health (NYCBH), Dairen, Ikeda, LC16M8, Western Reserve (WR), Copenhagen (Cop), Tashkent, Tian Tan, Wyeth, Dryvax, IHD-J, IHD-W, Brighton, Ankara, Modified Vaccinia Ankara (MVA), Dairen I, LIPV, LC16M0, LIVP, WR 65-16, EM63, Bern, Paris, CVA382, NYVAC, ACAM2000 and Connaught strains. Vaccinia viruses are oncolytic viruses that possess a variety of features that make them particularly suitable for use in wound and cancer gene therapy. For example, vaccinia is a cytoplasmic virus, thus, it does not insert its genome into the host genome during its life cycle. Unlike many other viruses that require the host's transcription machinery, vaccinia virus can support its own gene expression in the host cell cytoplasm using enzymes encoded in the viral genome. Vaccinia viruses also have a broad host and cell type range. In particular, vaccinia viruses can accumulate in immunoprivileged cells or immunoprivileged tissues, including tumors and/or metastases, and also including wounded tissues and cells. Yet, unlike other oncolytic viruses, vaccinia virus can typically be cleared from the subject to whom the viruses are administered by activity of the subject's immune system, and hence are less toxic than other viruses such as adenoviruses. Thus, while the viruses can typically be cleared from the subject to whom the viruses are administered by activity of the subject's immune system, viruses can nevertheless accumulate, survive and proliferate in immunoprivileged cells and tissues such as tumors, because such immunoprivileged areas are isolated from the host's immune system.

Vaccinia viruses also can be easily modified by insertion of heterologous genes. This can result in the attenuation of the virus and/or permit delivery of therapeutic proteins. For example, the vaccinia virus genome has a large carrying capacity for foreign genes, where up to 25 kb of exogenous DNA fragments (approximately 12% of the vaccinia genome size) can be inserted. The genomes of several of the vaccinia strains have been completely sequenced, and many essential and nonessential genes identified. Due to high sequence homology among different strains, genomic information from one vaccinia strain can be used for designing and generating modified viruses in other strains. Finally, the techniques for production of modified vaccinia strains by genetic engineering are well established (Moss (1993) *Curr. Opin. Genet. Dev.* 3:86-90; Broder and Earl (1999) *Mol. Biotechnol.* 13:223-245; Timiryasova et al. (2001) *Biotechniques* 31:534-540).

Various vaccinia viruses have been demonstrated to exhibit antitumor activities. In one study, for example, nude mice bearing non-metastatic colon adenocarcinoma cells were systemically injected with a WR strain of vaccinia virus modified by having a vaccinia growth factor deletion and an enhanced green fluorescence protein inserted into the thymidine kinase locus. The virus was observed to have antitumor effects, including one complete response, despite a lack of exogenous therapeutic genes in the modified virus (McCart et al. (2001) *Cancer Res.* 1:8751-8757). In another study, vaccinia melanoma oncolysate (VMO) was injected into sites near melanoma positive lymph nodes in a Phase III clinical trial of melanoma patients. As a control, a New York City Board of Health strain vaccinia virus (VV) was administered to melanoma patients. The melanoma patients treated with VMO had a survival rate better than that for untreated patients, but similar to patients treated with the VV control (Kim et al. (2001) *Surgical Oncol.* 10:53-59).

LIVP strains of vaccinia virus also have been used for the diagnosis and therapy of tumors, and for the treatment of wounded and inflamed tissues and cells (see e.g., Lin et al. (2007) *Surgery* 142:976-983; Lin et al. (2008) *J. Clin. Endocrinol. Metab.* 93:4403-7; Kelly et al. (2008) *Hum. Gene Ther.* 19:774-782; Yu et al. (2009) *Mol. Cancer Ther.* 8:141-151; Yu et al. (2009) *Mol. Cancer* 8:45; U.S. Pat. Nos. 7,588,767; 8,052,968; and U.S. Publication No. 2004/0234455). For example, when intravenously administered, LIVP strains have been demonstrated to accumulate in internal tumors at various loci in vivo, and have been demonstrated to effectively treat human tumors of various tissue origin, including, but not limited to, breast tumors, thyroid tumors, pancreatic tumors, metastatic tumors of pleural mesothelioma, squamous cell carcinoma, lung carcinoma and ovarian tumors. LIVP strains of vaccinia, including attenuated forms thereof, exhibit less toxicity than WR strains of vaccinia virus, and result in increased and longer survival of treated tumor-bearing animal models (see, e.g., U.S. Publication No. 2011/0293527).

Vaccinia is a cytoplasmic virus, thus, it does not insert its genome into the host genome during its life cycle. Vaccinia virus has a linear, double-stranded DNA genome of approximately 180,000 base pairs in length that is made up of a single continuous polynucleotide chain (Baroudy et al. (1982) *Cell* 28:315-324). The structure is due to the presence of 10,000 base pair inverted terminal repeats (ITRs). The ITRs are involved in genome replication. Genome replication involves self-priming, leading to the formation of high molecular weight concatemers (isolated from infected cells), which subsequently are cleaved and repaired to make virus genomes (see, e.g., Traktman, P., Chapter 27, Poxvirus DNA Replication, pp. 775-798, in DNA Replication in Eukaryotic Cells, Cold Spring Harbor Laboratory Press (1996)). The genome contains approximately 250 genes. In general, the non-segmented, non-infectious genome is arranged such that centrally located genes are essential for virus replication (and are thus conserved), while genes near the two termini effect more peripheral functions such as host range and virulence. Vaccinia viruses practice differential gene expression by utilizing open reading frames (ORFs) arranged in sets that, as a general principle, do not overlap.

Vaccinia virus possesses a variety of features for use in cancer gene therapy and vaccination including broad host and cell type range, and low toxicity. For example, while most oncolytic viruses are natural pathogens, vaccinia virus has a unique history in its widespread application as a smallpox vaccine that has resulted in an established track record of safety in humans. Toxicities related to vaccinia administration occur in less than 0.1% of cases, and can be effectively addressed with immunoglobulin administration. In addition, vaccinia virus possesses a large carrying capacity for foreign genes (up to 25 kb of exogenous DNA fragments, approximately 12% of the vaccinia genome size, can be inserted into the vaccinia genome) and high sequence homology among different strains for designing and generating modified viruses in other strains. Techniques for production of modified vaccinia strains by genetic engineering are well established (Moss (1993) *Curr. Opin. Genet. Dev.* 3: 86-90; Broder and Earl (1999) *Mol. Biotechnol.* 13: 223-245; Timiryasova et al. (2001) *Biotechniques* 31: 534-540). Vaccinia virus strains have been shown to specifically colonize solid tumors, while not infecting other organs (see, e.g., Zhang et al. (2007) *Cancer Res.* 67:10038-10046; Yu et al. (2004) *Nat. Biotech.* 22:313-320; Heo et al. (2011) *Mol. Ther.* 19:1170-1179; Liu et al. (2008) *Mol. Ther.* 16:1637-1642; Park et al. (2008) *Lancet Oncol.* 9:533-542).

Measles Virus

Measles virus (MV) is an enveloped, single-stranded RNA virus with a negative-sense genome that belongs to the family of Paramyxoviruses (Aref et al. (2016) *Viruses* 8:294; Hutzen et al. (2015) *Oncolytic Virotherapy* 4:109-118). Its non-segmented genome is stable, with a low risk of mutating and reverting to its pathogenic form, and due to its replication in the cytoplasm, poses no risk of insertional DNA mutagenesis in infected cells (Aref et al. (2016); Hutzen et al. (2015)). MV was first isolated from a patient called Edmonston in 1954, and developed into a live vaccine with an excellent safety profile, that has successfully protected over a billion individuals worldwide for 50 years, by attenuation following multiple in vitro passages (Aref et al. (2016) *Viruses* 8:294; Hutzen et al. (2015) *Oncolytic Virotherapy* 4:109-118). Derivatives of this strain, denoted as MV-Edm, are the most commonly utilized MV strains in oncolytic therapy studies. The Schwarz/Moraten measles vaccine strain is more attenuated and immunogenic than Edm derivatives, which makes them safer and more immunomodulatory (Veinalde et al. (2017) *Oncoimmunology* 6(4): e1285992). The oncolytic effects of wild-type MV were documented in the 1970s, with reports of improvements in patients with acute lymphoblastic leukemia, Burkitt's lymphoma and Hodgkin's lymphoma (Aref et al. (2016)).

MV uses three main receptors for entry into target cells: CD46, nectin-4 and signaling lymphocyte activation molecule (SLAM) (Aref et al. (2016); Hutzen et al. (2015)). Whereas SLAM, which is expressed on activated B and T cells, immature thymocytes, monocytes and dendritic cells, is the main receptor for wild-type strains, attenuated and tumor-selective MV-Edm strains primarily target the CD46 receptor, a regulator of complement activation that is overexpressed in many tumor cells (Aref et al. (2016); Hutzen et al. (2015); Jacobson et al. (2017) *Oncotarget* 8(38):63096-63109; Msaouel et al. (2013) *Expert Opin. Biol. Ther.* 13(4)). Nectin-4, which is predominantly expressed in the respiratory epithelium, is utilized by both wildtype and attenuated MV strains (Aref et al. (2016); Msaouel et al. (2013) *Expert Opin. Biol. Ther.* 13(4)). As with other oncolytic viruses, defects in the IFN antiviral response of tumor cells also facilitates the tumor-selectivity of MV (Aref et al. (2016); Jacobson et al. (2017) *Oncotarget* 8(38):63096-63109). Clinical trials investigating the MV in the treatment of several cancers, including multiple myeloma (NCT02192775, NCT00450814), head and neck cancer (NCT01846091), mesothelioma (NCT01503177), and ovarian cancer (NCT00408590, NCT02364713) have been conducted.

MV has been genetically engineered to express immune-stimulating and immunomodulatory genes, including those encoding IL-13, INF-beta, GM-CSF and *Heliobacter pylori* neutrophil-activating protein (NAP), for example (Aref et al. (2016), Hutzen et al. (2015); Msaouel et al. (2013) *Expert Opin. Biol. Ther.* 13(4)). Combination therapies utilizing oncolytic MV with anti-CTLA4 and anti-PD-L1 antibodies have been effective in melanoma mouse models (Aref et al. (2016); Hutzen et al. (2015)).

MV-CEA, which is genetically engineered to express the tumor marker carcinoembryonic antigen (CEA), results in the release of CEA into the blood stream of patients following infection of cancer cells, allowing the detection of CEA levels and thus, the tracking of in vivo viral infection (Aref et al. (2016); Hutzen et al. (2015)). The therapeutic use MV-CEA has been demonstrated pre-clinically, and is in Phase I clinical trials for the treatment of ovarian cancer (NCT00408590).

Reovirus

Respiratory Enteric Orphan virus, commonly known as Reovirus, is a non-enveloped double-stranded RNA virus of the Reoviridae family that is nonpathogenic to humans. Wild-type reovirus is ubiquitous throughout the environment, resulting in a 70-100% seropositivity in the general population (Gong et al. (2016) *World J. Methodol.* 6(1):25-42). There are three serotypes of reovirus, which include type 1 Lang, type 2 Jones, type 3 Abney and type 3 Dearing (T3D). T3D is the most commonly used naturally occurring oncolytic reovirus serotype in pre-clinical and clinical studies.

Oncolytic reovirus is tumor-selective due to activated Ras signaling that is characteristic of cancer cells (Gong et al. (2016)); Zhao et al. (2016) *Mol. Cancer Ther.* 15(5):767-773). Activation of the Ras signaling pathway disrupts the cell's antiviral responses, by inhibiting the phosphorylation of dsRNA-dependent protein kinase (PKR), a protein that is normally responsible for preventing viral protein synthesis (Zhao et al. (2016)). Ras activation also enhances viral un-coating and disassembly, results in enhanced viral progeny generation and infectivity, and accelerates the release of progeny through enhanced apoptosis (Zhao et al. (2016)). It is estimated that approximately 30% of all human tumors display aberrant Ras signaling (Zhao et al. (2016)). For example, the majority of malignant gliomas possess activated Ras signaling pathways, with reovirus demonstrating antitumor activity in 83% of malignant glioma cells in vitro, as well as in vivo in human malignant glioma models, and in 100% of glioma specimens ex vivo (Gong et al. (2016) *World J. Methodol.* 6(1):25-42). Additionally, pancreatic adenocarcinomas display a very high incidence of Ras mutations (approximately 90%), and reovirus has shown potent cytotoxicity in 100% of pancreatic cell lines tested in vitro and induced regression in 100% of subcutaneous tumor mouse models in vivo (Gong et al. (2016)).

Reovirus has demonstrated broad anticancer activity preclinically across a spectrum of malignancies including colon, breast, ovarian, lung, skin (melanoma), neurological, hematological, prostate, bladder, and head and neck cancer (Gong et al. (2016)). Reovirus therapy has been tested in combination with radiotherapy, chemotherapy, immunotherapy, and surgery. The combination of reovirus and radiation therapy has proven beneficial in the treatment of head and neck, colorectal and breast cancer cell lines in vitro, as well as colorectal cancer and melanoma models in vivo (Gong et al. (2016)). The combination of reovirus and gemcitabine, as well as reovirus, paclitaxel and cisplatin, have proven successful in mouse tumor models (Zhao et al. (2016)). Preclinical studies in B16 melanoma mouse models have shown that the combination of oncolytic reovirus and anti-PD-1 therapy demonstrated improved anticancer efficacy in comparison to reovirus alone (Gong et al. (2016); Zhao et al. (2016); Kemp et al. (2015) *Viruses* 8, 4).

The promising pre-clinical results demonstrated by reovirus have led to many clinical trials. Reolysin® reovirus, developed by the Canadian company Oncolytics Biotech Inc., is the only therapeutic wild-type reovirus in clinical development, and has demonstrated anticancer activity in many malignancies alone, and in combination with other therapeutics. For example, a phase I clinical study of the Reolysin® reovirus in the treatment of recurrent malignant gliomas (NCT00528684) found that the reovirus was well tolerated, while a phase I/II trial found that Reolysin® reovirus kills tumor cells without damaging normal cells in patients with ovarian epithelial cancer, primary peritoneal cancer, or fallopian tube cancer that did not respond to platinum chemotherapy (NCT00602277). A phase II clinical trial of Reolysin® reovirus demonstrated safety and efficacy in the treatment of patients with bone and soft tissue sarcomas metastatic to the lung (NCT00503295). A phase I clinical trial of Reolysin® reovirus in combination with FOLFIRI and bevacizumab in patients with metastatic colorectal cancer (NCT01274624) has been conducted. A phase II clinical trial of Reolysin® reovirus in combination with the chemotherapeutic gemcitabine was carried out in patients with advanced pancreatic adenocarcinoma (NCT00998322), a phase II clinical study investigated the therapeutic potential of Reolysin® in combination with docetaxel in metastatic castration resistant prostate cancer (NCT01619813), and a phase II clinical trial investigated the combination of Reolysin® reovirus with paclitaxel in patients with advanced/metastatic breast cancer (NCT01656538). A phase III clinical trial investigated the efficacy of Reolysin® in combination with paclitaxel and carboplatin in platinum-refractory head and neck cancers (NCT01166542), while phase II clinical studies employing this combination therapy were carried out in patients with non-small cell lung cancer (NCT00861627) and metastatic melanoma (NCT00984464). A phase I clinical trial of Reolysin® in combination with carfilzomib and dexamethasone in patients with relapsed or refractory multiple myeloma is ongoing (NCT02101944).

Vesicular Stomatitis Virus (VSV)

Vesicular stomatitis virus (VSV) is a member of the Vesiculovirus genus within the Rhabdoviridae family. Its genome, which consists of a single-stranded RNA with negative-sense polarity, consists of 11,161 nucleotides and encodes for five genes: nucleocapsid protein (N), phosphoprotein (P), matrix protein (M), glycoprotein (G), and large polymerase protein (Bishnoi et al. (2018) *Viruses* 10(2), 90). VSV is transmitted by insect vectors and disease is limited to its natural hosts, including horses, cattle and pigs, with mild and asymptomatic infection in humans (Bishnoi et al. (2018) *Viruses* 10(2), 90). VSV is a potent and rapid inducer of apoptosis in infected cells, and has been shown to sensitize chemotherapy-resistant tumor cells. VSV has been shown to infect tumor vasculature, resulting in a loss of blood flow to the tumor, blood-coagulation and lysis of neovasculature. This virus also is capable of replication and induction of cytopathic effects and cell lysis in hypoxic tissues. In addition, WT VSV grows to high titers in a variety of tissue culture cells lines, facilitating large-scale virus production, it has a small and easy to manipulate genome, and it replicates in the cytoplasm without risk of host cell transformation (Bishnoi et al. (2018); Felt and Grdzelishvili (2017) *Journal of General Virology* 98:2895-2911). These factors, together with the fact that it is not pathogenic to humans and there is generally no pre-existing human immunity to VSV, make it a good candidate for viral oncotherapy.

Although VSV can attach to ubiquitously expressed cell-surface molecules, making it "pantropic," it WT VSV is sensitive to type I IFN responses and thus displays oncoselectivity based on the defective or inhibited type I IFN signaling of tumors (Felt and Grdzelishvili (2017)). Due to its infectivity of normal cells, VSV can cause neuropathogenicity, but can be attenuated by modifying its matrix protein and/or glycoprotein. For example, the matrix protein can be deleted or the methionine residue at position 51 of the matrix protein can be deleted or substituted with arginine (Bishnoi et al. (2018); Felt and Grdzelishvili (2017)). Another approach replaces the glycoprotein of VSV with that of lymphocytic choriomeningitis virus (LCMV) (rVSV-GP) (Bishnoi et al. (2018); Felt and Grdzelishvili (2017)). VSV also can be genetically modified to include suicide genes, such as herpes virus thymidine kinase (TK), or to express immune-stimulatory cytokines such as IL-4, IL-12, IFNβ, or costimulatory agents such as granulocyte-macrophage-colony-stimulating factor 1 (GM-CSF1), to enhance oncolytic activity (Bishnoi et al. (2018)). VSV-IFNβ-sodium iodide symporter (VSV-IFNβ-NIS), which encodes NIS and IFNβ, is being tested in the USA in several phase I clinical trials (see details at ClinicalTrials.gov for trials NCT02923466, NCT03120624 and NCT03017820).

Vesicular stomatitis virus (VSV) is an effective oncolytic therapeutic when administered intravenously (IV) in a variety of murine cancer models. In one study, VSV-GP was successful in the intratumoral treatment of subcutaneously engrafted G62 human glioblastoma cells, as well as the intravenous treatment of orthotopic U87 human glioma cells, in immune-deficient mouse models. Intratumoral injection of VSV-GP also was effective against intracranial CT2A murine glioma cells (Muik et al. (2014) *Cancer Res.* 74(13):3567-3578). It was found that VSV-GP did not elicit a detectable neutralizing antibody response, and that this genetically modified oncolytic virus was insensitive to human complement, remaining stable over the length of the experiment (Muik et al. (2014)). In another example, intratumoral administration of VSV-GP was found to effectively infect and kill human Δ375 malignant melanoma cells transplanted in a mouse model, as well as the murine B16 melanoma cell line (Kimpel et al. (2018) *Viruses* 10, 108). Intravenous injection of the oncolytic virus was not successful, and even in the intratumorally-administered groups, the tumors all eventually grew, due to type I IFN responses (Kimpel et al. (2018)). In another study, a subcutaneous xenograft mouse model with Δ2780 human ovarian cancer cells was treated with intratumoral injection of VSV-GP, and although tumor remission was initially observed with no neurotoxicity, remission was temporary and the tumors recurred. This was found to be due to type I IFN responses, with an observed reversal of the antiviral state by combining VSV-GP with the JAK1/2 inhibitor ruxolitinib. (Dold et al. (2016) *Molecular Therapy—Oncolytics* 3, 16021).

Newcastle Disease Virus

Newcastle Disease Virus (NDV) is an avian paramyxovirus with a single-stranded RNA genome of negative polarity that infects poultry and is generally non-pathogenic to humans, but can cause flu-like symptoms (Tayeb et al. (2015) *Oncolytic Virotherapy* 4:49-62; Cheng et al. (2016) *J. Virol.* 90:5343-5352). Due to its cytoplasmic replication, lack of host genome integration and recombination and high genomic stability, NDV and other paramyxoviruses provide safer and more attractive alternatives to other oncolytic viruses, such as retroviruses or some DNA viruses (Matveeva et al. (2015) *Molecular Therapy—Oncolytics* 2, 150017). NDV has been shown to demonstrate tumor selectivity, with 10,000 times greater replication in tumor cells than normal cells, resulting in oncolysis due to direct cytopathic effects and induction of immune responses (Tayeb et al. (2015); Lam et al. (2011) *Journal of Biomedicine and Biotechnology*, Article ID: 718710). Though the mechanism of NDV's tumor selectivity is not entirely clear, defective interferon production and responses to IFN signaling in tumor cells allow the virus to replicate and spread (Cheng et al. (2016); Ginting et al. (2017) *Oncolytic Virotherapy* 6:21-30). The high affinity of paramyxoviruses towards cancer cells can also be due to overexpression of viral receptors on cancer cell surfaces, including sialic acid (Cheng et al. (2016); Matveeva et al. (2015); Tayeb et al. (2015)).

Non-engineered NDV strains are classified as lentogenic (avirulent), mesogenic (intermediate), or velogenic (virulent), based on their pathogenicity in chickens, with velogenic and mesogenic strains being capable of replication in (and lysis of) multiple human cancer cell lines, but not lentogenic strains (Cheng et al. (2016); Matveeva et al. (2015)). NDV strains also are categorized as lytic or non-lytic, with only the lytic strains being able to produce viable and infectious progeny (Ginting et al. (2017); Matveeva et al. (2015)). On the other hand, the oncolytic effects of non-lytic strains stems mainly from their ability to stimulate immune responses that result in antitumor activity (Ginting et al. (2017) *Oncolytic Virotherapy* 6:21-30). Mesogenic lytic strains commonly utilized in oncotherapy include PV701 (MK107), MTH-68/H and 73-T, and lentogenic non-lytic strains commonly utilized include HUJ, Ulster and Hitchner-B1 (Tayeb et al. (2015); Lam et al. (2011); Freeman et al. (2006) *Mol. Ther.* 13(1):221-228).

The NDV strain PV701 displayed activity against colorectal cancer in a phase 1 trial (Laurie et al. (2006) *Clin. Cancer Res.* 12(8):2555-2562), and NDV strain 73-T demonstrated in vitro oncolytic activity against various human cancer cell lines, including fibrosarcoma, osteosarcoma, neuroblastoma and cervical carcinoma, as well as in vivo therapeutic effects in mice bearing human neuroblastomas, fibrosarcoma xenografts and several carcinoma xenografts, including colon, lung, breast and prostate cancer xenografts (Lam et al. (2011)). NDV strain MTH-68/H resulted in significant regression of tumor cell lines, including PC12, MCF7, HCT116, DU-145, HT-29, A431, HELA, and PC3 cells, and demonstrated favorable responses in patients with advanced cancers when administered by inhalation (Lam et al. (2011)). The non-lytic strain Ulster demonstrated cytotoxic effects against colon carcinoma, while the lytic strain Italien effectively killed human melanomas (Lam et al. (2011)). Lentogenic NDV strain HUJ demonstrated oncolytic activity against recurrent glioblastoma multiforme when administered intravenously to patients, while lentogenic strain LaSota prolonged survival in colorectal cancer patients (Lam et al. (2011); Freeman et al. (2006) *Mol. Ther.* 13(1):221-228) and was capable of infecting and killing non-small cell lung carcinoma (A549), glioblastoma (U87MG and T98G), mammary gland adenocarcinoma (MCF7 and MDA-MB-453) and hepatocellular carcinoma (Huh7) cell lines (Ginting et al. (2017) *Oncolytic Virotherapy* 6:21-30).

Genetically engineered NDV strains also have been evaluated for oncolytic therapy. For example, the influenza NS1 gene, an IFN antagonist, was introduced into the genome of NDV strain Hitchner-B1, resulting in an enhanced oncolytic effect in a variety of human tumor cell lines and a mouse model of B16 melanoma (Tayeb et al. (2015)). The antitumor/immunostimulatory effects of NDV have been augmented by introduction of IL-2 or GM-CSF genes into the viral genome (Lam et al. (2011)). Combination therapy, utilizing intratumoral NDV injection with systemic CTLA-4 antibody administration resulted in the efficient rejection of pre-established distant tumors (Matveeva et al. (2015)).

Parvovirus

H-1 parvovirus (H-1PV) is a small, non-enveloped single-stranded DNA virus belonging to the family Parvoviridae, whose natural host is the rat (Angelova et al. (2017) *Front. Oncol.* 7:93; Angelova et al. (2015) *Frontiers in Bioengineering and Biotechnology* 3:55). H-1PV is nonpathogenic to humans, and is attractive as an oncolytic virus due to its favorable safety profile, the absence of preexisting H-1PV immunity in humans and their lack of host cell genome integration (Angelova et al. (2015)). H-1PV has demonstrated broad oncosuppressive activity against solid tumors, including preclinical modes of breast, gastric, cervical, brain, pancreatic and colorectal cancer, as well as hematological malignancies, including lymphoma and leukemia (Angelova et al. (2017)). H-1PV stimulates anti-tumor responses via the increased presentation of tumor-associated antigens, maturation of dendritic cells and the release of pro-inflammatory cytokines (Moehler et al. (2014) *Frontiers in Oncology* 4:92). H-1PV also displays tumor selectivity, which is thought to be due to the availability of cellular replication and transcription factors, the overexpression of cellular proteins that interact with the NS1 parvoviral protein, and the activation of metabolic pathways involved in the functional regulation of NS1 in tumor cells, but not normal cells (Angelova et al. (2015) *Frontiers in Bioengineering and Biotechnology* 3:55). Due to the innocuous nature of H-1PV, the wild type strain is often utilized, negating the need for attenuation by genetic engineering (Angelova et al. (2015)).

Studies have shown that oncolytic H-1PV infection of human glioma cells results in efficient cell killing, and high-grade glioma stem cell models were also permissive to lytic H-1PV infection. Enhanced killing of glioma cells has been observed when the virus was applied shortly after tumor cell irradiation, indicating that this protocol can be useful in non-resectable recurrent glioblastoma (Angelova et al. (2017)). Intracerebral or systemic H-1PV injection led to regression of gliomas without toxic side effects in immunocompetent rats with orthotopic RG-2 tumors, as well as immunodeficient animals implanted with human U87 gliomas (Angelova et al. (2015)). Del H-1PV, a fitness variant with higher infectivity and spreading in human transformed cell lines, demonstrated oncolytic effects in vivo in pancreatic cancer and cervix carcinoma xenograft models (Geiss et al. (2017) *Viruses* 9, 301). H-1PV also demonstrated oncolytic activity against a panel of five human osteosarcoma cell lines (CAL 72, H-OS, MG-63, SaOS-2, U-2OS) (Geiss et al. (2017) *Viruses* 9, 301) and against human melanoma cells (SK29-Mel-1, SK29-Mel-1.22) (Moehler et al. (2014) *Frontiers in Oncology* 4:92). In another study, nude rats bearing cervical carcinoma xenografts demonstrated dose-dependent tumor growth arrest and regression following treatment with H-1PV (Angelova et al. (2015)). The intratumoral and intravenous administration of H-1PV also demonstrated significant growth suppression in human mammary carcinoma xenografts in immunocompromised mice (Angelova et al. (2015)). Intratumoral H-1PV injection in human gastric carcinoma or human Burkitt lymphoma-bearing mice resulted in tumor regression and growth suppression (Angelova et al. (2015)).

The first phase I/IIa clinical trial of an oncolytic H-1PV (ParvOryx01) in recurrent glioblastoma multiforme patients (clinical trial NCT01301430), demonstrated favorable progression-free survival, clinical safety and patient tolerability with intratumoral or intravenous injection (Angelova et al. (2017); Geiss et al. (2017) *Viruses* 9, 301; Geletneky et al. (2017) *Mol. Ther.* 25(12):2620-2634). This trial demonstrated the ability of H-1PV to cross the blood-brain barrier in a dose-dependent manner and to establish an immunogenic anti-tumor response, characterized by leukocytic infiltration, predominantly by CD8+ and CD4+T lymphocytes, and the detection in locally treated tumors of several markers of immune cell activation, including perforin, granzyme B, IFNγ, IL-2, CD25 and CD40L (Geletneky et al. (2017) *Mol. Ther.* 25(12):2620-2634).

H-1PV also has demonstrated efficient killing of highly aggressive pancreatic ductal adenocarcinoma (PDAC) cells in vitro, including those resistant to gemcitabine, and intratumoral injection of H-1PV resulted in tumor regression and prolonged animal survival in an orthotopic rat model of PDAC (Angelova et al. (2017); Angelova et al. (2015)). Similar results, including selective tumor targeting and absence of toxicity, were observed in an immunodeficient nude rat PDAC model (Angelova et al. (2015)). The combination of H-1PV and cytostatic (cisplatin, vincristine) or targeted (sunitinib) drugs results in the synergistic induction of apoptosis in human melanoma cells (Moehler et al. (2014)). The combination of H-1PV and valproic acid, an HDAC inhibitor, resulted in synergistic cytotoxicity towards cervical and pancreatic cells (Angelova et al. (2017)), while the therapeutic efficiency of gemcitabine was improved when combined with H-1PV in a two-step protocol (Angelova et al. (2015)). As with other viruses, H-1PV can be engineered to express anti-cancer molecules. For example, studies have shown that a parvovirus-H1-derived vector expressing Apoptin had a greater capacity to induce apoptosis than wild-type H-1PV (Geiss et al. (2017)).

Coxsackie Virus

Coxsackie virus (CV) belongs to the genus Enterovirus and the family Picornaviridae and has a positive-sense single-stranded RNA genome that does not integrate into the host cell genome. CVs are classified into groups A and B, based on their effects in mice, and can cause mild upper respiratory tract infections in humans (Bradley et al. (2014) *Oncolytic Virotheraphy* 3:47-55). Commonly investigated coxsackie viruses for oncolytic virotherapy include attenuated coxsackie virus B3 (CV-B3), CV-B4, CV-A9 and CV-A21 (Yla-Pelto et al. (2016) *Viruses* 8, 57). CV-A21 infects cells via the ICAM-1 (or CD54) and DAF (or CD55) receptors, which are expressed at much higher levels in tumor cells, including melanoma, breast, colon, endometrial, head and neck, pancreatic and lung cancers, as well as in multiple myeloma and malignant glioma. CV-A21 has shown promising preclinical anticancer activity in vitro against malignant myeloma, melanoma, prostate, lung, head and neck, and breast cancer cells lines, and in vivo in mice bearing human melanoma xenografts, and against primary breast cancer tumors as well as their metastases in mice (Yla-Pelto et al. (2016); Bradley et al. (2014)). A derivative of CV-A21, CV-A21-DAFv, also known as CAVATAK™, was generated from the wild-type Kuykendall strain by serial passage of CV-A21 on DAF-expressing, ICAM-1-negative rhabdomyosarcoma (RD) cells and was found to possess enhanced oncolytic properties in comparison to the parent strain. CAVATAK™ binds only to the DAF receptor, which can contribute to its enhanced tropism towards cancer cells (Yla-Pelto et al. (2016)).

CV-A21 also has been studied in combination with doxorubicin hydrochloride, exhibiting enhanced oncolytic efficiency compared to either treatment alone against human breast, colorectal and pancreatic cancer cell lines, as well as in a xenograft mouse model of human breast cancer (Yla-Pelto et al. (2016)). Since a significant portion of the population has already developed neutralizing antibodies against CV, CV-A21 therapy has been combined with immunosuppressants such as cyclophosphamide (Bradley et al. (2014)) and is a good candidate for delivery via vehicle cells.

Clinical trials have investigated the use of CAVATAK™ in patients with stage IIIc or IV malignant melanoma (NCT01636882; NCT00438009; NCT01227551), and CAVATAK™ alone or in combination with low dose mitomycin C in patients with non-muscle invasive bladder cancer (NCT02316171). Clinical trials also have studied the effects of intravenous administration of CV-A21 in the treatment of solid tumors including melanoma, breast and prostate cancer (NCT00636558). Ongoing clinical trials include the investigation of CAVATAK™ alone or in combination with pembrolizumab for treatment of patients with non-small cell lung cancer (NCT02824965, NCT02043665) and bladder cancer (NCT02043665); CAVATAK™ in combination with ipilimumab in patients with uveal melanoma and liver metastases (NCT03408587) and in patients with advanced melanoma (NCT02307149); and CAVATAK™ in combination with pembrolizumab in patients with advanced melanoma (NCT02565992).

Seneca Valley Virus

Seneca Valley Virus (SVV) is a member of the Senecavirus genus within the family Picornaviridae, that has a positive-sense single-stranded RNA genome and is selective for neuroendocrine cancers including neuroblastoma, rhabdomyosarcoma, medulloblastoma, Wilms tumor, glioblastoma and small-cell lung cancer (Miles et al. (2017) *J. Clin. Invest.* 127(8):2957-2967; Qian et al. (2017) *J. Virol.* 91(16): e00823-17; Burke, M. J. (2016) *Oncolytic Virotherapy* 5:81-89). Studies have identified the anthrax toxin receptor 1 (ANTXR1) as the receptor for SVV, which is frequently expressed on the surface of tumor cells in comparison to normal cells, but prior studies also have indicated that sialic acid can be a component of the SVV receptor in pediatric glioma models (Miles et al. (2017)). SVV isolate 001 (SVV-001) is a potent oncolytic virus that can target and penetrate solid tumors following intravenous administration and is attractive due to its lack of insertional mutagenesis as well as its selective tropism for cancer cells and its non-pathogenicity in humans and animals. Additionally, previous exposure in humans is rare, resulting in low rates of preexisting immunity (Burke, M. J. (2016) *Oncolytic Virotherapy* 5:81-89).

SVV-001 has shown promising in vitro activity against small-cell lung cancer, adrenal gland cortical carcinoma, neuroblastoma, rhabdomyosarcoma, and Ewing sarcoma cell lines, and in vivo activity in orthotopic xenograft mouse models of pediatric GBM, medulloblastoma, retinoblastoma, rhabdomyosarcoma and neuroblastoma (Burke (2016)). NTX-010, an oncolytic SVV-001 developed by Neotropix®, is for the treatment of pediatric patients with relapsed/refractory solid tumors alone or in combination with cyclophosphamide, but was limited in its therapeutic efficacy due to the development of neutralizing antibodies (Burke et al. (2015) *Pediatr. Blood Cancer* 62(5):743-750). Clinical trials include studies using SV-001 in patients with solid tumors with neuroendocrine features (NCT00314925), NTX-010/SVV-001 in combination with cyclophosphamide in patients with relapsed or refractory neuroblastoma, rhabdomyosarcoma, Wilms tumor, retinoblastoma, adrenocortical carcinoma or carcinoid tumors (NCT01048892), and NTX-010/SVV-001 in patients with small cell lung cancer after chemotherapy (NCT01017601).

E. BACTERIAL CANCER IMMUNOTHERAPY

1. Bacterial Therapies

The recognition that bacteria have anticancer activity goes back to the 1800s, when several physicians observed regression of tumors in patients infected with *Streptococcus pyogenes*. William Coley began the first study utilizing bacteria for the treatment of end stage cancers, and developed a vaccine composed of *S. pyogenes* and *Serratia marcescens*, which was successfully used to treat a variety of cancers, including sarcomas, carcinomas, lymphomas and melanomas. Since then, a number of bacteria, including species of *Clostridium, Mycobacterium, Bifidobacterium, Listeria*, such as *L. monocytogenes*, and *Escherichia* species, have been studied as sources of anti-cancer vaccines (see, e.g., Published International PCT Application No. WO 1999/013053; Published International PCT Application No. WO 2001/025399; Bermudes et al. (2002) *Curr. Opin. Drug Discov. Devel.* 5:194-199; Patyar et al. (2010) *Journal of Biomedical Science* 17:21; Pawelek et al. (2003) *Lancet Oncol.* 4:548-556).

Bacteria can infect animal and human cells, and some possess the innate ability to deliver DNA into the cytosol of cells, and these are candidate vectors for gene therapy. Bacteria also are suitable for therapy because they can be administered orally, they propagate readily in vitro and in vivo, and they can be stored and transported in a lyophilized state. Bacterial genetics are readily manipulated, and the complete genomes for many strains have been fully characterized (Felgner et al. (2016) *mbio* 7(5):e01220-16). As a result, bacteria have been used to deliver and express a wide variety of genes, including those that encode cytokines, angiogenesis inhibitors, toxins and prodrug-converting enzymes. *Salmonella*, for example, has been used to express immune-stimulating molecules like IL-18 (Loeffler et al. (2008) *Cancer Gene Ther.* 15(12):787-794), LIGHT (Loeffler et al. (2007) *PNAS* 104(31):12879-12883), and Fas ligand (Loeffler et al. (2008) *J. Natl. Cancer Inst.* 100:1113-1116) in tumors. Bacterial vectors also are cheaper and easier to produce than viral vectors, and bacterial delivery is favorable over viral delivery because it can be quickly eliminated by antibiotics if necessary, rendering it a safer alternative.

To be used, however, the strains themselves must not be pathogenic or are not pathogenic after modification for use as a therapeutic. For example, in the treatment of cancer, the therapeutic bacterial strains must be attenuated or rendered sufficiently non-toxic so as to not cause systemic disease and/or septic shock, but still maintain some level of infectivity to effectively colonize tumors. Genetically modified bacteria have been described that are to be used as antitumor agents to elicit direct tumoricidal effects and/or to deliver tumoricidal molecules (Clairmont et al. (2000) *J. Infect. Dis.* 181:1996-2002; Bermudes et al. (2002) *Curr. Opin. Drug Discov. Devel.* 5:194-199; Zhao et al. (2005) *Proc. Natl. Acad. Sci. USA* 102:755-760; Zhao et al. (2006) *Cancer Res.* 66:7647-7652). Among these are bioengineered strains of *Salmonella enterica* serovar *Typhimurium* (*S. typhimurium*). These bacteria accumulate preferentially >1,000-fold greater in tumors than in normal tissues and disperse homogeneously in tumor tissues (Pawelek et al. (1997) *Cancer Res.* 57:4537-4544; Low et al. (1999) *Nat. Biotechnol.* 17:37-41). Preferential replication allows the bacteria to produce and deliver a variety of anticancer therapeutic agents at high concentrations directly within the tumor, while minimizing toxicity to normal tissues. These attenuated bacteria are safe in mice, pigs, and monkeys when administered i.v. (Zhao et al. (2005) *Proc. Natl. Acad. Sci. USA* 102:755-760; Zhao et al. (2006) *Cancer Res.* 66:7647-7652; Tjuvajev et al. (2001) *J. Control Release* 74:313-315; Zheng et al. (2000) *Oncol. Res.* 12:127-135), and certain live attenuated *Salmonella* strains have been shown to be well tolerated after oral administration in human clinical trials (Chatfield et al. (1992) *Biotechnology* 10:888-892; DiPetrillo et al. (1999) *Vaccine* 18:449-459; Hohmann et al. (1996) *J. Infect. Dis.* 173:1408-1414; Sirard et al. (1999) *Immunol. Rev.* 171:5-26). The *S. typhimurium* PhoP/PhoQ operon is a typical bacterial two-component regulatory system composed of a membrane-associated sensor kinase (PhoQ) and a cytoplasmic transcriptional regulator (PhoP: Miller et al. (1989) *Proc. Natl. Acad. Sci. USA* 86:5054-5058; Groisman et al. (1989) *Proc. Natl. Acad. Sci. USA* 86:7077-7081). PhoP/PhoQ is required for virulence, and its deletion results in poor survival of this bacterium in macrophages and a marked attenuation in mice and humans (Miller et al. (1989) *Proc. Natl. Acad. Sci. USA* 86:5054-5058; Groisman et al. (1989) *Proc. Natl. Acad. Sci. USA* 86:7077-7081; Galan, J. E. and Curtiss, R. III. (1989) *Microb. Pathog.* 6:433-443; Fields et al. (1986) *Proc. Natl. Acad. Sci. USA* 83: 5189-5193). PhoP/PhoQ deletion strains have been employed as effective vaccine delivery vehicles (Galan, J. E. and Curtiss, R. III. (1989) *Microb. Pathog.* 6:433-443; Fields et al. (1986) *Proc. Natl. Acad. Sci. USA* 83: 5189-5193; Angelakopoulos, H. and Hohmann, E. L. (2000) *Infect. Immun.* 68: 2135-2141). Attenuated Salmonellae have been used for targeted delivery of tumoricidal proteins (Bermudes et al. (2002) *Curr. Opin. Drug. Discov. Devel.* 5:194-199; Tjuvajev et al. (2001) *J. Control Release* 74:313-315).

Bacterially-based cancer therapies have demonstrated limited clinical benefit. A variety of bacterial species, including *Clostridium novyi* (Dang et al. (2001) *Proc. Natl. Acad. Sci. U.S.A.* 98(26):15155-15160; U.S. Patent Publications Nos. 2017/0020931, 2015/0147315; U.S. Pat. Nos. 7,344,710; 3,936,354), *Mycobacterium bovis* (U.S. Patent Publications Nos. 2015/0224151, 2015/0071873), *Bifidobacterium bifidum* (Kimura et al. (1980) *Cancer Res.* 40:2061-2068), *Lactobacillus casei* (Yasutake et al. (1984) *Med. Microbiol. Immunol.* 173(3):113-125), *Listeria monocytogenes* (Le et al. (2012) *Clin. Cancer Res.* 18(3):858-868; Starks et al. (2004) *J. Immunol.* 173:420-427; U.S. Patent Publication No. 2006/0051380) and *Escherichia coli* (U.S. Pat. No. 9,320,787) have been studied as possible agents for anticancer therapy.

The *Bacillus* Calmette-Guerin (BCG) strain, for example, is approved for the treatment of bladder cancer in humans, and is more effective than intravesical chemotherapy, often being used as a first-line treatment (Gardlik et al. (2011) *Gene Therapy* 18:425-431). Another approach utilizes *Listeria monocytogenes*, a live attenuated intracellular bacterium capable of inducing potent CD8$^+$ T cell priming to expressed tumor antigens in mice (Le et al. (2012) *Clin. Cancer Res.* 18(3):858-868). In a clinical trial of the *Listeria*-based vaccine incorporating the tumor antigen mesothelin, together with an allogeneic pancreatic cancer-based GVAX vaccine in a prime-boost approach, a median survival of 6.1 months was noted in patients with advanced pancreatic cancer, versus a median survival of 3.9 months for patients treated with the GVAX vaccine alone (Le et al. (2015) *J. Clin. Oncol.* 33(12):1325-1333). These results were not replicated in a larger phase 2b study, possibly pointing to the difficulties in attempting to induce immunity to a low affinity self-antigen such as mesothelin.

Bacterial strains can be modified as described and exemplified herein to express inhibitory RNA (RNAi), such as shRNAs and microRNAs, that inhibit or disrupt TREX1 and/or PD-L1 and optionally one or more additional immune checkpoint genes. The strains can be attenuated by standard methods and/or by deletion or modification of genes, and by alteration or introduction of genes that render the bacteria able to grow in vivo primarily in immunoprivilaged environments, such as the TME, in tumor cells and solid tumors. Strains for modification as described herein can be selected from among, for example, *Shigella, Listeria, E. coli*, Bifidobacteriae and *Salmonella*. For example, *Shigella sonnei, Shigella flexneri, Shigella dysenteriae, Listeria monocytogenes, Salmonella typhi, Salmonella typhimurium, Salmonella gallinarum*, and *Salmonella enteritidis*. Other suitable bacterial species include *Rickettsia, Klebsiella, Bordetella, Neisseria, Aeromonas, Francisella, Corynebacterium, Citrobacter, Chlamydia, Haemophilus, Brucella, Mycobacterium, Mycoplasma, Legionella, Rhodococcus, Pseudomonas, Helicobacter, Vibrio, Bacillus, and Erysipelothrix. For example, Rickettsia rickettsii, Rickettsia prowazekii, Rickettsia tsutsugamushi, Rickettsia mooseri, Rickettsia sibirica, Bordetella bronchiseptica, Neisseria meningitidis, Neisseria gonorrhoeae, Aeromonas eucrenophila, Aeromonas salmonicida, Francisella tularensis, Corynebacterium pseudotuberculosis, Citrobacter freundii, Chlamydia pneumoniae, Haemophilus somnus, Brucella abortus, Mycobacterium intracellulare, Legionella pneumophila, Rhodococcus equi, Pseudomonas aeruginosa, Helicobacter mustelae, Vibrio cholerae, Bacillus subtilis, Erysipelothrix rhusiopathiae, Yersinia enterocolitica, Rochalimaea quintana, and Agrobacterium tumefaciens. Any known therapeutic, including immunostimulatory, bacteria can be modified as described herein.

2. Comparison of the Immune Responses to Bacteria and Viruses

Bacteria, like viruses, have the advantage of being naturally immunostimulatory. Bacteria and viruses are known to contain conserved structures known as Pathogen-Associated Molecular Patterns (PAMPs), which are sensed by host cell Pattern Recognition Receptors (PRRs). Recognition of PAMPs by PRRs triggers downstream signaling cascades that result in the induction of cytokines and chemokines, and initiation of immune responses that lead to pathogen clearance (Iwasaki and Medzhitov (2010) Science 327(5963): 291-295). The manner in which the innate immune system is engaged by PAMPs, and from what type of infectious agent, determines the appropriate adaptive immune response to combat the invading pathogen.

A class of PRRs known as Toll Like Receptors (TLRs) recognize PAMPs derived from bacterial and viral origins, and are located in various compartments within the cell. TLRs bind a range of ligands, including lipopolysaccharide (TLR4), lipoproteins (TLR2), flagellin (TLR5), unmethylated CpG motifs in DNA (TLR9), double-stranded RNA (TLR3), and single-stranded RNA (TLR7 and TLR8) (Akira et al. (2001) Nat. Immunol. 2(8):675-680; Kawai and Akira (2005) Curr. Opin. Immunol. 17(4):338-344). Host surveillance of S. typhimurium for example, is largely mediated through TLR2, TLR4 and TLR5 (Arpaia et al. (2011) Cell 144(5):675-688). These TLRs signal through MyD88 and TRIF adaptor molecules to mediate induction of NF-kB dependent pro-inflammatory cytokines such as TNF-α, IL-6 and IFN-7 (Pandey et al. (2015) Cold Spring Harb. Perspect. Biol. 7(1):a016246).

Another category of PRRs are the nod-like receptor (NLR) family. These receptors reside in the cytosol of host cells and recognize intracellular PAMPS. For example, S. Typhimurium flagellin was shown to activate the NLRC4/NAIP5 inflammasome pathway, resulting in the cleavage of caspase-1 and induction of the pro-inflammatory cytokines IL-1β and IL-18, leading to pyroptotic cell death of infected macrophages (Fink et al. (2007) Cell Microbiol. 9(11):2562-2570).

While engagement of TLR2, TLR4, TLR5 and the inflammasome induces pro-inflammatory cytokines that mediate bacterial clearance, they activate a predominantly NF-κB-driven signaling cascade that leads to recruitment and activation of neutrophils, macrophages and CD4$^+$ T cells, but not the DCs and CD8$^+$ T cells that are required for anti-tumor immunity (Liu et al. (2017) Signal Transduct. Target Ther. 2:e17023). In order to activate CD8$^+$ T cell-mediated anti-tumor immunity, IRF3/IRF7-dependent type I interferon signaling is critical for DC activation and cross-presentation of tumor antigens to promote CD8$^+$ T cell priming (Diamond et al. (2011) J. Exp. Med. 208(10):1989-2003; Fuertes et al. (2011) J. Exp. Med. 208(10):2005-2016). Type I interferons (IFN-α, IFN-β) are the signature cytokines induced by two distinct TLR-dependent and TLR-independent signaling pathways. The TLR-dependent pathway for inducing IFN-β occurs following endocytosis of pathogens, whereby TLR3, 7, 8 and 9 detect pathogen-derived DNA and RNA elements within the endosomes. TLRs 7 and 8 recognize viral nucleosides and nucleotides, and synthetic agonists of these, such as resiquimod and imiquimod have been clinically validated (Chi et al. (2017) Frontiers in Pharmacology 8:304). Synthetic dsRNA, such as polyinosinic:polycytidylic acid (poly (I:C)) and poly ICLC, an analog that is formulated with poly L lysine to resist RNase digestion, is an agonist for TLR3 and MDA5 pathways and a powerful inducer of IFN-β (Caskey et al. (2011) J. Exp. Med. 208(12):2357-66). TLR9 detection of endosomal CpG motifs present in viral and bacterial DNA can also induce IFN-β via IRF3. Additionally, TLR4 has been shown to induce IFN-β via MyD88-independent TRIF activation of IRF3 (Owen et al. (2016) mBio 0.7:1 e02051-15). It subsequently was shown that TLR4 activation of DCs was independent of type I IFN, so the ability of TLR4 to activate DCs via type I IFN is not likely biologically relevant (Hu et al. (2015) Proc. Natl. Acad. Sci. U.S.A. 112(45): 13994-13999). Further, TLR4 signaling has not been shown to directly recruit or activate CD8$^+$ T cells.

Of the TLR-independent type I IFN pathways, one is mediated by host recognition of single-stranded (ss) and double-stranded (ds) RNA in the cytosol. These are sensed by RNA helicases, including retinoic acid-inducible gene I (RIG-I), melanoma differentiation-associated gene 5 (MDA-5), and through the IFN-β promoter stimulator 1 (IPS-1) adaptor protein-mediated phosphorylation of the IRF-3 transcription factor, leading to induction of IFN-β (Ireton and Gale (2011) Viruses 3(6):906-919). Synthetic RIG-I-binding elements have also been discovered unintentionally in common lentiviral shRNA vectors, in the form of an AA dinucleotide sequence at the U6 promoter transcription start site. Its subsequent deletion in the plasmid prevented confounding off-target type I IFN activation (Pebernard et al. (2004) Differentiation. 72:103-111).

The second type of TLR-independent type I interferon induction pathway is mediated through Stimulator of Interferon Genes (STING), a cytosolic ER-resident adaptor protein that is now recognized as the central mediator for sensing cytosolic dsDNA from infectious pathogens or aberrant host cell damage (Barber (2011) Immunol. Rev 243(1): 99-108). STING signaling activates the TANK binding kinase (TBK1)/IRF3 axis and the NF-kB signaling axis, resulting in the induction of IFN-β and other pro-inflammatory cytokines and chemokines that strongly activate innate and adaptive immunity (Burdette et al. (2011) Nature 478 (7370):515-518). Sensing of cytosolic dsDNA through STING requires cyclic GMP-AMP synthase (cGAS), a host cell nucleotidyl transferase that directly binds dsDNA, and in response, synthesizes a cyclic dinucleotide (CDN) second messenger, cyclic GMP-AMP (cGAMP), which binds and activates STING (Sun et al. (2013) Science 339(6121):786-791; Wu et al. (2013) Science 339(6121):826-830). CDNs derived from bacteria such as c-di-AMP produced from intracellular Listeria monocytogenes can also directly bind murine STING, but only 3 of the 5 human STING alleles. Unlike the CDNs produced by bacteria, in which the two purine nucleosides are joined by a phosphate bridge with 3'-3' linkages, the internucleotide phosphate bridge in the cGAM4P synthesized by mammalian cGAS is joined by a non-canonical 2'-3' linkage. These 2'-3' molecules bind to STING with 300-fold better affinity than bacterial 3'-3' CDNs, and thus are more potent physiological ligands of human STING (see, e.g., Civril et al. (2013) *Nature* 498 (7454):332-337; Diner et al. (2013) *Cell Rep.* 3(5):1355-1361; Gao et al. (2013) *Sci. Signal* 6(269):pl1; Ablasser et al. (2013) *Nature* 503(7477):530-534).

The cGAS/STING signaling pathway in humans may have evolved over time to preferentially respond to viral pathogens over bacterial pathogens, and this can explain why bacterial vaccines harboring host tumor antigens have made for poor CD8+ T cell priming vectors in humans. TLR-independent activation of CD8+ T cells by STING-dependent type I IFN signaling from conventional DCs is the primary mechanism by which viruses are detected, with TLR-dependent type I IFN production by plasmacytoid DCs operating only when the STING pathway has been virally-inactivated (Hervas-Stubbs et al. (2014) *J. Immunol.* 193: 1151-1161). Further, for bacteria such as *S. typhimurium*, while capable of inducing IFN-β via TLR4, CD8+ T cells are neither induced nor required for clearance or protective immunity (Lee et al. (2012) *Immunol. Lett.* 148(2): 138-143). The lack of physiologically relevant CD8+ T epitopes for many strains of bacteria, including *S. typhimurium*, has impeded both bacterial vaccine development and protective immunity to subsequent infections, even from the same genetic strains (Lo et al. (1999) *J. Immunol.* 162:5398-5406). Thus, bacterially-based cancer immunotherapies are biologically limited in their ability to induce type I IFN to recruit and activate CD8+ T cells, necessary to promote tumor antigen cross-presentation and durable anti-tumor immunity. Hence, engineering a bacterial immunotherapy provided herein to induce viral-like TLR-independent type I IFN signaling, rather than TLR-dependent bacterial immune signaling, will preferentially induce CD8+ T cell mediated anti-tumor immunity.

STING activates innate immunity in response to sensing nucleic acids in the cytosol. Downstream signaling is activated through binding of CDNs, which are synthesized by bacteria or by the host enzyme cGAS in response to binding to cytosolic dsDNA. Bacterial and host-produced CDNs have distinct phosphate bridge structures, which differentiates their capacity to activate STING. IFN-β is the signature cytokine of activated STING, and virally-induce type I IFN, rather than bacterially-induced IFN, is required for effective CD8+ T cell mediated anti-tumor immunity. Immunostimulatory bacteria provided herein include those that are STING agonists.

3. *Salmonella* Therapy

*Salmonella* is exemplary of a bacterial genus that can be used as a cancer therapeutic. The *Salmonella* exemplified herein is an attenuated species or one that by virtue of the modifications for use as a cancer therapeutic has reduced toxicity.

a. Tumor-Tropic Bacteria

A number of bacterial species have demonstrated preferential replication within solid tumors when injected from a distal site. These include, but are not limited to, species of *Salmonella, Bifidobacterium, Clostridium,* and *Escherichia.* The natural tumor-homing properties of the bacteria combined with the host's innate immune response to the bacterial infection is thought to mediate the anti-tumor response. This tumor tissue tropism has been shown to reduce the size of tumors to varying degrees. One contributing factor to the tumor tropism of these bacterial species is the ability to replicate in anoxic or hypoxic environments. A number of these naturally tumor-tropic bacteria have been further engineered to increase the potency of the antitumor response (reviewed in Zu et al. (2014) *Crit. Rev. Microbiol.* 40(3): 225-235; and Felgner et al. (2017) *Microbial Biotechnology* 10(5):1074-1078).

b. *Salmonella enterica* Serovar *typhimurium*

*Salmonella enterica* serovar *typhimurium* (*S. typhimurium*) is exemplary of a bacterial species for use as an anti-cancer therapeutic. One approach to using bacteria to stimulate host immunity to cancer has been through the Gram-negative facultative anaerobe *S. typhimurium*, which preferentially accumulates in hypoxic and necrotic areas in the body, including tumor microenvironments. *S. typhimurium* accumulates in these environments due to the availability of nutrients from tissue necrosis, the leaky tumor vasculature and their increased likelihood to survive in the immune system-evading tumor microenvironment (Baban et al. (2010) *Bioengineered Bugs* 1(6):385-394). *S. typhimurium* is able to grow under both aerobic and anaerobic conditions; therefore it is able to colonize small tumors that are less hypoxic and large tumors that are more hypoxic.

*S. typhimurium* is a Gram-negative, facultative pathogen that is transmitted via the fecal-oral route. It causes localized gastrointestinal infections, but also enters the bloodstream and lymphatic system after oral ingestion, infecting systemic tissues such as the liver, spleen and lungs. Systemic administration of wild-type *S. typhimurium* overstimulates TNF-α induction, leading to a cytokine cascade and septic shock, which, if left untreated, can be fatal. As a result, pathogenic bacterial strains, such as *S. typhimurium*, must be attenuated to prevent systemic infection, without completely suppressing their ability to effectively colonize tumor tissues. Attenuation is often achieved by mutating a cellular structure that can elicit an immune response, such as the bacterial outer membrane or limiting its ability to replicate in the absence of supplemental nutrients.

*S. typhimurium* is an intracellular pathogen that is rapidly taken up by myeloid cells such as macrophages or it can induce its own uptake in in non-phagocytic cells such as epithelial cells. Once inside cells, it can replicate within a *Salmonella* containing vacuole (SCV) and can also escape into the cytosol of some epithelial cells. Many of the molecular determinants of *S. typhimurium* pathogenicity have been identified and the genes are clustered in *Salmonella* pathogenicity islands (SPIs). The two best characterized pathogenicity islands are SPI-1 which is responsible for mediating bacterial invasion of non-phagocytic cells, and SPI-2 which is required for replication within the SCV (Agbor and McCormick (2011) *Cell Microbiol.* 13(12): 1858-1869). Both of these pathogenicity islands encode macromolecular structures called type three secretion systems (T3SS) that can translocate effector proteins across the host membrane (Galan and Wolf-Watz (2006) *Nature* 444: 567-573).

c. Bacterial Attenuation

Therapeutic bacteria for administration as a cancer treatment should be attenuated. Various methods for attenuation of bacterial pathogens are known in the art. Auxotrophic mutations, for example, render bacteria incapable of synthesizing an essential nutrient, and deletions/mutations in genes such as aro, pur, gua, thy, nad and asd (U.S. Patent Publication No. 2012/0009153) are widely used. Nutrients produced by the biosynthesis pathways involving these genes are often unavailable in host cells, and as such, bacterial survival is challenging. For example, attenuation of *Salmonella* and other species can be achieved by deletion of the aroA gene, which is part of the shikimate pathway, connecting glycolysis to aromatic amino acid biosynthesis (Felgner et al. (2016) *MBio* 7(5):e01220-16). Deletion of aroA therefore results in bacterial auxotrophy for aromatic amino acids and subsequent attenuation (U.S. Patent Publication Nos. 2003/0170276, 2003/0175297, 2012/0009153, 2016/0369282; International Application Publication Nos. WO 2015/032165 and WO 2016/025582). Similarly, other enzymes involved in the biosynthesis pathway for aromatic amino acids, including aroC and aroD have been deleted to achieve attenuation (U.S. Patent Publication No. 2016/0369282; International Application Publication No. WO 2016/025582). For example, *S. typhimurium* strain SL7207 is an aromatic amino acid auxotroph (aroA$^-$mutant); strains A1 and A1-R are leucine-arginine auxotrophs. VNP20009 is a purine auxotroph (purI$^-$ mutant). As shown herein, it is also auxotrophic for the immunosuppressive nucleoside adenosine.

Mutations that attenuate bacteria also include, but are not limited to, mutations in genes that alter the biosynthesis of lipopolysaccharide, such as rfaL, rfaG, rfaH, rfaD, rfaP, rFb, rfa, msbB, htrB, firA, pagL, pagP, lpxR, arnT, eptA, and lpxT; mutations that introduce a suicide gene such as sacB, nuk, hok, gef, kil or phlA; mutations that introduce a bacterial lysis gene such as hly and cly; mutations in virulence factors such as IsyA, pag, prg, iscA, virG, plc and act; mutations that modify the stress response such as recA, htrA, htpR, hsp and groEL; mutations that disrupt the cell cycle such as min; and mutations that disrupt or inactivate regulatory functions, such as cya, crp, phoP/phoQ, and ompR (U.S. Patent Publication Nos. 2012/0009153, 2003/0170276, 2007/0298012; U.S. Pat. No. 6,190,657; International Application Publication No. WO 2015/032165; Felgner et al. (2016) *Gut Microbes* 7(2):171-177; Broadway et al. (2014) *J. Biotechnology* 192:177-178; Frahm et al. (2015) *mBio* 6(2):e00254-15; Kong et al. (2011) *Infection and Immunity* 79(12):5027-5038; Kong et al. (2012) *Proc. Natl. Acad. Sci. U.S.A.* 109(47):19414-19419). Ideally, the genetic attenuations comprise gene deletions rather than point mutations to prevent spontaneous compensatory mutations that might result in reversion to a virulent phenotype.

i. msbB$^-$ Mutants

The enzyme lipid A biosynthesis myristoyltransferase, encoded by the msbB gene in *S. typhimurium*, catalyzes the addition of a terminal myristyl group to the lipid A domain of lipopolysaccharide (LPS) (Low et al. (1999) *Nat. Biotechnol.* 17(1):37-41). Deletion of msbB thus alters the acyl composition of the lipid A domain of LPS, the major component of the outer membranes of Gram-negative bacteria. This modification significantly reduces the ability of the LPS to induce septic shock, attenuating the bacterial strain and reducing the potentially harmful production of TNFα, thus lowering systemic toxicity. *S. typhimurium* msbB mutants maintain their ability to preferentially colonize tumors over other tissues in mice and retain anti-tumor activity, thus increasing the therapeutic index of *Salmonella* based immunotherapeutics (U.S. Patent Publication Nos. 2003/0170276, 2003/0109026, 2004/0229338, 2005/0255088, 2007/0298012).

For example, deletion of msbB in the *S. typhimurium* strain VNP20009 results in production of a predominantly penta-acylated LPS, which is less toxic than native hexa-acylated LPS and allows for systemic delivery without the induction of toxic shock (Lee et al. (2000) *International Journal of Toxicology* 19:19-25). Other LPS mutations can be introduced into the bacterial strains provided herein, including the *Salmonella* strains, that dramatically reduce virulence, and thereby provide for lower toxicity, and permit administration of higher doses.

ii. purI$^-$ Mutants

Immunostimulatory bacteria that can be attenuated by rendering them auxotrophic for one or more essential nutrients, such as purines (for example, adenine), nucleosides (for example, adenosine) or amino acids (for example, arginine and leucine), are employed. In particular, in embodiments of the immunostimulatory bacteria provided herein, such as *S. typhimurium*, the bacteria are rendered auxotrophic for adenosine, which preferentially accumulates in tumor microenvironments. Hence, strains of immunostimulatory bacteria described herein are attenuated because they require adenosine for growth, and they preferentially colonize TMEs, which, as discussed below, have an abundance of adenosine.

Phosphoribosylaminoimidazole synthetase, an enzyme encoded by the purI gene (synonymous with the purM gene), is involved in the biosynthesis pathway of purines. Disruption of the purI gene thus renders the bacteria auxotrophic for purines. In addition to being attenuated, purI$^-$ mutants are enriched in the tumor environment and have significant anti-tumor activity (Pawelek et al. (1997) *Cancer Research* 57:4537-4544). It was previously described that this colonization results from the high concentration of purines present in the interstitial fluid of tumors as a result of their rapid cellular turnover. Since the purI$^-$ bacteria are unable to synthesize purines, they require an external source of adenine, and it was thought that this would lead to their restricted growth in the purine-enriched tumor microenvironment (Rosenberg et al. (2002) *J. Immunotherapy* 25(3): 218-225). While the VNP20009 strain was initially reported to contain a deletion of the purI gene (Low et al. (2003) *Methods in Molecular Medicine* Vol. 90, *Suicide Gene Therapy* 47-59), subsequent analysis of the entire genome of VNP20009 demonstrated that the purI gene is not deleted, but is disrupted by a chromosomal inversion (Broadway et al. (2014) *Journal of Biotechnology* 192:177-178). The entire gene is contained within two parts of the VNP20009 chromosome that is flanked by insertion sequences (one of which has an active transposase).

It is shown herein, that, purI mutant *S. typhimurium* strains are auxotrophic for the nucleoside adenosine, which is highly enriched in tumor microenvironments. Hence, when using VNP20009, it is not necessary to introduce any further modification to achieve adenosine auxotrophy. For other strains and bacteria, the purI gene can be disrupted as it has been in VNP20009, or it can contain a deletion of all or a portion of the purI gene to prevent reversion to a wild-type gene.

iii. Combinations of Attenuating Mutations

A bacterium with multiple genetic attenuations by means of gene deletions on disparate regions of the chromosome is desirable for bacterial immunotherapies because the attenuation can be increased, while decreasing the possibility of reversion to a virulent phenotype by acquisition of genes by homologous recombination with a wild-type genetic material. Restoration of virulence by homologous recombination would require two separate recombination events to occur within the same organism. Ideally the combinations of attenuating mutations selected for use in an immunotherapeutic agent increases the tolerability without decreasing the potency, thereby increasing the therapeutic index. For example, disruption of the msbB and purI genes in *S. typhimurium* strain VNP20009, has been used for tumor-targeting and growth suppression, and elicits low toxicity in animal models (Clairmont et al. (2000) *J. Infect. Dis.* 181:1996-2002; Bermudes et al. (2000) *Cancer Gene Therapy: Past Achievements and Future Challenges*, edited by Habib Kluwer Academic/Plenum Publishers, New York, pp. 57-63; Low et al. (2003) *Methods in Molecular Medicine*, Vol. 90, *Suicide Gene Therapy* 47-59; Lee et al. (2000) *International Journal of Toxicology* 19:19-25; Rosenberg et al. (2002) *J. Immunotherapy* 25(3):218-225; Broadway et al. (2014) *J. Biotechnology* 192:177-178; Loeffler et al. (2007) *Proc. Natl. Acad. Sci. U.S.A.* 104(31):12879-12883; Luo et al. (2002) *Oncology Research* 12:501-508). When VNP20009 (msbB$^-$/purI$^-$) was administered to mice bearing syngeneic or human xenograft tumors, the bacteria accumulated preferentially within the extracellular components of tumors at ratios exceeding 300-1000 to 1, reduced TNFα induction, and demonstrated tumor regression and prolonged survival compared to control mice (Clairmont et al. (2000) *J. Infect. Dis.* 181:1996-2002). Results from the Phase 1 clinical trial in humans, however, revealed that while VNP20009 was relatively safe and well tolerated, poor accumulation was observed in human melanoma tumors, and very little anti-tumor activity was demonstrated (Toso et al. (2002) *J. Clin. Oncol.* 20(1):142-152). Higher doses, which are required to manifest any anti-tumor activity, were not possible due to toxicity.

Thus, further improvements are needed. The immunostimulatory bacteria provided herein address this problem.

iv. VNP20009 and Other Attenuated *S. typhimurium* Strains

Exemplary of a therapeutic bacterium that can be modified as described herein is the strain designated as VNP20009 (ATCC #202165, YS1646). The clinical candidate, VNP20009 (ATCC #202165; YS1646), was at least 50,000-fold attenuated for safety by deletion of both the msbB and purI genes (Clairmont et al. (2000) *J. Infect. Dis.* 181:1996-2002; Low et al. (2003) *Methods in Molecular Medicine*, Vol. 90, *Suicide Gene Therapy:*47-59; Lee et al. (2000) *International Journal of Toxicology* 19:19-25). Similar strains of *Salmonella* that are attenuated also are contemplated. As described above, deletion of msbB alters the composition of the lipid A domain of lipopolysaccharide, the major component of Gram-negative bacterial outer membranes (Low et al. (1999) *Nat. Biotechnol.* 17(1):37-41). This prevents lipopolysaccharide-induced septic shock, attenuating the bacterial strain and lowering systemic toxicity, while reducing the potentially harmful production of TNFα (Dinarello, C. A. (1997) *Chest* 112(6 Suppl):321S-329S; Low et al. (1999) *Nat. Biotechnol.* 17(1):37-41). Deletion of the purI gene renders the bacteria auxotrophic for purines, which further attenuates the bacteria and enriches it in the tumor micro environment (Pawelek et al. (1997) *Cancer Res.* 57:4537-4544; Broadway et al. (2014) *J. Biotechnology* 192:177-178).

The accumulation of VNP20009 in tumors results from a combination of factors including: the inherent invasiveness of the parental strain, ATCC14028, its ability to replicate in hypoxic environments, and its requirement for high concentrations of purines that are present in the interstitial fluid of tumors. Herein we will demonstrate that VNP20009 is also auxotrophic for the nucleoside adenosine, which can accumulate to pathologically high levels in the tumor microenvironment and contribute to an immunosuppressive tumor microenvironment (Peter Vaupel and Arnulf Mayer Oxygen Transport to Tissue XXXVII, Advances in Experimental Medicine and Biology 876 chapter 22, pp. 177-183). When VNP20009 was administered into mice bearing syngeneic or human xenograft tumors, the bacteria accumulated preferentially within the extracellular components of tumors at ratios exceeding 300-1000 to 1 and demonstrated tumor growth inhibition as well as prolonged survival compared to control mice (Clairmont et al. (2000) *J. Infect. Dis.* 181: 1996-2002). Results from the Phase 1 clinical trial revealed that while VNP20009 was relatively safe and well tolerated, poor accumulation was observed in human melanoma tumors, and very little anti-tumor activity was demonstrated (Toso et al. (2002) *J. Clin. Oncol.* 20(1):142-152). Higher doses, which would be required to affect any anti-tumor activity, were not possible due to toxicity that correlated with high levels of pro-inflammatory cytokines.

Other strains of *S. typhimurium* can be used for tumor-targeted delivery and therapy, such as, for example, leucine-arginine auxotroph A-1 (Zhao et al. (2005) *Proc. Natl. Acad. Sci. U.S.A.* 102(3):755-760; Yu et al. (2012) *Scientific Reports* 2:436; U.S. Pat. No. 8,822,194; U.S. Patent Publication No. 2014/0178341) and its derivative AR-1 (Yu et al. (2012) *Scientific Reports* 2:436; Kawaguchi et al. (2017) *Oncotarget* 8(12):19065-19073; Zhao et al. (2006) *Cancer Res.* 66(15):7647-7652; Zhao et al. (2012) *Cell Cycle* 11(1): 187-193; Tome et al. (2013) *Anticancer Research* 33:97-102; Murakami et al. (2017) *Oncotarget* 8(5):8035-8042; Liu et al. (2016) *Oncotarget* 7(16):22873-22882; Binder et al. (2013) *Cancer Immunol. Res.* 1(2):123-133); aroA$^-$mutant *S. typhimurium* strain SL7207 (Guo et al. (2011) *Gene Therapy* 18:95-105; U.S. Patent Publication Nos. 2012/0009153, 2016/0369282 and 2016/0184456) and its obligate anaerobe derivative YB1 (International Application Publication No. WO 2015/032165; Yu et al. (2012) *Scientific Reports* 2:436; Leschner et al. (2009) *PLoS ONE* 4(8): e6692); aroA$^-$/aroD$^-$ mutant *S. typhimurium* strain BRD509, a derivative of the SL1344 (WT) strain (Yoon et al. (2017) *European J. of Cancer* 70:48-61); asd$^-$/cya$^-$/crp$^-$ mutant *S. typhimurium* strain χ4550 (Sorenson et al. (2010) *Biologics: Targets & Therapy* 4:61-73) and phoP$^-$/phoQ$^-$ *S. typhimurium* strain LH430 (WO 2008/091375).

Although VNP20009 failed to show a clinical benefit in a study involving patients with advanced melanoma, a maximum tolerated dose (MTD) was established and the treatment was safely administered to advanced cancer patients. Hence, this strain, as well as other similarly engineered bacterial strains, can be used as tumor-targeting, therapeutic delivery vehicles. Modifications provided herein provide a strategy to increase efficacy, by increasing the anti-tumor efficiency and/or the safety and tolerability of the therapeutic agent.

v. Attenuated *S. typhimurium* Engineered to Deliver Macromolecules

The bacterial strains are engineered to deliver therapeutic molecules. The strains herein deliver RNAi targeted and inhibitory to immune checkpoints, and also to other such targets.

While the use of VNP20009 in clinical trials of metastatic melanoma resulted in no significant changes in metastatic burden, it did demonstrate some evidence of tumor colonization. VNP20009 and other *S. typhimurium* strains have been used as vectors to deliver a wide variety of genes, such as those encoding cytokines, anti-angiogenic factors, inhibitory enzymes and cytotoxic polypeptides (U.S. Patent Publication No. 2007/0298012). For example, the delivery of cytokine-encoding LIGHT using VNP20009 inhibited growth of primary tumors as well as pulmonary metastases of carcinoma cell lines in immunocompetent mice, with no significant toxicity observed (Loeffler et al. (2007) *Proc. Natl. Acad. Sci. U.S.A.* 104(31):12879-12883). In another study, VNP20009, expressing an *E. coli* cytosine deaminase gene was administered to patients who also received the prodrug 5-fluorocytosine (5-FC) orally. Two out of three patients showed intratumoral bacterial colonization for at least 15 days after initial injection, and the expressed cytosine deaminase converted the 5-FC to the anticancer drug 5-FU. No side effects from the *Salmonella* were observed, and direct IV administration of 5-FU resulted in lower tumor concentrations of the drug than with bacterial delivery of the cytosine deaminase gene (Nemunaitis et al. (2003) *Cancer Gene Therapy* 10:737-744).

In other examples, attenuated *Salmonella* expressing herpes simplex virus thymidine kinase (HSV TK) demonstrated a 2.5-fold reduction in B16 melanoma tumor size via ganciclovir-mediated tumor growth suppression (Pawelek, J. et al. (1997) *Cancer Res* 57:4537-4544), and the C-terminal p53 peptide (Cp53) was delivered using *S. typhimurium* and inducibly-expressed in MCF7 breast cancer cells, resulting in a decrease in tumor cell population (Camacho et al. (2016) *Scientific Reports* 6:30591: 1-12). *S. typhimurium* has also been utilized in the tumor-targeted expression of IFN-γ (Yoon et al. (2017) *European J. of Cancer* 70:48-61); SIINF antigen (Binder et al. (2013) *Cancer Immunol Res.* 1(2):123-133); *Vibrio vulnificus* flagellin B (Zheng et al. (2017) *Sci. Transl. Med.* 9, 9537); and truncated IL-2 (Sorenson et al. (2010) *Biology: Targets & Therapy* 4:61-73), for example.

*S. typhimurium* has also been modified to deliver the tumor-associated antigen (TAA) survivin (SVN) to APCs to prime adaptive immunity (U.S. Patent Publication No. 2014/0186401; Xu et al. (2014) *Cancer Res.* 74(21):6260-6270). SVN is an inhibitor of apoptosis protein (IAP) which prolongs cell survival and provides cell cycle control, and is overexpressed in all solid tumors and poorly expressed in normal tissues. This technology utilizes *Salmonella* Pathogenicity Island 2 (SPI-2) and its type III secretion system (T3SS) to deliver the TAAs into the cytosol of APCs, which then are activated to induce TAA-specific CD8+ T cells and anti-tumor immunity (Xu et al. (2014) *Cancer Res.* 74(21): 6260-6270). Similar to the *Listeria*-based TAA vaccines, this approach has shown promise in mouse models, but has yet to demonstrate effective tumor antigen-specific T cell priming in humans.

In addition to gene delivery, *S. typhimurium* also has been used for the delivery of small interfering RNAs (siRNAs) and short hairpin RNAs (shRNAs) for cancer therapy. For example, attenuated *S. typhimurium* have been modified to express certain shRNAs, such as those that target Stat 3 and IDO1 (PCT/US2007/074272, and U.S. Pat. No. 9,453,227). VNP20009 transformed with an shRNA plasmid against the immunosuppressive gene indolamine deoxygenase (IDO), successfully silenced IDO expression in a murine melanoma model, resulting in tumor cell death and significant tumor infiltration by neutrophils (Blache et al. (2012) *Cancer Res.* 72(24):6447-6456). Combining this vector with the co-administration of PEGPH20 (an enzyme that depletes extracellular hyaluronan), showed positive results in the treatment of pancreatic ductal adenocarcinoma tumors (Manuel et al. (2015) *Cancer Immunol. Res.* 3(9):1096-1107; U.S. Patent Publication No. 2016/0184456). In another study, an *S. typhimurium* strain attenuated by a phoP/phoQ deletion and expressing a signal transducer and activator of transcription 3 (STAT3)-specific shRNA, was found to inhibit tumor growth and reduce the number of metastatic organs, extending the life of C57BL6 mice (Zhang et al. (2007) *Cancer Res.* 67(12):5859-5864). In another example, *S. typhimurium* strain SL7207 has been used for the delivery of shRNA targeting CTNNB1, the gene that encodes 3-catenin (Guo et al. (2011) *Gene Therapy* 18:95-105; U.S. Patent Publication Nos. 2009/0123426, 2016/0369282), while *S. typhimurium* strain VNP20009 has been utilized in the delivery of shRNA targeting the STAT3 (Manuel et al. (2011) *Cancer Res.* 71(12):4183-4191; U.S. Patent Publication Nos. 2009/0208534, 2014/0186401, 2016/0184456; International Application Publication Nos. WO 2008/091375, WO 2012/149364). siRNAs targeting the autophagy genes Atg5 and Beclin1 have been delivered to tumor cells using *S. typhimurium* strains A1-R and VNP20009 (Liu et al. (2016) *Oncotarget* 7(16):22873-22882). Improvement of such strains is needed so that they more effectively stimulate the immune response, and have other advantageous properties, such as the immunostimulatory bacteria provided herein.

Any of the bacteria described above can be modified as described herein, such as by adding additional shRNA or microRNA encoding nucleic acids to target other checkpoints, such as TREX1. The bacteria can be modified as described herein to have reduced inflammatory effects, and, thus to be less toxic. As a result, for example, higher dosages can be administered. Any of these strains of *Salmonella*, as well as other species of bacteria, known to those of skill in the art and/or listed above and herein, can be modified as described herein, such as by introducing adenosine auxotrophy and/or shRNA for inhibiting TREX1 expression and other modifications as described herein. Exemplary are the *S. typhimurium* species described herein. It is shown herein that the *S. typhimurium* strain VNP20009 is auxotrophic for adenosine.

4. Enhancements of Immunostimulatory Bacteria to Increase Therapeutic Index

Provided herein are enhancements to immunostimulatory bacteria that reduce toxicity and improve the anti-tumor activity. Exemplary of such enhancements are the following. They are described with respect to *Salmonella*, particularly *S. typhimurium*; it is understood that the skilled person can effect similar enhancements in other bacterial species and other *Salmonella* strains.

a. asd Gene Deletion

The asd gene in bacteria encodes an aspartate-semialdehyde dehydrogenase. asd-mutants of: *S. typhimurium* have an obligate requirement for diaminopimelic acid (DAP) which is required for cell wall synthesis and will undergo lysis in environments deprived of DAP. This DAP auxotrophy can be used for plasmid selection and maintenance of plasmid stability in vivo without the use of antibiotics when the asd gene is complemented in trans on a plasmid. Non-antibiotic-based plasmid selection systems are advantageous and allow for 1) use of administered antibiotics as rapid clearance mechanism in the event of adverse symptoms, and 2) for antibiotic-free scale up of production, where such use is commonly avoided. The asd gene complementation system provides for such selection (Galan et al. (1990) *Gene* 94(1):29-35). The use of the asd gene complementation system to maintain plasmids in the tumor microenvironment is expected to increase the potency of *S. typhimurium* engineered to deliver plasmids encoding genes or interfering RNAs.

An alternative use for an asd mutant of *S. typhimurium* is to exploit the DAP auxotrophy to produce an autolytic (or suicidal) strain for delivery of macromolecules to infected cells without the ability to persistently colonize host tumors. Deletion of the asd gene makes the bacteria auxotrophic for DAP when grown in vitro or in vivo. An example described herein, provides an asd deletion strain that is auxotrophic for DAP and contains a plasmid suitable for delivery of RNAi, such as shRNA or miRNA, that does not contain an asd complementing gene, resulting in a strain that is defective for replication in vivo. This strain is propagated in vitro in the presence of DAP and grows normally, and then is administered as an immunotherapeutic agent to a mammalian host where DAP is not present. The suicidal strain is able to invade host cells but is not be able to replicate due to the absence of DAP in mammalian tissues, lysing automatically and delivering its cytosolic contents (e.g., plasmids or proteins). In examples provided herein, an asd gene deleted strain of VNP20009 was further modified to express an LLO protein lacking its endogenous periplasmic secretion signal sequence, causing it to accumulate in the cytoplasm of the *Salmonella*. LLO is a cholesterol-dependent pore forming hemolysin from *Listeria monocytogenes* that mediates phagosomal escape of bacteria. When the autolytic strain is introduced into tumor bearing mice, the bacteria are taken up by phagocytic immune cells and enter the *Salmonella* containing vacuole (SCV). In this environment, the lack of DAP will prevent bacterial replication, and result in autolysis of the bacteria in the SCV. Lysis of the suicidal strain will then allow for release of the plasmid and the accumulated LLO that will form pores in the cholesterol-containing SVC membrane, and allow for delivery of the plasmid into the cytosol of the host cell.

b. Adenosine Auxotrophy

Metabolites derived from the tryptophan and ATP/adenosine pathways are major drivers in forming an immunosuppressive environment within the tumor. Adenosine, which exists in the free form inside and outside of cells, is an effector of immune function. Adenosine decreases T-cell receptor induced activation of NF-κB, and inhibits IL-2, IL-4, and IFN-γ. Adenosine decreases T-cell cytotoxicity, increases T-cell anergy, and increases T-cell differentiation to Foxp3+ or Lag-3+ regulatory (T-reg) T-cells. On NK cells, adenosine decreases IFN-γ production, and suppresses NK cell cytotoxicity. Adenosine blocks neutrophil adhesion and extravasation, decreases phagocytosis, and attenuates levels of superoxide and nitric oxide. Adenosine also decreases the expression of TNF-α, IL-12, and MIP-1α on macrophages, attenuates MHC Class II expression, and increases levels of IL-1β and IL-6. Adenosine immunomodulation activity occurs after its release into the extracellular space of the tumor and activation of adenosine receptors (ADRs) on the surface of target immune cells, cancer cells or endothelial cells. The high adenosine levels in the tumor microenvironment result in local immunosuppression, which limits the capacity of the immune system to eliminate cancer cells.

Extracellular adenosine is produced by the sequential activities of membrane associated ectoenzymes, CD39 and CD73, which are expressed on tumor stromal cells, together producing adenosine by phosphohydrolysis of ATP or ADP produced from dead or dying cells. CD39 converts extracellular ATP (or ADP) to 5'AMP, which is converted to adenosine by 5'AMP. Expression of CD39 and CD73 on endothelial cells is increased under the hypoxic conditions of the tumor microenvironment, thereby increasing levels of adenosine. Tumor hypoxia can result from inadequate blood supply and disorganized tumor vasculature, impairing delivery of oxygen (Carroll and Ashcroft (2005) *Expert. Rev. Mol. Med.* 7(6):1-16). Hypoxia, which occurs in the tumor microenvironment, also inhibits adenylate kinase (AK), which converts adenosine to AMP, leading to very high extracellular adenosine concentrations. The extracellular concentration of adenosine in the hypoxic tumor microenvironment has been measured at 10-100 μM, which is up to about 100-1000 fold higher than the typical extracellular adenosine concentration of approximately 0.1 μM (Vaupel et al. (2016) *Adv. Exp. Med. Biol.* 876:177-183; Antonioli et al. (2013) *Nat. Rev. Can.* 13:842-857). Since hypoxic regions in tumors are distal from microvessels, the local concentration of adenosine in some regions of the tumor can be higher than others.

To direct effects to inhibit the immune system, adenosine also can control cancer cell growth and dissemination by effects on cancer cell proliferation, apoptosis and angiogenesis. For example, adenosine can promote angiogenesis, primarily through the stimulation of $A_{2A}$ and $A_{2B}$ receptors. Stimulation of the receptors on endothelial cells can regulate the expression of intercellular adhesion molecule 1 (ICAM-1) and E-selectin on endothelial cells, maintain vascular integrity, and promote vessel growth (Antonioli et al. (2013) *Nat. Rev. Can.* 13:842-857). Activation of one or more of $A_{2A}$, $A_{2B}$ or $A_3$ on various cells by adenosine can stimulate the production of the pro-angiogenic factors, such as vascular endothelial growth factor (VEGF), interleukin-8 (IL-8) or angiopoietin 2 (Antonioli et al. (2013) *Nat. Rev. Can.* 13:842-857).

Adenosine also can directly regulate tumor cell proliferation, apoptosis and metastasis through interaction with receptors on cancer cells. For example, studies have shown that the activation of $A_1$ and $A_{2A}$ receptors promote tumor cell proliferation in some breast cancer cell lines, and activation of $A_{2B}$ receptors have cancer growth-promoting properties in colon carcinoma cells (Antonioli et al. (2013) *Nat. Rev. Can.* 13:842-857). Adenosine also can trigger apoptosis of cancer cells, and various studies have correlated this activity to activation of the extrinsic apoptotic pathway through $A_3$ or the intrinsic apoptotic pathway through $A_{2A}$ and $A_{2B}$ (Antonioli et al. (2013)). Adenosine can promote tumor cell migration and metastasis, by increasing cell motility, adhesion to the extracellular matrix, and expression of cell attachment proteins and receptors to promote cell movement and motility.

The extracellular release of adenosine triphosphate (ATP) occurs from stimulated immune cells and damaged, dying or stressed cells. The NLR family pyrin domain-containing 3 (NLRP3) inflammasome, when stimulated by this extracellular release of ATP, activates caspase-1 and results in the secretion of the cytokines IL-1β and IL-18, which in turn activate innate and adaptive immune responses (Stagg and Smyth (2010) *Oncogene* 29:5346-5358). ATP is catabolized into adenosine by the enzymes CD39 and CD73. Activated adenosine acts as a highly immunosuppressive metabolite via a negative-feedback mechanism and has a pleiotropic effect against multiple immune cell types in the hypoxic tumor microenvironment (Stagg and Smyth (2010) *Oncogene* 29:5346-5358). Adenosine receptors $A_{2A}$ and $A_{2B}$ are expressed on a variety of immune cells and are stimulated by adenosine to promote cAMP-mediated signaling changes, resulting in immunosuppressive phenotypes of T-cells, B-cells, NK cells, dendritic cells, mast cells, macrophages, neutrophils, and NKT cells. As a result of this, adenosine levels can accumulate to over one hundred times their normal concentration in pathological tissues, such as solid tumors, which have been shown to overexpress ecto-nucleotidases, such as CD73. Adenosine has also been shown to promote tumor angiogenesis and development. An engineered bacterium that is auxotrophic for adenosine would thus exhibit enhanced tumor-targeting and colonization.

Immunostimulatory bacteria, such as *Salmonella typhi*, can be made auxotrophic for adenosine by deletion of the tsx gene (Bucarey et al. (2005) *Infection and Immunity* 73(10): 6210-6219) or by deletion of purD (Husseiny (2005) *Infection and Immunity* 73(3):1598-1605). In the Gram negative bacteria *Xanthomonas oryzae*, a purD gene knockout was shown to be auxotrophic for adenosine (Park et al. (2007) *FEMS Microbiol Lett* 276:55-59). As exemplified herein, *S. typhimurium* strain VNP20009, is auxotrophic for adenosine due to its purI deletion, hence, further modification to render it auxotrophic for adenosine is not required. Hence, embodiments of the immunostimulatory bacterial strains, as provided herein, are auxotrophic for adenosine. Such auxotrophic bacteria selectively replicate in the tumor microenvironment, further increasing accumulation and replication of the administered bacteria in tumors and decreasing the levels of adenosine in and around tumors, thereby reducing or eliminating the immunosuppression caused by accumulation of adenosine. Exemplary of such bacteria, provided herein is a modified strain of *S. typhimurium* containing purI–/msbB– mutations to provide adenosine auxotrophy.

c. Flagellin Deficient Strains

Flagella are organelles on the surface of bacteria that are composed of a long filament attached via a hook to a rotary motor that can rotate in a clockwise or counterclockwise manner to provide a means for locomotion. Flagellin is the generic name for the main structural protein that makes up bacterial flagella. They are cylindrical structures of variable length (approximately 530 nm) and about 21 nm in diameter. Flagella occur in Gram-positive and Gram-negative bacteria; they are structures of variable length that allow bacteria to move in liquid media. In addition to flagellin, the bacterial flagella contain other proteins that intervene in the assembly, the interaction with the cell's external envelopes, or that participate in chemotactic processes. Bacterial flagellin can activate interactions with specific receptors. Most are recognized by the "Toll-like-5" receptor (TLR5), which is located in the membrane of epithelial cells and immune system cells: monocytes, T lymphocytes, NK cells and immature dendritic cells. Once the flagellin is bound to TLR5, a signal transduction cascade is initiated through MyD88 (Myeloid differentiation primary response gene 88) in order to mediate the production of cytokines necessary for the development and regulation of an innate and adaptive immune response.

Flagella in *S. typhimurium* are important for chemotaxis and for establishing an infection via the oral route, due to the ability to mediate motility across the mucous layer in the gastrointestinal tract. While flagella have been demonstrated to be required for chemotaxis to and colonization of tumor cylindroids in vitro (Kasinskas and Forbes (2007) *Cancer Res.* 67(7):3201-3209), and motility has been shown to be important for tumor penetration (Toley and Forbes (2012) *Integr. Biol. (Camb).* 4(2):165-176), flagella are not required for tumor colonization in animals when the bacteria are administered intravenously (Stritzker et al. (2010) *International Journal of Medical Microbiology* 300:449-456). Each flagellar filament is composed of tens of thousands of flagellin subunits. The *S. typhimurium* chromosome contains two genes, fliC and fljB, that encode antigenically distinct flagellin monomers. Mutants defective for both fliC and fljB are non-motile and avirulent when administered via the oral route of infection, but maintain virulence when administered parenterally.

Flagellin is a major pro-inflammatory determinant of *Salmonella* (Zeng et al. (2003) *J. Immunol.* 171:3668-3674), and is directly recognized by TLR5 on the surface of cells, and by NLCR4 in the cytosol (Lightfield et al. (2008) *Nat. Immunol.* 9(10):1171-1178). Both pathways lead to pro-inflammatory responses resulting in the secretion of cytokines, including IL-1β, IL-18, TNF-α and IL-6. Attempts have been made to make *Salmonella*-based cancer immunotherapy more potent by increasing the pro-inflammatory response to flagellin by engineering the bacteria to secrete *Vibrio vulnificus* flagellin B, which induces greater inflammation than flagellin encoded by fliC and fljB (Zheng et al. (2017) *Sci. Transl. Med.* 9(376):eaak9537).

For use in the methods herein, immunostimulatory bacteria, such as *Salmonella* bacteria, such as *S. typhimurium*, are engineered to lack both flagellin subunits fliC and fljB, to reduce pro-inflammatory signaling. For example, as shown herein, a *Salmonella* strain lacking msbB, which results in reduced TNF-alpha induction, is combined with fliC and fljB knockouts. This results in a *Salmonella* strain that has a combined reduction in TNF-alpha induction and reduction in TLR5 recognition. These modifications can be combined with msbB⁻,fliC⁻ and fljB⁻, and transformed with an immunostimulatory plasmid, optionally containing CpGs, and also inhibitory RNAi molecule(s), such as shRNA or miRNA, targeting an immune checkpoint. The resulting bacteria have reduced pro-inflammatory signaling, but robust anti-tumor activity.

For example, as provided herein, a fliC and fljB double mutant was constructed in a wild-type *Salmonella typhimurium* strain, and in the asd deleted strain of *S. typhimurium* designated VNP20009. VNP20009, which is attenuated for virulence by disruption of purI/purM, also contains an msbB deletion that results in production of a lipid A subunit that is less toxigenic than wild-type lipid A. This results in reduced TNF-α production in the mouse model after intravenous administration, compared to strains with wild-type lipid A. The resulting strain is exemplary of strains that are attenuated for bacterial inflammation by modification of lipid A to reduce TLR2/4 signaling, and deletion of the flagellin subunits to reduce TLR5 recognition and inflammasome induction. Deletion of the flagellin subunits combined with modification of the LPS allows for greater tolerability in the host, and directs the immuno-stimulatory response towards delivery of RNA interference against desired targets in the TME which elicit an anti-tumor response and promote an adaptive immune response to the tumor.

d. *Salmonella* Engineered to Escape the *Salmonella* Containing Vacuole (SCV)

*Salmonella*, such as *S. typhimurium*, are intracellular pathogens that replicate primarily in a membrane bound compartment called a *Salmonella* containing vacuole (SCV). In some epithelial cell lines and at a low frequency, *S. typhimurium* have been shown to escape into the cytosol where they can replicate. *Salmonella* engineered to escape the SCV with higher efficiency will be more efficient at delivering macromolecules, such as plasmids, as the lipid bilayer of the SCV is a potential barrier. Provided herein are *Salmonella* and methods that have enhanced frequency of SCV escape. This is achieved by deletion of genes required for *Salmonella* induced filament (SIF) formation. These mutants have an increased frequency of SCV escape and can replicate in the cytosol.

For example, enhanced plasmid delivery using a sifA mutant of *S. typhimurium* has been demonstrated. The sifA gene encodes SPI-2, T3SS-2 secreted effector protein that mimics or activates a RhoA family of host GTPases (Ohlson et al. (2008) *Cell Host & Microbe* 4:434-446). Other genes encoding secreted effectors involved in SIF formation can be targeted. These include, for example, sseJ, sseL, sopD2, pipB2, sseF, sseG, spvB, and steA. Enhancing the escape of *S. typhimurium* by prevention of SIF formation releases live bacteria into the cytosol, where they can replicate.

Another method to enhance *S. typhimurium* escape from the SCV and increase the delivery of macromolecules such as plasmids, is the expression of a heterologous hemolysin that results in pore formation in, or rupture of, the SCV membrane. One such hemolysin is the Listeriolysin O protein (LLO) from *Listeria monocytogenes*, which is encoded by the hlyA gene. LLO is a cholesterol-dependent pore-forming cytolysin that is secreted from *L. monocytogenes* and is primarily responsible for phagosomal escape and entry into the cytosol of host cells. Secretion of LLO from *S. typhimurium* can result in bacterial escape and lead to replication in the cytosol. To prevent intact *S. typhimurium* from escaping the SCV and replicating in the cytosol, the nucleotides encoding the signal sequence can be removed from the gene. In this manner, the active LLO is contained within the cytoplasm of the *S. typhimurium* and LLO is only released when the bacteria undergo lysis. As provided herein, VNP20009 engineered to express cytoLLO to enhance delivery of plasmids for expression of interfering RNAs to targets, such as TREX1, can increase the therapeutic potency of the immunostimulatory bacteria.

e. Deletions in *Salmonella* Genes Required for Biofilm Formation

Bacteria and fungi are capable of forming multicellular structures called biofilms. Bacterial biofilms are encased within a mixture of secreted and cell wall-associated polysaccharides, glycoproteins, and glycolipids, as well as extracellular DNA, known collectively as extracellular polymeric substances. These extracellular polymeric substances protect the bacteria from multiple insults, such as cleaning agents, antibiotics, and antimicrobial peptides. Bacterial biofilms allow for colonization of surfaces, and are a cause of significant infection of prosthetics, such as injection ports and catheters. Biofilms can also form in tissues during the course of an infection, which leads to increases in the duration of bacterial persistence and shedding, and limits the effectiveness of antibiotic therapies. Chronic persistence of bacteria in biofilms is associated with increased tumorigenesis, for example in *S. typhi* infection of the gall bladder (Di Domenico et al. (2017) *Int. J. Mol. Sci.* 18:1887).

*S. typhimurium* biofilm formation is regulated by CsgD. CsgD activates the csgBAC operon, which results in increased production of the curli fimbrial subunits CsgA and CsgB (Zakikhani et al. (2010) *Molecular Microbiology* 77(3):771-786). CsgA is recognized as a PAMP by TLR2 and induces production of IL-8 from human macrophages (Tukel et al. (2005) *Molecular Microbiology* 58(1):289-304). Further, CsgD indirectly increases cellulose production by activating the adrA gene that encodes for di-guanylate cyclase. The small molecule cyclic di-guanosine monophosphate (c-di-GMP) generated by AdrA is a ubiquitous secondary messenger found in almost all bacterial species. The AdrA-mediated increase in c-di-GMP enhances expression of the cellulose synthetase gene bcsA, which in turn increases cellulose production via stimulation of the bcsABZC and bcsEFG operons. Reduction in the capability of immunostimulatory bacteria such as *S. typhimurium* to form biofilms can be achieved through deletion of genes involved in biofilm formation such as, for example, csgD, csgA, csgB, adrA, bcsA, bcsB, bcsZ, bcsE, bcsF, bcsG, dsbA or dsbB (Anwar et al. (2014) *Plos One* 9(8):e106095).

*S. typhimurium* biofilm formation is regulated by CsgD. CsgD activates the csgBAC operon, which results in increased production of the curli fimbrial subunits CsgA and CsgB (Zakikhany et al. (2010) *Molecular Microbiology* 77(3):771-786). CsgA is recognized as a PAMP by TLR2 and induces production of IL-8 from human macrophages (Tukel et al. (2005) *Molecular Microbiology* 58(1): 289-304). Further, CsgD indirectly increases cellulose production by activating the adrA gene that encodes for di-guanylate cyclase. The small molecule cyclic di-guanosine monophosphate (c-di-GMP) generated by AdrA is a ubiquitous secondary messenger found in almost all bacterial species. The AdrA-mediated increase in c-di-GMP enhances expression of the cellulose synthetase gene bcsA, which in turn increases cellulose production via stimulation of the bcsABZC and bcsEFG operons. Reduction in the capability of immunostimulatory bacteria such as *S. typhimurium* to form biofilms can be achieved through deletion of genes involved in biofilm formation such as, for example, csgD, csgA, csgB, adrA, bcsA, bcsB, bcsZ, bcsE, bcsF, bcsG, dsbA or dsbB (Anwar et al. (2014) *Plos One* 9(8):e106095).

The adrA gene encodes a di-guanylate cyclase that produces c-di-GMP, which is required for *S. typhimurium* biofilm formation. c-di-GMP binds to and is an agonist for the host cytosolic protein STING. As described above, STING agonists are pursued as anti-cancer treatments, vaccine adjuvants, and bacteria engineered to secrete cyclic di-nucleotides for use in immunotherapies (Libanova 2012, Synlogic 2018 AACR poster). Immunostimulatory bacteria that are reduced in c-di-GMP production via the deletion of adrA appears to be counterintuitive, but bacterial mutants, such as *S. typhimurium* mutants that are unable to form biofilms (including an adrA mutant), have demonstrated reduced therapeutic potential in mouse tumor models (Crull et al. (2011) *Cellular Microbiology* 13(8):1223-1233). Further, several human alleles of STING are refractory to binding bacterially-produced 3'3' CDNs (Corrales et al. (2015) *Cell Reports* 11:1022-1023).

As described herein, bacterial strains, such as *S. typhimurium* strains, that are engineered to be adenosine auxotrophic, and are reduced in their ability to induce pro-inflammatory cytokines by modification of the LPS and/or deletion of flagellin, and/or deletion of genes required for biofilm formation, and further modified to deliver interfering RNAs, promote robust anti-tumor immune responses.

f. Deletions in Genes in the LPS Biosynthetic Pathway

The LPS of Gram negative bacteria is the major component of the outer leaflet of the bacterial membrane. It is composed of three major parts, lipid A, a non-repeating core oligosaccharide, and the O antigen (or O polysaccharide). O antigen is the outermost portion on LPS and serves as a protective layer against bacterial permeability, however, the sugar composition of O antigen varies widely between strains. The lipid A and core oligosaccharide vary less, and are more typically conserved within strains of the same species. Lipid A is the portion of LPS that contains endotoxin activity. It is typically a disaccharide decorated with multiple fatty acids. These hydrophobic fatty acid chains anchor the LPS into the bacterial membrane, and the rest of the LPS projects from the cell surface. The lipid A domain is responsible for much of the toxicity of Gram-negative bacteria. Typically, LPS in the blood is recognized as a significant pathogen associated molecular pattern (PAMP) and induces a profound pro-inflammatory response. LPS is the ligand for a membrane-bound receptor complex comprising CD14, MD2 and TLR4. TLR4 is a transmembrane protein that can signal through the MyD88 and TRIF pathways to stimulate the NFκB pathway and result in the production of pro-inflammatory cytokines such as TNF-α and IL-1β, the result of which can be endotoxic shock, which can be fatal. LPS in the cytosol of mammalian cells can bind directly to the CARD domains of caspases 4, 5, and 11, leading to autoactivation and pyroptotic cell death (Hagar et al. (2015) *Cell Research* 25:149-150). The composition of lipid A and the toxigenicity of lipid A variants is well documented. For example, a monophosphorylated lipid A is much less inflammatory than lipid A with multiple phosphate groups. The number and length of the acyl chains on lipid A can also have a profound impact on the degree of toxicity. Canonical lipid A from *E. coli* has six acyl chains, and this hexa-acylation is potently toxic. *S. typhimurium* lipid A is similar to that of *E. coli*; it is a glucosamine disaccharide that carries four primary and two secondary hydroxyacyl chains (Raetz and Whitfield (2002) *Annu. Rev. Biochem.* 71:635-700). As described above, msbB mutants of *S. typhimurium* cannot undergo the terminal myristoylation of its LPS and produces predominantly penta-acylated LPS that is significantly less toxic than hexa-acylated lipid A. The modification of lipid A with palmitate is catalyzed by palmitoyl transferase (PagP). Transcription of the pagP gene is under control of the PhoP/PhoQ system which is activated by low concentrations of magnesium, e.g., inside the SCV. Thus, the acyl content of *S. typhimurium* is variable, and with wild type bacteria it can be hexa- or penta-acylated. The ability of *S. typhimurium* to palmitate its lipid A increases resistance to antimicrobial peptides that are secreted into phagolysozomes.

In wild type *S. typhimurium*, expression of pagP results in a lipid A that is hepta-acylated. In an msbB mutant (in which the terminal acyl chain of the lipid A cannot be added), the induction of pagP results in a hexa-acylated LPS (Kong et al. (2011) *Infection and Immunity* 79(12):5027-5038). Hexa-acylated LPS has been shown to be the most pro-inflammatory. While other groups have sought to exploit this pro-inflammatory signal, for example, by deletion of pagP to allow only hexa-acylated LPS to be produced (Felgner et al. (2016) *Gut Microbes* 7(2):171-177; (Felgner et al. (2018) *Oncoimmunology* 7(2): e1382791), this can lead to poor tolerability, due to the TNF-α-mediated pro-inflammatory nature of the LPS and paradoxically less adaptive immunity (Kocijancic et al. (2017) *Oncotarget* 8(30):49988-50001). Provided herein, is a live attenuated strain of *S. typhimurium* that can only produce penta-acylated LPS, that contains a deletion of the msbB gene (that prevents the terminal myristoylation of lipid A, as described above), and is further modified by deletion of pagP (preventing palmitoylation). A strain modified to produce penta-acylated LPS will allow for lower levels of pro-inflammatory cytokines, increased sensitivity to antimicrobial peptides, enhanced tolerability, and increased anti-tumor immunity when further modified to express interfering RNAs against immune checkpoints such as TREX1.

g. Deletions of SPI-1 Genes

As described above, in *Salmonella* species, such as *S. typhimurium*, pathogenesis involves a cluster of genes referred to as *Salmonella* pathogenicity islands (SPIs). SPI-1 mediates invasion of epithelial cells. SPI-1 encodes a type 3 secretion system (T3SS) that is responsible for translocation of effector proteins into the cytosol of host cells that can cause actin rearrangements that lead to uptake of *Salmonella*. The SPI-1 T3SS is essential for crossing the gut epithelial layer, but is dispensable for infection when bacteria are injected parenterally. The injection of some proteins and the needle complex itself can also induce inflammasome activation and pyroptosis of phagocytic cells. This pro-inflammatory cell death can limit the initiation of a robust adaptive immune response by directly inducing the death of antigen-presenting cells (APCs), as well as modifying the cytokine milieu to prevent the generation of memory T-cells. SPI-1 genes comprise a number of operons including: sit-ABCD, sprB, avrA, hilC, orgABC, prgKJIH, hilD, hilA, iagB, sptP, sicC, iacP, sipADCB, sicA, spaOPQRS, invFGE-ABCIJ, and invH.

As exemplified herein, a live attenuated strain of *S. typhimurium* that contains a purI deletion, an msbB deletion, an asd gene deletion and is engineered to deliver plasmids encoding interfering RNA, is further modified to delete SPI-1 genes. For example, deletion of a regulatory gene (e.g., hilA or invF) required for expression of the SPI-1-associated type 3 secretion system (T3SS-1), a T3SS-1 structural gene (e.g., invG orprgH), or a T3SS-1 effector gene (e.g., sipA or avrA). This secretion system is responsible for injecting effector proteins into the cytosol of non-phagocytic host cells such as epithelial cells that cause the uptake of the bacteria. In this example, the additional deletion of the hilA gene from a therapeutic *Salmonella typhimurium* strain that is administered either intravenously or intratumorally focuses the *S. typhimurium* infection towards phagocytic cells that do not require the SPI-1 T3SS for uptake, and prolongs the longevity of these phagocytic cells. The hilA mutation also reduces the quantity of pro-inflammatory cytokines, increasing the tolerability of the therapy, as well as the quality of the adaptive immune response.

h. Endonuclease I (endA) Mutations to Increase Plasmid Delivery

The endA gene (for example, SEQ ID NO:250) encodes an endonuclease I (for example, SEQ ID NO:251) that mediates degradation of double stranded DNA in the periplasm of Gram negative bacteria. Most common strains of laboratory *E. coli* are endA⁻, as a mutation in the endA gene allows for higher yields of plasmid DNA. This gene is conserved among species. To facilitate intact plasmid DNA delivery, the endA gene of the engineered immunostimulatory bacteria is deleted or mutated to prevent its endonuclease activity. Exemplary of such mutations is an E208K amino acid substitution (Durfee et al. (2008) *J. Bacteriol.* 190(7):2597-2606) or a corresponding mutation in the species of interest. endA, including E208, is conserved among bacterial species, including *Salmonella*. Thus, the E208K mutation can be used to eliminate endonuclease activity in other species, including *Salmonella* species. Those of skill in the art can introduce other mutations or deletions to eliminate endA activity. Effecting this mutation or deleting or disrupting the gene to eliminate activity of the endA in the immunostimulatory bacteria herein, such as in *Salmonella*, increases efficiency of intact plasmid DNA delivery, thereby increasing expression of the RNAs, such as the shRNA and/or miRNA, targeting any or two or more of the immune checkpoints, encoded in the plasmid, thereby increasing RNAi-mediated knockdown of checkpoint genes and enhancing anti-tumor efficacy.

i. RIG-I Inhibition

Of the TLR-independent type I IFN pathways, one is mediated by host recognition of single-stranded (ss) and double-stranded (ds) RNA in the cytosol. These are sensed by RNA helicases, including retinoic acid-inducible gene I (RIG-I), melanoma differentiation-associated gene 5 (MDA-5), and through the IFN-β promoter stimulator 1 (IPS-1) adaptor protein-mediated phosphorylation of the IRF-3 transcription factor, leading to induction of type I IFN (Ireton and Gale (2011) *Viruses* 3(6):906-919). RIG-I recognizes dsRNA and ssRNA bearing 5'-triphosphates. This moiety can directly bind RIG-I, or be synthesized from a poly(dA-dT) template by the poly DNA-dependent RNA polymerase III (Pol III) (Chiu, Y. H. et al. (2009) *Cell* 138(3):576-91). A poly(dA-dT) template containing two AA dinucleotide sequences occurs at the U6 promoter transcription start site in a common lentiviral shRNA cloning vector. Its subsequent deletion in the plasmid prevents type I IFN activation (Pebernard et al. (2004) *Differentiation* 72:103-111). A RIG-I binding sequence can be included in the plasmids provided herein; inclusion can increase immunostimulation that increases anti-tumoral activity of the immunostimulatory bacteria herein.

j. DNase II Inhibition

Another nuclease responsible for degrading foreign and self DNA is DNase II, an endonuclease, which resides in the endosomal compartment and degrades DNA following apoptosis. Lack of DNase II (Dnase2a in mice) results in the accumulation of endosomal DNA that escapes to the cytosol and activates cGAS/STING signaling (Lan et al. (2014) *Cell Rep.* 9(1):180-192). Similar to TREX1, DNase II-deficiency in humans presents with autoimmune type I interferonopathies. In cancer, dying tumor cells that are engulfed by tumor-resident macrophages prevent cGAS/STING activation and potential autoimmunity through DNase II digestion of DNA within the endosomal compartment (Ahn et al. (2018) *Cancer Cell* 33:862-873). Hence, embodiments of the immunostimulatory bacterial strains, as provided herein, encode RNAi, such as shRNA or miRNA that inhibit, suppress or disrupt expression of DNase II, which can inhibit DNase II in the tumor microenvironment, thereby provoking accumulation of endocytosed apoptotic tumor DNA in the cytosol, where it can act as a potent cGAS/STING agonist.

k. RNase H2 Inhibition

While TREX1 and DNase II function to clear aberrant DNA accumulation, RNase H2 functions similarly to eliminate pathogenic accumulation of RNA:DNA hybrids in the cytosol. Similar to TREX1, deficiencies in RNase H2 also contribute to the autoimmune phenotype of Aicardi-Goutières syndrome (Rabe, B. (2013) *J Mol Med.* 91:1235-1240). Specifically, loss of RNase H2 and subsequent accumulation of RNA:DNA hybrids or genome-embedded ribonucleotide substrates has been shown to activate cGAS/STING signaling (Mackenzie et al. (2016) *EMBO J.* 35(8): 831-44). Hence, embodiments of the immunostimulatory bacterial strains, as provided herein, encode RNAi, such as shRNA or miRNA that inhibit, suppress or disrupt expression of RNase H2, to thereby inhibit RNase H2, resulting in tumor-derived RNA:DNA hybrids and derivatives thereof, which activate cGAS/STING signaling and anti-tumor immunity.

l. Stabilin-1/CLEVER-1 Inhibition

Another molecule expressed primarily on monocytes and involved in regulating immunity is stabilin-1 (gene name STAB1, also known as CLEVER-1, FEEL-1). Stabilin-1 is a type I transmembrane protein that is upregulated on endothelial cells and macrophages following inflammation, and in particular, on tumor-associated macrophages (Kzhyshkowska et al. (2006) *J. Cell. Mol. Med.* 10(3):635-649). Upon inflammatory activation, stabilin-1 acts as a scavenger and aids in wound healing and apoptotic body clearance, and can prevent tissue injury, such as liver fibrosis (Rantakari et al. (2016) *Proc. Natl. Acad. Sci. U.S.A.* 113 (33):9298-9303). Upregulation of stabilin-1 directly inhibits antigen-specific T cell responses, and knockdown by siRNA in monocytes was shown to enhance their pro-inflammatory function (Palani et al. (2016) *J. Immunol.* 196:115-123). Hence, embodiments of the immunostimulatory bacterial strains, as provided herein, encode RNAi, such as shRNA or miRNA that inhibit, suppress or disrupt expression of Stabilin-1/CLEVER-1 in the tumor microenvironment, thereby enhancing the pro-inflammatory functions of tumor-resident macrophages.

m. Bacterial Culture Conditions

Culture conditions for bacteria can influence their gene expression. It has been documented that *S. typhimurium* can induce rapid pro-inflammatory caspase-dependent cell death of macrophages, but not epithelial cells, within 30 to 60 min of infection by a mechanism involving the SPI-1 and its associated T3SS-1 (Lundberg et al. (1999) *Journal of Bacteriology* 181(11):3433-3437). It is now known that this cell death is mediated by activation of the inflammasome that subsequently activates caspase-1, which promotes the maturation and release of IL-1β and IL-18 and initiates a novel form of cell death called pyroptosis (Broz and Monack (2011) *Immunol. Rev.* 243(1):174-190). This pyroptotic activity can be induced by using log phase bacteria, whereas stationary phase bacteria do not induce this rapid cell death in macrophages. The SPI-1 genes are induced during log phase growth. Thus, by harvesting *S. typhimurium* to be used therapeutically at stationary phase, rapid pyroptosis of macrophages can be prevented. Macrophages are important mediators of the innate immune system and they can act to secrete cytokines that are critical for establishing appropriate anti-tumor responses. In addition, limiting pro-inflammatory cytokines such as IL-1β and IL-18 secretion will improve the tolerability of administered *S. typhimurium* therapy. As provided herein, immunostimulatory *S. typhimurium* harvested at stationary phase will be used to induce anti-tumor responses.

F. BACTERIAL ATTENUATION AND COLONIZATION

1. Deletion of Flagellin (fliC⁻/fljB⁻)

Provided are immunostimulatory bacteria, such as the *Salmonella* species *S. typhimurium*, engineered to lack both flagellin subunits fliC and fljB, to reduce pro-inflammatory signaling. For example, as shown herein, a *Salmonella* strain lacking msbB, which results in reduced TNF-alpha induction, is combined with fliC and fljB knockouts. The resulting *Salmonella* strain has a combined reduction in TNF-alpha induction and reduction in TLR5 recognition. These modifications, msbB⁻, fliC⁻ and fljB⁻, can be combined with a bacterial plasmid, optionally containing CpGs, and also a cDNA expression cassette to provide expression of a therapeutic protein under the control of a eukaryotic promoter, such as for example, an immunostimulatory protein, such as a cytokine or chemokine, such as IL-2, and/or also inhibitory molecules, such as antibodies, including antibody fragments, such as nanobodies, and/or RNAi molecule(s), targeting an immune checkpoint, such as TREX1, PD-L1, VISTA, SIRP-alpha, TGF-beta, beta-catenin, CD47, VEGF, and combinations thereof. The resulting bacteria have reduced proinflammatory signaling, and robust anti-tumor activity.

For example, as exemplified herein, a fliC⁻ and fljB⁻ double mutant was constructed in the asd-deleted strain of *S. typhimurium* strain VNP20009 or in a wild-type *Salmonella typhimurium*, such as one having all of the identifying characteristics of the strain deposited under ATCC accession no. 14028. VNP20009, which is a derivative of ATCC 14028, was attenuated for virulence by disruption of purI/purM, and was also engineered to contain an msbB deletion that results in production of a lipid A subunit of LPS that is less toxigenic than wild-type lipid A. This results in reduced TNF-α production in the mouse model after intravenous administration, compared to strains with wild-type lipid A.

A fliC⁻ and fljB⁻ double mutant was constructed on a wild-type strain of S. typhimurium and also engineered to contain the asd, purI/purM and msbB deletions. The bacterium is optionally pagP⁻. The resulting strains are exemplary of strains that are attenuated for bacterial inflammation by modification of lipid A to reduce TLR2/4 signaling, and deletion of the flagellin subunits to reduce TLR5 recognition and inflammasome induction. Deletion of the flagellin subunits combined with modification of the LPS allows for greater tolerability in the host, and directs the immunostimulatory response towards production of immunostimulatory proteins. The delivery of RNA interference by the modified bacteria against desired targets in the TME elicits an anti-tumor response and promotes an adaptive immune response to the tumor.

2. Deletion of Genes in the LPS Biosynthetic Pathway

The LPS of Gram-negative bacteria is the major component of the outer leaflet of the bacterial membrane. It is composed of three major parts, lipid A, a nonrepeating core oligosaccharide, and the O antigen (or O polysaccharide). O antigen is the outermost portion on LPS and serves as a protective layer against bacterial permeability, however, the sugar composition of O antigen varies widely between strains. The lipid A and core oligosaccharide vary less, and are more typically conserved within strains of the same species. Lipid A is the portion of LPS that contains endotoxin activity. It is typically a disaccharide decorated with multiple fatty acids. These hydrophobic fatty acid chains anchor the LPS into the bacterial membrane, and the rest of the LPS projects from the cell surface. The lipid A domain is responsible for much of the toxicity of Gram-negative bacteria. Typically, LPS in the blood is recognized as a significant pathogen associated molecular pattern (PAMP), and induces a profound pro-inflammatory response. LPS is the ligand for a membrane-bound receptor complex comprising CD14, MD2 and TLR4. TLR4 is a transmembrane protein that can signal through the MyD88 and TRIF pathways to stimulate the NFκB pathway and result in the production of pro-inflammatory cytokines such as TNF-α and IL-1β, the result of which can be endotoxic shock, which can be fatal. LPS in the cytosol of mammalian cells can bind directly to the CARD domains of caspases 4, 5, and 11, leading to autoactivation and pyroptotic cell death (Hagar et al. (2015) *Cell Research* 25:149-150). The composition of lipid A and the toxigenicity of lipid A variants is well documented. For example, a monophosphorylated lipid A is much less inflammatory than lipid A with multiple phosphate groups. The number and length of the acyl chains on lipid A can also have a profound impact on the degree of toxicity. Canonical lipid A from *E. coli* has six acyl chains, and this hexa-acylation is potently toxic. *S. typhimurium* lipid A is similar to that of *E. coli*; it is a glucosamine disaccharide that carries four primary and two secondary hydroxyacyl chains (Raetz and Whitfield (2002) Annu. Rev. Biochem. 71:635-700). As described above, msbB⁻ mutants of *S. typhimurium* cannot undergo the terminal myristoylation of its LPS and produce predominantly penta-acylated lipid A that is significantly less toxic than hexa-acylated lipid A. The modification of lipid A with palmitate is catalyzed by palmitoyl transferase (PagP). Transcription of the pagP gene is under control of the PhoP/PhoQ system, which is activated by low concentrations of magnesium, e.g., inside the SCV. Thus, the acyl content of *S. typhimurium* is variable, and with wild-type bacteria, it can be hexa- or penta-acylated. The ability of *S. typhimurium* to palmitate its lipid A increases resistance to antimicrobial peptides that are secreted into phagolysozomes.

In wild-type *S. typhimurium*, expression of pagP results in a lipid A that is hepta-acylated. In an msbB⁻ mutant (in which the terminal acyl chain of the lipid A cannot be added), the induction of pagP results in a hexa-acylated LPS (Kong et al. (2011) *Infection and Immunity* 79(12):5027-5038). Hexa-acylated LPS has been shown to be the most pro-inflammatory. While other groups have sought to exploit this pro-inflammatory signal, for example, by deletion of pagP to allow only hexa-acylated LPS to be produced (Felgner et al. (2016) *Gut Microbes* 7(2):171-177; Felgner et al. (2018) *Oncoimmunology* 7(2): e1382791), this can lead to poor tolerability, due to the TNF-α-mediated pro-inflammatory nature of the LPS and paradoxically less adaptive immunity (Kocijancic et al. (2017) *Oncotarget* 8(30):49988-50001). Exemplified herein, is a live attenuated strain of *S. typhimurium* that can only produce penta-acylated LPS, that contains a deletion of the msbB gene (that prevents the terminal myristoylation of lipid A, as described above), and is further modified by deletion of pagP (preventing palmitoylation). A strain modified to produce penta-acylated LPS will allow for lower levels of pro-inflammatory cytokines, improved stability in the blood and resistance to complement fixation, increased sensitivity to antimicrobial peptides, enhanced tolerability, and increased anti-tumor immunity when further modified to express heterologous immune-stimulatory proteins and/or interfering RNAs against immune checkpoints.

As provided herein, a pagP⁻ mutant was also constructed on an asd, msbB, purI/purM and fliC/fljB deleted strain of *S. typhimurium* VNP20009 or wild-type *S. typhimurium*. The resulting strains are exemplary of strains that are attenuated for bacterial inflammation by modification of lipid A to reduce TLR2/4 signaling, and deletion of the flagellin subunits to reduce TLR5 recognition and inflammasome induction, and deletion of pagP to produce penta-acylated LPS. Deletion of the flagellin subunits combined with modification of the LPS allows for greater tolerability in the host, and greater stability in the blood and resistance to complement fixation, providing for improved trafficking to the tumor site, in order to direct the immuno-stimulatory response towards production of any gene product, such as immune-stimulatory proteins and/or delivery of RNA interference against desired targets in the TME to elicit an anti-tumor response and promote an adaptive immune response to the tumor.

3. Colonization

VNP20009 is an attenuated *S. typhimurium*-based microbial cancer therapy that was developed for the treatment of cancer. VNP20009 is attenuated through deletion of the genes msbB and purI (purM). The purI deletion renders the microbe auxotrophic for purines or adenosine. Deletion of the msbB gene reduced the toxicity associated with lipopolysaccharide (LPS) by preventing the addition of a terminal myristyl group to the lipid A domain (Khan et al. (1998) *Mol. Microbiol.* 29:571-579).

There is a difference between mouse and humans in the ability of VNP20009 to colonize tumors. Systemic administration of VNP20009 resulted in colonization of mouse tumors; whereas systemic administration of VNP20009 in human patients resulted in very little colonization. It was shown that in mice, VNP20009 showed a high degree of tumor colonization after systemic administration (Clairmont et al. (2000) *J. Infect. Dis.* 181:1996-2002; and Bermudes et al. (2001) *Biotechnol. Genet. Eng. Rev.* 18:219-33). In a Phase 1 Study in advanced melanoma patients, however, very little VNP20009 was detected in human tumors after a 30-minute intravenous infusion (see, Toso et al. (2002) *J. Clin. Oncol.* 20:142-52). Patients that entered into a follow-up study evaluating a longer, four-hour infusion of VNP20009, also demonstrated a lack of detectable VNP20009 after tumor biopsy (Heimann et al. (2003) *J. Immunother.* 26:179-180). Following intratumoral administration, colonization of a derivative of VNP20009 was detected (Nemunaitis et al. (2003) *Cancer Gene Ther.* 10:737-44). Direct intratumoral administration of VNP20009 to human tumors resulted in tumor colonization, indicating that human tumors can be colonized at a high level, and that the difference in tumor colonization between mice and humans occurs only after systemic administration.

It is shown herein, (see, e.g., Example 22) that VNP20009 is inactivated by human complement, which leads to low tumor colonization. The data demonstrate that complement inactivates such strains. Strains that provide improved resistance to complement are provided. These strains contain modifications in the bacterial genome and also can carry a plasmid, typically in low or medium copy number, to encode genes to provide for replication (asd under the control of a eukaryotic promoter), and nucleic acid(s) encoding a therapeutic product(s), such as, but not limited to, RNAi, immunostimulatory protein, such as cytokines, and other such therapeutic genes, as described elsewhere herein. The table below summarizes the bacterial genotypes/modifications, their functional effects, and the effects/benefits.

| Genotype/Modification | Functional effect | Effect/Benefit |
|---|---|---|
| ΔpurI | Purine/adenosine auxotrophy | Tumor-specific enrichment Limited replication in healthy tissue |
| ΔmsbB | LPS surface coat modification | Decreased TLR4 recognition Reduced cytokine profile Improved safety |
| ΔFLG | Flagella knockout | Removes major inflammatory and immune-suppressive element Decreased TLR5 recognition Reduced cytokine profile Improved safety |
| ΔpagP | LPS surface coat modifications | Removes major inflammatory and immune-suppressive element Decreased TLR4 recognition Reduced IL-6 profile Improved safety |
| Δasd (in genome) | Plasmid maintenance | Improved plasmid delivery Plasmid maintenance |
| plasmid | Express gene products under control of host-recognized promoter | Eukaryotic promoter limits expression to cells containing the plasmid Long term expression in the TME (i.e., asd encoded on plasmid under control of host-recognized promoter) Expression of therapeutic product(s) |

Strains provided herein are ΔFLG and/or ΔpagP. Additionally, the strains are one or more of ΔpurI (ΔpurM), ΔmsbB, and Δasd (in the bacterial genome). The plasmid is modified to encode products under control of host-recognized promoters (e.g., eukaryotic promoters, such as RNA polymerase II promoters, including those from eukaryotes, and animal viruses). The plasmids can encode asd to permit replication in vivo, as well as nucleic acids with other beneficial functions and gene products as described elsewhere herein.

The immunostimulatory bacteria are derived from suitable bacterial strains. Bacterial strains can be attenuated strains, or strains that are attenuated by standard methods, or that, by virtue of the modifications provided herein, are attenuated in that their ability to colonize is limited primarily to immunoprivileged tissues and organs, particularly immune and tumor cells, including solid tumors. Bacteria include, but are not limited to, for example, strains of *Salmonella, Shigella, Listeria, E. coli*, and *Bifidobacteriae*. For example, species include *Shigella sonnei, Shigella flexneri, Shigella dysenteriae, Listeria monocytogenes, Salmonella typhi, Salmonella typhimurium, Salmonella gallinarum*, and *Salmonella enteritidis*. Other suitable bacterial species include *Rickettsia, Klebsiella, Bordetella, Neisseria, Aeromonas, Francisella, Corynebacterium, Citrobacter, Chlamydia, Haemophilus, Brucella, Mycobacterium, Mycoplasma, Legionella, Rhodococcus, Pseudomonas, Helicobacter, Vibrio, Bacillus*, and *Erysipelothrix*. For example, *Rickettsia rickettsii, Rickettsia prowazekii, Rickettsia tsutsugamushi, Rickettsia mooseri, Rickettsia sibirica, Bordetella bronchiseptica, Neisseria meningitidis, Neisseria gonorrhoeae, Aeromonas eucrenophila, Aeromonas salmonicida, Francisella tularensis, Corynebacterium pseudotuberculosis, Citrobacter freundii, Chlamydia pneumoniae, Haemophilus somnus, Brucella abortus, Mycobacterium intracellulare, Legionella pneumophila, Rhodococcus equi, Pseudomonas aeruginosa, Helicobacter mustelae, Vibrio cholerae, Bacillus subtilis, Erysipelothrix rhusiopathiae, Yersinia enterocolitica, Rochalimaea quintana*, and *Agrobacterium tumefaciens*.

Exemplary of the immunostimulatory bacteria provided herein are species of *Salmonella*. Exemplary of bacteria for modification as described herein are wild-type strains of *Salmonella*, such as the strain that has all of the identifying characteristics of the strain deposited in the ATCC as accession #14028. Engineered strains of *Salmonella typhimurium*, such as strain YS1646 (ATCC Catalog #202165; also referred to as VNP20009, see, International Application Publication No. WO 99/13053) that is engineered with plasmids to complement an asd gene knockout and antibiotic-free plasmid maintenance. The strains then are modified to delete the flagellin genes and/or to delete pagP. The strains also are rendered auxotrophic for purines, particularly the purine nucleoside base adenosine, and are asd$^-$ and msbB$^-$. The asd gene can be provided on a plasmid for replication in the eukaryotic host. These deletions and plasmids are described elsewhere herein. Any of the nucleic acid encoding therapeutic products and immunostimulatory proteins and products, described elsewhere herein and/or known to those of skill in the art, can be included on the plasmid. The plasmid generally is present in low to medium copy number as described elsewhere herein. Therapeutic products include immunostimulatory proteins, such as cytokines, that promote an anti-tumor immune response in the tumor microenvironment and other such products described herein.

G. CONSTRUCTING EXEMPLARY PLASMIDS

The immunostimulatory bacteria provided herein are modified. They include modifications to the bacterial genome and bacterial gene expression, and also, to include plasmids that encode products that are expressed in the bacteria by including a bacterial promoter, or in the host by including an appropriate eukaryotic promoter and other regulatory regions as appropriate.

To introduce the plasmids, the bacteria are transformed using standard methods, such as electroporation with purified DNA plasmids constructed with routine molecular biology tools (DNA synthesis, PCR amplification, DNA restriction enzyme digestion and ligation of compatible cohesive end fragments with ligase).

As discussed below, the plasmids encode one or more short hairpin (sh) RNA construct(s), or other inhibitory RNA modalities, whose expression inhibits or disrupts expression of targeted genes. The RNAi, such as shRNA or microRNA constructs, are expressed under control of a eukaryotic promoter, such as an RNA polymerase (RNAP) II or III promoter. Typically, RNAPIII (also referred to as POLIII) promoters are constitutive, and RNAPII (also referred to as POLII) can be regulated. In some examples, the shRNAs target the gene TREX1, to inhibit its expression. In some embodiments the plasmids encode a plurality of shRNAs that target to inhibit two or more checkpoint genes, such as shRNAs for inhibiting PD-L1, VISTA, SIRPα, CTNNB1, TGF-beta, and/or VEGF and any others known to those of skill in the art. Where a plurality of RNAi's, such as shRNAs, are encoded, expression of each is under control of different promoters.

As provided herein, bacterial strains, such as strains of Salmonella, including S. typhimurium, are modified or identified to be auxotrophic for adenosine in the tumor microenvironment, and to carry plasmids containing genes encoding shRNAs or microRNAs capable of knocking down gene expression of TREX1, PD-L1, VISTA, SIRP-alpha, beta-catenin, TGF-beta and VEGF. S. typhimurium is capable of infecting multiple cell types, including both tumor cells and macrophages. For cells infected with S. typhimurium, the plasmid is released and capable of being transcribed by RNA polymerases. shRNAs generated are then processed and capable of interfering with target mRNA gene expression.

1. Interfering RNAs (RNAi)

The plasmids herein encode the RNAi nucleic acids targeting the checkpoints and other targets of interest, as described above. RNAi includes shRNA, siRNA, and microRNA. RNA interference (RNAi) allows for the sequence-selective suppression of gene expression in eukaryotic cells using small interfering RNAs (siRNAs), which are short, synthetic, dsRNA molecules with a sequence homologous to the target gene. RNAi technology provides a powerful tool for the depletion of disease-related transcripts.

a. shRNA

The siRNAs, which are typically about 19-29 base pairs long, function by degrading specific host mRNA sequences, precluding translation into their respective protein products, effectively silencing the expression of the target gene. Short hairpin RNAs (shRNAs), containing a tight hairpin loop, are widely used in RNAi. shRNAs contain of two complementary RNA sequences, each 19-29 bps long, linked by a loop spacer of 4-15 nucleotides. The RNA sequence that is complementary to the target gene sequence (and is thus identical to the mRNA sequence), is known as the "sense" strand, while the strand which is complementary to the mRNA (and identical to the target gene sequence) is known as the "antisense" or "guide" strand. shRNA transcripts are processed by an RNase III enzyme known as Dicer into siRNA duplexes. The product is then loaded into the RNA-induced silencing complex (RISC) with Argonaute (Ago) proteins and other RNA-binding proteins. RISC then localizes the antisense, or "guide" strand to its complimentary mRNA sequence, which is subsequently cleaved by Ago (U.S. Pat. No. 9,624,494). The use of shRNA is preferred over siRNA, because it is more cost effective, high intracellular concentrations of siRNA are associated with off-target effects, and because the concentration of siRNA becomes diluted upon cell division. The use of shRNA, on the other hand, results in stable, long-term gene knockdown, without the need for multiple rounds of transfection (Moore et al. (2010) Methods Mol. Bio. 629:141-158).

Targets of interest for RNAi, such as micro-RNA and siRNA/shRNA-mediated silencing include, but are not limited to, developmental genes such as cytokines and their receptors, cyclin kinase inhibitors, neurotransmitters and their receptors, growth/differentiation factors and their receptors; oncogenes such as BCL2, ERBA, ERBB, JUN, KRAS, MYB, MYC; tumor suppressor genes such as BRCA1, BRCA2, MCC, p53; and enzymes such as ACC synthases and oxidases, ATPases, alcohol dehydrogenases, amylases, catalases, DNA polymerases, RNA polymerases, kinases, lactases and lipases (U.S. Pat. Nos. 7,732,417, 8,829,254, 8,383,599, 8,426,675, 9,624,494; U.S. Patent Publication No. 2012/0009153). Of particular interest are immune checkpoint targets, such as PD-1, PD-2, PD-L1, PD-L2, CTLA-4, IDO 1 and 2, CTNNB1 (β-catenin), SIRPα, VISTA, RNase H2, DNase II, CLEVER-1/Stabilin-1, LIGHT, HVEM, LAG3, TIM3, TIGIT, Galectin-9, KIR, GITR, TIM1, TIM4, CEACAM1, CD27, CD40, CD40L, CD48, CD70, CD80, CD86, CD112, CD137 (4-1BB), CD155, CD160, CD200, CD226, CD244 (2B4), CD272 (BTLA), B7-H2, B7-H3, B7-H4, B7-H6, ICOS, A2aR, A2bR, HHLA2, TLT-2, ILT-4, gp49B, PIR-B, HLA-G, ILT-2/4, OX40 and OX-40L. Other targets include MDR1, Arginase1, iNOs, IL-10, TGF-β, pGE2, STAT3, VEGF, KSP, HER2, Ras, EZH2, NIPP1, PP1, TAK1 and PLK1 (U.S. Patent Publication Nos. 2008/091375, 2009/0208534, 2014/0186401, 2016/0184456, 2016/0369282; International Application Publication Nos. WO 2012/149364, WO 2015/002969, WO 2015/032165, WO 2016/025582).

Bacteria are attractive vectors for the tumor-targeted delivery of siRNAs and shRNAs. Salmonella, for example, can be used for the delivery of shRNA plasmids against genetic targets such as DO (Blache et al. (2012) Cancer Res. 72(24):6447-6456; Manuel et al. (2015) Cancer Immunol. Res. 3(9):1096-1107; U.S. Patent Publication Nos. 2014/0186401, 2016/0184456; International Application Publication Nos. WO 2012/149364, WO 2015/002969); STAT3 (Manuel et al. (2011) Cancer Res. 71(12):4183-4191; Zhang et al. (2007) Cancer Res. 67(20):10038-10046; U.S. Patent Publication Nos. 2014/0186401, 2016/0184456; International Application Publication Nos. WO 2008/091375, WO 2012/149364, WO 2015/002969, WO 2015/032165); β-catenin (Guo et al. (2011) Gene Therapy 18:95-105; International Application Publication No. WO 2015/032165) and CTLA-4 (U.S. Patent Publication Nos. 2014/0186401, 2016/0184456; International Application Publication Nos. WO 2012/149364, WO 2015/002969).

Expressed RNAi, such as shRNAs, mediate long-term, stable knockdown of their target transcripts for as long as the shRNAs are transcribed. RNA Pol II and III promoters are used to drive expression of shRNA constructs, depending on the type of expression required. Consistent with their normal cellular roles in producing abundant, endogenous small RNAs, Pol III promoters (such as U6 or H1) drive high levels of constitutive shRNA expression, and their transcription initiation points and termination signals (4-6 thymidines) are well defined. Pol II promoter-driven shRNAs can be expressed tissue-specifically and are transcribed as longer precursors that mimic pri-miRNAs and have cap and polyA signals that must be processed. Such artificial miRNAs/shRNAs are efficiently incorporated into RISC, contributing to a more potent inhibition of target-gene expression; this allows lower levels of shRNA expression and might prevent saturation of components in the RNAi pathway. An additional advantage of Pol II promoters is that a single transcript can simultaneously express several miRNA and mimic shRNAs. This multiplexing strategy can be used to simultaneously knock down the expression of two or more therapeutic targets, or to target several sites in a single gene product (see, e.g., U.S. Publication No. 2009/0208534).

b. MicroRNA

MicroRNAs (miRNAs) are short, non-coding single-stranded RNA molecules that are about or are 20-24 nucleotides long. Naturally-occurring miRNAs are involved in the post-transcriptional regulation of gene expression; miRNAs do not encode genes. miRNAs have been shown to regulate cell proliferation and survival, as well as cellular differentiation. miRNAs inhibit translation or promote RNA degradation by binding to target mRNAs that share sequence complementarity. They affect the stability and translation of mRNAs; miRNAs inhibit translation, and/or promote RNA degradation, by binding to target mRNAs that share sequence complementarity. miRNAs, which occur in eukaryotes, are transcribed by RNA Pol II into capped and polyadenylated hairpin-containing primary transcripts, known as primary miRNAs, or pri-miRNAs. These pri-miRNAs are cleaved by the enzyme Drosha ribonuclease III and its cofactor Pasha/DGCR8 into ~70 nucleotide long precursor miRNA hairpins, known as precursor miRNAs, or pre-miRNAs, which are then transported from the nucleus into the cytoplasm, and cleaved by Dicer ribonuclease III into the miRNA: miRNA* duplex, with sense and antisense strand products that are approximately 22 nucleotides long. The mature miRNA is incorporated into the RNA-induced silencing complex (RISC), which recognizes and binds target mRNAs, usually at the 3-untranslated region (UTR), through imperfect base pairing with the miRNA, resulting in the inhibition of translation, or destabilization/degradation of the target mRNA (see, e.g., Auyeung et al. (2013) *Cell* 152(4):844-85).

As described herein, regulating gene expression by RNA interference (RNAi), often uses short hairpin RNAs (shRNAs) to inhibit, disrupt or other interfere with expression of targeted genes. While advantageously used, and used herein, in some instances, shRNAs can be poor substrates for small RNA biogenesis factors, they can be processed into a heterogeneous mix of small RNAs, and their precursor transcripts can accumulate in cells, resulting in the induction of sequence-independent, non-specific effects and leading to in vivo toxicity. miRNAs are contemplated for use herein. miRNA-like scaffolds, or artificial miRNAs (amiRNAs) can be used to reduce sequence-independent non-specific effects (Watanabe et al. (2016) *RNA Biology* 13(1):25-33; Fellmann et al. (2013) *Cell Reports* 5:1704-1713). In addition to improved safety profiles, amiRNAs are more readily transcribed by Pol II than shRNAs, allowing for regulated and cell-specific expression. Artificial miRNAs (amiRNAs), in comparison to shRNAs, can effectively, and in some cases, more potently, silence gene expression without generating large amounts of inhibitory RNAs (McBride et al. (2008) *Proc. Natl. Acad. Sci. U.S.A.* 105(15):5868-5873). This effect was determined to be due to the more effective processing of siRNA from pre-miRNA precursors than from shRNA transcripts (Boden et al. (2004) *Nucl. Acid Res.* 32(3):1154-1158).

miRNAs have been shown to regulate several cellular processes, including cell proliferation and survival, intracellular signaling, cellular metabolism, and cellular differentiation. In 1993, the first miRNA was identified in *C. elegans* (Lee et al. (1993) *Cell* 75:843-854), and later, mammalian miRNAs were identified (Pasquinelli et al. (2000) *Nature* 408(6808):86-89). More than 17,000 miRNAs in 142 species have been identified, with more than 1900 miRNAs identified in humans, many of which have been associated with a variety of diseases, including cancer (e.g., miR-15 and miR-16 in B-CLL, miR-125b, miR-145, miR-21, miR-155 and miR-210 in breast cancer, miR-155 and let-7a in lung cancer, miR-145 in gastric cancer, miR-29b in liver cancer); viral infections (e.g., miR-122 and miR-155 in HCV infection, mir-28, miR-125b, miR-150, miR-223 and miR-382 in HIV-1 infection, miR-21 and miR-223 in influenza virus infection); immune-related diseases (e.g., miR-145, miR-34a, miR-155 and miR-326 in multiple sclerosis, miR-146a in systemic lupus erythematosus, miR-144, miR-146a, miR-150, miR-182, miR-103 and miR-107 in type II diabetes, miR-200a, miR-200b, miR-429, miR-122, miR-451 and miR-27 in nonalcoholic fatty liver disease, miR-29c, miR-34a, miR-155 and miR-200b in non-alcoholic steatohepatitis); and neurodegenerative diseases (e.g., miR-30b, miR-30c, miR-26a, miR-133b, miR-184* and let-7 in Parkinson's disease, miR-29b-1, miR-29a and miR-9 in Alzheimer's disease) (Li and Kowdley (2012) *Genomics Proteomics Bioinformatics* 10:246-253).

Studies have shown that specific endogenous miRNAs are up-regulated or down-regulated in certain cancers. For example, miR-140 is down-regulated in non-small cell lung cancer (NSCLC) and its overexpression was found to suppress PD-L1 (Xie et al. (2018) *Cell Physiol. Biochem.* 46:654-663); miR-197 is downregulated in platinum-based chemotherapy resistant NSCLC, resulting in chemoresistance, tumorigenicity and metastasis (Fujita et al. (2015) *Mol. Ther.* 23(4):717-727); and several miRNAs have been found to be down-regulated in cancer cells to allow PD-L1 expression, including miR-200, miR-34a and miR-138 (Yee et al. (2017) *J. Biol. Chem.* 292(50):20683-20693). Several miRNAs also are upregulated, for example miR-21, miR-17 and miR-221 in lung cancer (Xie et al. (2018) *Cell Physiol. Biochem.* 46:654-663).

MicroRNA-103 (miR-103) was identified as the most upregulated microRNA in endothelial cells as a result of genotoxic stress and DNA damage following radiation. It was found that miR-103 led to the downregulation of the TREX1, TREX2 and FANCF genes, and the decrease in TREX1 expression was identified as the major mechanism by which miR-103 mediates cell death and suppresses angiogenesis (Wilson et al. (2016) *Nature Communications* 7:13597). Since the loss of TREX1 results in the accumulation of ds and ssDNA, defective DNA repair, and release of cytokines, Wilson et al. examined whether miR-103 regulates the expression of cytokines. Results showed that miR-103 expression significantly upregulated the pro-inflammatory chemokines IP-10, RANTES, MIG, and the cytokines IL-15, IL-12 and IFN-γ, and this upregulation was due to a miR-103 mediated decrease in TREX1 levels. Studies also revealed a significant increase in costimulatory receptors CD40 and CD160, and a decrease in the numbers of PD-L1$^+$ macrophages and neutrophils in the 4T1 tumors. miR-103 regulation of TREX1 is therefore a potent modulator of the immune TME. Other miRNAs that target TREX1 include miR-107 (U.S. Pat. No. 9,242,000), miR-27a and miR-148b (U.S. Pat. No. 8,580,757). miRNA-103 can be used in the plasmids herein to inhibit TREX1.

Artificial miRNAs (amiRNAs) can be delivered to cells and used to silence target genes by creating a microRNA-based siRNA or shRNA vector (shRNAmir). The miR-30a backbone is often used in mammals, and approximately 200-300 bases of the primary miRNA transcript are included in the vector, with the miRNA hairpin placed at the center of the fragment, and the natural miRNA stem sequence being replaced with the siRNA/shRNA-encoding sequence of interest. Viral promoters, such as CMV, MSCV and TLR promoters; cellular promoters, such as EIF-1a; inducible chimeric promoters, such as tet-CMV; and tissue-specific promoters, can be used (Chang et al. (2013) *Cold Spring Harb Protoc*; doi:10.1101/pdb.prot075853). Other miRNAs that can be used include mir-16-2 (Watanabe et al. (2016) *RNA Biology* 13(1):25-33), miR-155 (Chung et al. (2006) *Nuc Acids Res.* 34:e53), miR17-92 (Liu et al. (2008) *Nuc Acids Res.* 36(9):2811-2824), miR-15a, miR-16, miR-19b, miR-20, miR-23a, miR-27b, miR-29a, miR-30b, miR-30c, miR-104, miR-132s, miR-181, miR-191, miR-223 (U.S. Pat. No. 8,426,675), and Let-7 miRNA (International Application Publication Nos. WO 2009/006450, WO 2015/032165).

shRNAmirs are limited by the low effectiveness of computationally-predicted shRNA sequences, particularly when expressed under low or single copy conditions. Third generation artificial miRNAs, such as miR-E (based on miR-30a) and miR-3G (based on miR-16-2) have been developed, and were found to exhibit stronger gene silencing in both Pol II- and Pol III-based expression vectors in comparison to shRNAmirs, due to the enhanced processing and accumulation of precisely-defined guide RNAs. miR-E, which was developed by the discovery of the conserved CNNC motif that enhances the processing of miRNA within the stem 3p flanking sequences, is different from endogenous miR-30a in three aspects: the stem of miR-E has no bulge and has the intended guide on the opposite strand; two conserved base pairs flanking the loop were mutated from CU/GG to UA/UA; and XhoI/EcoRI restriction sites were introduced into the flanking regions for shRNA cloning (Fellmann et al. (2013) *Cell Reports* 5:1704-1713). miR-E was found to be more potent than miR-30a, but symmetric processing of both the 3p and 5p strands of miR-30a does not favor guide strand delivery over passenger strand delivery, which is not optimal. Additionally, cloning into miR-E using oligos longer than 100 nt is costly and time consuming (Watanabe et al. (2016) *RNA Biology* 13(1):25-33).

The amiRNA designated miR-16-2 (see, e.g., Watanabe et al. (2016) *RNA Biology* 13(1):25-33, see FIG. 1) is a third generation (3G) amiRNA scaffold alternative; it is expressed in several tissues, is naturally asymmetric (the mature strand is derived exclusively from the 5p or 3p arm of the stem), and its stem and loop segments are small and rigid, simplifying vector cloning. miR-3G is generated by cloning the ~175 bp fragment containing the native miR-16-2 stem and loop, and the flanking 35 bps on either side of the stem, into the vector. miR-3G includes further modification of miR-16-2 by introducing cloning sites, such as MluI and EcoRI, into the 5p and 3p arm-flanking sequences, respectively, and fully base-pairing the guide (antisense) and passenger (sense) strand stem, with the exception of a mismatch at position 1 relative to the guide strand. The restriction sites allow for the generation of new targeting constructs via 88-mer duplexed DNA oligonucleotides without compromising the predicted secondary structure of the miR-16-2 hairpin and flanking elements. Additionally, one of the two CNNC motifs and the GHG motif (small RNA processing enhancers) are modified in the 3p flanking sequence of miR-16-2. siRNAs targeting the gene(s) of interest are then exchanged with the first 21 nucleotides of the mature 5p guide and 3p passenger sequences. Studies determined that miR-E and miR-3G were equally potent. miR-3G provides an attractive RNAi system, due to the smaller size of its expression cassette (~175 nts vs. ~375 for miR-E), and the simplified and cost effective single step cloning method for its production. As with shRNAs, bacteria can be used as vectors for the in vivo delivery of micro-RNAs. For example, it was shown that attenuated *S. typhimurium* can be used as a vector for the oral delivery of plasmids expressing miRNA against CCL22 in mice with inflammation. Down-regulation of CCL22 gene expression by this method was successful both in vitro and in vivo in mouse models of atopic dermatitis (Yoon et al. (2012) *DNA and Cell Biology* 31(3):289-296). For purposes herein a miRNA 16-2 can be used to produce miRNAs to be used in place of the shRNA. The sequences for the shRNA can be used for design of miRNAs.

DNA encoding RNAi for disrupting and/or inhibiting and/or targeting any of selected target genes, such as any immune checkpoint described herein or known to the skilled artisan, is inserted into a microRNA backbone, such as the microRNA backbone set forth in SEQ ID NO:249, and below. Any suitable microRNA backbone known to the skilled artisan can be used; generally such backbones are based on a naturally-occurring microRNA and are modified for expression of the RNAi. Exemplary of such backbones is one based on miR-16-2 (SEQ ID NO:248). The sequence of the modified microRNA backbone is:

```
                                        (SEQ ID NO: 249)
5'-CCGGATC AACGCCCTAG GTTTATGTTT GGATGAACTG

ACATACGCGT ATCCGTC NNNNNNNNNNNNNNNNNNNNNN GTAG

TGAAATATAT ATTAAAC NNNNNNNNNNNNNNNNNNNNN

TACGGTAACGCG GAATTCGCAA CTATTTTATC AATTTTTTGC

GTCGAC-3',
``` where the N's represent complementary, generally 18-26, such as 19-24, 19-22, 19-20, base pair long anti-sense and sense nucleotide sequences that target the gene to be silenced, and are inserted before and after the microRNA loop. RNAs, such as ARI-205 (SEQ ID NO:214) and ARI-206 (SEQ ID NO:215) are exemplary constructs based on the microRNA backbone of SEQ ID NO:249, that encode 21 and 22 base pair homology sequences, respectively. ARI-207 (SEQ ID NO:216) and ARI-208 (SEQ ID NO:217) are exemplary constructs based on the microRNA backbone of SEQ ID NO:249, that encode 19 base pair homology sequences. Another example, is the construct designated ARI-201, which is microRNA construct ARI-205, wherein the N's are replaced with a sequence of nucleotides targeting mouse PD-L1. The construct designated ARI-202 represents microRNA construct ARI-206, where the N's are replaced with sequences targeting mouse PD-L1. The skilled person readily can construct microRNAs for inclusion in plasmids as described and exemplified herein using the miR-16-2 backbone, or other suitable backbones known to the skilled artisan.

2. Origin of Replication and Plasmid Copy Number

Plasmids are autonomously-replicating extra-chromosomal circular double stranded DNA molecules that are maintained within bacteria by means of a replication origin. Copy number influences the plasmid stability. High copy number generally results in greater stability of the plasmid when the random partitioning occurs at cell division. A high number of plasmids generally decreases the growth rate, thus possibly allowing for cells with few plasmids to dominate the culture, since they grow faster. The origin of replication also determines the plasmid's compatibility: its ability to replicate in conjunction with another plasmid within the same bacterial cell. Plasmids that utilize the same replication system cannot co-exist in the same bacterial cell. They are said to belong to the same compatibility group. The introduction of a new origin, in the form of a second plasmid from the same compatibility group, mimics the result of replication of the resident plasmid. Thus, any further replication is prevented until after the two plasmids have been segregated to different cells to create the correct pre-replication copy number.

| Origin of Replication | Copy Number | SEQ ID NO. |
|---|---|---|
| pMB1 | 15-20 | 254 |
| p15A | 10-12 | 255 |
| pSC101 | ~5 | 256 |
| pBR322 | 15-20 | 243 |
| ColE1 | 15-20 | 257 |
| pPS10 | 15-20 | 258 |
| RK2 | ~5 | 259 |
| R6K (alpha origin) | 15-20 | 260 |
| R6K (beta origin) | 15-20 | 261 |
| R6K (gamma origin) | 15-20 | 262 |
| P1 (oriR) | Low | 263 |
| R1 | Low | 264 |
| pWSK | Low | 265 |
| ColE2 | 10-15 | 266 |
| pUC (pMB1) | 500-700 | 267 |
| F1 | 300-500 | 268 |

Numerous bacterial origins of replication are known to those of skill in the art. The origin can be selected to achieve a desired copy number. Origins of replication contain sequences that are recognized as initiation sites of plasmid replication via DNA dependent DNA polymerases (Del Solar et al. (1998) *Microbiology And Molecular Biology Reviews* 62(2):434-464). Different origins of replication provide for varying plasmid copy numbers within each cell and can range from 1 to hundreds of copies per cell. Commonly used bacterial plasmid origins of replication include, but are not limited to, pMB1 derived origins, which have very high copy derivatives, ColE1 origins, p15A, pSC101, pBR322, and others, which have low copy numbers. Such origins are well known to those of skill in the art. The pUC19 origin results in copy number of 500-700 copies per cell. The pBR322 origin has a known copy number of 15-20. These origins only vary by a single base pair. The ColE1 origin copy number is 15-20, and derivatives such as pBluescript have copy numbers ranging from 300-500. The p15A origin that is in pACYC184, for example, results in a copy number of approximately 10. The pSC101 origins confer a copy number of approximately 5. Other low copy number vectors from which origins can be obtained, include, for example, pWSK29, pWKS30, pWKS129 and pWKS130 (see, Wang et al. (1991) Gene 100:195-199). Medium to low copy number is less than 150, or less than 100. Low copy number is less than 20, 25, or 30. Those of skill in the art can identify plasmids with low or high copy number. For example, one way to determine experimentally if the copy number is high or low is to perform a miniprep. A high-copy number plasmid should yield between 3-5 µg DNA per 1 ml LB culture; a low-copy number plasmid will yield between 0.2-1 µg DNA per ml of LB culture.

Sequences of bacterial plasmids, including identification of and sequence of the origin of replication, are well known (see, e.g., snapgene.com/resources/plasmid_files/basic_cloning_vectors/pBR322/).

High copy number plasmids are selected for heterologous expression of proteins in vitro because the gene dosage is increased relative to chromosomal genes and higher specific yields of protein, and for therapeutic bacteria, higher therapeutic dosages of encoded therapeutics. It is shown, herein, however, that for delivery of plasmids encoding RNA interference (RNAi), such as by *S. typhimurium*, as described herein, while it would appear that a high copy plasmid would be ideally suited, therapeutically, a lower copy number is more effective.

The requirement for bacteria to maintain the high copy plasmids can be a problem if the expressed molecule is toxic to the organism. The metabolic requirements for maintaining these plasmids can come at a cost of replicative fitness in vivo. Optimal plasmid copy number for delivery of interfering RNAs can depend on the mechanism of attenuation of the strain engineered to deliver the plasmid. If needed, the skilled person, in view of the disclosure herein, can select an appropriate copy number for a particular immunostimulatory species and strain of bacteria. It is shown herein, that low copy number can be advantageous.

3. CpG Motifs and CpG Islands

Unmethylated cytidine-phosphate-guanosine (CpG) motifs are prevalent in bacterial, but not vertebrate, genomic DNA. Pathogenic DNA and synthetic oligodeoxynucleotides (ODN) containing CpG motifs activate host defense mechanisms, leading to innate and acquired immune responses. The unmethylated CpG motifs contain a central unmethylated CG dinucleotide plus flanking regions. In humans, four distinct classes of CpG ODN have been identified based on differences in structure and the nature of the immune response they induce. K-type ODNs (also referred to as B-type) contain from 1 to 5 CpG motifs typically on a phosphorothioate backbone. D-type ODNs (also referred to as A-type) have a mixed phosphodiester/phosphorothioate backbone and have a single CpG motif, flanked by palindromic sequences that enables the formation of a stem-loop structure, as well as poly G motifs at the 3' and 5' ends. C-type ODNs have a phosphorothioate backbone and contain multiple palindromic CpG motifs that can form stem loop structures or dimers. P-Class CpG ODN have a phosphorothioate backbone and contain multiple CpG motifs with double palindromes that can form hairpins at their GC-rich 3' ends (Scheiermann and Klinman (2014) *Vaccine* 32(48):6377-6389). For purposes herein, the CpGs are encoded in the plasmid DNA; they can be introduced as a motif, or in a gene.

Toll-like receptors (TLRs) are key receptors for sensing pathogen-associated molecular patterns (PAMPs) and activating innate immunity against pathogens (Akira et al. (2001) *Nat. Immunol.* 2(8):675-680). TLR9 recognizes hypomethylated CpG motifs in DNA of prokaryotes that do not occur naturally in mammalian DNA (McKelvey et al. (2011) *J. Autoimmunity* 36:76-86). Recognition of CpG motifs upon phagocytosis of pathogens into endosomes in immune cell subsets induces IRF7-dependent type I interferon signaling and activates innate and adaptive immunity.

Immunostimulatory bacteria, such as *Salmonella* species, such as *S. typhimurium*, strains carrying plasmids containing CpG islands, are provided herein. These bacteria can activate TLR9 and induce type I IFN-mediated innate and adaptive immunity. As exemplified herein, bacterial plasmids that contain hypomethylated CpG islands can elicit innate and adaptive anti-tumor immune responses that, in combination with RNAi encoded in the plasmid, such as RNAi that targets immune checkpoints, such as the shRNA or miRNA that targets TREX1, and hence, TREX1-mediated STING pathway activation, can have synergistic or enhanced anti-tumor activity. For example, the asd gene (SEQ ID NO:48) encodes a high frequency of hypomethylated CpG islands. CpG motifs can be included in combination with any of the RNAi described or apparent from the description herein in the immunostimulatory bacteria, and thereby enhance or improve anti-tumor immune responses in a treated subject.

Immunostimulatory CpGs can be included in the plasmids, by including a nucleic acid, typically from a bacterial gene, that encodes a gene product, and also by adding a nucleic acid that encodes CpG motifs. The plasmids herein can include CpG motifs. Exemplary CpG motifs are known (see, e.g., U.S. Pat. Nos. 8,232,259, 8,426,375 and 8,241,844). These include, for example, synthetic immunostimulatory oligonucleotides, between 10 and 100, 10 and 20, 10 and 30, 10 and 40, 10 and 50, 10 and 75, base pairs long, with the general formula:

$(CpG)_n$, where n is the number of repeats.

Generally, at least one or two repeats are used; non-CG bases can be interspersed. Those of skill in the art are very familiar with the general use of CpG motifs for inducing an immune response by modulating TLRs, particularly TLR9.

4. Plasmid Maintenance/Selection Components

The maintenance of plasmids in laboratory settings is usually ensured by inclusion of an antibiotic resistance gene on the plasmid and use of antibiotics in growth media. As described above, the use of an asd deletion mutant complimented with a functional asd gene on the plasmid allows for plasmid selection in vitro without the use of antibiotics, and allows for plasmid selection in vivo. The asd gene complementation system provides for such selection (Galan et al. (1990) *Gene* 94(1):29-35). The use of the asd gene complementation system to maintain plasmids in the tumor microenvironment increases the potency of *S. typhimurium* engineered to deliver plasmids encoding genes or interfering RNAs.

5. RNA Polymerase Promoters

Plasmids provided herein are designed to encode interfering RNAs targeting immunological checkpoints as described above. The RNA expression cassette contains a promoter for transcription in human cells such as an H1 promoter or a U6 promoter, or a CMV promoter. U6 and H1 are RNA polymerase III (RNAP III) promoters, which are for production and processing of small RNAs. The CMV promoter is recognized by RNA polymerase II, and is more amenable for expression of long RNA stretches than is RNAP III. The promoter precedes the interfering RNA, such as an shRNA, siRNA or miRNA, as described above.

In eukaryotic cells, DNA is transcribed by three types of RNA polymerases; RNA Pol I, II and III. RNA Pol I transcribes only ribosomal RNA (rRNA) genes, RNA Pol II transcribes DNA into mRNA and small nuclear RNAs (snRNAs), and RNA Pol III transcribes DNA into ribosomal 5S rRNA (type I), transfer RNA (tRNA) (type II) and other small RNAs such as U6 snRNAs (type III). shRNAs are typically transcribed in vivo under the control of eukaryotic type III RNA Pol III promoters, such as the human U6 promoter, which transcribes the U6 snRNA component of the spliceosome, and the H1 human promoter, which transcribes the RNA component of RNase P. U6 and H1 promoters are more suitable than other Pol III or Pol II promoters because they are structurally simple, with a well-defined transcription start-site, and naturally drive the transcription of small RNAs. U6 and H1 promoters do not carry the sequences necessary for transcribing anything downstream from the transcription start site (Makinen et al. (2006) *J. Gene Med.* 8:433-441). They are thus the most straightforward promoters for use in shRNA expression.

The use of other promoters such as type II pol III tRNA promoters, while successful in expressing shRNAs, results in longer dsRNA transcripts, which can induce an interferon response. RNA pol II promoters, such as the human cytomegalovirus (CMV) promoter also may be used (U.S. Pat. Nos. 8,202,846; 8,383,599), but are more often utilized for expression of long RNA stretches. Studies have shown that the addition of the enhancer from the CMV promoter near the U6 promoter can increase its activity, increasing shRNA synthesis and improving gene silencing (Xia et al. (2003) *Nucleic Acids Res.* 31(17):e100; Nie et al. (2010) *Genomics Proteomics Bioinformatics* 8(3):170-179). RNA pol II promoters are typically avoided in shRNA transcription due to the generation of cytoplasmic DNA, which leads to a pro-inflammatory interferon response. In this case, a cytoplasmic DNA mediated interferon response in *S. typhimurium*-infected tumor cells has anti-tumor benefit, especially in the context of TREX1 inhibition as provided herein. Prokaryotic promoters, including T7, pBAD and pepT promoters can be utilized when transcription occurs in a bacterial cell (Guo et al. (2011) *Gene Therapy* 18:95-105; U.S. Patent Publication Nos. 2012/0009153, 2016/0369282; International Application Publication Nos. WO 2015/032165, WO 2016/025582).

RNA pol III promoters generally are used for constitutive shRNA expression. For inducible expression, RNA pol II promoters are used. Examples include the pBAD promoter, which is inducible by L-arabinose; tetracycline-inducible promoters such as TRE-tight, IPT, TRE-CMV, Tet-ON and Tet-OFF; retroviral LTR; IPTG-inducible promoters such as Lad, Lac-O responsive promoters; LoxP-stop-LoxP system promoters (U.S. Pat. No. 8,426,675; International Application Publication No. WO 2016/025582); and pepT, which is a hypoxia-induced promoter (Yu et al. (2012) *Scientific Reports* 2:436). These promoters are well known. Exemplary of these promoters are human U6 (SEQ ID NO:73) and human H1 (SEQ ID NO:74).

| SEQ ID NO. | Name | Sequence |
|---|---|---|
| 73 | human U6 RNA pol III promoter | aa ggtcgggcag gaagagggcc 721 tatttcccat gattccttca tatttgcata tacgatacaa ggctgttaga gagataatta 781 gaattaattt gactgtaaac acaaagatat tagtacaaaa tacgtgacgt agaaagtaat 841 aatttcttgg gtagtttgca gttttaaaat tatgttttaa aatggactat catatgctta |

```
SEQ ID
NO.    Name         Sequence
                    901 ccgtaacttg aaagtatttc gatttcttgg ctttatatat cttgtggaaa ggacgaaact
                    961 ag 74     human H1 RNA                                                  atatttgca tgtcgctatg
       pol III promoter 721 tgttctggga aatcaccata aacgtgaaat gtctttggat ttgggaatct tataagttct
                    781 gtatgagacc actccctagg
```

Tissue specific promoters include TRP2 promoter for melanoma cells and melanocytes; MMTV promoter or WAP promoter for breast and breast cancer cells, Villin promoter or FABP promoter for intestinal cells, RIP promoter for pancreatic beta cells, Keratin promoter for keratinocytes, Probasin promoter for prostatic epithelium, Nestin promoter or GFAP promoter for CNS cells/cancers, Tyrosine Hydroxylase S100 promoter or neurofilament promoter for neurons, Clara cell secretory protein promoter for lung cancer, and Alpha myosin promoter in cardiac cells (U.S. Pat. No. 8,426,675).

6. DNA Nuclear Targeting Sequences

DNA nuclear targeting sequences (DTS)s such as the SV40 DTS mediate the translocation of DNA sequences through the nuclear pore complex. The mechanism of this transport is reported to be dependent on the binding of DNA binding proteins that contain nuclear localization sequences. The inclusion of a DTS on a plasmid to increase nuclear transport and expression has been demonstrated (Dean et al. (1999) *Exp. Cell Res.* 253(2):713-722), and has been used to increase gene expression from plasmids delivered by *S. typhimurium* (Kong et al. (2012) *Proc. Natl. Acad. Sci. U.S.A.* 109(47):19414-19419).

Rho-independent or class I transcriptional terminators such as the T1 terminator of the rrnB gene of *E. coli* contain sequences of DNA that form secondary structures that cause dissociation of the transcription elongation complex. Transcriptional terminators shall be included in the plasmid in order to prevent expression of interfering RNAs by the *S. typhimurium* transcriptional machinery. This ensures that expression of the encoded interfering RNA, such as shRNA, micro-RNA and siRNA, is confined to the host cell transcriptional machinery.

Plasmids used for transformation of *Salmonella*, such as *S. typhimurium*, as a cancer therapy described herein, contain all or some of the following attributes: 1) a CpG island, 2) a bacterial origin of replication, 3) an asd gene selectable marker for plasmid maintenance, 4) one or more human interfering RNA expression cassettes, 5) DNA nuclear targeting sequence, and 6) transcriptional terminators.

H. TUMOR TARGETING IMMUNOSTIMULATORY BACTERIA CONTAIN RNAI AGAINST EXEMPLARY IMMUNE TARGET GENES TO STIMULATE ANTI-TUMOR IMMUNITY

RNAi against any immune target can be encoded in the plasmids. These include, but are not limited to, any discussed in the disclosure herein, and any known to those of skill in the art. The following discussion describes exemplary targets. The plasmids can contain any RNAi against such targets, including, but not limited to, shRNA, siRNA and microRNA.

1. TREX1

In certain embodiments provided herein, the TREX1 antagonist is immunostimulatory bacteria that encode inhibitory RNA, such as shRNA, that inhibit or disrupt or suppress TREX1 expression. The enzyme product encoded by TREX1, located upstream from cGAS, is a mediator of the type I interferon pathway. TREX1 encodes the major 3' DNA exonuclease in mammalian cells (also called DNase III). Human TREX1 proteins are as catalytically efficient as bacterial exonucleases (Mazur and Perrino (2001) *J. Biol. Chem.* 276:17022-17029). Immunostimulatory bacterium that inhibit TREX1 expression by processes other than RNA silencing also are contemplated herein.

For the immunostimulatory bacteria for use as provided herein, such as bacteria that express shRNA against TREX1, it is shown that loss of TREX1 activity and subsequent activation of cGAS/STING-induced vascular disruption enhances tumor colonization of *S. typhimurium*. The TREX1 gene encodes a protein that is 314 amino acids long (Mazur et al. (2001) *J. Biol. Chem* 276:17022-17029), exists as a homodimer, and lacks endonuclease activity. TREX1 is among several proteins involved in the repair of DNA that is damaged by exogenous genotoxic stress, including UV irradiation and DNA-damaging compounds. TREX1 can function as an editing exonuclease for DNA pol R by excising mispaired nucleotides from the 3' end (Mazur et al. (2001) *J. Biol. Chem* 276:17022-17029). ssDNA is degraded 3-4 times more efficiently than dsDNA (Lindahl et al. (2009) *Biochem. Soc. Trans.* 37 (Pt 3), 535-538). Mutations in residues D18 and D200, frequently associated with autoimmune diseases, disable TREX1 enzyme from degrading dsDNA and reduces its ability to degrade ssDNA. TREX1 enzyme translocates from the endoplasmic reticulum to the nucleus following DNA damage, indicating its involvement in the replication of damaged DNA. Promoter activation and upregulation of TREX1 has been observed as a result of UVC exposure in mouse fibroblasts, and TREX1 null mouse cells have demonstrated hypersensitivity to UVC light (Tomicic et al. (2013) *Bioch. Biophys. Acta* 1833:1832-1843).

Mutations resulting in loss of TREX1 have been identified in patients with the inherited rare disease, Aicardi-Goutieres syndrome (AGS), which has phenotypic overlap with the autoimmune diseases systemic lupus erythematosus (SLE) and chilblain lupus (Aicardi and Goutieres (2000) *Neuropediatrics* 31(3):113). Mutations in TREX1 also are associated with retinal vasculopathy with cerebral leukodystrophy. TREX1-mediated autoimmune diseases are associated with the cell's inability to prevent autoimmunity via the degradation of ssDNA and dsDNA that accumulates in the cytoplasm. TREX1 null mice suffer from inflammatory myocarditis, resulting in circulatory failure, which is caused by chronic cytokine production (Morita et al. (2004) *Mol. Cell Biol.* 24(15):6719-6727; Yang et al. (2007) *Cell* 131(5):873-886; Tomicic et al. (2013) *Bioch. Biophys. Acta* 1833(8): 1832-1843). Hence, TREX1 deficiency induces innate immunity following the cytoplasmic accumulation of DNA, resulting in an inflammatory response (Wang et al. (2009) *DNA Repair(Amst)* 8:1179-1189). The source of the DNA that accumulates in the cytosol of TREX1-deficient cells was found to be in part derived from endogenous retroelements that escape from the damaged nucleus, as TREX1 is known to metabolize reverse-transcribed (RT) DNA (Stetson et al. (2008) *Cell* 134(4):587-598). In HIV infection, HIV RT DNA accumulates in the cytosol of infected T cells and macrophages, and would normally trigger cGAS/STING activation of antiviral immunity. TREX1 digests this viral DNA and permits HIV immune escape (Yan et al. (2010) *Nat. Immunol.* 11(11):1005-1013). Thus, TREX1 acts as a negative regulator of STING, and can be exploited to evade detection by several retroviruses, such as murine leukemia virus (MLV), simian immunodeficiency virus (SIV), and many others (Hasan et al. (2014) *Front. Microbiol.* 5:193).

Like STING, TREX1 is expressed in most mammalian cell types, with the key producers of cytokines in TREX1 null mice originating from macrophages and dendritic cells (Ahn et al. (2014) *J. Immunol.* 193(9):4634-4642). Data indicate that TREX1 is responsible for degrading self-DNA that can leak from a damaged nucleus into the cytosol, where it would otherwise bind and activate cGAS and lead to autoimmunity (Barber (2015) *Nat. Rev. Immunol.* 15(12): 760-770). In support of this, TREX1 null mice and TREX1-deficient cells that also lack cGAS are completely protected from type I interferon activation and lethal autoimmunity (Ablasser et al. (2014) *J. Immunol.* 192(12):5993-5997; Gray et al. (2015) *J. Immunol.* 195(5):1939-1943). In a negative feedback loop, type I interferon and type II IFNγ can also induce TREX1, and TREX1 thus serves to limit aberrant autoimmune activation (Tomicic et al. (2013) *Bioch. Biophys. Acta* 1833:1832-1843).

Lymphocytes derived from an Aicardi-Goutieres syndrome patient, containing mutated TREX1, were found to inhibit angiogenesis and the growth of neuroblastoma cells, the effect being enhanced by the presence of IFN-α (Pulliero et al. (2012) *Oncology Reports* 27:1689-1694). The use of microRNA-103 also has been shown to inhibit the expression of TREX1, disrupting DNA repair and angiogenesis, and resulting in decreased tumor growth in vivo (see, U.S. Patent Publication No. 2014/0127284, Cheresh et al.).

TREX1 is a negative regulator of macrophage activation and pro-inflammatory function. TREX1 null macrophages were found to exhibit increased TNF-α and IFN-α production, higher levels of CD86, and increased antigen presentation to T cells, as well as impaired apoptotic T cell clearance (Pereira-Lopes et al. (2013) *J. Immunol.* 191: 6128-6135). The inability to adequately digest apoptotic DNA in TREX1 null macrophages generates high amounts of aberrant cytosolic DNA, which binds to cGAS and activates the STING pathway to produce higher levels of type I interferon (Ahn et al. (2014) *J. Immunol.* 193:4634-4642). Not all cell types are sensitive to the immunostimulatory effects of Trex1 knockdown, however. In a study of individual cell types, dendritic cells, macrophages, fibroblasts and keratinocytes were found to produce type I IFN upon Trex1 knockdown, while B cells, cardiomyocytes, neurons and astrocytes did not (Peschke et al. (2016) *J. Immunol.* 197:2157-2166). Thus, inhibiting the function of TREX1 in phagocytic cells that have engulfed *S. typhimurium* would enhance their pro-inflammatory activity, while driving an accumulation of cytosolic DNA from phagocytosed tumor cells that can then activate the cGAS/STING pathway. The use of microRNA-103 inhibits the expression of TREX1, disrupting DNA repair and angiogenesis, and resulting in decreased tumor growth in vivo (see, U.S. Publication No. 2014/0127284, Cheresh et al.).

Studies have shown that the expression of cGAS and/or STING is inhibited in over a third of colorectal cancers, while STING expression is lost in many primary and metastatic melanomas and HPV[+] cancers. STING signaling remains intact in all tumor-resident APCs that continuously sample the antigenic milieu of the TME, including Batf3-lineage CD103/CD8α[+] DCs that cross-present tumor antigens to CD8[+] T cells, and these APCs will also readily phagocytose *S. typhimurium* or be activated by type I IFN from neighboring macrophages that have phagocytosed *S. typhimurium* containing TREX1 gene knockdown.

Inactivation of TREX1 enhances an immune response by enabling cytosolic accumulation of dsDNA to bind to the enzyme cyclic GMP-AMP (cGAMP) synthase (cGAS), a cytosolic DNA sensor that triggers the production of type I interferons and other cytokines through activation of the STING signaling pathway (Sun et al. (2013) *Science* 339 (6121):786-791; Wu et al. (2013) *Science* 339(6121):826-830). Activation of the STING pathway has been shown to induce potent innate and adaptive antitumor immunity (Corrales et al. (2015) *Cell Reports* 11:1018-1030).

Hence, embodiments of the immunostimulatory bacterial strains, as provided herein, are administered to inhibit TREX1 in tumor-resident APCs and induce cGAS/STING activation, thereby activating these DCs to cross-present host tumor antigens to CD8[+] T cells and induce local and systemic tumor regression and durable anti-tumor immunity (Corrales et al. (2015) *Cell Reports* 11:1018-1030; Zitvogel et al. (2015) *Nature Reviews Immunology* 15:405-414).

The clinical activity of the strain VNP20009 was disappointing in part due to its poor ability to colonize human tumors, a phenomenon that was not observed in mouse models (Nemunaitis et al. (2003) *Cancer Gene Ther.* 10(10): 737-744; Toso et al. (2002) *J. Clin. Oncol.* 20(1):142-152; Heimann et al. (2003) *J. Immunother.* 26(2):179-180). A reason for the discrepancy between human and mouse tumor colonization was that orthotopically transplanted syngeneic mouse tumors are much more vascularized than human tumors. In order to more closely model the lack of human tumor vascularization in mice, autochthonous tumor models were treated with VNP20009 and found to only provide tumor colonization with pre-treatment of a vascular disrupting agent (Drees et al. (2015) *J. of Cancer* 6(9):843-848; Drees et al. (2015) *Anticancer Res.* 35(2):843-849). Vascular disrupting agents such as 5,6-Dimethylxanthenone-4-acetic acid (DMXAA) have been shown to mediate tumor collapse in mice (but not humans) by directly binding STING and inducing type I interferon signaling (Baguley (2003) *Lancet Oncol.* 4(3):141-148; Corrales and Glickman et al. (2015) *Cell Reports* 11(7):1018-1030). STING signaling induces TNF-α and IFN-γ production, cytokines which have been shown to directly promote vascular disruption by downregulating αVβ3 integrin adhesion receptors on endothelial cells (Rüegg et al. (1998) *Nat. Medicine* 4(4):408-414). Production of innate pro-inflammatory cytokines such as TNF-α, IL-12p40 and IFN-γ that are induced upon STING activation are critical for activating anti-tumor immunity (Burdette et al. (2011) *Nature* 478(7370):515-518).

The immunostimulatory bacteria provided herein have enhanced ability to colonize tumors, and to accumulate in tumors, in the tumor microenvironment, and/or in tumor-resident immune cells. The immunostimulatory bacteria provided herein express RNAi, such as shRNA, against TREX1, resulting in loss of TREX1 and subsequent activation of cGAS/STING-induced vascular disruption. This further enhances tumor colonization.

2. PD-L1

Programmed cell death protein 1 (PD-1) is an immune-inhibitory receptor that is involved in the negative regulation of immune responses. Its cognate ligand, programmed death-ligand 1 (PD-L1), is expressed on APCs, and upon binding to PD-1 on T cells, leads to loss of $CD8^+$ T cell effector function, inducing T cell tolerance. The expression of PD-L1 is often associated with tumor aggressiveness and reduced survival in certain human cancers (Gao et al. (2009) *Clin. Cancer Res.* 15(3):971-979).

Antibodies designed to block immune checkpoints, such as anti-PD-1 (for example, pembrolizumab, nivolumab) and anti-PD-L1 (for example, atezolizumab, avelumab, durvalumab) antibodies have had durable success in preventing T cell anergy and breaking immune tolerance. Only a fraction of treated patients exhibit clinical benefit, and those that do often present with autoimmune-related toxicities (Ribas (2015) *N. Engl. J. Med.* 373(16):1490-1492; Topalian et al. (2012) *N. Engl. J. Med.* 366(26):2443-54). Besides acquiring toxicity, PD-1/PD-L1 therapy often leads to resistance, and the concomitant use of anti-CTLA-4 antibodies (for example, ipilimumab) has shown limited success in clinical trials with significantly additive toxicity. To limit the toxicity and enhance the potency of PD-L1 blockade, immunostimulatory bacteria with an shRNA to PD-L1, as provided herein, will synergize with TLR activation of immune cells to both activate and potentiate anti-tumor immunity.

3. VISTA

Other non-redundant checkpoints in immune activation can synergize with PD-1/PD-L1 and CTLA-4, such as V-domain immunoglobulin (Ig) suppressor of T cell activation (VISTA). VISTA is expressed primarily on APCs, particularly on tumor-infiltrating myeloid cells and myeloid-derived suppressor cells (MDSC), and to a lesser extent on regulatory T cells ($CD4^+$ $Foxp3^+$ Tregs) (Wang et al. (2011) *J. Exp. Med.* 208(3):577-592). Similar to PD-L1, VISTA upregulation directly suppresses T cell proliferation and cytotoxic function (Liu et al. (2015) *Proc. Natl. Acad. Sci. U.S.A.* 112(21):6682-6687). Monoclonal antibody targeting of VISTA was shown to remodel the tumor microenvironment in mice, increasing APC activation and enhancing anti-tumor immunity (LeMercier et al. (2014) *Cancer Res.* 74(7):1933-1944). Clinically, VISTA expression was shown to be upregulated on tumor-resident macrophages following treatment with anti-CTLA-4 therapy in prostate cancer, demonstrating compensatory regulation of immune checkpoints (Gao et al. (2017) *Nat. Med.* 23(5):551-555). The majority of VISTA expression is purported to be located in the intracellular compartment of myeloid cells, rather than on the surface, which may limit the effectiveness of the monoclonal antibody approach (Deng et al. (2016) *J. Immunother. Cancer* 4:86). The ability to inhibit VISTA from within the APC using a tumor-targeting bacteria containing shRNA to VISTA, as provided herein, will more efficiently and completely inhibit the T cell-suppressing function of VISTA, leading to activation of T cell-mediated anti-tumor immunity and tumor regression.

4. SIRPα

One mechanism by which tumor cells evade removal is to prevent their phagocytosis by innate immune cells. Phagocytosis is inhibited by surface expression of CD47, which is widely expressed on hematopoietic and non-hematopoietic cells (Liu et al. (2015) *PLoS ONE* 10(9):e0137345). Upon CD47 binding its receptor, signal regulatory protein alpha (SIRPα), an inhibitory signal for phagocytosis, is initiated. SIRPα is abundantly expressed on phagocytic cells, including macrophages, granulocytes and DCs. As such, the protein-protein interaction between CD47 and SIRPα represents another class of immune checkpoints unique to APCs, and tumor-resident macrophages in particular. The effectiveness of CD47 in preventing phagocytosis is evidenced by the fact that it is often upregulated in a wide variety of tumors, which allow them to avoid being phagocytosed by APCs in the tumor microenvironment (Liu et al. (2015) *Nat. Med.* 21(10):1209-1215). Several methods to block the CD47/SIRPα interaction have been examined, including the development of anti-CD47 or anti-SIRPα antibodies or antibody fragments, the use of small peptides that bind either protein, or the knockdown of CD47 expression (U.S. Patent Publication Nos. 2013/0142786, 2014/0242095; International Application Publication No. WO 2015/191861; McCracken et al. (2015) *Clin. Cancer Res.* 21(16):3597-3601). To this end, several monoclonal antibodies that directly target SIRPα are in clinical development, either alone or in combination with tumor-targeting antibodies (e.g., Rituximab, Daratumumab, Alemtuzumab, Cetuximab) that can enhance phagocytosis of antibody-opsonized tumor cells, in a process known as antibody-dependent cellular phagocytosis (ADCP) (McCracken et al. (2015) *Clin. Cancer Res.* 21(16): 3597-3601; Yanagita et al. (2017) *JCI Insight* 2(1):e89140).

The CD47/SIRPα interaction also serves to preserve the longevity of red blood cells by preventing their phagocytic elimination (Murata et al. (2014) *J. Biochem.* 155(6):335-344). Thus, systemically administered therapies such as anti-CD47 antibodies that broadly disrupt this interaction have resulted in anemia toxicities (Huang et al. (2017) *J. Thorac. Dis.* 9(2):E168-E174). Systemic SIRPα-based therapies also risk adverse events, such as organ damage by creating systemic hyperphagocytic self-eating macrophages. Using a tumor-targeting immunostimulatory bacteria containing an shRNA to SIRPα, such as provided herein, will localize the CD47/SIRPα disruption to the tumor microenvironment and eliminate these adverse events. Further, inhibition of SIRPα in the context of bacterial activation of TLR-mediated pro-inflammatory signaling pathways will potently activate these macrophages to become hyperphagocytic towards neighboring tumor cells (Bian et al. (2016) *PNAS.* 113(37):E5434—E5443).

5. β-catenin

Immune checkpoint pathways exemplify the multiple layers of regulation that exist to prevent immune hyperactivation and autoimmunity, and the difficulties in subverting these pathways to promote anti-tumor immunity. One mechanism by which tumors have evolved to be refractory to checkpoint therapies is through their lack of T cell and dendritic cell (DC) infiltration, described as non-T-cell-inflamed, or "cold tumors" (Sharma et al. (2017) *Cell* 168(4):707-723). Several tumor-intrinsic mechanisms have been identified that lead to the exclusion of anti-tumor T cells and resistance to immunotherapy. In melanoma, in particular, molecular profiling of checkpoint therapy-refractory tumors revealed a signature of elevated β-catenin and its downstream target genes, correlating with a lack of tumor-infiltrating lymphocytes (Gajewski et al. (2011) *Curr. Opin. Immunol.* 23(2):286-292).

CTNNB1 is an oncogene that encodes β-catenin, and can induce the expression of the genes c-Myc and cyclin D1, resulting in tumor proliferation. Mutations in CTNNB1 are associated with certain cancers. Gene silencing of CTNNB1/β-catenin using *S. typhimurium* shRNA vectors can be used in the treatment of cancer (Guo et al. (2011) *Gene Therapy* 18:95-105; U.S. Patent Publication Nos. 2012/0009153, 2016/0369282; International Patent Publication No. WO 2015/032165). For example, shRNA silencing of CTNNB1, using *S. typhimurium* strain SL7207 as a delivery vector, reduced tumor proliferation and growth in SW480 xenograft mice, when compared to control cells, and reduced expression of c-Myc and cyclin D1 (Guo et al. (2011) *Gene Therapy* 18:95-105). Silencing of CTNNB1 for the treatment of hepatoblastoma also can be achieved using miRNA, with or without antibody therapeutics against the immune checkpoints PD-1 and PD-L1 (International Application Publication No. WO 2017/005773). The use of siRNA or shRNA targeting CTNNB1, delivered via alternative vectors, such as liposomes, for the treatment of CTNNB1-related cancers, including adenocarcinomas and squamous cell carcinomas, also can be affected (U.S. Patent Publication Nos. 2009/0111762, 2012/0294929).

Elevated β-catenin signaling directly inhibits the chemokine CCL4 from recruiting Batf3-lineage CD103/CD8a DCs, thereby preventing them from priming tumor antigen-specific $CD8^+$ T cells (Spranger et al. (2015) *Nature* 523 (7559):231-235). β-catenin is the major downstream mediator of the WNT signaling pathway, a key embryonic developmental pathway that is also critical for adult tissue regeneration, homeostasis and hematopoiesis (Clevers et al. (2012) *Cell* 149(6):1192-1205). Excessive WNT/β-catenin signaling has been implicated in a variety of cancers (Tai et al. (2015) *Oncologist* 20(10):1189-1198). Accordingly, several strategies to target WNT/β-catenin signaling have been pursued, but success has been hampered by a lack of specificity to the tumor microenvironment, resulting in off-target toxicities to intestinal stem cells, bone turnover and hematopoiesis (Kahn (2014) *Nat. Rev. Drug Dis.* 13(7): 513-532). The immunostimulatory bacteria provided herein overcome these problems.

For example, an advantage of using immunostimulatory bacteria with shRNA to β-catenin as provided herein, is enhancing chemokine-mediated infiltration of T cell-priming DCs and the conversion of a cold tumor to a T-cell-inflamed tumor microenvironment, without the systemic toxicities of existing therapeutic modalities. Further, bacterial activation of TLR innate immune signaling pathways synergize with β-catenin inhibition to further promote immune activation and anti-tumor immunity.

6. TGF-β

Transforming growth factor beta (TGF-β) is a pleiotropic cytokine with numerous roles in embryogenesis, wound healing, angiogenesis and immune regulation. It exists in three isoforms in mammalian cells, TGF-β1, TGF-β2 and, TGF-β3; TGF-β1 is the most predominant in immune cells (Esebanmen et al. (2017) *Immunol Res.* 65:987-994). TGF-β's role as an immunosuppressant is arguably its most dominant function. Its activation from a latent form in the tumor microenvironment, in particular, has profound immunosuppressive effects on DCs and their ability to tolerize antigen-specific T cells. TGF-β can also directly convert Th1 $CD4^+$ T cells to immunosuppressive Tregs, furthering promoting tumor tolerance (Travis et al. (2014) *Annu. Rev. Immunol.* 32: 51-82). Based on its tumor-specific immunosuppressive functions, and irrespective of its known cancer cell growth and metastasis-promoting properties, inhibition of TGF-β is a cancer therapy target. High TGF-β signaling has been demonstrated in several human tumor types, including CRC, HCC, PDAC and NSCLC (Colak et al. (2017) *Trends Cancer* 3(1):56-71). Systemic inhibition of TGF-β can lead to unacceptable autoimmune toxicities, and its inhibition should be localized to the tumor microenvironment. As such, a tumor-targeting immunostimulatory bacteria with RNAi, such as shRNA, to TGF-β, provided herein, or an shRNA to TGF-βRII, breaks tumor immune tolerance and stimulates anti-tumor immunity.

7. VEGF

Angiogenesis, or the development of new blood vessels, is an essential step for any tumor microenvironment to become established. Vascular endothelial growth factor (VEGF) is the critical mitogen for endothelial proliferation and angiogenesis, and inhibition of VEGF in the tumor microenvironment markedly decreases tumor vascularity, thereby starving the tumor of its blood supply (Kim et al. (1993) *Nature* 362(6423):841-4). This early research led to the development of the monoclonal antibody inhibitor of VEGF, bevacizumab (Avastin; Genentech), which in combination with chemotherapy, has become the standard of care for metastatic CRC. Systemic administration of bevacizumab also demonstrated significant toxicities, including multiple fatalities in a Phase II trial of NSCLC, largely due to hemorrhaging. As such, several next generation anti-angiogenics have been evaluated, such as the anti-VEGF receptor 2 antibody ramucirumab (Cyramza, Imclone) and the anti-angiogenic tyrosine kinase inhibitor axitinib (Inlyta, Pfizer), yet none have been able to overcome systemic toxicity or markedly improve progression-free survival (Alshangiti et al. (2018) *Curr. Oncol.* 25(Suppl 1):S45-S58). While the anti-tumor activity of anti-VEGF therapy has shown some promise, systemic toxicity is clearly limiting. As such, a therapy that targets only the tumor microenvironment, such as an immunostimulatory tumor-targeting bacteria with shRNA to VEGF, provided herein, delivers local anti-angiogenic therapy while preventing systemic toxicity. This therapeutic modality has the additional advantage of being taken up into myeloid cells, which predominantly produce VEGF in the tumor microenvironment, where it will have maximum impact on tumor progression (Osterberg et al. (2016) *Neuro-Oncology.* 18(7):939-949).

8. Additional Exemplary Checkpoint Targets

Exemplary checkpoint targets for which RNAi, such as micro-RNA and shRNA, can be prepared or are exemplified herein include, but are not limited to:

| Checkpoint target |
| --- |
| CTLA-4 |
| PD-L1 (B7-H1) |
| PD-L2 |
| PD-1, PD-2 |
| IDO1 |
| IDO2 |
| SIRP alpha (SIRPα) |
| VISTA (B7-H5) |
| LIGHT |
| HVEM |
| CD28 |
| LAG3, TIM3, TIGIT |
| Galectin-9 |
| CEACAM1, CD155, CD112, |
| CD226, CD244 (2B4), |
| B7-H2, B7-H3, CD137, |
| ICOS, GITR, B7-H4. B7-H6 |
| CD137, CD27, |
| CD40/CD40L, CD48, CD70, |
| CD80, CD86, CD137(4-1BB), CD200, CD272 |
| (BTLA), CD160 |
| A2a receptor, A2b receptor, |
| HHLA2, ILT-2, ILT-4, |

| Checkpoint target |
| --- |
| gp49B, PIR-B |
| OX40/OX-40L, BTLA, |
| ICOS, HLA-G, ILT-2/4 |
| KIR, GITR, TIM1, TIM4 |

Other exemplary targets include, but are not limited to:

| Target |
| --- |
| CTNNB1 (beta-catenin) |
| STAT3 |
| BCL-2 |
| MDR1 |
| Arginase 1 |
| iNOS |
| TGF-β |
| IL-10 |
| pGE2 |
| VEGF |
| KSP |
| HER2 |
| KRAS |
| TAK1 |
| PLK1 |
| K-Ras (Ras) |
| Stablin-1/CLEVER-1 |
| RNase H2 |
| DNase II |

I. COMBINATIONS OF RNAI/shRNAS TO MULTIPLE IMMUNE TARGETS WITHIN A SINGLE THERAPEUTIC MODALITY AND COMBINATION THERAPY

Combinations of RNAi, such as shRNAs or microRNAs, that inhibit different targets in one bacterium, are contemplated. Combinations of such targets can be selected to act synergistically. RNAi's that target any two immune checkpoints can be combined, and introduced into the immunostimulatory bacterial hosts modified as described herein, or into therapeutic bacterial hosts of others.

1. TREX1 and Other Targets

In order to mitigate the induction of compensatory immune checkpoint pathways that can be upregulated upon STING activation and enhance anti-tumor immunity, the modified immunostimulatory bacteria used herein can contain short hairpin (sh)-RNA sequences against TREX1 in combination with shRNA to other immune targets, including but not limited to PD-L1, VISTA and SIRPα. Knockdown of TREX1 and SIRPα in tumor-resident phagocytic cells enables blockade of "don't eat me" interactions with CD47 on tumor cells, as well as further enhances the susceptibility of the tumor microenvironment to *S. typhimurium* infection (Li et al. (2012) *J. Immunol.* 189(5):2537-2544), and is provided herein. The combination of enhanced phagocytosis enabled by SIRPα inhibition and simultaneous knockdown of TREX1, facilitates greater cytosolic delivery and stabilization of tumor DNA that can more potently activate cGAS/STING signaling. Notably, the anti-tumor effects of CD47/SIRPα blockade were shown to require intact STING signaling, demonstrating the potential synergy of combining TREX1-mediated STING activation with SIRPα inhibition (Liu et al. (2015) *Nat. Med.* 21(10):1209-1215). Knockdown of TREX1 in combination with shRNA to PD-L1, provided herein, enhances the pathogenesis and immune-stimulatory properties of the modified *S. typhimurium* (Lee et al. (2010) *J. Immunol.* 185(4):2442-2449), thereby igniting a more inflamed and immunogenic tumor microenvironment. shRNA targets against β-catenin and TGF-β also lead to a more T cell inflamed tumor microenvironment and synergize well with shRNA to PD-L1, and are provided herein. Combining immune activation with local checkpoint blockade within the macrophage/myeloid compartment in particular, such as through combined shRNAs to TREX1 and VISTA, provided herein, potentiates the immune response by enhancing both tumor neoantigen presentation by *S. typhimurium*-infected APCs and enhanced activation of tumor-specific T cells.

2. TREX1 and Radiotherapy

The success of anticancer radiotherapy depends on the induction of type I interferon-dependent innate and adaptive immunity. TREX1 has been shown to attenuate anti-tumor immunity following high levels of Gy radiation by degrading the cytosolic DNA that is produced in the damaged cancer cells, thus inhibiting the type I interferon pathway mediated by cGAS and STING (Vanpouille-Box et al. (2017) *Nature Communications* 8:15618). Thus, the overexpression of TREX1, or the knockout of cGAS/STING, which prevents activation of the IFN-I pathway, attenuates the abscopal tumor response upon irradiation. In order to activate STING-mediated Batf3-DC priming of $CD8^+$ T cells and achieve maximal abscopal anti-tumor immunity, a lower dose of radiation was required that would not induce TREX1 (Vanpouille-Box et al. (2017) *Nature Communications* 8:15618). The downregulation of TREX1 has been shown to restore the sensitivity of tumor cells towards ionizing radiation. For example, high dose irradiation induced TREX1 expression and prevented cytoplasmic accumulation of dsDNA, thereby inhibiting abscopal tumor regression (Vanpouille-Box et al. (2017) *Nature Communications* 8:15618). The immunostimulatory strains provided herein that block or inhibit TREX1 expression can reduce or eliminate or blunt the expression of TREX1 upon high dose radiation treatment, significantly extending the therapeutic window.

While radiotherapy (RT) has an abscopal effect at lower doses, the lower doses are not necessarily effective. At higher doses, however, the abscopal effect is no longer observed. This is a known problem with RT. Radiotherapy has been shown to promote the upregulation of TREX1 that degrades cytosolic dsDNA, precluding IFN-β secretion secondary to cGAS/STING signaling (see, Vanpouille-Box et al. (2017) *Nat. Commun.* 8:15618). Hence, the immunostimulatory bacterium provided herein can be administered with RT to prevent upregulation of TREX1. Administration of an immunostimulatory bacterium, provided herein, that encodes shRNA or other product that inhibits TREX1 abrogates this response, thereby improving and complementing RT. Hence, provided herein are combination therapies in which the immunostimulatory bacteria that encode shRNA or other products that inhibit or reduce expression of TREX1 are administered with RT, either before, in conjunction with, or after, or intermittently with RT. The combination therapy of the immunostimulatory bacteria and RT therapy also can include other anti-cancer therapies, such as administration of a checkpoint inhibitor, and/or inclusion of shRNA against other checkpoints, such as PD-L1, as described herein.

3. TREX1 and Immunogenic Chemotherapy

Induction of TREX1 was observed following DNA-damaging UV irradiation of mouse and human fibroblasts, as well as treatment of glioma and malignant melanoma cells with the DNA alkylating agents nimustine, carmustine and fotemustine, and the topoisomerase I inhibitor topotecan. These tumor cells were re-sensitized to these anti-cancer therapeutics following siRNA knockdown of TREX1 (Tomicic et al. (2013) *Biochimica et Biophysica Acta* 1833:1832-1843). TREX1 was only induced by damage agents that induce AP-1 efficiently, while agents that are weak inducers of Fos/Jun/AP-1, such as the methylating agent temozolomide and the topoisomerase II inhibitor etoposide, did not induce TREX1.

A separate study found that dsDNA accumulates and activates type I IFN upon treatment with chemotherapies that stall DNA replication in the S phase, such as cisplatin, irinotecan, doxorubicin and etoposide, but not agents that act in M phase, such as vinorelnine and paclitaxel (Wilkinson R. presented at ESMO TAT Conference 2018). S phase agents likely lead to the release of damaged DNA fragments that accumulate in the cytosol and upregulate TREX1. These chemotherapeutic agents, which include those that cause DNA strand breaks, such as nucleotide analogs, alkylating agents, platinum drugs, and intercalating agents (see, e.g., Swift et al. (2014) *Int. J. Mol. Sci.* 15:3403-3431), can induce TREX1 at levels sufficient to degrade the DNA, thereby precluding activation of the type-I interferon (IFN-I) pathway mediated via cyclic GMP-AMP (cGAMP) synthase (cGAS) and its downstream adaptor stimulator of interferon genes (STING). Treatment with the immunostimulatory bacteria provided herein can be combined with chemotherapeutic agents, and further with other checkpoint inhibitors. Hence, the immunostimulatory bacteria provided herein can advantageously be used in combination therapy with a variety of anti-cancer agents and treatments.

4. Combination Therapy with Anti-Checkpoint Antibodies

Therapy with the immunostimulatory bacteria provided herein can be combined with any other anti-cancer therapy, including checkpoint inhibitor therapies and, as discussed above, other cancer treatments and chemotherapy.

J. IDENTIFICATION AND TREATMENT OF TUMORS SUSCEPTIBLE TO TREATMENT WITH A TREX1 ANTAGONIST

It is shown herein that tumors that have a high mutational burden and/or are virally driven, such as HPV positive tumors, are susceptible to treatment with a TREX1 antagonist, such as an immunostimulatory bacterium or oncolytic virus, provided herein, that encodes an RNAi that inhibits, suppresses, disrupts or otherwise silences or reduces TREX1 expression, or that encodes an anti-TREX1 antibody or antigen-binding fragment thereof. Methods for treating such tumors are provided, as are uses of immunostimulatory bacteria that inhibit, disrupt or suppress expression of TREX1, or inhibit TREX1. Also provided are methods for identifying subjects for treatment by determining whether the subject's tumor or cancer is HPV positive and/or assessing tumor mutational burden (TMB) to identify whether the subject has a high tumor mutational burden (TMB; generally at least or about 10 mutations/megabase of genome). Subjects with HPV positive cancers or tumors, or with high mutational load are treated with a TREX1 antagonist.

1. Tumor Mutational Burden (TMB)

Tumor mutational burden (TMB) refers to the number of somatic cell mutations in the tumor genome, which for example, can be evaluated by assessing mutations per megabase using Next-Generation/Whole-Exome Sequencing. High tumor mutational burden (TMB) is more than 10 mutations per megabase (Mb), and low tumor mutational burden is less than 1 mutation/Mb (see, e.g., Bethune and Joglekar (2017) *Current Opinion in Biotechnology* 18:142-152). Tumors with high TMB, have neoantigens that form when somatic mutations result in the expression of epitopes. The epitopes are processed, presented by MHC molecules, and recognized by a specific subset of T-cells. The neoantigens are thus targets of endogenous immunity (Bethune and Joglekar (2017) *Current Opinion in Biotechnology* 18:142-152).

High tumor mutational burden (TMB), i.e., more than about 10 mutations per megabase (Mb), is associated with higher levels of neoantigens (neoantigen load) that are subject to recognition by the immune system. It can be a biomarker for tumors susceptible to immunotherapy. For example, patients with advanced non-small cell lung carcinoma (NSCLC), that had a TMB of ≥10 mutations per megabase, demonstrated longer progression-free survival after treatment with a combination of nivolumab and ipilimumab, than after chemotherapy. Other tumors with high TMB, such as melanoma, multiple myeloma, head and neck squamous cell carcinoma (HNSCC) and bladder cancer, have demonstrated improved response rates to immune checkpoint inhibition (ICI), compared to tumors with a low TMB, such as pancreatic and prostate cancer (Zhu et al. (2018) *Cancer Management and Research* 10:2475-2488; Gibney et al. (2016) *Lancet Oncol.* 17(12):e542-e551). In a study of patients with advanced melanoma treated with ipilimumab or tremilimumab, a mutational load of over 100 non-synonymous somatic mutations, based on tumor whole-exome sequencing, was associated with longer overall survival than patients with a lower mutational load, while patients with NSCLC characterized by a high TMB (>178 non-synonymous mutations) displayed longer progression-free survival following treatment with pembrolizumab (Gibney et al. (2016) *Lancet Oncol.* 17(12):e542-e551).

Herein, it is shown that there is a correlation between high TMB and TREX1 expression, indicating that the TMB can be exploited to select or identify cancer subjects who will respond to therapies, such as the immunostimulatory bacteria and oncolytic viruses provided herein, that antagonize TREX1. For example, provided herein are methods of treating a tumor, comprising administering an oncolytic virus or immunostimulatory bacterium, wherein the virus or bacterium comprises a sequence of nucleotides encoding RNAi; the RNAi inhibits, suppresses or disrupts expression of TREX1; and the tumor is HPV positive and/or has a high mutational burden. The methods can include a step of testing a tumor sample, such as a biopsy or body fluid, to determine TMB, and then treating such subjects with a TREX1 antagonist as described herein.

2. Virally Driven Tumors

It is shown herein that virally driven tumors, or tumors that are positive for a cancer-driving virus, are susceptible to treatment with a TREX1 antagonist, such as the immunostimulatory bacteria and oncolytic viruses that encode an RNA that inhibits, suppresses, disrupts or otherwise silences or reduces TREX1 expression. Hence, provided are methods for treatment of such cancers, which include cervical cancers and head and neck cancers. The tumors can be identified by standard, including commercially available assays, to detect the virus or virus markers in a tumor sample, such as a biopsy or biological fluid sample.

3. Oncoviruses

It is estimated that 12% of all cancers are caused by oncoviruses. Oncoviruses that have viral oncogenes contributing directly to neoplastic cellular transformation are known as direct carcinogens, whereas indirect carcinogenic viruses result in chronic inflammation that leads to oncogenic transformation (Mui et al. (2017) *J. Clin. Med.* 6, 111).

Oncogenic DNA viruses include, but are not limited to, Epstein-Barr virus (EBV), hepatitis B virus (HBV), human papillomavirus (HPV), human herpes virus-8 (HHV-8, also known as Kaposi sarcoma-associated herpesvirus) and Merkel cell polyomavirus (MCPyV), while oncogenic RNA viruses include, but are not limited to, hepatitis C virus (HCV) and human T-cell lymphotropic virus-1 (HTLV-1). Oncoviruses typically promote tumorigenesis by inhibiting tumor suppressor pathways, such as p53 and retinoblastoma (Rb) pathways. Other targets include tumor necrosis-associated factors (TRAFs), telomerase reverse transcriptase (TERT), cytoplasmic PI3K-AKT-mTOR, NF-κB, beta-catenin, interferon signaling pathways, MHC-1, JAK/STAT, and the host DNA damage response pathway (DDR) (Mui et al. (2017) *J. Clin. Med.* 6, 111).

a. Human Papillomavirus (HPV)

Human papillomavirus (HPV) belongs to the Papillomaviridae family, with over 200 different types, and is the most common sexually transmitted infection. HPV infects epithelial cells, and is categorized into low-risk and high-risk types, with high-risk types being associated with an increased risk of cancer development. The most common high risk types are HPV 16, 18, 31, 33, 52 and 58, and the most common low risk types are HPV 6, 11 and 53. HPV 16 and HPV 18 are the most common worldwide, and the primary types linked to cancer. HPV-associated malignancies include cervical, penile, vulvar, vaginal, anal, rectal and oropharyngeal carcinoma, with HPV infection accounting for more than half of infectious cancers in women, and 5% in men. HPV oncoproteins include E6 and E7, which inhibit tumor suppressor pathways, including p53 and Rb pathways, alter cytokine expression, and activate PI3K/AKT, Wnt/beta-catenin and Notch signaling pathways, resulting in increased cellular proliferation, decreased apoptosis, altered cell cycle regulation and telomere maintenance, and induction of DNA damage and genomic instability.

Therapeutic vaccines for the treatment of HPV-induced cancers are ongoing, with the goal of inducing antigen-specific cellular-mediated immunity. Vaccine-induced CD8$^+$ cytotoxic T cells and CD4$^+$ helper T cells target epithelial cells containing viral oncoproteins E6 and E7. Combinations using monoclonal antibodies, such as nivolumab, and therapeutic vaccines are also being explored (Mui et al. (2017) *J. Clin. Med.* 6, 111).

Cervical Cancer

Cervical cancer is the fourth leading cause of cancer in women, and the most common types are squamous cell carcinoma and adenocarcinoma of the cervix. HPVs cause almost 100% of cervical cancers. HPV 16 is found in approximately 59% of squamous cell carcinomas and 36% of adenocarcinomas, while HPV 18 is found in approximately 13% of squamous cell carcinomas and 39% of adenocarcinomas (Mui et al. (2017) *J. Clin. Med.* 6, 111).

Head and Neck Cancer (Oropharyngeal Cancer)

Head and neck cancer (HNSCC), particularly oropharyngeal squamous cell carcinoma (OPSCC) also can be caused by HPV infection. It is estimated that approximately 25% of HNSCC tumors are related to HPV infection (McBride, A. A. (2017) *Phil. Trans. R. Soc. B* 372:20160273), and HPV 16 is found in 90% and 96% of HPV-positive oropharyngeal and oral cancers, respectively (Mui et al. (2017) *J. Clin. Med.* 6, 111).

b. Human Herpesvirus-8 (HHV-8)

Human herpesvirus-8 (HHV-8), or Kaposi's sarcoma-associated herpesvirus (KSHV), belongs to the Herpesviridae family and is associated with Kaposi sarcoma (KS), as well as two B-cell lymphoproliferative diseases: multicentric Castleman's disease (MCD) and primary effusion lymphoma (PEL). HHV-8 is transmitted mostly via salivary, blood and sexual contact, with worldwide seroprevalence estimated to be between 5-20%. miRNAs and oncogenic proteins, such as LANA, viral cyclin, viral FLICE inhibitory protein (v-FLIP) and kaposin are associated with HHV-8-related malignancies and target signaling pathways such as MAPK, JAK/STAT, ERK, PI3K/AKT, Notch, Wnt, and NF-κB, as well as tumor suppressor proteins, including p53 and Rb. Additionally, kaposins promote tumorigenesis by increasing the expression of cytokines such as IL-6, IL-8, TNF-alpha, MIP-1alpha, and MIP-1beta. HHV-8 associated malignancies such as KS and PEL are currently treated by combination antiretroviral therapy (ART) and chemotherapy, but molecular-targeted therapies are being explored in clinical and pre-clinical trials (Mui et al. (2017) *J. Clin. Med.* 6, 111).

c. Hepatitis B Virus (HBV)

Hepatitis B virus (HBV) is a member of the family Hepadnaviridae and is associated with a 40% increased risk in the development of hepatocellular carcinoma (HCC). HBV infection accounts for 20% of HCC cases in the U.S., Europe and Japan, and 60% of HCC cases in Asia and Africa. Other malignancies associated with HBV include B-cell non-Hodgkin lymphoma (B-NHL) and nasopharyngeal carcinoma (NPC).

HBV exhibits oncogenesis primarily due to the insertion of viral DNA into the host cellular genome at sites prone to mutation, resulting in chromosomal instability and altered host gene expression, with integrated viral DNA being detected in approximately 80-90% of HBV-associated HCC. HBx and preS/S genes are commonly integrated viral genes, and TERT, MLL4, CCNE1, NTRK2, IRAK2 and MAPK1 are commonly altered human genes, which are responsible for telomerase activity, cell cycle progression, cell proliferation, apoptosis and stress response. HBx targets p53, DNMT, Wnt/beta-catenin, NF-κB, E2F1 and AP-1. It also has been demonstrated that autophagy, induced by HBx, promotes HBV DNA replication. Additionally, it has been found that preS/S HBV mutants increase the risk of HCC by 3.77-fold, via the induction of endoplasmic reticulum stress, which promotes oxidative DNA damage, and activation of signal transduction pathways that are responsible for cell cycle progression, cell proliferation, and anchorage-independent growth. NF-κB and STAT3 signaling pathways also have been shown to be activated in HBV-associated HCC by inflammatory cytokines, such as interleukins and TNF, as well as HBx.

Due to liver cirrhosis, radiation and chemotherapy, which further damage surrounding normal hepatocytes, are not optimal for the treatment of HCC. Surgical resection is only possible in less than 5-10% of cases, and other therapies include liver transplant and local ablative therapies, but are limited to small, localized tumors. Sorafenib and regorafenib are FDA-approved systemic chemotherapies for advanced HCC (Mui et al. (2017) *J. Clin. Med.* 6, 111).

d. Hepatitis C Virus (HCV)

Hepatitis C virus (HCV) belongs to the family Flaviviridae and HCV infection is the major risk factor for HCC in developed countries, accounting for up to 60% of HCC cases in the U.S. and 25% of HCC cases in Asia and Africa. HCV-induced hepatocarcinogenesis is associated with inflammation, and HCV infection also has been linked to B-cell Non-Hodgkin Lymphoma (B-NHL) and carcinomas of the head and neck, biliary duct, bladder, kidneys, pancreas, thyroid, breast and prostate, but its role in these malignancies remains unclear. HCV viral proteins activate the Wnt/beta-catenin signaling pathway, inhibit tumor suppressor proteins such as p53, p21, p73, Rb, ATM, and nibrin (NBS1), and induce oxidative stress and angiogenesis. HCV-associated HCC is treated using the same therapies as HBV-induced HCC (Mui et al. (2017) *J. Clin. Med.* 6, 111).

e. Merkel Cell Polyomavirus (MCPyV)

Merkel Cell Polyomavirus (MCPyV) belongs to the family Polyomaviridae and is found in 80-97% of Merkel cell carcinomas (MCCs), which is an extremely rare and aggressive cutaneous cancer. MCPyV infection usually occurs during childhood, with 80% of the adult population being seropositive. MCPyV oncoproteins include large T (LT) antigen, which promotes tumorigenesis by inhibiting apoptosis, stimulating telomerase activity and inducing angiogenesis, and small T (ST) antigen, which promotes tumorigenesis by promoting the cap-dependent translation downstream of the mTOR phosphorylation pathway, promoting aerobic glycolysis and ST-mediated c-Jun phosphorylation. The FDA recently approved avelumab, a human anti-PD-L1 monoclonal antibody, for the treatment of stage IV MCC. Other anti-PD-L1 antibodies, such as pembrolizumab and nivolumab have shown promise as therapies for MCC in clinical trials (Mui et al. (2017) *J. Clin. Med.* 6, 111).

f. Human T-Cell Lymphotropic Virus-1 (HTLV-1)

Human T-cell lymphotropic virus-1 (HTLV-1) is a delta RNA virus with a low seroprevalence, that causes peripheral T cell neoplasm adult T-cell lymphoma (ATLL), which is a clonal proliferation of CD4 T regulatory cells. The oncogenic HTLV-1 protein Tax interacts with factors such as AP-1, NF-B, CREB/ATF, CBP/p300, and p300/CBP-associated factor (P-CAF) serum responsive factor (SRF), inducing cytokines and receptors such as IL-2/IL-2 receptor (IL-2R), IL-9, IL-13, and IL-15/IL-15R, and repressing p53, cycin A and c-myb genes. HBZ is another oncogenic HTLV-1 protein, which stimulates lymphocyte proliferation through the upregulation of the E2F1 gene, prevents apoptosis by inhibiting the Bim gene, inhibits the NF-κB pathway, and induces microRNAs that compromise host genomic integrity. Chemotherapy is traditionally used for the treatment of ATLL, but monoclonal antibodies, such as anti-CD25 antibodies, and mogamulizumab (anti-CCR4 antibody) have been successful in clinical trials, whereas Δ24, an anti-transferrin receptor antibody, has shown promise in preclinical studies. Other promising therapies include vorinostat and romidepsin (HDAC inhibitors), alemtazumab (anti-CD52 antibody), and brentuximab vedotin (anti-CD30 antibody) (Mui et al. (2017) *J. Clin. Med.* 6, 111).

K. PHARMACEUTICAL PRODUCTION, COMPOSITIONS, AND FORMULATIONS

Provided herein are methods for manufacturing, pharmaceutical compositions and formulations containing any of the immunostimulatory bacteria provided herein and pharmaceutically acceptable excipients or additives. The pharmaceutical compositions can be used in treatment of diseases, such as hyperproliferative diseases or conditions, such as a tumor or cancer. The immunostimulatory bacteria can be administered in a single agent therapy, or can be administered in a combination therapy with a further agent or treatment. The compositions can be formulated for single dosage administration or for multiple dosage administration. The agents can be formulated for direct administration. The compositions can be provided as a liquid or dried formulation.

1. Manufacturing a. Cell Bank Manufacturing

As the active ingredient of the immunotherapeutic described herein is composed of engineered self-replicating bacteria, the selected composition will be expanded into a series of cell banks that will be maintained for long-term storage and as the starting material for manufacturing of drug substance. Cell banks are produced under current good manufacturing practices (cGMP) in an appropriate manufacturing facility per the Code of Federal Regulations (CFR) 21 part 211 or other relevant regulatory authority. As the active agent of the immunotherapeutic is a live bacterium, the products described herein are, by definition, non-sterile and cannot be terminally sterilized. Care must be taken to ensure that aseptic procedures are used throughout the manufacturing process to prevent contamination. As such, all raw materials and solutions must be sterilized prior to use in the manufacturing process.

A master cell bank (MCB) is produced by sequential serial single colony isolation of the selected bacterial strain to ensure no contaminants are present in the starting material. A sterile culture vessel containing sterile media (can be complex media e.g., LB or MSBB or defined media e.g., M9 supplemented with appropriate nutrients) is inoculated with a single well-isolated bacterial colony and the bacteria are allowed to replicate e.g., by incubation at 37° C. with shaking. The bacteria are then prepared for cryopreservation by suspension in a solution containing a cryoprotective agent or agents.

Examples of cryoprotective agents include: proteins such as human or bovine serum albumin, gelatin, and immunoglobulins; carbohydrates including monosaccharides (galactose, D-mannose, sorbose, etc.) and their non-reducing derivatives (e.g., methylglucoside), disaccharides (trehalose, sucrose, etc.), cyclodextrins, and polysaccharides (raffinose, maltodextrins, dextrans, etc.); amino-acids (glutamate, glycine, alanine, arginine or histidine, tryptophan, tyrosine, leucine, phenylalanine, etc.); methylamines such as betaine; polyols such as trihydric or higher sugar alcohols, e.g., glycerin, erythritol, glycerol, arabitol, xylitol, sorbitol, and mannitol; propylene glycol; polyethylene glycol; surfactants e.g., pluronic; or organo-sulfur compounds such as dimethyl sulfoxide (DMSO), and combinations thereof. Cryopreservation solutions may include one or more cryoprotective agents in a solution that may also contain salts (e.g., sodium chloride, potassium chloride, magnesium sulfate), and/or buffering agents such as sodium phosphate, tris(hydroxymethyl)aminomethane (TRIS), 4-(2-hydroxyethyl)-1-piperazineethanesulfonic acid (HEPES), and other such buffering agents known to those of skill in the art.

Suspension of the bacteria in cryopropreservation solution can be achieved either by addition of a concentrated cryoprotective agent or agents to the culture material to achieve a final concentration that preserves viability of the bacteria during the freezing and thawing process (e.g., 0.5% to 20% final concentration of glycerol), or by harvesting the bacteria (e.g., by centrifugation) and suspending in a cryopreservative solution containing the appropriate final concentration of cryoprotective agent(s). The suspension of bacteria in cryopreservation solution is then filled into appropriate sterile vials (plastic or glass) with a container closure system that is capable of maintaining closure integrity under frozen conditions (e.g., butyl stoppers and crimp seals). The vials of master cell bank are then frozen (either slowly by means of a controlled rate freezer, or quickly by means of placing directly into a freezer). The MCB is then stored frozen at a temperature that preserves long-term viability (e.g., at or below −60° C.). Thawed master cell bank material is thoroughly characterized to ensure identity, purity, and activity per regulation by the appropriate authorities.

Working cell banks (WCBs) are produced much the same way as the master cell bank, but the starting material is derived from the MCB. MCB material can be directly transferred into a fermentation vessel containing sterile media and expanded as above. The bacteria are then suspended in a cryopreservation solution, filled into containers, sealed, and frozen at or below −20° C. Multiple WCBs can be produced from MCB material, and WCB material can be used to make additional cell banks (e.g., a manufacturer's working cell bank MWCB). WCBs are stored frozen and characterized to ensure identity, purity, and activity. WCB material is typically the starting material used in production of the drug substance of biologics such as engineered bacteria.

b. Drug Substance Manufacturing

Drug substance is manufactured using aseptic processes under cGMP as described above. Working cell bank material is typically used as starting material for manufacturing of drug substance under cGMP, however other cell banks can be used (e.g., MCB or MWCB). Aseptic processing is used for production of all cell therapies including bacterial cell-based therapies. The bacteria from the cell bank are expanded by fermentation, this can be achieved by production of a pre-culture (e.g., in a shake flask) or by direct inoculation of a fermenter. Fermentation is accomplished in a sterile bioreactor or flask that can be single-use disposable or re-usable. Bacteria are harvested by concentration (e.g., by centrifugation, continuous centrifugation, or tangential flow filtration). Concentrated bacteria are purified from media components and bacterial metabolites by exchange of the media with buffer (e.g., by diafiltration). The bulk drug product is formulated and preserved as an intermediate (e.g., by freezing or drying) or is processed directly into a drug product. Drug substance is tested for identity, strength, purity, potency, and quality.

c. Drug Product Manufacturing

Drug product is defined as the final formulation of the active substance contained in its final container. Drug product is manufactured using aseptic processes under cGMP. Drug product is produced from drug substance. Drug substance is thawed or reconstituted if necessary, then formulated at the appropriate target strength. Because the active component of the drug product is live, engineered bacteria, the strength is determined by the number of CFU contained within the suspension. The bulk product is diluted in a final formulation appropriate for storage and use as described below. Containers are filled, and sealed with a container closure system and the drug product is labeled. The drug product is stored at an appropriate temperature to preserve stability and is tested for identity, strength, purity, potency, and quality and released for human use if it meets specified acceptance criteria.

2. Compositions

Pharmaceutically acceptable compositions are prepared in view of approvals for a regulatory agency or other agency prepared in accordance with generally recognized pharmacopeia for use in animals and in humans. The compositions can be prepared as solutions, suspensions, powders, or sustained release formulations. Typically, the compounds are formulated into pharmaceutical compositions using techniques and procedures well known in the art (see e.g., Ansel *Introduction to Pharmaceutical Dosage Forms*, Fourth Edition, 1985, 126). The formulation should suit the mode of administration.

Compositions can be formulated for administration by any route known to those of skill in the art including intramuscular, intravenous, intradermal, intralesional, intraperitoneal injection, subcutaneous, intratumoral, epidural, nasal, oral, vaginal, rectal, topical, local, otic, inhalational, buccal (e.g., sublingual), and transdermal administration or any route. Other modes of administration also are contemplated. Administration can be local, topical or systemic depending upon the locus of treatment. Local administration to an area in need of treatment can be achieved by, for example, but not limited to, local infusion during surgery, topical application, e.g., in conjunction with a wound dressing after surgery, by injection, by means of a catheter, by means of a suppository, or by means of an implant. Compositions also can be administered with other biologically active agents, either sequentially, intermittently or in the same composition. Administration also can include controlled release systems including controlled release formulations and device controlled release, such as by means of a pump.

The most suitable route in any given case depends on a variety of factors, such as the nature of the disease, the progress of the disease, the severity of the disease and the particular composition which is used. Pharmaceutical compositions can be formulated in dosage forms appropriate for each route of administration. In particular, the compositions can be formulated into any suitable pharmaceutical preparations for systemic, local intraperitoneal, oral or direct administration. For example, the compositions can be formulated for administration subcutaneously, intramuscularly, intratumorally, intravenously or intradermally. Administration methods can be employed to decrease the exposure of the active agent to degradative processes, such as immunological intervention via antigenic and immunogenic responses. Examples of such methods include local administration at the site of treatment or continuous infusion.

The immunostimulatory bacteria can be formulated into suitable pharmaceutical preparations such as solutions, suspensions, tablets, dispersible tablets, pills, capsules, powders, sustained release formulations or elixirs, for oral administrations, as well as transdermal patch preparation and dry powder inhalers. Typically, the compounds are formulated into pharmaceutical compositions using techniques and procedures well known in the art (see e.g., Ansel *Introduction to Pharmaceutical Dosage Forms*, Fourth Edition, 1985, 126). Generally, the mode of formulation is a function of the route of administration. The compositions can be formulated in dried (lyophilized or other forms of vitrification) or liquid form. Where the compositions are provided in dried form they can be reconstituted just prior to use by addition of an appropriate buffer, for example, a sterile saline solution.

3. Formulations a. Liquids, Injectables, Emulsions

The formulation generally is made to suit the route of administration. Parenteral administration, generally characterized by injection or infusion, either subcutaneously, intramuscularly, intratumorally, intravenously or intradermally is contemplated herein. Preparations of bacteria for parenteral administration include suspensions ready for injection (direct administration) or frozen suspensions that are thawed prior to use, dry soluble products, such as lyophilized powders, ready to be combined with a resuspension solution just prior to use, and emulsions. Dried thermostable formulations such as lyophilized formulations can be used for storage of unit doses for later use.

The pharmaceutical preparation can be in a frozen liquid form, for example a suspension. If provided in frozen liquid form, the drug product can be provided as a concentrated preparation to be thawed and diluted to a therapeutically effective concentration before use.

The pharmaceutical preparations also can be provided in a dosage form that does not require thawing or dilution for use. Such liquid preparations can be prepared by conventional means with pharmaceutically acceptable additives, as appropriate, such as suspending agents (e.g., sorbitol, cellulose derivatives or hydrogenated edible fats); emulsifying agents (e.g., lecithin or acacia); non-aqueous vehicles (e.g., almond oil, oily esters, or fractionated vegetable oils); and preservatives suitable for use with microbial therapeutics. The pharmaceutical preparations can be presented in dried form, such as lyophilized or spray-dried, for reconstitution with water or other sterile suitable vehicle before use.

Suitable excipients are, for example, water, saline, dextrose, or glycerol. The solutions can be either aqueous or non-aqueous. If administered intravenously, suitable carriers include physiological saline or phosphate buffered saline (PBS), and other buffered solutions used for intravenous hydration. For intratumoral administration solutions containing thickening agents such as glucose, polyethylene glycol, and polypropylene glycol, oil emulsions and mixtures thereof may be appropriate to maintain localization of the injectant.

Pharmaceutical compositions can include carriers or other excipients. For example, pharmaceutical compositions provided herein can contain any one or more of a diluents(s), adjuvant(s), antiadherent(s), binder(s), coating(s), filler(s), flavor(s), color(s), lubricant(s), glidant(s), preservative(s), detergent(s), or sorbent(s) and a combination thereof or vehicle with which a modified therapeutic bacteria is administered. For example, pharmaceutically acceptable carriers or excipients used in parenteral preparations include aqueous vehicles, non-aqueous vehicles, isotonic agents, buffers, antioxidants, local anesthetics, suspending and dispersing agents, emulsifying agents, sequestering or chelating agents and other pharmaceutically acceptable substances. Formulations, including liquid preparations, can be prepared by conventional means with pharmaceutically acceptable additives or excipients.

Pharmaceutical compositions can include carriers such as a diluent, adjuvant, excipient, or vehicle with which the compositions are administered. Examples of suitable pharmaceutical carriers are described in "Remington's Pharmaceutical Sciences" by E. W. Martin. Such compositions will contain a therapeutically effective amount of the compound or agent, generally in purified form or partially purified form, together with a suitable amount of carrier so as to provide the form for proper administration to the patient. Such pharmaceutical carriers can be sterile liquids, such as water and oils, including those of petroleum, animal, vegetable or synthetic origin, such as peanut oil, soybean oil, mineral oil, and sesame oil. Water is a typical carrier. Saline solutions and aqueous dextrose and glycerol solutions also can be employed as liquid carriers, particularly for injectable solutions. Compositions can contain along with an active ingredient: a diluent such as lactose, sucrose, dicalcium phosphate, or carboxymethylcellulose; a lubricant, such as magnesium stearate, calcium stearate and talc; and a binder such as starch, natural gums, such as gum acacia, gelatin, glucose, molasses, polyvinylpyrrolidine, celluloses and derivatives thereof, povidone, crospovidones and other such binders known to those of skill in the art. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. For example, suitable excipients are, for example, water, saline, dextrose, glycerol or ethanol. A composition, if desired, also can contain other minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Pharmaceutically acceptable carriers used in parenteral preparations include aqueous vehicles, non-aqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Non-aqueous parenteral vehicles include fixed oils of vegetable origin, cottonseed oil, corn oil, sesame oil and peanut oil. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include, for example, polysorbates, such as Polysorbate 80 (TWEEN 80). Sequestering or chelating agents of metal ions, such as EDTA, can be included. Pharmaceutical carriers also include polyethylene glycol and propylene glycol for water miscible vehicles and sodium hydroxide, hydrochloric acid, citric acid or lactic acid for pH adjustment. Non-antimicrobial preservatives can be included.

The pharmaceutical compositions also can contain other minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) also is contemplated herein. The percentage of active compound contained in such parenteral compositions is highly dependent on the specific nature thereof, as well as the activity of the compound and the needs of the subject.

b. Dried Thermostable Formulations

The bacteria can be dried. Dried thermostable formulations, such as lyophilized or spray dried powders and vitrified glass can be reconstituted for administration as solutions, emulsions and other mixtures. The dried thermostable formulation can be prepared from any of the liquid formulations, such as the suspensions, described above. The pharmaceutical preparations can be presented in lyophilized or vitrified form for reconstitution with water or other suitable vehicle before use.

The thermostable formulation is prepared for administration by reconstituting the dried compound with a sterile solution. The solution can contain an excipient which improves the stability or other pharmacological attribute of the active substance or reconstituted solution, prepared from the powder. The thermostable formulation is prepared by dissolving an excipient, such as dextrose, sorbitol, fructose, corn syrup, xylitol, glycerin, glucose, sucrose or other suitable agent, in a suitable buffer, such as citrate, sodium or potassium phosphate or other such buffer known to those of skill in the art. Then, the drug substance is added to the resulting mixture, and stirred until it is mixed. The resulting mixture is apportioned into vials for drying. Each vial will contain a single dosage containing $1\times10^5$-$1\times10^{11}$ CFU per vial. After drying, the product vial is sealed with a container closure system that prevents moisture or contaminants from entering the sealed vial. The dried product can be stored under appropriate conditions, such as at −20° C., 4° C., or room temperature. Reconstitution of this dried formulation with water or a buffer solution provides a formulation for use in parenteral administration. The precise amount depends upon the indication treated and selected compound. Such amount can be empirically determined.

4. Compositions for Other Routes of Administration

Depending upon the condition treated, other routes of administration in addition to parenteral, such as topical application, transdermal patches, oral and rectal administration are also contemplated herein. The suspensions and powders described above can be administered orally or can be reconstituted for oral administration. Pharmaceutical dosage forms for rectal administration are rectal suppositories, capsules and tablets and gel capsules for systemic effect. Rectal suppositories include solid bodies for insertion into the rectum which melt or soften at body temperature releasing one or more pharmacologically or therapeutically active ingredients. Pharmaceutically acceptable substances in rectal suppositories are bases or vehicles and agents to raise the melting point. Examples of bases include cocoa butter (*theobroma* oil), glycerin-gelatin, carbowax (polyoxyethylene glycol) and appropriate mixtures of mono-, di- and triglycerides of fatty acids. Combinations of the various bases can be used. Agents to raise the melting point of suppositories include spermaceti and wax. Rectal suppositories can be prepared either by the compressed method or by molding. The typical weight of a rectal suppository is about 2 to 3 gm. Tablets and capsules for rectal administration are manufactured using the same pharmaceutically acceptable substance and by the same methods as for formulations for oral administration. Formulations suitable for rectal administration can be provided as unit dose suppositories. These can be prepared by admixing the drug substance with one or more conventional solid carriers, for example, cocoa butter, and then shaping the resulting mixture.

For oral administration, pharmaceutical compositions can take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well-known in the art.

Formulations suitable for buccal (sublingual) administration include, for example, lozenges containing the active compound in a flavored base, usually sucrose and acacia or tragacanth; and pastilles containing the compound in an inert base such as gelatin and glycerin or sucrose and acacia.

Topical mixtures are prepared as described for the local and systemic administration. The resulting mixtures can be solutions, suspensions, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compositions can be formulated as aerosols for topical application, such as by inhalation (see, e.g., U.S. Pat. Nos. 4,044,126; 4,414,209 and 4,364,923, which describe aerosols for delivery of a steroid useful for treatment of lung diseases). These formulations, for administration to the respiratory tract, can be in the form of an aerosol or solution for a nebulizer, or as a microfine powder for insufflation, alone or in combination with an inert carrier such as lactose. In such a case, the particles of the formulation will typically have diameters of less than 50 microns, or less than 10 microns.

The compounds can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients also can be administered.

Formulations suitable for transdermal administration are provided. They can be provided in any suitable format, such as discrete patches adapted to remain in intimate contact with the epidermis of the recipient for a prolonged period of time. Such patches contain the active compound in an optionally buffered aqueous solution of, for example, 0.1 to 0.2 M concentration with respect to the active compound. Formulations suitable for transdermal administration also can be delivered by iontophoresis (see, e.g., Tyle, P, (1986) *Pharmaceutical Research* 3(6):318-326) and typically take the form of an optionally buffered aqueous solution of the active compound.

Pharmaceutical compositions also can be administered by controlled release formulations and/or delivery devices (see e.g., in U.S. Pat. Nos. 3,536,809; 3,598,123; 3,630,200; 3,845,770; 3,916,899; 4,008,719; 4,769,027; 5,059,595; 5,073,543; 5,120,548; 5,591,767; 5,639,476; 5,674,533 and 5,733,566).

5. Dosages and Administration

The compositions can be formulated as pharmaceutical compositions for single dosage or multiple dosage administration. The immunostimulatory bacteria can be included in an amount sufficient to exert a therapeutically useful effect in the absence of undesirable side effects on the patient treated. For example, the concentration of the pharmaceutically active compound is adjusted so that an injection provides an effective amount to produce the desired pharmacological effect. The therapeutically effective concentration can be determined empirically by testing the immunostimulatory bacteria in known in vitro and in vivo systems such as by using the assays described herein or known in the art. For example, standard clinical techniques can be employed. In vitro assays and animal models can be employed to help identify optimal dosage ranges. The precise dose, which can be determined empirically, can depend on the age, weight, body surface area, and condition of the patient or animal, the particular immunostimulatory bacteria administered, the route of administration, the type of disease to be treated and the seriousness of the disease.

Hence, it is understood that the precise dosage and duration of treatment is a function of the disease being treated and can be determined empirically using known testing protocols or by extrapolation from in vivo or in vitro test data. Concentrations and dosage values also can vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or use of compositions and combinations containing them. The compositions can be administered hourly, daily, weekly, monthly, yearly or once. Generally, dosage regimens are chosen to limit toxicity. It should be noted that the attending physician would know how to and when to terminate, interrupt or adjust therapy to lower dosage due to toxicity, or bone marrow, liver or kidney or other tissue dysfunctions. Conversely, the attending physician would also know how to and when to adjust treatment to higher levels if the clinical response is not adequate (precluding toxic side effects).

The immunostimulatory bacteria are included in the composition in an amount sufficient to exert a therapeutically useful effect. For example, the amount is one that achieves a therapeutic effect in the treatment of a hyperproliferative disease or condition, such as cancer.

Pharmaceutically and therapeutically active compounds and derivatives thereof are typically formulated and administered in unit dosage forms or multiple dosage forms. Each unit dose contains a predetermined quantity of therapeutically active compound sufficient to produce the desired therapeutic effect, in association with the required pharmaceutical carrier, vehicle or diluent. Unit dosage forms, include, but are not limited to, tablets, capsules, pills, powders, granules, parenteral suspensions, and oral solutions or suspensions, and oil water emulsions containing suitable quantities of the compounds or pharmaceutically acceptable derivatives thereof. Unit dose forms can be contained in vials, ampoules and syringes or individually packaged tablets or capsules. Unit dose forms can be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses that are not segregated in packaging. Generally, dosage forms or compositions containing active ingredient in the range of 0.005% to 100% with the balance made up from non-toxic carrier can be prepared. Pharmaceutical compositions can be formulated in dosage forms appropriate for each route of administration.

The unit-dose parenteral preparations are packaged in an ampoule, a vial or a syringe with a needle. The volume of liquid solution or reconstituted powder preparation, containing the pharmaceutically active compound, is a function of the disease to be treated and the particular article of manufacture chosen for package. All preparations for parenteral administration must be sterile, as is known and practiced in the art.

As indicated, compositions provided herein can be formulated for any route known to those of skill in the art including, but not limited to, subcutaneous, intramuscular, intravenous, intradermal, intralesional, intraperitoneal injection, epidural, vaginal, rectal, local, otic, transdermal administration or any route of administration. Formulations suited for such routes are known to one of skill in the art. Compositions also can be administered with other biologically active agents, either sequentially, intermittently or in the same composition.

Pharmaceutical compositions can be administered by controlled release formulations and/or delivery devices (see, e.g., in U.S. Pat. Nos. 3,536,809; 3,598,123; 3,630,200; 3,845,770; 3,847,770; 3,916,899; 4,008,719; 4,687,660; 4,769,027; 5,059,595; 5,073,543; 5,120,548; 5,354,556; 5,591,767; 5,639,476; 5,674,533 and 5,733,566). Various delivery systems are known and can be used to administer selected compositions, are contemplated for use herein, and such particles can be easily made.

6. Packaging and Articles of Manufacture

Also provided are articles of manufacture containing packaging materials, any pharmaceutical composition provided herein, and a label that indicates that the compositions are to be used for treatment of diseases or conditions as described herein. For example, the label can indicate that the treatment is for a tumor or cancer.

Combinations of immunostimulatory bacteria described herein and another therapeutic agent also can be packaged in an article of manufacture. In one example, the article of manufacture contains a pharmaceutical composition containing the immunostimulatory bacteria composition and no further agent or treatment. In other examples, the article of manufacture contains another further therapeutic agent, such as a different anti-cancer agent. In this example, the agents can be provided together or separately, for packaging as articles of manufacture.

The articles of manufacture provided herein contain packaging materials. Packaging materials for use in packaging pharmaceutical products are well known to those of skill in the art. See, for example, U.S. Pat. Nos. 5,323,907, 5,052,558 and 5,033,252, each of which is incorporated herein in its entirety. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. Exemplary of articles of manufacture are containers including single chamber and dual chamber containers. The containers include, but are not limited to, tubes, bottles and syringes. The containers can further include a needle for intravenous administration.

The choice of package depends on the agents, and whether such compositions will be packaged together or separately. In general, the packaging is non-reactive with the compositions contained therein. In other examples, some of the components can be packaged as a mixture. In other examples, all components are packaged separately. Thus, for example, the components can be packaged as separate compositions that, upon mixing just prior to administration, can be directly administered together. Alternatively, the components can be packaged as separate compositions for administration separately.

Selected compositions including articles of manufacture thereof also can be provided as kits. Kits can include a pharmaceutical composition described herein and an item for administration provided as an article of manufacture. The compositions can be contained in the item for administration or can be provided separately to be added later. The kit can, optionally, include instructions for application including dosages, dosing regimens and instructions for modes of administration. Kits also can include a pharmaceutical composition described herein and an item for diagnosis.

L. METHODS OF TREATMENT AND USES

The methods provided herein include methods of administering or using the immunostimulatory bacteria, for treating subjects having a disease or condition whose symptoms can be ameliorated or lessened by administration of such bacteria, such as cancer. In particular examples, the disease or condition is a tumor or a cancer. Additionally, methods of combination therapies with one or more additional agents for treatment, such as an anticancer agent or an antihyaluronan agent, also are provided. The bacteria can be administered by any suitable route, including, but not limited to, parenteral, systemic, topical and local, such as intra-tumoral, intravenous, rectal, oral, intramuscular, mucosal and other routes. Formulations suitable for each are provided. The skilled person can establish suitable regimens and doses and select routes.

1. Cancers and Tumors

The immunostimulatory bacteria, combinations, uses and methods provided herein are applicable to treating all types of tumors, including cancers, particularly solid tumors including lung cancer, bladder, non-small cell lung cancer, gastric cancers, head and neck cancers, ovarian cancer, liver cancer, pancreatic cancer, kidney cancer, breast cancer, colorectal cancer, and prostate cancer. The methods also can be used for hematological cancers. In particular, the immunostimulatory bacteria and oncolytic viruses herein are for treating viral-driven tumors and/or tumors with a high TMB (see section J, above).

Tumors and cancers subject to treatment by the uses methods provided herein include, but are not limited to, those that originate in the immune system, skeletal system, muscles and heart, breast, pancreas, gastrointestinal tract, central and peripheral nervous system, renal system, reproductive system, respiratory system, skin, connective tissue systems, including joints, fatty tissues, and circulatory system, including blood vessel walls. Examples of tumors that can be treated with the immunostimulatory bacteria provided herein include carcinomas, gliomas, sarcomas (including liposarcoma), adenocarcinomas, adenosarcomas, and adenomas. Such tumors can occur in virtually all parts of the body, including, for example, breast, heart, lung, small intestine, colon, spleen, kidney, bladder, head and neck, ovary, prostate, brain, pancreas, skin, bone, bone marrow, blood, thymus, uterus, testicles, cervix or liver.

Tumors of the skeletal system include, for example, sarcomas and blastomas such as osteosarcoma, chondrosarcoma, and chondroblastoma. Muscle and heat tumors include tumors of both skeletal and smooth muscles, e.g., leiomyomas (benign tumors of smooth muscle), leiomyosarcomas, rhabdomyomas (benign tumors of skeletal muscle), rhabdomyosarcomas, cardiac sarcoma. Tumors of the gastrointestinal tract include e.g., tumors of the mouth, esophagus, stomach, small intestine, colon and colorectal tumors, as well as tumors of gastrointestinal secretory organs such as salivary glands, liver, pancreas, and the biliary tract. Tumors of the central nervous system include tumors of the brain, retina, and spinal cord, and can also originate in associated connective tissue, bone, blood vessels or nervous tissue. Treatment of tumors of the peripheral nervous system are also contemplated. Tumors of the peripheral nervous system include malignant peripheral nerve sheath tumors. Tumors of the renal system include those of the kidneys, e.g., renal cell carcinoma, as well as tumors of the ureters and bladder. Tumors of the reproductive system include tumors of the cervix, uterus, ovary, prostate, testes and related secretory glands. Tumors of the immune system include both blood based and solid tumors, including lymphomas, e.g., both Hodgkin's and non-Hodgkin's. Tumors of the respiratory system include tumors of the nasal passages, bronchi and lungs. Tumors of the breast include, e.g., both lobular and ductal carcinoma.

Other examples of tumors that can be treated by the immunostimulatory bacteria and methods provided herein include Kaposi's sarcoma, CNS neoplasms, neuroblastomas, capillary hemangioblastomas, meningiomas and cerebral metastases, melanoma, gastrointestinal and renal carcinomas and sarcomas, rhabdomyosarcoma, glioblastoma (such as glioblastoma multiforme) and leiomyosarcoma. Examples of other cancer that can be treated as provided herein include but are not limited to lymphoma, blastoma, neuroendocrine tumors, mesothelioma, schwannoma, meningioma, melanoma, and leukemia or lymphoid malignancies. Examples of such cancers include hematologic malignancies, such as Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplasmacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histiocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia; tumors of the central nervous system such as glioma, glioblastoma, neuroblastoma, astrocytoma, medulloblastoma, ependymoma, and retinoblastoma; solid tumors of the head and neck (e.g., nasopharyngeal cancer, salivary gland carcinoma, and esophageal cancer), lung (e.g., small-cell lung cancer, non-small cell lung cancer, adenocarcinoma of the lung and squamous carcinoma of the lung), digestive system (e.g., gastric or stomach cancer including gastrointestinal cancer, cancer of the bile duct or biliary tract, colon cancer, rectal cancer, colorectal cancer, and anal carcinoma), reproductive system (e.g., testicular, penile, or prostate cancer, uterine, vaginal, vulval, cervical, ovarian, and endometrial cancer), skin (e.g., melanoma, basal cell carcinoma, squamous cell cancer, actinic keratosis, cutaneous melanoma), liver (e.g., liver cancer, hepatic carcinoma, hepatocellular cancer, and hepatoma), bone (e.g., osteoclastoma, and osteolytic bone cancers) additional tissues and organs (e.g., pancreatic cancer, bladder cancer, kidney or renal cancer, thyroid cancer, breast cancer, cancer of the peritoneum, and Kaposi's sarcoma), tumors of the vascular system (e.g., angiosarcoma and hemangiopericytoma), Wilms' tumor, retinoblastoma, osteosarcoma and Ewing's sarcoma.

2. Administration

In practicing the uses and methods herein, immunostimulatory bacteria provided herein can be administered to a subject, including a subject having a tumor or having neoplastic cells, or a subject to be immunized. One or more steps can be performed prior to, simultaneously with or after administration of the immunostimulatory bacteria to the subject including, but not limited to, diagnosing the subject with a condition appropriate for administering immunostimulatory bacteria, determining the immunocompetence of the subject, immunizing the subject, treating the subject with a chemotherapeutic agent, treating the subject with radiation, or surgically treating the subject.

For embodiments that include administering immunostimulatory bacteria to a tumor-bearing subject for therapeutic purposes, the subject typically has previously been diagnosed with a neoplastic condition. Diagnostic methods also can include determining the type of neoplastic condition, determining the stage of the neoplastic conditions, determining the size of one or more tumors in the subject, determining the presence or absence of metastatic or neoplastic cells in the lymph nodes of the subject, or determining the presence of metastases of the subject.

Some embodiments of therapeutic methods for administering immunostimulatory bacteria to a subject can include a step of determination of the size of the primary tumor or the stage of the neoplastic disease, and if the size of the primary tumor is equal to or above a threshold volume, or if the stage of the neoplastic disease is at or above a threshold stage, an immunostimulatory bacterium is administered to the subject. In a similar embodiment, if the size of the primary tumor is below a threshold volume, or if the stage of the neoplastic disease is at or below a threshold stage, the immunostimulatory bacterium is not yet administered to the subject; such methods can include monitoring the subject until the tumor size or neoplastic disease stage reaches a threshold amount, and then administering the immunostimulatory bacterium to the subject. Threshold sizes can vary according to several factors, including rate of growth of the tumor, ability of the immunostimulatory bacterium to infect a tumor, and immunocompetence of the subject. Generally the threshold size will be a size sufficient for an immunostimulatory bacterium to accumulate and replicate in or near the tumor without being completely removed by the host's immune system, and will typically also be a size sufficient to sustain a bacterial infection for a time long enough for the host to mount an immune response against the tumor cells, typically about one week or more, about ten days or more, or about two weeks or more. Exemplary threshold stages are any stage beyond the lowest stage (e.g., Stage I or equivalent), or any stage where the primary tumor is larger than a threshold size, or any stage where metastatic cells are detected.

Any mode of administration of a microorganism to a subject can be used, provided the mode of administration permits the immunostimulatory bacteria to enter a tumor or metastasis. Modes of administration can include, but are not limited to, intravenous, intraperitoneal, subcutaneous, intramuscular, topical, intratumoral, multipuncture, inhalation, intranasal, oral, intracavity (e.g., administering to the bladder via a catheter, administering to the gut by suppository or enema), aural, rectal, and ocular administration.

One skilled in the art can select any mode of administration compatible with the subject and the bacteria, and that also is likely to result in the bacteria reaching tumors and/or metastases. The route of administration can be selected by one skilled in the art according to any of a variety of factors, including the nature of the disease, the kind of tumor, and the particular bacteria contained in the pharmaceutical composition. Administration to the target site can be performed, for example, by ballistic delivery, as a colloidal dispersion system, or systemic administration can be performed by injection into an artery.

The dosage regimen can be any of a variety of methods and amounts, and can be determined by one skilled in the art according to known clinical factors. A single dose can be therapeutically effective for treating a disease or disorder in which immune stimulation effects treatment. Exemplary of such stimulation is an immune response, that includes, but is not limited to, one or both of a specific immune response and non-specific immune response, both specific and non-specific responses, innate response, primary immune response, adaptive immunity, secondary immune response, memory immune response, immune cell activation, immune cell proliferation, immune cell differentiation, and cytokine expression.

As is known in the medical arts, dosages for a subject can depend on many factors, including the subject's species, size, body surface area, age, sex, immunocompetence, and general health, the particular bacteria to be administered, duration and route of administration, the kind and stage of the disease, for example, tumor size, and other compounds such as drugs being administered concurrently. In addition to the above factors, such levels can be affected by the infectivity of the bacteria and the nature of the bacteria, as can be determined by one skilled in the art. In the present methods, appropriate minimum dosage levels of bacteria can be levels sufficient for the bacteria to survive, grow and replicate in a tumor or metastasis. Exemplary minimum levels for administering a bacterium to a 65 kg human can include at least about $5 \times 10^6$ colony forming units (CFU), at least about $1 \times 10^7$ CFU, at least about $5 \times 10^7$ CFU, at least about $1 \times 10^8$ CFU, or at least about $1 \times 10^9$ CFU. In the present methods, appropriate maximum dosage levels of bacteria can be levels that are not toxic to the host, levels that do not cause splenomegaly of 3× or more, and/or levels that do not result in colonies or plaques in normal tissues or organs after about 1 day or after about 3 days or after about 7 days. Exemplary maximum levels for administering a bacterium to a 65 kg human can include no more than about $5 \times 10^{11}$ CFU, no more than about $1 \times 10^{11}$ CFU, no more than about $5 \times 10^{10}$ CFU, no more than about $1 \times 10^{10}$ CFU, or no more than about $1 \times 10^9$ CFU.

The methods and uses provided herein can include a single administration of immunostimulatory bacteria to a subject or multiple administrations of immunostimulatory bacteria to a subject or others of a variety of regimens, including combination therapies with other anti-tumor therapeutics and/or treatments. These include, cellular therapies, such as administration of modified immune cells, CAR-T therapy, CRISPR therapy, checkpoint inhibitors, such as antibodies, and chemotherapeutic compounds, such as nucleoside analogs, surgery and radiotherapy.

In some embodiments, a single administration is sufficient to establish immunostimulatory bacteria in a tumor, where the bacteria can colonize and can cause or enhance an anti-tumor response in the subject. In other embodiments, the immunostimulatory bacteria provided for use in the methods herein can be administered on different occasions, separated in time typically by at least one day. Separate administrations can increase the likelihood of delivering a bacterium to a tumor or metastasis, where a previous administration may have been ineffective in delivering the bacterium to a tumor or metastasis. In embodiments, separate administrations can increase the locations on a tumor or metastasis where bacterial colonization/proliferation can occur or can otherwise increase the titer of bacteria accumulated in the tumor, which can increase eliciting or enhancing a host's anti-tumor immune response.

When separate administrations are performed, each administration can be a dosage amount that is the same or different relative to other administration dosage amounts. In one embodiment, all administration dosage amounts are the same. In other embodiments, a first dosage amount can be a larger dosage amount than one or more subsequent dosage amounts, for example, at least 10× larger, at least 100× larger, or at least 1000× larger than subsequent dosage amounts. In one example of a method of separate administrations in which the first dosage amount is greater than one or more subsequent dosage amounts, all subsequent dosage amounts can be the same, smaller amount relative to the first administration.

Separate administrations can include any number of two or more administrations, including two, three, four, five or six administrations. One skilled in the art readily can determine the number of administrations to perform, or the desirability of performing one or more additional administrations, according to methods known in the art for monitoring therapeutic methods and other monitoring methods provided herein. Accordingly, the methods provided herein include methods of providing to the subject one or more administrations of immunostimulatory bacteria, where the number of administrations can be determined by monitoring the subject, and, based on the results of the monitoring, determining whether or not to provide one or more additional administrations. Deciding whether or not to provide one or more additional administrations can be based on a variety of monitoring results, including, but not limited to, indication of tumor growth or inhibition of tumor growth, appearance of new metastases or inhibition of metastasis, the subject's anti-bacterial antibody titer, the subject's anti-tumor antibody titer, the overall health of the subject and the weight of the subject.

The time period between administrations can be any of a variety of time periods. The time period between administrations can be a function of any of a variety of factors, including monitoring steps, as described in relation to the number of administrations, the time period for a subject to mount an immune response, the time period for a subject to clear bacteria from normal tissue, or the time period for bacterial colonization/proliferation in the tumor or metastasis. In one example, the time period can be a function of the time period for a subject to mount an immune response; for example, the time period can be more than the time period for a subject to mount an immune response, such as more than about one week, more than about ten days, more than about two weeks, or more than about a month; in another example, the time period can be less than the time period for a subject to mount an immune response, such as less than about one week, less than about ten days, less than about two weeks, or less than about a month. In another example, the time period can be a function of the time period for bacterial colonization/proliferation in the tumor or metastasis; for example, the time period can be more than the amount of time for a detectable signal to arise in a tumor or metastasis after administration of a microorganism expressing a detectable marker, such as about 3 days, about 5 days, about a week, about ten days, about two weeks, or about a month.

The methods used herein also can be performed by administering compositions, such as suspensions and other formulations, containing the immunostimulatory bacteria provided herein. Such compositions contain the bacteria and a pharmaceutically acceptable excipient or vehicle, as provided herein or known to those of skill in the art.

As discussed above, the uses and methods provided herein also can include administering one or more therapeutic compounds, such as anti-tumor compounds or other cancer therapeutics, to a subject in addition to administering immunostimulatory bacteria to the subject. The therapeutic compounds can act independently, or in conjunction with the immunostimulatory bacteria, for tumor therapeutic effects. Therapeutic compounds that can act independently include any of a variety of known chemotherapeutic compounds that can inhibit tumor growth, inhibit metastasis growth and/or formation, decrease the size of a tumor or metastasis, or eliminate a tumor or metastasis, without reducing the ability of the immunostimulatory bacteria to accumulate in a tumor, replicate in the tumor, and cause or enhance an anti-tumor immune response in the subject. Examples of such chemotherapeutic agents include, but are not limited to, alkylating agents such as thiotepa and cyclosphosphamide; alkyl sulfonates such as busulfan, improsulfan, and piposulfan; androgens such as calusterone, dromostanolone propionate, epitiostanol, mepitiostane, and testolactone; anti-adrenals such as aminoglutethimide, mitotane, and trilostane; anti-androgens such as flutamide, nilutamide, bicalutamide, leuprolide, and goserelin; antibiotics such as aclacinomycins, actinomycin, anthramycin, azaserine, bleomycins, cactinomycin, calicheamicin, carubicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti estrogens including for example tamoxifen, raloxifene, aromatase inhibiting 4(5)-imidazoles, 4-hydroxytamoxifen, trioxifene, keoxifene, LY 117018, onapristone, and toremifene (Fareston); anti-metabolites such as methotrexate and 5-fluorouracil (5-FU); folic acid analogues such as denopterin, methotrexate, pteropterin, and trimetrexate; aziridines such as benzodepa, carboquone, meturedepa, and uredepa; ethylenimines and methylmelamines including altretamine, triethylenemelamine, triethylenephosphoramide, triethylenethiophosphoramide and trimethylol melamine; folic acid replenisher such as folinic acid; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, fotemustine, lomustine, nimustine, and ranimustine; platinum analogs such as cisplatin and carboplatin; vinblastine; platinum; proteins such as arginine deiminase and asparaginase; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, floxuridine, and 5-FU; taxanes, such as paclitaxel and docetaxel and albuminated forms thereof (i.e., nab-paclitaxel and nab-docetaxel), topoisomerase inhibitor RFS 2000; thymidylate synthase inhibitor (such as Tomudex); and additional chemotherapeutics including aceglatone; aldophosphamide glycoside; aminolevulinic acid; amsacrine; bestrabucil; bisantrene; edatrexate; defosfamide; demecolcine; diaziquone; difluoromethylornithine (DFMO); eflornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2', 2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; chlorambucil; gemcitabine; 6-thioguanine; mercaptopurine; methotrexate; etoposide (VP-16); ifosfamide; mitomycin C; mitoxantrone; vincristine; vinorelbine; Navelbine; Novantrone; teniposide; daunomycin; aminopterin; Xeloda; ibandronate; CPT-11; retinoic acid; esperamycins; capecitabine; and topoisomerase inhibitors such as irinotecan. Pharmaceutically acceptable salts, acids or derivatives of any of the above can also be used.

Therapeutic compounds that act in conjunction with the immunostimulatory bacteria include, for example, compounds that increase the immune response eliciting properties of the bacteria, e.g., by increasing expression of the RNAi, such as shRNA and miRNA, that inhibit, suppress or disrupt expression of the checkpoint genes, such as PD-L1, or TREX1 or other checkpoint genes, or compounds that can further augment bacterial colonization/proliferation. For example, a gene expression-altering compound can induce or increase transcription of a gene in a bacterium, such as an exogenous gene, e.g., encoding shRNA that inhibit, suppress or disrupt expression of one or more checkpoint genes, thereby provoking an immune response. Any of a wide variety of compounds that can alter gene expression are known in the art, including IPTG and RU486. Exemplary genes whose expression can be up-regulated include proteins and RNA molecules, including toxins, enzymes that can convert a prodrug to an anti-tumor drug, cytokines, transcription regulating proteins, shRNA, siRNA, and ribozymes. In other embodiments, therapeutic compounds that can act in conjunction with the immunostimulatory bacteria to increase the colonization/proliferation or immune response eliciting properties of the bacteria are compounds that can interact with a bacteria-expressed gene product, and such interaction can result in an increased killing of tumor cells or an increased anti-tumor immune response in the subject. A therapeutic compound that can interact with a bacteria-expressed gene product can include, for example a prodrug or other compound that has little or no toxicity or other biological activity in its subject-administered form, but after interaction with a bacteria-expressed gene product, the compound can develop a property that results in tumor cell death, including but not limited to, cytotoxicity, ability to induce apoptosis, or ability to trigger an immune response. A variety of prodrug-like substances are known in the art, including ganciclovir, 5-fluorouracil, 6-methylpurine deoxyriboside, cephalosporin-doxorubicin, 4-[(2-chloroethyl)(2-mesuloxyethyl)amino]benzoyl-L-glutamic acid, acetaminophen, indole-3-acetic acid, CB1954, 7-ethyl-10-[4-(1-piperidino)-1-piperidino]carbonyloxycampotothecin, bis-(2-chloroethyl)amino-4-hydroxyphenylaminomethanone 28, 1-chloromethyl-5-hydroxy-1,2-dihyro-3H-benz[e]indole, epirubicin-glucuronide, 5'-deoxy5-fluorouridine, cytosine arabinoside, and linamarin.

3. Monitoring

The methods provided herein can further include one or more steps of monitoring the subject, monitoring the tumor, and/or monitoring the immunostimulatory bacteria administered to the subject. Any of a variety of monitoring steps can be included in the methods provided herein, including, but not limited to, monitoring tumor size, monitoring the presence and/or size of metastases, monitoring the subject's lymph nodes, monitoring the subject's weight or other health indicators including blood or urine markers, monitoring anti-bacterial antibody titer, monitoring bacterial expression of a detectable gene product, and directly monitoring bacterial titer in a tumor, tissue or organ of a subject.

The purpose of the monitoring can be simply for assessing the health state of the subject or the progress of therapeutic treatment of the subject, or can be for determining whether or not further administration of the same or a different immunostimulatory bacterium is warranted, or for determining when or whether or not to administer a compound to the subject where the compound can act to increase the efficacy of the therapeutic method, or the compound can act to decrease the pathogenicity of the bacteria administered to the subject.

In some embodiments, the methods provided herein can include monitoring one or more bacterially expressed genes. Bacteria, such as those provided herein or otherwise known in the art, can express one or more detectable gene products, including but not limited to, detectable proteins.

As provided herein, measurement of a detectable gene product expressed in a bacterium can provide an accurate determination of the level of bacteria present in the subject. As further provided herein, measurement of the location of the detectable gene product, for example, by imaging methods including tomographic methods, can determine the localization of the bacteria in the subject. Accordingly, the methods provided herein that include monitoring a detectable bacterial gene product can be used to determine the presence or absence of the bacteria in one or more organs or tissues of a subject, and/or the presence or absence of the bacteria in a tumor or metastases of a subject. Further, the methods provided herein that include monitoring a detectable bacterial gene product can be used to determine the titer of bacteria present in one or more organs, tissues, tumors or metastases. Methods that include monitoring the localization and/or titer of bacteria in a subject can be used for determining the pathogenicity of bacteria since bacterial infection, and particularly the level of infection, of normal tissues and organs can indicate the pathogenicity of the bacteria. The methods that include monitoring the localization and/or titer of immunostimulatory bacteria in a subject can be performed at multiple time points and, accordingly, can determine the rate of bacterial replication in a subject, including the rate of bacterial replication in one or more organs or tissues of a subject; accordingly, methods that include monitoring a bacterial gene product can be used for determining the replication competence of the bacteria. The methods provided herein also can be used to quantitate the amount of immunostimulatory bacteria present in a variety of organs or tissues, and tumors or metastases, and can thereby indicate the degree of preferential accumulation of the bacteria in a subject; accordingly, the bacterial gene product monitoring can be used in methods of determining the ability of the bacteria to accumulate in tumor or metastases in preference to normal tissues or organs. Since the immunostimulatory bacteria used in the methods provided herein can accumulate in an entire tumor or can accumulate at multiple sites in a tumor, and can also accumulate in metastases, the methods provided herein for monitoring a bacterial gene product can be used to determine the size of a tumor or the number of metastases present in a subject. Monitoring such presence of bacterial gene product in a tumor or metastasis over a range of time can be used to assess changes in the tumor or metastases, including growth or shrinking of a tumor, or development of new metastases or disappearance of metastases, and also can be used to determine the rate of growth or shrinking of a tumor, or development of new metastases or disappearance of metastases, or the change in the rate of growth or shrinking of a tumor, or development of new metastases or disappearance of metastases. Accordingly, monitoring a bacterial gene product can be used for monitoring a neoplastic disease in a subject, or for determining the efficacy of treatment of a neoplastic disease, by determining rate of growth or shrinking of a tumor, or development of new metastases or disappearance of metastases, or the change in the rate of growth or shrinking of a tumor, or development of new metastases or disappearance of metastases.

Any of a variety of detectable proteins can be detected by monitoring, exemplary of which are any of a variety of fluorescence proteins (e.g., green fluorescence proteins), any of a variety of luciferases, transferrin or other iron binding proteins; or receptors, binding proteins, and antibodies, where a compound that specifically binds the receptor, binding protein or antibody can be a detectable agent or can be labeled with a detectable substance (e.g., a radionuclide or imaging agent).

Tumor and/or metastasis size can be monitored by any of a variety of methods known in the art, including external assessment methods or tomographic or magnetic imaging methods. In addition to the methods known in the art, methods provided herein, for example, monitoring bacterial gene expression, can be used for monitoring tumor and/or metastasis size.

Monitoring size over several time points can provide information regarding the increase or decrease in size of a tumor or metastasis, and can also provide information regarding the presence of additional tumors and/or metastases in the subject. Monitoring tumor size over several time points can provide information regarding the development of a neoplastic disease in a subject, including the efficacy of treatment of a neoplastic disease in a subject.

The methods provided herein also can include monitoring the antibody titer in a subject, including antibodies produced in response to administration of immunostimulatory bacteria to a subject. The bacteria administered in the methods provided herein can elicit an immune response to endogenous bacterial antigens. The bacteria administered in the methods provided herein also can elicit an immune response to exogenous genes expressed by the bacteria. The bacteria administered in the methods provided herein also can elicit an immune response to tumor antigens. Monitoring antibody titer against bacterial antigens, bacterially expressed exogenous gene products, or tumor antigens can be used to monitor the toxicity of the bacteria, the efficacy of treatment methods, or the level of gene product or antibodies for production and/or harvesting.

Monitoring antibody titer can be used to monitor the toxicity of the bacteria. Antibody titer against a bacteria can vary over the time period after administration of the bacteria to the subject, where at some particular time points, a low anti-(bacterial antigen) antibody titer can indicate a higher toxicity, while at other time points a high anti-(bacterial antigen) antibody titer can indicate a higher toxicity. The bacteria used in the methods provided herein can be immunogenic, and can, therefore, elicit an immune response soon after administering the bacteria to the subject. Generally, immunostimulatory bacteria against which the immune system of a subject can mount a strong immune response can be bacteria that have low toxicity when the subject's immune system can remove the bacteria from all normal organs or tissues. Thus, in some embodiments, a high antibody titer against bacterial antigens soon after administering the bacteria to a subject can indicate low toxicity of the bacteria.

In other embodiments, monitoring antibody titer can be used to monitor the efficacy of treatment methods. In the methods provided herein, antibody titer, such as anti-(tumor antigen) antibody titer, can indicate the efficacy of a therapeutic method such as a therapeutic method to treat neoplastic disease. Therapeutic methods provided herein can include causing or enhancing an immune response against a tumor and/or metastasis. Thus, by monitoring the anti-(tumor antigen) antibody titer, it is possible to monitor the efficacy of a therapeutic method in causing or enhancing an immune response against a tumor and/or metastasis.

In other embodiments, monitoring antibody titer can be used for monitoring the level of gene product or antibodies for production and/or harvesting. As provided herein, methods can be used for producing proteins, RNA molecules or other compounds, particularly RNA molecules such as shRNA, by expressing an exogenous gene in a microorganism that has accumulated in a tumor. Monitoring antibody titer against the protein, RNA molecule or other compound can indicate the level of production of the protein, RNA molecule or other compound by the tumor-accumulated microorganism, and also can directly indicate the level of antibodies specific for such a protein, RNA molecule or other compound.

The methods provided herein also can include methods of monitoring the health of a subject. Some of the methods provided herein are therapeutic methods, including neoplastic disease therapeutic methods. Monitoring the health of a subject can be used to determine the efficacy of the therapeutic method, as is known in the art. The methods provided herein also can include a step of administering to a subject an immunostimulatory bacterium, as provided herein. Monitoring the health of a subject can be used to determine the pathogenicity of an immunostimulatory bacterium administered to a subject. Any of a variety of health diagnostic methods for monitoring disease such as neoplastic disease, infectious disease, or immune-related disease can be monitored, as is known in the art. For example, the weight, blood pressure, pulse, breathing, color, temperature or other observable state of a subject can indicate the health of a subject. In addition, the presence or absence or level of one or more components in a sample from a subject can indicate the health of a subject. Typical samples can include blood and urine samples, where the presence or absence or level of one or more components can be determined by performing, for example, a blood panel or a urine panel diagnostic test. Exemplary components indicative of a subject's health include, but are not limited to, white blood cell count, hematocrit, and c-reactive protein concentration.

The methods provided herein can include monitoring a therapy, where therapeutic decisions can be based on the results of the monitoring. Therapeutic methods provided herein can include administering to a subject immunostimulatory bacteria, where the bacteria can preferentially accumulate in a tumor and/or metastasis, and where the bacteria can cause or enhance an anti-tumor immune response. Such therapeutic methods can include a variety of steps including multiple administrations of a particular immunostimulatory bacterium, administration of a second immunostimulatory bacterium, or administration of a therapeutic compound. Determination of the amount, timing or type of immunostimulatory bacteria or compound to administer to the subject can be based on one or more results from monitoring the subject. For example, the antibody titer in a subject can be used to determine whether or not it is desirable to administer an immunostimulatory bacterium and, optionally, a compound, the quantity of bacteria and/or compound to administer, and the type of bacteria and/or compound to administer, where, for example, a low antibody titer can indicate the desirability of administering an additional immunostimulatory bacterium, a different immunostimulatory bacterium, and/or a therapeutic compound such as a compound that induces bacterial gene expression or a therapeutic compound that is effective independent of the immunostimulatory bacteria.

In another example, the overall health state of a subject can be used to determine whether or not it is desirable to administer an immunostimulatory bacterium and, optionally, a compound, the quantity of bacterium or compound to administer, and the type of bacterium and/or compound to administer where, for example, determining that the subject is healthy can indicate the desirability of administering additional bacteria, different bacteria, or a therapeutic compound such as a compound that induces bacterial gene (e.g., shRNA that inhibits one or more checkpoint gene(s)) expression. In another example, monitoring a detectable bacterially expressed gene product can be used to determine whether it is desirable to administer an immunostimulatory bacterium and, optionally, a compound, the quantity of bacterium and/or compound to administer, and the type of bacterium and/or compound to administer where, for example, determining that the subject is healthy can indicate the desirability of administering additional bacteria, different bacteria, or a therapeutic compound such as a compound that induces bacterial gene (e.g., shRNA that inhibits one or more checkpoint gene(s)) expression. Such monitoring methods can be used to determine whether or not the therapeutic method is effective, whether or not the therapeutic method is pathogenic to the subject, whether or not the bacteria have accumulated in a tumor or metastasis, and whether or not the bacteria have accumulated in normal tissues or organs. Based on such determinations, the desirability and form of further therapeutic methods can be derived.

In another example, monitoring can determine whether or not immunostimulatory bacteria have accumulated in a tumor or metastasis of a subject. Upon such a determination, a decision can be made to further administer additional bacteria, a different immunostimulatory bacterium and, optionally, a compound to the subject.

M. EXAMPLES

The following examples are included for illustrative purposes only and are not intended to limit the scope of the invention.

Summary of Exemplary Engineered Immunostimulatory Bacterial Strains and Nomenclature:

| Strain # | Plasmid | Strain Background | RNAi Targets | Alternate name |
|---|---|---|---|---|
| AST-100 | None | YS1646 | none | VNP 20009 |
| AST-101 | None | YS1646-ASD | none | ASD (asd gene knockout) |
| AST-102 | pEQU6 | YS1646 | none | YS1646 (pEQU6 - plasmid) |
| AST-103 | pEQU6 | YS1646 | Scrambled (shRNA) | YS1646 (pEQU6-shSCR) |
| AST-104 | pEQU6 | YS1646 | muTREX1 (shRNA) ARI-108 | YS1646 (pEQU6-shTREX1) |
| AST-105 | pEQU6 | YS1646 | muPD-L1 (shRNA) ARI-115 | YS1646 (pEQU6-shPDL1) |
| AST-106 | pEQU6 | YS1646 | muTREX1 (microRNA) ARI-203 | YS1646 (pEQU6-miTREX1) |
| AST-107 | pATI-U6 | YS1646-ASD | Scrambled (shRNA) | ASD (pATI-shSCR) |
| AST-108 | pATI-U6 | YS1646-ASD | muTREX1 (shRNA) ARI-108 | ASD (pATI-shTREX1) |
| AST-109 | pATIKAN-U6 | YS1646-ASD | Scrambled (shRNA) | ASD (pATIKan-shSCR) |
| AST-110 | pATIKAN-U6 | YS1646-ASD | muTREX1 (shRNA) ARI-108 | ASD (pATIKan-shTREX1) |
| AST-111 | None | YS1646-ASD-fljb-fliC | None | ASD/FLG (asd and flagellin knockout) |
| AST-112 | pATI-U6 | YS1646-ASD-fljb-fliC | muTREX1 (shRNA) ARI-108 | ASD/FLG (pATI-shTREX1) |
| AST-113 | pATI-U6 | YS1646-ASD-fljb-fliC | muTREX1 (shRNA) ARI-108 | ASD/FLG (pATI-U6 Kan shTREX1) |
| AST-114 | None | YS1646-ASD-LLO | None | ASD/LLO (asd knockout/ cytoLLO knock-in) |
| AST-115 | pATI-U6 | YS1646-ASD-LLO | muTREX1 (shRNA) ARI-108 | ASD/LLO (pATIKan-shTREX1) |
| AST-116 | pATIKanpBRori-U6 | YS1646-ASD | Scrambled | ASD (pATIKanLow-shSCR) |
| AST-117 | pATIKanpBRori-U6 | YS1646-ASD | muTREX1 (shRNA) ARI-108 | ASD (pATIKanLow-shTREX1) |
| AST-118 | pATIKanpBRori-U6 | YS1646-ASD-fljb-fliC | muTREX1 (shRNA) ARI-108 | ASD/FLG (pATIKanLow-shTREX1) |
| AST-119 | pATIKanpBRori-U6 | YS1646-ASD-pMTL-LLO | muTREX1 (shRNA) ARI-108 | ASD/LLO (pATIKanLow-shTREX1) |
| AST-120 | pEQU6 | YS1646-ASD-pMTL-LLO | muTREX1 (microRNA) ARI-203 | ASD/LLO (pEQU6-miTREX1) Suicidal |
| AST-121 | pEQU6 | YS1646 | muVISTA ARI-157 | YS1646 (pEQU6-shVISTA) |
| AST-122 | pEQU6 | YS1646 | muTGF-beta ARI-149 | YS1646 (pEQU6-TGF-beta) |
| AST-123 | pEQU6 | YS1645 | muBeta-Catenin ARI-166 | YS1646 (pEQU6-Beta-Catenin) |

Example 1

*Salmonella* asd Gene Knockout Strain Engineering

Strain AST-101 was prepared. It is an attenuated *Salmonella typhimurium* derived from YS1646 (which can be purchased from ATCC, Catalog #202165) that has been engineered to be asd⁻ (an asd gene knockout). In this example, the *Salmonella typhimurium* strain YS1646 asd⁻ gene deletion was engineered using modifications of the method of Datsenko and Wanner (*Proc Natl Acad Sci USA* 97:6640-6645 (2000)) as outlined in FIG. 1, and described below.

Introduction of the Lambda Red Helper Plasmid into YS1646

The YS1646 strain was prepared to be electrocompetent as described previously (Sambrook J., (1998) *Molecular Cloning, A Laboratory Manual*, 2nd edn. Cold Spring Harbor, NY Cold Spring Harbor Laboratory) by growing a culture in LB and concentrating 100-fold and washing three times with ice-cold 10% glycerol. The electrocompetent strain was electroporated with the Lambda red helper plasmid pKD46 (SEQ ID NO:218) using a 0.2 cm gap cuvette at the following settings: 2.5 kV, 186 ohms, 50 μF. Transformants carrying pKD46 were grown in 5 mL SOC medium with ampicillin and 1 mM L-arabinose at 30° C. and selected on LB agar plates containing ampicillin. A YS1646 clone containing the lambda red helper plasmid pKD46 then was made electrocompetent, as described above for YS1646.

Construction of asd Gene Knockout Cassette

The asd gene from the genome of YS1646 (Broadway et al. (2014) J. Biotechnology 192:177-178) was used for designing the asd gene knockout cassette. A plasmid containing 204 and 203 bp of homology to the left hand and right hand regions, respectively, of the asd gene, was transformed into DH5-alpha competent cells. A kanamycin gene cassette flanked by lox P sites was cloned into this plasmid. The asd gene knockout cassette then was PCR amplified using primers asd-1 and asd-2 (Table 1) and gel purified.

Execution of asd Gene Deletion

The YS1646 strain carrying plasmid pKD46 was electroporated with the gel-purified linear asd gene knock-out cassette. Electroporated cells were recovered in SOC medium and plated onto LB Agar plates supplemented with Kanamycin (20 μg/mL) and diaminopimelic acid (DAP, 50 μg/ml). During this step, lambda red recombinase induces homologous recombination of the chromosomal asd gene with the kan cassette (due to the presence of homologous flanking sequences upstream and downstream of the chromosomal asd gene), and knockout of the chromosomal copy of the asd gene occurs. The presence of the disrupted asd gene in the selected kanamycin resistant clones was confirmed by PCR amplification with primers from the YS1646 genome flanking the sites of disruption (primer asd-3) and from the multi-cloning site (primer scFv-3) (Table 1). Colonies were also replica plated onto LB plates with and without supplemental DAP to demonstrate DAP auxotrophy. All clones with the asd gene deletion were unable to grow in the absence of supplemental DAP, demonstrating DAP auxotrophy.

TABLE 1

Primer information

| Primer name | Primer sequence | SEQ ID NO. |
|---|---|---|
| asd-1 | ccttcctaacgcaaattccctg | 219 |
| asd-2 | ccaatgctctgcttaactcctg | 220 |
| asd-3 | gcctcgccatgtttcagtacg | 221 |
| asd-4 | ggtctggtgcattccgagtac | 222 |
| scFv-3 | cataatctgggtccttggtctgc | 223 |

Kanamycin Gene Cassette Removal

The kan selectable marker was removed by using the Cre/loxP site-specific recombination system. The YS1646 asd⁻ gene Kan$^R$ mutant was transformed with pJW168 (a temperature sensitive plasmid expressing the cre recombinase, SEQ ID NO:224). Amp$^R$ colonies were selected at 30° C.; pJW168 was subsequently eliminated by growth at 42° C. A selected clone (AST-101) then was tested for loss of kan by replica plating on LB agar plates with and without kanamycin, and confirmed by PCR verification using primers from YS1646 genome flanking the sites of disruption (primer asd-3 and asd-4, for primer sequence, see Table 1).

Characterization of the asd Deletion Mutant Strain AST-101

The asd mutant AST-101 was unable to grow on LB agar plates at 37° C., but was able to grow on LB plates containing 50 μg/mL diaminopimelic acid (DAP). The asd mutant growth rate was evaluated in LB liquid media and it was unable to grow in liquid LB but was able to grow in LB supplemented with 50 μg/mL DAP, as determined by measuring absorbance at 600 nM.

Sequence Confirmation of the AST-101 asd Locus Sequence after asd Gene Deletion

The AST-101 asd gene deletion strain was verified by DNA sequencing using primer asd-3 and asd-4. Sequencing of the region flanking the asd locus was performed and the sequence confirmed that the asd gene was deleted from the YS1646 chromosome.

Generation of Modified Salmonella typhimurium Strains from Wild-Type Salmonella typhimurium The purI, msbB and asd genes were individually deleted from the genome of wild-type Salmonella typhimurium strain ATCC 14028 using the lambda-derived Red recombination system as described in Datsenko and Wanner (Proc. Natl. Acad Sci. USA 97:6640-6645 (2000)), to generate a base-strain designated 14028:ΔpurI/ΔmsbB/Δasd. The flagellin genes fljB and fliC were subsequently deleted to generate the strain 14028:ΔpurI/ΔmsbB/Δasd/ΔfljB/ΔfliC, and the pagP gene was then deleted to generate the strain 14028:ΔpurI/ΔmsbB/Δasd/ΔfljB/ΔfliC/ΔpagP. Strains 14028:ΔpurI/ΔmsbB/Δasd/ΔfljB/ΔfliC and 14028:ΔpurI/ΔmsbB/Δasd/ΔfljB/ΔfliC/ΔpagP were electroporated with a plasmid containing a functional asd gene, to complement the chromosomal deletion of asd and ensure plasmid maintenance in vivo, and a eukaryotic expression cassette encoding the red fluorescent protein mCherry under control of the EF1-α promoter.

Example 2

Design and Characterization of Exemplary shRNAs

In order to generate recombinant Salmonella typhimurium transformed with plasmids encoding shRNAs against desired target genes, a set of 6 shRNAs were designed against each of human PD-L1, SIRP-alpha, beta-catenin, VISTA, TREX1, and VEGF. A total of 9 shRNAs were designed against human TGF-beta isoform 1. The shRNAs were subcloned into the pEQU6 vector (SEQ ID NO:41), for a total of 45 shRNAs.

| Proteins targeted by shRNA | |
|---|---|
| SEQ ID NO. | Protein |
| 31 | Human PD-L1 |
| 32 | Human CTNNB1 |
| 33 | Human SIRP-alpha |
| 34 | Human TREX1 |
| 35 | Human VISTA |
| 193 | Human TGF-beta, isoform 1 |
| 194 | Human VEGF |

The target sequences in each gene are as follows:

| SEQ ID NO. | Target | Target Sequence | Reference |
|---|---|---|---|
| 1 | Human PD-L1 | gtagagtatggtagcaata | ARI-122 |
| 2 | Human PD-L1 | gccgactacaagcgaatta | ARI-123 |
| 3 | Human PD-L1 | gacaagcagtgaccatcaa | ARI-124 |
| 4 | Human PD-L1 | gaatcaacacaacaactaa | ARI-125 |
| 5 | Human PD-L1 | gcacatcctccaaatgaaa | ARI-126 |
| 6 | Human PD-L1 | gtagcactgacattcatct | ARI-127 |
| 7 | Human CTNNB1 | gacagactgccttcaaatt | ARI-168 |
| 8 | Human CTNNB1 | gcagctggaattctttcta | ARI-169 |
| 9 | Human CTNNB1 | gactaccagttgtggttaa | ARI-170 |
| 10 | Human CTNNB1 | ggacacagcagcaatttgt | ARI-171 |
| 11 | Human CTNNB1 | ggatgttcacaaccgaatt | ARI-172 |
| 12 | Human CTNNB1 | gccacaagattacaagaaa | ARI-173 |
| 13 | Human SIRP-alpha | gccaggtgaggaagttcta | ARI-174 |
| 14 | Human SIRP-alpha | gagctggctcctggtgaat | ARI-175 |
| 15 | Human SIRP-alpha | gctgagaacactggatcta | ARI-176 |
| 16 | Human SIRP-alpha | gaagaatgccagagaaata | ARI-177 |
| 17 | Human SIRP-alpha | ggacacaaatgatatcaca | ARI-178 |
| 18 | Human SIRP-alpha | ggagtatgccagcattcag | ARI-179 |
| 19 | Human TREX1 | gcagcgcatgggcgtcaat | ARI-109 |
| 20 | Human TREX1 | ggcccaaggaagagctata | ARI-110 |
| 21 | Human TREX1 | gcaccatcaggcccatgta | ARI-111 |
| 22 | Human TREX1 | gccacaaccaggaacacta | ARI-112 |
| 23 | Human TREX1 | gcaggggtaccaaggatct | ARI-113 |
| 24 | Human TREX1 | gccacactgtatggactat | ARI-114 |
| 25 | Human VISTA | gatgtgaccttctacaaga | ARI-195 |
| 26 | Human VISTA | gaccaccatggcaacttct | ARI-196 |
| 27 | Human VISTA | ggtgcagacaggcaaagat | ARI-197 |
| 28 | Human VISTA | gtgcctgcatcgtaggaat | ARI-198 |
| 29 | Human VISTA | gcaacattcaagggattga | ARI-199 |
| 30 | Human VISTA | gtccctgactctccaaact | ARI-200 |
| 195 | Human TGF-beta isoform 1 | gaaacccacaacgaaatct | ARI-180 |
| 196 | Human TGF-beta isoform 1 | gtacacacagcatatatat | ARI-181 |
| 197 | Human TGF-beta isoform 1 | ctgctgaggctcaagttaa | ARI-182 |
| 198 | Human TGF-beta isoform 1 | gtggagctgtaccagaaat | ARI-183 |
| 199 | Human TGF-beta isoform 1 | gactcgccagagtggttat | ARI-184 |
| 200 | Human TGF-beta isoform 1 | gagccgtggagggggaaatt | ARI-185 |
| 201 | Human TGF-beta isoform 1 | cctgtgacagcagggataa | ARI-186 |
| 202 | Human TGF-beta isoform 1 | gccctggacaccaactatt | ARI-187 |

-continued

| SEQ ID NO. | Target | Target Sequence | Reference |
|---|---|---|---|
| 203 | Human TGF-beta isoform 1 | ccctgtacaaccagcataa | ARI-188 |
| 204 | Human VEGF | gagatcgagtacatcttca | ARI-189 |
| 205 | Human VEGF | gcagattatgcggatcaaa | ARI-190 |
| 206 | Human VEGF | gatagagcaagacaagaaa | ARI-191 |
| 207 | Human VEGF | ggagaaagcatttgtttgt | ARI-192 |
| 208 | Human VEGF | gatccgcagacgtgtaaat | ARI-193 |
| 209 | Human VEGF | gcgaggcagcttgagttaa | ARI-194 |

To generate each shRNA, a pair of designed oligonucleotides was synthesized to form a cassette encoding the shRNA. The oligonucleotides were allowed to anneal to each other to form the cassette and ligated to linearized pEQU6 vector that was predigested with the restriction enzymes Spe1 and Xho1. The linked DNA fragments were transformed into E. coli cells and the positive clones were selected with restriction enzyme digestion. The shRNA sequences were purified and sequenced. Six sequences for RNA interference were selected from different cDNA-coding regions and analyzed by a BLAST search to ensure that they did not have significant sequence homology with other genes. The six exemplary shRNA encoding sequences are as follows:

| SEQ ID NO | Target Protein | shRNA-encoding Sequence |
|---|---|---|
| 36 | Human PD-L1 | gtagagta tggtagcaat atctagagta ttgctaccat actctac |
| 37 | Human CTNNB1 | g acagactgcc ttcaaatttc tagagaattt gaaggcagtc tgtc |
| 38 | Human SIRP-alpha | g ccaggtgagg aagttctatc tagagtagaa cttcctcacc tggc |
| 39 | Human TREX1 | g cagcgcatgg gcgtcaattc tagagattga cgcccatgcg ctgc |
| 40 | Human VISTA | g accaccatgg caacttcttc tagagagaag ttgccatggt ggtc |

The sequences of the resulting vectors, designated pEQU6-shPDL1-shRNA, pEQU6-shPDL1-H1-shCTNNB1, pEQU6-shPDL1-H1-shSIRP-alpha, pEQU6-shPDL1-H1-shTREX1, and pEQU6-shPDL1-H1-shVISTA, are set forth in SEQ ID NOs: 43-47. Each shRNA then is individually screened to identify the best shRNA against each target protein. The plasmid used for screening contains a bacterial origin of replication, a kanamycin resistance marker, and a human U6 promoter sequence, followed by the individual shRNA, which then is followed by a terminator poly-T sequence. The vector can employ an H1 promoter instead of a U6 promoter. U6 and H1 are RNA polymerase III promoters, which generally are used for production and processing of small RNAs (see, Sequence Listing). Each shRNA was designed to hybridize with a 19 nucleotide overlap to the target sequence, and contains a 7 nucleotide loop-spacer, followed by the reverse complement of the initial target sequence. The shRNA designs are not limited to these nucleotide lengths. Complementary shRNA sequences range from 19-29 nucleotides (the "sense" sequence derived from the target gene), followed by a loop spacer of 4-15 nucleotides, and then completed with a 19-29 nucleotide sequence, which is the "antisense" sequence of the primary target sequence.

A second vector was used to achieve knockdown of gene expression for separate targets. This vector uses a second promoter, H1, which is separated by a length of at least 75 nucleotides, which can be from about 60-100, from the U6 promoter, in order to achieve effective gene knockdown by both target shRNAs. As an example, one particular vector carries shRNA sequences to PD-L1 and SIRP-alpha, with the anti-PD-L1 shRNA under the U6 promoter, followed by an anti-SIRP-alpha shRNA under an H1 promoter. Multiple targeting shRNAs can be added to a plasmid by utilizing additional promoters, such as U6 or H1 promoters from orthologous species.

In order to identify the top performing shRNAs against each target, individual shRNAs subcloned into pEQU6 were tested for their ability to knockdown gene expression. First, HEK293 cells are co-transfected with both the pEQU6 plasmid (encoding a distinct shRNA sequence) and a cDNA expression plasmid (expressing target protein cDNA under a CMV promoter). For example, the pEQU6 plasmid encoding shRNA to PD-L1, clone 1, is co-transfected with a PD-L1 cDNA expressing plasmid. shRNA-mediated knockdown of gene expression is measured by Western blot and qPCR. Commercially available cDNAs are available from GE/Dharmacon or Origene, and are subcloned into a CMV expression vector that results in a fused HA tag to the C-terminus of the target protein. This allows for uniform measurement of gene knockdown using an anti-HA antibody-HRP fusion. The cDNA molecules correspond to portions of the cDNA encoding genes.

In addition to shRNAs targeting human genes, shRNAs for use for testing in in vivo models are provided. shRNAs are generated that target orthologous murine genes, in order to test in syngeneic murine transplant and autochthonous murine tumor models. Murine targeting shRNA sequences (SIGMA) are subcloned into the pEQU6 vector described above and characterized for gene knockdown propensity by Western blot and qPCR. Furthermore, a combination of shRNAs against PD-L1 and TREX1 were subcloned into pEQU6-H1 (SEQ ID NO:42), with the shRNA against PD-L1 under the U6 promoter and the shRNA against TREX1 under the H1 promoter. For use in the mouse models the following shRNA-encoding sequences were designed:

| SEQ ID NO. | Target (mouse) | shRNA encoding sequence (SIGMA) | Reference |
|---|---|---|---|
| 75 | muPD-L1 | ccggccgaaatgatacacaattcgactcgagtcgaattgtgtatcatttcggtttttg | ARI-115 |
| 76 | muSIRP-alpha | ccggccacaactggaatgtcttcatctcgagatgaagacattccagttgtggttttt | ARI-138 |
| 77 | muTREX1-clone1 | ccggacaaccaacctaaggccacatctcgagatgtggccttaggttggttgtttttg | ARI-101 |
| 78 | muTREX1-clone2 | ccggcctagatggtaccttctgtgtctcgagacacagaaggtaccatctaggtttttg | ARI-102 |

For screening individual shRNA performance against each target, the positive control for Western blot corresponds to beta-tubulin expression, and the negative control for both Western blot and qPCR screening corresponds to a scrambled shRNA that lacks homology to any mammalian sequences. Each shRNA is individually tested by western blot. For qPCR gene expression, knockdown is quantified as % gene knockdown, and triplicate testing with error bars is generated.

Western blot screening was performed as follows. First, the co-transfection experiment was setup with the target gene expression plasmid (pCMV-cDNA-HA) and each of 6 designed shRNA vectors, as individual reactions, using Lipofectamine 2000 (Invitrogen). The chart below describes the component of each reaction. 48 hours after transfection, cells were lysed in SDS-PAGE buffer and subjected to 4-20% SDS-PAGE gel electrophoresis and Western blot analyses. The Western blot was carried out using the anti-HA-antibody purchased from Santa Cruz Biotechnology at a 1:1000 dilution. The membranes were detected by ECL reagents. For each 6-well:

|  | 293 cells | cDNA | shRNA 1 | shRNA 2 | shRNA 3 | shRNA 4 | shRNA 5 | shRNA6 |
|---|---|---|---|---|---|---|---|---|
| DNA |  | 1.0 µg | 1.0 µg | 1.0 µg | 1.0 µg | 1.0 µg | 1.0 µg | 1.0 µg |
| pEQ-shRNA |  |  | 2.0 µg | 2.0 µg | 2.0 µg | 2.0 µg | 2.0 µg | 2.0 µg |
| pEQ-scramble-sliRNA | 3.0 µg | 2.0 µg |  |  |  |  |  |  |
| Total DNA | 3.0 µg | 3.0 µg | 3.0 µg | 3.0 µg | 3.0 µg | 3.0 µg | 3.0 µg | 3.0 µg |

The gene silencing assessment by qPCR was performed as follows. First, the co-transfection experiment was setup with the target gene expression plasmid pCMV-cDNA-HA and 6 shRNA vectors using Lipofectamine™ 2000 (Invitrogen). The chart below describes the component of each reaction. The cDNA to shRNA ratio is 1:6. 48 hours after transfection, RNA was extracted using the RNeasy Plus kit (Qiagen). cDNA was synthesized from mRNA using oligo (dT)$_{20}$ primer, SuperScript™ IV reverse transcriptase (ThermoFisher) and 100 ng of total RNA. The real time PCR assay was performed with PowerUP™ SYBR™ master mix (ThermoFisher) on an Applied Biosystems StepOne™ Real-Time PCR System against cDNA-HA and GAPDH (endogenous control) targets. For each 6-well:

|  | 293 cells | cDNA | shRNA 1 | shRNA 2 | shRNA 3 | shRNA 4 | shRNA 5 | shRNA6 |
|---|---|---|---|---|---|---|---|---|
| cDNA |  | 0.2 µg | 0.2 µg | 0.2 µg | 0.2 µg | 0.2 µg | 0.2 µg | 0.2 µg |
| pEQ-shRNA |  |  | 1.2 µg | 1.2 µg | 1.2 µg | 1.2 µg | 1.2 µg | 1.2 µg |
| pEQ-plasmid control | 1.2 µg | 1.2 µg |  |  |  |  |  |  |
| Total DNA | 1.2 µg | 2.2 µg | 2.2 µg | 2.2 µg | 2.2 µg | 2.2 µg | 2.2 µg | 2.2 µg |

Figure 2A:
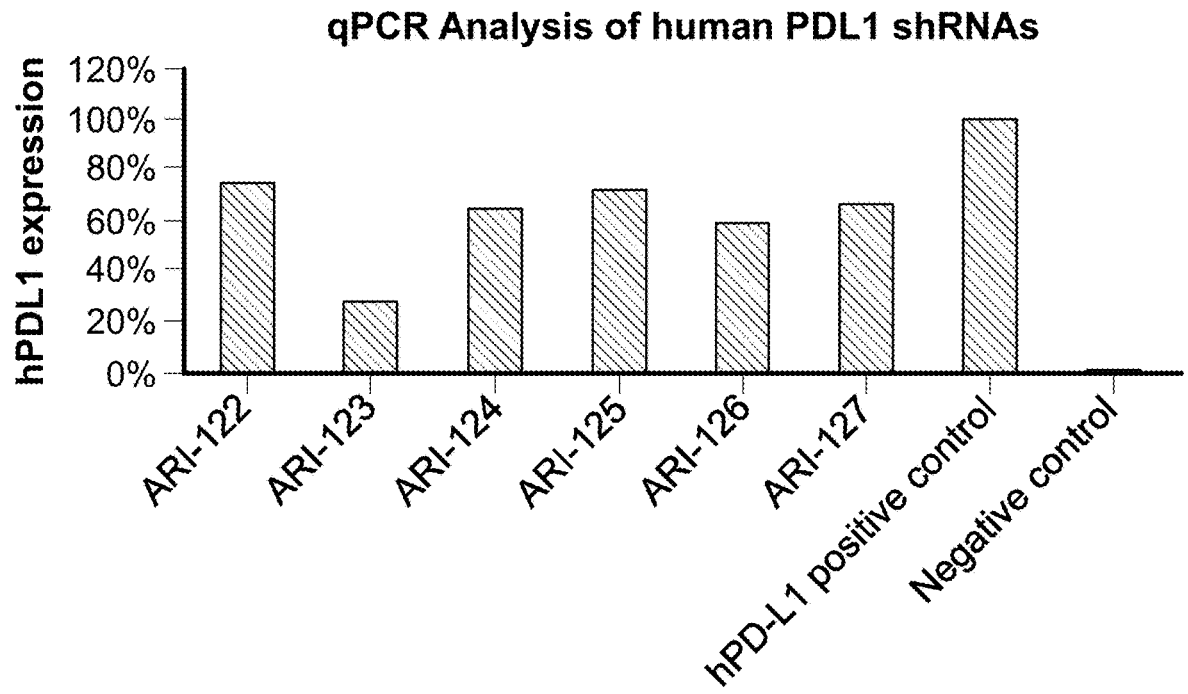
FIGS. 2A-2B depict the results of human PD-L1 shRNA screening using qPCR and Western blot. HEK 293 cells were co-transfected with a PD-L1 cDNA expression plasmid and various pEQU6 plasmids encoding distinct shRNAs targeting PDL1.
Figure 2B:
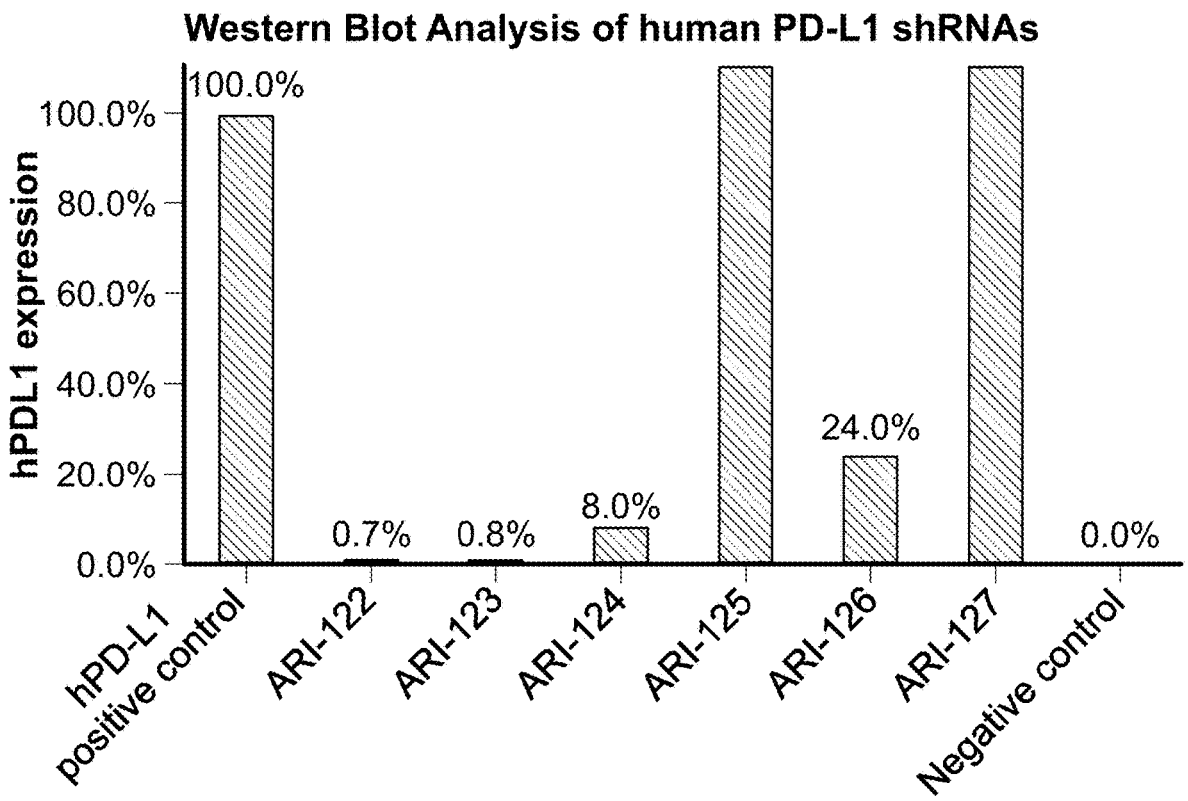

The shRNA-mediated gene knockdown with these shRNAs were functionally characterized. See, *Methods Mol. Biol.* (2010) 629:141-158 for a description of the methods used. Using the human PD-L1 gene as a reference, a set of 6 shRNAs were designed with a 19 base pair complementary region to the PD-L1 gene (SEQ ID NO: 31), and cloned into the pEQU6 screening vector (SEQ ID NO:41) behind the U6 promoter, utilizing the cloning strategy that is described above. Each shRNA construct was screened for disruption of human PD-L1 gene expression by using the qPCR and western blot protocols described above. As shown in FIG. 2A, several shRNAs were effective at knocking down PD-L1 gene expression. ARI-123 (SEQ ID NO:2) resulted in the highest potency, with approximately 75% knockdown of human PD-L1 gene expression. This was confirmed by western blot (FIG. 2B), where ARI-123 demonstrated >99% knockdown of PD-L1 gene expression. In addition, ARI-122 (SEQ ID NO:1) showed >99% knockdown of PD-L1 gene expression by Western blot.

Figure 3A:
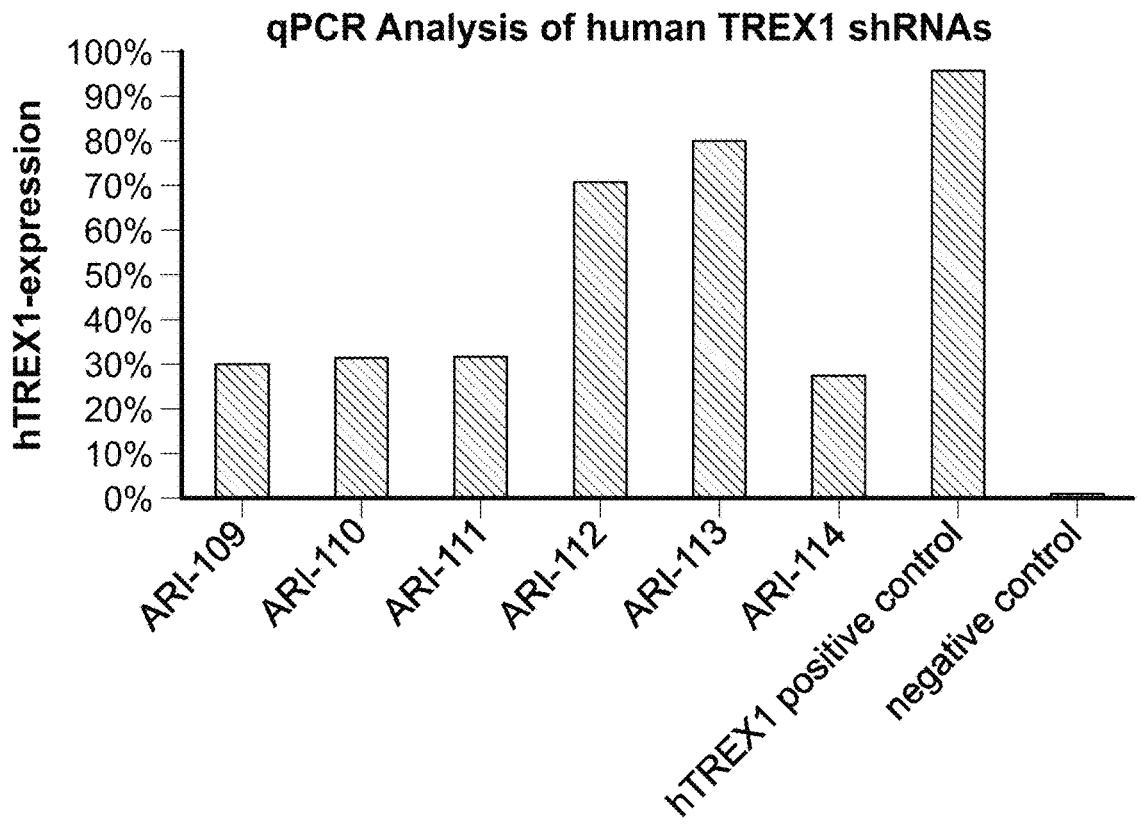
FIGS. 3A-3B depict the results of human TREX1 shRNA screening using qPCR and Western blot. HEK 293 cells were co-transfected with a TREX1 cDNA expression plasmid and various pEQU6 plasmids encoding distinct shRNAs targeting TREX1.
Figure 3B:
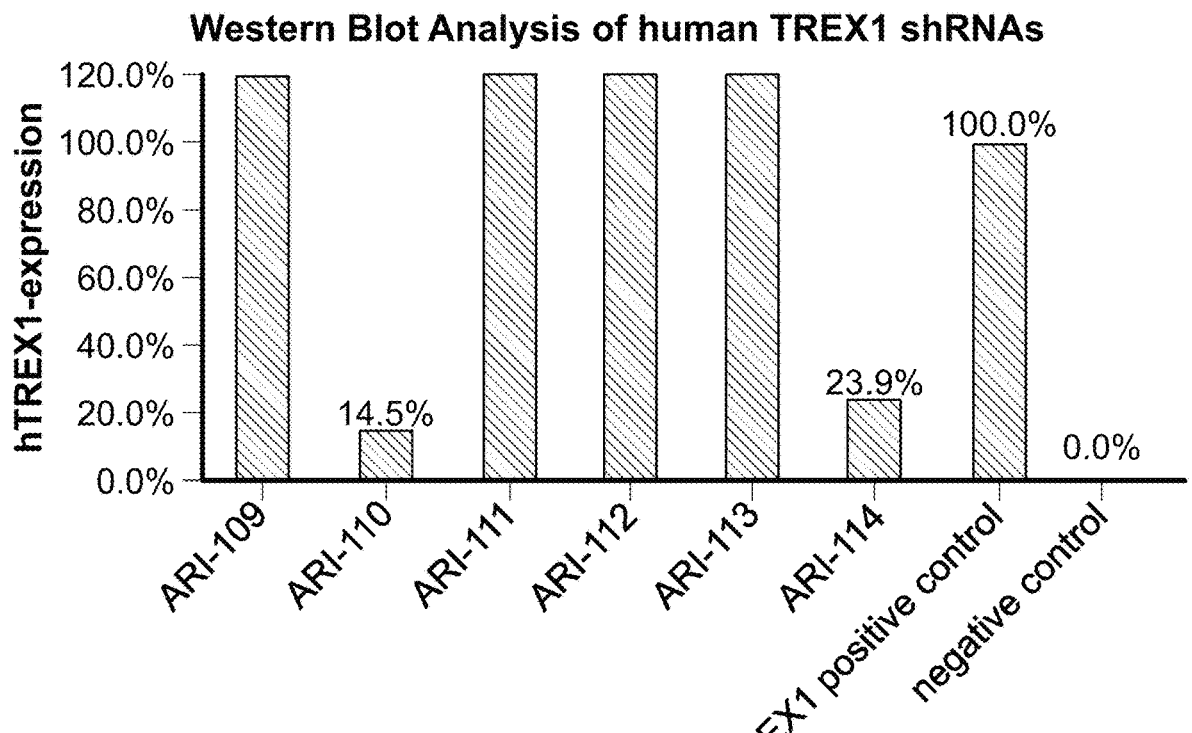

A set of 6 shRNAs with 19 bp complementary regions were designed to disrupt the expression of the human TREX1 gene (SEQ ID NO:34), and cloned into the pEQU6 screening vector (SEQ ID NO:41) behind the U6 promoter in the manner described above. As shown in FIG. 3A, ARI-109 (SEQ ID NO:19), ARI-110 (SEQ ID NO:20), ARI-111 (SEQ ID NO:21) and ARI-114 (SEQ ID NO:24) all showed approximately 70% knockdown of TREX1 gene expression by qPCR. Western blot analysis was used to confirm the gene disruption findings identified by qPCR (FIG. 3B). Both ARI-110 (SEQ ID NO:20) and ARI-114 (SEQ ID NO:24) showed a high degree of gene knockdown, 85.5% and 76.1%, respectively.

Figure 4A:
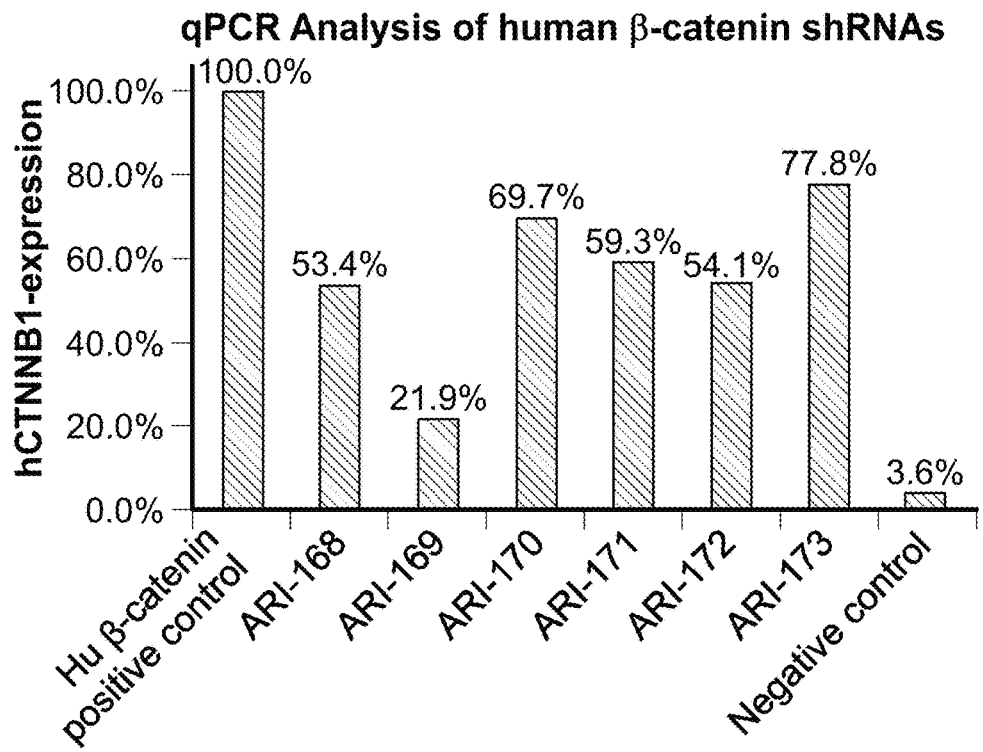
FIGS. 4A-4B depict the results of human beta-catenin shRNA screening using qPCR and Western blot. HEK 293 cells were co-transfected with a beta-catenin cDNA expression plasmid and various pEQU6 plasmids encoding distinct shRNAs targeting beta-catenin.
Figure 4B:
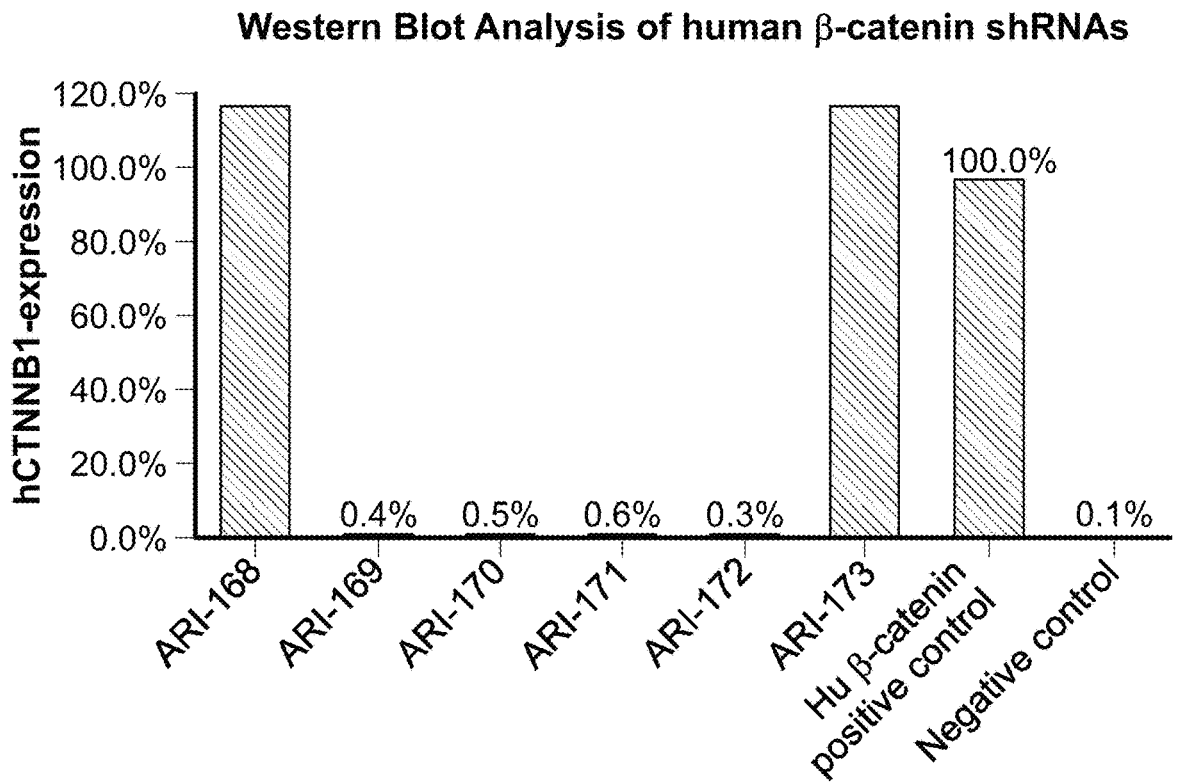

Using the human beta-catenin gene (SEQ ID NO:32) as a reference, a set of 6 shRNAs were designed with a 19 base complementary region to the beta-catenin gene and cloned into the pEQU6 screening vector (SEQ ID NO:41) behind the U6 promoter as described above. Each shRNA construct was screened for disruption of human beta-catenin gene expression by both qPCR and Western blot. As shown in FIG. 4A, several shRNAs were effective at knocking down beta-catenin gene expression. ARI-169 (SEQ ID NO:8) demonstrated >75% knockdown of human beta-catenin gene expression. In the Western blot analysis (FIG. 4B) ARI-169 (SEQ ID NO:8), ARI-170 (SEQ ID NO:9), ARI-171 (SEQ ID NO:10), and ARI-172 (SEQ ID NO:11), each showed >99% knockdown of beta-catenin gene expression.

Figure 5A:
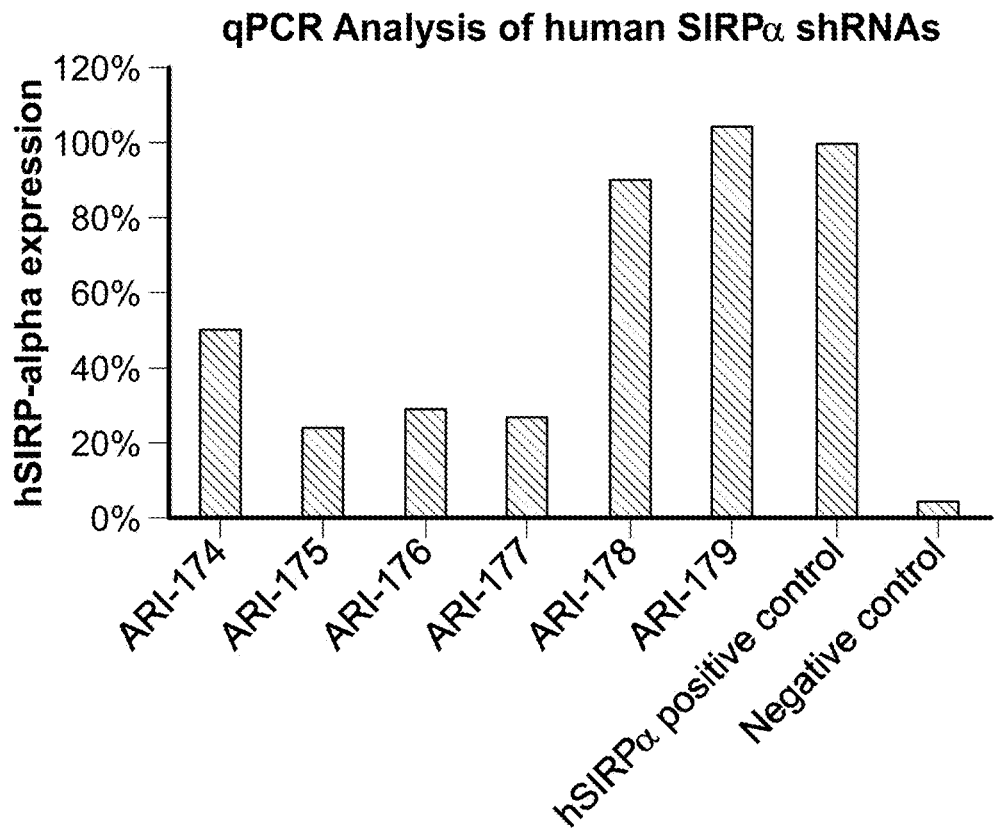
FIGS. 5A-5B depict the results of human SIRP-alpha shRNA screening using qPCR and Western blot. HEK 293 cells were co-transfected with a SIRP-alpha cDNA expression plasmid and various pEQU6 plasmids encoding distinct shRNAs targeting SIRP-alpha.
Figure 5B:
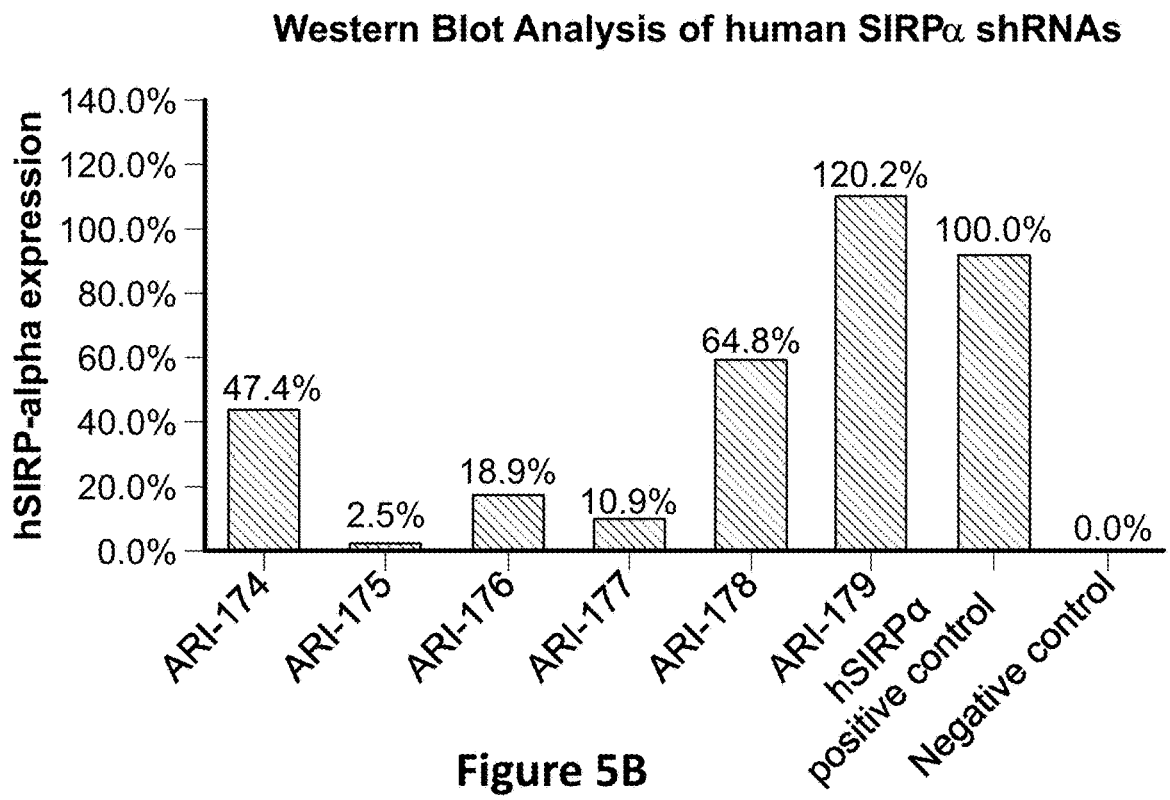

The human SIRP-alpha gene (SEQ ID NO:33) was also screened for shRNAs that disrupt gene expression. A set of 6 shRNAs with 19 bp complementary regions were designed and cloned into the pEQU6 screening vector (SEQ ID NO:41) behind the U6 promoter as described above. As shown in FIG. 5A, several shRNA constructs were able to significantly knockdown SIRP-alpha gene expression. ARI-175 (SEQ ID NO:14), ARI-176 (SEQ ID NO:15), and ARI-177 (SEQ ID NO:16) all showed approximately greater than 70% knockdown of SIRP-alpha gene expression by qPCR. In the Western blot analysis (FIG. 5B), a high degree of knockdown was observed for several constructs: ARI-175 (>95% knockdown), ARI-176 (>80% knockdown), and ARI-177 (approximately 90% knockdown), which was consistent with the findings by these three constructs when screened by qPCR.

Figure 6:
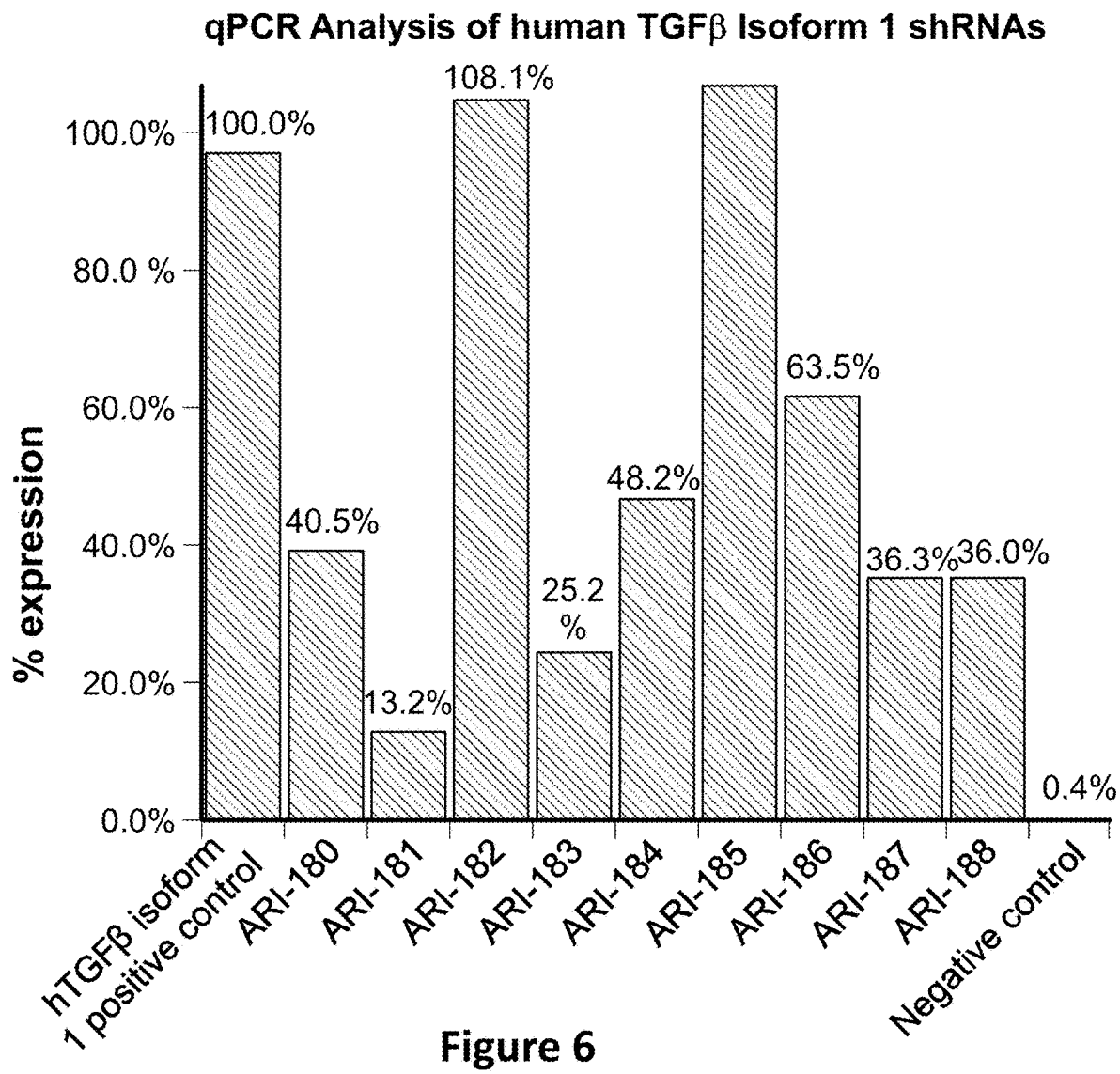
FIG. 6 depicts the results of human TGF-beta isoform 1 shRNA screening using qPCR. HEK 293 cells were co-transfected with a TGF-beta isoform 1 cDNA expression plasmid and various pEQU6 plasmids encoding distinct shRNAs targeting TGF-beta. qPCR was used to determine the level of mRNA knockdown.

Using the human TGF-beta isoform 1 gene (SEQ ID NO:193) as a reference, a set of nine shRNAs were designed and cloned into the pEQU6 screening vector (SEQ ID NO:41) behind the U6 promoter as described above. Each shRNA construct was screened for disruption of human TGF-beta isoform 1 gene expression by qPCR. As shown in FIG. 6, several shRNAs were effective at knocking down TGF-beta gene expression. ARI-181 (SEQ ID NO:196) was the most potent shRNA, with approximately >85% knockdown of human TGF-beta gene expression. This was followed by ARI-183 (SEQ ID NO:198), which showed approximately 75% knockdown of TGF-beta gene expression.

Figure 7:
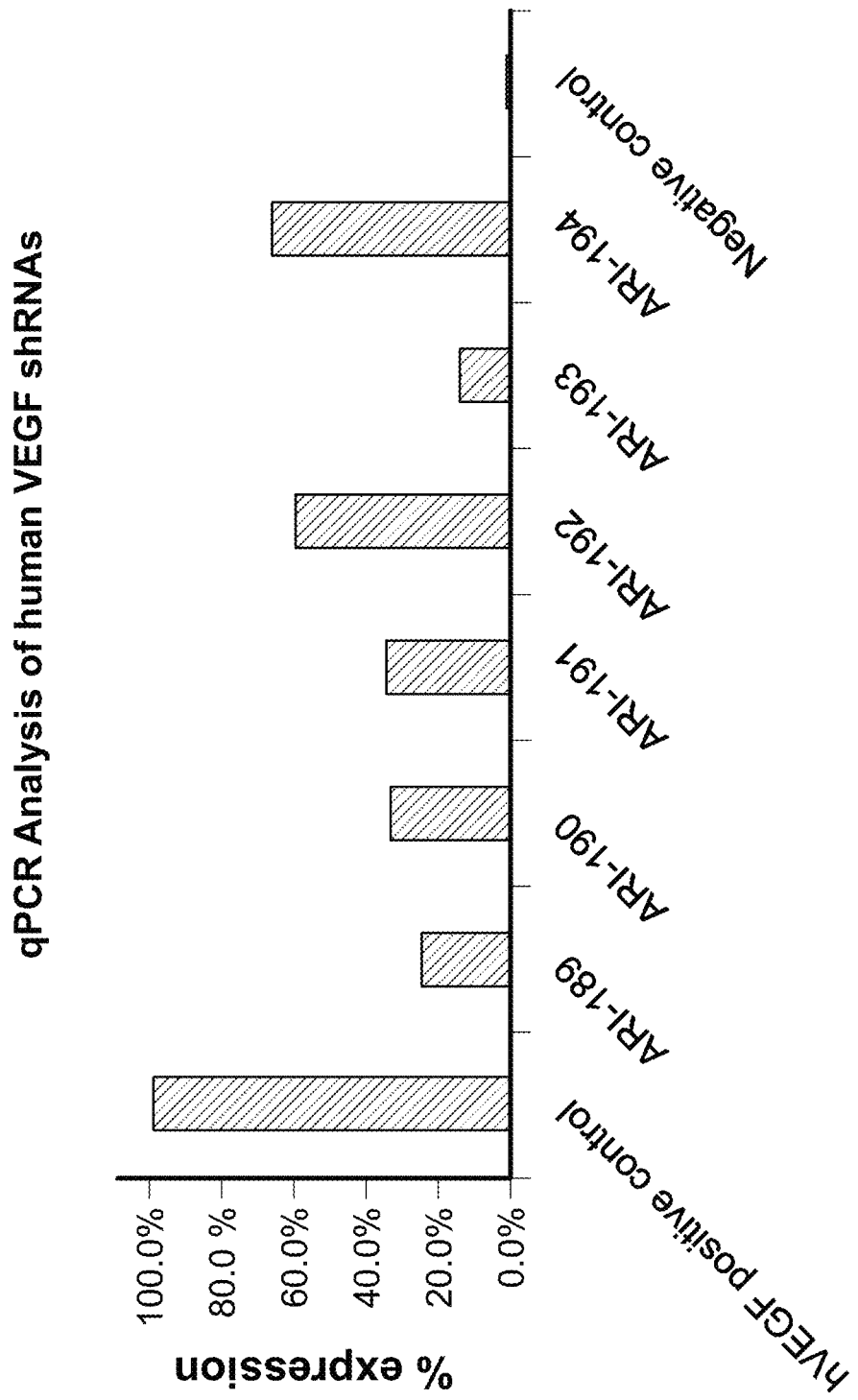
FIG. 7 depicts the results of human VEGF shRNA screening using qPCR. HEK 293 cells were co-transfected with a VEGF cDNA expression plasmid and various pEQU6 plasmids encoding distinct shRNAs targeting VEGF. qPCR was used to determine the level of mRNA knockdown.

A set of 6 shRNAs with 19 bp complementary regions were designed to disrupt the expression of human VEGF (SEQ ID NO:194), and cloned into the pEQU6 screening vector (SEQ ID NO:41) behind the U6 promoter as described above. As shown in FIG. 7, several shRNA constructs possessed a high degree of knockdown efficiency against VEGF gene expression, when assessed by qPCR. ARI-189 (SEQ ID NO:204), ARI-190 (SEQ ID NO:205), and ARI-191 (SEQ ID NO:206) all showed approximately equal to, or greater than, 70% knockdown of VEGF gene expression by qPCR. In addition, ARI-193 (SEQ ID NO:208) showed greater than 80% knockdown of VEGF gene expression. Western blot analysis was used to confirm the gene disruption findings identified by qPCR, with ARI-189 (SEQ ID NO:204), ARI-190 (SEQ ID NO:205), ARI-191 (SEQ ID NO:206), ARI-193 (SEQ ID NO:208) all showing very faint VEGF Western blot bands as individual lanes on a gel when compared to a positive control, a VEGF lane that lacked a cognate shRNA to VEGF in the transfection reaction. Therefore, the findings from the Western blot analysis confirmed the findings from the qPCR reaction.

Figure 8A:
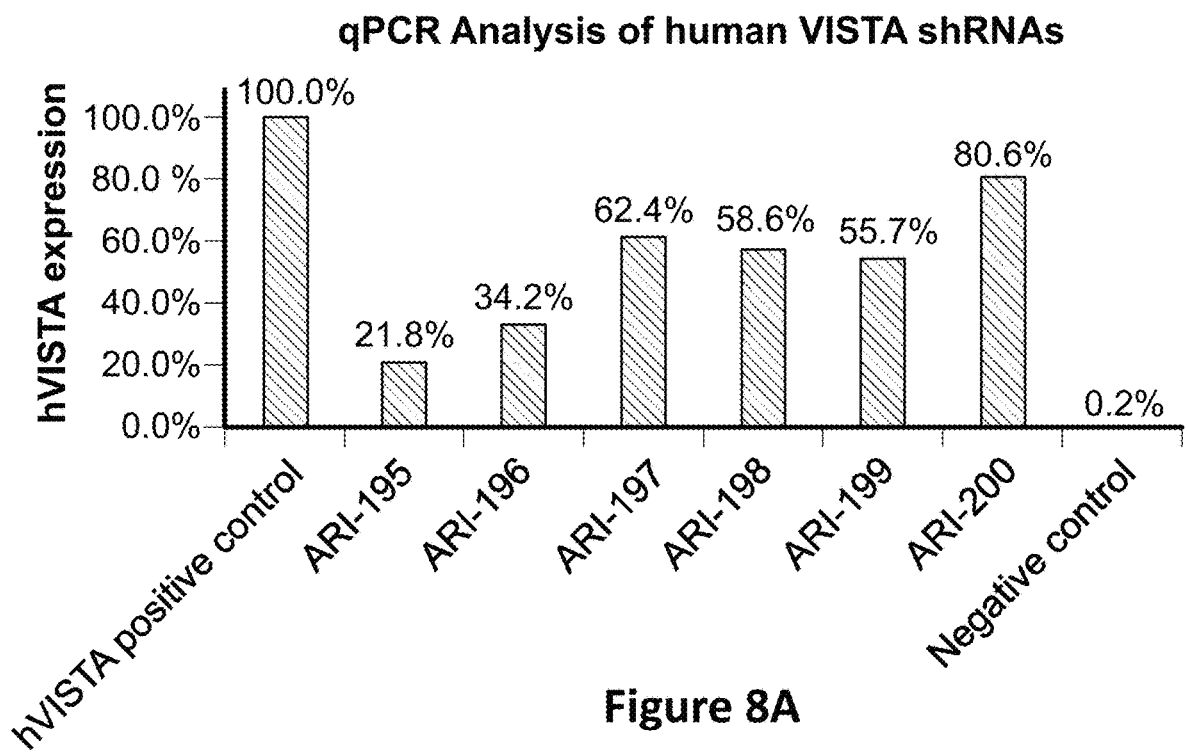
FIGS. 8A-8B depict the results of human VISTA shRNA screening using qPCR and Western blot. HEK 293 cells were co-transfected with a VISTA cDNA expression plasmid and various pEQU6 plasmids encoding distinct shRNAs targeting VISTA.
Figure 8B:
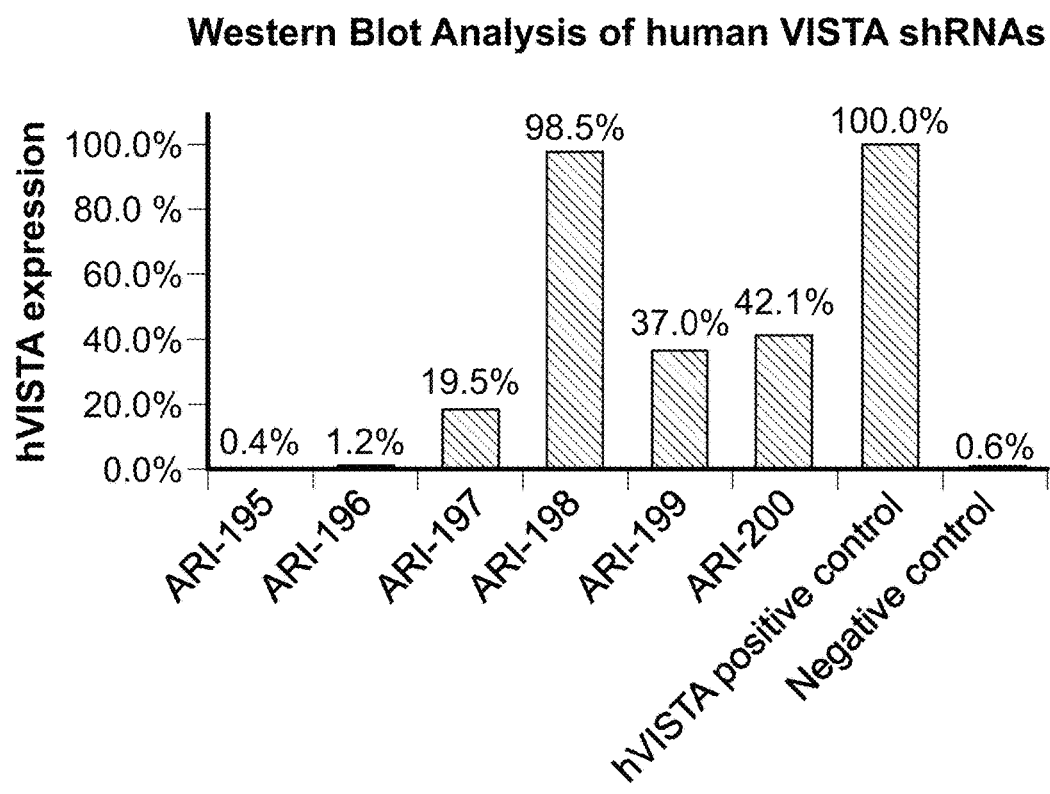

Using the human VISTA gene as a reference (SEQ ID NO:35), a set of six shRNAs were designed and cloned into the pEQU6 screening vector (SEQ ID NO:41) behind the U6 promoter as described above. Each shRNA construct was screened for disruption of VISTA gene expression in a qPCR knockdown experiment. As shown in FIG. 8A, several shRNAs were effective at knocking down human VISTA gene expression. ARI-195 (SEQ ID NO:25) and ARI-196 (SEQ ID NO:26) were the most potent shRNAs, with approximately 80% and 65% knockdown of human VISTA gene expression, respectively. These results were confirmed by Western blot analysis, which demonstrated nearly complete knockdown (approximately 99%) for ARI-195 and ARI-196 (FIG. 8B).

Combination RNAi

Figures 9A, 9B:
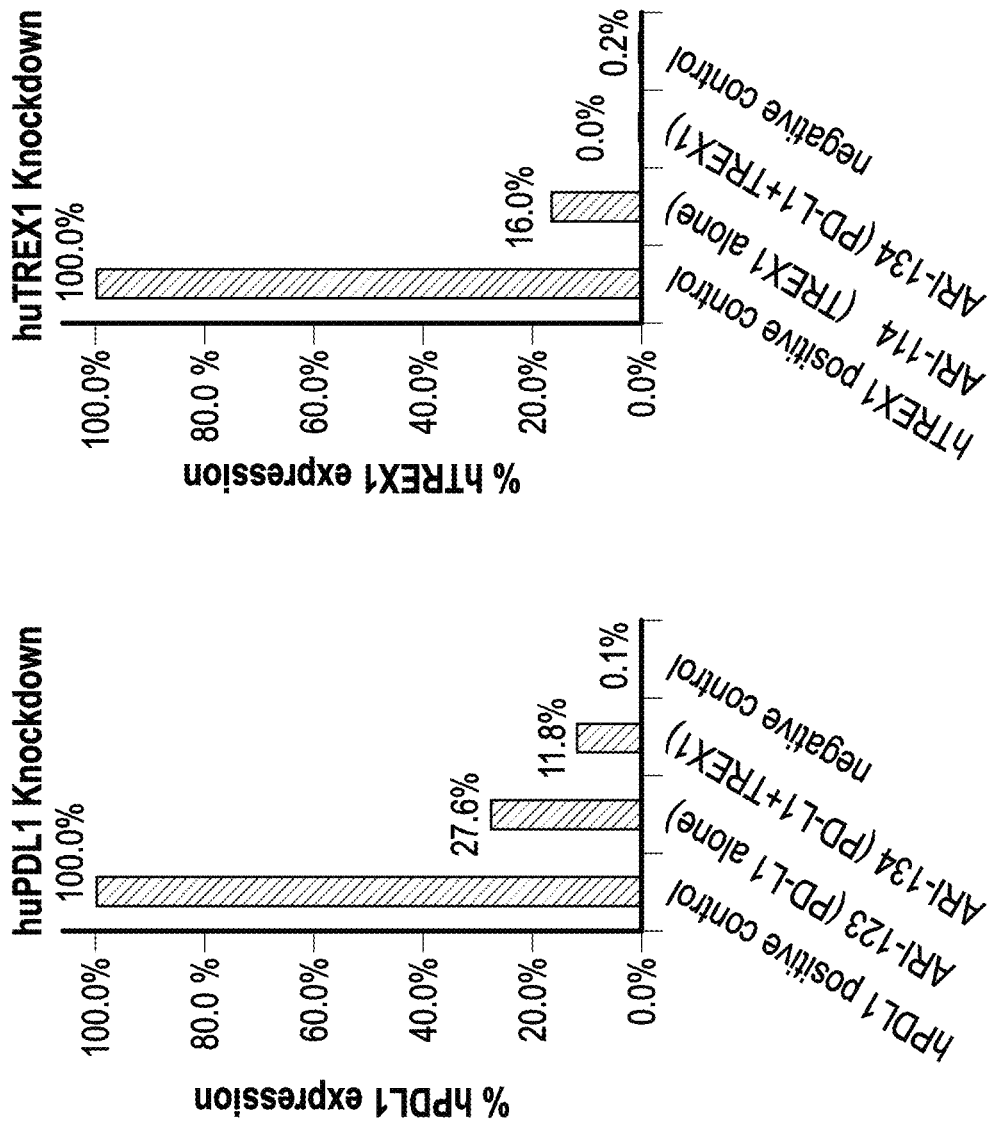
FIGS. 9A-9B depict the results of qPCR assessment of combination gene knockdown with HuPD-L1+HuTREX1 RNAi's. HEK 293 cells were co-transfected with a TREX1 cDNA expression plasmid, a PD-L1 cDNA expression plasmid, and pEQU6-H1 plasmid encoding ARI-134 shRNAs targeting PD-L1 and TREX1, or pEQU6 plasmid encoding ARI-123 shRNA targeting PD-L1 alone, or pEQU6 plasmid encoding ARI-114 shRNA targeting TREX1.

Combined RNAi knockdown of two separate gene targets by separate shRNAs expressed from the same plasmid was tested using an engineered plasmid carrying both a U6 and H1 promoter (SEQ ID NO:42). Individual shRNAs each targeting PD-L1 (ARI-123, SEQ ID NO:2) and TREX1 (ARI-114, SEQ ID NO:24) were subcloned to generate the combination RNAi ARI-134 (SEQ ID NO:210). ARI-134 then was tested for the ability to simultaneously express two separate shRNAs in situ, that can each individually knockdown expression of their respective targets (PD-L1 and TREX1). As a control, knockdown of human PD-L1 expression in HEK293 cells by ARI-134 was compared to ARI-123 (the single RNAi targeting solely PD-L1 (SEQ ID NO:2)), and knockdown of human TREX1 in HEK 293 cells by ARI-134 was compared to ARI-14 (a single RNAi solely targeting TREX1 (SEQ ID NO:24)). Whereas the ARI-123 knockdown had 27.6% of wild type human PD-L1 gene expression, knockdown of human PD-L1 by ARI-134 (the combination vector) was improved with 11.8% of wild type human PD-L1 gene expression (FIG. 9A). Likewise, whereas human TREX1 knockdown with ARI-114 had 16% of wild type TREX1 expression, the knockdown of human TREX1 with ARI-134 was 100% (FIG. 9B). When knockdown against PD-L1 and TREX1 by ARI-134 was analyzed by Western blot, there was no detectable expression of either human PD-L1 or human TREX1 versus their respective positive controls (individual human PD-L1 and human TREX1 expression reactions lacking any RNAi). Therefore, the combination RNAi ARI-134 is able to knockdown expression of PD-L1 and TREX1.

Figure 10B:
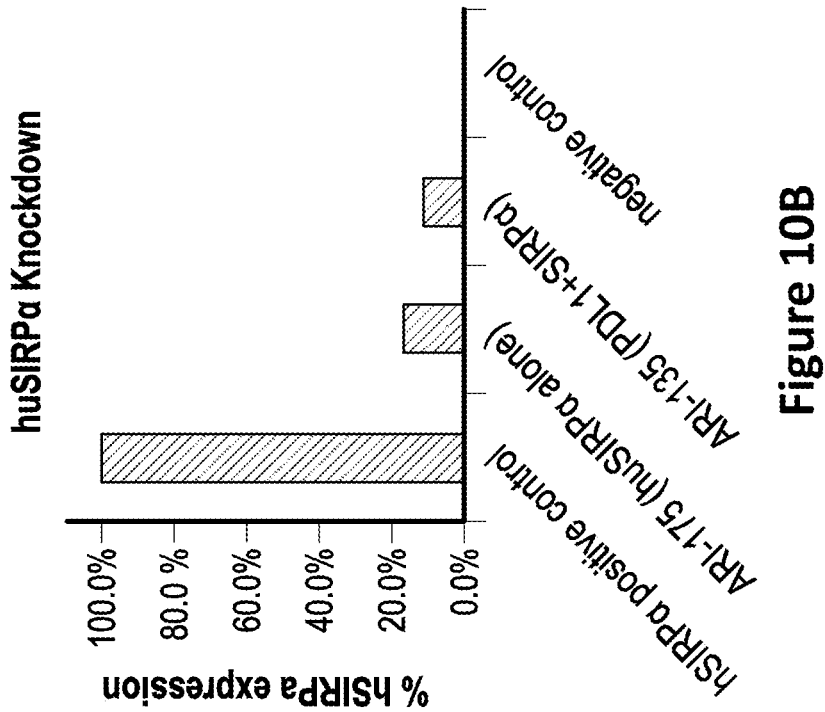
FIGS. 10A-10B depict the results of qPCR assessment of combination gene knockdown with HuPD-L1+HuSIRP-alpha RNAi's. HEK 293 cells were co-transfected with a PD-L1 cDNA expression plasmid, a SIRP-alpha cDNA expression plasmid, and pEQU6-H1 plasmid encoding ARI-135 containing shRNAs targeting PD-L1 and SIRP-alpha, or pEQU6 plasmid encoding ARI-123 shRNA targeting PD-L1 alone, or pEQU6 plasmid encoding ARI-175 shRNA targeting SIRPalpha.
Figure 10A:
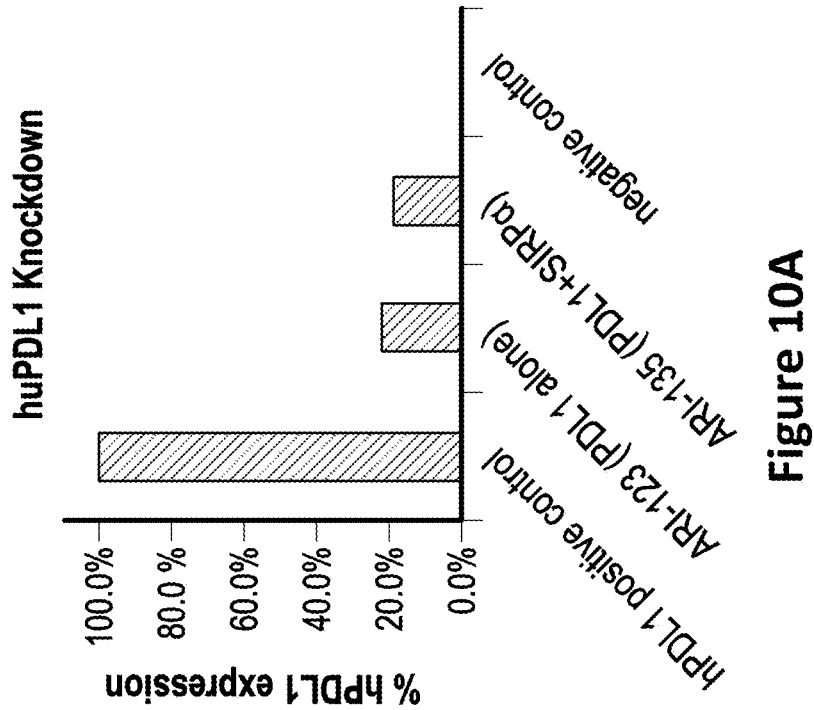

Similarly, the individual RNAi's, each targeting PD-L1 (ARI-123, SEQ ID NO:2) and SIRP-alpha (ARI-175, SEQ ID NO:14) described above, were subcloned into an engineered plasmid carrying both a U6 and H1 promoter (SEQ ID NO:42) to generate the combination RNAi, ARI-135 (SEQ ID NO:211). ARI-135 was tested for the ability to simultaneously express two separate shRNAs in situ that can each individually knockdown expression of PD-L1 and SIRP-alpha. As a control, knockdown of human PD-L1 expression in HEK293 cells by ARI-135 was compared to ARI-123 (a single RNAi solely targeting PD-L1 alone (SEQ ID NO:2), described above). Likewise, knockdown of human SIRP-alpha in HEK 293 cells by ARI-135 was compared to ARI-175 (a single RNAi targeting SIRP-alpha alone (SEQ ID NO:14), described above). Knockdown of PD-L1 by both ARI-123 and ARI-135 resulted in approximately 20% of wild type human PD-L1 gene expression (FIG. 10A). Likewise, knockdown of SIRP-alpha with both ARI-175 and ARI-135 resulted in <20% wild type SIRP-alpha expression (FIG. 10B). When knockdown against both PD-L1 and SIRP-alpha by ARI-135 was analyzed by Western blot, there was no detectable expression of either human PD-L1 or human SIRP-alpha versus their respective positive controls (human PD-L1 and human SIRP-alpha expression reactions lacking any RNAi). Therefore, the combination RNAi ARI-135 is able to knockdown expression of PD-L1 and SIRP-alpha.

Figure 11B:
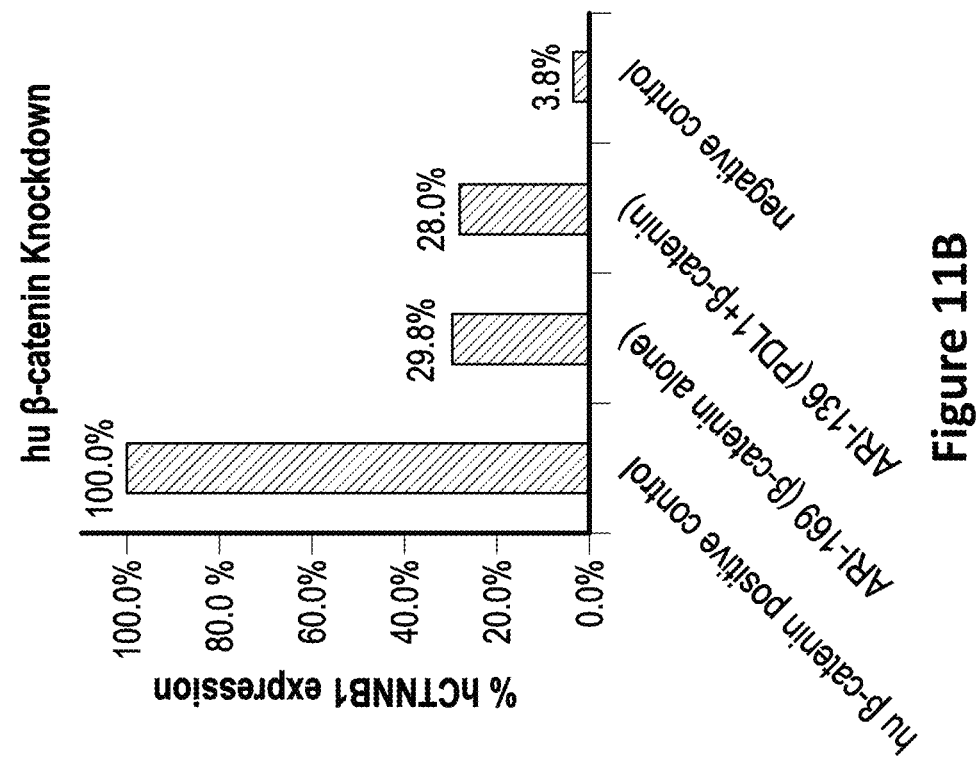
FIGS. 11A-11B depict the results of qPCR assessment of combination gene knockdown with HuPD-L1+Hu beta-catenin RNAi's. HEK 293 cells were co-transfected with a PD-L1 cDNA expression plasmid, a beta-catenin cDNA expression plasmid, and pEQU6-H1 plasmid encoding ARI-136 containing shRNAs targeting PD-L1 and beta-catenin, or pEQU6 plasmid encoding ARI-123 shRNA targeting PD-L1 alone, or pEQU6 plasmid encoding ARI-169 shRNA targeting beta-catenin.
Figure 11A:
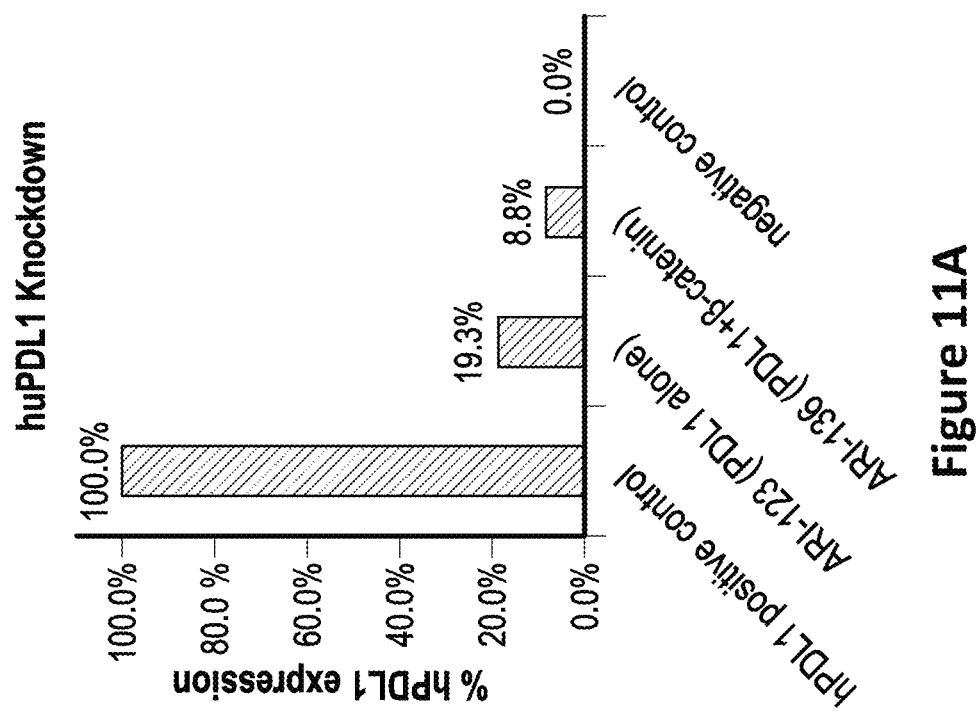

Next, the individual RNAi's, each targeting PD-L1 (ARI-123, SEQ ID NO:2) and beta-catenin (ARI-169, SEQ ID NO:8) described above, were subcloned into the engineered combination RNAi plasmid carrying the U6 and H1 promoter (SEQ ID NO:42) to generate the combination RNAi ARI-136 (SEQ ID NO:212). ARI-136 then was tested for the ability to simultaneously express two separate RNAi's in situ that can each individually knockdown expression of PD-L1 and beta-catenin. As a control, knockdown of human PD-L1 expression in HEK293 cells by ARI-136 was compared to ARI-123 (the single RNAi targeting PD-L1 alone (SEQ ID NO:2), described above). Likewise, knockdown of human beta-catenin in HEK 293 cells by ARI-136 was compared to ARI-169 (the single RNAi targeting beta-catenin alone (SEQ ID NO:8), described above). Knockdown of PD-L1 by ARI-123 resulted in approximately 20% of wild type human PD-L1 gene expression (FIG. 11A). Knockdown of PD-L1 by ARI-136 resulted in approximately 10% of wild type human PD-L1 gene expression, which is approximately two-fold better than ARI-123 (FIG. 11A). Knockdown of beta-catenin with ARI-136 and ARI-169 resulted in approximately 30% of wild type beta-catenin expression (FIG. 11B). When knockdown against PD-L1 and beta-catenin by ARI-136 was analyzed by Western blot, there was no detectable expression of either human PD-L1 or human beta-catenin versus their respective positive controls (human PD-L1 and human beta-catenin expression reactions lacking any RNAi). Therefore, the combination RNAi ARI-136 is able to knockdown expression of PD-L1 and beta-catenin.

Figure 12B:
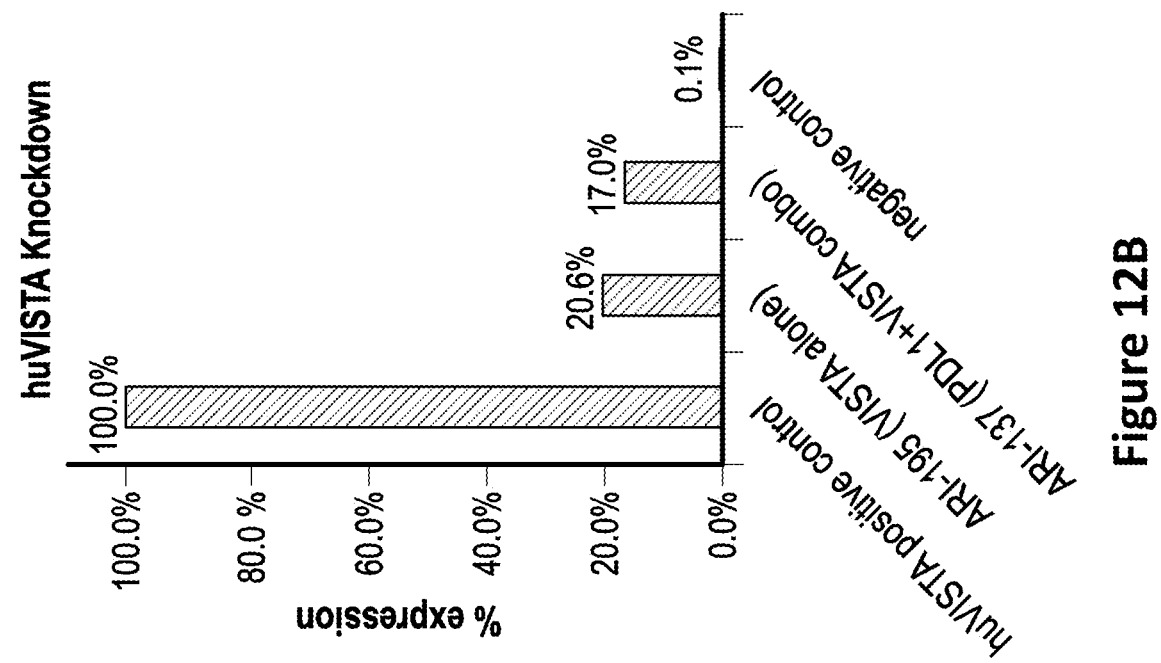
FIGS. 12A-12B depict the results of qPCR assessment of combination gene knockdown with HuPD-L1+HuVISTA RNAi's. HEK 293 cells were co-transfected with a PD-L1 cDNA expression plasmid, a VISTA cDNA expression plasmid, and pEQU6-H1 plasmid encoding ARI-137 (SEQ ID NO:213) containing shRNAs targeting PD-L1 and VISTA, or pEQU6 plasmid encoding ARI-123 (SEQ ID NO:2) shRNA targeting PD-L1 alone, or pEQU6 plasmid encoding ARI-195 (SEQ ID NO:25) shRNA targeting VISTA.
Figure 12A:
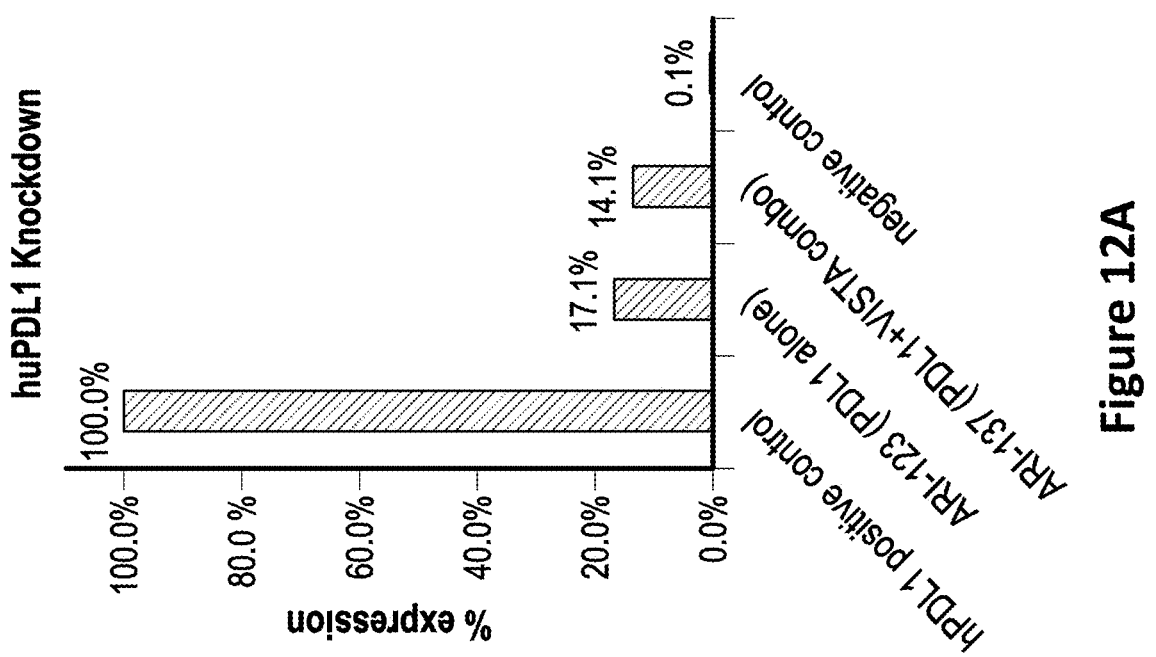

The individual RNAi's, each targeting PD-L1 (ARI-123, SEQ ID NO:2) and VISTA (ARI-195, SEQ ID NO:25) described above, were subcloned into an engineered plasmid carrying both a U6 and H1 promoter (SEQ ID NO:42) to generate the combination RNAi, ARI-137 (SEQ ID NO:213). ARI-137 was tested for the ability to simultaneously express two separate shRNAs in situ that can each individually knockdown expression of PD-L1 and VISTA. As a control, knockdown of human PD-L1 expression in HEK293 cells by ARI-137 was compared to ARI-123 (a single RNAi solely targeting PD-L1 alone (SEQ ID NO:2), described above). Likewise, knockdown of human VISTA in HEK 293 cells by ARI-137 was compared to ARI-195 (a single RNAi targeting VISTA alone, described above, SEQ ID NO:25). Knockdown of PD-L1 by both ARI-123 and ARI-137 resulted in approximately 20% of wild type human PD-L1 gene expression (FIG. 12A). Likewise, knockdown of VISTA with both ARI-195 and ARI-137 resulted in less than, or approximately equal to, 20% wild type VISTA expression (FIG. 12B). When knockdown against PD-L1 and VISTA by ARI-137 was analyzed by Western blot, there was no detectable expression of either human PD-L1 or human VISTA versus their respective positive controls (human PD-L1 and human VISTA expression reactions lacking any RNAi). Therefore, the combination RNAi ARI-137 is able to knockdown expression of PD-L1 and VISTA.

Figures 13A, 13B:
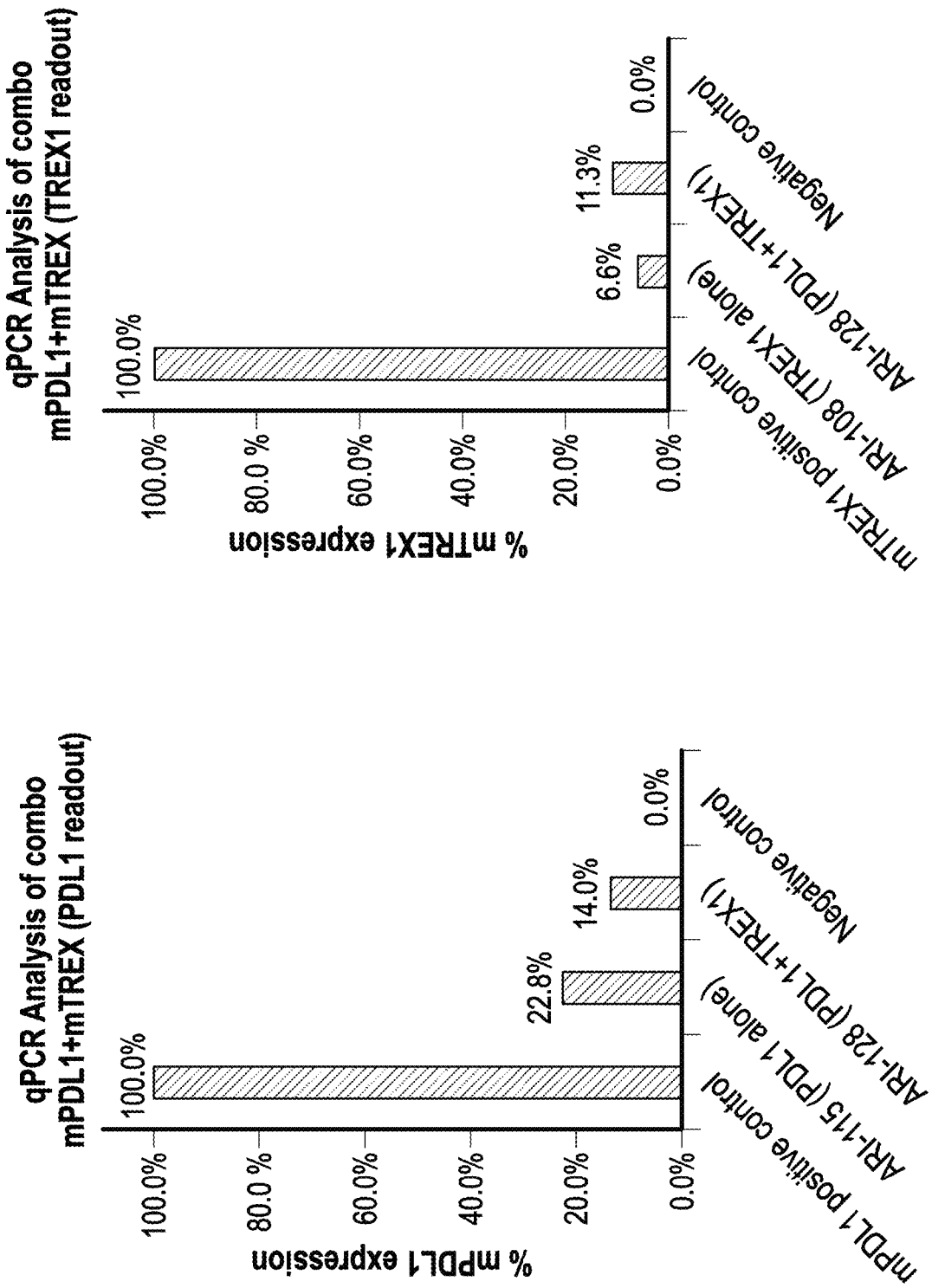
FIGS. 13A-13B depict the results of qPCR assessment of combination gene knockdown with mouse TREX1+mouse PD-L1 RNAi's. HEK 293 cells were co-transfected with a mouse TREX1 cDNA expression plasmid, a mouse PD-L1 cDNA expression plasmid, and pEQU6-H1 plasmid encoding containing shRNA (designated ARI-128) targeting mouse TREX1 and mouse PD-L1, or pEQU6 plasmid encoding shRNA (designated ARI-15 targeting mouse PD-L1 alone, or pEQU6 plasmid encoding shRNA (designated ARI-108) targeting mouse TREX1.

In addition to human targets, combined RNAi knockdown of two mouse gene targets by separate shRNAs expressed from the same plasmid was tested using the engineered plasmid carrying both a U6 and H1 promoter (SEQ ID NO:42). Individual shRNAs each targeting mouse PD-L1 (ARI-115, SEQ ID NO:75) and mouse TREX1 (ARI-108) were subcloned to generate the combination RNAi ARI-128. ARI-128 then was tested for the ability to simultaneously express two separate shRNAs in situ that can each individually knockdown expression of their respective targets (mouse PD-L1 and mouse TREX1). As a control, knockdown of mouse PD-L1 expression in HEK293 cells by ARI-128 was compared to ARI-115 (the single RNAi targeting solely targeting PD-L1 (SEQ ID NO:75)), and knockdown of mouse TREX1 in HEK 293 cells by ARI-128 was compared to ARI-108 (a single RNAi solely targeting TREX1). Whereas the ARI-115 knockdown had 22.8% of wild type mouse PD-L1 gene expression, knockdown of mouse PD-L1 by ARI-128 (the combination vector) was improved, allowing only 14.0% of wild type mouse TREX1 gene expression (FIG. 13A). Knockdown of mouse TREX1 with either ARI-108 or ARI-128 was very efficient (6.6% and 11.3%, respectively, of wild-type mouse TREX1 expression) (FIG. 13B). When knockdown against both mouse PD-L1 and mouse TREX1 by ARI-128 was analyzed by Western blot, there was no detectable expression of either mouse PD-L1 or mouse TREX1 versus their respective positive controls (individual mouse PD-L1 and mouse TREX1 expression reactions lacking any RNAi).

Figure 14B:
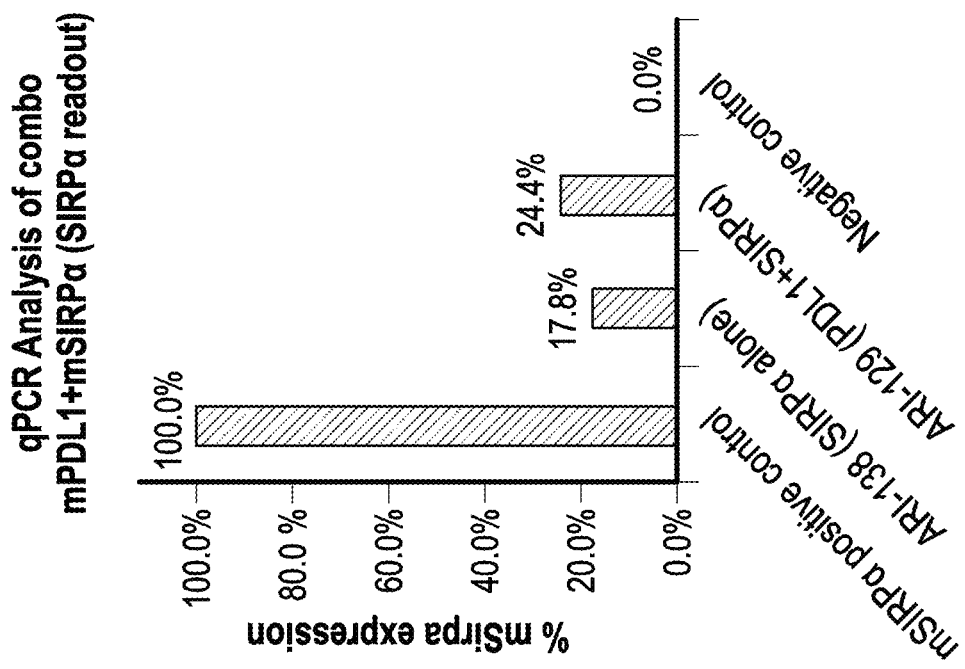
FIGS. 14A-14B depict the results of qPCR assessment of combination gene knockdown with mouse PD-L1+mouse SIRP-alpha RNAi's. HEK 293 cells were co-transfected with a mouse PD-L1 cDNA expression plasmid, a mouse SIRP-alpha cDNA expression plasmid, and pEQU6-H1 plasmid encoding shRNA (designated ARI-129) targeting mouse PD-L1 and SIRP-alpha, or pEQU6 plasmid encoding shRNA (designated ARI-115) targeting PD-L1 alone, or pEQU6 plasmid encoding shRNA (designated ARI-138) targeting SIRP-alpha.
Figure 14A:
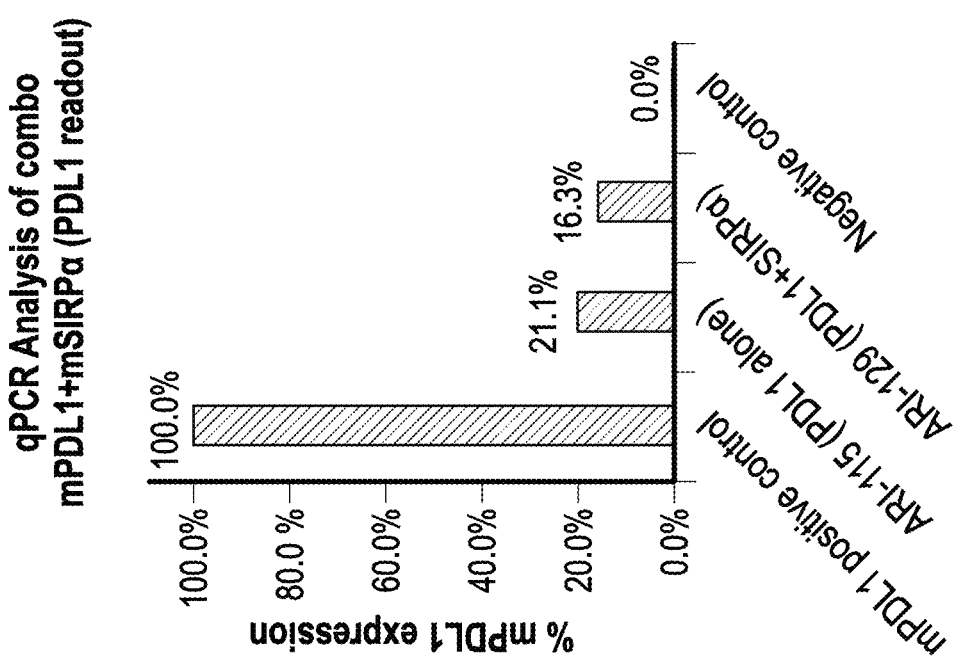

A combination RNAi was generated for targeting mouse PD-L1 and mouse SIRP-alpha using the engineered plasmid carrying both a U6 and H1 promoter (SEQ ID NO:42). Individual shRNAs each targeting mouse PD-L1 (ARI-115, SEQ ID NO:75) and mouse SIRP-alpha (ARI-138, SEQ ID NO:76) were subcloned to generate the combination RNAi ARI-129. ARI-129 then was tested for the ability to simultaneously express two separate shRNAs in situ that can each individually knockdown expression of their respective targets (mouse PD-L1 and mouse SIRP-alpha). As a control, knockdown of mouse PD-L1 expression in HEK293 cells by ARI-129 was compared to ARI-115 (the single RNAi targeting solely targeting PD-L1), and knockdown of mouse SIRP-alpha in HEK 293 cells by ARI-129 was compared to ARI-138 (a single RNAi solely targeting SIRP-alpha). ARI- 115 and ARI-129 had knockdown of approximately 20% or less of wild type mouse PD-L1 gene expression (FIG. 14A). Knockdown of mouse SIRP-alpha with either ARI-138 or ARI-129 was approximately 25% or less of wild-type mouse SIRP-alpha expression (FIG. 14B). When knockdown against both mouse PD-L1 and mouse SIRP-alpha by ARI-129 was analyzed by Western blot, there was no detectable expression of either mouse PD-L1 or mouse SIRP-alpha versus their respective positive controls (individual mouse PD-L1 and mouse SIRP-alpha expression reactions lacking any RNAi).

Figures 15A, 15B:
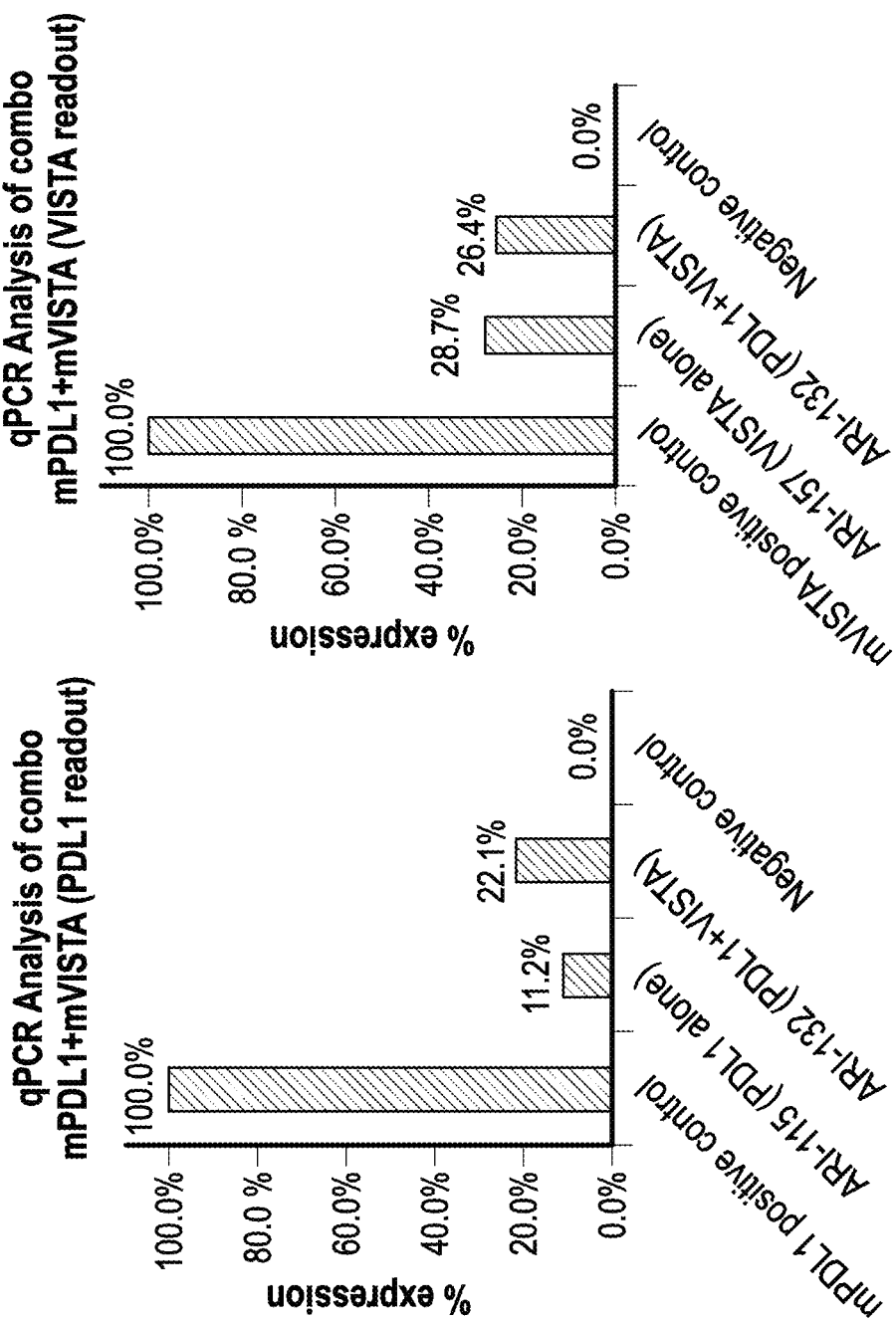
FIGS. 15A-15B depict the results of qPCR assessment of combination gene knockdown with mouse PD-L1+mouse VISTA RNAi's. HEK 293 cells were co-transfected with a mouse PD-L1 cDNA expression plasmid, a mouse VISTA cDNA expression plasmid, and pEQU6-H1 plasmid encoding containing shRNA (designated ARI-132) targeting PD-L1 and VISTA, or pEQU6 plasmid encoding shRNA (designated ARI-115) targeting PD-L1 alone, or pEQU6 plasmid encoding shRNA (designated ARI-157) targeting VISTA.

Next, a combination RNAi was generated for targeting mouse PD-L1 and mouse VISTA using the engineered plasmid carrying both a U6 and H1 promoter (SEQ ID NO:42). Individual shRNAs each targeting mouse PD-L1 (ARI-115, SEQ ID NO:75) and mouse VISTA (ARI-157) were subcloned to generate the combination RNAi ARI-132. ARI-132 then was tested for the ability to simultaneously express two separate shRNAs in situ that can each individually knockdown expression of their respective targets (mouse PD-L1 and mouse VISTA). As a control, knockdown of mouse PD-L1 expression in HEK293 cells by ARI-132 was compared to ARI-115 (the single RNAi targeting solely targeting PD-L1), and knockdown of mouse VISTA in HEK 293 cells by ARI-132 was compared to ARI-157 (a single RNAi solely targeting VISTA). Both ARI-115 and ARI-132 had knockdown of approximately 20% or less of wild type mouse PD-L1 gene expression (FIG. 15A). Knockdown of mouse VISTA with either ARI-157 or ARI-132 was approximately 30% or less of wild-type mouse VISTA expression (FIG. 15B). When knockdown against both mouse PD-L1 and mouse VISTA by ARI-132 was analyzed by Western blot, there was no detectable expression of either mouse PD-L1 or mouse VISTA versus their respective positive controls (individual mouse PD-L1 and mouse VISTA expression reactions lacking any RNAi).

Figure 16A:
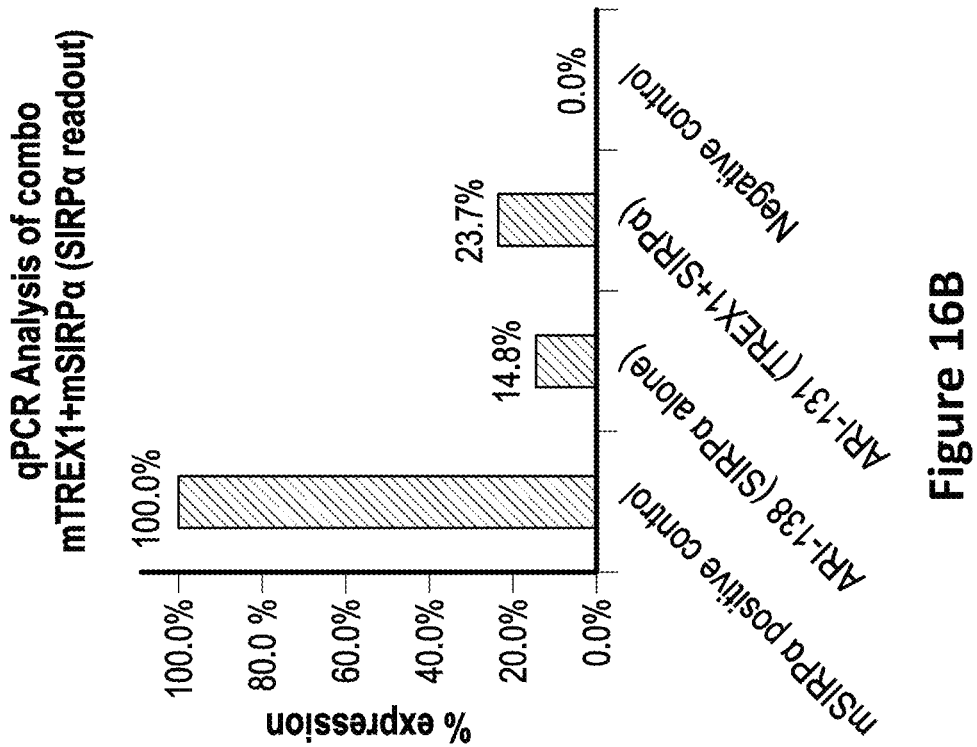
FIGS. 16A-16B depict the results of qPCR assessment of combination gene knockdown with mouse TREX1+mouse SIRP-alpha RNAi's. HEK 293 cells were co-transfected with a mouse TREX1 cDNA expression plasmid, a mouse VISTA cDNA expression plasmid, and pEQU6-H1 plasmid encoding containing shRNA (designated ARI-131) targeting PD-L1 and VISTA, or pEQU6 plasmid encoding shRNA (designated ARI-108) targeting TREX1 alone, or pEQU6 plasmid encoding shRNA (designated ARI-138) targeting SIRP-alpha.
Figure 16B:
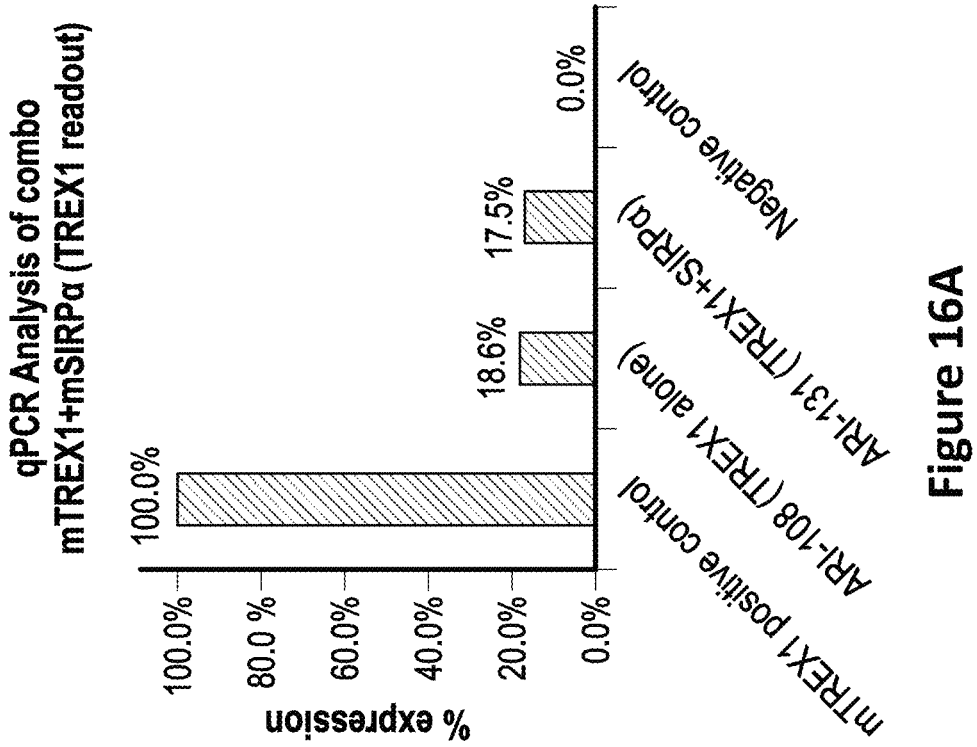

A combination of RNAi was generated for targeting mouse TREX1 and mouse SIRP-alpha using the engineered plasmid carrying a U6 and H1 promoter (SEQ ID NO:42). Individual shRNAs, one targeting mouse TREX1 (ARI-108) and the other targeting mouse SIRP-alpha (ARI-138, SEQ ID NO:76), were subcloned to generate the combination RNAi designated ARI-131. ARI-131 was tested for the ability to simultaneously express two separate shRNAs in situ that can each individually knockdown expression of the respective targets (mouse TREX1 and mouse SIRP-alpha). As a control, knockdown of mouse TREX1 expression in HEK293 cells by ARI-131 was compared to ARI-108 (the single RNAi targeting solely targeting TREX1), and knockdown of mouse SIRP-alpha in HEK 293 cells by ARI-131 was compared to ARI-138 (a single RNAi solely targeting SIRP-alpha). ARI-108 and ARI-131 had knockdown of approximately 20% or less of wild type mouse TREX1 gene expression (FIG. 16A). Knockdown of mouse SIRP-alpha with either ARI-138 or ARI-131 was approximately 25% or less than wild-type mouse SIRP-alpha expression (FIG. 16B).

Figure 17B:
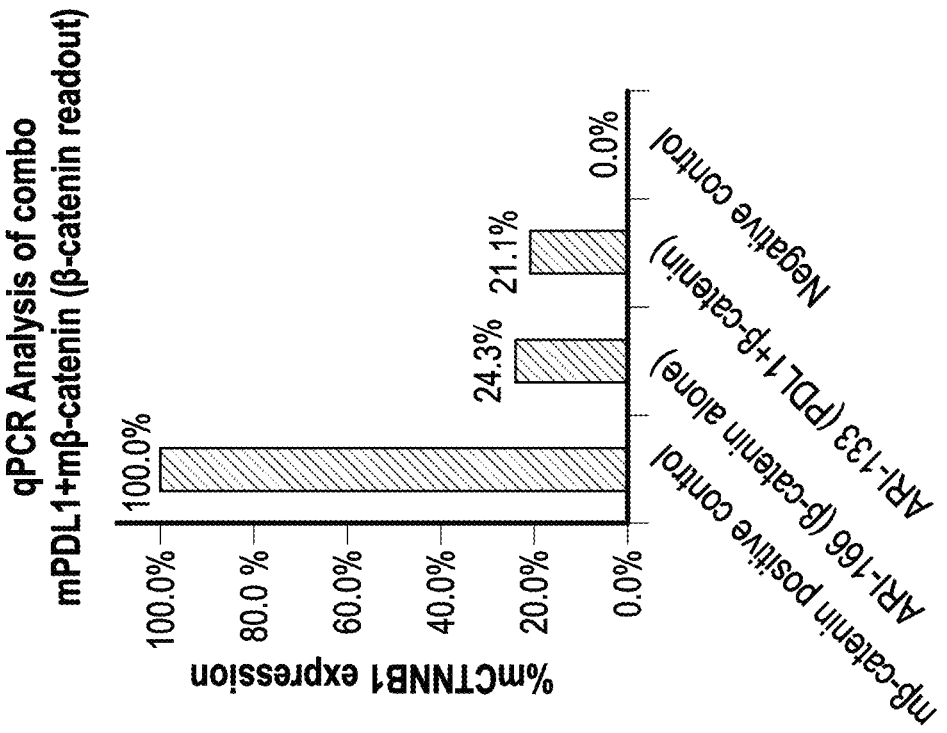
FIGS. 17A-17B depict the results of qPCR assessment of combination gene knockdown with mouse PD-L1+mouse beta-catenin RNAi's. HEK 293 cells were co-transfected with a mouse PD-L1 cDNA expression plasmid, a mouse beta-catenin cDNA expression plasmid, and pEQU6-H1 plasmid encoding containing shRNA (designated ARI-133) targeting PD-L1 and VISTA, or pEQU6 plasmid encoding shRNA (designated ARI-115) targeting PD-L1 alone, or pEQU6 plasmid encoding shRNA (designated ARI-166) targeting beta catenin.
Figure 17A:
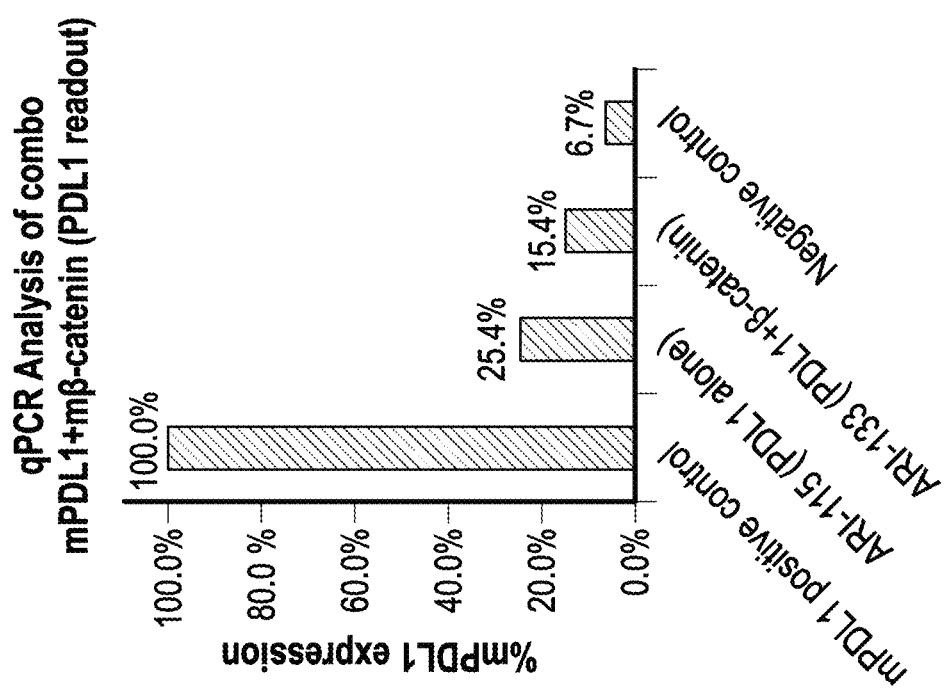

A combination RNAi was generated that targets mouse PD-L1 and mouse beta-catenin using the engineered plasmid carrying a U6 and H1 promoter (SEQ ID NO:42). Individual shRNAs each targeting mouse PD-L1 (ARI-115, SEQ ID NO:75) and mouse beta-catenin (ARI-166) were subcloned to generate the combination RNAi ARI-133. ARI-133 then was tested for the ability to simultaneously express two separate shRNAs in situ that can each individually knockdown expression of their respective targets (mouse PD-L1 and mouse beta-catenin). As a control, knockdown of mouse PD-L1 expression in HEK293 cells by ARI-133 was compared to ARI-115 (the single RNAi targeting solely targeting PD-L1), and knockdown of mouse beta-catenin in HEK 293 cells by ARI-133 was compared to ARI-166 (a single RNAi solely targeting beta-catenin). ARI-115 and ARI-133 had knockdown of approximately 25% or less of wild type mouse PD-L1 gene expression (FIG. 17A). Knockdown of mouse beta-catenin with either ARI-166 or ARI-133 was approximately 25% or less of wild-type mouse beta-catenin expression (FIG. 17B). When knockdown against mouse PD-L1 and mouse beta-catenin by ARI-133 was analyzed by Western blot, there was no detectable expression of either mouse PD-L1 or mouse beta-catenin versus their respective positive controls (individual mouse PD-L1 and mouse beta-catenin expression reactions lacking any RNAi).

Figures 18A, 18B:
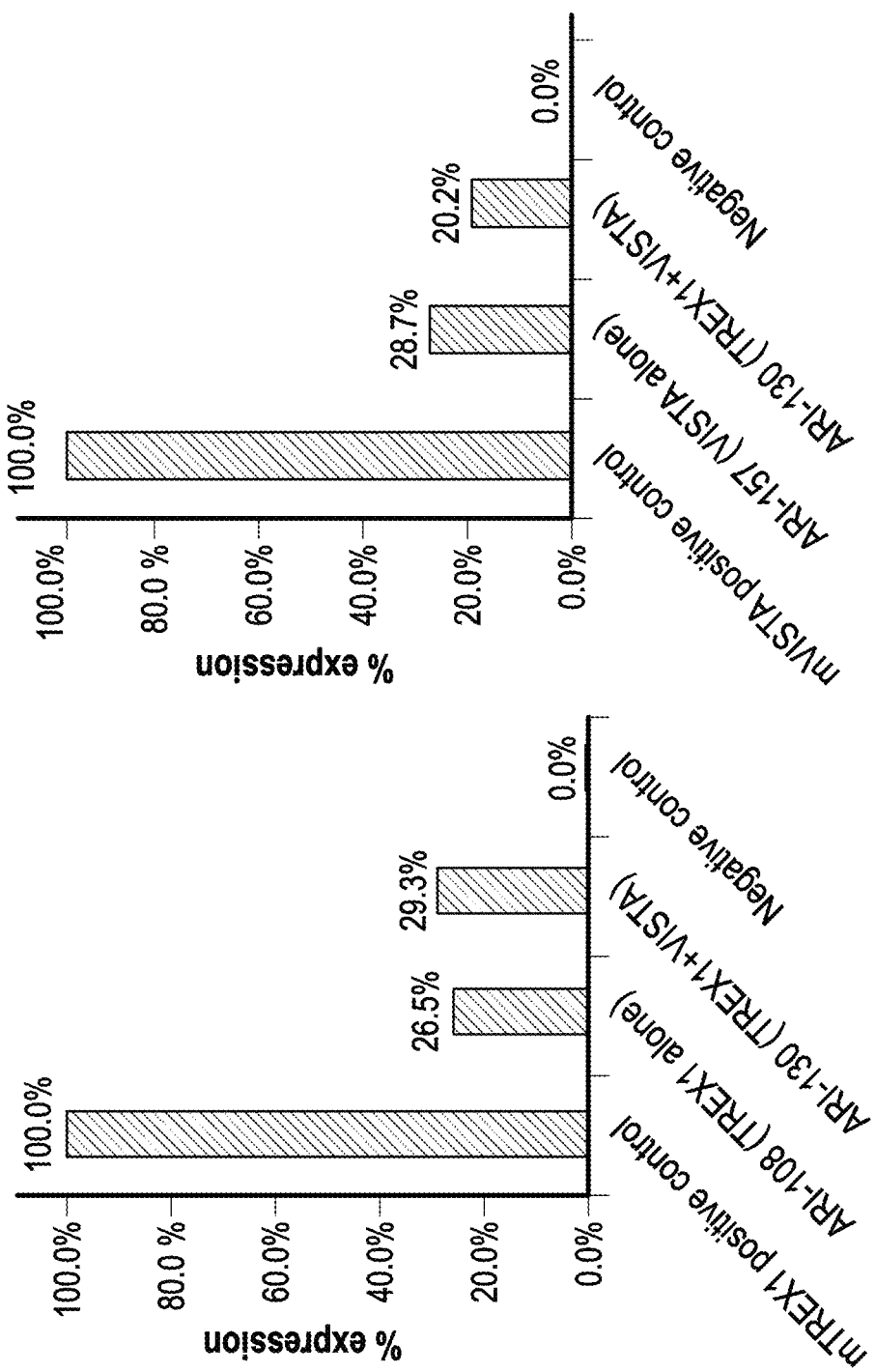
FIGS. 18A-18B depict the results of qPCR assessment of combination gene knockdown with mouse TREX1+mouse VISTA RNAi's. HEK 293 cells were co-transfected with a mouse TREX1 cDNA expression plasmid, a mouse VISTA cDNA expression plasmid, and pEQU6-H1 plasmid encoding shRNA (designated ARI-130) targeting PD-L1 and VISTA, or pEQU6 plasmid encoding shRNA (designated ARI-108) targeting TREX1 alone, or pEQU6 plasmid encoding shRNA (designated ARI-157) targeting VISTA.

Next, a combination RNAi was generated for targeting mouse TREX1 and mouse VISTA using the engineered plasmid carrying both a U6 and H1 promoter (SEQ ID NO:42). Individual shRNAs each targeting mouse TREX1 (ARI-108) and mouse VISTA (ARI-157) were subcloned to generate the combination RNAi ARI-130. ARI-130 then was tested for the ability to simultaneously express two separate shRNAs in situ that can each individually knockdown expression of their respective targets (mouse TREX1 and mouse VISTA). As a control, knockdown of mouse TREX1 expression in HEK293 cells by ARI-130 was compared to ARI-108 (a RNAi targeting solely targeting TREX1), and knockdown of mouse VISTA in HEK 293 cells by ARI-130 was compared to ARI-157 (a single RNAi solely targeting VISTA). Both ARI-108 and ARI-130 had knockdown of approximately 30% or less of wild type mouse TREX1 gene expression (FIG. 18A). Knockdown of mouse VISTA with either ARI-157 or ARI-130 was approximately 30% or less of wild-type mouse VISTA expression (FIG. 18B). When knockdown against both mouse TREX1 and mouse VISTA by ARI-130 was analyzed by Western blot, there was no detectable expression of either mouse TREX1 or mouse VISTA versus their respective positive controls (individual mouse TREX1 and mouse VISTA expression reactions lacking any RNAi).

Micro RNA (mi-RNA)

Figures 19A, 19B:
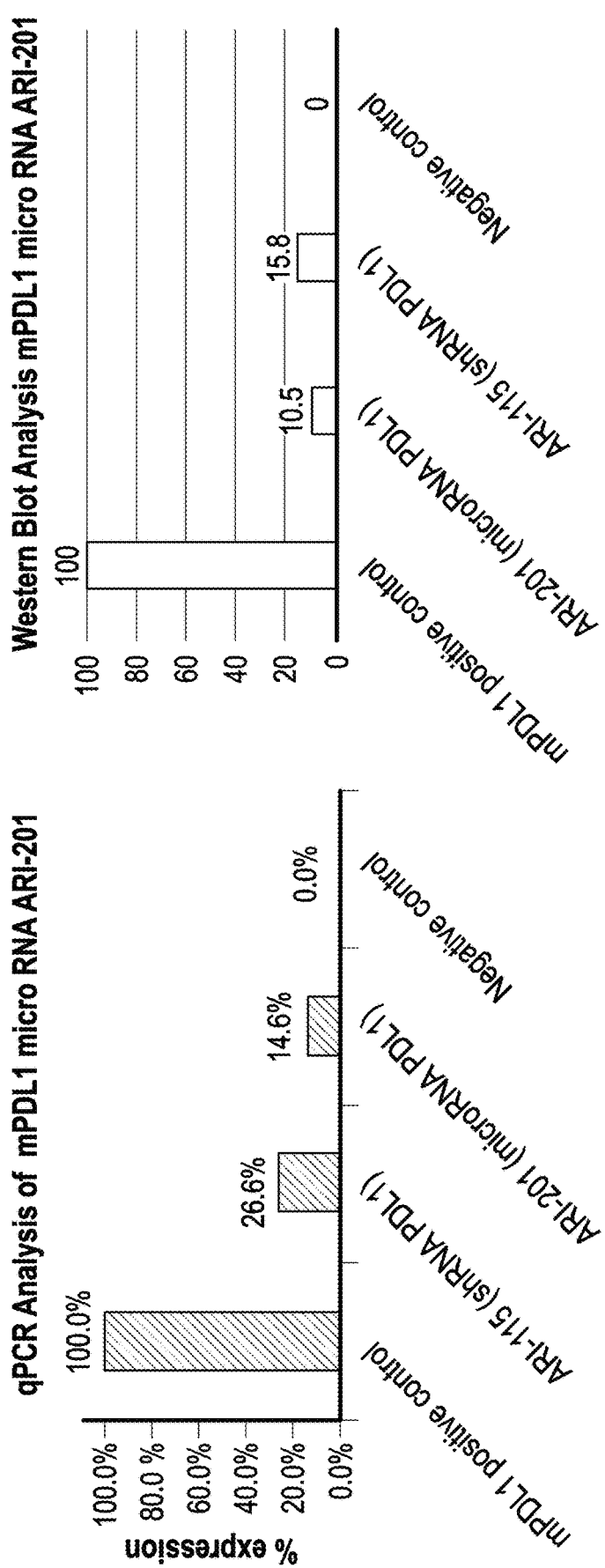
FIGS. 19A-19B depict a comparison of micro-RNA and shRNA-mediated knockdown of mouse PD-L1. HEK 293 cells were co-transfected with a mouse PD-L1 cDNA expression plasmid and either pEQU6 plasmids encoding micro-RNA (ARI-201) or shRNA (designated ARI-115) targeting PD-L1.

A microRNA construct, ARI-205 (SEQ ID NO:214), was used to generate a mouse PD-L1 targeting microRNA, ARI-201, by inserting RNAi targeting mouse PD-L1 into the microRNA backbone of SEQ ID NO:249, and compared to the PD-L1 targeting shRNA construct ARI-115 (SEQ ID NO:75) by qPCR and Western blot analysis, as described above. Whereas ARI-115 knockdown was 26.6% of wild-type PD-L1 expression, knockdown by ARI-201 was improved, with 14.6% of PD-L1 expression (FIG. 19A). By Western blot, ARI-115 was able to knockdown PD-L1 to 15.8% of wild type PD-L1 expression, and knockdown by ARI-201 was improved, with 10.5% of PD-L1 expression (FIG. 19B).

Figure 20:
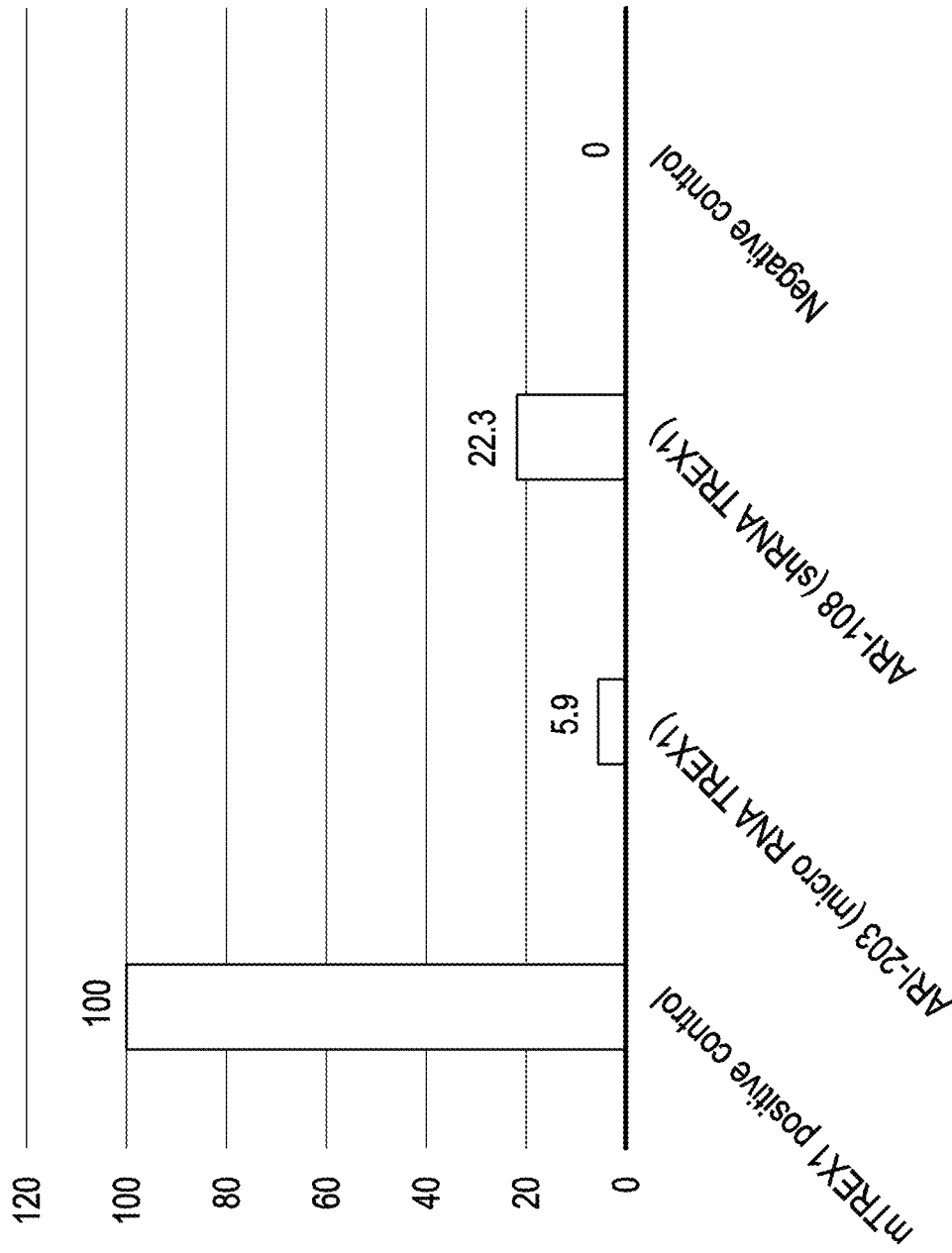
FIG. 20 depicts a comparison of micro-RNA and shRNA-mediated knockdown of mouse TREX1. HEK 293 cells were co-transfected with a mouse TREX1 cDNA expression plasmid and pEQU6 plasmids encoding micro-RNA (designated ARI-203) or shRNA (designated ARI-108) targeting TREX1. Western blot was used to determine the level of mRNA knockdown.

A microRNA was generated against mouse TREX1, ARI-203, based on the microRNA construct described above, ARI-205 (SEQ ID NO:214), using oligonucleotide synthesis, overlapping PCR and restriction digest cloning, and tested by qPCR. Whereas ARI-108, a shRNA that targets mouse TREX1, had a gene knockdown efficiency of 22.3% versus wild-type TREX1, ARI-203 possessed a knockdown efficiency of 5.9% (FIG. 20). Therefore, the microRNA was approximately three to four-fold improved in its knockdown efficiency of mouse TREX1, when compared to the shRNA.

Figure 21A:
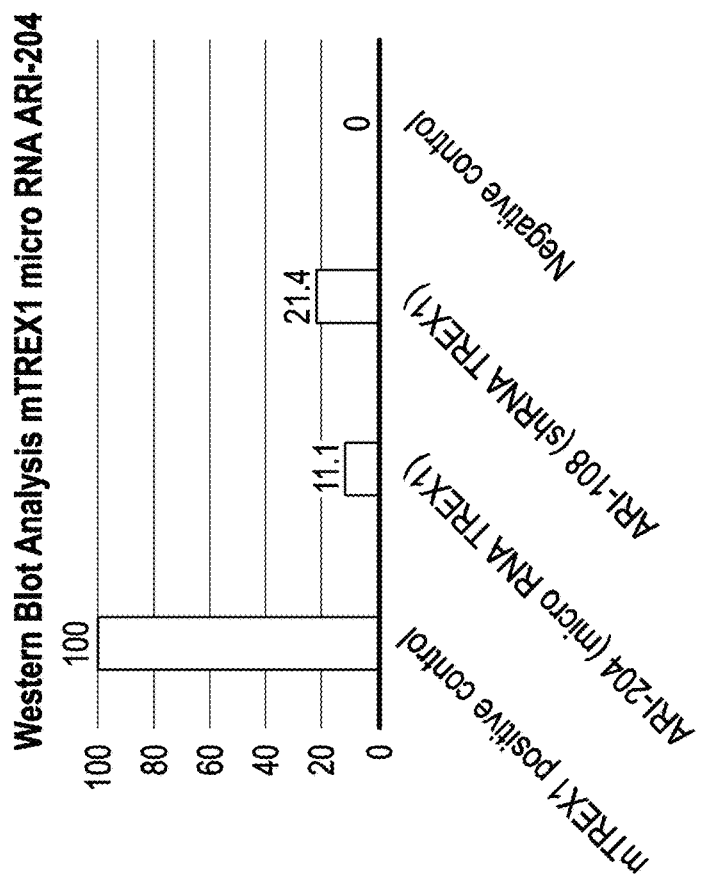
FIGS. 21A-21B depict the results of TREX1 knockdown with RNA Pol II expression of micro-RNA. HEK 293 cells were co-transfected with a mouse TREX1 cDNA expression plasmid and pEQU6 plasmid shRNA targeting mouse TREX1 (designated ARI-108) or a pEQ plasmid encoding a CMV promoter and micro-RNA targeting mouse TREX1 (designated ARI-204).
Figure 21B:
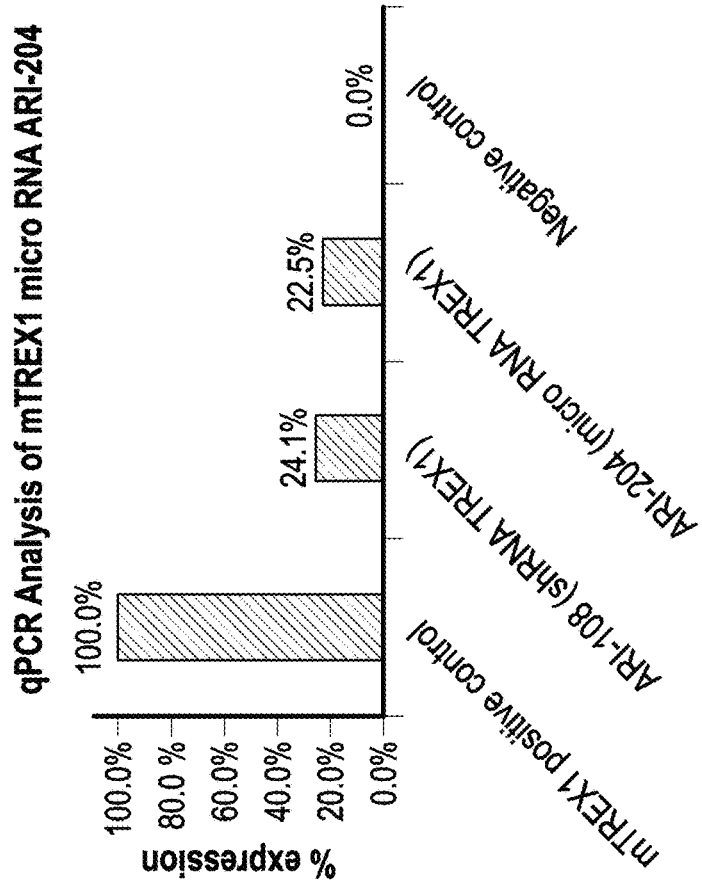

A large microRNA construct, ARI-206 (SEQ ID NO:215), requiring expression under an RNA polymerase II promoter, was constructed for testing knockdown of target genes and testing by qPCR and Western blot analysis. A mouse TREX1 targeting version of this microRNA, ARI-204, was tested against ARI-108, the mouse TREX1 targeting shRNA described above. ARI-204 and ARI-108 were able to efficiently knock down expression of mouse TREX1 (22.5% and 24.1% of wild type mouse TREX1 expression, respectively, FIG. 21A). The activity of ARI-204 mouse TREX1 targeting microRNA was slightly improved over the ARI-108 mouse TREX1 targeting shRNA, when assessed for knockdown of mouse TREX1 gene expression by Western blot (11.1% for ARI-204, versus 21.4% for ARI-108, FIG. 21B).

Figures 22A, 22B:
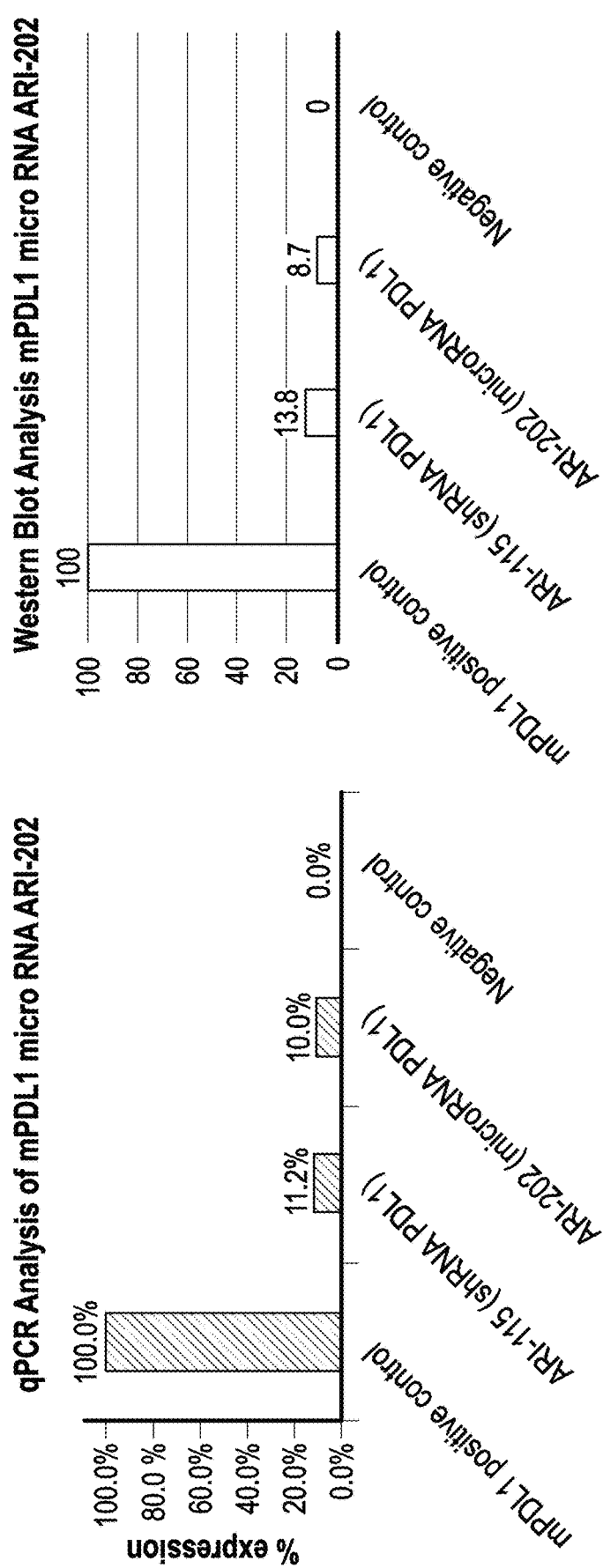
FIGS. 22A-22B depict the results of PD-L1 knockdown with RNA Pol II expression of micro-RNA. HEK 293 cells were co-transfected with a mouse PD-L1 cDNA expression plasmid and pEQU6 plasmid shRNA targeting mouse PD-L1 (designated ARI-115) or a pEQ plasmid encoding a CMV promoter and micro-RNA targeting mouse TREX1 (designated ARI-202).

A mouse PD-L1 targeting version of microRNA construct ARI-206, ARI-202, was tested against ARI-115, the mouse PD-L1 targeting shRNA described above. ARI-202 and ARI-I 15 were able to efficiently knock down expression of mouse PD-L1 (10.0 and 11.2% of wild type mouse PD-L1 expression, respectively, FIG. 22A). The ARI-202 mouse PD-L1 targeting microRNA was slightly improved over the ARI-115 mouse PD-L1 targeting shRNA, when assessed for knockdown of mouse PD-L1 gene expression by Western blot (8.7% for ARI-202, versus 13.8% for ARI-115, FIG. 22B).

The shRNA gene knockdown can be directly measured in tumor cell lines that are known to overexpress the target gene. For example, the following are known tumor cell lines with high PD-L1 expression: PC-3 (prostate), MDA-MB-231 (breast), and ASPC-1 (pancreatic) (Grenga et al. (2014) *J. Immuno Therapy of Cancer* 2(Suppl 3):P102). Cells can be stimulated with IFN-gamma to see induction of PD-L1 expression. The U937 tumor cell line overexpresses SIRP-alpha (Irandoust et al. (2013) *PLoS ONE* 8(1):e52143). Simultaneous knockdown of gene expression against PD-L1 and SIRP-alpha can be performed in U937 cells induced with IFN-gamma.

The microRNA constructs above, ARI-205 (SEQ ID NO:214) and ARI-206 (SEQ ID NO:215) encode 21 and 22 base pair homology sequences, respectively. Alternatively, microRNA constructs can be used that encode 19 base pair homology sequences, for example, ARI-207 (SEQ ID NO: 216) and ARI-208 (SEQ ID NO:217). The individual microRNAs against target genes can be generated by gene synthesis, PCR amplification with primers containing restriction sites and subcloning into the expression vector with matched restriction enzyme generated overhangs.

Example 3

Modified *Salmonella typhimurium* Targets Demonstrate Robust Tumor Growth Inhibition in Multiple Syngeneic Murine Tumor Models

TREX1

Delivery of an shRNA to TREX1, following tumor microenvironment uptake of systemically administered attenuated *Salmonella*, results in activation of STING-mediated anti-tumor immunity and tumor growth inhibition. To assess the ability of AST-104 (strain YS1646 transformed with pEQU6-shTREX1) to induce tumor growth inhibition in a murine colon carcinoma model, 6-8 week-old female BALB/c mice (8 mice per group) were inoculated subcutaneously (SC) in the right flank with CT26 murine colon carcinoma ($2 \times 10^5$ cells in 100 µL PBS). Mice bearing established flank tumors were intravenously (IV) injected twice, four days apart, with $1 \times 10^7$ CFUs of AST-104, or AST-102 (strain YS1646 transformed with pEQU6 plasmid control), and compared to PBS control. Six hours following the first IV dose, mice were bled, and plasma was collected and assessed for pro-inflammatory cytokines, using the Mouse Inflammation Cytometric Bead Array kit and analyzed by FACS (BD Biosciences).

Figure 23:
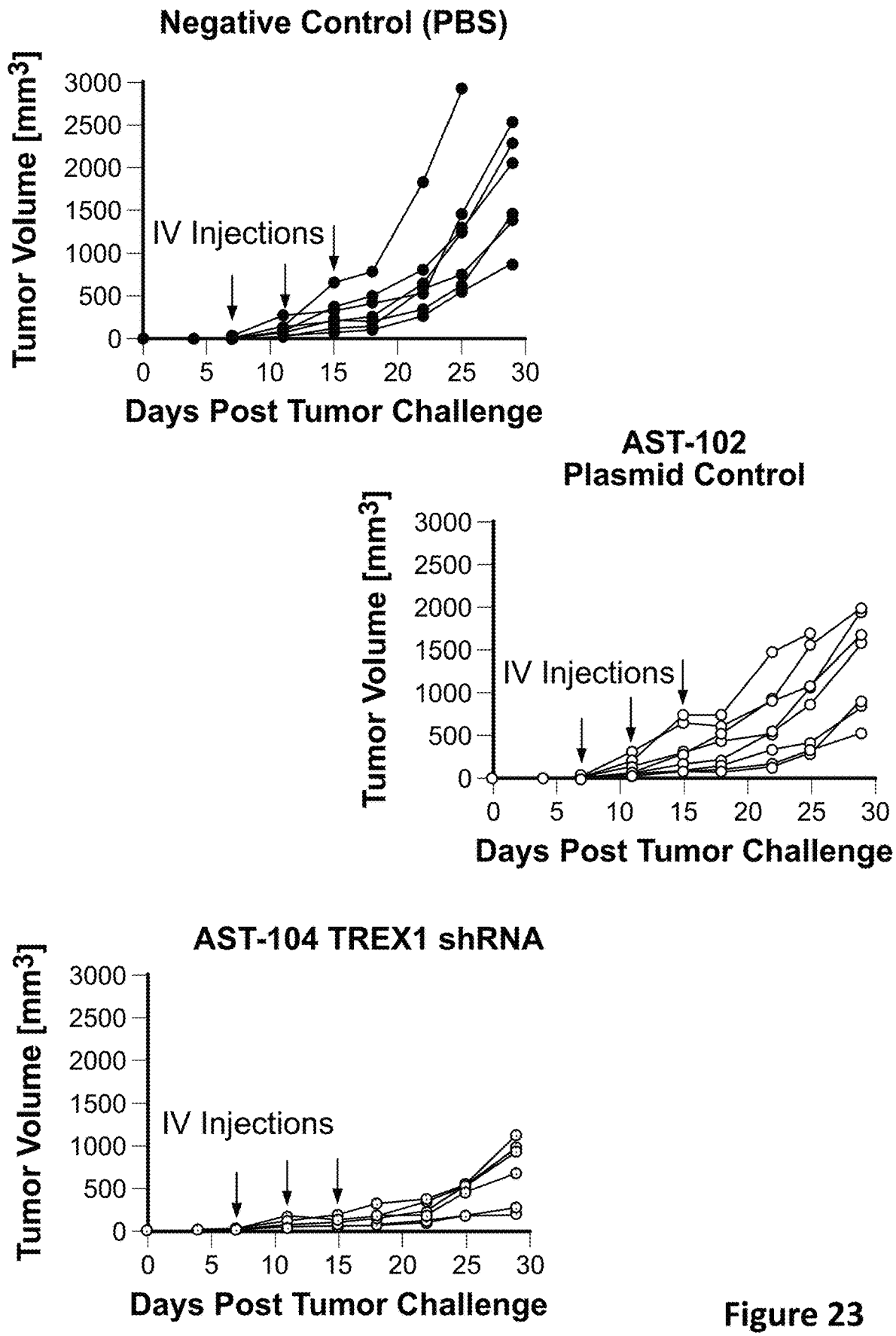
FIG. 23 depicts the efficacy of systemically administered strain AST-104 in a CT26 colon tumor model. BALB/c mice were implanted with a single CT26 ($2\times10^5$ cells) subcutaneous flank tumor (n=8 per group). Mice with established tumors were IV injected with 1×10⁷ CFU of YS1646 strains containing either plasmid control (strain AST-102) or the TREX1 shRNA plasmid (of strain AST-104), or PBS control, on the days indicated by the arrows. Spaghetti plots depict tumor growth, each line representing an individual mouse. Tumor measurements were performed using electronic calipers (Fowler, Newton, MA). Tumor volume was calculated using the modified ellipsoid formula ½(length×width²). Mice were euthanized when tumor size reached >20% of body weight or became necrotic, as per IACUC regulations. % Tumor Growth Inhibition (TGI) was calculated as 1−(mean test tumor volume/mean control tumor volume)×100. *p<0.05 vs. plasmid control, student's t-test.

As shown in FIG. 23, the control strain, AST-102 demonstrated modest tumor control, compared to PBS (18% tumor growth inhibition (TGI), p=ns at day 25). The shTREX1-containing strain, AST-104, demonstrated significant tumor growth inhibition compared to PBS (66% TGI, p=0.01 at day 25, calculated over the average of 8 animals per group), and significant tumor control compared to AST-102 (p=0.02 at day 28). The percent tumor growth inhibition (TGI) is calculated as 1−(mean test tumor volume/mean control tumor volume)×100.

Activation of Pro-Inflammatory Cytokines
TREX1

The level of systemic serum cytokines at 6 hours post IV injection were assessed. The immune-activating cytokines TNF-alpha, IL-12, and interferon-gamma, elicited by AST-104 (containing an shTREX1 plasmid that includes the asd complementation in the plasmid; asd contains CpG elements) were significantly higher, compared to the AST-102 plasmid control (also containing CpG from the asd) and PBS groups (FIG. 24A). IL-1β, a cytokine known to suppress immunity (see, e.g., Wang et al. (2012) *Scand. J. Immunol.* 3:273-281), trended lower in the shTREX1 group compared to the plasmid control (FIG. 24B). These data demonstrate that inhibiting TREX1 activates known STING pathway-induced cytokines that promote anti-tumor immunity and potent tumor growth inhibition in a murine model of colon carcinoma.

To assess the ability of AST-104 (containing an shTREX1 plasmid with CpG elements) to induce tumor growth inhibition in a separate aggressive murine colon carcinoma model, as well as a checkpoint therapy-resistant melanoma model, 6-8 week-old female C57BL/6 mice (10 mice per group) were inoculated SC in the right flank with MC38 colon carcinoma cells or B16.F10 melanoma cells (5 and $2 \times 10^5$ cells, respectively, in 100 µL PBS). Mice bearing established flank tumors were IV injected twice, four days apart, with $5 \times 10^6$ CFUs of AST-104, or AST-102, and compared to PBS control.

Figure 25:
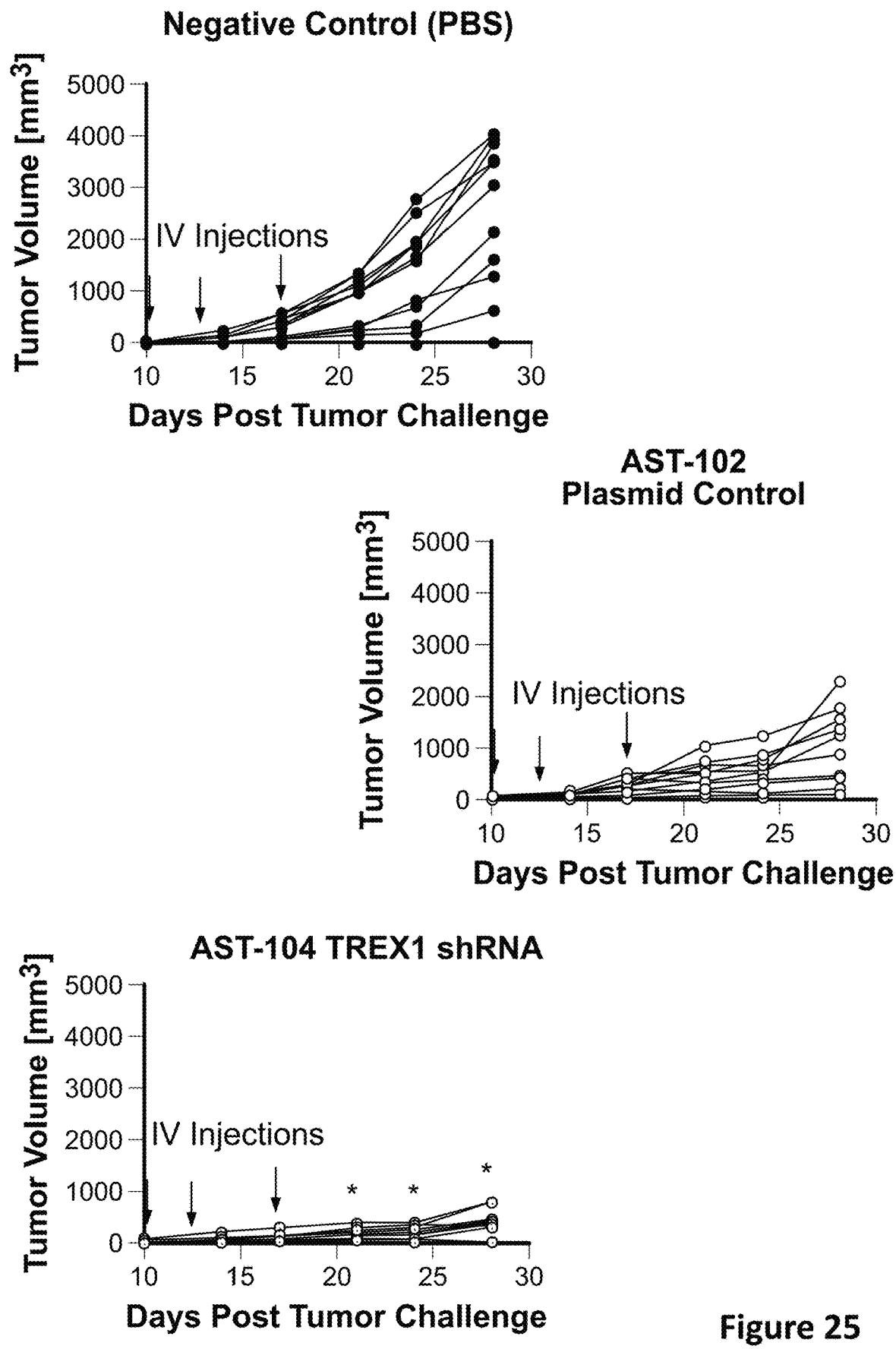
FIG. 25 depicts the efficacy of systemically administered strain AST-104 in a MC38 colon tumor model. C57Bl/6 mice (6-8 wk old) were implanted with a single MC38 (2×10⁵ cells) subcutaneous flank tumor (n=10 per group). Mice with established tumors were IV injected with 5×10⁶ CFU of YS1646 strains containing either plasmid control (strain AST-102) or the TREX1 shRNA plasmid (strain AST-104), or PBS control, on the days indicated by the arrows. Spaghetti plots depict tumor growth, each line representing an individual mouse. Tumor measurements were performed using electronic calipers (Fowler, Newton, MA). Tumor volume was calculated using the modified ellipsoid formula ½(length×width²). Mice were euthanized when tumor size reached >20% of body weight or became necrotic, as per IACUC regulations. TGI was calculated as 1−(mean test tumor volume/mean control tumor volume)×100. *p<0.05 vs. plasmid control, student's t-test.
Figure 26:
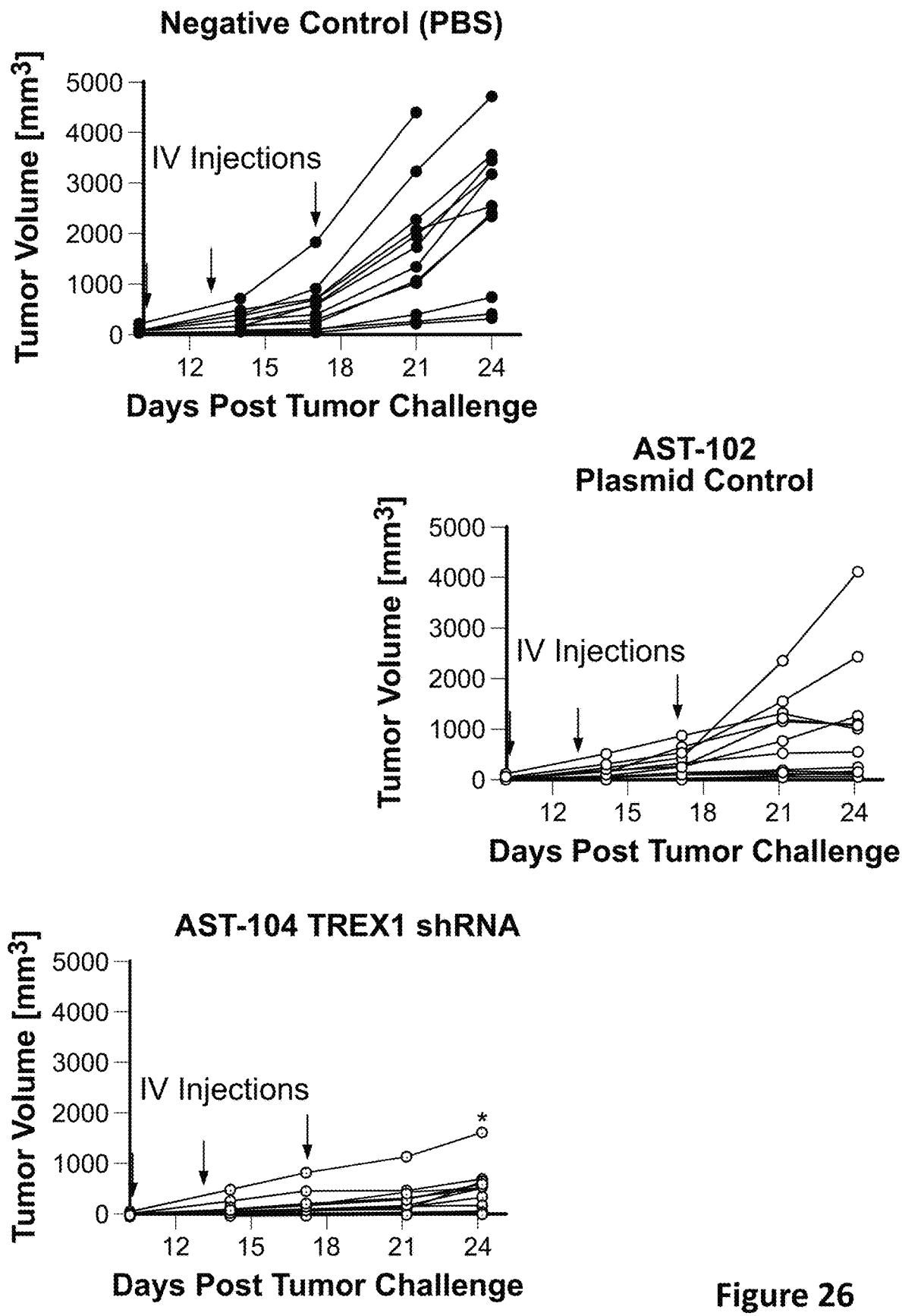
FIG. 26 depicts the efficacy of AST-104 in a checkpoint-resistant B16.F10 melanoma model. C57Bl/6 mice (6-8 wk old) were implanted with a single B16.F10 (5×10⁵ cells) subcutaneous flank tumor (n=10 per group). Mice with established tumors were IV injected with 5×10⁶ CFU of YS1646 strains containing either plasmid control (AST-102) or the TREX1 shRNA plasmid (AST-104), or PBS control, on the days indicated by the arrows. Spaghetti plots depict tumor growth, each line representing an individual mouse. Tumor measurements were performed using electronic calipers (Fowler, Newton, MA). Tumor volume was calculated using the modified ellipsoid formula ½(length×width²). Mice were euthanized when tumor size reached >20% of body weight or became necrotic, as per IACUC regulations. TGI was calculated as 1−(mean test tumor volume/mean control tumor volume)×100. *p<0.05 vs. plasmid control, student's t-test.

As shown in FIG. 25, strain AST-104, containing shRNA to TREX1, induced potent tumor growth inhibition of MC38 tumors (85% TGI, p<0.0001, day 28), and significant tumor growth inhibition compared to the plasmid control (p=0.049, day 28). Similarly, as shown in FIG. 26, AST-104 induced highly significant tumor growth inhibition in B16.F10 melanoma compared to PBS (83% TGI, p=0.0012, day 24), and greater tumor growth inhibition compared to plasmid control strain AST-102, which had significant efficacy in this model compared to PBS (p=0.019, day 24). These results also show that plasmids containing CpG elements, in combination with shTREX1-mediated STING activation demonstrate synergy and efficacy, and have the benefit of systemic, instead of intratumoral, administration.

In summary, in multiple aggressive murine tumor models, the addition of a plasmid encoding shRNA against TREX1 in the YS1646 strain significantly enhanced anti-tumor responses compared to the YS1646 strain containing a control plasmid. These data demonstrate the potency of activating the STING pathway through systemic administration of an immunostimulatory tumor-targeting bacteria.

PD-L1

The immune system has evolved several checks and balances to limit autoimmunity. Programmed cell death protein 1 (PD-1) and programmed death-ligand 1 (PD-L1)

are two examples of numerous inhibitory "immune checkpoints," which function by downregulating immune responses. The binding of PD-L1 to PD-1 interferes with $CD8^+$ T cell signaling pathways, impairing the proliferation and effector function of $CD8^+$ T cells, and inducing T cell tolerance (Topalian et al. (2012) *N. Engl. J. Med.* 366: 2443-2454).

Tumor colonization of a modified *Salmonella typhimurium* strain delivering shRNA to knockdown the PD-L1 gene disrupts its binding to PD-1, and its inhibition of $CD8^+$ T cell function. PD-L1/PD-1 checkpoint inhibition synergizes well with the immunostimulatory *S. typhimurium* containing CpG plasmid DNA, all in one therapeutic modality. To demonstrate the in vivo efficacy of the YS1646 strain containing a plasmid encoding shRNA to PD-L1 (AST-105), this strain, in comparison to the AST-102 strain (containing a control plasmid that also contains CpG motifs) in a murine colon carcinoma model was evaluated. For this experiment, 6-8 week-old female BALB/c mice (10 mice per group) were inoculated SC in the right flank with CT26 murine colon carcinoma ($2 \times 10^5$ cells in 100 µL PBS). Mice bearing established flank tumors were IV injected twice, four days apart, with $5 \times 10^6$ CFUs of AST-105, AST-102, or IV administration of anti-PD-L1 antibody (4 mg/kg, BioXCell clone 10F.9G2). Six hours following the first IV dose, mice were bled, and plasma was collected and assessed for pro-inflammatory cytokines using the Mouse Inflammation Cytometric Bead Array kit and analyzed by FACS (BD Biosciences).

Figure 27:
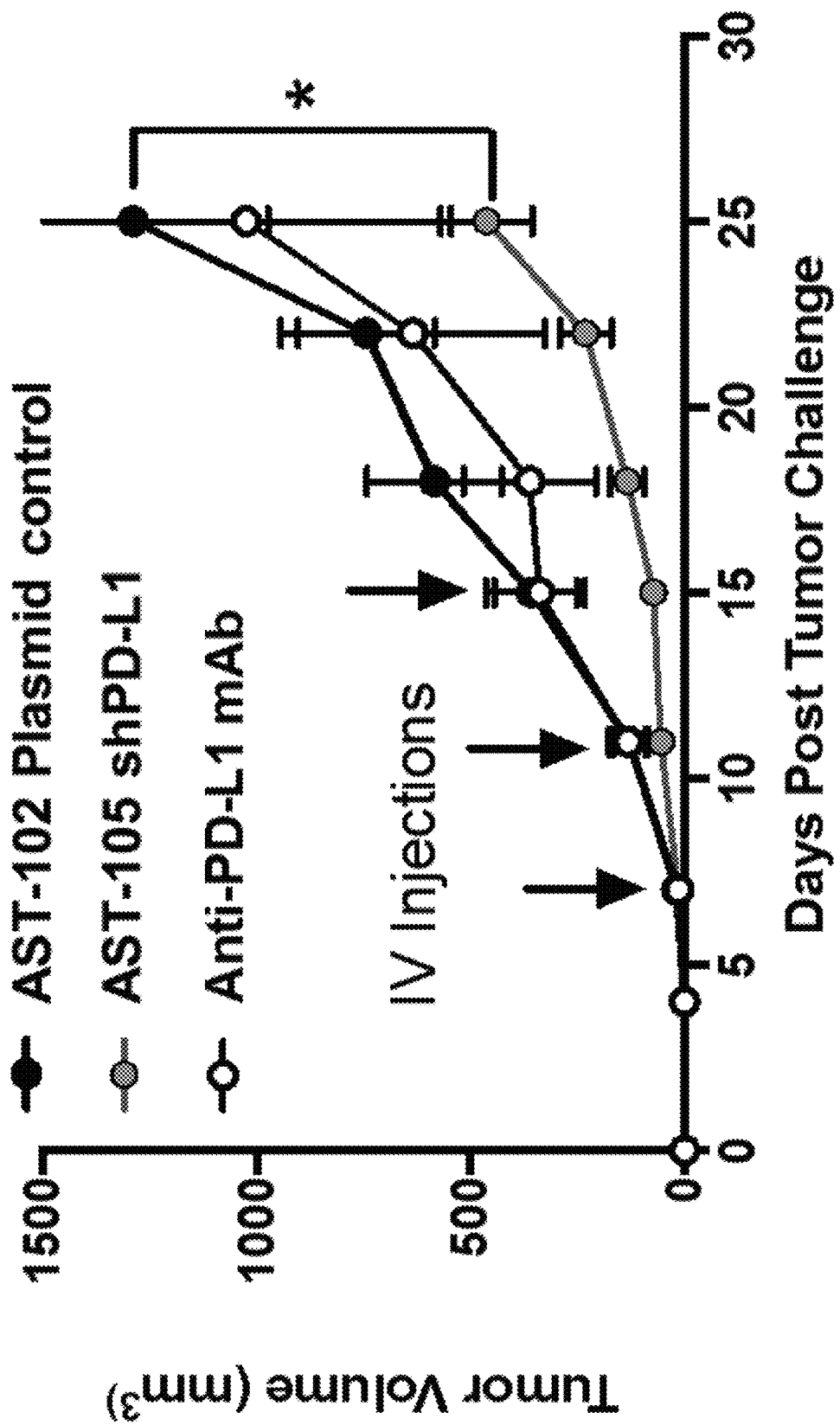
FIG. 27 depicts the efficacy of systemically administered AST-105 (shPD-L1) in a CT26 tumor model. BALB/c (6-8 wk old) were implanted with a single CT26 (2×10⁵ cells) subcutaneous flank tumor (n=8 per group). Mice with established tumors were IV injected with 5×10⁶ CFU of YS1646 strains containing either plasmid control (AST-102) or the PD-L1 shRNA plasmid (AST-105), or PBS control, on the days indicated by the arrows. A separate group was administered 100 µg anti-PD-L1 antibody (clone 10F.9G2 clone, BioXCell) by IP injection weekly, beginning with the first IV injection. Spaghetti plots depicting tumor growth, each line representing an individual mouse. Tumor measurements were performed using electronic calipers (Fowler, Newton, MA). Tumor volume was calculated using the modified ellipsoid formula ½(length×width²). Mice were euthanized when tumor size reached >20% of body weight or became necrotic, as per IACUC regulations. TGI was calculated as 1−(mean test tumor volume/mean control tumor volume)×100. *p<0.05 vs. plasmid control, student's t-test.

As shown in FIG. 27, treatment with strain AST-105 demonstrated statistically significant tumor control compared to treatment with the plasmid-containing control strain AST-102 (69% TGI, p=0.05, day 25). Tumor growth inhibition was also greater for treatment with AST-105 (expressing shPD-L1) than from systemic administration of an anti-PD-L1 antibody (68% TGI vs. anti-PD-L1).

Figure 28:
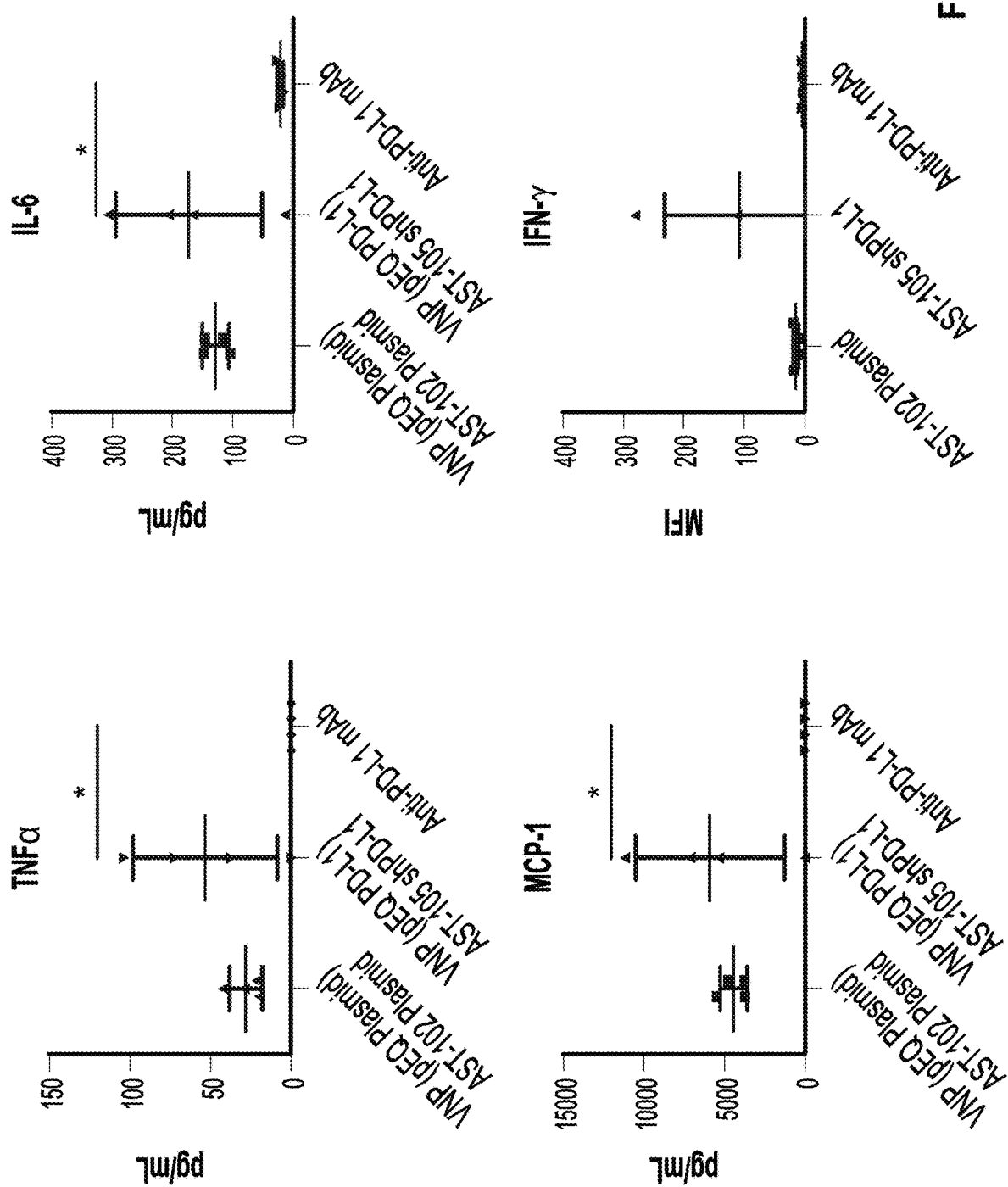
FIG. 28 depicts results showing that AST-105 induces significant cytokine responses observed over PD-L1 mAb. BALB/c mice (6-8 wk old) were implanted with a single CT26 (2×10⁵ cells) subcutaneous flank tumor (n=8 per group). Mice with established tumors were IV injected with 5×10⁶ CFU of YS1646 strains containing either plasmid control (AST-102) or the PD-L1 shRNA plasmid (AST-105), or PBS control, on the days indicated by the arrows. A separate group was administered 100 µg anti-PD-L1 antibody IP (clone 10F.9G2 clone, BioXCell) weekly, beginning with the first IV injection. Mice were bled 6 hrs following the first dose and systemic serum cytokines tested by Luminex (BD bead array and Luminex 200) and mouse cytometric bead array (FACS Fortessa, FCAP software, all BD Biosciences). *p<0.05, **p<0.01, student's t-test.

Comparing the production of innate pro-inflammatory cytokines at 6 hours post IV injection, the cytokines elicited by strain AST-105 were significantly higher compared to the anti-PD-L1 antibody (p<0.05, FIG. 28), and much higher than those from AST-102. These data demonstrate that inhibiting PD-L1 within the tumor microenvironment, compared to systemic administration of anti-PD-L1 antibody, uniquely activates potent pro-inflammatory cytokines that induce anti-tumor immunity and promote tumor growth inhibition in a murine model of colon carcinoma.

Example 4

Intratumoral Administration of Modified *S. typhimurium* shTREX1 Provides Distal Tumor Colonization and Complete Anti-Tumor Responses in a Dual Flank Murine Colon Carcinoma Model A hallmark of inducing adaptive immunity to a tumor is the ability to induce regression of a distal, untreated tumor. To assess the ability of the YS1646 strain containing the pEQU6 shRNA plasmids to induce primary and distal tumor growth inhibition in a dual flank murine colon carcinoma model, 6-8 week-old female BALB/c mice (10 mice per group) were inoculated SC in the right and left flanks with CT26 murine colon carcinoma ($2 \times 10^5$ cells in 100 µL PBS). Mice bearing established flank tumors were intratumorally (IT) injected twice, four days apart, into the right flank tumor with $5 \times 10^6$ CFUs of AST-104, (pEQU6 shTREX1 in YS1646), AST-105 (pEQU6 shPD-L1 in YS1646) or AST-102 (plasmid control in YS1646), and compared to PBS control.

Figure 29:
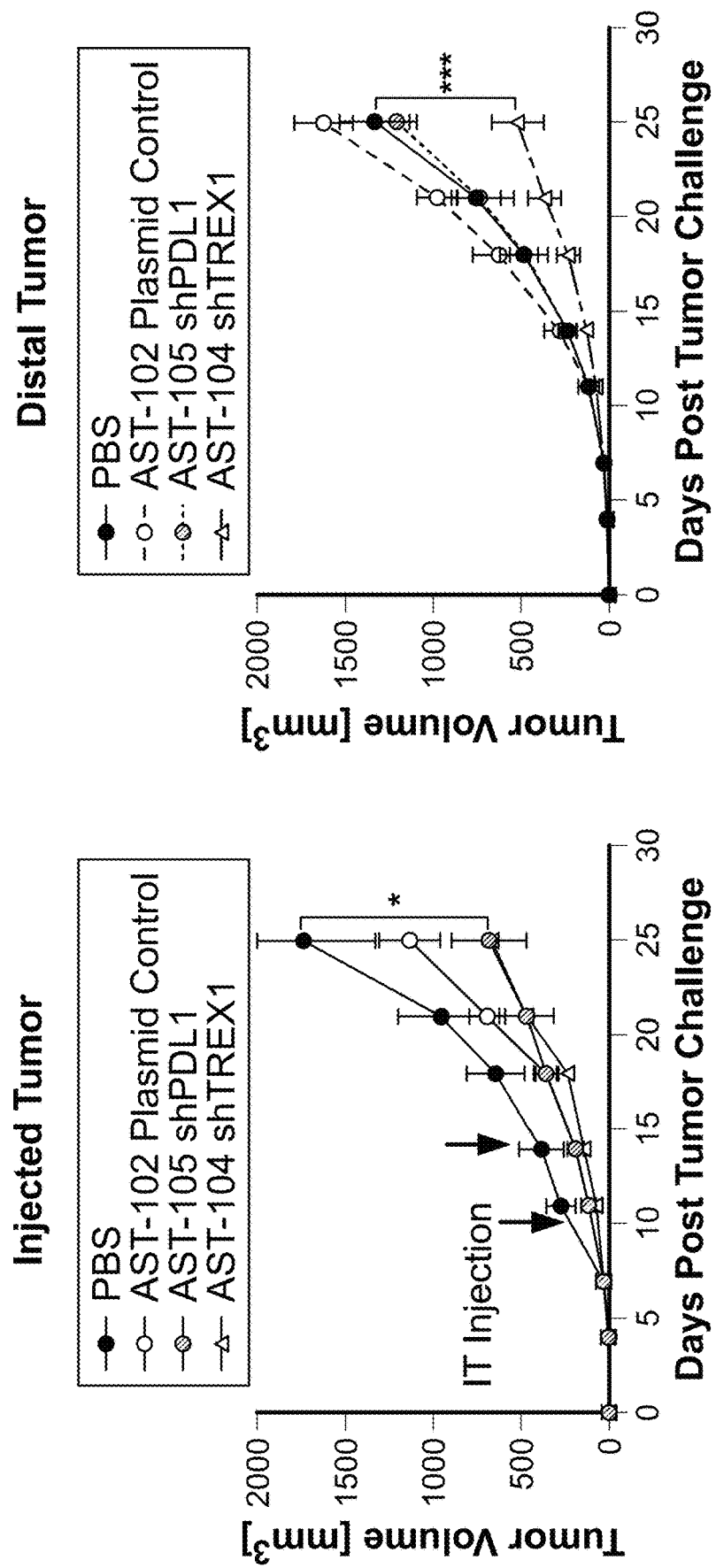
FIG. 29 depicts the effects of intratumoral administration of strains AST-104 and AST-105 in dual flank colon tumors on tumor volume. BALB/c mice (6-8 wk old) were implanted with dual CT26 (2×10⁵ cells) subcutaneous flank tumors on the right and left flanks (n=10 per group). Mice with established tumors were IT injected into the right flank with 5×10⁶ CFU of YS1646 strains containing either plasmid control (AST-102) or the strain containing TREX1 shRNA plasmid (AST-104), or PD-L1 shRNA plasmid (AST-105), or PBS control, on the days indicated by the arrows. Tumor measurements were performed using electronic calipers (Fowler, Newton, MA). Tumor volume was calculated using the modified ellipsoid formula ½(length×width²). Mice were euthanized when tumor size reaches >20% of body weight or became necrotic, as per IACUC regulations. % Tumor Growth Inhibition (TGI) is calculated as 1−(mean test tumor volume/mean control tumor volume)×100. The plots depict mean tumor growth of each group in the injected (left graph) and distal (right graph) groups, ±SEM. *p<0.05, ***p<0.001, student's t-test.
Figure 30:
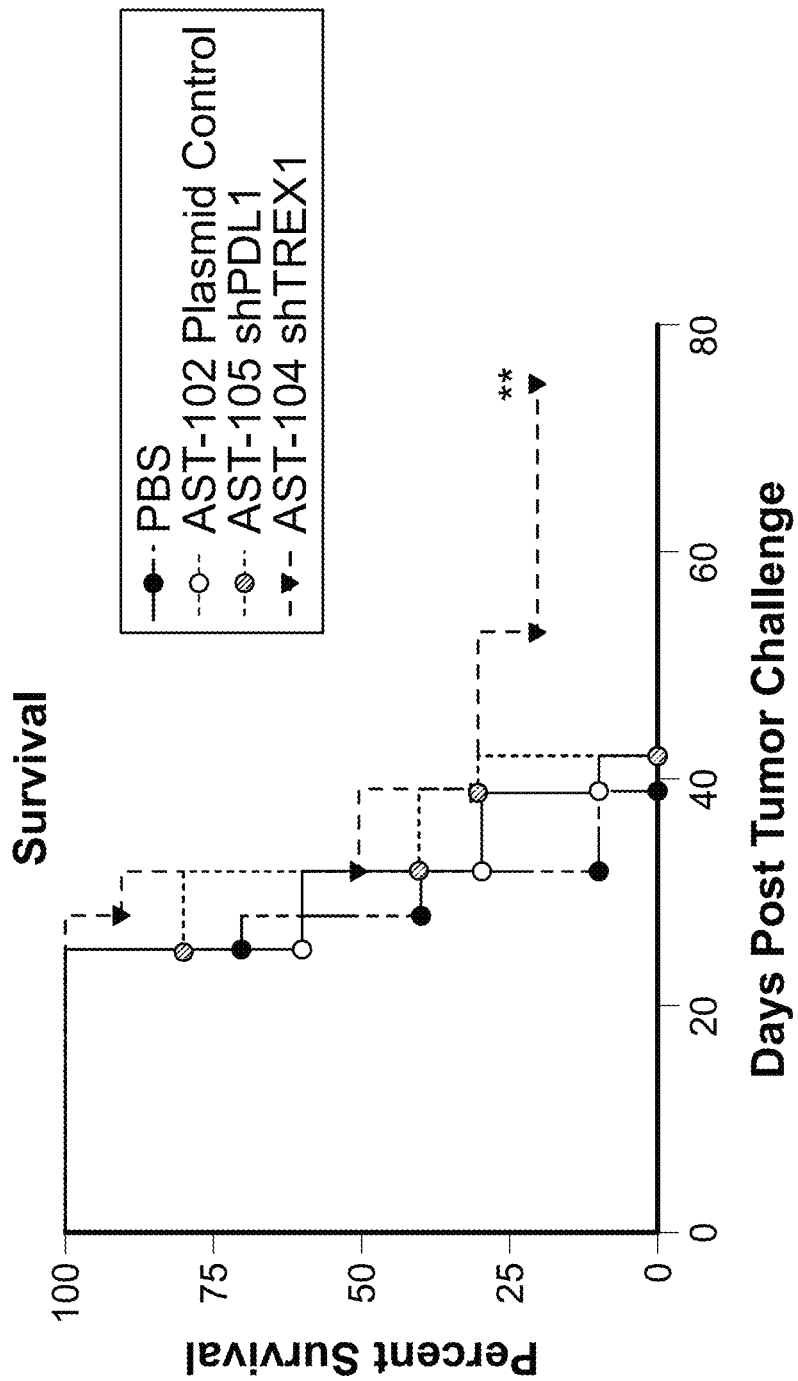
FIG. 30 depicts the curative effects of intratumoral AST-104 administration in dual flank colon tumors in mice. BALB/c mice (6-8 wk old) were implanted with dual CT26 (2×10⁵ cells) subcutaneous flank tumors on the right and left flanks (n=10 per group). Mice with established tumors were IT injected into the right flank with 5×10⁶ CFU of YS1646 strains containing either plasmid control (AST-102) or the TREX1 shRNA plasmid (AST-104), or the shPD-L1 plasmid (AST-105), or PBS control on days 10 and 14 after tumor implantation. Mice were euthanized when tumor size reached >20% of body weight or became necrotic, as per IACUC regulations. The figure depicts the overall survival of the mice, **p<0.01, log-rank (Mantel-Cox) test.

As shown in FIG. 29, IT injection of AST-104 and AST-105 induced significant tumor growth inhibition in the injected tumor, compared to the PBS control (AST-105-60.5% TGI, p=0.03; AST-104-61.4% TGI, p=0.03 day 25). Unlike AST-105, only AST-104 induced significant growth inhibition of the distal, untreated tumor compared to PBS (60% TGI, p<0.0001, day 25), and significant distal tumor growth inhibition compared to AST-102 containing the plasmid control (p=0.004, day 25). The AST-104 strain also demonstrated significant tumor regression and increased survival compared to PBS control (p=0.0076, Log-rank (Mantel-Cox) test) with 2/10 complete remissions (FIG. 30).

Figure 31:
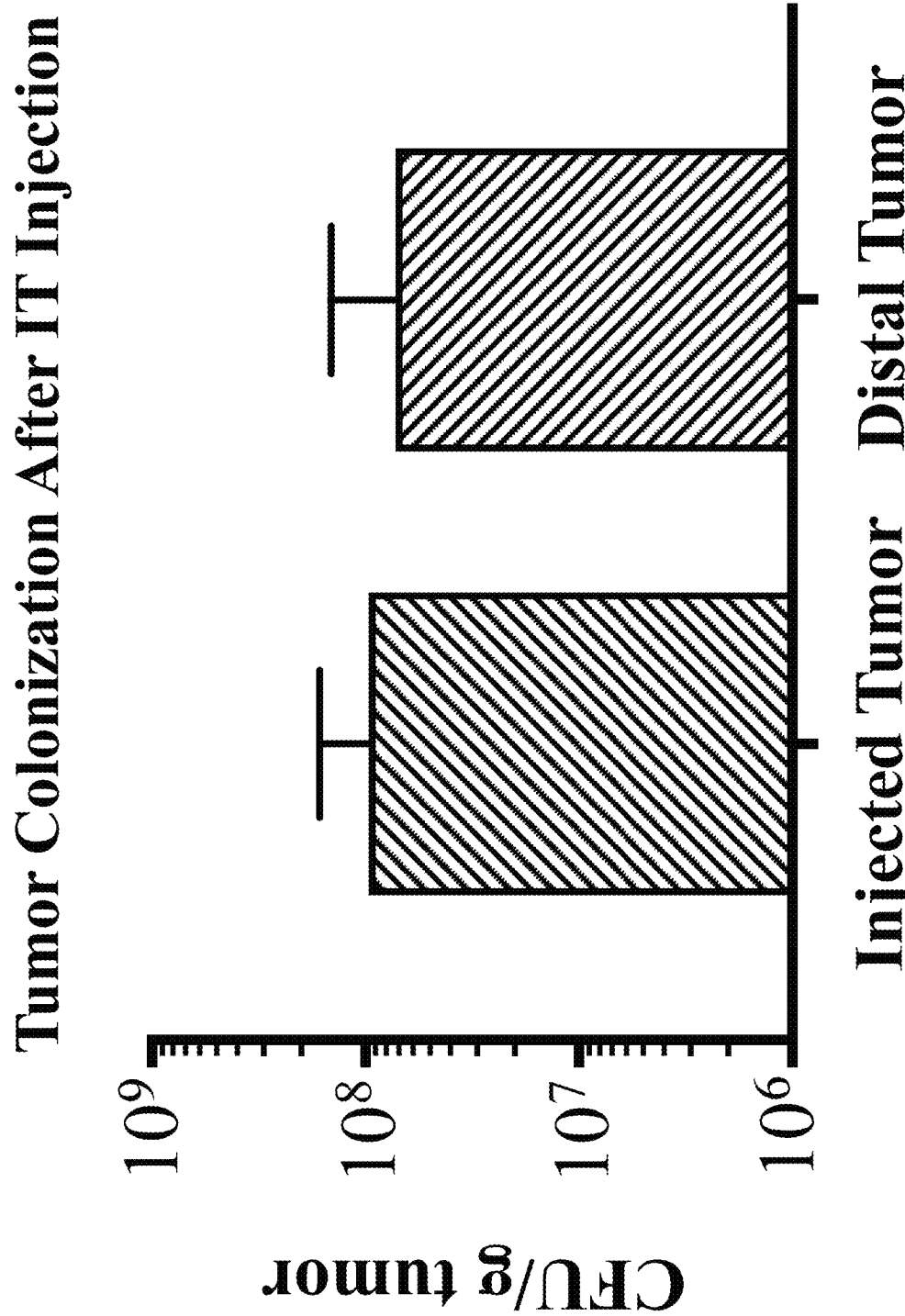
FIG. 31 depicts the levels of tumor colonization in injected and distal tumors after IT administration of AST-104. BALB/c mice (6-8 wk old) were implanted with dual CT26 (2×10⁵ cells) subcutaneous flank tumors on the right and left flanks (n=10 per group). Mice with established tumors were IT injected into the right flank with 5×10⁶ CFU of the YS1646 strain containing a TREX1 shRNA plasmid (AST-104). At 35 days post tumor implantation (12 days after the last dose of AST-104), three mice were sacrificed, and injected and distal tumors were homogenized (GentleMACs™, Miltenyi Biotec) and plated on LB plates to enumerate the number of colony forming units (CFU) per gram of tumor tissue. The figure depicts the mean CFU per gram of tissue, SD.

To determine whether the bacteria colonize injected, as well as distal tumors, tumor-bearing mice treated with AST-104 were sacrificed and tumors were collected. Injected and distal tumors were transferred to M tubes and were homogenized in PBS using a gentleMACS™ Dissociator (Miltenyi Biotec). Tumor homogenates were serially diluted and plated on LB agar plates and incubated at 37° C. for colony forming unit (CFU) determination. As shown in FIG. 31, the distal tumor was colonized to the same extent as the injected tumor, indicating that the engineered *Salmonella* strains dosed with an intratumoral route of administration are able to transit and colonize distal lesions. These data demonstrate the potency of administering immunostimulatory bacteria IT with the ability to systemically colonize distal tumor lesions preferentially over other organs, and the potency of activating the STING Type I Interferon pathway, leading to systemic tumor regression and complete remissions.

Example 5

Modified *S. typhimurium* Strains with Plasmids Containing CpG Elements Demonstrate Enhanced Anti-Tumor Activity Compared to YS1646 Parental Strain Toll-like receptors (TLRs) are key receptors for sensing pathogen-associated molecular patterns (PAMPs) and activating innate immunity against pathogens (Akira et al. (2001) *Nat Immunol.* 2(8):675-680). Of these, TLR9 is responsible for recognizing hypomethylated CpG motifs in pathogenic DNA which do not occur naturally in mammalian DNA (McKelvey et al. (2011) *J. Autoimmunity* 36:76). Recognition of CpG motifs upon phagocytosis of pathogens into endosomes in immune cell subsets induces IFR7-dependent type I interferon signaling and activates innate and adaptive immunity. It is shown herein, that the *S. typhimurium* strain YS1646 carrying modified *Salmonella typhimurium* plasmids containing CpG motifs (YS1646 pEQU6 Scramble) similarly activate TLR9 and induce type I IFN-mediated innate and adaptive immunity, as compared to the YS1646 strain without a plasmid.

The CpG motifs in the engineered plasmids used here are shown in Table 2. The pEQU6 shSCR (non-cognate shRNA) plasmid in strain AST-103 possesses 362 CpG motifs, indicating that *Salmonella*-based plasmid delivery can be immuno-stimulatory and have an anti-tumor effect, when compared to the same *Salmonella* lacking transformation with this plasmid. To assess the ability of CpG-containing plasmids within YS1646 to induce tumor growth inhibition in a murine colon carcinoma model, 6-8 week-old female BALB/c mice (9 mice per group) were inoculated SC in the right flank with CT26 ($2 \times 10^5$ cells in 100 µL PBS). Mice bearing established flank tumors were IV injected weekly with three doses of $5 \times 10^6$ CFUs of YS1646 (AST-100) or YS1646 containing an shRNA scrambled plasmid with CpG motifs (AST-103), and compared to PBS control.

TABLE 2

CpG motifs in the engineered plasmids

| Sequence name | Number of CpG Motifs | SEQ ID NO. |
|---|---|---|
| pBR322 Origin | 80 | 243 |
| pEQU6 (shSCR) | 362 | 244 |
| Asd Gene ORF | 234 | 242 |
| pATI-2.0 | 538 | 245 |

Figure 32:
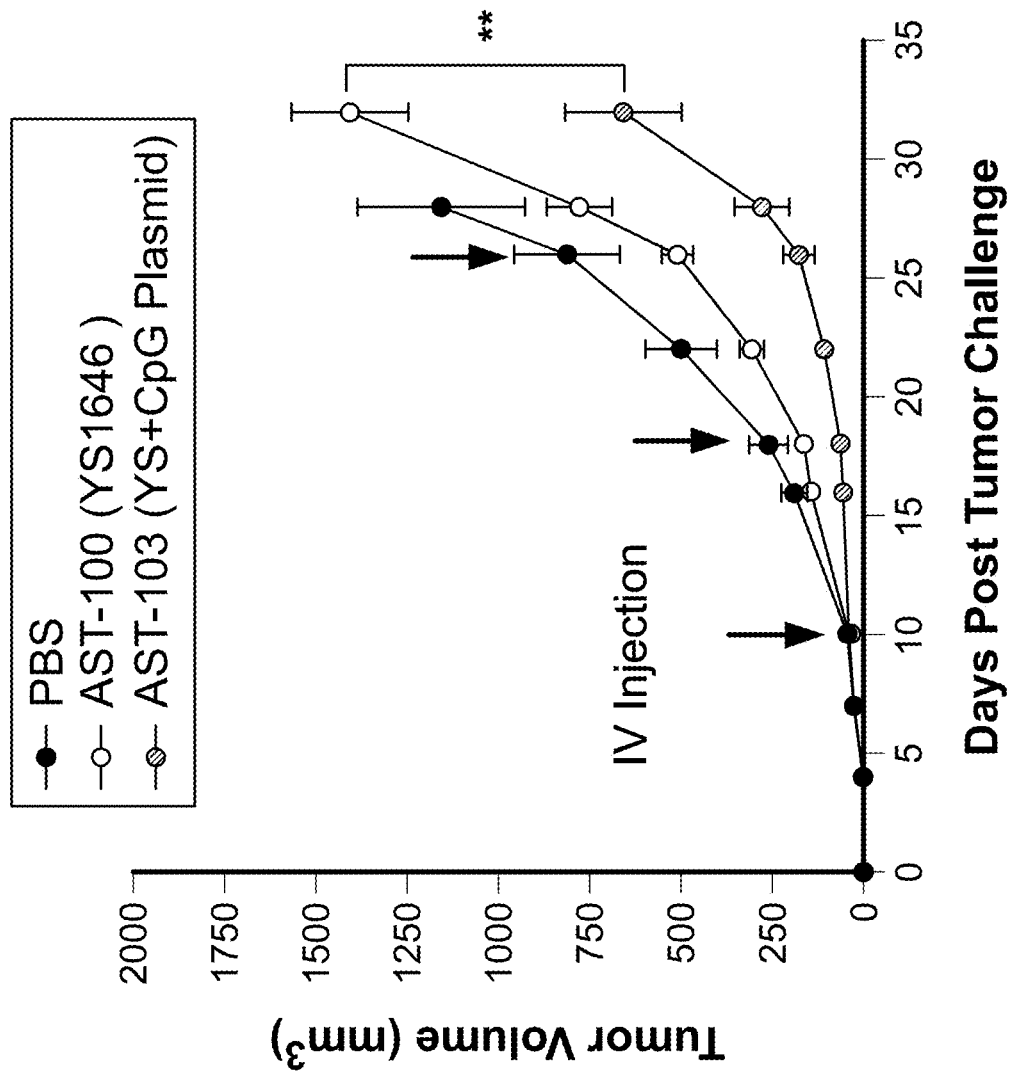
FIG. 32 depicts that CpG scrambled plasmid has immunostimulatory anti-tumor properties. BALB/c mice (6-8 wk old) were implanted with a single CT26 ($2 \times 10^5$ cells) subcutaneous flank tumor (n=9 per group). Mice with established tumors were IV injected with $5 \times 10^6$ CFU of the YS1646 strain (AST-100), or the YS1646 strain containing the scrambled shRNA control plasmid (AST-103), or PBS control, on the days indicated by the arrows. Tumor measurements were performed using electronic calipers (Fowler, Newton, MA). Tumor volume was calculated using the modified ellipsoid formula 1/2 (length×width$^2$). Mice were euthanized when tumor size reached >20% of body weight or became necrotic, as per IACUC regulations. TGI is calculated as 1−(mean test tumor volume/mean control tumor volume)×100. The figure depicts mean tumor growth of each group, ±SEM. **$p<0.01$, student's t-test.

As shown in FIG. 32, the YS1646 (AST-100) strain demonstrated modest tumor control (32% TGI, p=ns, day 28) as compared to PBS. The AST-103 strain, that varies from YS1646 only by the addition of the CpG-containing plasmid encoding a non-cognate scrambled shRNA, demonstrated highly significant tumor growth inhibition compared to YS1646 alone, untransformed and therefore lacking a plasmid (p=0.004, day 32).

Figure 46:
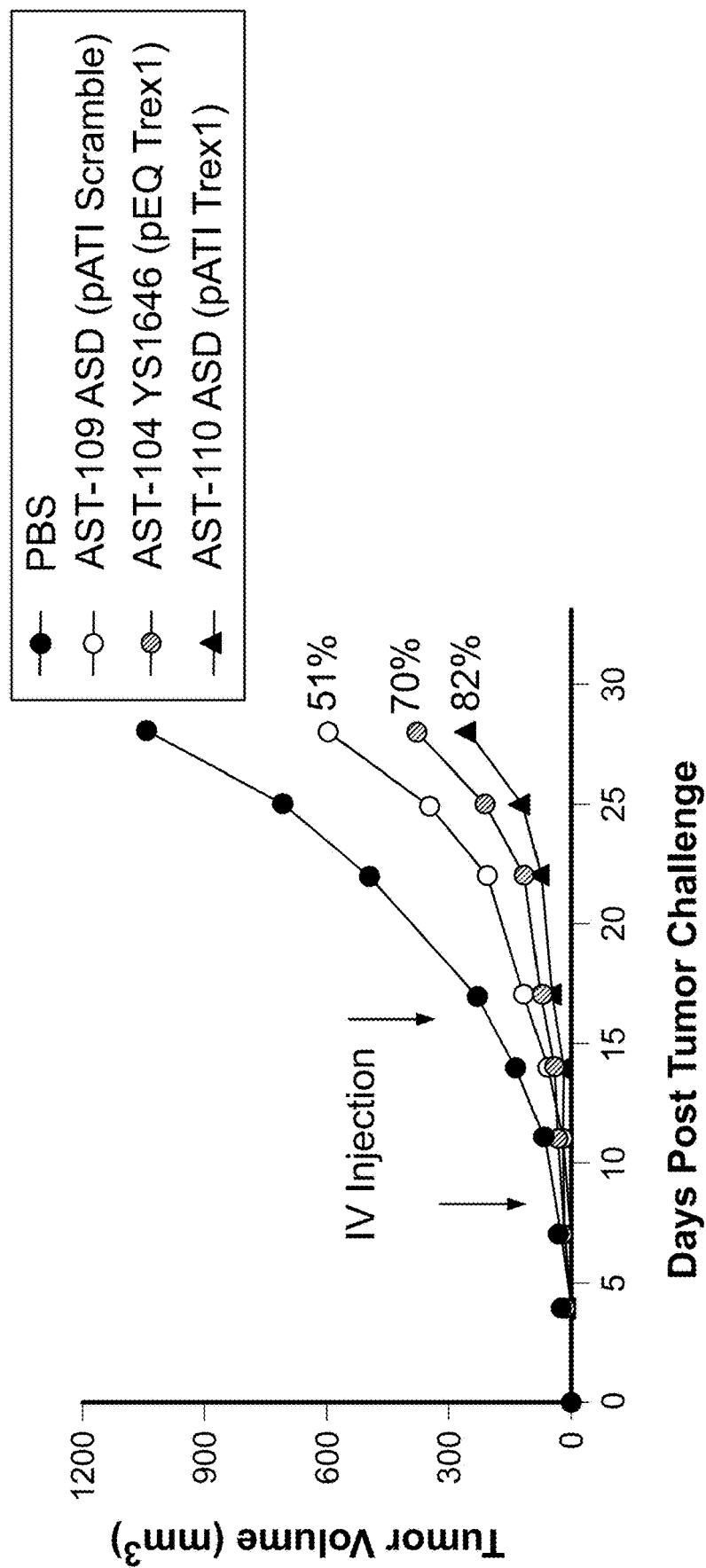
FIG. 46 depicts that the therapeutic efficacy of a strain containing a plasmid with asd gene complementation system and shTREX1 (AST-110) is improved. BALB/c mice (6-8 wk old) were implanted with a single CT26 ($2\times10^5$ cells) subcutaneous flank tumor (n=9 per group). Mice with established tumors were IV injected with $5\times10^6$ CFU of the asd knockout strain containing the pATI-shTREX1 plasmid (AST-110) or the asd knockout strain containing the pATI-scramble plasmid (AST-109), or the YS1646 strain containing a pEQ-shTREX-1 plasmid without an asd gene (AST-104), or PBS control, on the days indicated by the arrows. Tumor measurements were performed using electronic calipers (Fowler, Newton, MA). Tumor volume was calculated using the modified ellipsoid formula ½(length×width²). Mice were euthanized when tumor size reaches >20% of body weight or became necrotic, as per IACUC regulations. TGI was calculated as 1−(mean test tumor volume/mean control tumor volume)×100. The figure depicts the mean tumor growth of each group, ±SEM.

The asd gene possesses 234 CpG motifs (Table 2), indicating that a plasmid containing it can have immunostimulatory properties. As shown in FIG. 46, AST-109 (YS1646-ASD) had 51% tumor growth inhibition vs PBS alone, indicative of a strong immunostimulatory effect.

These data demonstrate the potent immunostimulatory properties of plasmid DNA containing TLR9-activating CpG motifs within a tumor-targeting attenuated strain of *S. typhimurium*.

Example 6

The Modified *Salmonella typhimurium* Strains Containing MicroRNA Inhibition Demonstrate Enhanced Anti-Tumor Activity Compared to shRNA Superior TREX1 gene knockdown was achieved in vitro with microRNA ARI-203 (see Example 2, FIG. 20). The microRNA strain AST-106 was generated by transforming YS1646 with ARI-203, pEQU6 plasmid encoding a microRNA (miRNA) against TREX1. AST-106 was compared to the shRNA strain, AST-104 (YS1646 transformed with pEQU6 shTREX1). In vivo potency in a murine colon carcinoma model was tested. For this experiment, 6-8 week-old female BALB/c mice (10 mice per group) were inoculated SC in the right flank with CT26 ($2\times10^5$ cells in 100 µL PBS). Mice bearing established flank tumors were IV injected weekly on day 8, day 15 and day 23 with $5\times10^6$ CFUs of AST-104 or AST-106 and compared to PBS control.

Figure 33:
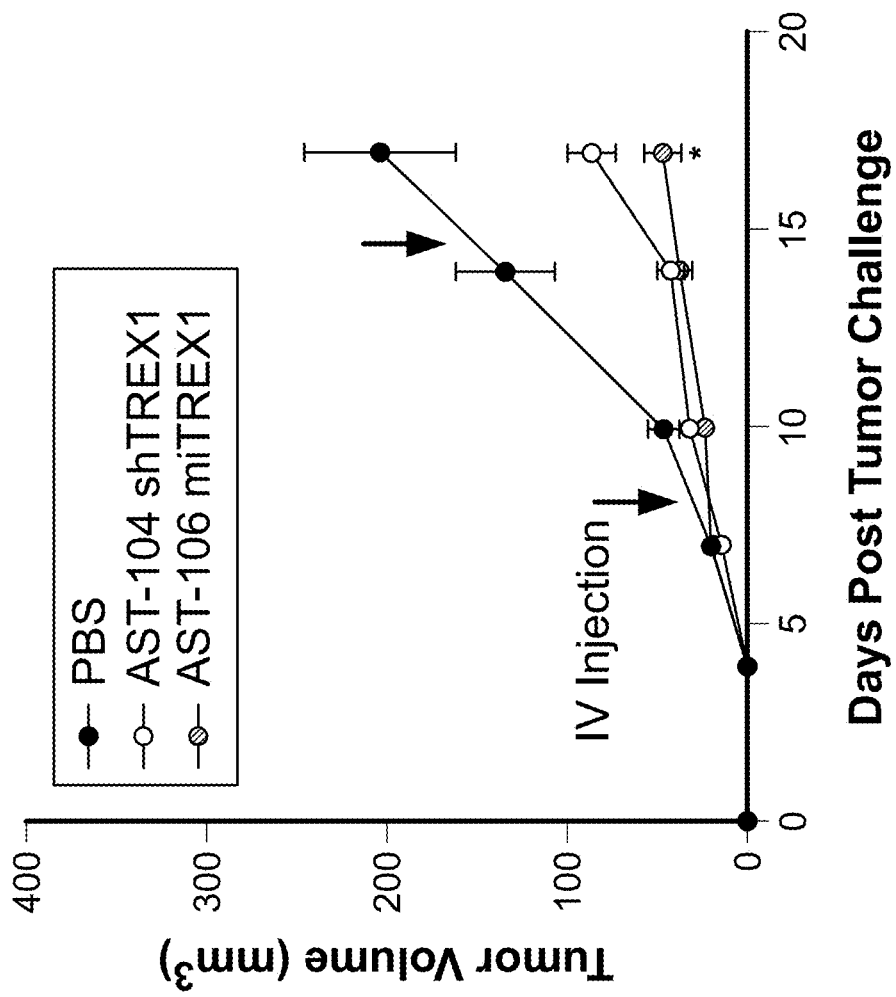
FIG. 33 depicts the efficacy of AST-106 (microRNA TREX1) vs. AST-104 (shRNA TREX1). BALB/c mice (6-8 wk old) were implanted with a single CT26 ($2 \times 10^5$ cells) subcutaneous flank tumor (n=9 per group). Mice with established tumors were IV injected with $5 \times 10^6$ CFU of the YS1646 containing the TREX1 shRNA plasmid (AST-104) or the YS1646 strain containing a TREX1 microRNA plasmid (AST-106), or PBS control, on the days indicated by the arrows. Tumor measurements were performed using electronic calipers (Fowler, Newton, MA). Tumor volume was calculated using the modified ellipsoid formula ½(length× width$^2$). Mice were euthanized when tumor size reached >20% of body weight or became necrotic, as per IACUC regulations. TGI was calculated as 1−(mean test tumor volume/mean control tumor volume)×100. The figure depicts the mean tumor growth of each group, ±SEM. *$p<0.05$, student's t-test.

As shown in FIG. 33, both versions of the TREX1 knockdown strains demonstrated significant tumor growth inhibition compared to PBS control (AST-104 58% TGI, p=0.014; AST-106 77% TGI, p=0.003, day 17), with the AST-106 miTREX1 exhibiting the most potent tumor control after the second dose, which was significantly better than the shTREX1 strain AST-104 (p=0.036, day 17). These data demonstrate that the microRNA based inhibitory RNAs can deliver more potent gene knockdown in vivo and outperform the shRNA-based inhibitory RNAs in a tumor growth inhibition model.

Example 7

Vector Synthesis

Complementation of Asd Deletion by Asd Expression from Plasmids

A plasmid (pATIU6) was chemically synthesized and assembled (SEQ ID NO:225). The plasmid contained the following features: a high copy (pUC19) origin of replication, a U6 promoter for driving expression of a short hairpin, an ampicillin resistance gene flanked by HindIII restriction sites for subsequent removal, and the asd gene containing 85 base pairs of sequence upstream of the start codon (SEQ ID NO:246). Into this vector, shRNAs targeting murine TREX1 or a scrambled, non-cognate shRNA sequence were introduced by restriction digestion with SpeI and XhoI and ligation and cloning into *E. coli* DH5-alpha. The resulting plasmids, designated pATI-shTREX1 and pATI-shSCR, respectively, were amplified in *E. coli* and purified for transformation into the asd knockout strain AST-101 by electroporation and clonal selection on LB amp plates to produce strains AST-108, and AST-107, respectively. asd-mutants complemented with pATIU6-derived plasmids were able to grow on LB agar and liquid media in the absence of DAP.

In a subsequent iteration, the ampicillin resistance gene (AmpR) from pATI-shTREX1 was replaced with a kanamycin resistance gene. This was accomplished by digestion of pATI-shTREX1 plasmid with HindIII followed by gel purification to remove the AmpR gene, PCR amplification of the kanamycin resistance (KanR) gene using primers APR-001 and APR-002 (SEQ ID NO:226 and SEQ ID NO:227, respectively), digestion with HindIII and ligation into the gel purified, digested pATIU6 plasmid.

In subsequent iterations, a single point mutation was introduced into the pATIKan plasmid at the pUC19 origin of replication using the Q5® Site-Directed Mutagenesis Kit (New England Biolabs) and the primers APR-003 (SEQ ID NO:228) and APR-004 (SEQ ID NO:229) to change the nucleotide T at position 148 to a C. This mutation makes the origin of replication homologous to the pBR322 origin of replication in order to reduce the plasmid copy number.

| Primer ID | Description | Sequence | SEQ ID NO |
|---|---|---|---|
| APR-001 | Kan primerF | AAAAAAGCTTGCAGCTCTGGCCCGTG | 226 |
| APR-002 | Kan PrimerR | AAAAAAGCTTTTAGAAAAACTCATCG AGCATCAAATGA | 227 |
| APR-003 | pATI ori T148CF | ACACTAGAAGgACAGTATTTGGTATC TG | 228 |
| APR-004 | pATI ori T148CR | AGCCGTAGTTAGGCCACC | 229 | pATI2.0

A plasmid was designed and synthesized that contains the following features: a pBR322 origin of replication, an SV40 DNA nuclear targeting sequence (DTS), an rrnB terminator, a U6 promoter for driving expression of shRNAs followed by flanking restriction sites for cloning the promoter and shRNAs or microRNAs, the asd gene, an rrnG terminator, a kanamycin resistance gene flanked by HindIII sites for curing, and a multicloning site (SEQ ID NO:247). In addition, a plasmid was designed and synthesized for expression of two separate shRNA or microRNAs. This plasmid contains the following features: a pBR322 origin of replication, an SV40 DNA nuclear targeting sequence (DTS), an rrnB terminator, a U6 promoter for driving expression of shRNAs followed by flanking restriction sites for cloning the promoter and shRNAs or microRNAs, an H1 promoter for driving the expression of a 2$^{nd}$ shRNA or microRNA, a 450 bp randomly generated stuffer sequence placed between the H1 and U6 promoters, the asd gene, an rrnG terminator, and a kanamycin resistance gene flanked by HindIII sites for curing, and a multicloning site (SEQ ID NO:245).

Example 8

Figure 34:
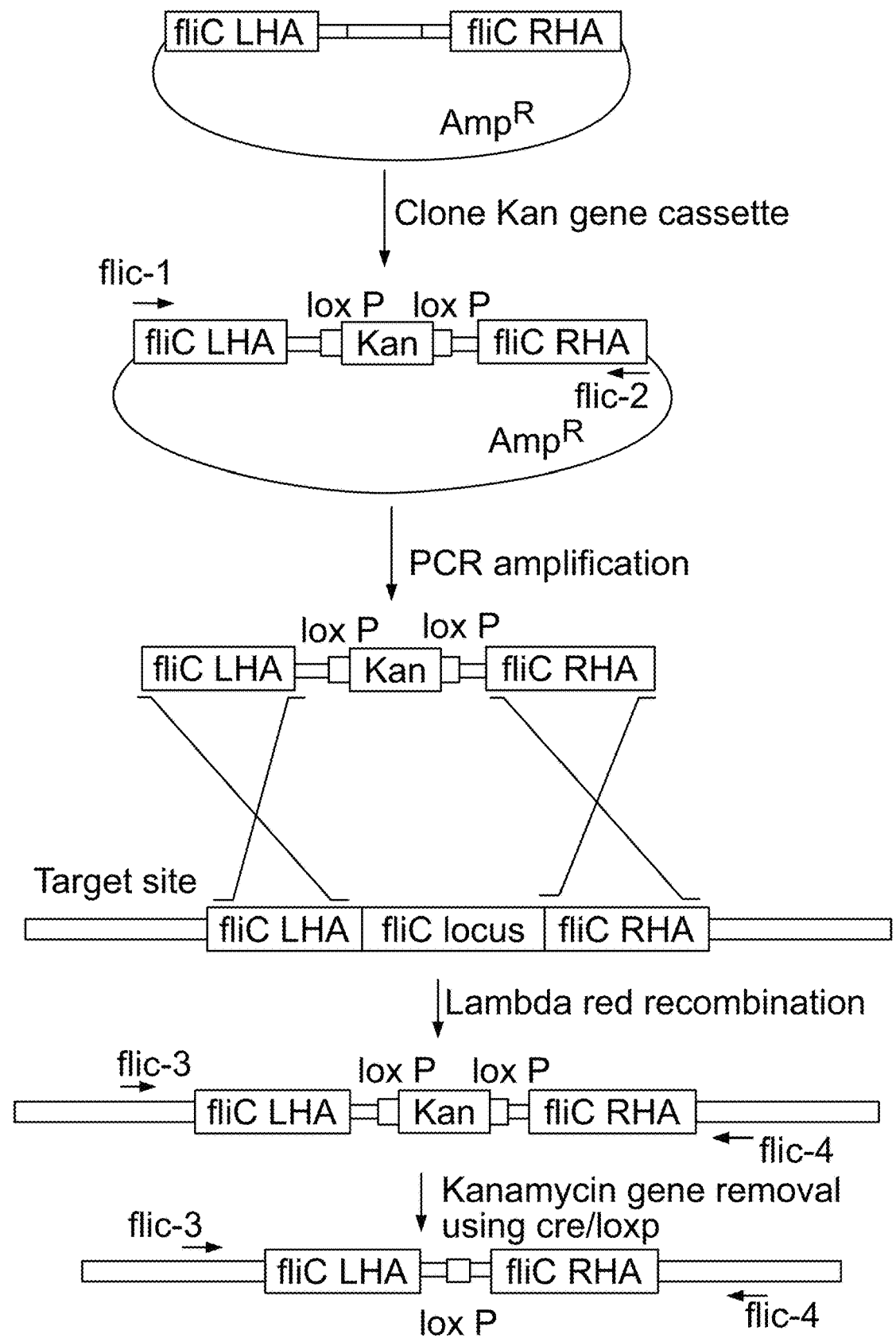
FIG. 34 depicts a schematic of the process used to delete the fliC gene. The flic gene was deleted from the chromosome of *S. typhimurium* strain AST-101 (asd deleted strain of YS1646) using lambda-derived Red recombination system as described in Datsenko and Wanner (*Proc. Natl. Acad. Sci. U.S.A.* 97:6640-6645 (2000)).

S. typhimurium Flagellin Knockout Strain Engineering by Deletion of the fliC and fljB Genes In the example herein, *S. typhimurium* strains were engineered to lack both flagellin subunits fliC and fljB to reduce pro-inflammatory signaling. Deletions of fliC and fljB were sequentially engineered into the chromosome of the asd gene deleted strain of YS1646 (AST-101).
Deletion of fliC In this example, fliC was deleted from the chromosome of the AST-101 strain using modifications of the method of Datsenko and Wanner (*Proc. Natl. Acad. Sci. USA* 97:6640-6645 (2000)) as described in detail in Example 1 and schematically depicted in FIG. 34. Synthetic fliC gene homology arm sequences were ordered that contained 224 and 245 bases of homologous sequence flanking the fliC gene, cloned into a plasmid called pSL0147 (SEQ ID NO:230). A kanamycin gene cassette flanked by cre/lox p sites then was cloned into pSL0147, the fliC gene knockout cassette was then PCR amplified with primer flic-1 (SEQ ID NO:232) and flic-2 (SEQ ID NO:233) and gel purified and introduced into the AST-101 strain carrying the temperature sensitive lambda red recombination plasmid pKD46 by electroporation. Electroporated cells were recovered in SOC+DAP medium and plated onto LB Agar plates supplemented with Kanamycin (20 μg/mL) and diaminopimelic acid (DAP, 50 μg/ml). Colonies were selected and screened for insertion of the knockout fragment by PCR using primers flic-3 (SEQ ID NO:234) and flic-4 (SEQ ID NO:235). pKD46 then was cured by culturing the selected kanamycin resistant strain at 42° C. and screening for loss of ampicillin resistance. The Kanamycin resistance marker then was cured by electroporation of a temperature sensitive plasmid expressing the Cre recombinase (pJW1680) and Amp$^R$ colonies were selected at 30° C.; pJW168 was subsequently eliminated by growing cultures at 42° C. Selected fliC knockout clones were then tested for loss of kanamycin marker by PCR using primers flanking the sites of disruption (flic-3 and flic-4) and evaluation of the electrophoretic mobility on agarose gels.
Deletion of fljB fljB was then deleted in the asd/fliC deleted YS1646 strain using modifications of the methods described above. Synthetic fljB gene homology arm sequences that contained 249 and 213 bases of the left hand and right hand sequence, respectively, flanking the fljB gene, were synthesized and cloned into a plasmid called pSL0148 (SEQ ID NO:231). A kanamycin gene cassette flanked by cre/loxP sites then was cloned into pSL0148 and the fljB gene knockout cassette then was PCR amplified with primer fljb-1 (SEQ ID NO:236) and fljb-2 (SEQ ID NO:237) and gel purified and introduced into AST-101 carrying the temperature sensitive lambda red recombination plasmid pKD46 by electroporation. The kanamycin resistance gene then was cured by cre-mediated recombination as described above, and the temperature-sensitive plasmids were cured by growth at non-permissive temperature. The fliC and fljB gene knockout sequences were amplified by PCR using primers flic-3 and flic-4 or fljb-3 (SEQ ID NO:238) and fljb-4 (SEQ ID NO:239), and verified by DNA sequencing. This asd⁻/fliC⁻/fljB⁻ mutant derivative of YS1646 was designated AST-111.

| Primer sequence information | | |
|---|---|---|
| Primer name | Primer sequence | SEQ ID NO. |
| flic-1 | CGTTATCGGCAATCTGGAGGC | 232 |
| flic-2 | CCAGCCCTTACAACAGTGGTC | 233 |
| flic-3 | GTCTGTCAACAACTGGTCTAACGG | 234 |
| flic-4 | AGACGGTCCTCATCCAGATAAGG | 235 |
| fljb-1 | TTCCAGACGACAAGAGTATCGC | 236 |
| fljb-2 | CCTTTAGGTTTATCCGAAGCCAGAATC | 237 |
| fljb-3 | CACCAGGTTTTTCACGCTGC | 238 |
| fljb-4 | ACACGCATTTACGCCTGTCG | 239 |

Figure 35:
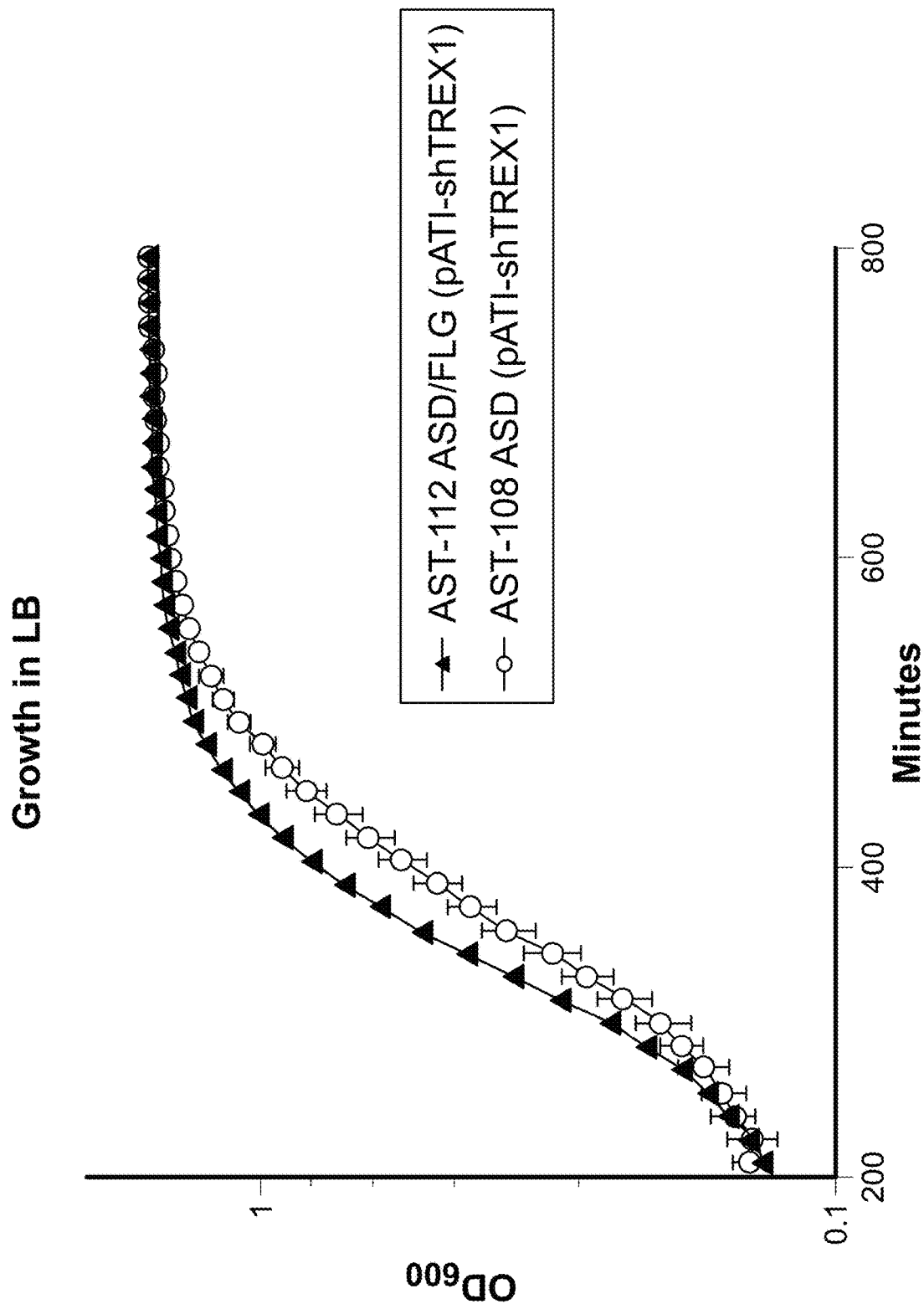
FIG. 35 depicts that the Flagellin deletion strain grows normally in LB. The figure depicts the growth of strains AST-108 ASD (pATI-shTREX1) and AST-112 ASD/FLG (pATI-shTREX1) at 37° C. in LB broth, as measured by OD600 using a SpectraMax® 96-well plate reader (Molecular devices).

In Vitro Characterization of Engineered *S. typhimurium* Flagellin Knockout Strain The YS1646 derived asd mutant strain harboring the deletions of both fliC and fljB, herein referred to as AST-111 or ASD/FLG, was evaluated for swimming motility by spotting 10 microliters of overnight cultures onto swimming plates (LB containing 0.3% agar and 50 mg/mL DAP). While motility was observed for YS1646 and the asd deleted strain AST-101, no motility was evident with the asd/fliC/fljB-deleted strain AST-111. The AST-111 strain then was electroporated with pATIshTREX1 (a plasmid containing an asd gene and an shRNA targeting TREX1), to produce AST-112, and its growth rate in the absence of DAP was assessed. As shown in FIG. 35 ASD/FLG (pATI-shTREX1) strain AST-112 was able to replicate in LB in the absence of supplemental DAP, and grew at a rate comparable to the asd strain containing pATIshTREX1(AST-108). These data demonstrate that the elimination of flagellin does not decrease the fitness of *S. typhimurium* in vitro.

Elimination of flagellin subunits decreases pyroptosis in macrophages. To demonstrate this, 5×10⁵ mouse RAW-Dual™ macrophage cells (InvivoGen, San Diego, Ca.) were infected with the asd/fliC/fljB deleted strain harboring a low copy shTREX1 plasmid, designated AST-118, or the asd deleted strain harboring the same plasmid (AST-117) at an MOI of approximately 100 in a gentamycin protection assay. After 24 hours of infection, culture supernatants were collected and assessed for lactate dehydrogenase release as a marker of cell death using a Pierce™ LDH Cytotoxicity Assay Kit (Thermo Fisher Scientific, Waltham, Ma.). AST-117 induced 75% maximal LDH release, while AST-118 induced 54% maximal LDH release, demonstrating that the deletion of the flagellin genes reduce the *S. typhimurium*-induced pyroptosis.

ASD/FLG Knockout Strain Containing shTrex1 Plasmid Demonstrates Enhanced Anti-Tumor Activity, Enhanced Interferon Gamma Responses, and Increased Tumor Colonization in Mice Compared to Parental Asd Strain.

To assess the impact of the flagellin knockout strains administered in a murine model of colon carcinoma, 6-8 week-old female BALB/c mice (10 mice per group) were inoculated SC in the right flank with CT26 (2×10⁵ cells in 100 μL PBS). Mice bearing established flank tumors were IV injected with three weekly doses of 5×10⁶ CFUs of the ASD/FLG strain containing the pATIKan-shTREX1 plasmid (AST-113) or the ASD strain with the same pATIKan-shTREX1 plasmid (AST-110), and compared to PBS control. Six hours following the first IV dose, mice were bled, and plasma was collected and assessed for pro-inflammatory cytokines using the Mouse Inflammation Cytometric Bead Array kit and analyzed by FACS (BD Biosciences).

Figure 36:
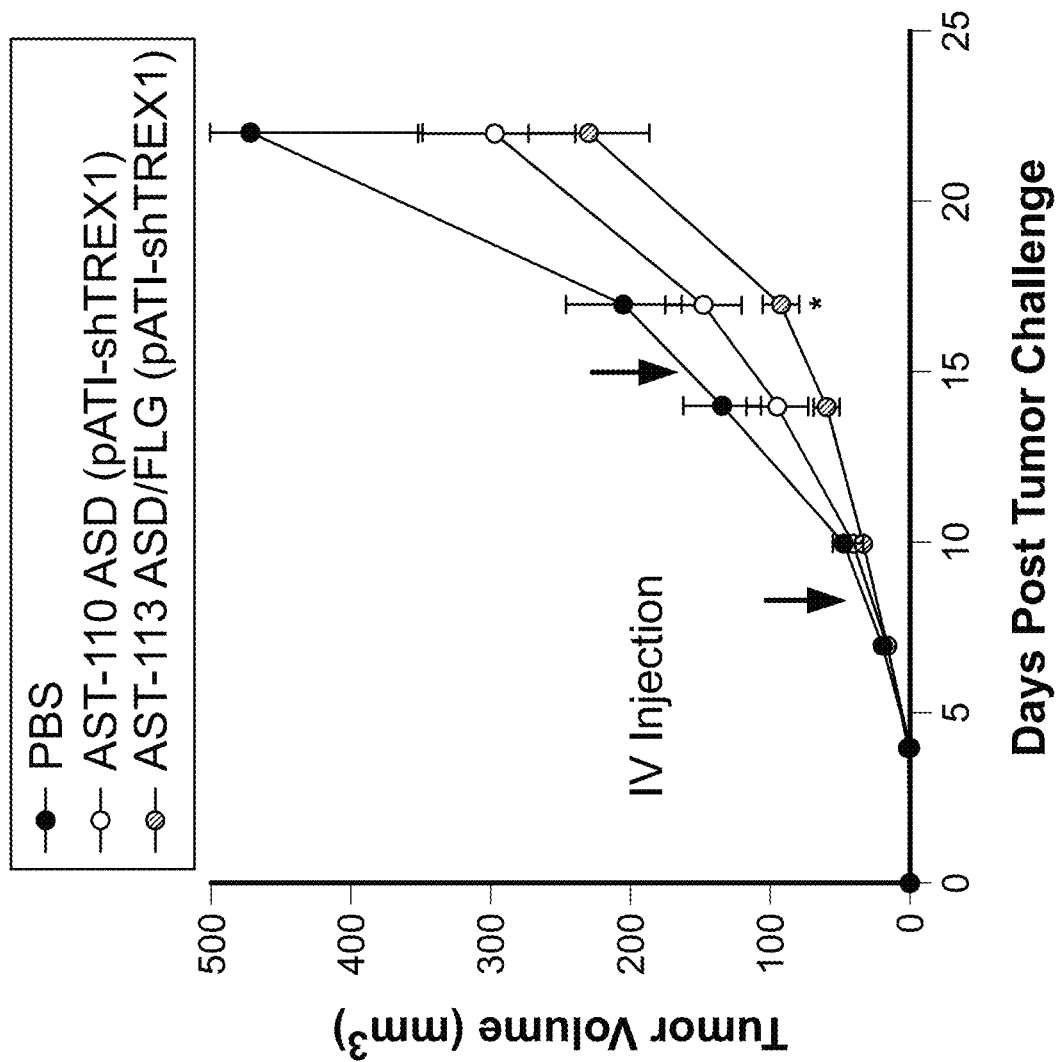
FIG. 36 depicts that Flagellin knockout improves anti-tumor efficacy. BALB/c mice (6-8 wk old) were implanted with a single CT26 ($2 \times 10^5$ cells) subcutaneous flank tumor (n=9 per group). Mice with established tumors were IV injected with $5 \times 10^6$ CFU of the asd/fljB/fliC knockout strain containing the pATI shTREX1 plasmid (AST-113), or asd knockout strain containing the pATI shTREX1 plasmid (AST-110), or PBS control, on the days indicated by the arrows. Tumor measurements were performed using electronic calipers (Fowler, Newton, MA). Tumor volume was calculated using the modified ellipsoid formula ½(length× width$^2$). Mice were euthanized when tumor size reached >20% of body weight or became necrotic, as per IACUC regulations. TGI was calculated as 1−(mean test tumor volume/mean control tumor volume)×100. The figure depicts the mean tumor growth of each group, ±SEM. *$p<0.05$, student's t-test.

As shown in FIG. 36, The AST-113 strain, incapable of making flagella and containing the pATIshTrex1 plasmid (ASD/FLG pATI-shTREX1), demonstrated enhanced tumor control compared to the parental ASD pATI-shTREX1 strain AST-110, and significant tumor control compared to the PBS control (54% TGI, p=0.02, day 17).

Figure 37:
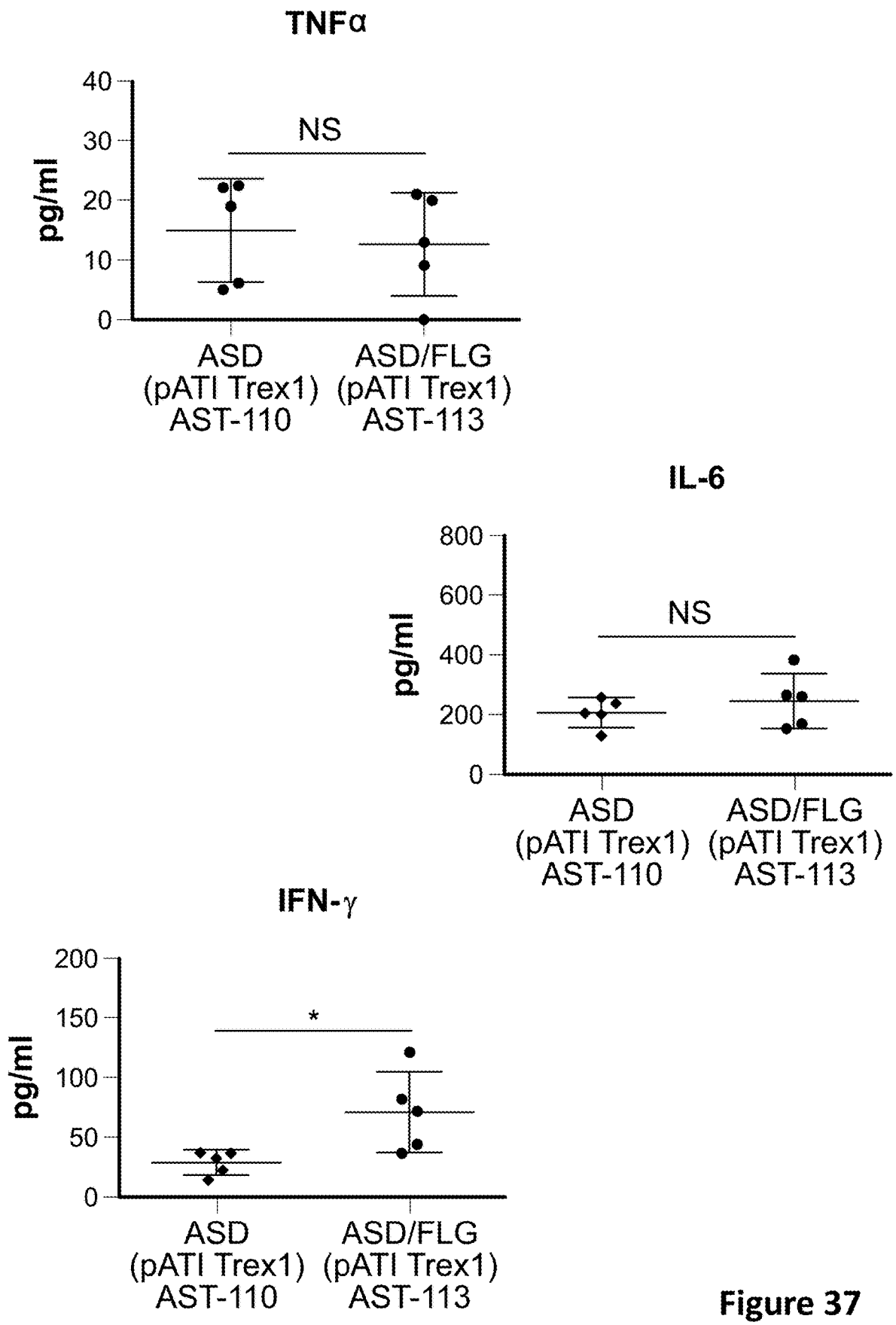
FIG. 37 depicts that Flagellin knockout shows an increased IFN-gamma signature. BALB/c mice (6-8 wk old) were implanted with a single CT26 ($2 \times 10^5$ cells) subcutaneous flank tumor (n=9 per group). Mice with established tumors were IV injected with $5 \times 10^6$ CFU of the asd/fljB/fliC knockout strain containing the pATI shTREX1 plasmid (AST-113), or asd knockout strain containing the pATI shTREX1 plasmid (AST-110), or PBS control. Mice were bled 6 hrs following the first dose and systemic serum cytokines tested by Luminex 200 device (Luminex Corporation) and mouse cytometric bead array (BD bead array, FACS Fortessa, FCAP software, all BD Biosciences). *$p<0.05$, $p<0.01$, *$p<0.001$, student's t-test.

Comparing the levels of systemic serum cytokines at 6 hours post IV injection, the cytokines elicited by the AST-113 strain were comparable for TNF-α and IL-6 as compared to the parental AST-110 strain capable of making flagella. The levels of the potent anti-tumor immune cytokine IFN-γ were significantly higher with AST-113 compared to AST-110, indicating that the flagellin deficient strain can provide for superior anti-tumor potency over the parental asd knockout strain (FIG. 37).

Figure 38:
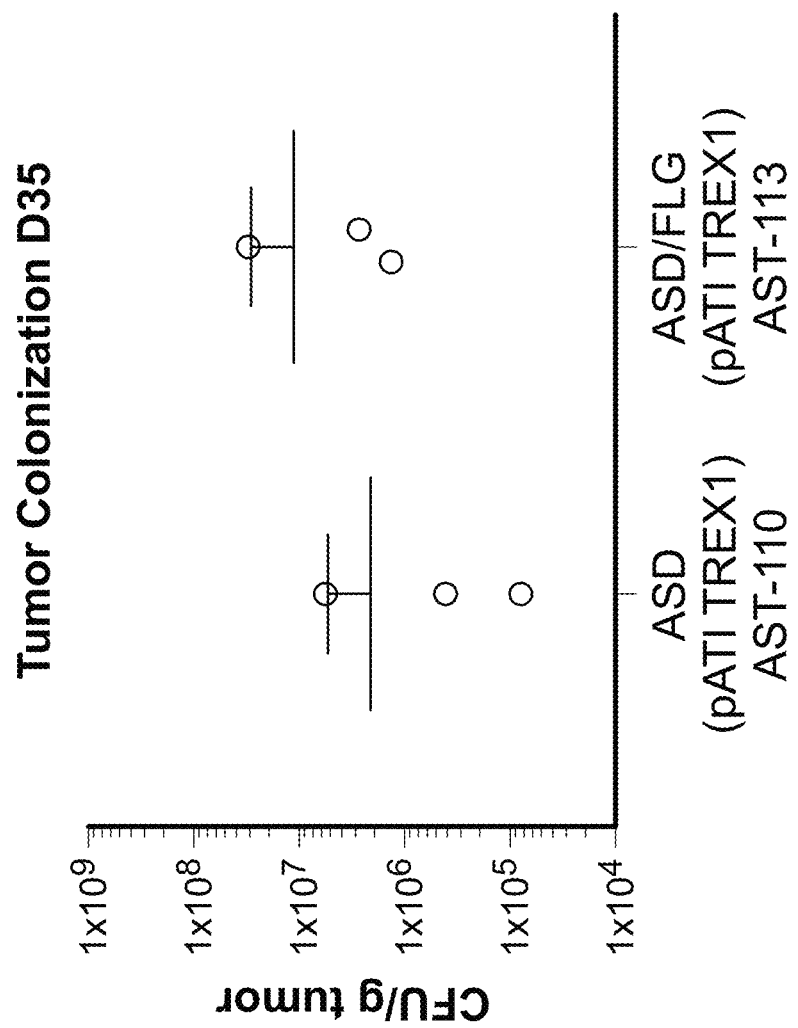
FIG. 38 depicts that Flagellin is not required for tumor colonization. BALB/c mice (6-8 wk old) were implanted with a single CT26 ($2 \times 10^5$ cells) subcutaneous flank tumor (n=9 per group). Mice with established tumors were IV injected with $5 \times 10^6$ CFU of the asd/fljB/fliC knockout strain containing the pATI shTREX1 plasmid (AST-113), or asd knockout strain containing the pATI shTREX1 plasmid (AST-110), or PBS control. At 35 days post tumor implantation (12 days after the last dose of engineered *Salmonella* therapy), three mice per group were sacrificed, and tumors were homogenized (GentleMACs™, Miltenyi Biotec) and plated on LB plates to enumerate the number of colony forming units per gram of tumor tissue. The figure depicts the mean colony forming units (CFU) per gram of tissue, ±SD.

At 35 days post tumor implantation (12 days after the last dose of engineered *Salmonella* therapy), three mice per group were euthanized, and tumors were homogenized and plated on LB plates to enumerate the number of colony forming units (CFUs) per gram of tumor tissue as described above. As shown in FIG. 38, the AST-113 strain, deleted of fliC and fljB and containing the pATIshTREX1 plasmid, was able to colonize tumors at least as well as the strain that only had the asd gene deletion and contained the same plasmid (AST-110). AST-113 colonized tumors with a mean of $1.2 \times 10^7$ CFU per gram of tissue compared with a mean of $2.1 \times 10^6$ cfu/g of tumor for AST-110, indicating that the absence of flagellin can lead to an increased tumor colonization by greater than 5 times that of strains with a functional flagella. Together, these data demonstrate that, contrary to the expectation from the art, not only is the flagella not required for tumor colonization, but its loss can enhance tumor colonization and anti-tumor immunity.

Example 9

*S. typhimurium* Engineered to Express cytoLLO for Enhanced Plasmid Delivery

In this example, the asd deleted strain of YS1646 described in Example 1 (AST-101) was further modified to express the listeriolysin O (LLO) protein lacking the signal sequence that accumulates in the cytoplasm of the *Salmonella* strain (referred to herein as cytoLLO). LLO is a cholesterol-dependent pore-forming cytolysin that is secreted from *Listeria monocytogenes* and mediates phagosomal escape of bacteria. A gene encoding LLO, with codons 2-24 deleted, was synthesized with codons optimized for expression in *Salmonella*. The sequence of the open reading frame of cytoLLO is in SEQ ID NO:240. The cytoLLO gene was placed under control of a promoter that induces transcription in *S. typhimurium* (SEQ ID NO: 241, reproduced below). The cytoLLO expression cassette was inserted in single copy into the knockout-out asd locus of the asd deleted strain AST-101 using modifications of the method of Datsenko and Wanner (*Proc. Natl. Acad. Sci. USA* (2000) 97:6640-6645), as described in Example 1.

| Sequence of promoter driving expression of cytoLLO | | |
|---|---|---|
| LLO promoter | attatgtcttgacatgtagtgag tgggctggtataatgcagcaag | SEQ ID NO: 241 |

Figure 39:
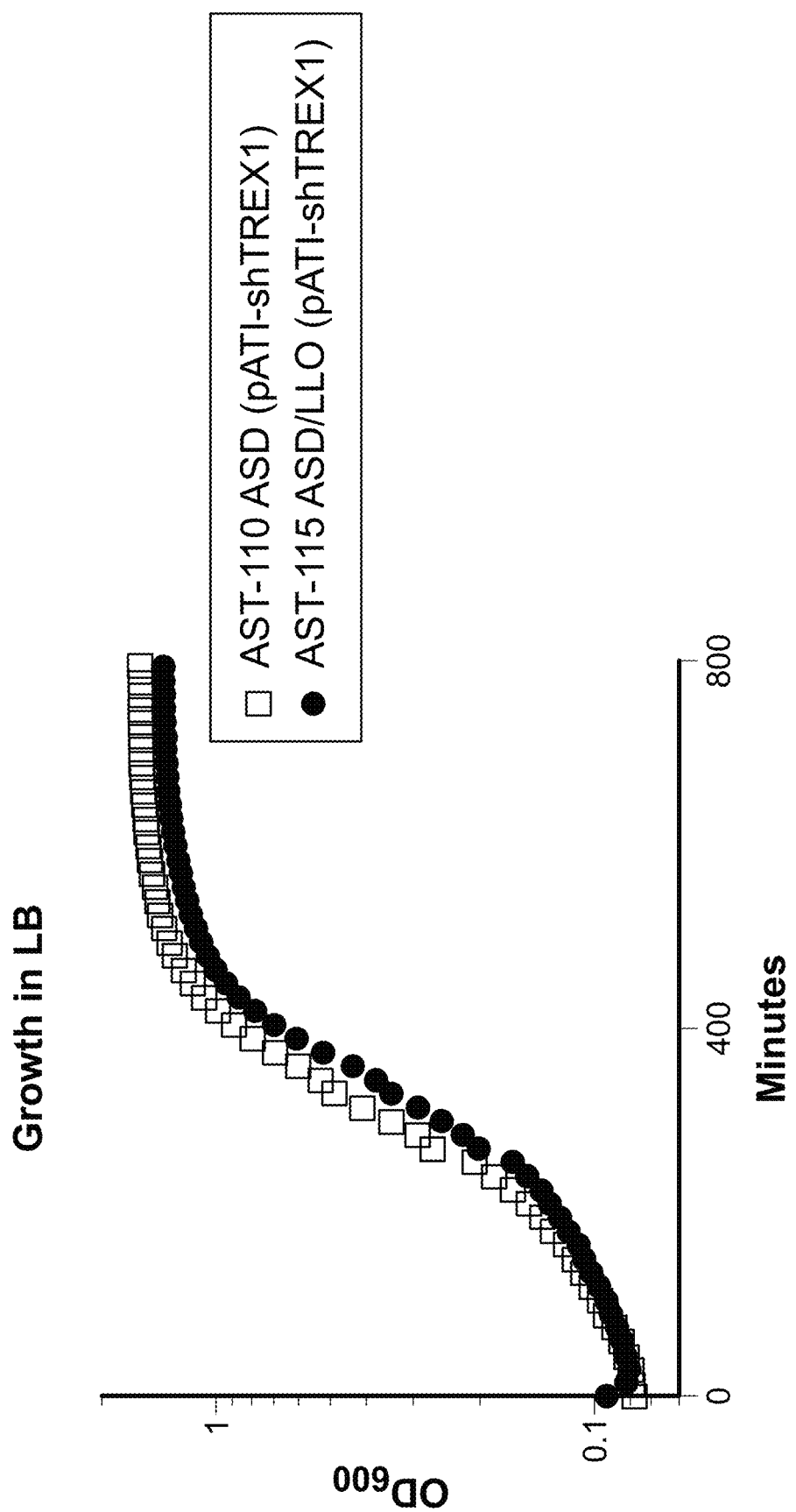
FIG. 39 depicts that a cytoLLO expressing strain grows normally in vitro. The figure depicts the growth of strains AST-110 (YS1646 with asd deletion containing (pATI-shTREX1)) and AST-115 (YS1646 with asd deletion and knock-in of cytoLLO expression cassette containing (pATI-shTREX1)) at 37° C. in LB broth, as measured by OD600 using a SpectraMax® 96-well plate reader (Molecular devices).

The asd deleted strain with the cytoLLO expression cassette inserted at the asd locus (referred to herein as ASD/LLO or AST-114) was further modified by electroporation with a pATI plasmid encoding an asd gene that allows the strain to grow in the absence of exogenous DAP and selects for plasmid maintenance, and also contains a U6 promoter driving expression of shTREX1 as described in Example 7 (referred to herein as ASD/LLO (pATI-shTREX1) or AST-115). As shown in FIG. 39, the ASD/LLO (pATI-shTREX1) strain AST-115 grew at a comparable rate to the asd deleted strain containing the same plasmid (pATI-shTREX1), AST-110, demonstrating that the LLO knock-in does not impact bacterial fitness in vitro.

*S. typhimurium* Engineered to Produce cytoLLO Demonstrate Potent Anti-Tumor Activity To determine whether the cytoLLO gene knock-in provided anti-tumor efficacy, the ASD/LLO (pATI-shTREX1) strain AST-115 was evaluated in a murine model of colon carcinoma. For this study, 6-8 week-old female BALB/c mice (8 mice per group) were inoculated SC in the right flank with CT26 ($2 \times 10^5$ cells in 100 µL PBS). Mice bearing established flank tumors were IV injected with a single dose of $5 \times 10^6$ CFUs of AST-115, and compared to PBS control.

Figure 40:
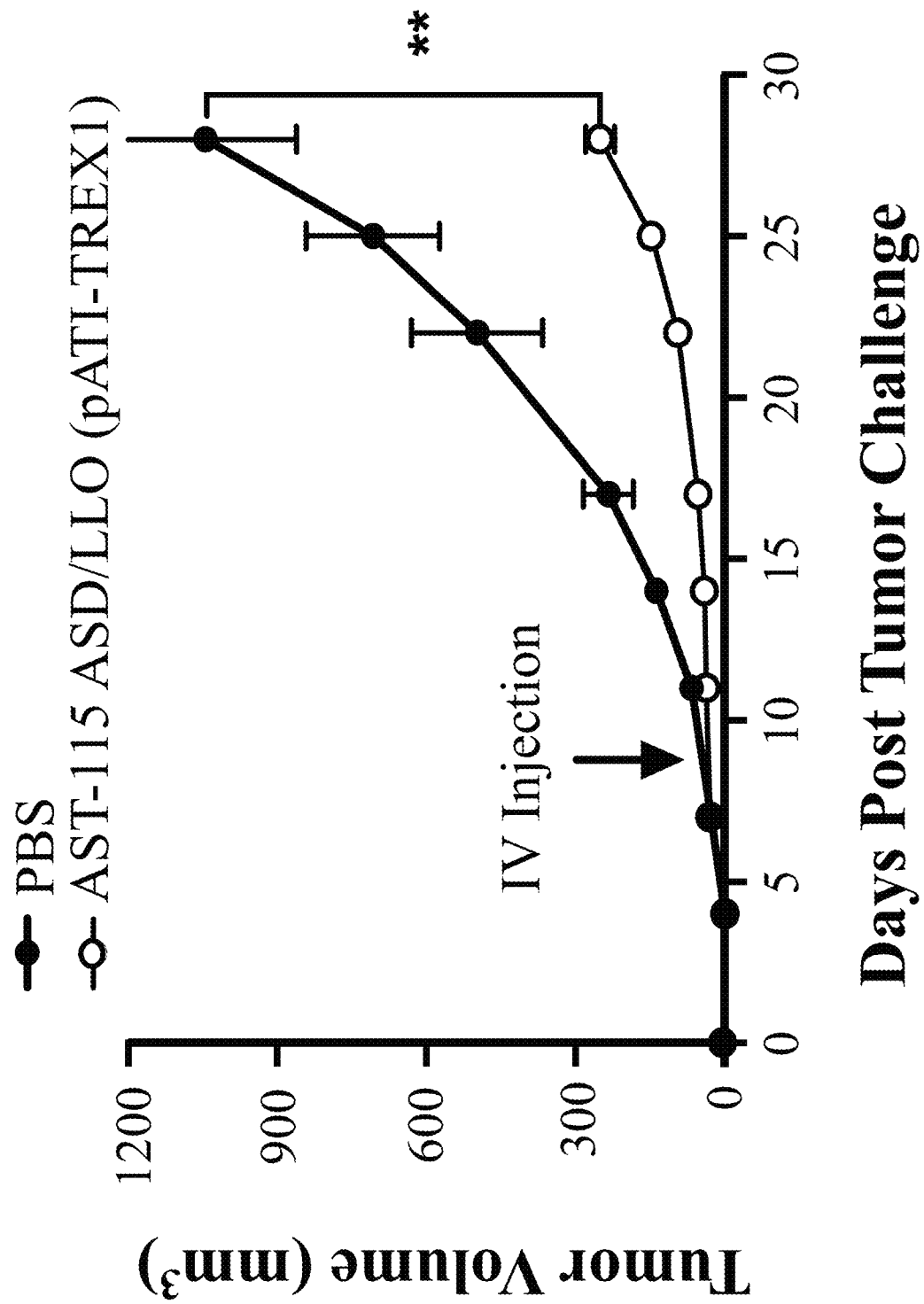
FIG. 40 depicts that AST-115 (ASD knockout+CytoLLO Knock-in strain carrying shTREX1 plasmid) demonstrates potent, single-dose efficacy in a murine CT26 tumor model. BALB/c mice (6-8 wk old) were implanted with a single CT26 ($2 \times 10^5$ cells) subcutaneous flank tumor (n=9 per group). Mice with established tumors were IV injected with $5 \times 10^6$ CFU of AST-115 (YS1646 with asd deletion and knock-in of cytoLLO expression cassette at asd locus containing (pATI-shTREX1), or PBS control, on the days indicated by the arrows. Tumor measurements were performed using electronic calipers (Fowler, Newton, MA). Tumor volume was calculated using the modified ellipsoid formula ½(length×width$^2$). Mice were euthanized when tumor size reached >20% of body weight or became necrotic, as per IACUC regulations. TGI was calculated as 1−(mean test tumor volume/mean control tumor volume)× 100. The figure depicts the mean tumor growth of each group, ±SEM. **$p<0.01$, student's t-test.

As shown in FIG. 40, the addition of the cytoLLO gene into the asd strain ASD/LLO (pATI-shTREX1) demonstrated highly significant tumor control compared to PBS control (76% TGI, p=0.002, day 28), and comparable efficacy after a single dose to previous studies where the TREX1 shRNA plasmid containing strains were given at multiple doses. These data demonstrate the cytoLLO-mediated advantage of delivering more plasmid into the cytosol, resulting in greater gene knockdown, thereby improving the therapeutic efficacy of RNAi against targets such as TREX1.

Example 10

Adenosine Auxotrophic Strains of *S. typhimurium*

Strains provided herein are engineered to be auxotrophic for adenosine. As a result, they are attenuated in vivo because they are unable to replicate in the low adenosine concentrations of normal tissue, therefore colonization occurs primarily in the solid tumor microenvironment where adenosine levels are high. The *Salmonella* strain YS1646 (AST-100) is a derivative of the wild type strain ATCC14028, and was engineered to be auxotrophic for purine due to disruption of the purI gene (Low et al. (2003) *Methods Mol. Med* 90:47-60). Subsequent analysis of the entire genome of YS1646 demonstrated that the purI gene (synonymous with purM) was not in fact deleted, but was instead disrupted by a chromosomal inversion (Broadway et al. (2014) *J. Biotechnol.* 192:177-178), and that the entire gene is still contained within two parts of the YS1646 chromosome that is flanked by insertion sequences (one of which has an active transposase). The presence of the complete genetic sequence of the purI gene disrupted by means of a chromosomal reengagement leaves open the possibility of reversion to a wild type gene. While it has previously been demonstrated that purine auxotrophy of YS1646 was stable after serial passage in vitro, it was not clear what the reversion rate is (Clairmont et al. (2000) *J. Infect. Dis.* 181:1996-2002).

It is shown herein that, when provided with adenosine, YS1646 is able to replicate in minimal medium; whereas the wild-type parental strain ATCC14028 can grow in minimal media that is not supplemented with adenosine. YS1646 was grown overnight in LB medium washed with M9 minimal medium and diluted into M9 minimal media containing no adenosine, or increasing concentrations of adenosine. Growth was measured using a SpectraMax® M3 spectrophotometer (Molecular Devices) at 37° C., reading the $OD_{600}$ every 15 minutes.

Figure 41:
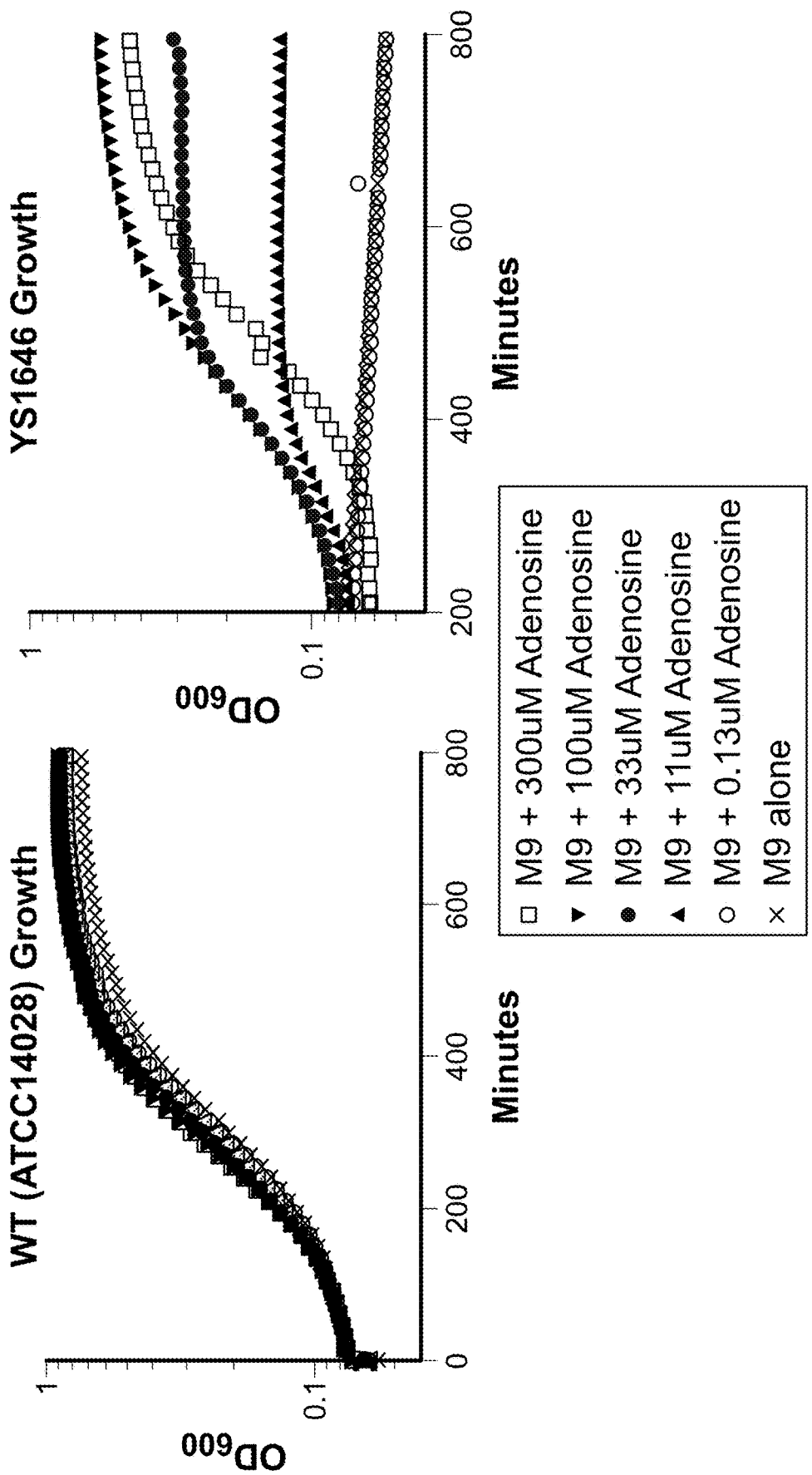
FIG. 41 depicts that strain YS1646 requires tumor microenvironment levels of adenosine for growth. Growth of strains YS1646 (purI−/msbB−) and the wild-type parental strain ATCC14028 at 37° C. in LB broth are shown, as measured by OD600 using a SpectraMax® 96-well plate reader (Molecular devices).

As shown in FIG. 41, YS1646 was able to replicate when adenosine was provided at concentrations ranging from 11 to 300 micromolar, but was completely unable to replicate in M9 alone or M9 supplemented with 130 nanomolar adenosine. These data demonstrate that purI mutants are able to replicate in concentrations of adenosine that are found in the tumor microenvironment, but not at concentrations found in normal tissues. Engineered adenosine auxotrophic strains exemplified herein include strains wherein all, or portions of the purI open reading frame are deleted from the chromosome to prevent reversion to wild-type. Such gene deletions can be achieved utilizing the lambda red system as described in Example 1.

Figure 42:
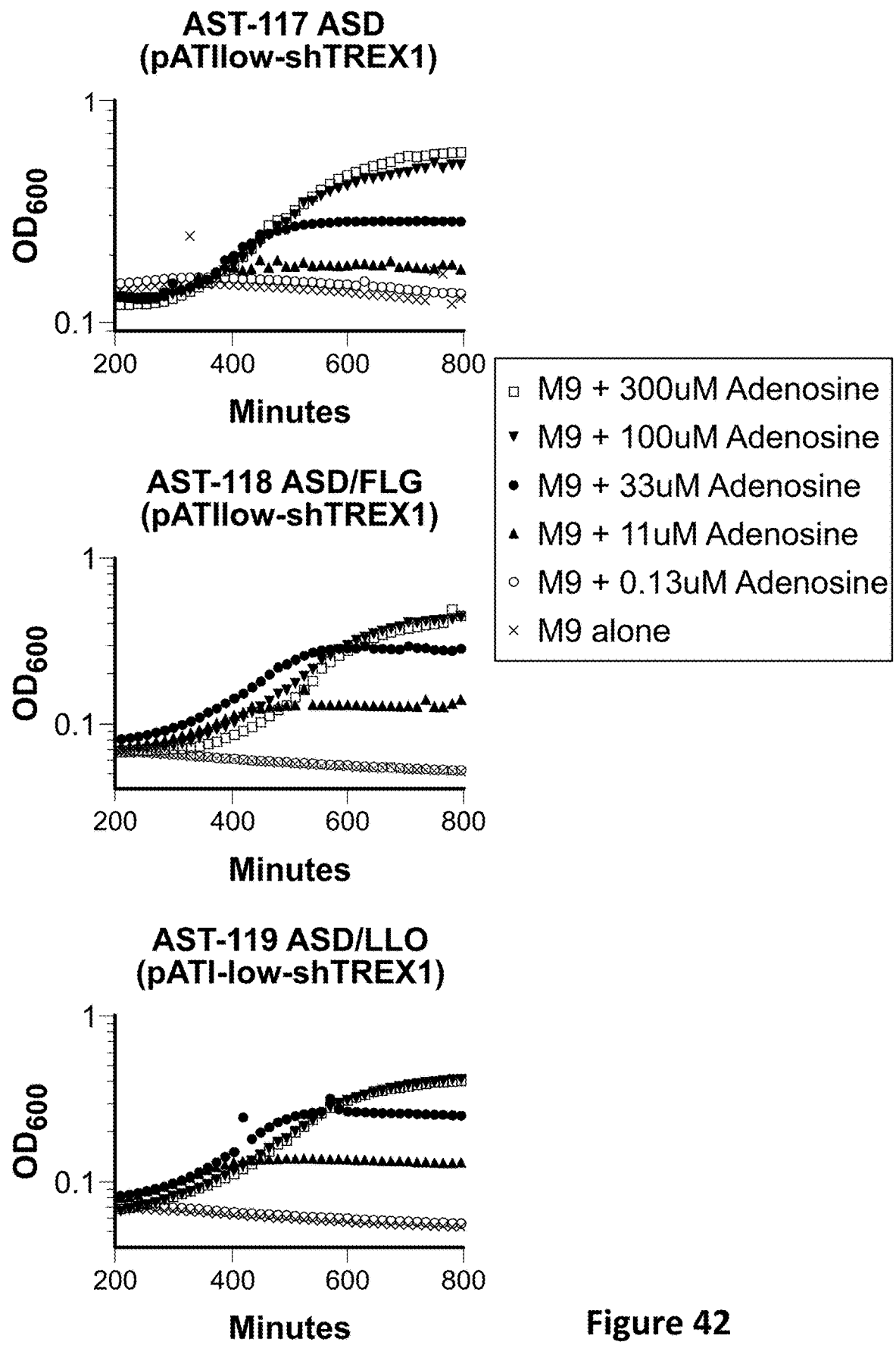
FIG. 42 depicts that ASD, FLG, and CytoLLO engineered strains require high adenosine for growth. The growth of strains AST-117 (YS1646 Δasd containing a low copy shTREX-1 plasmid), AST-118 (YS1646 Δasd/filC/fljB containing a low copy shTREX-1 plasmid), and AST-119 (YS1646 Δasd:LLO containing a low copy shTREX-1 plasmid) at 37° C. in LB broth are shown, as measured by $OD_{600}$ using a SpectraMax® 96-well plate reader (Molecular devices).

*Salmonella* strains containing a purI disruption, further engineered to contain an asd gene deletion (ASD) as described in Example 1, or asd gene deletion further engineered to have deletions of fliC and fljB and (ASD/FLG), as described in Example 8, or asd mutants further engineered to express cytoLLO (ASD/cLLO) as described in Example 9 and complemented with a low copy number plasmid (pATIlow) expressing asd as described in Example 7 (Strains AST-117, AST-118, and AST-119, respectively), were also evaluated for growth in M9 minimal media. The data in FIG. 42 show that each strain was able to replicate when adenosine was provided at concentrations ranging from 11 to 300 micromolar, but was completely unable to replicate in M9 alone or M9 supplemented with 130 nanomolar adenosine.

Example 11

Figure 43:
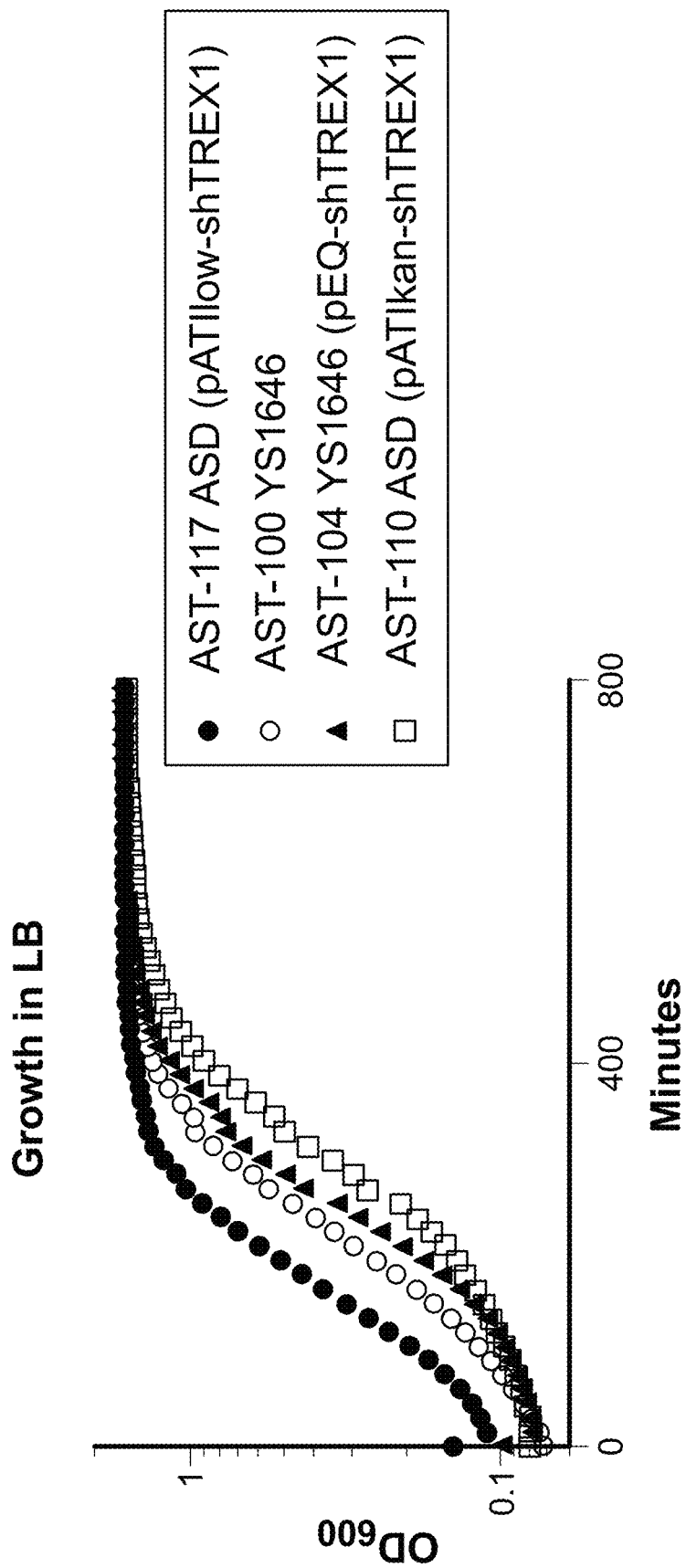
FIG. 43 depicts that a strain with a low copy origin of replication asd-encoding plasmid has superior growth kinetics than a strain with a high copy origin of replication asd-encoding plasmid. The growth of strains YS1646, AST-117 (YS1646 Δasd containing a low copy shTREX-1 plasmid with a functional asd gene), AST-104 (YS1646 containing a low copy pEQ shTREX-1 plasmid without an asd gene), and AST-110 (YS1646 Δasd containing a high copy pATI-shTREX-1 plasmid with a functional asd gene) at 37° C. in LB broth are shown, as measured by $OD_{600}$ using a SpectraMax® 96-well plate reader (Molecular devices).

Characterization and use of the asd *Gene* Complementation System in vitro Growth of Strains with asd *Gene* Complementation To assess fitness of the bacterial strains containing plasmids, growth curves were performed in LB liquid media using a SpectraMax® plate reader at 37° C., reading the $OD_{600}$ every 15 minutes. As Shown in FIG. 43, YS1646 containing a low copy plasmid pEQU6-shTREX1 (AST-104) grew comparably to YS1646 that did not contain a plasmid (AST-100). An asd mutant strain harboring a high copy shTREX1 plasmid with an asd gene that can complement the asd auxotrophy (AST-110) was able to replicate in LB in the absence of DAP, but grew slower than YS1646. An asd deleted strain containing an shTREX-1 expression plasmid with low copy number origin of replication and an asd gene that can complement the asd auxotrophy (pATIlow-shTREX1), strain AST-117, grew at a faster rate than AST-110. These data demonstrate that low copy number plasmids that complement the asd gene auxotrophy are superior to high copy number plasmids, as they allow for more rapid replication rates of *S. typhimurium* in vitro.

Intracellular Growth of asd Complemented Strains

To measure fitness of the asd mutants complemented with asd on high and low copy plasmids, the ability of bacterial strains to replicate intracellularly in mouse tumor cell lines was assessed using a gentamycin protection assay. In this assay, mouse melanoma B16.F10 cells or mouse colon cancer CT26 cells were infected with asd mutant *Salmonella* strains containing plasmids that contain a complementary asd gene and have either a high copy origin of replication, AST-110 (ASD pATI-shTREX1) or a low copy origin of replication, AST-117 (ASD pATI low copy-shTREX1). Cells were infected at a multiplicity of approximately 5 bacteria per cell for 30 minutes, then cells were washed with PBS, and medium containing gentamicin was added to kill extracellular bacteria. Intracellular bacteria are not killed by gentamicin, as it cannot cross the cell membrane. At various time points after infection, cell monolayers were lysed by osmotic shock with water and the cell lysates were diluted and plated on LB agar to enumerate surviving colony forming units (CFU).

Figure 44:
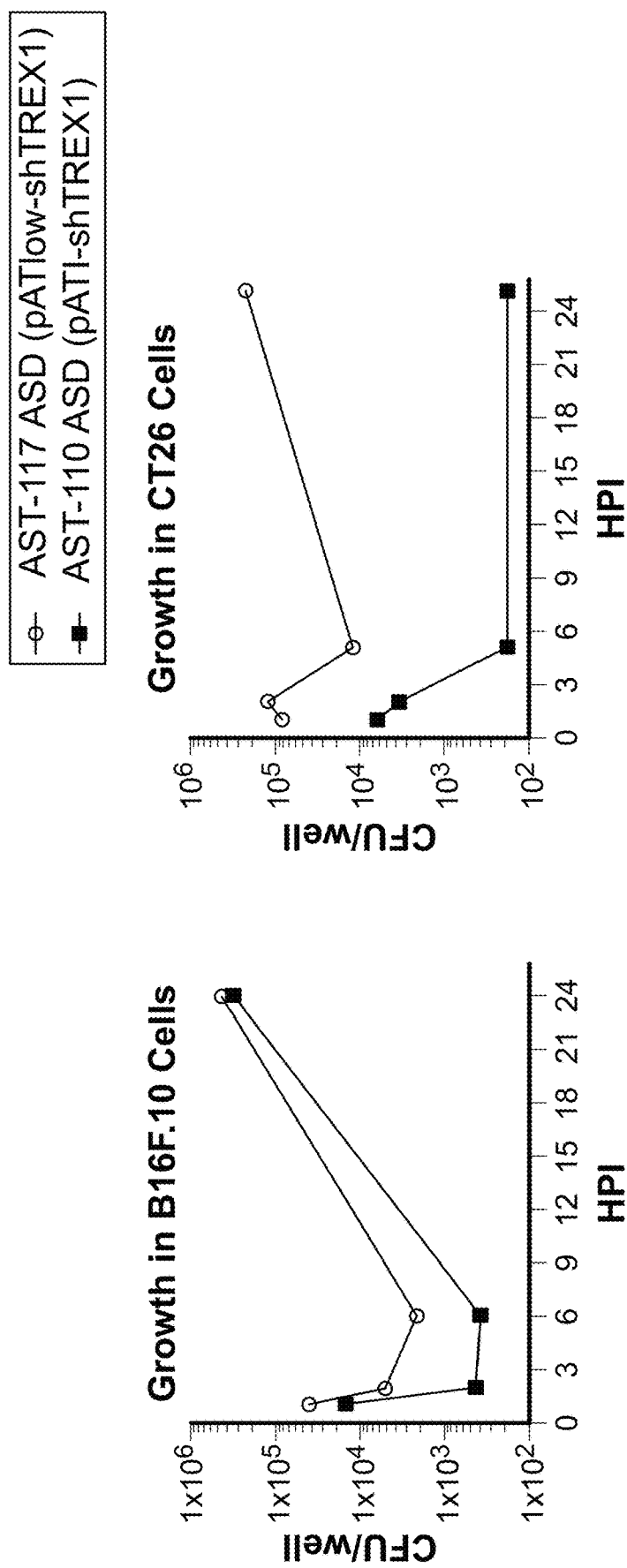
FIG. 44 depicts that a strain with a low copy number asd plasmid is more fit than a strain with a high copy number asd plasmid in mouse tumor cells. The intracellular growth of strains AST-117 (YS1646 Δasd containing a low copy number shTREX-1 plasmid with a functional asd gene) and AST-110 (YS1646 Δasd containing a high copy number pATI-shTREX-1 plasmid with a functional asd gene) are shown in B16F.10 mouse melanoma cells and CT26 mouse colon carcinoma cells. $5\times10^5$ cells in a 24 well dish were infected with the *S. typhimurium* strains at a MOI of 5. After 30 minutes of infection, media was replaced with media containing gentamycin to kill extracellular bacteria. At indicated time points, cell monolayers were lysed by osmotic shock the cell lysates were diluted and plated on LB agar to enumerate CFU.

As shown in FIG. 44, the asd mutant strain complemented with a high copy plasmid, AST-110, had an initial decline in CFU, but was able to grow in B16.F10 cells but not in CT26 cells, demonstrating that the asd gene complementation system is sufficient to support growth inside mammalian tumor cells. The asd mutant strain containing the low copy plasmid, AST-117, was able to invade and replicate in both cell types, demonstrating that asd gene complementation on a low copy plasmid allows for robust asd mutant growth inside mammalian cells. The strain with low copy plasmid replicated to higher numbers in both tumor cell types compared to the strain with a high copy plasmid. This demonstrates that *Salmonella* strains with low copy plasmids have enhanced fitness over strains with high copy plasmids.

Plasmid Maintenance in Tumors Using asd Complementation System

In this example, CT26 tumor-bearing mice were treated with YS1646 containing a plasmid that expresses an shRNA targeting TREX1 (pEQU6-TREX1), strain AST-104, or an asd deleted strain of YS1646 containing a plasmid with a functional asd gene and an shRNA targeting TREX1 (pATI-shTREX1), strain AST-110. At 12 days after the final *Salmonella* injection, tumors were homogenized, and homogenates were serially diluted and plated on LB agar plates to enumerate the total number of CFUs present, or on LB plates containing kanamycin to enumerate the number of kanamycin resistant colonies.

Figure 45:
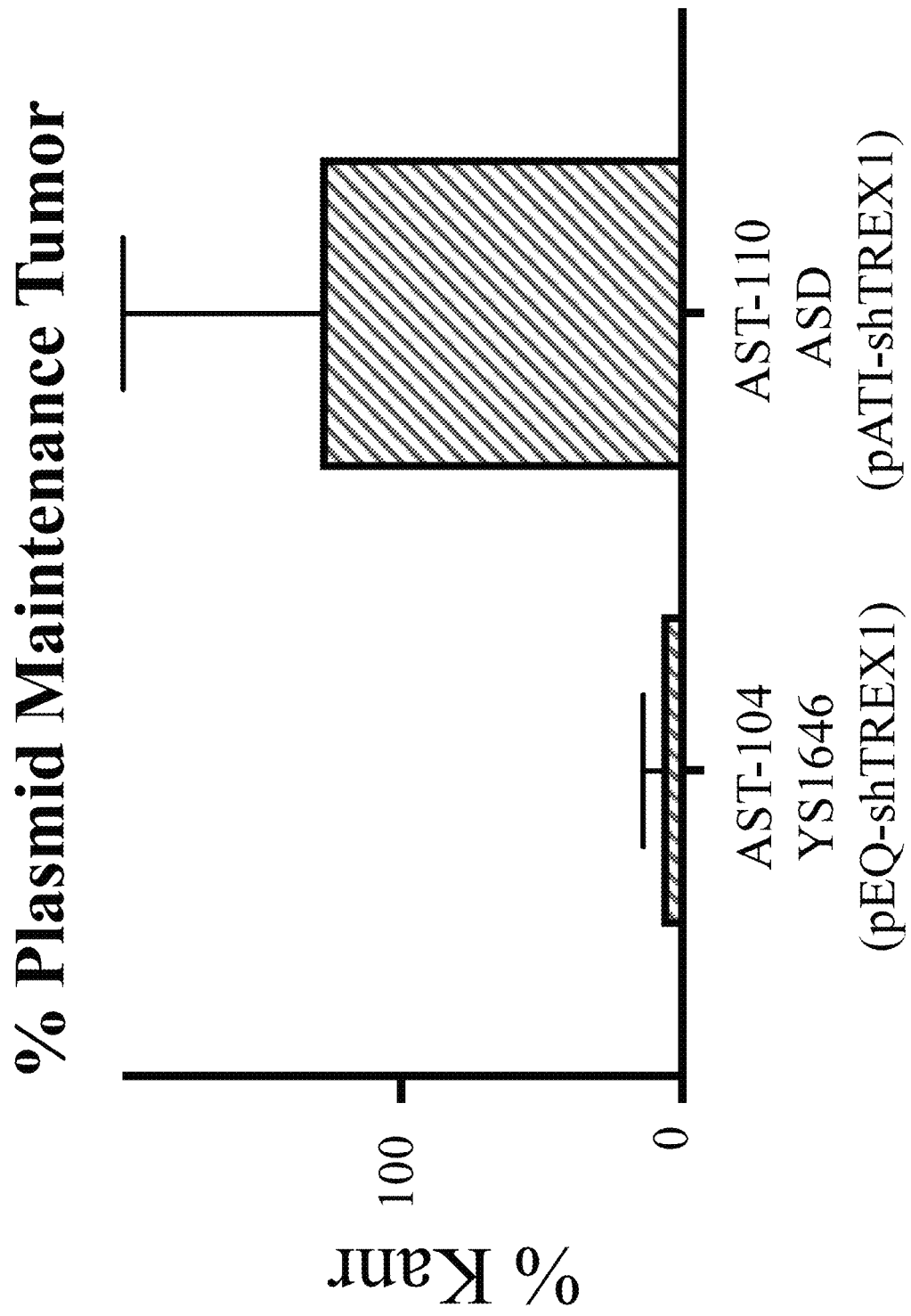
FIG. 45 depicts that in vivo, asd gene complementation systems result in retention of plasmids in *S. typhimurium*-infected tumors. BALB/c mice (6-8 wk old) were implanted with a single CT26 ($2\times10^5$ cells) subcutaneous flank tumor (n=9 per group). Mice with established tumors were IV injected with $5\times10^6$ CFU of the asd knockout strain containing the pATI shTREX1 plasmid (AST-110) or the YS1646 containing a pEQ shTREX-1 plasmid without an asd gene (AST-104). At 35 days post tumor implantation (12 days after the last dose of engineered *Salmonella* therapy), three mice per group were sacrificed, and tumors were homogenized using a GentleMACs™ homogenizer (Miltenyi Biotec) and plated on LB agar plates or LB agar plates with 50 ug/mL of Kanamycin. The figure depicts the percentage of Kanamycin resistant CFU in tumor tissue homogenates, ±SD.

As shown in FIG. 45, *S. typhimurium* that did not have selective pressure to maintain the shRNA plasmid, AST-104, demonstrated plasmid loss, as the percent kanamycin resistant (KanR) colonies was less than 10%. The strain that used the asd gene complementation system for plasmid maintenance, AST-110, had nearly identical numbers of kanamycin resistant and kanamycin sensitive CFUs. These data demonstrate that the asd gene complementation system is sufficient to maintain the plasmid in the context of the tumor microenvironment in mice.

Enhanced Anti-Tumor Efficacy Using asd Complementation System

The asd complementation system is designed to prevent plasmid loss and potentiate the anti-tumor efficacy of the inhibitory RNA delivery by *S. typhimurium* strains in vivo. To test this, asd deleted strains containing shTREX1 plasmid (AST-110) or scrambled control (AST-109) that contain a functional asd gene cassette were compared to YS1646 containing pEQU6-shTREX1 (AST-104, a plasmid that lacks an asd gene cassette and therefore does not have a mechanism for plasmid maintenance) for anti-tumor efficacy in a murine colon carcinoma model. For this experiment, 6-8 week-old female BALB/c mice (8 mice per group) were inoculated SC in the right flank with CT26 ($2\times10^5$ cells in 100 µL PBS). Mice bearing established flank tumors were IV injected twice, on day 8 and day 18, with $5\times10^6$ CFUs of AST-109 (ASD transformed with pATI-shScramble), AST-110 (ASD transformed with pATI-shTREX1), or AST-104 (YS1646 transformed with pEQU6-shTREX1) and compared to PBS control.

As shown in FIG. 46, the YS1646 strain AST-104 demonstrated tumor control compared to PBS (70% TGI, day 28) despite its demonstrated plasmid loss over time. The asd strain containing the scramble control in a pATI plasmid with the asd gene complementation system (AST-109) demonstrated tumor control compared to PBS (51% TGI, day 25), indicating that maintained delivery of CpG plasmids stimulates an anti-tumor response. The asd strain containing plasmid with the asd gene complementation system and shTREX1 (AST-110) demonstrated the highest tumor growth inhibition compared to PBS (82% TGI, p=0.002, day 25). These data demonstrate that improved potency is achieved by preventing plasmid loss using the asd complementation system and delivery of shTREX1, as compared to YS1646 containing plasmids without gene complementation systems or shTREX1.

Figure 47:
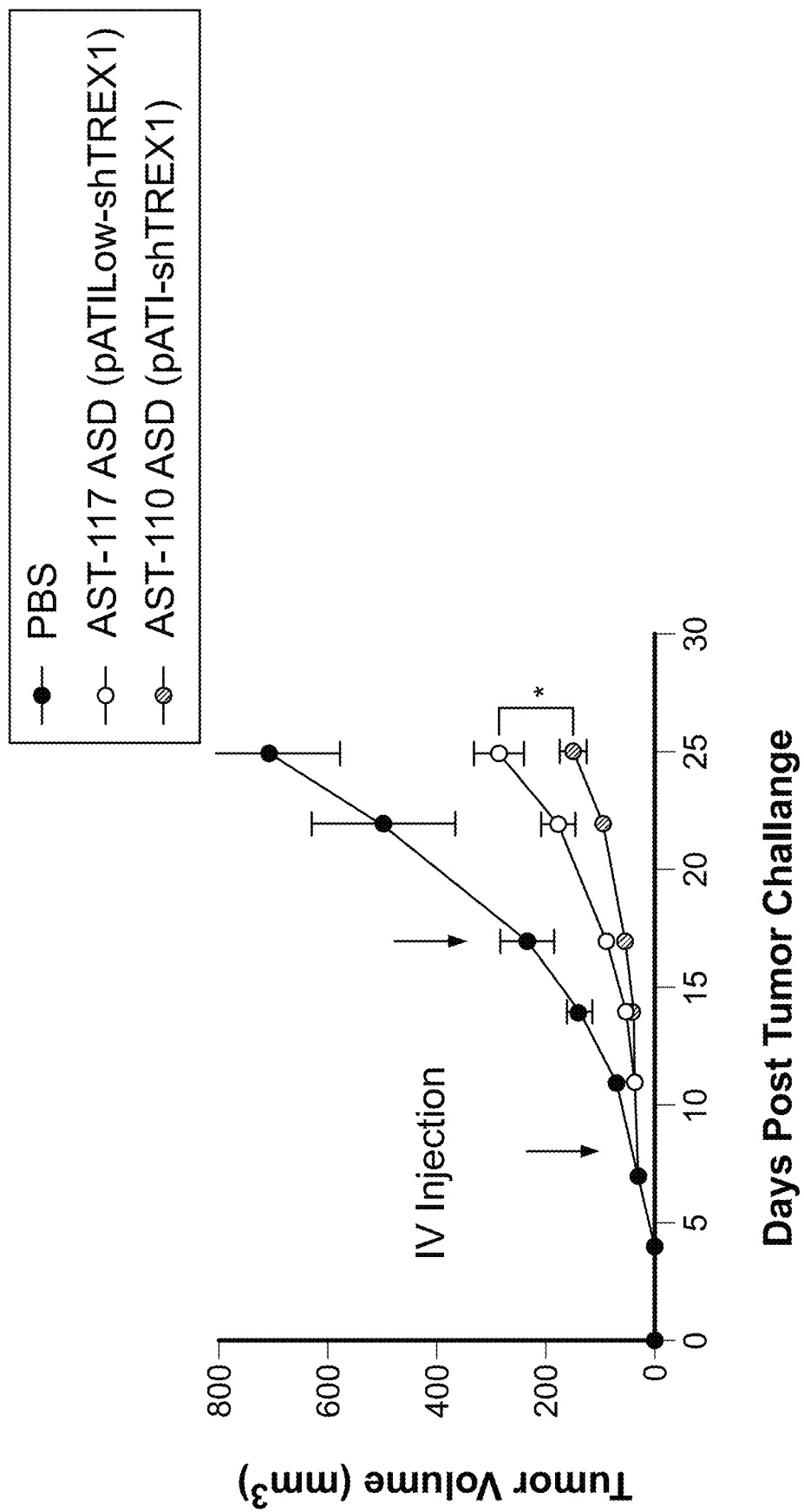
FIG. 47 depicts that a strain containing a low copy number shTREX1 plasmid (AST-117) has superior anti-tumor properties compared to a strain containing a high copy number plasmid (AST-110). BALB/c mice (6-8 wk old) were implanted with a single CT26 ($2\times10^5$ cells) subcutaneous flank tumor (n=9 per group). Mice with established tumors were IV injected with $5\times10^6$ CFU of the asd knockout strain containing the pATI-shTREX1 plasmid with a high copy number origin of replication (AST-110) or the asd knockout strain containing the pATI-shTREX1 plasmid with a low copy number origin of replication (AST-117), or PBS control, on the days indicated by the arrows. Tumor measurements were performed using electronic calipers (Fowler, Newton, MA). Tumor volume was calculated using the modified ellipsoid formula ½(length×width²). Mice were euthanized when tumor size reached >20% of body weight or became necrotic, as per IACUC regulations. TGI was calculated as 1−(mean test tumor volume/mean control tumor volume)×100. The figure depicts the mean tumor growth of each group, ±SEM. *p<0.05, student's t-test.

S. typhimurium Strains with Low Copy Plasmids Demonstrate Superior Anti-Tumor Efficacy and Tumor Colonization Compared to High Copy Plasmids In order to compare the anti-tumor efficacy of the low copy shTREX1 plasmid with the asd complementation system, relative to the high copy shTREX1 plasmid in a murine model of colon carcinoma, 6-8 week-old female BALB/c mice (10 mice per group) were inoculated SC in the right flank with CT26 ($2\times10^5$ cells in 100 µL PBS). Mice bearing established flank tumors were IV injected with two weekly doses of $5\times10^6$ CFUs of AST-117 (ASD (pATI Low-shTREX1)) or AST-110 (ASD (pATI-shTREX1) and were compared to PBS injections as a negative control. As shown in FIG. 47, the strain with the low copy plasmid, AST-117, demonstrated superior anti-tumor efficacy compared to the strain with the high copy plasmid AST-110 (High 59% TGI, Low 79% TGI, p=0.042, day 25).

Figure 48B:
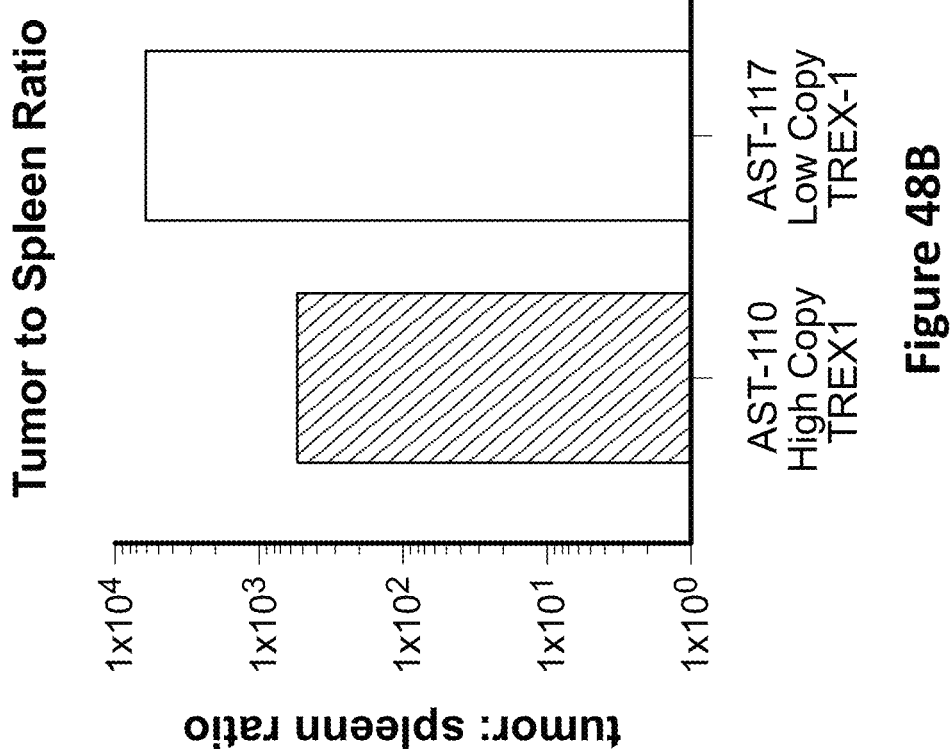
FIGS. 48A-48B depict that the AST-117 low copy number plasmid strain colonizes tumors better and has a higher tumor to spleen colonization ratio than the AST-110 high copy number plasmid strain. BALB/c mice (6-8 wk old) were implanted with a single CT26 ($2\times10^5$ cells) subcutaneous flank tumor (n=9 per group). Mice with established tumors were IV injected with $5\times10^6$ CFU of the asd knockout strain containing the pATI-shTREX1 plasmid with a high copy number origin of replication (AST-110) or the asd knockout strain containing the pATI-shTREX1 plasmid with a low copy number origin of replication (AST-117). At 35 days post tumor implantation (12 days after the last dose of engineered *Salmonella* therapy), 3 mice per group were sacrificed, and tumors were homogenized using a GentleMACs™ homogenizer (Miltenyi Biotec) and plated on LB plates to enumerate the number of CFU per gram of tumor tissue.
Figure 48A:
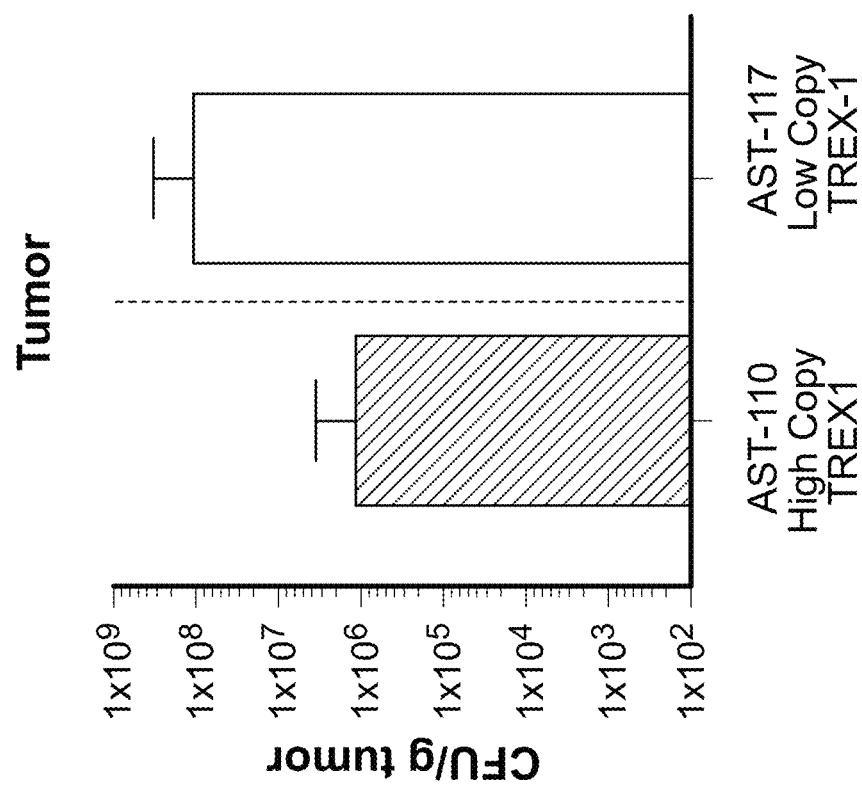

At the end of this tumor growth inhibition study, 4 mice from each group were euthanized, and tumors and spleens were homogenized as described above to evaluate tumor colonization and tumor to spleen colonization ratios. As shown in FIG. 48A, the strain containing the low copy plasmid, AST-117, colonized tumors at a level greater than 100 times higher than the strain with the high copy plasmid, AST-110. When the ratio of colonies recovered from tumor and spleen were calculated, AST-117 had a greater than 10-fold higher tumor to spleen colonization ratio compared to AST-110 (FIG. 48B), demonstrating that the strain with the low copy plasmid had greater specificity for tumor colonization than the strain with the high copy plasmid. These data demonstrate a previously unknown attribute that S typhimurium engineered to deliver plasmids encoding interfering RNAs have improved tumor colonizing capabilities and anti-tumor efficacy when the plasmids have low copy number origins of replication.

Example 12

S. typhimurium Harvested at Log Vs Stationary Phase Production of Log Vs Stationary Injection Stocks It has been demonstrated that the Salmonella pathogenicity island-1 (SPI-1) genes of Salmonella typhimurium are induced during logarithmic growth (Lundberg et al. (1999) Journal Of Bacteriology 181:3433-3437). This pathogenicity island is essential for uptake in non-phagocytic cells, such as epithelial cells, or cells derived from solid tumors. Induction of SPI-1 genes during late log has also been demonstrated to result in rapid pyroptosis (caspase-1-dependent proinflammatory programmed cell death) of macrophages (Fink et al. (2007) Cell Microbiol. 9(11): 2562-2570).

To determine the optimal phase of growth for production of Salmonella typhimurium-based immunotherapy, strains were produced by growing overnight cultures in LB at 37° C. with agitation. The overnight cultures were diluted into fresh LB in disposable shaker flasks and grown until the $OD_{600}$ reached 1.0 for late-log phase, or until the culture stopped increasing in OD for stationary phase (approximately 2 hours). The cultures were washed in PBS and suspended in a volume of PBS+15% glycerol that result in a stock concentration $OD_{600}$ of 1.0 for cryopreservation to produce injection stocks at approximately $1\times10^9$ CFU/mL. The injection stocks were then stored at −80° C.

Modified S. typhimurium Strains Grown to Stationary Phase Demonstrate Equivalent Anti-Tumor Potency with and Superior Tolerability Compared to Strains Grown to Log Phase To determine the impact that the phase of culture at harvest has on in vivo activity, log vs stationary phase cultures of the modified Salmonella typhimurium strains were evaluated in a murine model of colon carcinoma. 6-8 week-old female BALB/c mice (10 mice per group) were inoculated SC in the right flank with CT26 ($2\times10^5$ cells in 100 µL PBS). Mice bearing established flank tumors were IV injected with three weekly doses of $5\times10^6$ CFUs of AST-104 (YS1646 transformed with pEQU6-shTREX1) strains harvested at log or stationary phase, and compared to PBS control. Six hours following the first IV dose, mice were bled, and plasma was collected and assessed for pro-inflammatory cytokines using the Mouse Inflammation Cytometric Bead Array kit and analyzed by FACS (BD Biosciences).

Figure 49A:
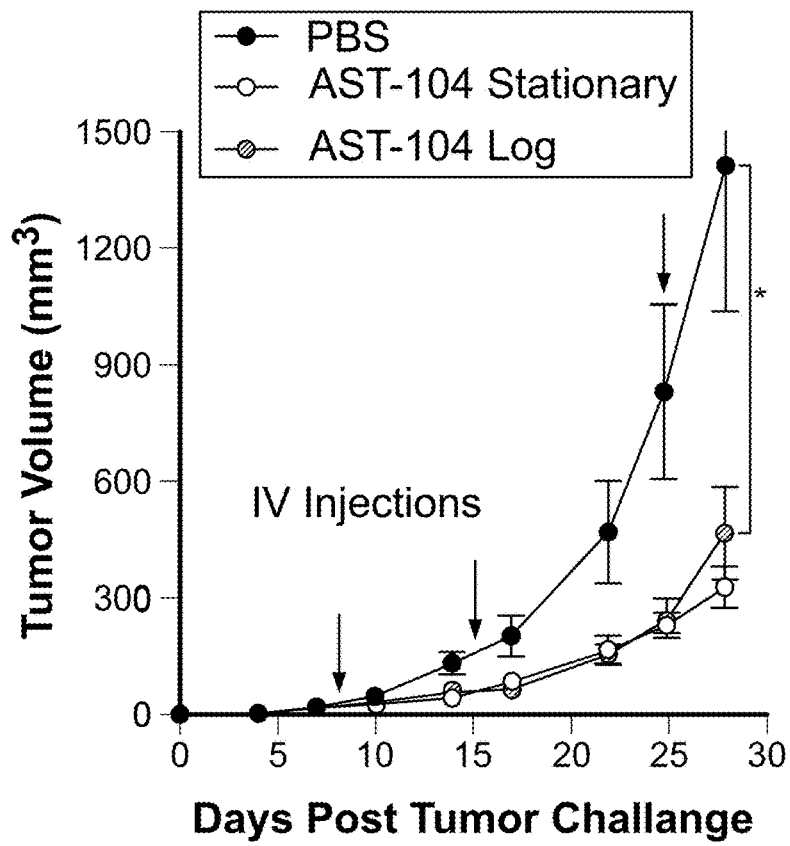
FIGS. 49A-49B depict that a strain grown to stationary phase is equivalently potent, and less inflammatory than the same strain grown to log phase. BALB/c mice (6-8 wk old) were implanted with a single CT26 ($2\times10^5$ cells) subcutaneous flank tumor (n=9 per group). Mice with established tumors were IV injected with $5\times10^6$ CFU of the YS1646 strain containing a pEQ-shTREX-1 plasmid (AST-104) harvested at log phase or stationary phase, or PBS control, on the days indicated by the arrows. Tumor measurements were performed using electronic calipers (Fowler, Newton, MA). Tumor volume was calculated using the modified ellipsoid formula ½(length×width²). Mice were euthanized when tumor size reached >20% of body weight or became necrotic, as per IACUC regulations. TGI was calculated as 1−(mean test tumor volume/mean control tumor volume)×100.
Figure 49B:
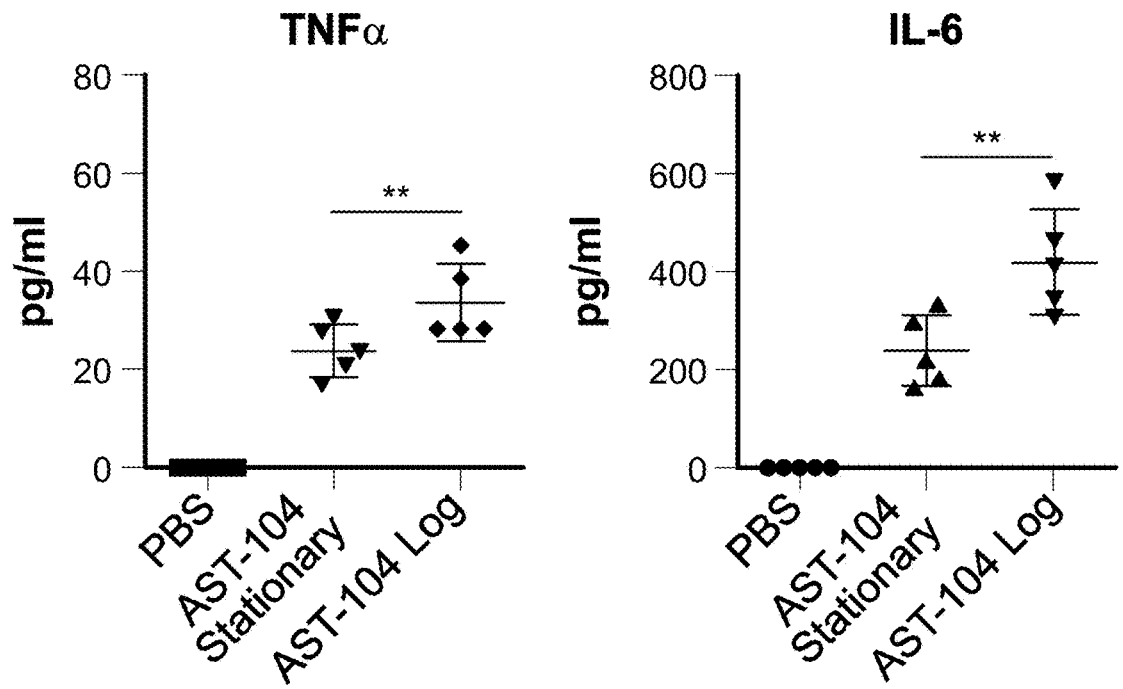

As shown in FIG. 49A, the AST-104 log and AST-104 stationary phase injection stocks demonstrated comparable anti-tumor efficacy compared to the PBS control group (log—67% TGI, p=0.04, stationary—77% p=0.01, day 28), with the stationary phase injection stock demonstrating slightly better tumor growth inhibition. Comparing the levels of systemic serum cytokines at 6 hours post IV injection, the inflammatory cytokines elicited by the log phase injection stock were significantly higher for both TNF-α (p=0.007), and IL-6 (p=0.016), compared to the AST-104 stationary phase strain (FIG. 49B). These data demonstrate that growing bacterial therapeutic strains to stationary phase prior to IV administration can significantly reduce inflammatory toxicity and can improve tumor growth inhibition, indicating that the therapeutic index can be improved with material harvested at stationary phase.

Example 13

Engineering of an Autolytic S. typhimurium Strain for Delivery of RNAi

As described above, the asd gene in S. typhimurium encodes aspartate semialdehyde dehydrogenase. Deletion of this gene renders the bacteria auxotrophic for diaminopimelic acid (DAP) when grown in vitro or in vivo. This example employs an asd deletion strain (described in Example 1) that is auxotrophic for DAP and contains a plasmid suitable for delivery of RNAi that does not contain an asd-complementing gene so that the strain is defective for replication in vivo. This strain is propagated in vitro in the presence of DAP and grows normally, and then is administered as an immunotherapeutic agent to mammalian hosts where DAP is not present, which results in autolysis of the bacteria. Autolytic strains are able to invade host cells, but are not able to replicate due to the absence of DAP in mammalian tissues; this combination of attributes allows for RNAi-mediated gene knockdown and increased safety relative to replicating strains.

In this example, the asd deleted strain of YS1646 (AST-101, described in Example 1) was further modified to express cytoLLO to generate strain AST-114 (described in Example 9), was electroporated to contain a plasmid encoding ARI-203 (a microRNA targeting TREX1, described in Example 2), to make strain AST-120 (ASD/LLO (pEQU6-miTREX1)). When this strain is introduced into tumor bearing mice, the bacteria are taken up by host cells and enter the Salmonella containing vacuole (SCV). In this environment, the lack of DAP prevents replication, and result in lysis of the bacteria in the SCV. Lysis of AST-120 allows for release of the plasmid, and the accumulated cytoLLO that form pores in the cholesterol-containing SVC membrane, resulting in efficient delivery of the plasmid into the cytosol of the host cell.

Figure 50:
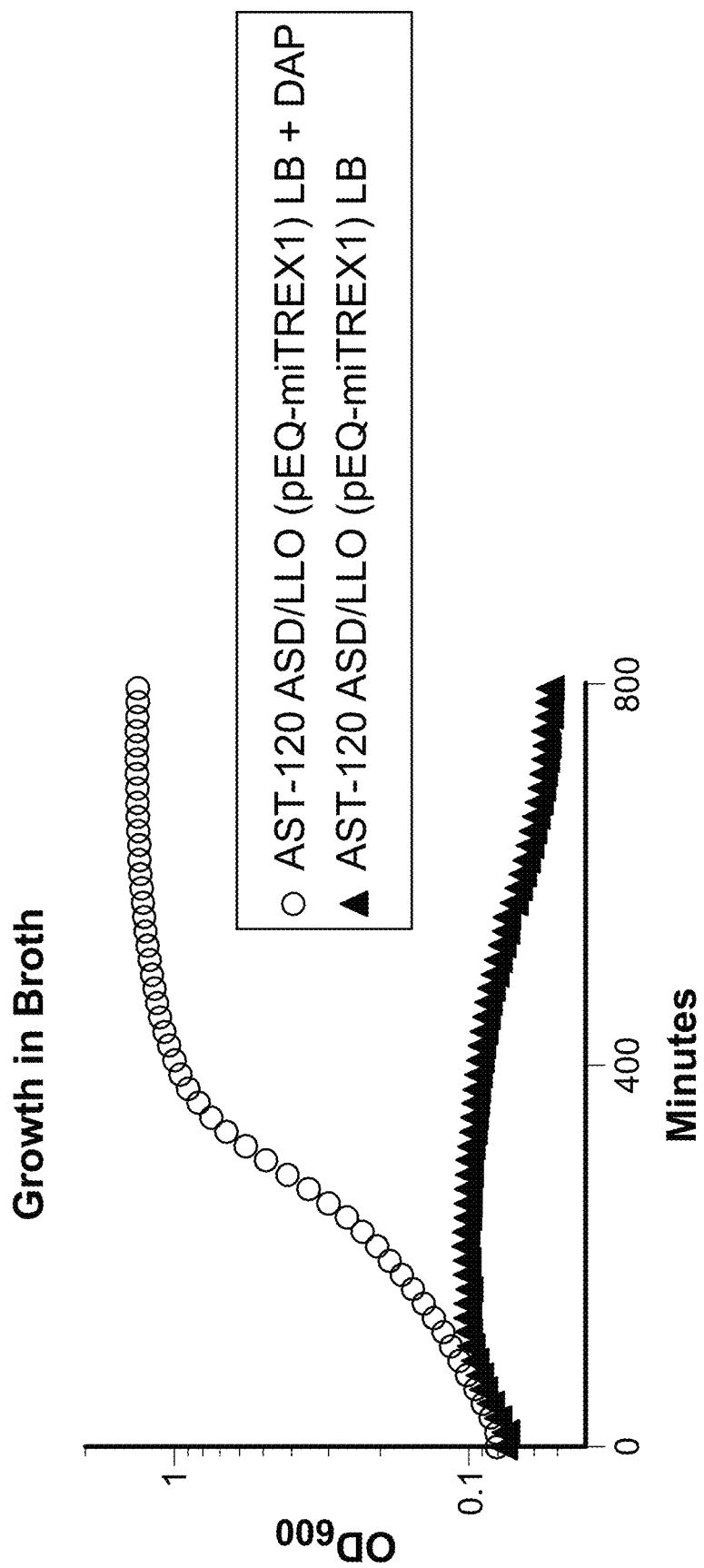
FIG. 50 depicts that an autolytic strain (AST-120) cannot grow in the absence of DAP. The figure depicts the growth of Δasd:cytoLLO strain containing a pEQU6-shTREX1 plasmid that does not contain an asd gene (AST-120), over time in LB broth alone, or in LB broth supplemented with 50 ug/mL DAP, as measured by $OD_{600}$ using a SpectraMax® 96-well plate reader (Molecular devices).

The ability of the autolytic strain AST-120, to replicate in LB in the presence or absence of DAP was assessed using a SpectraMax® M3 spectrophotometer (Molecular Devices) at 37° C., reading the $OD_{600}$ every 15 minutes. As shown in FIG. 50, AST-120 is able to grow robustly in LB supplemented with 50 µg/mL DAP, but cannot replicate in LB alone.

Increased Attenuation of Autolytic *S. typhimurium* in Mice

To determine whether the autolytic strain AST-120, engineered to deliver cytoLLO and a microRNA targeting TREX1, was attenuated for virulence, a median lethal dose ($LD_{50}$) study was performed. Increasing doses of AST-120, ranging from $1×10^6$ to $5×10^7$ CFU, were administered IV to C57BL/6 mice (a strain of mouse that is highly sensitive to LPS). After IV administration, AST-120 was well tolerated at all doses with transient weight loss observed after a single dose. A second dose was administered 7 days after the first dose and one mouse out of four, at the highest dose level ($5×10^7$ CFU), was found moribund and required euthanasia. All other mice administered AST-120 experienced transient weight loss, but recovered. These data indicate that the $LD_{50}$ for the autolytic strain of *S. typhimurim* delivering a microRNA targeting TREX1 (AST-120) is greater than $5×10^7$ CFU. The $LD_{50}$ for the VNP20009 strain is known to be approximately $5×10^6$ in C57BL/6 mice (Lee et al. (2000) *International Journal of Toxicology* 19:19-25), demonstrating that AST-120 is at least 10-fold attenuated compared to VNP20009.

Antitumor Activity of Autolytic *S. typhimurium*

Figure 51:
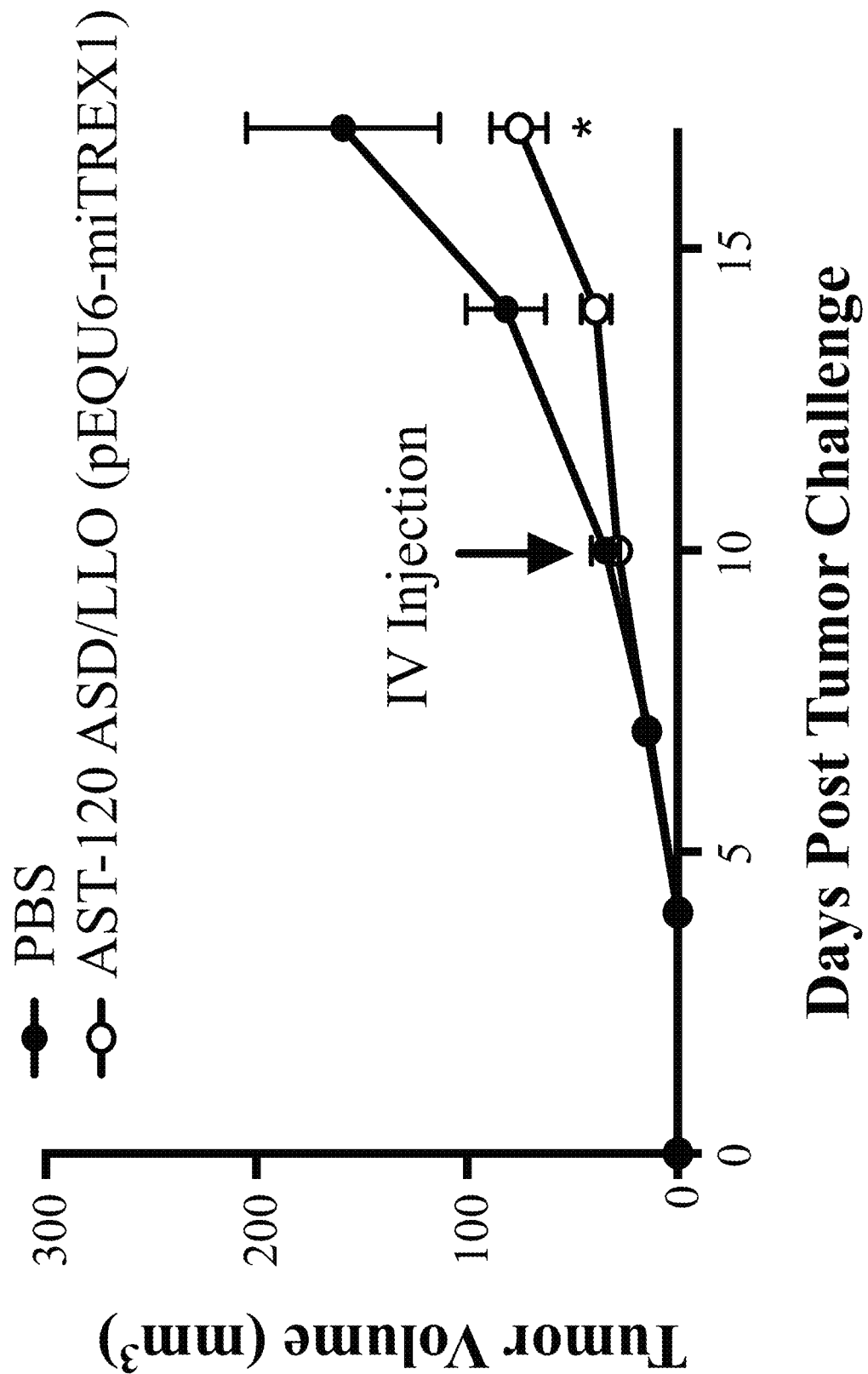
FIG. 51 depicts the anti-tumor activity of the autolytic strain (AST-120). BALB/c mice (6-8 wk old) were implanted with a single CT26 ($2 \times 10^5$ cells) subcutaneous flank tumor (n=9 per group). Mice with established tumors were IV injected with $5 \times 10^6$ CFU of the of Δasd:cytoLLO strain containing a pEQU6-shTREX1 plasmid that does not contain an asd gene (AST-120), or PBS control, on the days indicated by the arrows. Tumor measurements were performed using electronic calipers (Fowler, Newton, MA). Tumor volume was calculated using the modified ellipsoid formula ½(length×width$^2$). Mice were euthanized when tumor size reached >20% of body weight or became necrotic, as per IACUC regulations. TGI was calculated as 1−(mean test tumor volume/mean control tumor volume)× 100. The figure depicts the mean tumor growth of each group, ±SEM. *$p<0.05$, student's t-test.

To determine whether the autolytic strain AST-120, engineered to deliver cytoLLO and a microRNA targeting TREX1, was able to provide an anti-tumor response, 6-8 week-old female BALB/c mice (10 mice per group) were inoculated SC in the right flank with CT26 ($2×10^5$ cells in 100 µL PBS). Mice bearing established flank tumors were IV injected with a single dose of $5×10^6$ CFUs of the autolytic strain AST-120 (ASD/LLO (pEQU6-miTREX1)) and compared to mice treated with PBS as a control. As shown in FIG. 51, an antitumor response was detected after only a single dose, compared to animals treated with PBS alone (52.4% TGI, p=0.02, day 17). Together, these data demonstrate that *S. typhimurium* engineered to be autolytic by means of DAP auxotrophy and engineered to contain a plasmid for delivery of RNAi targeting TREX1, are exquisitely attenuated and can elicit an anti-tumor response.

Example 14

Exemplary Strains Engineered for Increased Tolerability adrA or csgD Deletion

In this example, a live attenuated strain of *Salmonella typhimurium* that contains a purI deletion, an msbB deletion, an asd gene deletion and is engineered to deliver plasmids encoding interfering RNA, is further modified to delete adrA, a gene required for *Salmonella typhimurium* biofilm formation. *Salmonella* that cannot form biofilms are taken up more rapidly by host phagocytic cells and are cleared more rapidly. This increase in intracellular localization enhances the effectiveness of plasmid delivery and gene knockdown by RNA interference. The increased clearance rate from tumors/tissues increases the tolerability of the therapy, and the lack of biofilm formation prevents colonization of prosthetics and gall bladders in patients. In another example, a live attenuated strain of *Salmonella typhimurium* that contains a purI deletion, an msbB deletion, an asd gene deletion and is engineered to deliver plasmids encoding interfering RNA, is further modified to delete csgD. This gene is responsible for activation of adrA, and also induces expression of the curli fimbriae, a TLR2 agonist. Loss of csgD also prevents biofilm formation, with the added benefit of inhibiting TLR2 activation, thereby further reducing the bacterial virulence and enhancing delivery of RNAi.

pagP Deletion

In this example a live attenuated strain of *S. typhimurium* that contains a purI deletion, an msbB deletion, and an asd gene deletion, and is engineered to deliver plasmids encoding interfering RNA, is further modified to delete pagP. The pagP gene is induced during the infectious life cycle of *S. typhimurium* and encodes an enzyme that palmitoylates lipid A. In wild type *S. typhimurium*, expression of pagP results in a lipidA that is hepta-acylated. In an msbB-mutant in which the terminal acyl chain of the lipid A cannot be added, the expression of pagP results in a hexa-acylated LPS. Hexa-acylated LPS has been shown to be the most pro-inflammatory. In this example, a strain deleted of pagP and msbB can produce only penta-acylated LPS, allowing for lower pro-inflammatory cytokines, enhanced tolerability, and increased adaptive immunity when the bacteria are engineered to deliver interfering RNAs.

hilA Deletion

In this example a live attenuated strain of *Salmonella typhimurium* that contains a purI deletion, an msbB deletion, an asd gene deletion and is engineered to deliver plasmids encoding interfering RNA, is further modified to delete hilA. hilA is a regulatory gene that is required for expression of the *salmonella* pathogenicity island-1 (SPI-1)-associated type 3 secretion system (T3SS). This secretion system is responsible for injecting effector proteins into the cytosol of non-phagocytic host cells, such as epithelial cells, that cause the uptake of modified *S. typhimurium*. The SPI-1 T3SS has been shown to be essential for crossing the gut epithelial layer, but is dispensable for infection when bacteria are injected parenterally. The injection of some proteins and the needle complex itself can also induce inflammasome activation and pyroptosis of phagocytic cells. This pro-inflammatory cell death can limit the initiation of a robust adaptive immune response by directly inducing the death of antigen-presenting cells (APCs), as well as modifying the cytokine milieu to prevent the generation of memory T-cells. In this example, the additional deletion of the hilA gene from a therapeutic *Salmonella typhimurium* strain that is administered either intravenously or intratumorally focuses the *Salmonella typhimurium* infection towards phagocytic cells that do not require the SPI-1 T3SS for uptake, and then prolongs the longevity of these phagocytic cells. The hilA mutation reduces the quantity of pro-inflammatory cytokines, increasing the tolerability of the therapy, as well as the quality of the adaptive immune response.

Example 15

TREX1 Expression is Upregulated in Multiple Human Tumor Types

Figure 52:
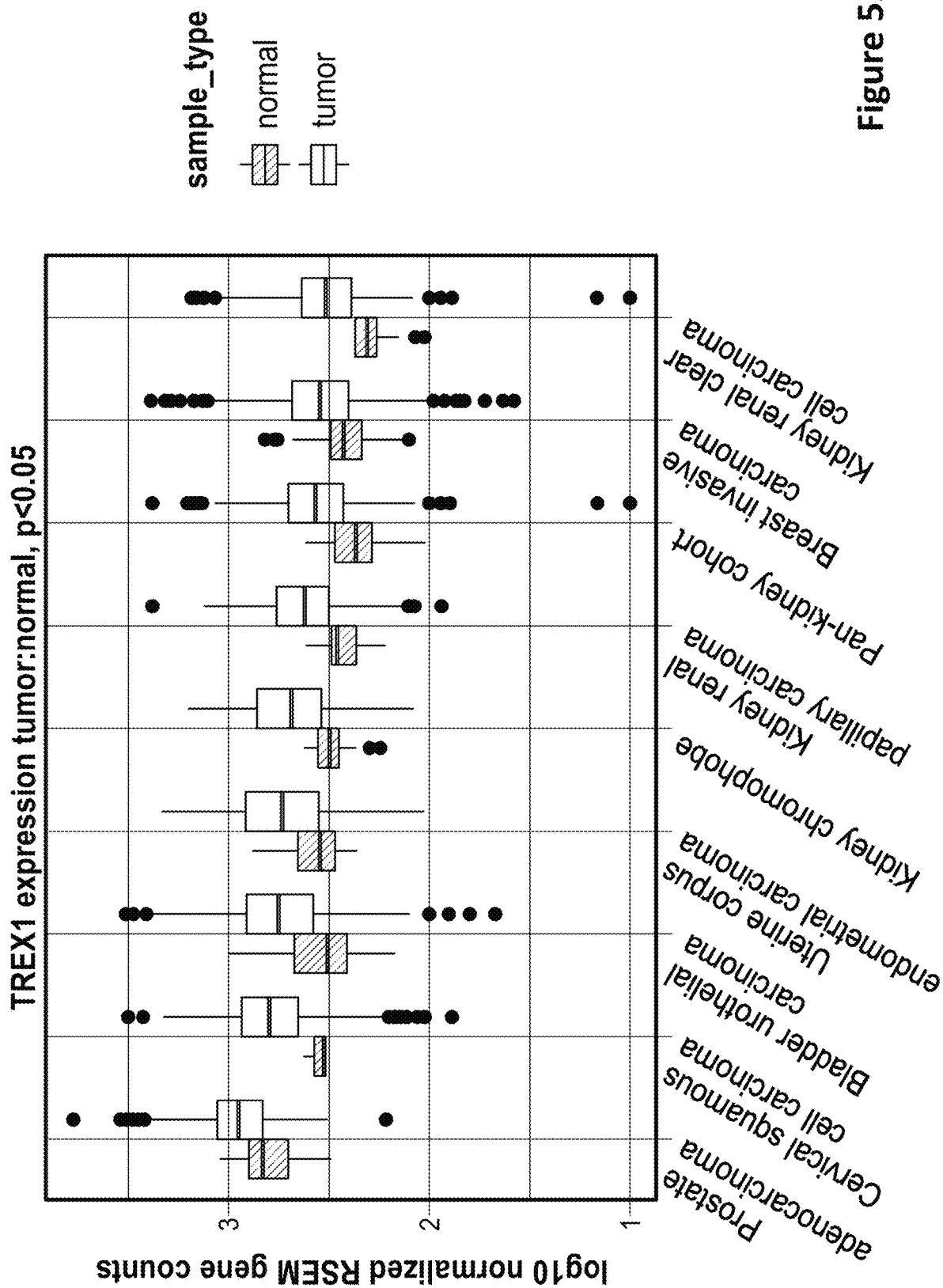
FIG. 52 depicts that TREX1 expression is increased in several human tumor types. Analysis of the relative gene expression of the TREX1 gene using the TCGA database was performed from a broad array of tumor types. Tumor types with a significant upregulation of TREX1 compared to normal tissue are displayed: prostate, breast, cervical, uterine and bladder (p values: BRCA—7.7e-16; PRAD—9.4e-12; UCEC—2.5e-05; BLCA—3.7e-03; CESC—7.7e-03) and multiple forms of kidney cancer (p values: KIPAN—8.9e-39; KIRC—9.6e-35; KTRP—5.8e-14; KICH—4.9e-08).

In order to evaluate whether TREX1 is found upregulated in tumor tissue as compared to normal human tissue, an analysis was performed to assess the relative gene expression of the TREX1 gene using the cancer genome atlas (TCGA) database. As shown in FIG. 52, a broad array of tumor types demonstrated significant upregulation of TREX1 compared to normal tissue, including breast, prostate, uterine, bladder and cervical (p values: BRCA: 7.7e-16; PRAD: 9.4e-12; UCEC: 2.5e-05; BLCA: 3.7e-03; CESC: 7.7e-03). In addition, TREX1 was found upregulated in multiple forms of kidney cancer (p values: KIPAN: 8.9e-39; KIRC: 9.6e-35; KTRP: 5.8e-14; KICH: 4.9e-08). These data validate the phenomenon of TREX1 upregulation broadly correlating with tumor progression, and support its targeting as a promising cancer therapeutic strategy, as provided herein.

Example 16

The Modified *Salmonella typhimurium* pEQU6 Strains Containing shRNA to Multiple Immune Targets Demonstrate Potent Anti-Tumor Growth Inhibition To compare the efficacy of a set of shRNA immune targets in a murine colon tumor flank model, 6-8 week-old female BALB/c mice (10 mice per group) were inoculated SC in the right and left flanks with CT26 ($2\times10^5$ cells in 100 µL PBS). Mice bearing established flank tumors were intratumorally (IT) injected twice, four days apart, on days 10 and 14 post tumor implantation into the right flank tumor with $5\times10^6$ CFUs each of YS1646, YS1646 (pEQU6-shVISTA), YS1646 (pEQU6-shBeta-catenin), or YS1646 (pEQU6-shTGF-beta), and compared to PBS control.

IT injection of AST-121 (YS1646 carrying pEQU6-shVISTA) induced significant tumor growth inhibition in the injected and distal tumors compared to the PBS control (injected tumor=75% TGI, p=0.01; distal tumor TGI=57% TGI, p=0.04), including one complete response, demonstrating the in vivo potency of inhibiting this immune checkpoint using this therapeutic modality. AST-122, (YS1646 carrying pEQU6-shTGF-beta) also demonstrated potent tumor inhibition of both the injected and distal lesions (injected tumor=52%; distal TGI=48.4%). AST-123 (YS1646 carrying pEQU6-shBeta-catenin) demonstrated tumor growth inhibition (injected TGI=33.1%, distal TGI=17% TGI), including one complete response. These strains were prepared in stationary phase instead of log-phase. In log-phase, SPI-1 would be expected to be maximally upregulated, which would have enhanced tumor cell targeting and improved the efficacy of targeting beta-catenin.

Example 17

Radiotherapy Enhances Tumor Colonization of Immunostimulatory Bacteria Containing a Plasmid Encoding a microRNA to TREX1 and Enhances Efficacy in Combination with Immune Checkpoint Blockade Radiation therapy has been shown to synergize with *S. typhimurium* to promote tumor growth inhibition. A previous study demonstrated enhanced tumor growth inhibition with the combination of a single IV administration of $5\times10^5$ CFU of *S. typhimurium* (YS1646) followed by 15 Gy radiation by in a murine B16.F10 melanoma flank model (Bermudes et al. (2001) *Biotechnol Genet Eng Rev.* 18:1).

To determine the effect of radiation on bacterial tumor colonization, 6-8 week-old female BALB/c mice were inoculated subcutaneously in the right flank with $1\times10^5$ mouse TSA breast carcinoma cells (in 100 µL PBS). Mice bearing established tumors were administered the following: 1) PBS IV followed by 0 Gy radiation (1 mouse); 2) IV injection of $5\times10^6$ CFUs of AST-106 (YS1646 transformed with pEQU6-miTREX1, ARI-203), followed 4 hours later with 0 Gy (3 mice); 3) $5\times10^6$ CFUs of AST-106, followed 4 hours later with 20 Gy (3 mice); 4) 20 Gy, followed 4 hours later with $5\times10^6$ CFUs of AST-106 (3 mice). Radiotherapy was administered using an XStrahl SARRP as described in Vanpouille-Box et al. (2017) *Nat. Commun.* 8:15618. Mice were sacrificed 24 hours later, and tumors were harvested and weighed. Tumors were homogenized in 10 mL sterile PBS (M tubes, GentleMACs™ Miltenyi Biotec), then 10-fold serial dilutions were performed and plated on LB (Luria Broth) agar plates containing kanamycin. The following day, colony forming units (CFUs) were counted and CFU per gram of tumor tissue was calculated.

Figure 53:
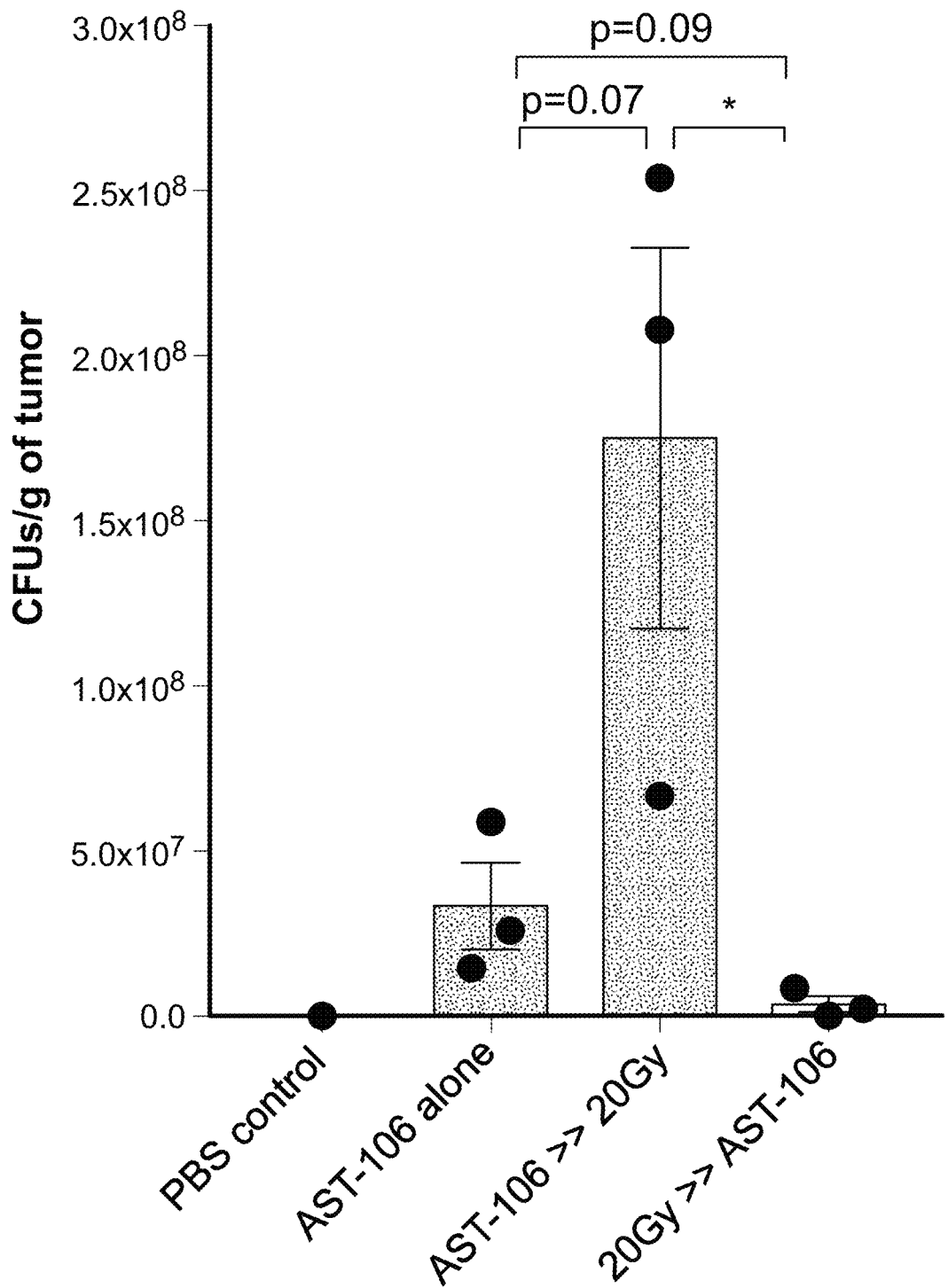
FIG. 53 depicts that radiotherapy after administration of *S. typhimurium* strain AST-106 increases tumor colonization. BALB/c mice (6-8 wk old) were inoculated subcutaneously in the right flank with $1 \times 10^5$ mouse TSA breast carcinoma cells. Mice bearing established tumors were administered the following: IV injection of $5 \times 10^6$ CFUs of AST-106 (YS1646 transformed with pEQU6-miTREX1) followed 4 hours later with 0 Gy (3 mice), or $5 \times 10^6$ CFUs of AST-106 followed 4 hours later with 20 Gy (3 mice); 20 Gy irradiation followed 4 hours later with $5 \times 10^6$ CFUs of AST-106 (3 mice), or PBS IV followed by 0 Gy radiation (1 mouse). Focal radiotherapy was administered using a small animal radiation research platform (SARRP) device (XStrahl Life Sciences). Mice were sacrificed 24 hours later, and tumors were harvested and weighed. Tumors were homogenized in 10 mL sterile PBS using M tubes in a GentleMACs™ device (Miltenyi Biotec), then 10-fold serial dilutions were performed and plated on LB agar plates containing kanamycin. The following day, colony forming units (CFU) were counted and CFU per gram of tumor tissue was calculated. *$p<0.05$, student's t-test.

As shown in FIG. 53, administration of 20 Gy of radiation prior to IV administration of AST-106 resulted in fewer CFU/g than administering AST-106 IV alone, with no radiation. Administration of 20 Gy of radiation after administration of AST-106 IV demonstrated significantly enhanced tumor colonization, compared to the opposite regimen (p<0.05).

Experiments are performed to determine whether IV administration of *S. typhimurium* containing shTREX1, prior to administering 20 Gy of radiation, would inhibit the activity of TREX1 and potentiate the abscopal activity of the radiation therapy. As discussed in the detailed description, TREX1 has been shown to suppress the abscopal anti-tumor efficacy of radiation, even with the addition of the checkpoint inhibitor anti-CTLA4. The potentiating effects of administration of the *S. typhimurium* containing shTREX1 prior to administration of the radiation therapy is further enhanced in the presence of anti-CTLA4 or anti-PD-1 therapy.

To demonstrate this, administration of the modified *S. typhimurium* shTREX1 is combined with 20 Gy of radiotherapy in the presence or absence of anti-CTLA4 or anti-PD-1 immune checkpoint blockade in a dual flank TSA murine mammary carcinoma model. For these studies, 6-8 week-old female BALB/c mice are inoculated subcutaneously in the right and left flanks with $1\times10^5$ mouse TSA breast carcinoma cells (in 100 µL PBS). Mice bearing established tumors are administered radiotherapy to the right flank tumor on concurrent days using an XStrahl SARRP as described in Vanpouille-Box et al. ((2017) Nat. Commun. 8:15618), in two doses of 20 Gy, or 3 fractions of 8 Gy on consecutive days. Mice are administered IV injections beginning 4 hours post the initial radiation treatment and repeated 4 and 7 days later with 1-5×10⁶ CFUs of the modified *Salmonella typhimurium* shTREX1, or the modified *Salmonella typhimurium* containing a scrambled shRNA control (modified *Salmonella typhimurium* scr). Some groups of mice are concurrently administered the checkpoint therapy anti-CTLA4 or anti-PD-1 (100 µg) or isotype control IP twice weekly. Mice are bled seven days following the last IV modified *Salmonella typhimurium* injection and PBMCs assessed for the ability to produce IFN-γ in response to the immunodominant $CD8^+$ T cell epitope AH1 [SPSYVYHQF]-specific tetramer by flow cytometry. Separate groups of mice are harvested for spleen, tumor and tumor-draining lymph nodes 48 hours and 7 days post modified *Salmonella typhimurium* IV treatment and assessed for lymphoid and myeloid populations by flow cytometry, and tissue is assessed for CFUs by homogenization and plating on LB agar plates. Remaining mice are assessed for tumor growth in the primary irradiated tumor and the distal (abscopal) tumor by caliper measurements, and mice that demonstrate complete tumor regression are re-challenged with autologous tumors and compared to age-matched, tumor-naïve mice. Separate groups of mice are depleted of $CD4^+$ and/or $CD8^+$ T cells prior to re-challenge, to demonstrate the requirement for adaptive immunity. These data demonstrate that inhibition of Trex1 in the context of high dose radiation therapy enhances the anti-tumor immunity of the combined immunotherapies.

Example 18

The Addition of Anti-PD-1 Antibody to Modified *Salmonella typhimurium* Therapy Containing Plasmid Encoding Anti-TREX1 microRNA Enhances Distal Tumor Regression in a CD8-Dependent Manner in the Dual Flank Murine Colon Carcinoma Model To demonstrate that addition of anti-PD-1 checkpoint therapy can enhance the efficacy of AST-106 (YS1646 carrying a plasmid encoding a microRNA to TREX1), 6-8 week-old female BALB/c mice (10 mice per group) were inoculated subcutaneously (SC) in the right and left flanks with CT26 (2×10⁵ cells in 100 µL PBS) to establish tumors. Mice bearing established flank tumors were intratumorally (IT) injected on days 10 and 14 post tumor implantation into the right flank tumor with 5×10⁶ CFUs of AST-106 (YS1646 transformed with pEQU6-miTREX1, ARI-203), or AST-103 (YS1646 transformed with pEQU6-scrambled shRNA), and compared to PBS control, either alone or in combination with weekly IP injections of anti-PD-1 (4 mg/kg, clone RMP1-14, BioXCell). To determine whether the primary and distal tumor efficacy was dependent on CD8a T cells and DCs, groups were administered anti-CD8a depleting antibody IP on days 5 and 7, prior to IT injection, and then on days 10, 14 and 17 (4 mg/kg, clone 2.43, BioXCell).

IT injection of AST-106, the YS1646 strain containing a plasmid encoding a miTREX1, induced significant tumor growth inhibition in the injected tumor and distal tumors, compared to PBS control (injected TGI: 67.5%, distal TGI: 67.2%; p=0.027). This anti-tumor activity was completely abrogated with depletion of $CD8\alpha^+$ cells (injected TGI: 14.6%, distal TGI: 0%), demonstrating the requirement for cytolytic $CD8^+$ T cells and $CD8\alpha^+$ DCs for AST-106 anti-tumor activity. The administration of anti-PD-1 antibody with AST-106 further enhances the activity of the AST-106, resulting in 2/10 complete remissions. This effect also was completely reversed upon $CD8\alpha^+$ cell depletion. No other groups of mice, other than those treated with the combination of AST-106 miTREX1 with anti-PD1 mAb, resulted in complete dual flank remissions, including the scramble control (AST-103) with anti-PD-1 antibody, or the anti-PD-1 antibody alone. These data demonstrate that engineered *S. typhimurium* containing a plasmid encoding an anti-TREX1 inhibitory microRNA induces a potent, CD8α-dependent adaptive immune response. This activity is synergistic with anti-PD-1 checkpoint therapy.

Example 19

Examples of Additional Therapeutic Bacteria and Combination Therapy

The table below sets forth, in the first column, targets of the RNA; the second column sets forth combinations of targets encoded by RNA in the plasmid; the third column sets forth the types (format) of the encoded RNA in the plasmids; and the fourth column sets forth exemplary additional therapeutic agents that can be used in combination therapy with the immunostimulatory bacteria in the table, or herein. The next column lists modifications to the genome of the bacterial strain, and the last column describes features of plasmids that can be used. Each of the listed elements in the columns can be matched with any other elements/features listed in the table and provided throughout the disclosure herein. The bacterium can be any therapeutic bacterium, particularly any listed throughout the disclosure herein, such as, but not limited to, *Salmonella, Shigella, E. coli, Bifidobacteriae, Rickettsia, Vibrio, Listeria, Klebsiella, Bordetella, Neisseria, Aeromonas, Francisella, Cholera, Corynebacterium, Citrobacter, Chlamydia, Haemophilus, Brucella, Mycobacterium, Mycoplasma, Legionella, Rhodococcus, Pseudomonas, Helicobacter, Bacillus*, and *Erysipelothrix*. Exemplary of such bacteria are *Salmonella* strains, such as *S. typhimurium*. Among the *Salmonella typhimurium* strains are the well known strains designated VNP20009 (ATCC #202165), RE88, SL7207, χ8429, χ8431, and χ8468.

| Target | RNAi + RNAi Combinations | RNAi format | Therapeutic Combinations | Therapeutic Strains | Plasmid features |
|---|---|---|---|---|---|
| TREX1 | TREX1 + PD-L1 | shRNA | anti-PD-1 mAb | asd knockout | encodes asd gene |
| PD-L1 | TREX1 + VISTA | microRNA | anti-CTLA4 mAb | purI (purM) knockout | low copy origin |
| VISTA | TREX1 + SIRP-alpha | shRNA with RIG-I binding element | anti-VEGF mAb | msbB knockout | medium copy origin |

-continued

| Target | RNAi + RNAi Combinations | RNAi format | Therapeutic Combinations | Therapeutic Strains | Plasmid features |
|---|---|---|---|---|---|
| TGF-beta | PD-L1 + TGF-beta | micro RNA with RIG-I binding element (polyA) | Radiation Therapy | cytoLLO knock-in | U6 Promoter |
| beta-catenin | PD-L1 + beta-catenin | | Immunogenic chemotherapy: nimustine, carmustine, fotemustine, topotecan, cisplatin, irinotecan, doxorubicin and etoposide | purD knockout | H1 Promoter |
| SIRP-alpha | PD-L1 + VISTA | | | flagellin (fliC/FljB) knockout | CMV Promoter for RNAi expression |
| VEGF | TGF-beta + VISTA | | | pagP knockout | removable Kan Cassette |
| Rnase H2 | SIRP-alpha + VISTA | | | adrA knockout | SV40 DNA nuclear targeting sequence |
| Dnase II | TREX1 + Rnase H2 | | | hilA knockout | CpG sequences |
| CLEVER-1/Stabilin-1 | | | | | |

These RNAi's and any described herein can be encoded in any oncolytic virus for use in anti-tumor therapy.

Example 20

Figure 54:
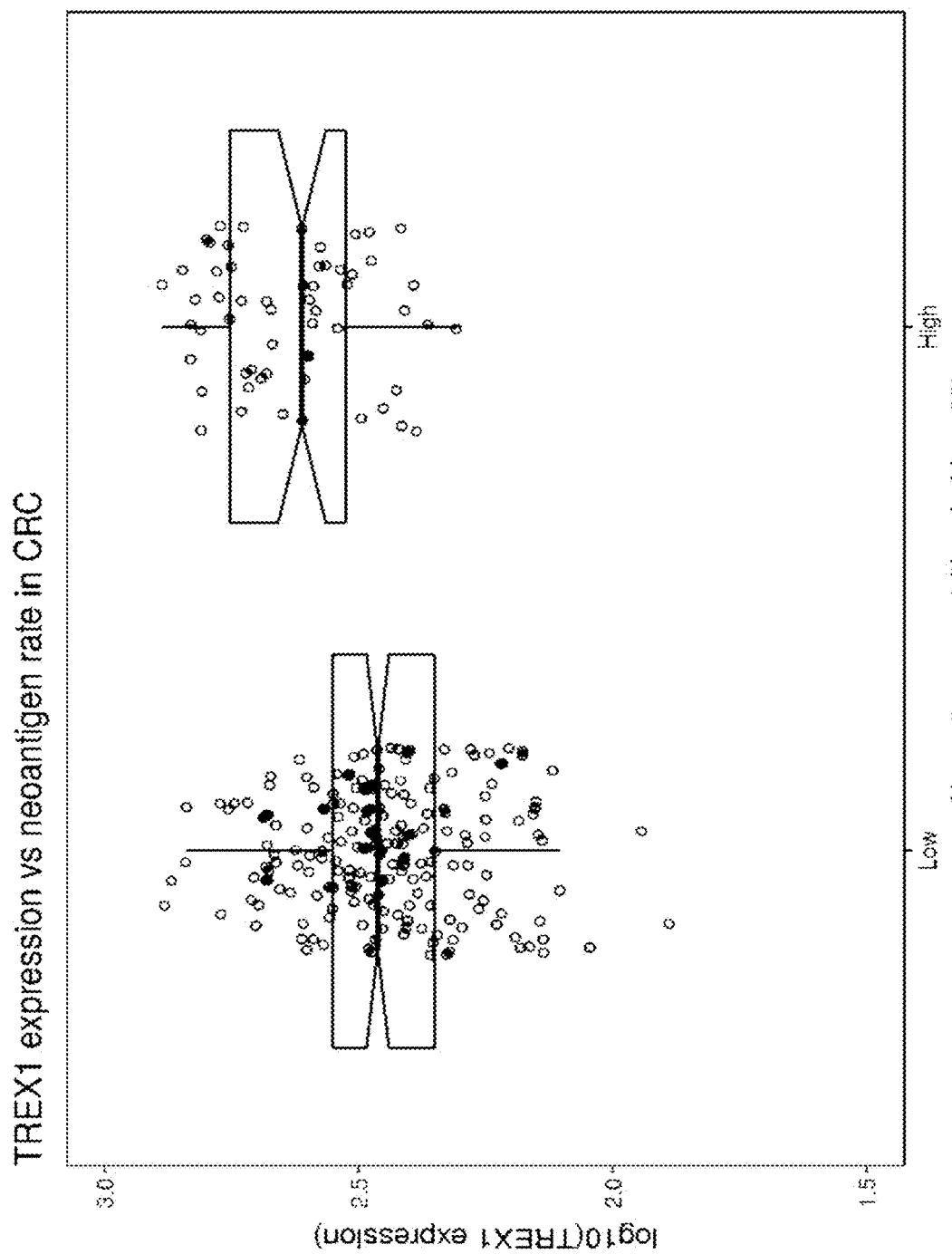
FIG. 54 depicts the correlation between TREX1 expression and neoantigen rate in colorectal cancer. TREX1 expression was correlated with non-silent and silent mutational burden, across the Cancer Genome Atlas (TCGA), and by tumor type. The number of single nucleotide variants predicted to generate neoantigen peptides (SNV neoantigen rate) was correlated with TREX1 expression in colorectal cancers (COAD) and compared to normal tissue.

TREX1 Expression is Correlated with Mutational Burden in Human Colorectal Cancer An analysis was performed to assess the relative gene expression of the TREX1 gene using the Cancer Genome Atlas (TCGA) database. TREX1 expression was correlated with non-silent and silent mutational burden, across TCGA and by tumor type. The number of single nucleotide variants predicted to generate neoantigen peptides (SNV neoantigen rate) correlated with TREX1 expression in colorectal cancers (COAD). As shown in FIG. 54, when binned with a neoantigen threshold of 100, COAD demonstrated significant upregulation of TREX1 compared to normal tissue, (a t-test of log 10 TREX1 expression calculated the 95% confidence interval for the difference in means to be between 0.14 and 0.23, i.e., an expression fold change of 1.4 to 1.7). These data validate the phenomenon of TREX1 upregulation correlating with mutation rate in colorectal cancer, and the use of TREX1 as a target for a cancer therapeutic strategy.

Example 21

Figure 55:
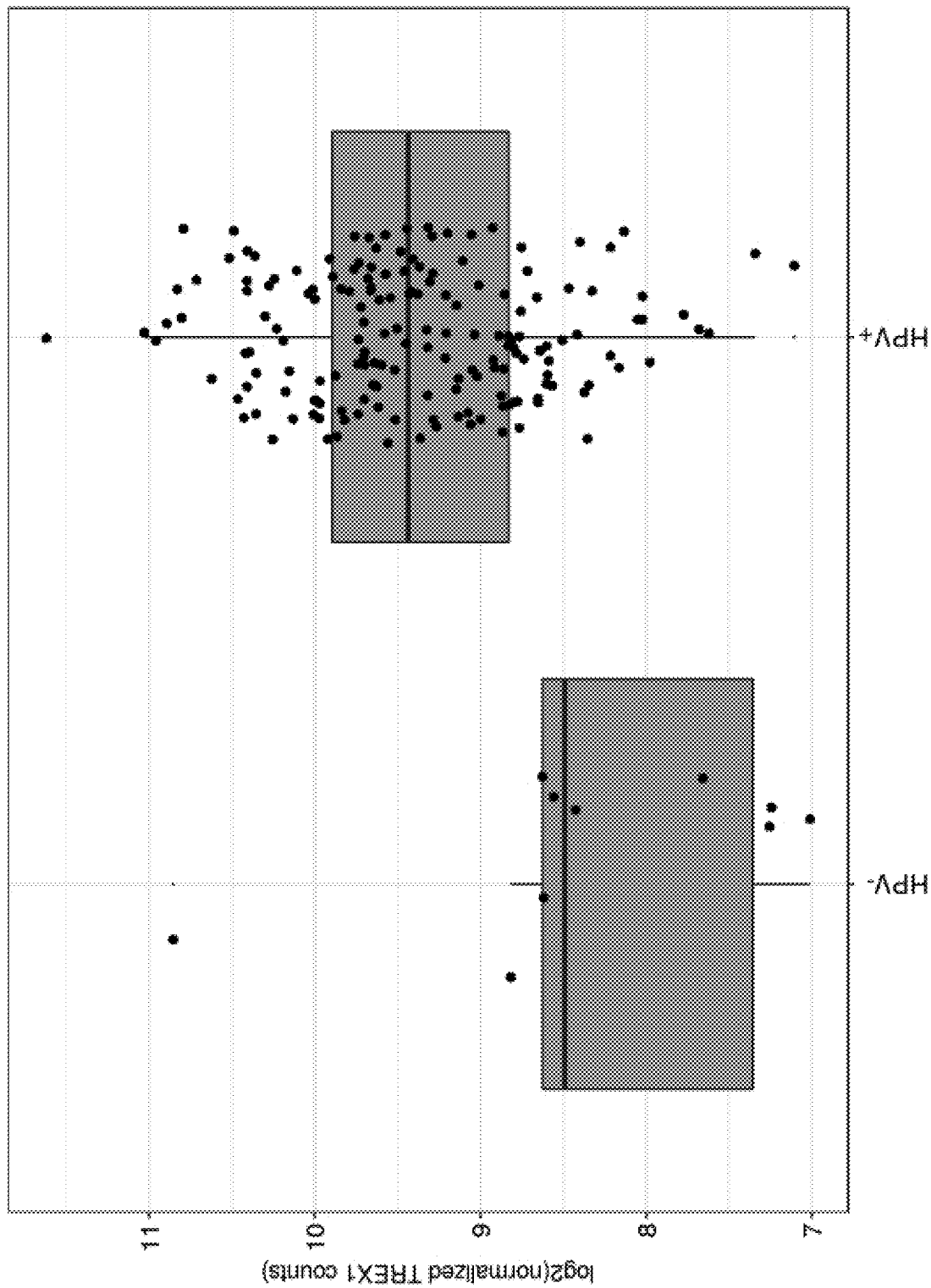
FIG. 55 depicts the correlation between TREX1 expression in HPV negative vs. HPV positive cervical carcinoma (CESC) tumor samples in the Cancer Genome Atlas (TCGA) database (p=0.01).
Figure 56:
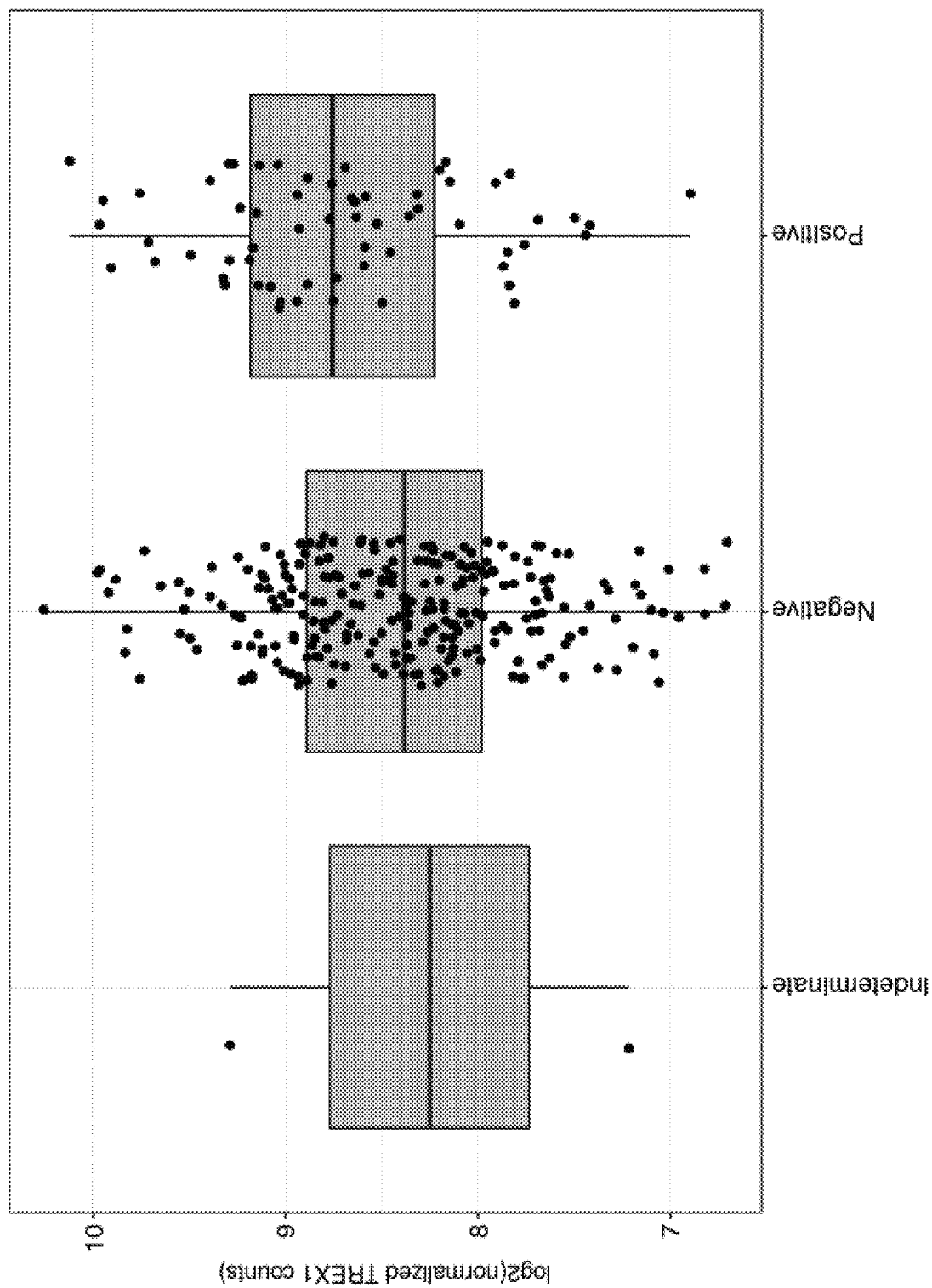
FIG. 56 depicts the correlation between TREX1 expression in HPV negative vs. HPV positive Head and Neck Cancer (HNSCC) tumor samples in the Cancer Genome Atlas (TCGA) database (p=0.002).
Figure 57:
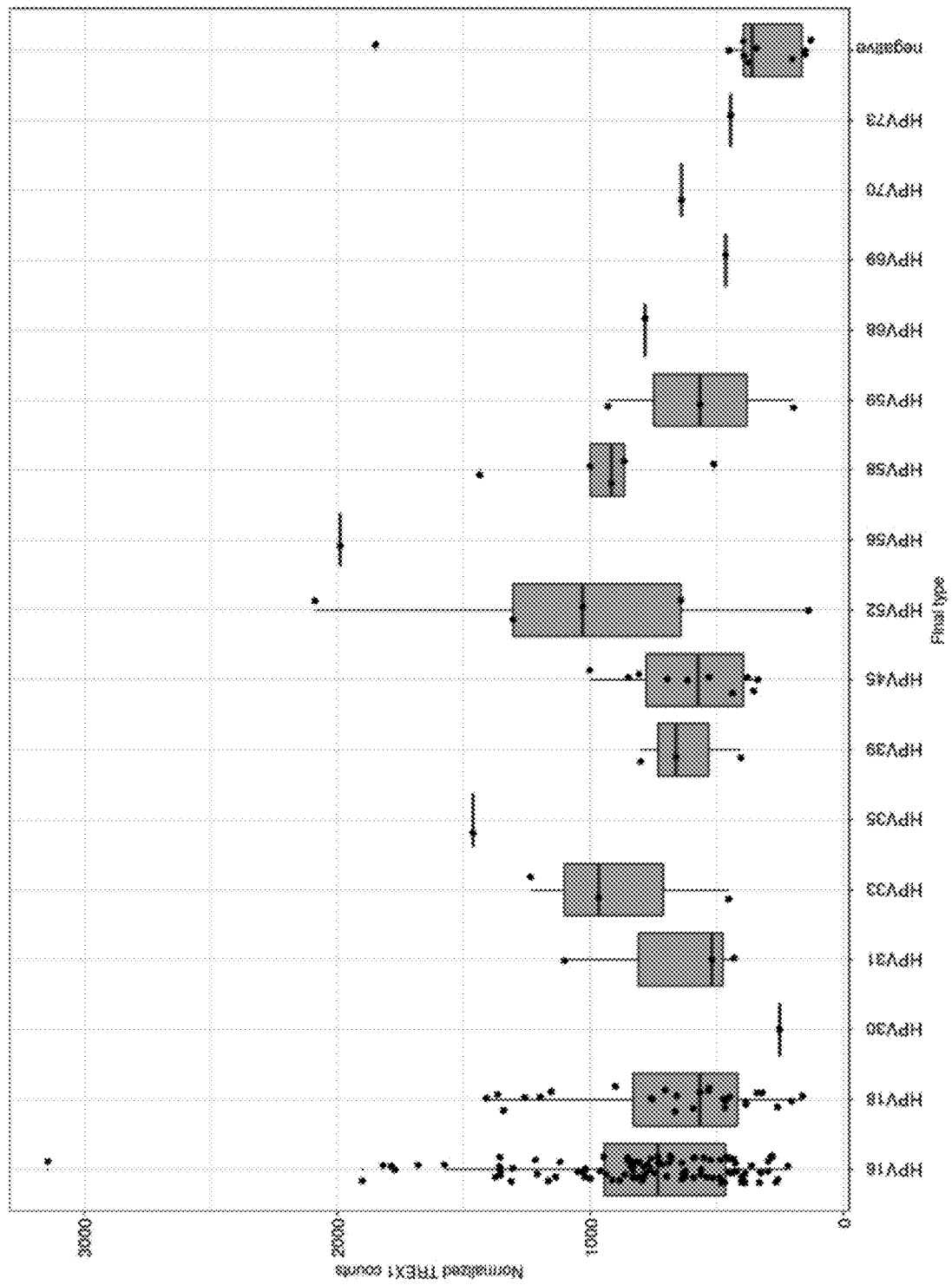
FIG. 57 depicts the correlation between TREX1 expression and HPV serotype in HPV positive cervical carcinoma (CESC) tumor samples in the Cancer Genome Atlas (TCGA) database. HPV16+, HPV18+, HPV30+, HPV31+, HPV33+, HPV35+, HPV39+, HPV45+, HPV52+, HPV56+, HPV58+, HPV59+, HPV68+, HPV69+, HPV70+ and HPV73+ serotype driven CESC tumors and HPV negative CESC tumors were evaluated.
Figure 58:
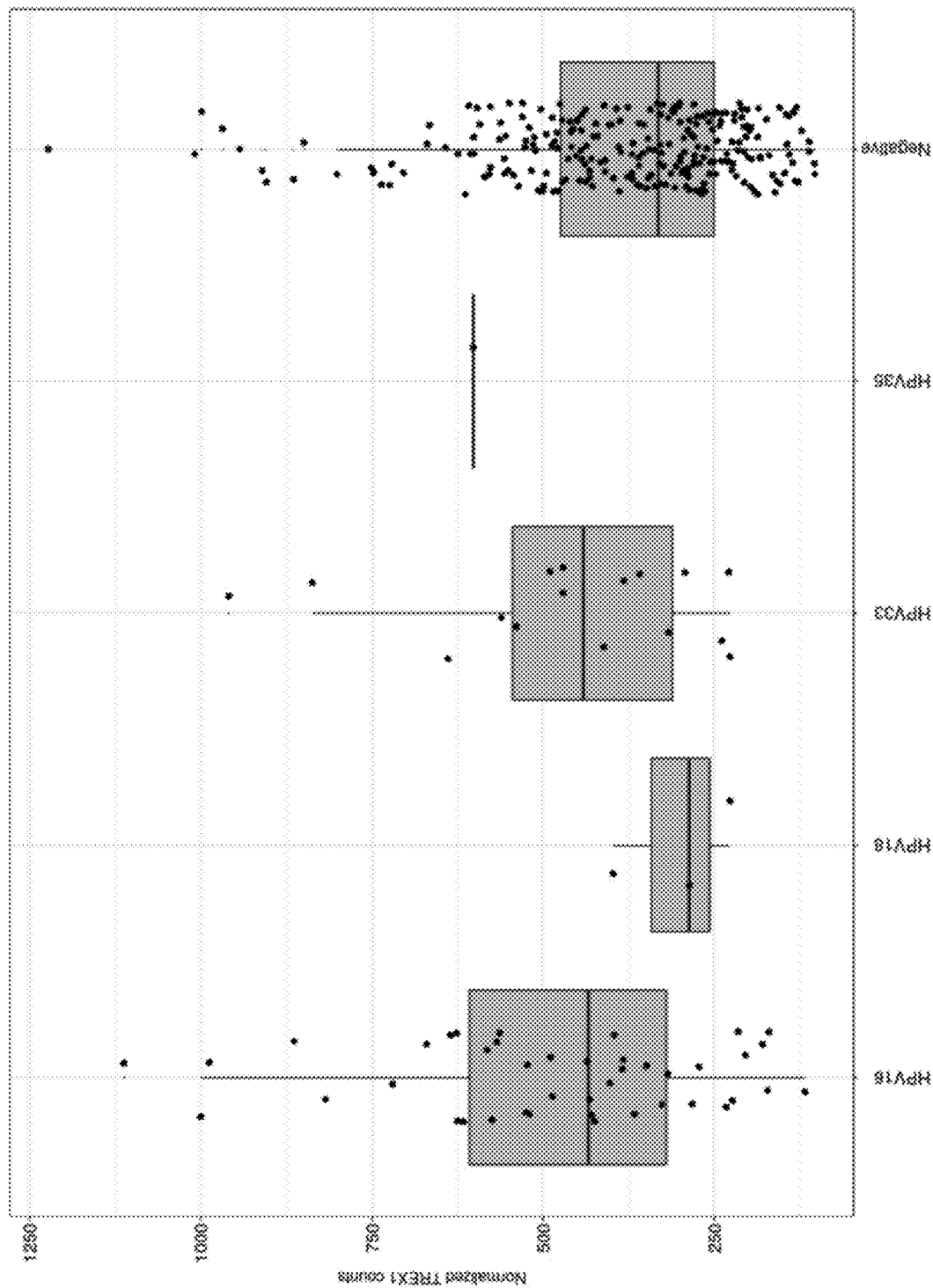
FIG. 58 depicts the correlation between TREX1 expression and HPV serotype in HPV positive Head and Neck Cancer (HNSCC) tumor samples in the Cancer Genome Atlas (TCGA) database. HPV16+, HPV18+, HPV33+ and HPV35+ serotype driven HNSCC tumors and HPV negative HNSCC tumors were evaluated.

TREX1 Expression is Correlated with Virally-Driven Human Cervical and Head and Neck Cancers An analysis was performed to correlate the relative gene expression of the TREX1 gene in viral negative vs. positive tumor samples in the Cancer Genome Atlas (TCGA) database. For cervical carcinoma (CESC) and Head and Neck Cancer (HNSCC), there is a correlation of increased TREX1 expression in human papillomavirus (HPV) infected patients (FIG. 55 and FIG. 56, respectively). In CESC, the p-value was 0.01, and in HNSCC, the p-value was 0.002. In cervical carcinoma (CESC), TREX1 expression is most correlated with HPV18+ and HPV16+ serotype driven cancer (HPV18+, p-value=0.009; HPV16+, p-value=0.0005, Mann Whitney U test) (FIG. 57). In head and neck carcinoma (HNSCC), TREX1 expression is most correlated with HPV16+ tumors (HPV16+, p-value=0.004; HPV33+, p-value=0.08, Mann Whitney U test) (FIG. 58). These data validate and demonstrate that TREX1 upregulation broadly correlates with virally-driven cancers, demonstrating that TREX1 is a therapeutic target for HPV-driven cervical and head and neck cancers, as provided herein.

Example 22

PagP Deletion Mutants have Penta-Acylated LPS and Induce Reduced Inflammatory Cytokines The pagP gene was deleted from the asd gene-deleted strain of S. typhimurium YS1646 (which contains a purI/M and msbB deletion), using the lambda-derived Red recombination system as described in Datsenko and Wanner (Proc. Natl. Acad. Sci. USA 97:6640-6645 (2000)) to generate the strain PagP/ASD. This strain was then electroporated with a plasmid containing a functional asd gene (to complement the deleted asd gene and to ensure plasmid maintenance in vivo) and a eukaryotic expression cassette containing the U6 promoter driving expression of a microRNA targeting murine TREX-1 (pATI-miTREX1) to generate the strain PagP/ASD (pATI-miTREX1). The Lipid A was then extracted from this strain and evaluated by matrix-assisted laser desorption/ionization mass spectrometry (MALDI MS) and compared to wild-type S. typhimurium strain ATCC 14028, strain YS1646 (which is deleted for msbB and purM), and strain YS1646 deleted for the asd gene and complimented with the pATI-miTREX1 plasmid. Wild-type Salmonella had a minor lipid A peak with a mass of 2034, and a major peak with a mass of 1796, corresponding to the hepta-acylated and hexa-acylated species, respectively, due to the presence of functional msbB and purM genes. The msbB deleted strains YS1646 and ASD (pATI-miTREX1) had major peaks at 1828 and 1585, corresponding to a mixture of hexa-acylated and penta-acylated LPS. The msbB and pagP deleted strain, PagP/ASD (pATI-miTREX1) had only a single peak with a mass of 1585. These data demonstrate that deletion of pagP prevents palmitoylation of the LPS, thereby restricting it to a single penta-acylated species.

To determine whether the penta-acylated LPS from the pagP mutant strains reduced TLR-4 signaling, 4 μg of purified LPS from the strains described above were added to THP-1 human monocytic cells, and the supernatants were evaluated 24 hours later for the presence of inflammatory cytokines using a cytometric bead array (CBA) kit (BD Biosciences). The LPS from the pagP⁻ strain induced ¼ the amount of TNF-alpha compared to wild-type LPS, and 7-fold less IL-6 than wild-type. The pagP⁻ mutant LPS induced 22-fold less IL-6 than YS1646, demonstrating that the penta-acylated LPS species from a pagP⁻ mutant is significantly less inflammatory in human cells, and indicating that the pagP⁻ mutant would be better tolerated in humans.

Example 23

FLG, HilA and PagP Deletion Mutants are More Attenuated than Strain YS1646 in Mice To determine whether the modified strains described above are more attenuated than strain YS1646, a median lethal dose ($LD_{50}$) study was conducted. C57BL/6 mice were injected intravenously with increasing concentrations of strains YS1646, FLG/ASD (pATI-TREX1), HilA/ASD (pATI-TREX1), or PagP/ASD (pATI-TREX1). The $LD_{50}$ for strain YS1646 was found to be $1.6 \times 10^6$ CFUs, which is consistent with published reports of this strain. The $LD_{50}$ for the HilA/ASD (pATI-TREX1) strain was determined to be $5.3 \times 10^6$ CFUs, demonstrating a 3-fold reduction in virulence. The $LD_{50}$ for the PagP/ASD (pATI-TREX1) strain was determined to be $6.9 \times 10^6$ CFUs, demonstrating a 4-fold reduction in virulence. The $LD_{50}$ for the FLG/ASD (pATI-TREX1) strain was determined to be $>7 \times 10^6$ CFUs, demonstrating a >4.4-fold reduction in virulence compared to strain YS1646. These data indicate that the genetic modifications described above reduce the virulence of the *S. typhimurium* therapy and will lead to increased tolerability in humans. In the Phase I clinical trial of VNP20009 (Toso et al. (2002) *J. Clin. Oncol.* 20(1):142-152), the presence of the bacteria in patients' tumors was only partially observed at the two highest doses tested, 3E8 CFU/m² (33% presence), and 1E9 CFU/m² (50% presence), indicating that the tolerable dose of VNP20009 was too low to achieve colonization. By improving the tolerability of the strains through the modifications described above, higher doses can be administered than VNP20009. This improves both the percentage of patients that will have their tumors colonized, and the level of therapeutic colonization per tumor.

Example 24 pagP⁻/fljB⁻/fliC⁻, and pagP⁻/fljB⁻/fliC⁻ Strains Demonstrate Significantly Higher Viability in Human Serum Compared to VNP20009 (YS1646)

As described herein, VNP20009 (YS1646) exhibits limited tumor colonization in humans after systemic administration. It is shown herein that VNP20009 is inactivated by complement factors in human blood. To demonstrate this, strains YS1646 and *E. coli* D10B were compared to exemplary immunostimulatory bacteria provided herein that contain additional mutations that alter the surface of the bacteria. These strains were YS1646 (pagP⁻), YS1646 (fljB⁻/fliC⁻), and YS1646 (pagP⁻/fljB⁻/fliC⁻). These three strains, in addition to YS1646 and *E. coli* D10B cultures, were incubated with serum or heat-inactivated (HI) serum from either pooled mouse blood or pooled healthy human donors (n=3), for 3 hours at 37° C. After incubation with serum, bacteria were serially diluted and plated on LB agar plates, and the colony forming units (CFUs) were measured.

In mouse serum, all strains remained 100% viable and were completely resistant to complement inactivation. In human serum, all strains were 100% viable in the heat-inactivated serum. The *E. coli* D10B strain was completely eliminated after 3 hours in whole human serum. The YS1646 strain exhibited only 6.37% of live colonies, demonstrating that tumor colonization of the YS1646 clinical strain was limited due to complement inactivation in human blood. For the YS1646 (fljB⁻/fliC⁻) strain, 31.47% of live colonies remained, and for the YS1646 (pagP⁻) strain, 72.9% of live colonies remained, after incubation with human serum for 3 hours. The combined YS1646 (pagP⁻/fljB⁻/fliC⁻) strain was completely resistant to complement in human serum.

These data show why VNP20009 had very low tumor colonization when systemically administered. It is shown herein that VNP20009 (YS1646) is highly sensitive to complement inactivation in human serum, but not mouse serum. These data explain why limited tumor colonization was observed in humans, while mouse tumors were colonized at a high level. The fljB/fliC or pagP deletions, or the combination of these mutations, partially or completely rescues this phenotype. Thus, the enhanced stability observed in human serum with the fljB/fliC, pagP, or pagP/fljB/fliC deletion strains provides for increased human tumor colonization.

These data and other provided herein (see, e.g., Examples 8, 22 and 23, above), show that deletion of the flagella and/or pagP increases tumor colonization, improves tolerability, and increases the anti-tumor activity of the immunostimulatory bacteria. Example 22 demonstrates that LPS from immunostimulatory bacteria that are pagP⁻ induced 22-fold less TL-6 than LPS from YS1646, and therefore, pagP⁻ bacteria are less inflammatory in human cells. Example 23 demonstrates that each and all of FLG, hilA and pagP deletion mutants are more attenuated than YS1646.

Immunostimulatory bacteria, such as *Salmonella* strains, including wild-type strains, that are one or both of flagellin and pagP exhibit properties that increase tumor/tumor microenvironment colonization and increase anti-tumor activity. Such strains can be used to deliver a therapeutic payload, such as an immunotherapeutic product and/or other anti-tumor product, and also can include modifications that improve therapeutic properties, such as deletion of hilA and/or msbB, adenosine auxotrophy, and other properties as described elsewhere herein. The resulting strains are more effectively targeted to the tumor/tumor microenvironment, by virtue of the modifications that alter infectivity, toxicity to certain cells, and nutritional requirements, such as auxotrophy for purines, that are provided in the tumor environment.

Example 25 fljB−/fliC− Immunostimulatory Bacterial Strain Demonstrates Tumor Myeloid Cell-Specific Colonization In Vivo The asd and flagellin (fljB/fliC) genes were deleted from strain YS1646, which is purI−/msbB−, using the lambda-derived Red recombination system as described previously (see, Datsenko and Wanner (2000) *Proc. Natl. Acad. Sci. USA* 97:6640-6645), to generate the strain YS1646 ΔFLG/ΔASD. Strain YS1646 ΔFLG/ΔASD was then transformed by electroporation with the bacterial plasmid pRPSM-mCherry, containing 1) a functional asd expression cassette to complement the chromosomal deletion of asd for in vivo plasmid maintenance, and 2) a constitutive mCherry expression cassette under control of the bacterial rpsm promoter (rpsm-mCherry). Bacterial colonies transformed with this plasmid were visibly red in color, due to expression of the mCherry red fluorescent protein. To evaluate tumor colonization, the transformed bacterial strain (YS1646 ΔFLG/ΔASD (pRPSM-mCherry)) was tested in vivo in a murine colon carcinoma model. 6-8 week-old female C57BL/6 mice (3 mice per group) were inoculated subcutaneously in the right flank with MC38 cells ($5\times10^5$ cells in 100 μL PBS). Mice bearing large, established flank tumors were intravenously injected with $1\times10^6$ CFUs of YS1646 ΔFLG/ΔASD (pRPSM-mCherry). Tumors were harvested 3 days later and dissociated into a single cell suspension (Miltenyi Biotec). Cells were stained with Zombie Aqua™ fixable viability dye (BioLegend), which penetrates dead, but not live, cells. The cells were incubated with the following antibodies: Brilliant Violet 510™ anti-mouse CD45 (clone 30-F11, BioLegend); Brilliant Violet 421™ anti-mouse CD8a (clone 53-6.7, BioLegend); PE anti-mouse CD3F (clone 145-2C11, BioLegend); FITC anti-mouse CD4 (clone RM4-5, BioLegend); PE/Cy7 anti-mouse/human CD11b (clone M1/70, BioLegend); Brilliant Violet 785™ anti-mouse Ly6C (clone HK1.4, BioLegend); Brilliant Violet 605™ anti-mouse Ly6G (clone 1A8, BioLegend); APC anti-mouse F4/80 (clone BM8, BioLegend); and PercP/Cy5.5 anti-mouse CD24 (clone M1/69, Biolegend). The cells were then sorted by flow cytometry (Novocyte) using the various surface markers and mCherry+ (PE Texas Red), to determine/localize bacterial uptake by the harvested cells.

CD45− cells, which include stromal and tumor cells, demonstrated no detectable bacterial colonization, with 0.076% cells being positive for mCherry, compared to a background staining level of 0.067%. CD45+ tumor-infiltrating myeloid cells were positive for mCherry, with 7.27% of monocytes, 3.33% of dendritic cells (DCs), and 8.96% of macrophages being positive for mCherry, indicating uptake of the YS1646 ΔFLG/ΔASD (pRPSM-mCherry) bacteria. A control strain, containing intact flagella, was tested in parallel. Unlike the ΔFLG strain, the flagellin+ control strain infected CD45− cells, with 0.36% of CD45− cells being positive for mCherry, which was 5.37-fold greater than background staining (0.067%). The flagellin+ control strain also infected CD45+ myeloid populations, with 5.71% of monocytes, 5.56% of DCs, and 9.52% of macrophages being positive for mCherry. These data indicate that flagella knockout strains accumulate in the myeloid cell populations of the tumor, but not in the tumor or stromal cells, whereas strains with intact flagella infect all cell types. Thus, flagella knockout strains demonstrate tumor myeloid-specific colonization in vivo.

Example 26

Flagella Knockout (ΔfljB/ΔfliC) and ΔpagP Strains Demonstrate Increased Tolerability and Decreased Immunogenicity In Vivo The pagP gene was deleted from the *S. typhimurium* strains YS1646 ΔASD and YS1646 ΔFLG/ΔASD, generating the strains YS1646 ΔPagP/ΔASD and YS1646 ΔPagP/ΔFLG/ΔASD, respectively. Strains YS1646 ΔFLG/ΔASD, YS1646 ΔPagP/ΔASD, and YS1646 ΔPagP/ΔFLG/ΔASD were transformed by electroporation with plasmids encoding the asd gene, as well as a eukaryotic expression cassette encoding murine IL-2 (muIL-2). To test the tolerability of these strains in vivo, an $LD_{50}$ study was performed in 6-8 week old female BALB/c mice. The mice were intravenously injected with $3\times10^5$, $1\times10^6$, $3\times10^6$, $1\times10^7$, or $3\times10^7$ CFUs of strains YS1646, YS1646 ΔFLG/ΔASD (muIL-2), YS1646 ΔPagP/ΔASD (muIL-2), or YS1646 ΔPagP/ΔFLG/ΔASD (muIL-2). The mice were then monitored for morbidity and mortality, and the $LD_{50}$ values were calculated. The results are shown in the table below.

| Bacterial Strain | $LD_{50}$ (CFUs) |
| --- | --- |
| YS1646 | $7.24 \times 10^6$ |
| YS1646 ΔFLG/ΔASD (muIL-2) | $2.07 \times 10^7$ |
| YS1646 ΔPagP/ΔASD (muIL-2) | $1.39 \times 10^7$ |
| YS1646 ΔPagP/ΔFLG/ΔASD (muIL-2) | Not calculated |

The $LD_{50}$ values for the YS1646 ΔFLG/ΔASD (muIL-2) and YS1646 ΔPagP/ΔASD (muIL-2) strains were higher than the $LD_{50}$ value for the parental YS1646 strain, indicating that the tolerability of the flagellin− and pagP deletion mutants, expressing murine IL-2, was higher in vivo. The $LD_{50}$ for strain YS1646 ΔPagP/ΔFLG/ΔASD (muIL-2) was not calculated, as no animals died during the duration of the study, but was greater than $6.2\times10^7$ CFUs, representing a near 10-fold improvement in the tolerability, compared to the parental YS1646 strain.

To compare the immunogenicity of the different bacterial strains, mice that survived the $3\times10^6$ CFU dose (N=5, except YS1646, where N=4) were bled at day 40 post intravenous dosing, and anti-*Salmonella* serum antibodies were titered. Sera from mice treated with the various mutant bacterial strains, and from control mice, were seeded in a 96-well PCR plate and serially diluted in PBS. Cultures of the *S. typhimurium* strains containing the pRPSM-mCherry plasmid were spun down and washed, then resuspended in flow-cytometry fixation buffer. For the assay, 25 μl of the mCherry+ bacterial cultures, containing $1\times10^6$ CFUs, were added to the sera and incubated for 25 minutes at room temperature. Following incubation, the bacterial samples were centrifuged and washed twice with PBS by spinning them at 4000 RPM for 5 min, and then resuspended in PBS containing a secondary goat anti-mouse Fc Alexa Fluor® 488 antibody (1/400 dilution from stock), and incubated for 25 minutes at room temperature in the dark. The samples were then washed three times with PBS by spinning them at 4000 RPM for 5 min, resuspended in PBS, and analyzed by flow cytometry (Novocyte). The results showed that the mice injected with parental strain YS1646 had the highest serum antibody titers, with an average mean fluorescence intensity (MFI) of 29,196±20,730. Sera from mice injected with strain YS1646 ΔFLG/ΔASD (muIL-2) had an MFI of 7,941±9,290; sera from mice injected with strain YS1646 ΔPagP/ΔASD (muIL-2) had an MFI of 3,454±3,860; and sera from mice injected with strain YS1646 ΔPagP/ΔFLG/

ΔASD (muIL-2), had the lowest serum antibody titers, with an MFI of 2,295±2,444. The data demonstrate that deletion of the genes encoding the flagella (fljB/fliC) or pagP result in strains with decreased immunogenicity, and that the combination of mutations (ΔPagP/ΔFLG) further decreases the immunogenicity, compared to the parental strain without the deletions.

Overall, the data demonstrate the improved tolerability and decreased immunogenicity of the ΔFLG and ΔPagP strains, with the ΔPagP/ΔFLG/ΔASD strain demonstrating the most favorable tolerability and lowest immunogenicity.

Since modifications will be apparent to those of skill in the art, it is intended that this invention be limited only by the scope of the appended claims.

What is claimed:

1. A method for treating a subject with cancer with a three prime repair exonuclease 1 (TREX1) antagonist, comprising administering the TREX1 antagonist to a subject identified as having a tumor that will be responsive to treatment with a TREX1 antagonist, wherein:
   the identified subject is one whose tumor has a high tumor mutational burden (TMB) or whose tumor is positive for human papillomavirus (HPV);
   the TREX1 antagonist inhibits the expression of TREX1 or inhibits TREX1;
   TMB in a tumor is the number of somatic mutations per megabase (Mb) of the genome of the tumor; and
   high TMB is at least 10 mutations per Mb of the genome of the tumor.

2. The method of claim 1, wherein the TREX1 antagonist is encoded in an immunostimulatory bacterium or oncolytic virus.

3. The method of claim 2, wherein:
   the TREX1 antagonist is encoded on a plasmid in an immunostimulatory bacterium;
   the immunostimulatory bacterium contains the plasmid that encodes the TREX1 antagonist under control of a eukaryotic promoter;
   the genome of the immunostimulatory bacterium is modified whereby the bacterium lacks flagella, wherein the wild-type bacterium comprises flagella; and
   the bacterium is auxotrophic for adenosine.

4. The method of claim 3, wherein the genome of the bacterium is modified whereby the bacterium is pagP⁻ and msbB⁻.

5. The method of claim 3, wherein the immunostimulatory bacterium is a *Salmonella* species.

6. The method of claim 5, wherein the *Salmonella* species is a *Salmonella typhimurium* strain.

7. The method of claim 3, wherein the immunostimulatory bacterium is aspartate-semialdehyde dehydrogenase⁻ (asd⁻).

8. The method of claim 2, wherein the TREX1 antagonist encoded by the immunostimulatory bacterium or oncolytic virus comprises a sequence of nucleotides encoding RNAi that suppresses, inhibits, disrupts or otherwise silences or reduces expression of TREX1, or comprises an antibody or antigen-binding fragment thereof that inhibits TREX1.

9. The method of claim 1, wherein the cancer comprises a tumor that is HPV positive.

10. The method of claim 1, wherein the cancer comprises a tumor with a high tumor mutational burden.

11. The method of claim 1, wherein the cancer comprises a hematological malignancy, solid tumor, or metastases thereof.

12. The method of claim 1, wherein the cancer comprises a tumor that has a high TMB or is HPV positive, and is selected from among lung cancer, head and neck cancer, gastric cancer, liver cancer, kidney cancer, pancreatic cancer, ovarian cancer, bladder cancer, breast cancer, colorectal cancer, prostate cancer, cervical cancer, and chronic lymphoblastic leukemia.

13. The method of claim 12, wherein the cancer is an ovarian cancer or cervical cancer.

14. The method of claim 2, wherein:
the TREX1 antagonist is an antibody or antigen-binding fragment thereof;
the antibody or antigen-binding fragment thereof binds to TREX1 to inhibit its activity; and
the antibody or antigen-binding fragment thereof is encoded on a plasmid in an immunostimulatory bacterium.

15. The method of claim 2, wherein:
the TREX1 antagonist is encoded in an immunostimulatory bacterium; and
the genome of the immunostimulatory bacterium is modified so that it preferentially infects tumor-resident immune cells and/or so that it induces less cell death in tumor-resident immune cells.

16. The method of claim 2, wherein:
the TREX1 antagonist is encoded in an immunostimulatory bacterium; and
the genome of the immunostimulatory bacterium is modified, whereby the bacterium is flagellin deficient and pagP⁻, wherein the wild-type bacterium comprises flagella.

17. The method of claim 2, wherein:
the TREX1 antagonist is a therapeutic product that inhibits, suppresses or disrupts expression of TREX1, or that inhibits TREX1; and
the therapeutic product is encoded in a plasmid in an immunostimulatory bacterium.

18. The method of claim 11, wherein the immunostimulatory bacterium is auxotrophic for adenosine.

19. The method of claim 11, wherein:
the immunostimulatory bacterium has a deletion or disruption or both in a gene(s) encoding the flagella, whereby the bacterium is flagellin deficient; and
the wild-type bacterium comprises flagella.

20. The method of claim 11, wherein:
the immunostimulatory bacterium that encodes the TREX1 antagonist is a *Salmonella* species; and
the immunostimulatory bacterium comprises deletions or disruptions or both in the genes encoding both flagellin subunits fliC and fljB, whereby the bacterium is flagellin deficient.

21. The method of claim 2, wherein:
the TREX1 antagonist is RNAi that is encoded on a plasmid in an immunostimulatory bacterium; and
the RNAi is short hairpin RNA (shRNA) or micro-RNA (miRNA).

22. The method of claim 2, wherein:
the TREX1 antagonist is a therapeutic product that inhibits expression of TREX1 or that inhibits TREX1; and
the TREX1 antagonist is encoded in an oncolytic virus.

23. The method of claim 2, wherein:
the TREX1 antagonist is encoded in an immunostimulatory bacterium; and
the immunostimulatory bacterium is one or more of purI⁻ (purM⁻), msbB⁻, purD⁻, flagellin⁻ (fliC⁻/fljB⁻), pagP⁻, adrA⁻, csgD⁻, and hilA⁻.

24. The method of claim 2, wherein:
the TREX1 antagonist is encoded in an immunostimulatory bacterium; and
the immunostimulatory bacterium is a strain of *Salmonella, Shigella, E. coli*, Bifidobacteriae, *Rickettsia, Vibrio, Listeria, Klebsiella, Bordetella, Neisseria, Aeromonas, Francisella, Cholera, Corynebacterium, Citrobacter, Chlamydia, Haemophilus, Brucella, Mycobacterium, Mycoplasma, Legionella, Rhodococcus, Pseudomonas, Helicobacter, Bacillus*, or *Erysipelothrix*, or is an attenuated strain thereof, or is a modified strain thereof of any of the preceding list of bacterial strains.

25. The method of claim 24, wherein the immunostimulatory bacterium is a strain of *Salmonella*.

26. The method of claim 25, wherein the immunostimulatory bacterium is a *Salmonella typhimurium* strain.

27. The method of claim 26, wherein the *Salmonella typhimurium* strain is derived from strain AST-100 (VNP20009 or YS1646), or a wild-type strain having all of the identifying characteristics of the strain deposited under ATCC accession number 14028, or is the strain deposited under ATCC accession number 14028.

28. The method of claim 1, wherein the subject with the cancer is human.

29. The method of claim 1, wherein administration of the TREX1 antagonist is parenteral.

30. The method of claim 1, wherein:
the TREX1 antagonist is encoded in an immunostimulatory bacterium or in an oncolytic virus; and
the immunostimulatory bacterium or oncolytic virus is formulated in a pharmaceutical composition that is administered by oral administration, or by rectal administration, or by aerosol into the lung, or by intratumoral, intravenous, intramuscular, or subcutaneous administration.

31. The method of claim 30, wherein the TREX1 antagonist is encoded in an immunostimulatory bacterium.

32. The method of claim 1, wherein:
the subject has a cancer that comprises a solid tumor or hematological malignancy; and
the TREX1 antagonist is encoded in an oncolytic virus.

* * * * *

SEQUENCE LISTING

```
<160> NUMBER OF SEQ ID NOS: 268

<210> SEQ ID NO 1
<211> LENGTH: 19
<212> TYPE: DNA
<213> ORGANISM: Homo sapiens
<220> FEATURE:
<223> OTHER INFORMATION: Human PD-L1 shRNA target 1

<400> SEQUENCE: 1
gtagagtatg gtagcaata                                                   19

<210> SEQ ID NO 2
<211> LENGTH: 19
<212> TYPE: DNA
<213> ORGANISM: Homo sapiens
<220> FEATURE:
<223> OTHER INFORMATION: Human PD-L1 shRNA target 2

<400> SEQUENCE: 2
gccgactaca agcgaatta                                                   19

<210> SEQ ID NO 3
<211> LENGTH: 19
<212> TYPE: DNA
<213> ORGANISM: Homo sapiens
<220> FEATURE:
<223> OTHER INFORMATION: Human PD-L1 shRNA target 3

<400> SEQUENCE: 3
gacaagcagt gaccatcaa                                                   19

<210> SEQ ID NO 4
<211> LENGTH: 19
<212> TYPE: DNA
<213> ORGANISM: Homo sapiens
<220> FEATURE:
<223> OTHER INFORMATION: Human PD-L1 shRNA target 4

<400> SEQUENCE: 4
gaatcaacac aacaactaa                                                   19

<210> SEQ ID NO 5
<211> LENGTH: 19
<212> TYPE: DNA
<213> ORGANISM: Homo sapiens
<220> FEATURE:
<223> OTHER INFORMATION: Human PD-L1 shRNA target 5

<400> SEQUENCE: 5
gcacatcctc caaatgaaa                                                   19

<210> SEQ ID NO 6
<211> LENGTH: 19
<212> TYPE: DNA
<213> ORGANISM: Homo sapiens
```

```
<220> FEATURE:
<223> OTHER INFORMATION: Human PD-L1 shRNA target 6

<400> SEQUENCE: 6
gtagcactga cattcatct                                                    19

<210> SEQ ID NO 7
<211> LENGTH: 19
<212> TYPE: DNA
<213> ORGANISM: Homo sapiens
<220> FEATURE:
<223> OTHER INFORMATION: Human CTNNB1 shRNA target 1

<400> SEQUENCE: 7
gacagactgc cttcaaatt                                                    19

<210> SEQ ID NO 8
<211> LENGTH: 19
<212> TYPE: DNA
<213> ORGANISM: Homo sapiens
<220> FEATURE:
<223> OTHER INFORMATION: Human CTNNB1 shRNA target 2

<400> SEQUENCE: 8
gcagctggaa ttctttcta                                                    19

<210> SEQ ID NO 9
<211> LENGTH: 19
<212> TYPE: DNA
<213> ORGANISM: Homo sapiens
<220> FEATURE:
<223> OTHER INFORMATION: Human CTNNB1 shRNA target 3

<400> SEQUENCE: 9
gactaccagt tgtggttaa                                                    19

<210> SEQ ID NO 10
<211> LENGTH: 19
<212> TYPE: DNA
<213> ORGANISM: Homo sapiens
<220> FEATURE:
<223> OTHER INFORMATION: Human CTNNB1 shRNA target 4

<400> SEQUENCE: 10
ggacacagca gcaatttgt                                                    19

<210> SEQ ID NO 11
<211> LENGTH: 19
<212> TYPE: DNA
<213> ORGANISM: Homo sapiens
<220> FEATURE:
<223> OTHER INFORMATION: Human CTNNB1 shRNA target 5

<400> SEQUENCE: 11
ggatgttcac aaccgaatt                                                    19

<210> SEQ ID NO 12
<211> LENGTH: 19
<212> TYPE: DNA
<213> ORGANISM: Homo sapiens
<220> FEATURE:
<223> OTHER INFORMATION: Human CTNNB1 shRNA target 6

<400> SEQUENCE: 12
gccacaagat tacaagaaa                                                    19
```

<210> SEQ ID NO 13
<211> LENGTH: 19
<212> TYPE: DNA
<213> ORGANISM: Homo sapiens
<220> FEATURE:
<223> OTHER INFORMATION: Human SIRP-alpha shRNA target 1

<400> SEQUENCE: 13
gccaggtgag gaagttcta                                                    19

<210> SEQ ID NO 14
<211> LENGTH: 19
<212> TYPE: DNA
<213> ORGANISM: Homo sapiens
<220> FEATURE:
<223> OTHER INFORMATION: Human SIRP-alpha shRNA target 2

<400> SEQUENCE: 14
gagctggctc ctggtgaat                                                    19

<210> SEQ ID NO 15
<211> LENGTH: 19
<212> TYPE: DNA
<213> ORGANISM: Homo sapiens
<220> FEATURE:
<223> OTHER INFORMATION: Human SIRP-alpha shRNA target 3

<400> SEQUENCE: 15
gctgagaaca ctggatcta                                                    19

<210> SEQ ID NO 16
<211> LENGTH: 19
<212> TYPE: DNA
<213> ORGANISM: Homo sapiens
<220> FEATURE:
<223> OTHER INFORMATION: Human SIRP-alpha shRNA target 4

<400> SEQUENCE: 16
gaagaatgcc agagaaata                                                    19

<210> SEQ ID NO 17
<211> LENGTH: 19
<212> TYPE: DNA
<213> ORGANISM: Homo sapiens
<220> FEATURE:
<223> OTHER INFORMATION: Human SIRP-alpha shRNA target 5

<400> SEQUENCE: 17
ggacacaaat gatatcaca                                                    19

<210> SEQ ID NO 18
<211> LENGTH: 19
<212> TYPE: DNA
<213> ORGANISM: Homo sapiens
<220> FEATURE:
<223> OTHER INFORMATION: Human SIRP-alpha shRNA target 6

<400> SEQUENCE: 18
ggagtatgcc agcattcag                                                    19

<210> SEQ ID NO 19
<211> LENGTH: 19
<212> TYPE: DNA
<213> ORGANISM: Homo sapiens
<220> FEATURE:
<223> OTHER INFORMATION: Human Trex1 shRNA target 1

-continued

<400> SEQUENCE: 19
gcagcgcatg ggcgtcaat                                                19

<210> SEQ ID NO 20
<211> LENGTH: 19
<212> TYPE: DNA
<213> ORGANISM: Homo sapiens
<220> FEATURE:
<223> OTHER INFORMATION: Human Trex1 shRNA target 2

<400> SEQUENCE: 20
ggcccaagga agagctata                                                19

<210> SEQ ID NO 21
<211> LENGTH: 19
<212> TYPE: DNA
<213> ORGANISM: Homo sapiens
<220> FEATURE:
<223> OTHER INFORMATION: Human Trex1 shRNA target 3

<400> SEQUENCE: 21
gcaccatcag gcccatgta                                                19

<210> SEQ ID NO 22
<211> LENGTH: 19
<212> TYPE: DNA
<213> ORGANISM: Homo sapiens
<220> FEATURE:
<223> OTHER INFORMATION: Human Trex1 shRNA target 4

<400> SEQUENCE: 22
gccacaacca ggaacacta                                                19

<210> SEQ ID NO 23
<211> LENGTH: 19
<212> TYPE: DNA
<213> ORGANISM: Homo sapiens
<220> FEATURE:
<223> OTHER INFORMATION: Human Trex1 shRNA target 5

<400> SEQUENCE: 23 gcagggtac caaggatct                                                 19

<210> SEQ ID NO 24
<211> LENGTH: 19
<212> TYPE: DNA
<213> ORGANISM: Homo sapiens
<220> FEATURE:
<223> OTHER INFORMATION: Human Trex1 shRNA target 6

<400> SEQUENCE: 24
gccacactgt atggactat                                                19

<210> SEQ ID NO 25
<211> LENGTH: 19
<212> TYPE: DNA
<213> ORGANISM: Homo sapiens
<220> FEATURE:
<223> OTHER INFORMATION: Human VISTA shRNA target 1

<400> SEQUENCE: 25
gatgtgacct tctacaaga                                                19

<210> SEQ ID NO 26

```
<211> LENGTH: 19
<212> TYPE: DNA
<213> ORGANISM: Homo sapiens
<220> FEATURE:
<223> OTHER INFORMATION: Human VISTA shRNA target 2

<400> SEQUENCE: 26
gaccaccatg gcaacttct                                              19

<210> SEQ ID NO 27
<211> LENGTH: 19
<212> TYPE: DNA
<213> ORGANISM: Homo sapiens
<220> FEATURE:
<223> OTHER INFORMATION: Human VISTA shRNA target 3

<400> SEQUENCE: 27
ggtgcagaca ggcaaagat                                              19

<210> SEQ ID NO 28
<211> LENGTH: 19
<212> TYPE: DNA
<213> ORGANISM: Homo sapiens
<220> FEATURE:
<223> OTHER INFORMATION: Human VISTA shRNA target 4

<400> SEQUENCE: 28
gtgcctgcat cgtaggaat                                              19

<210> SEQ ID NO 29
<211> LENGTH: 19
<212> TYPE: DNA
<213> ORGANISM: Homo sapiens
<220> FEATURE:
<223> OTHER INFORMATION: Human VISTA shRNA target 5

<400> SEQUENCE: 29
gcaacattca agggattga                                              19

<210> SEQ ID NO 30
<211> LENGTH: 19
<212> TYPE: DNA
<213> ORGANISM: Homo sapiens
<220> FEATURE:
<223> OTHER INFORMATION: Human VISTA shRNA target 6

<400> SEQUENCE: 30
gtccctgact ctccaaact                                              19

<210> SEQ ID NO 31
<211> LENGTH: 870
<212> TYPE: DNA
<213> ORGANISM: Homo sapiens
<220> FEATURE:
<223> OTHER INFORMATION: programmed death-ligand 1 (PD-L1), isoform 1

<400> SEQUENCE: 31
atgaggatat ttgctgtctt tatattcatg acctactggc atttgctgaa cgcatttact      60
gtcacggttc ccaaggacct atatgtggta gagtatggta gcaatatgac aattgaatgc     120
aaattcccag tagaaaaaca attagacctg gctgcactaa ttgtctattg ggaaatggag     180
gataagaaca ttattcaatt tgtgcatgga gaggaagacc tgaaggttca gcatagtagc     240
tacagacaga gggcccggct gttgaaggac cagctctccc tgggaaatgc tgcacttcag     300
atcacagatg tgaaattgca ggatgcaggg gtgtaccgct gcatgatcag ctatggtggt     360
```

-continued

```
gccgactaca agcgaattac tgtgaaagtc aatgccccat acaacaaaat caaccaaaga      420
attttggttg tggatccagt cacctctgaa catgaactga catgtcaggc tgagggctac      480
cccaaggccg aagtcatctg acaagcagt gaccatcaag tcctgagtgg taagaccacc      540
accaccaatt ccaagagaga ggagaagctt ttcaatgtga ccagcacact gagaatcaac      600
acaacaacta atgagatttt ctactgcact tttaggagat tagatcctga ggaaaaccat      660
acagctgaat tggtcatccc agaactacct ctggcacatc ctccaaatga aggactcac       720 ttggtaattc tgggagccat cttattatgc cttggtgtag cactgacatt catcttccgt      780
ttaagaaaag ggagaatgat ggatgtgaaa aaatgtggca tccaagatac aaactcaaag      840
aagcaaagtg atacacattt ggaggagacg                                      870
```

<210> SEQ ID NO 32
<211> LENGTH: 2343
<212> TYPE: DNA
<213> ORGANISM: Homo sapiens
<220> FEATURE:
<223> OTHER INFORMATION: CTNNB1 (Beta-catenin), isoform 1

<400> SEQUENCE: 32

```
atggctactc aagctgattt gatggagttg gacatggcca tggaaccaga cagaaaagcg      60
gctgttagtc actggcagca acagtcttac ctggactctg gaatccattc tggtgccact      120
accacagctc cttctctgag tggtaaaggc aatcctgagg aagaggatgt ggatacctcc      180
caagtcctgt atgagtggga cagggatttt tctcagtcct tcactcaaga caagtagct       240 gatattgatg acagtatgc aatgactcga gctcagaggg tacgagctgc tatgttccct      300
gagacattag atgagggcat gcagatccca tctacacagt ttgatgctgc tcatcccact      360
aatgtccagc gtttggctga accatcacag atgctgaaac atgcagttgt aaacttgatt      420
aactatcaag atgatgcaga acttgccaca cgtgcaatcc ctgaactgac aaaactgcta      480
aatgacgagg accaggtggt ggttaataag gctgcagtta tggtccatca gctttctaaa      540
aaggaagctt ccagacacgc tatcatgcgt tctcctcaga tggtgtctgc tattgtacgt      600
accatgcaga atacaaatga tgtagaaaca gctcgttgta ccgctgggac cttgcataac      660
ctttcccatc atcgtgaggg cttactggcc atctttaagt ctggaggcat tcctgccctg      720
gtgaaaatgc ttggttcacc agtggattct gtgttgtttt atgccattac aactctccac      780
aaccttttat tacatcaaga aggagctaaa atggcagtgc gtttagctgg tgggctgcag      840
aaaatggttg ccttgctcaa caaaacaaat gttaaattct tggctattac gacagactgc      900
cttcaaattt tagcttatgg caaccaagaa agcaagctca tcatactggc tagtggtgga      960
ccccaagctt tagtaaatat aatgaggacc tatacttacg aaaaactact gtggaccaca     1020
agcagagtgc tgaaggtgct atctgtctgc tctagtaata agccggctat tgtagaagct     1080
ggtggaatgc aagcttttagg acttcacctg acagatccaa gtcaacgtct tgttcagaac     1140
tgtctttgga ctctcaggaa tctttcagat gctgcaacta acaggaagg gatggaaggt     1200 ctccttggga ctcttgttca gcttctgggt tcagatgata taaatgtggt cacctgtgca     1260
gctggaattc tttctaacct cacttgcaat aattataaga acaagatgat ggtctgccaa     1320
gtgggtggta tagaggctct tgtgcgtact gtccttcggg ctggtgacag ggaagacatc     1380
actgagcctg ccatctgtgc tcttcgtcat ctgaccagcc acaccaaga agcagagatg     1440 gcccagaatg cagttcgcct tcactatgga ctaccagttg tggttaagct cttacaccca     1500
```

```
ccatcccact ggcctctgat aaaggctact gttggattga ttcgaaatct tgccctttgt    1560
cccgcaaatc atgcaccttt gcgtgagcag ggtgccattc cacgactagt tcagttgctt    1620
gttcgtgcac atcaggatac ccagcgccgt acgtccatgg gtgggacaca gcagcaattt    1680 gtggagggggg tccgcatgga agaaatagtt gaaggttgta ccggagccct tcacatccta   1740
gctcgggatg ttcacaaccg aattgttatc agaggactaa ataccattcc attgtttgtg    1800
cagctgcttt attctcccat tgaaaacatc caaagagtag ctgcagggggt cctctgtgaa   1860 cttgctcagg acaaggaagc tgcagaagct attgaagctg agggagccac agctcctctg    1920
acagagttac ttcactctag gaatgaaggt gtggcgacat atgcagctgc tgttttgttc    1980
cgaatgtctg aggacaagcc acaagattac aagaaacggc tttcagttga gctgaccagc    2040
tctctcttca gaacagagcc aatggcttgg aatgagactg ctgatcttgg acttgatatt    2100
ggtgcccagg agaaccccct tggatatcgc caggatgatc ctagctatcg ttcttttcac    2160
tctggtggat atggccagga tgccttgggt atggacccca tgatggaaca tgagatgggt    2220
ggccaccacc ctggtgctga ctatccagtt gatgggctgc cagatctggg gcatgcccag    2280
gacctcatgg atgggctgcc tccaggtgac agcaatcagc tggcctggtt tgatactgac    2340
ctg                                                                   2343
```

<210> SEQ ID NO 33
<211> LENGTH: 1512
<212> TYPE: DNA
<213> ORGANISM: Homo sapiens
<220> FEATURE:
<223> OTHER INFORMATION: signal regulatory protein alpha (SIRP-alpha)
      isoform 1

<400> SEQUENCE: 33

```
atggagcccg ccggcccggc ccccggccgc ctcgggccgc tgctctgcct gctgctcgcc      60
gcgtcctgcg cctggtcagg agtggcgggt gaggaggagc tgcaggtgat tcagcctgac    120
aagtccgtgt tggttgcagc tggagagaca gccactctgc gctgcactgc gacctctctg    180
atccctgtgg ggcccatcca gtggttcaga ggagctggac caggccggga attaatctac    240
aatcaaaaag aaggccactt cccccgggta acaactgttt cagacctcac aaagagaaac    300
aacatggact tttccatccg catcggtaac atcaccccag cagatgccgg cacctactac    360
tgtgtgaagt tccggaaagg gagccccgat gacgtggagt ttaagtctgg agcaggcact    420
gagctgtctg tgcgcgccaa accctctgcc ccgtggtat cgggccctgc ggcgagggcc     480
acacctcagc acacagtgag cttcacctgc gagtcccacg gcttctcacc cagagacatc    540
accctgaaat ggttcaaaaa tgggaatgag ctctcagact tccagaccaa cgtggacccc    600
gtaggagaga gcgtgtccta cagcatccac agcacagcca aggtggtgct gacccgcgag    660
gacgttcact ctcaagtcat ctgcgaggtg gcccacgtca ccttgcaggg ggaccctctt    720
cgtgggactg ccaacttgtc tgagaccatc cgagttccac ccaccttgga ggttactcaa    780
cagcccgtga gggcagagaa ccaggtgaat gtcacctgcc aggtgaggaa gttctacccc    840
cagagactac agctgacctg gttggagaat ggaaacgtgt cccggacaga aacggcctca    900
accgttacag agaacaagga tggtacctac aactggatga gctggctcct ggtgaatgta    960
tctgccacac gggatgatgt gaagctcacc tgccaggtgg agcatgacgg gcagccagcg   1020
gtcagcaaaa gccatgacct gaaggtctca gcccacccga aggagcaggg ctcaaatacc   1080
gccgctgaga acactggatc taatgaacgg aacatctata ttgtggtggg tgtggtgtgc   1140
```

| | |
|---|---|
| accttgctgg tggccctact gatggcggcc ctctacctcg tccgaatcag acagaagaaa | 1200 |
| gcccagggct ccacttcttc tacaaggttg catgagcccg agaagaatgc cagagaaata | 1260 |
| acacaggaca caaatgatat cacatatgca gacctgaacc tgcccaaggg gaagaagcct | 1320 |
| gctcccagg ctgcggagcc caacaaccac acggagtatg ccagcattca gaccagcccg | 1380 |
| cagcccgcgt cggaggacac cctcacctat gctgacctgg acatggtcca cctcaaccgg | 1440 |
| accccaagc agccggcccc caagcctgag ccgtccttct cagagtacgc cagcgtccag | 1500 |
| gtcccgagga ag | 1512 |

<210> SEQ ID NO 34
<211> LENGTH: 1108
<212> TYPE: DNA
<213> ORGANISM: Homo sapiens
<220> FEATURE:
<223> OTHER INFORMATION: TREX1 isoform 1

<400> SEQUENCE: 34

| | |
|---|---|
| aatgggccct ggagctcgca gacagggcag gattgtgcag ggaaggcctg agatgtgctt | 60 |
| ctgcccaccc cctaccccac tccctcccct tcggatctta acactgggca ctcacacacc | 120 |
| caccccatgc tcctctccag gctcagcagc aggtacgtac ccaaccatgg gctcgcaggc | 180 |
| cctgccccg gggcccatgc agaccctcat cttttcgac atggaggcca ctggcttgcc | 240 |
| cttctcccag cccaaggtca cggagctgtg cctgctggct gtccacagat gtgccctgga | 300 |
| gagccccccc acctctcagg ggccacctcc cacagttcct ccaccaccgc gtgtggtaga | 360 |
| caagctctcc ctgtgtgtgg ctccggggaa ggcctgcagc cctgcagcca gcgagatcac | 420 |
| aggtctgagc acagctgtgc tggcagcgca tgggcgtcaa tgttttgatg acaacctggc | 480 |
| caacctgctc ctagccttcc tgcggcgcca gccacagccc tggtgcctgg tgcacacaa | 540 |
| tggtgaccgc tacgacttcc ccctgctcca agcagagctg gctatgctgg gcctcaccag | 600 |
| tgctctggat ggtgccttct gtgtggatag catcactgcg ctgaaggccc tggagcgagc | 660 |
| aagcagcccc tcagaacacg gcccaaggaa gagctatagc ctaggcagca tctacactcg | 720 |
| cctgtatggg cagtcccctc cagactcgca cacggctgag ggtgatgtcc tggccctgct | 780 |
| cagcatctgt cagtggagac cacaggccct gctgcggtgg gtggatgctc acgccaggcc | 840 |
| tttcggcacc atcaggccca tgtatgggggt cacagcctct gctaggacca agccaagacc | 900 |
| atctgctgtc acaaccactg cacacctggc cacaaccagg aacactagtc ccagccttgg | 960 |
| agagagcagg ggtaccaagg atcttcctcc agtgaaggac cctggagccc tatccaggga | 1020 |
| ggggctgctg gccccactgg gtctgctggc catcctgacc ttggcagtag ccacactgta | 1080 |
| tggactatcc ctggccacac ctggggag | 1108 |

<210> SEQ ID NO 35
<211> LENGTH: 933
<212> TYPE: DNA
<213> ORGANISM: Homo sapiens
<220> FEATURE:
<223> OTHER INFORMATION: V-domain Ig suppressor of T cell activation
       (VISTA)

<400> SEQUENCE: 35

| | |
|---|---|
| atgggcgtcc ccacggccct ggaggccggc agctggcgct ggggatccct gctcttcgct | 60 |
| ctcttcctgg ctgcgtccct aggtccggtg gcagccttca aggtcgccac gccgtattcc | 120 |
| ctgtatgtct gtcccgaggg gcagaacgtc accctcacct gcaggctctt gggccctgtg | 180 |

```
gacaaagggc acgatgtgac cttctacaag acgtggtacc gcagctcgag gggcgaggtg    240
cagacctgct cagagcgccg gcccatccgc aacctcacgt tccaggacct tcacctgcac    300
catggaggcc accaggctgc aacaccagc cacgacctgg ctcagcgcca cgggctggag     360
tcggcctccg accaccatgg caacttctcc atcaccatgc gcaacctgac cctgctggat    420
agcggcctct actgctgcct ggtggtggag atcaggcacc accactcgga gcacagggtc    480
catggtgcca tggagctgca ggtgcagaca ggcaaagatg caccatccaa ctgtgtggtg    540
tacccatcct cctcccagga tagtgaaaac atcacggctg cagccctggc tacgggtgcc    600
tgcatcgtag gaatcctctg cctccccctc atcctgctcc tggtctacaa gcaaaggcag    660
gcagcctcca accgccgtgc ccaggagctg gtgcggatgc acagcaacat tcaagggatt    720
gaaaaccccg gctttgaagc ctcaccacct gcccagggga tacccgaggc caaagtcagg    780
caccccctgt cctatgtggc ccagcggcag ccttctgagt ctgggcggca tctgctttcg    840
gagcccagca ccccctgtc tcctccaggc cccggagacg tcttcttccc atccctggac    900
cctgtccctg actctccaaa ctttgaggtc atc                                 933
```

<210> SEQ ID NO 36
<211> LENGTH: 45
<212> TYPE: DNA
<213> ORGANISM: Artificial Sequence
<220> FEATURE:
<223> OTHER INFORMATION: shRNA-encoding sequence for huPD-L1

<400> SEQUENCE: 36

```
gtagagtatg gtagcaatat ctagagtatt gctaccatac tctac               45
```

<210> SEQ ID NO 37
<211> LENGTH: 45
<212> TYPE: DNA
<213> ORGANISM: Artificial Sequence
<220> FEATURE:
<223> OTHER INFORMATION: shRNA-encoding sequence for huCTNNB1

<400> SEQUENCE: 37

```
gacagactgc cttcaaattt ctagagaatt tgaaggcagt ctgtc               45
```

<210> SEQ ID NO 38
<211> LENGTH: 45
<212> TYPE: DNA
<213> ORGANISM: Artificial Sequence
<220> FEATURE:
<223> OTHER INFORMATION: shRNA-encoding sequence for huSIRPalpha

<400> SEQUENCE: 38

```
gccaggtgag gaagttctat ctagagtaga acttcctcac ctggc               45
```

<210> SEQ ID NO 39
<211> LENGTH: 45
<212> TYPE: DNA
<213> ORGANISM: Artificial Sequence
<220> FEATURE:
<223> OTHER INFORMATION: shRNA-encoding sequence for huTREX1

<400> SEQUENCE: 39

```
gcagcgcatg ggcgtcaatt ctagagattg acgcccatgc gctgc               45
```

<210> SEQ ID NO 40
<211> LENGTH: 45
<212> TYPE: DNA
<213> ORGANISM: Artificial Sequence
<220> FEATURE:
<223> OTHER INFORMATION: shRNA-encoding sequence for huVISTA

<400> SEQUENCE: 40

```
gaccaccatg gcaacttctt ctagagagaa gttgccatgg tggtc          45
```

<210> SEQ ID NO 41
<211> LENGTH: 3220
<212> TYPE: DNA
<213> ORGANISM: Artificial Sequence
<220> FEATURE:
<223> OTHER INFORMATION: pEQU6 vector

<400> SEQUENCE: 41

```
ctttcctgcg ttatccctg attctgtgga taaccgtatt accgcctttg agtgagctga      60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca atccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggcccca aataatgatt ttattttgac tgatagtgac    600
ctgttcgttg caacaaattg atgagcaatg ctttttata atgccaactt tgtacaaaaa    660
agcaggcttt aaaggaacca attcagtcga ctggatccaa ggtcgggcag gaagagggcc    720
tatttcccat gattccttca tatttgcata tacgatacaa ggctgttaga gagataatta    780
gaattaattt gactgtaaac acaaagatat tagtacaaaa tacgtgacgt agaaagtaat    840
aatttcttgg gtagtttgca gttttaaaat tatgttttaa aatggactat catatgctta    900
ccgtaacttg aaagtatttc gatttcttgg ctttatatat cttgtggaaa ggacgaaact    960
agttttttct cgagtagcta gagaattcat ggtaatagcg atgactaata cgtagatgta   1020
ctgccaagta ggaaagtccc ataaggtcat gtactgggca taatgccagg cgggccattt   1080
accgtcattg acgtcaatag ggggcgtact tggcatatga tacacttgat gtactgccaa   1140
gtgggcagtt taccgtaaat agtccaccca ttgacgtcaa tggaaagtcc ctattggcgt   1200
tactatggga acatacgtca ttattgacgt caatgggcgg gggtcgttgg gcggtcagcc   1260
aggcgggcca tttaccgtaa gttatgtaac gcggaactcc atatatgggc tatgaactaa   1320
tgaccccgta attgattact attaataact agacccagct tcttgtaca aagttggcat   1380 tataagaaag cattgcttat caatttgttg caacgaacag gtcactatca gtcaaaataa   1440 atcattatt tgccatccag ctgatatccc ctatagtgag tcgtattaca tggtcatagc   1500
tgtttcctgg cagctctggc ccgtgtctca aaatctctga tgttacattg cacaagataa   1560
aaatatatca tcatgaacaa taaaactgtc tgcttacata acagtaata caaggggtgt   1620 tatgagccat attcaacggg aaacgtcgag gccgcgatta aattccaaca tggatgctga   1680
tttatatggg tataaatggg ctcgcgataa tgtcgggcaa tcaggtgcga caatctatcg   1740
cttgtatggg aagcccgatg cgccagagtt gtttctgaaa catggcaaag gtagcgttgc   1800
caatgatgtt acagatgaga tggtcagact aaactggctg acggaattta tgcctcttcc   1860
```

-continued

| | |
|---|---|
| gaccatcaag cattttatcc gtactcctga tgatgcatgg ttactcacca ctgcgatccc | 1920 |
| cggaaaaaca gcattccagg tattagaaga atatcctgat tcaggtgaaa atattgttga | 1980 |
| tgcgctggca gtgttcctgc gccggttgca ttcgattcct gtttgtaatt gtccttttaa | 2040 |
| cagcgatcgc gtatttcgtc tcgctcaggc gcaatcacga atgaataacg gtttggttga | 2100 |
| tgcgagtgat tttgatgacg agcgtaatgg ctggcctgtt gaacaagtct ggaaagaaat | 2160 |
| gcataaactt tgccattct caccggattc agtcgtcact catggtgatt tctcacttga | 2220 |
| taaccttatt tttgacgagg ggaaattaat aggttgtatt gatgttggac gagtcggaat | 2280 |
| cgcagaccga taccaggatc ttgccatcct atggaactgc ctcggtgagt tttctccttc | 2340 |
| attacagaaa cggctttttc aaaaatatgg tattgataat cctgatatga ataaattgca | 2400 |
| gtttcatttg atgctcgatg agttttcta atcagaattg gttaattggt tgtaacactg | 2460 |
| gcagagcatt acgctgactt gacgggacgg cgcaagctca tgaccaaaat cccttaacgt | 2520 |
| gagttacgcg tcgttccact gagcgtcaga ccccgtagaa aagatcaaag gatcttcttg | 2580 |
| agatcctttt tttctgcgcg taatctgctg cttgcaaaca aaaaaaccac cgctaccagc | 2640 |
| ggtggtttgt ttgccggatc aagagctacc aactctttt ccgaaggtaa ctggcttcag | 2700 |
| cagagcgcag ataccaaata ctgtccttct agtgtagccg tagttaggcc accacttcaa | 2760 |
| gaactctgta gcaccgccta catacctcgc tctgctaatc ctgttaccag tggctgctgc | 2820 |
| cagtggcgat aagtcgtgtc ttaccgggtt ggactcaaga cgatagttac cggataaggc | 2880 |
| gcagcggtcg ggctgaacgg ggggttcgtg cacacagccc agcttggagc gaacgaccta | 2940 |
| caccgaactg agatacctac agcgtgagca ttgagaaagc gccacgcttc ccgaagggag | 3000 |
| aaaggcggac aggtatccgg taagcggcag ggtcggaaca ggagagcgca cgagggagct | 3060 |
| tccaggggga aacgcctggt atctttatag tcctgtcggg tttcgccacc tctgacttga | 3120 |
| gcgtcgattt ttgtgatgct cgtcaggggg gcggagccta tggaaaaacg ccagcaacgc | 3180 |
| ggccttttta cggttcctgg ccttttgctg gcttttgct | 3220 |

<210> SEQ ID NO 42
<211> LENGTH: 3802
<212> TYPE: DNA
<213> ORGANISM: Artificial Sequence
<220> FEATURE:
<223> OTHER INFORMATION: pEQU6-H1 Vector

<400> SEQUENCE: 42

| | |
|---|---|
| ctttcctgcg ttatccctg attctgtgga taaccgtatt accgcctttg agtgagctga | 60 |
| taccgctcgc cgcagccgaa cgaccgagcg cagcgagtca gtgagcgagg aagcggaaga | 120 |
| gcgcccaata cgcaaaccgc ctctccccgc gcgttggccg attcattaat gcagctggca | 180 |
| cgacaggttt cccgactgga aagcgggcag tgagcgcaac gcaattaata cgcgtaccgc | 240 |
| tagccaggaa gagtttgtag aaacgcaaaa aggccatccg tcaggatggc cttctgctta | 300 |
| gtttgatgcc tggcagttta tggcgggcgt cctgcccgcc accctccggg ccgttgcttc | 360 |
| acaacgttca atccgctcc cggcggattt gtcctactca ggagagcgtt caccgacaaa | 420 |
| caacagataa acgaaaggc ccagtcttcc gactgagcct tcgtttat ttgatgcctg | 480 |
| gcagttccct actctcgcgt taacgctagc atggatgttt tcccagtcac gacgttgtaa | 540 |
| aacgacggcc agtcttaagc tcgggcccca ataatgatt ttattttgac tgatagtgac | 600 |
| ctgttcgttg caacaaattg atgagcaatg cttttttata atgccaactt tgtacaaaaa | 660 |
| agcaggcttt aaaggaacca attcagtcga gaattggtac catatttgca tgtcgctatg | 720 |

```
tgttctggga aatcaccata aacgtgaaat gtctttggat ttgggaatct tataagttct      780
gtatgagacc actccctagg tttttgtcga cagatctggc gcgccatagt ggccagcggc      840
cgcaggtaag ccagcccagg cctcgccctc cagctcaagg cgggacaggt gccctagagt      900
agcctgcatc cagggacagg ccccagccgg gtgctgacac gtccacctcc atctcttcct      960
caggtctgcc cgggtggcat ccctgtgacc cctccccagt gcctctcctg gccctggaag     1020
ttgccactcc agtgcccacc agccttgtcc taataaaatt aagttgcatc attttgtctg     1080
actaggtgtc cttctataat attatggggt ggaggggggt ggtatggagc aaggggccca     1140
agttaacttg tttattgcag cttataatgg ttacaaataa agcaatagca tcacaaattt     1200
cacaaataaa gcattttttt cactgcattc tagttgtggt ttgtccaaac tcatcaatgt     1260
atcttatcat gtctggatcc aaggtcgggc aggaagaggg cctatttccc atgattcctt     1320
catatttgca tatacgatac aaggctgtta gagagataat tagaattaat ttgactgtaa     1380
acacaaagat attagtacaa atacgtgacg tagaaagta ataatttctt gggtagtttg     1440
cagttttaaa attatgtttt aaaatggact atcatatgct taccgtaact tgaaagtatt     1500
tcgatttctt ggctttatat atcttgtgga aaggacgaaa ctagtttttt ctcgagtagc     1560
tagagaattc atggtaatag cgatgactaa tacgtagatg tactgccaag taggaaagtc     1620
ccataaggtc atgtactggg cataatgcca ggcgggccat ttaccgtcat tgacgtcaat     1680 aggggggcgta cttggcatat gatacacttg atgtactgcc aagtgggcag tttaccgtaa     1740
atagtccacc cattgacgtc aatggaaagt ccctattggc gttactatgg gaacatacgt     1800
cattattgac gtcaatgggc ggggtcgtt gggcggtcag ccaggcgggc catttaccgt     1860
aagttatgta acgcggaact ccatatatgg gctatgaact aatgacccg taattgatta     1920 ctattaataa ctagacccag cttcttgta caaagttggc attataagaa agcattgctt     1980
atcaatttgt tgcaacgaac aggtcactat cagtcaaaat aaaatcatta tttgccatcc     2040
agctgatatc ccctatagtg agtcgtatta catggtcata gctgtttcct ggcagctctg     2100
gcccgtgtct caaaatctct gatgttacat tgcacaagat aaaaatatat catcatgaac     2160
aataaaactg tctgcttaca taaacagtaa tacaaggggt gttatgagcc atattcaacg     2220
ggaaacgtcg aggccgcgat taaattccaa catggatgct gatttatatg ggtataaatg     2280
ggctcgcgat aatgtcgggc aatcaggtgc gacaatctat cgcttgtatg ggaagcccga     2340
tgcgccagag ttgtttctga acatggcaa aggtagcgtt gccaatgatg ttacagatga     2400
gatggtcaga ctaaactggc tgacggaatt tatgcctctt ccgaccatca agcatttat      2460 ccgtactcct gatgatgcat ggttactcac cactgcgatc cccggaaaaa cagcattcca     2520
ggtattagaa gaatatcctg attcaggtga aaatattgtt gatgcgctgg cagtgttcct     2580
gcgccggttg cattcgattc ctgtttgtaa ttgtcctttt aacagcgatc gcgtatttcg     2640
tctcgctcag gcgcaatcac gaatgaataa cggtttggtt gatgcgagtg attttgatga     2700
cgagcgtaat ggctggcctg ttaacaagt ctggaaagaa atgcataaac ttttgccatt     2760
ctcaccggat tcagtcgtca ctcatggtga tttctcactt gataaccta ttttgacga     2820 ggggaaatta ataggttgta ttgatgttgg acgagtcgga atcgcagacc gataccagga     2880
tcttgccatc ctatggaact gcctcggtga gttttctcct tcattacaga aacggctttt     2940
tcaaaaatat ggtattgata atcctgatat gaataaattg cagtttcatt tgatgctcga     3000
tgagtttttc taatcagaat tggttaattg gttgtaacac tggcagagca ttacgctgac     3060
```

```
ttgacgggac ggcgcaagct catgaccaaa atcccttaac gtgagttacg cgtcgttcca   3120
ctgagcgtca gacccgtag aaaagatcaa aggatcttct tgagatcctt tttttctgcg    3180
cgtaatctgc tgcttgcaaa caaaaaaacc accgctacca gcggtggttt gtttgccgga   3240
tcaagagcta ccaactcttt ttccgaaggt aactggcttc agcagagcgc agataccaaa   3300
tactgtcctt ctagtgtagc cgtagttagg ccaccacttc aagaactctg tagcaccgcc   3360
tacatacctc gctctgctaa tcctgttacc agtggctgct gccagtggcg ataagtcgtg   3420
tcttaccggg ttggactcaa gacgatagtt accggataag gcgcagcggt cgggctgaac   3480
ggggggttcg tgcacacagc ccagcttgga gcgaacgacc tacaccgaac tgagatacct   3540
acagcgtgag cattgagaaa gcgccacgct tcccgaaggg agaaaggcgg acaggtatcc   3600
ggtaagcggc agggtcggaa caggagagcg cacgagggag cttccagggg gaaacgcctg   3660
gtatctttat agtcctgtcg ggtttcgcca cctctgactt gagcgtcgat ttttgtgatg   3720
ctcgtcaggg gggcggagcc tatggaaaaa cgccagcaac gcggccttttt tacggttcct   3780 ggccttttgc tggccttttg ct                                             3802
```

<210> SEQ ID NO 43
<211> LENGTH: 3263
<212> TYPE: DNA
<213> ORGANISM: Artificial Sequence
<220> FEATURE:
<223> OTHER INFORMATION: pEQU6-shPDL1-shRNA Vector

<400> SEQUENCE: 43

```
ctttcctgcg ttatcccctg attctgtgga taaccgtatt accgcctttg agtgagctga     60
taccgctcgc cgcagccgaa cgaccgagcg cagcgagtca gtgagcgagg aagcggaaga   120
gcgcccaata cgcaaaccgc ctctccccgc gcgttggccg attcattaat gcagctggca   180
cgacaggttt cccgactgga aagcgggcag tgagcgcaac gcaattaata cgcgtaccgc   240
tagccaggaa gagtttgtag aaacgcaaaa aggccatccg tcaggatggc cttctgctta   300
gtttgatgcc tggcagttta tggcgggcgt cctgcccgcc accctccggg ccgttgcttc   360
acaacgttca aatccgctcc cggcggattt gtcctactca ggagagcgtt caccgacaaa   420
caacagataa aacgaaaggc ccagtcttcc gactgagcct ttcgttttat ttgatgcctg   480
gcagttccct actctcgcgt taacgctagc atggatgttt tcccagtcac gacgttgtaa   540
aacgacggcc agtcttaagc tcgggcccca ataatgatt ttattttgac tgatagtgac   600
ctgttcgttg caacaaattg atgagcaatg cttttttata tgccaactt tgtacaaaaa     660 agcaggcttt aaaggaacca attcagtcga ctggatccaa ggtcgggcag gaagagggcc   720
tatttcccat gattccttca tatttgcata tacgatacaa ggctgttaga gagataatta   780
gaattaattt gactgtaaac acaaagatat tagtacaaaa tacgtgacgt agaaagtaat   840
aatttcttgg gtagtttgca gttttaaaat tatgttttaa aatggactat catatgctta   900
ccgtaacttg aaagtatttc gatttcttgg ctttatatat cttgtggaaa ggacgaaact   960
aggtagagta tggtagcaat atctagagta ttgctaccat actctacttt tttcgagtag  1020
ctagagaatt catggtaata gcgatgacta atacgtagat gtactgccaa gtaggaaagt  1080
cccataaggt catgtactgg gcataatgcc aggcgggcca tttaccgtca ttgacgtcaa  1140 taggggggcgt acttggcata tgatacactt gatgtactgc caagtgggca gtttaccgta  1200
aatagtccac ccattgacgt caatggaaag tccctattgg cgttactatg gaacatacg   1260 tcattattga cgtcaatggg cggggtcgt tgggcggtca gccaggcggg ccatttaccg  1320
```

```
taagttatgt aacgcggaac tccatatatg ggctatgaac taatgacccc gtaattgatt    1380
actattaata actagaccca gctttcttgt acaaagttgg cattataaga aagcattgct    1440
tatcaatttg ttgcaacgaa caggtcacta tcagtcaaaa taaaatcatt atttgccatc    1500
cagctgatat cccctatagt gagtcgtatt acatggtcat agctgtttcc tggcagctct    1560
ggcccgtgtc tcaaaatctc tgatgttaca ttgcacaaga taaaaatata tcatcatgaa    1620
caataaaact gtctgcttac ataaacagta atacaagggg tgttatgagc catattcaac    1680
gggaaacgtc gaggccgcga ttaaattcca acatggatgc tgatttatat gggtataaat    1740
gggctcgcga taatgtcggg caatcaggtg cgacaatcta tcgcttgtat gggaagcccg    1800
atgcgccaga gttgtttctg aaacatggca aaggtagcgt tgccaatgat gttacagatg    1860
agatggtcag actaaactgg ctgacggaat ttatgcctct tccgaccatc aagcatttta    1920
tccgtactcc tgatgatgca tggttactca ccactgcgat ccccggaaaa acagcattcc    1980
aggtattaga agaatatcct gattcaggtg aaaatattgt tgatgcgctg gcagtgttcc    2040
tgcgccggtt gcattcgatt cctgtttgta attgtccttt taacagcgat cgcgtatttc    2100
gtctcgctca ggcgcaatca cgaatgaata acggtttggt tgatgcgagt gattttgatg    2160
acgagcgtaa tggctggcct gttgaacaag tctggaaaga atgcataaa cttttgccat    2220 tctcaccgga ttcagtcgtc actcatggtg atttctcact tgataacctt attttttgacg    2280 aggggaaatt aataggttgt attgatgttg gacgagtcgg aatcgcagac cgataccagg    2340
atcttgccat cctatggaac tgcctcggtg agttttctcc ttcattacag aaacggcttt    2400
ttcaaaaata tggtattgat aatcctgata tgaataaatt gcagtttcat ttgatgctcg    2460
atgagttttt ctaatcagaa ttggttaatt ggttgtaaca ctggcagagc attacgctga    2520
cttgacggga cggcgcaagc tcatgaccaa aatcccttaa cgtgagttac gcgtcgttcc    2580
actgagcgtc agaccccgta gaaaagatca aaggatcttc ttgagatcct ttttttctgc    2640
gcgtaatctg ctgcttgcaa acaaaaaaac caccgctacc agcggtggtt tgtttgccgg    2700
atcaagagct accaactctt tttccgaagg taactggctt cagcagagcg cagataccaa    2760
atactgtcct tctagtgtag ccgtagttag gccaccactt caagaactct gtagcaccgc    2820
ctacatacct cgctctgcta atcctgttac cagtggctgc tgccagtggc gataagtcgt    2880
gtcttaccgg gttggactca agacgatagt taccggataa ggcgcagcgg tcgggctgaa    2940
cggggggttc gtgcacacag cccagcttgg agcgaacgac ctacaccgaa ctgagatacc    3000
tacagcgtga gcattgagaa agcgccacgc ttcccgaagg gagaaaggcg gacaggtatc    3060
cggtaagcgg cagggtcgga acaggagagc gcacgaggga gcttccaggg ggaaacgcct    3120
ggtatcttta tagtcctgtc gggtttcgcc acctctgact tgagcgtcga tttttgtgat    3180
gctcgtcagg ggggcggagc ctatggaaaa acgccagcaa cgcggccttt ttacggttcc    3240
tggccttttg ctggcctttt gct                                           3263
```

<210> SEQ ID NO 44
<211> LENGTH: 3888
<212> TYPE: DNA
<213> ORGANISM: Artificial Sequence
<220> FEATURE:
<223> OTHER INFORMATION: pEQU6-shPDL1-H1-shCTNNB1 Vector

<400> SEQUENCE: 44

```
ctttcctgcg ttatcccctg attctgtgga taaccgtatt accgcctttg agtgagctga    60
```

```
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt cccagtcac gacgttgtaa     540 aacgacggcc agtcttaagc tcgggcccca ataatgatt ttattttgac tgatagtgac     600
ctgttcgttg caacaaattg atgagcaatg cttttttata atgccaactt tgtacaaaaa    660
agcaggcttt aaaggaacca attcagtcga gaattggtac catatttgca tgtcgctatg    720
tgttctggga atcaccata aacgtgaaat gtctttggat ttgggaatct tataagttct      780
gtatgagacc actccctagg acagactgcc ttcaaatttc tagagaattt gaaggcagtc    840
tgtctttttt cgacagatct ggcgcgccat agtggccagc ggccgcaggt aagccagccc    900
aggcctcgcc ctccagctca aggcgggaca ggtgccctag agtagcctgc atccagggac    960
aggccccagc cgggtgctga cacgtccacc tccatctctt cctcaggtct gccgggtgg    1020 catccctgtg acccctcccc agtgcctctc ctggccctgg aagttgccac tccagtgccc   1080
accagccttg tcctaataaa attaagttgc atcatttgt ctgactaggt gtccttctat    1140
aatattatgg ggtggagggg ggtggtatgg agcaagggc ccaagttaac ttgtttattg     1200
cagcttataa tggttacaaa taaagcaata gcatcacaaa tttcacaaat aaagcatttt   1260
tttcactgca ttctagttgt ggtttgtcca aactcatcaa tgtatcttat catgtctgga   1320
tccaaggtcg ggcaggaaga gggcctattt cccatgattc cttcatattt gcatatacga   1380
tacaaggctg ttagagagat aattagaatt aatttgactg taaacacaaa gatattagta   1440
caaaatacgt gacgtagaaa gtaataattt cttgggtagt ttgcagtttt aaaattatgt   1500
tttaaaatgg actatcatat gcttaccgta acttgaaagt atttcgattt cttggcttta   1560
tatatcttgt ggaaaggacg aaactaggta gagtatggta gcaatatcta gagtattgct   1620
accatactct acttttttcg agtagctaga gaattcatgg taatagcgat gactaatacg   1680
tagatgtact gccaagtagg aaagtcccat aaggtcatgt actgggcata atgccaggcg   1740
ggccatttac cgtcattgac gtcaataggg gcgtacttg gcatatgata cacttgatgt    1800
actgccaagt gggcagttta ccgtaaatag tccacccatt gacgtcaatg gaaagtccct   1860
attggcgtta ctatgggaac atacgtcatt attgacgtca atgggcgggg tcgttgggc    1920 ggtcagccag gcgggccatt taccgtaagt tatgtaacgc ggaactccat atatgggcta   1980
tgaactaatg acccgtaat tgattactat taataactag acccagcttt cttgtacaaa    2040
gttggcatta taagaaagca ttgcttatca atttgttgca acgaacaggt cactatcagt    2100
caaaataaaa tcattatttg ccatccagct gatatcccct atagtgagtc gtattacatg    2160
gtcatagctg tttcctggca gctctggccc gtgtctcaaa atctctgatg ttacattgca    2220
caagataaaa atatatcatc atgaacaata aaactgtctg cttacataaa cagtaataca   2280 agggggtgtta tgagccatat tcaacgggaa acgtcgaggc cgcgattaaa ttccaacatg   2340
gatgctgatt tatatgggta taaatgggct cgcgataatg tcgggcaatc aggtgcgaca   2400
atctatcgct tgtatgggaa gcccgatgcg ccagagttgt ttctgaaaca tggcaaaggt   2460
```

```
agcgttgcca atgatgttac agatgagatg gtcagactaa actggctgac ggaatttatg    2520
cctcttccga ccatcaagca tttatccgt actcctgatg atgcatggtt actcaccact    2580
gcgatccccg aaaaacagc attccaggta ttagaagaat atcctgattc aggtgaaaat    2640
attgttgatg cgctggcagt gttcctgcgc cggttgcatt cgattcctgt ttgtaattgt    2700 cctttaaca gcgatcgcgt atttcgtctc gctcaggcgc aatcacgaat gaataacggt    2760
ttggttgatg cgagtgattt tgatgacgag cgtaatggct ggcctgttga caagtctgg     2820 aaagaaatgc ataaacttt gccattctca ccggattcag tcgtcactca tggtgatttc    2880
tcacttgata accttatttt tgacgagggg aaattaatag ttgtattga tgttggacga     2940 gtcggaatcg cagaccgata ccaggatctt gccatcctat ggaactgcct cggtgagttt    3000
tctccttcat tacagaaacg cttttcaa aaatatggta ttgataatcc tgatatgaat      3060
aaattgcagt tcatttgat gctcgatgag ttttctaat cagaattggt taattggttg      3120
taacactggc agagcattac gctgacttga cgggacggcg caagctcatg accaaaatcc    3180
cttaacgtga gttacgcgtc gttccactga gcgtcagacc ccgtagaaaa gatcaaagga    3240
tcttcttgag atccttttt tctgcgcgta atctgctgct tgcaaacaaa aaaaccaccg    3300
ctaccagcgg tggtttgttt gccggatcaa gagctaccaa ctctttttcc gaaggtaact    3360
ggcttcagca gagcgcagat accaaatact gtccttctag tgtagccgta gttaggccac    3420
cacttcaaga actctgtagc accgcctaca tacctcgctc tgctaatcct gttaccagtg    3480
gctgctgcca gtggcgataa gtcgtgtctt accgggttgg actcaagacg atagttaccg    3540
gataaggcgc agcggtcggg ctgaacgggg ggttcgtgca cacagcccag cttggagcga    3600
acgacctaca ccgaactgag atacctacag cgtgagcatt gagaaagcgc cacgcttccc    3660
gaagggagaa aggcggacag gtatccggta agcggcaggg tcggaacagg agagcgcacg    3720
agggagcttc cagggggaaa cgcctggtat ctttatagtc ctgtcgggtt tcgccacctc    3780
tgacttgagc gtcgattttt gtgatgctcg tcagggggc ggagcctatg gaaaaacgcc     3840
agcaacgcgg cctttttacg gttcctggcc ttttgctggc ttttgct                  3888
```

<210> SEQ ID NO 45
<211> LENGTH: 3888
<212> TYPE: DNA
<213> ORGANISM: Artificial Sequence
<220> FEATURE:
<223> OTHER INFORMATION: pEQU6-shPDL1-H1-shSIRPalpha Vector

<400> SEQUENCE: 45

```
ctttcctgcg ttatcccctg attctgtgga taaccgtatt accgcctttg agtgagctga      60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca atccgctcc cggcggattt gtcctactca ggagagcgtt caccgacaaa     420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggcccca ataatgatt ttatttgac tgatagtgac     600
```

```
ctgttcgttg caacaaattg atgagcaatg cttttttata atgccaactt tgtacaaaaa    660
agcaggcttt aaaggaacca attcagtcga gaattggtac catatttgca tgtcgctatg    720
tgttctggga atcaccata aacgtgaaat gtctttggat ttgggaatct tataagttct    780
gtatgagacc actccctagg ccaggtgagg aagttctatc tagagtagaa cttcctcacc    840
tggctttttt cgacagatct ggcgcgccat agtggccagc ggccgcaggt aagccagccc    900
aggcctcgcc ctccagctca aggcgggaca ggtgccctag agtagcctgc atccagggac    960
aggccccagc cgggtgctga cacgtccacc tccatctctt cctcaggtct gcccgggtgg   1020
catccctgtg accctcccc agtgcctctc ctggccctgg aagttgccac tccagtgccc   1080
accagccttg tcctaataaa attaagttgc atcattttgt ctgactaggt gtccttctat   1140
aatattatgg ggtggagggg ggtggtatgg agcaaggggc ccaagttaac ttgtttattg   1200
cagcttataa tggttacaaa taaagcaata gcatcacaaa tttcacaaat aaagcatttt   1260
tttcactgca ttctagttgt ggtttgtcca aactcatcaa tgtatcttat catgtctgga   1320
tccaaggtcg ggcaggaaga gggcctattt cccatgattc cttcatattt gcatatacga   1380
tacaaggctg ttagagagat aattagaatt aatttgactg taaacacaaa gatattagta   1440
caaaatacgt gacgtagaaa gtaataattt cttgggtagt ttgcagtttt aaaattatgt   1500
tttaaaatgg actatcatat gcttaccgta acttgaaagt atttcgattt cttggcttta   1560
tatatcttgt ggaaaggacg aaactaggta gagtatggta gcaatatcta gagtattgct   1620
accatactct actttttcg agtagctaga gaattcatgg taatagcgat gactaatacg   1680
tagatgtact gccaagtagg aaagtcccat aaggtcatgt actgggcata atgccaggcg   1740
ggccatttac cgtcattgac gtcaataggg ggcgtacttg gcatatgata cacttgatgt   1800
actgccaagt gggcagttta ccgtaaatag tccacccatt gacgtcaatg gaaagtccct   1860
attggcgtta ctatgggaac atacgtcatt attgacgtca atgggcgggg gtcgttgggc   1920
ggtcagccag gcgggccatt taccgtaagt tatgtaacgc ggaactccat atatgggcta   1980
tgaactaatg acccccgtaat tgattactat taataactag acccagcttt cttgtacaaa   2040
gttggcatta taagaaagca ttgcttatca atttgttgca acgaacaggt cactatcagt   2100
caaaataaaa tcattatttg ccatccagct gatatcccct atagtgagtc gtattacatg   2160
gtcatagctg tttcctggca gctctggccc gtgtctcaaa atctctgatg ttacattgca   2220
caagataaaa atatatcatc atgaacaata aaactgtctg cttacataaa cagtaataca   2280
agggggtgtta tgagccatat tcaacgggaa acgtcgaggc cgcgattaaa ttccaacatg   2340
gatgctgatt tatatgggta taaatgggct cgcgataatg tcgggcaatc aggtgcgaca   2400
atctatcgct tgtatgggaa gcccgatgcg ccagagttgt ttctgaaaca tggcaaaggt   2460
agcgttgcca atgatgttac agatgagatg gtcagactaa actggctgac ggaatttatg   2520
cctcttccga ccatcaagca ttttatccgt actcctgatg atgcatggtt actcaccact   2580
gcgatccccg gaaaaacagc attccaggta ttagaagaat atcctgattc aggtgaaaat   2640
attgttgatg cgctggcagt gttcctgcgc cggttgcatt cgattcctgt ttgtaattgt   2700
ccttttaaca gcgatcgcgt atttcgtctc gctcaggcgc aatcacgaat gaataacggt   2760
ttggttgatg cgagtgattt tgatgacgag cgtaatggct ggcctgttga acaagtctgg   2820
aaagaaatgc ataaactttt gccattctca ccggattcag tcgtcactca tggtgatttc   2880
tcacttgata accttatttt tgacgagggg aaattaatag gttgtattga tgttggacga   2940
gtcggaatcg cagaccgata ccaggatctt gccatcctat ggaactgcct cggtgagttt   3000
```

```
tctccttcat tacagaaacg gcttttttcaa aaatatggta ttgataatcc tgatatgaat    3060
aaattgcagt ttcatttgat gctcgatgag tttttctaat cagaattggt taattggttg    3120
taacactggc agagcattac gctgacttga cgggacggcg caagctcatg accaaaatcc    3180
cttaacgtga gttacgcgtc gttccactga gcgtcagacc ccgtagaaaa gatcaaagga    3240
tcttcttgag atcctttttt tctgcgcgta atctgctgct tgcaaacaaa aaaaccaccg    3300
ctaccagcgg tggtttgttt gccggatcaa gagctaccaa ctcttttttcc gaaggtaact    3360 ggcttcagca gagcgcagat accaaatact gtccttctag tgtagccgta gttaggccac    3420
cacttcaaga actctgtagc accgcctaca tacctcgctc tgctaatcct gttaccagtg    3480
gctgctgcca gtggcgataa gtcgtgtctt accgggttgg actcaagacg atagttaccg    3540
gataaggcgc agcggtcggg ctgaacgggg ggttcgtgca cacagcccag cttggagcga    3600
acgacctaca ccgaactgag atacctacag cgtgagcatt gagaaagcgc cacgcttccc    3660
gaagggagaa aggcggacag gtatccggta agcggcaggg tcggaacagg agagcgcacg    3720
agggagcttc caggggggaaa cgcctggtat ctttatagtc ctgtcgggtt tcgccacctc    3780
tgacttgagc gtcgattttt gtgatgctcg tcagggggggc ggagcctatg gaaaaacgcc    3840
agcaacgcgg cctttttacg gttcctggcc ttttgctggc cttttgct                3888
```

<210> SEQ ID NO 46
<211> LENGTH: 3888
<212> TYPE: DNA
<213> ORGANISM: Artificial Sequence
<220> FEATURE:
<223> OTHER INFORMATION: pEQU6-shPDL1-H1-shTREX1

<400> SEQUENCE: 46

```
ctttcctgcg ttatcccctg attctgtgga taaccgtatt accgcctttg agtgagctga    60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggcccca ataatgatt ttattttgac tgatagtgac    600
ctgttcgttg caacaaattg atgagcaatg cttttttata atgccaactt tgtacaaaaa    660
agcaggcttt aaaggaacca attcagtcga gaattggtac catatttgca tgtcgctatg    720
tgttctggga aatcaccata aacgtgaaat gtctttggat ttgggaatct tataagttct    780
gtatgagacc actccctagg cagcgcatgg gcgtcaattc tagagattga cgcccatgcg    840
ctgctttttt cgacagatct ggcgcgccat agtggccagc ggccgcaggt aagccagccc    900
aggcctcgcc ctcagctca aggcgggaca ggtgccctag agtagcctgc atccaggggac    960 aggccccagc cgggtgctga cacgtccacc tccatctctt cctcaggtct gccgggtgg    1020 catccctgtg accctccccc agtgcctctc ctggccctgg aagttgccac tccagtgccc    1080
accagccttg tcctaataaa attaagttgc atcatttgt ctgactaggt gtccttctat    1140
```

```
aatattatgg ggtggagggg ggtggtatgg agcaagggc ccaagttaac ttgtttattg    1200
cagcttataa tggttacaaa taaagcaata gcatcacaaa tttcacaaat aaagcatttt    1260
tttcactgca ttctagttgt ggtttgtcca aactcatcaa tgtatcttat catgtctgga    1320
tccaaggtcg ggcaggaaga gggcctattt cccatgattc cttcatattt gcatatacga    1380
tacaaggctg ttagagagat aattagaatt aatttgactg taaacacaaa gatattagta    1440
caaaatacgt gacgtagaaa gtaataattt cttgggtagt ttgcagtttt aaaattatgt    1500
tttaaaatgg actatcatat gcttaccgta acttgaaagt atttcgattt cttggctta    1560 tatatcttgt ggaaaggacg aaactaggta gagtatggta gcaatatcta gagtattgct    1620
accatactct actttttttcg agtagctaga gaattcatgg taatagcgat gactaatacg    1680
tagatgtact gccaagtagg aaagtcccat aaggtcatgt actgggcata atgccaggcg    1740
ggccatttac cgtcattgac gtcaataggg ggcgtacttg gcatatgata cacttgatgt    1800
actgccaagt gggcagttta ccgtaaatag tccacccatt gacgtcaatg gaaagtccct    1860
attggcgtta ctatgggaac atacgtcatt attgacgtca atgggcgggg gtcgttgggc    1920
ggtcagccag gcgggccatt taccgtaagt tatgtaacgc ggaactccat atatgggcta    1980
tgaactaatg accccgtaat tgattactat taataactag acccagcttt cttgtacaaa    2040
gttggcatta taagaaagca ttgcttatca atttgttgca acgaacaggt cactatcagt    2100
caaaataaaa tcattatttg ccatccagct gatatcccct atagtgagtc gtattacatg    2160
gtcatagctg tttcctggca gctctggccc gtgtctcaaa atctctgatg ttacattgca    2220
caagataaaa atatatcatc atgaacaata aaactgtctg cttacataaa cagtaataca    2280
aggggtgtta tgagccatat tcaacgggaa acgtcgaggc cgcgattaaa ttccaacatg    2340
gatgctgatt tatatgggta taaatgggct cgcgataatg tcgggcaatc aggtgcgaca    2400
atctatcgct tgtatgggaa gcccgatgcg ccagagttgt ttctgaaaca tggcaaaggt    2460
agcgttgcca atgatgttac agatgagatg gtcagactaa actggctgac ggaatttatg    2520
cctcttccga ccatcaagca ttttatccgt actcctgatg atgcatggtt actcaccact    2580 gcgatcccg gaaaaacagc attccaggta ttagaagaat atcctgattc aggtgaaaat    2640
attgttgatg cgctggcagt gttcctgcgc cggttgcatt cgattcctgt ttgtaattgt    2700
ccttttaaca gcgatcgcgt atttcgtctc gctcaggcgc aatcacgaat gaataacggt    2760
ttggttgatg cgagtgattt tgatgacgag cgtaatggct ggcctgttga caagtctgg    2820 aaagaaatgc ataaactttt gccattctca ccggattcag tcgtcactca tggtgatttc    2880
tcacttgata accttatttt tgacgagggg aaattaatag gttgtattga tgttggacga    2940
gtcggaatcg cagaccgata ccaggatctt gccatcctat ggaactgcct cggtgagttt    3000
tctccttcat tacagaaacg ctttttcaa aaatatggta ttgataatcc tgatatgaat    3060
aaattgcagt ttcatttgat gctcgatgag ttttttctaat cagaattggt taattggttg    3120
taacactggc agagcattac gctgacttga cgggacggcg caagctcatg accaaaatcc    3180
cttaacgtga gttacgcgtc gttccactga gcgtcagacc ccgtagaaaa gatcaaagga    3240
tcttcttgag atcctttttt tctgcgcgta atctgctgct tgcaaacaaa aaaaccaccg    3300
ctaccagcgg tggtttgttt gccggatcaa gagctaccaa ctctttttcc gaaggtaact    3360
ggcttcagca gagcgcagat accaaatact gtccttctag tgtagccgta gttaggccac    3420
cacttcaaga actctgtagc accgcctaca tacctcgctc tgctaatcct gttaccagtg    3480
gctgctgcca gtggcgataa gtcgtgtctt accgggttgg actcaagacg atagttaccg    3540
```

```
gataaggcgc agcggtcggg ctgaacgggg ggttcgtgca cacagcccag cttggagcga    3600
acgacctaca ccgaactgag atacctacag cgtgagcatt gagaaagcgc cacgcttccc    3660
gaagggagaa aggcggacag gtatccggta agcggcaggg tcggaacagg agagcgcacg    3720
agggagcttc caggggaaa cgcctggtat ctttatagtc ctgtcgggtt tcgccacctc    3780
tgacttgagc gtcgattttt gtgatgctcg tcagggggc ggagcctatg gaaaaacgcc    3840
agcaacgcgg cctttttacg gttcctggcc ttttgctggc cttttgct               3888
```

<210> SEQ ID NO 47
<211> LENGTH: 3888
<212> TYPE: DNA
<213> ORGANISM: Artificial Sequence
<220> FEATURE:
<223> OTHER INFORMATION: pEQU6-shPDL1-H1-shVISTA

<400> SEQUENCE: 47

```
ctttcctgcg ttatcccctg attctgtgga taaccgtatt accgcctttg agtgagctga      60
taccgctcgc cgcagccgaa cgaccgagcg cagcgagtca gtgagcgagg aagcggaaga     120
gcgcccaata cgcaaaccgc ctctccccgc gcgttggccg attcattaat gcagctggca     180
cgacaggttt cccgactgga aagcgggcag tgagcgcaac gcaattaata cgcgtaccgc     240
tagccaggaa gagtttgtag aaacgcaaaa aggccatccg tcaggatggc cttctgctta     300
gtttgatgcc tggcagttta tggcgggcgt cctgcccgcc accctccggg ccgttgcttc     360
acaacgttca aatccgctcc cggcggattt gtcctactca ggagagcgtt caccgacaaa     420
caacagataa aacgaaaggc ccagtcttcc gactgagcct ttcgttttat ttgatgcctg     480
gcagttccct actctcgcgt taacgctagc atggatgttt tcccagtcac gacgttgtaa     540
aacgacggcc agtcttaagc tcgggcccca ataatgatt ttatttgac tgatagtgac     600 ctgttcgttg caacaaattg atgagcaatg cttttttata atgccaactt tgtacaaaaa     660
agcaggcttt aaaggaacca attcagtcga gaattggtac catatttgca tgtcgctatg     720
tgttctggga atcaccata aacgtgaaat gtctttggat ttgggaatct tataagttct     780
gtatgagacc actccctagg accaccatgg caacttcttc tagagagaag ttgccatggt     840
ggtctttttt cgacagatct ggcgcgccat agtggccagc ggccgcaggt aagccagccc     900
aggcctcgcc ctccagctca aggcgggaca ggtgccctag gtagcctgc atccaggac     960 aggccccagc cgggtgctga cacgtccacc tccatctctt cctcaggtct gcccgggtgg    1020
catccctgtg accctccccc agtgcctctc ctggccctgg aagttgccac tccagtgccc    1080
accagccttg tcctaataaa attaagttgc atcattttgt ctgactaggt gtccttctat    1140
aatattatgg ggtggagggg ggtggtatgg agcaagggc caagttaac ttgtttattg    1200 cagcttataa tggttacaaa taaagcaata gcatcacaaa tttcacaaat aaagcatttt    1260
tttcactgca ttctagttgt ggtttgtcca aactcatcaa tgtatcttat catgtctgga    1320
tccaaggtcg ggcaggaaga gggcctattt cccatgattc cttcatattt gcatatacga    1380
tacaaggctg ttagagagat aattagaatt aatttgactg taaacacaaa gatattagta    1440
caaaatacgt gacgtagaaa gtaataattt cttgggtagt ttgcagtttt aaaattatgt    1500
tttaaaatgg actatcatat gcttaccgta acttgaaagt atttcgattt cttggcttta    1560
tatatcttgt ggaaaggacg aaactaggta gagtatggta gcaatatcta gagtattgct    1620
accatactct acttttttcg agtagctaga gaattcatgg taatagcgat gactaatacg    1680
```

```
tagatgtact gccaagtagg aaagtcccat aaggtcatgt actgggcata atgccaggcg    1740
ggccatttac cgtcattgac gtcaataggg ggcgtacttg gcatatgata cacttgatgt    1800
actgccaagt gggcagttta ccgtaaatag tccacccatt gacgtcaatg aaagtccct     1860 attggcgtta ctatgggaac atacgtcatt attgacgtca atgggcgggg gtcgttgggc    1920
ggtcagccag gcgggccatt taccgtaagt tatgtaacgc ggaactccat atatgggcta   1980
tgaactaatg accccgtaat tgattactat taataactag acccagcttt cttgtacaaa   2040
gttggcatta taagaaagca ttgcttatca atttgttgca acgaacaggt cactatcagt   2100
caaaataaaa tcattatttg ccatccagct gatatcccct atagtgagtc gtattacatg   2160
gtcatagctg tttcctggca gctctggccc gtgtctcaaa atctctgatg ttacattgca   2220
caagataaaa atatatcatc atgaacaata aaactgtctg cttacataaa cagtaataca   2280
aggggtgtta tgagccatat tcaacgggaa acgtcgaggc cgcgattaaa ttccaacatg   2340
gatgctgatt tatatgggta taaatgggct cgcgataatg tcgggcaatc aggtgcgaca   2400
atctatcgct tgtatgggaa gcccgatgcg ccagagttgt ttctgaaaca tggcaaaggt   2460
agcgttgcca atgatgttac agatgagatg gtcagactaa actggctgac ggaatttatg   2520
cctcttccga ccatcaagca tttatccgt actcctgatg atgcatggtt actcaccact    2580
gcgatccccg aaaacagc attccaggta ttagaagaat atcctgattc aggtgaaaat     2640
attgttgatg cgctggcagt gttcctgcgc cggttgcatt cgattcctgt ttgtaattgt   2700
ccttttaaca gcgatcgcgt atttcgtctc gctcaggcgc aatcacgaat gaataacggt   2760
ttggttgatg cgagtgattt tgatgacgag cgtaatggct ggcctgttga acaagtctgg   2820
aaagaaatgc ataaacttttt gccattctca ccggattcag tcgtcactca tggtgatttc   2880
tcacttgata accttatttt tgacgagggg aaattaatag gttgtattga tgttggacga   2940
gtcggaatcg cagaccgata ccaggatctt gccatcctat ggaactgcct cggtgagttt   3000
tctccttcat tacagaaacg gcttttttcaa aaatatggta ttgataatcc tgatatgaat   3060
aaattgcagt ttcatttgat gctcgatgag ttttttctaat cagaattggt taattggttg   3120
taacactggc agagcattac gctgacttga cgggacggcg caagctcatg accaaaatcc   3180
cttaacgtga gttacgcgtc gttccactga gcgtcagacc ccgtagaaaa gatcaaagga   3240
tcttcttgag atcctttttt tctgcgcgta atctgctgct tgcaaacaaa aaaaccaccg   3300
ctaccagcgg tggtttgttt gccggatcaa gagctaccaa ctcttttcc gaaggtaact    3360 ggcttcagca gagcgcagat accaaatact gtccttctag tgtagccgta gttaggccac   3420
cacttcaaga actctgtagc accgcctaca tacctcgctc tgctaatcct gttaccagtg   3480
gctgctgcca gtggcgataa gtcgtgtctt accgggttgg actcaagacg atagttaccg   3540
gataaggcgc agcggtcggg ctgaacgggg ggttcgtgca cacagcccag cttggagcga   3600
acgacctaca ccgaactgag atacctacag cgtgagcatt gagaaagcgc cacgcttccc   3660
gaagggagaa aggcggacag gtatccggta agcggcaggg tcggaacagg agagcgcacg   3720
agggagcttc caggggggaaa cgcctggtat ctttatagtc ctgtcgggtt tcgccacctc   3780
tgacttgagc gtcgattttt gtgatgctcg tcagggggggc ggagcctatg gaaaaacgcc   3840
agcaacgcgg cctttttacg gttcctggcc ttttgctggc cttttgct                3888
```

<210> SEQ ID NO 48
<211> LENGTH: 1104
<212> TYPE: DNA
<213> ORGANISM: Salmonella typhimurium
<220> FEATURE:
<223> OTHER INFORMATION: Strain LT2 Aspartate-semialdehyde dehydrogenase
      (asd)

<400> SEQUENCE: 48

| | | | | | |
|---|---|---|---|---|---|
| atgaaaaatg | ttggttttat | cggctggcgc | ggaatggtcg | gctctgttct | catgcaacgc | 60 |
| atggtagagg | agcgcgattt | cgacgctatt | cgccctgttt | tcttttctac | ctcccagttt | 120 |
| ggacaggcgg | cgcccacctt | cggcgacacc | tccaccggca | cgctacagga | cgcttttgat | 180 |
| ctggatgcgc | taaaagcgct | cgatatcatc | gtgacctgcc | agggcggcga | ttataccaac | 240 |
| gaaatttatc | aaagctgcg | cgaaagcgga | tggcagggtt | actggattga | tgcggcttct | 300 |
| acgctgcgca | tgaaagatga | tgccattatt | attctcgacc | cggtcaacca | ggacgtgatt | 360 |
| accgacggcc | tgaacaatgg | cgtgaagacc | tttgtgggcg | gtaactgtac | cgttagcctg | 420 |
| atgttgatgt | cgctgggcgg | tctctttgcc | cataatctcg | ttgactgggt | atccgtcgcg | 480 |
| acctatcagg | ccgcctccgg | cggcggcgcg | cgccatatgc | gcgagctgtt | aacccagatg | 540 |
| ggtcagttgt | atggccatgt | cgccgatgaa | ctggcgacgc | cgtcttccgc | aattcttgat | 600 |
| attgaacgca | aagttacggc | attgacccgc | agcggcgagc | tgccggttga | taactttggc | 660 |
| gtaccgctgg | cgggaagcct | gatccctgg | atcgacaaac | agctcgataa | cggccagagc | 720 |
| cgcgaagagt | ggaaaggcca | ggcggaaacc | aacaagattc | tcaatactgc | ctctgtgatt | 780 |
| ccggttgatg | gtttgtgtgt | gcgcgtcggc | gcgctgcgct | gtcacagcca | ggcgttcacc | 840 |
| atcaagctga | aaaagaggt | atccattccg | acggtggaag | aactgctggc | ggcacataat | 900 |
| ccgtgggcga | agtggtgcc | gaacgatcgt | gatatcacta | tgcgcgaatt | aaccccggcg | 960 |
| gcggtgaccg | gcacgttgac | tacgccggtt | ggtcgtctgc | gtaagctgaa | catggggcca | 1020 |
| gagttcttgt | cggcgtttac | cgtaggcgac | cagttgttat | ggggcgccgc | cgagccgctg | 1080 |
| cgtcgaatgc | tgcgccagtt | ggcg | | | | 1104 |

<210> SEQ ID NO 49
<211> LENGTH: 861
<212> TYPE: DNA
<213> ORGANISM: Salmonella typhimurium
<220> FEATURE:
<223> OTHER INFORMATION: Strain LT2 TSX

<400> SEQUENCE: 49

| | | | | | |
|---|---|---|---|---|---|
| atgaaaaaaa | ctttactcgc | agtcagcgca | gcgctggcgc | tcacctcatc | ttttactgct | 60 |
| aacgcagcag | aaaatgatca | gccgcagtat | ttgtccgact | ggtggcacca | gagcgtaaac | 120 |
| gtggtaggca | gctaccatac | ccgtttctcg | ccgaaattga | caacgacgt | ctatctggaa | 180 |
| tatgaagcat | ttgccaaaaa | agactggttt | gatttctacg | gctatatcga | tattcccaaa | 240 |
| acctttgatt | ggggtaacgg | caacgataaa | ggtatctggt | ccgacggttc | tccgctgttc | 300 |
| atggaaatcg | aaccgcgttt | ctcaattgat | aagctgaccg | cgcagacct | gagcttcggc | 360 |
| ccgtttaaag | agtggtattt | cgccaacaac | tacatctacg | atatgggcga | taacaaagcc | 420 |
| agccgccaga | gcacgtggta | tatgggtctg | gggaccgata | tcgacaccgg | cctgccgatg | 480 |
| ggtctgtcgc | tgaacgtgta | tcgaaatat | cagtggcaaa | actacggcgc | gtccaatgaa | 540 |
| aacgaatggg | acggctaccg | tttcaaagtg | aaatacttcg | tccccatcac | cgatctgtgg | 600 |
| ggcggtaaac | tgagctatat | cggctttacc | aactttgact | ggggatctga | tttaggcgac | 660 |
| gatccgaacc | gtaccagcaa | ctccatcgct | tccagccata | tcctggcgct | gaactacgat | 720 |
| cactggcact | actcggtcgt | tgcgcgttac | ttccataacg | gcggacagtg | gcagaatggc | 780 |

-continued

```
gcaaaactga actggggcga cggcgatttc agcgcgaaat ctaccggctg gggcggctac    840
ctggtcgtgg gttacaactt c                                              861
```

<210> SEQ ID NO 50
<211> LENGTH: 864
<212> TYPE: DNA
<213> ORGANISM: Homo sapiens
<220> FEATURE:
<223> OTHER INFORMATION: programmed cell death protein 1 (PD-1)

<400> SEQUENCE: 50

```
atgcagatcc cacaggcgcc ctggccagtc gtctgggcgg tgctacaact gggctggcgg     60
ccaggatggt tcttagactc cccagacagg ccctggaacc cccccacctt ctccccagcc    120
ctgctcgtgg tgaccgaagg ggacaacgcc accttcacct gcagcttctc caacacatcg    180
gagagcttcg tgctaaactg gtaccgcatg agccccagca accagacgga caagctggcc    240
gccttccccg aggaccgcag ccagcccggc caggactgcc gcttccgtgt cacacaactg    300
cccaacgggc gtgacttcca catgagcgtg gtcagggccc ggcgcaatga cagcggcacc    360
tacctctgtg gggccatctc cctggccccc aaggcgcaga tcaaagagag cctgcgggca    420
gagctcaggg tgacagagag aagggcagaa gtgcccacag cccaccccag cccctcaccc    480
aggccagccg ccagttccaa accctggtg gttggtgtcg tgggcggcct gctgggcagc    540
ctggtgctgc tagtctgggt cctggccgtc atctgctccc gggccgcacg agggacaata    600
ggagccaggc gcaccggcca gccctgaag gaggacccct cagccgtgcc tgtgttctct    660
gtggactatg gggagctgga tttccagtgg cgagagaaga cccggagcc cccgtgccc    720 tgtgtccctg agcagacgga gtatgccacc attgtctttc tagcggaat gggcacctca    780 tcccccgccc gcagggctc agctgacggc ctcggagtg cccagccact gaggcctgag    840
gatggacact gctcttggcc cctc                                          864
```

<210> SEQ ID NO 51
<211> LENGTH: 933
<212> TYPE: DNA
<213> ORGANISM: Homo sapiens
<220> FEATURE:
<223> OTHER INFORMATION: programmed cell death protein 2 (PD-2), isoform 1

<400> SEQUENCE: 51

```
atggctgccg ccggggccag gcctgtggag ctgggcttcg ccgagtcggc gccggcgtgg     60
cgactgcgca gcgagcagtt ccccagcaag gtgtatgcgc cgctgcctgg ccgcccggac    120
gccttccacc gctgcatctt cctcttctgc tgccgcgagc agccgtgctg tgccggcctg    180 cgagtttta ggaatcaact acccaggaaa aacgattttt actcatatga gccaccttct    240
gagaatcctc cccagaaaac aggagaatca gtgtgtctcc agcttaagtc tggtgctcat    300
ctctgcaggg tttgtggctg tttaggcccc aaaacgtgct ccagatgcca caaagcatat    360
tactgcagca aggagcatca gaccctagac tggagattgg acataagca ggcttgtgca    420 caaccagatc atctggacca tataattcca gaccacaact tcctttttcc agaatttgaa    480
attgtaatag aaacagaaga tgagattatg cctgaggttg tggaaaagga agattactca    540
gagattatag ggagcatggg tgaagcactt gaggaagaac tggattccat ggcaaaacat    600
gaatccaggg aagataaat tttcagaag tttaaaactc agatagccct tgaaccagaa    660
cagattctta gatatggcag aggtattgcc cccatctgga tttctggtga aaatattcct    720
```

```
caagaaaagg atattccaga ttgcccctgt ggtgccaaga gaatattgga attccaggtc    780
atgcctcagc tcctaaacta cctgaaggct gacagactgg gcaagagcat tgactggggc    840
atcctggctg tcttcacctg tgctgagagc tgcagcttgg gtactggcta tacagaagaa    900
tttgtgtgga agcaggatgt aacagataca ccg                                 933
```

<210> SEQ ID NO 52
<211> LENGTH: 819
<212> TYPE: DNA
<213> ORGANISM: Homo sapiens
<220> FEATURE:
<223> OTHER INFORMATION: programmed death-ligand 2 (PD-L2), isoform 1

<400> SEQUENCE: 52

```
atgatcttcc tcctgctaat gttgagcctg aattgcagc ttcaccagat agcagcttta     60
ttcacagtga cagtccctaa ggaactgtac ataatagagc atggcagcaa tgtgaccctg    120
gaatgcaact ttgacactgg aagtcatgtg aaccttggag caataacagc cagtttgcaa    180
aaggtggaaa atgatacatc cccacaccgt gaaagagcca ctttgctgga ggagcagctg    240
cccctaggga aggcctcgtt ccacatacct caagtccaag tgaggacga aggacagtac     300 caatgcataa tcatctatgg ggtcgcctgg gactacaagt acctgactct gaaagtcaaa    360
gcttcctaca ggaaaataaa cactcacatc ctaaaggttc agaaacaga tgaggtagag     420 ctcacctgcc aggctacagg ttatcctctg gcagaagtat cctggccaaa cgtcagcgtt    480
cctgccaaca ccagccactc caggaccct gaaggcctct accaggtcac cagtgttctg    540
cgcctaaagc caccccctgg cagaaacttc agctgtgtgt tctggaatac tcacgtgagg    600
gaacttactt tggccagcat tgaccttcaa agtcagatgg aacccaggac ccatccaact    660
tggctgcttc acattttcat ccctcctgc atcattgctt tcattttcat agccacagtg     720
atagccctaa gaaaacaact ctgtcaaaag ctgtattctt caaaagacac aacaaaaaga    780
cctgtcacca caacaaagag ggaagtgaac agtgctatc                           819
```

<210> SEQ ID NO 53
<211> LENGTH: 669
<212> TYPE: DNA
<213> ORGANISM: Homo sapiens
<220> FEATURE:
<223> OTHER INFORMATION: cytotoxic T-lymphocyte-associated protein 4
      (CTLA-4), isoform 1

<400> SEQUENCE: 53

```
atggcttgcc ttggatttca gcggcacaag gctcagctga acctggctac caggacctgg     60
ccctgcactc tcctgttttt tcttctcttc atccctgtct tctgcaaagc aatgcacgtg    120
gcccagcctg ctgtggtact ggccagcagc cgaggcatcg ccagctttgt gtgtgagtat    180
gcatctccag gcaaagccac tgaggtccgg gtgacagtgc ttcggcaggc tgacagccag    240
gtgactgaag tctgtgcggc aacctacatg atggggaatg agttgacctt cctagatgat    300
tccatctgca cgggcacctc cagtggaaat caagtgaacc tcactatcca aggactgagg    360
gccatggaca cgggactcta catctgcaag gtggagctca tgtacccacc gccatactac    420
ctgggcatag gcaacggaac ccagatttat gtaattgatc cagaaccgtg cccagattct    480
gacttcctcc tctggatcct tgcagcagtt agttcgggt tgttttttta tagctttctc    540
ctcacagctg tttctttgag caaaatgcta agaaaagaa gccctcttac aacagggtc     600 tatgtgaaaa tgcccccaac agagccagaa tgtgaaaagc aatttcagcc ttattttatt    660
```

```
cccatcaat                                                              669

<210> SEQ ID NO 54
<211> LENGTH: 969
<212> TYPE: DNA
<213> ORGANISM: Homo sapiens
<220> FEATURE:
<223> OTHER INFORMATION: CD47 transcript variant 1

<400> SEQUENCE: 54
atgtggcccc tggtagcggc gctgttgctg ggctcggcgt gctgcggatc agctcagcta      60
ctatttaata aaacaaaatc tgtagaattc acgttttgta atgacactgt cgtcattcca     120
tgctttgtta ctaatatgga ggcacaaaac actactgaag tatacgtaaa gtggaaattt     180
aaaggaagag atatttacac ctttgatgga gctctaaaca agtccactgt ccccactgac     240
tttagtagtg caaaaattga agtctcacaa ttactaaaag gagatgcctc tttgaagatg     300
gataagagtg atgctgtctc acacacagga aactacactt gtgaagtaac agaattaacc     360
agagaaggtg aaacgatcat cgagctaaaa tatcgtgttg tttcatggtt ttctccaaat     420
gaaaatattc ttattgttat tttcccaatt tttgctatac tcctgttctg gggacagttt     480
ggtattaaaa cacttaaata tagatccggt ggtatggatg agaaaacaat tgctttactt     540
gttgctggac tagtgatcac tgtcattgtc attgttggag ccattctttt cgtcccaggt     600
gaatattcat taagaatgc tactggcctt ggtttaattg tgacttctac agggatatta     660
atattacttc actactatgt gtttagtaca gcgattggat taacctcctt cgtcattgcc     720
atattggtta ttcaggtgat agcctatatc ctcgctgtgg ttggactgag tctctgtatt     780
gcggcgtgta taccaatgca tggccctctt ctgatttcag gtttgagtat cttagctcta     840
gcacaattac ttggactagt ttatatgaaa tttgtggctt ccaatcagaa gactatacaa     900
cctcctagga aagctgtaga ggaacccctt aatgcattca agaatcaaa aggaatgatg     960 aatgatgaa                                                              969

<210> SEQ ID NO 55
<211> LENGTH: 1209
<212> TYPE: DNA
<213> ORGANISM: Homo sapiens
<220> FEATURE:
<223> OTHER INFORMATION: indoleamine 2,3-dioxygenase (IDO) 1

<400> SEQUENCE: 55
atggcacacg ctatggaaaa ctcctggaca atcagtaaag agtaccatat tgatgaagaa      60
gtgggctttg ctctgccaaa tccacaggaa atctacctg attttttataa tgactggatg     120 ttcattgcta acatctgcc tgatctcata gagtctggcc agcttcgaga aagagttgag     180
aagttaaaca tgctcagcat tgatcatctc acagaccaca gtcacagcg ccttgcacgt     240 ctagttctgg gatgcatcac catggcatat gtgtggggca aggtcatgg agatgtccgt     300 aaggtcttgc caagaaatat tgctgttcct tactgccaac tctccaagaa actggaactg     360 cctcctatt tggtttatgc agactgtgtc ttggcaaact ggaagaaaaa ggatcctaat     420
aagcccctga cttatgagaa catggactt tgttctcat tcgtgatgg agactgcagt     480 aaaggattct tcctggtctc tctattggtg aaatagcag ctgcttctgc aatcaaagta     540
attcctactg tattcaaggc aatgcaaatg caagaacggg acactttgct aaaggcgctg     600
ttggaaatag cttcttgctt ggagaaagcc cttcaagtgt tcaccaaat ccacgatcat     660
```

```
gtgaacccaa aagcatttt  cagtgttctt cgcatatatt tgtctggctg gaaaggcaac    720
ccccagctat cagacggtct ggtgtatgaa aggttctggg aagacccaaa ggagtttgca    780
gggggcagtg caggccaaag cagcgtcttt cagtgctttg acgtcctgct gggcatccag    840
cagactgctg gtggaggaca tgctgctcag ttcctccagg acatgagaag atatatgcca    900
ccagctcaca ggaacttcct gtgctcatta gagtcaaatc cctcagtccg tgagtttgtc    960
ctttcaaaag gtgatgctgg cctgcgggaa gcttatgacg cctgtgtgaa agctctggtc   1020
tccctgagga gctaccatct gcaaatcgtg actaagtaca tcctgattcc tgcaagccag   1080
cagccaaagg agaataagac ctctgaagac ccttcaaaac tggaagccaa aggaactgga   1140
ggcactgatt taatgaattt cctgaagact gtaagaagta caactgagaa atcccttttg   1200
aaggaaggt                                                           1209

<210> SEQ ID NO 56
<211> LENGTH: 1260
<212> TYPE: DNA
<213> ORGANISM: Homo sapiens
<220> FEATURE:
<223> OTHER INFORMATION: indoleamine 2,3-dioxygenase (IDO) 2

<400> SEQUENCE: 56
atgttgcatt tcattatta tgatacttca aacaaaataa tggagcccca cagaccgaat     60
gtgaagacag cagtgccatt gtctttggaa agctatcaca tatctgaaga gtatggcttt    120
cttcttccag attctctgaa agaacttcca gatcattata ggccttggat ggaaattgcc    180
aacaaacttc ctcaattgat tgatgctcac cagcttcaag ctcatgtgga caagatgccc    240
ctgctgagct gccagttcct gaagggtcac cgggagcagc gcctggccca cctggtcctg    300
agcttcctca ccatgggtta tgtctggcag gaaggagagg cgcagcctgc agaggtcctg    360
ccaaggaatc ttgcccttcc atttgtcgaa gtctccagga acttggggct ccctcctatc    420
ctggtccact cagacttggt gctgacgaac tggaccaaaa aagatccaga cggattcctg    480
gaaattggga acctggagac catcatctca tttcctgggg gagagagcct gcatggtttt    540
atactggtga ctgctttggt agagaaagaa gcagtgcctg ggataaaggc tcttgttcag    600
gccacgaatg ctatcttgca gcccaaccag gaggccctgc tccaagccct gcagcgactg    660
agactgtcta ttcaggacat caccaaaacc ttaggacaga tgcatgatta tgtagatcca    720 gacatattt atgcaggcat ccggatctt ctctctggat ggaaagacaa cccagcaatg    780
cctgcagggc tgatgtatga aggagtttcc aagagcccc tgaaatactc cggcgggagt    840
gcagctcaga gcacagtgct tcatgccttt gatgagttct taggcattcg tcatagcaag    900
gaaagtggtg actttctgta cagaatgagg gattacatgc ctccttccca taaggccttc    960
atagaagaca tccactcagc accttccctg agggactaca tcctgtcatc tggacaggac   1020
cacttgctga cagcttataa ccagtgtgtg caggccctgg cagagctgcg gagctatcac   1080
atcaccatgg tcaccaaata cctcatcaca gctgcagcca aggcaaagca tgggaagcca   1140
aaccatctcc cagggcctcc tcaggcttta aaagacaggg gcacaggtgg aaccgcagtt   1200
atgagctttc ttaagagtgt cagggataag accttggagt caatccttca cccacgtggt   1260

<210> SEQ ID NO 57
<211> LENGTH: 2310
<212> TYPE: DNA
<213> ORGANISM: Homo sapiens
<220> FEATURE:
<223> OTHER INFORMATION: signal transducer and activator of
``` transcription 3 (STAT3)

<400> SEQUENCE: 57

```
atggcccaat ggaatcagct acagcagctt gacacacggt acctggagca gctccatcag       60
ctctacagtg acagcttccc aatggagctg cggcagtttc tggccccttg gattgagagt      120
caagattggg catatgcggc cagcaaagaa tcacatgcca ctttggtgtt tcataatctc      180
ctgggagaga ttgaccagca gtatagccgc ttcctgcaag agtcgaatgt tctctatcag      240
cacaatctac gaagaatcaa gcagtttctt cagagcaggt atcttgagaa gccaatggag      300
attgcccgga ttgtgcccg tgcctgtgg aagaatcac gccttctaca gactgcagcc         360
actgcggccc agcaagggg ccaggccaac cacccacag cagccgtggt gacggagaag        420
cagcagatgc tggagcagca ccttcaggat gtccggaaga gagtgcagga tctagaacag      480
aaaatgaaag tggtagagaa tctccaggat gactttgatt tcaactataa aaccctcaag      540
agtcaaggag acatgcaaga tctgaatgga acaaccagt cagtgaccag gcagaagatg       600
cagcagctgg aacagatgct cactgcgctg accagatgc ggagaagcat cgtgagtgag       660
ctggcggggc ttttgtcagc gatggagtac gtgcagaaaa ctctcacgga cgaggagctg      720
gctgactgga agaggcggca acagattgcc tgcattggag gccgcccaa catctgccta      780
gatcggctag aaaactggat aacgtcatta gcagaatctc aacttcagac ccgtcaacaa      840
attaagaaac tggaggagtt gcagcaaaaa gtttcctaca aggggaccc cattgtacag      900
caccggccga tgctggagga gagaatcgtg gagctgttta gaaacttaat gaaaagtgcc      960
tttgtggtgg agcggcagcc ctgcatgccc atgcatcctg accggccct cgtcatcaag     1020
accggcgtcc agttcactac taaagtcagg ttgctggtca aattccctga gttgaattat     1080
cagcttaaaa ttaaagtgtg cattgacaaa gactctgggg acgttgcagc tctcagagga     1140
tcccggaaat ttaacattct gggcacaaac acaaaagtga tgaacatgga agaatccaac     1200
aacggcagcc tctctgcaga attcaaacac ttgaccctga gggagcagag atgtgggaat     1260
gggggccgag ccaattgtga tgcttccctg attgtgactg aggagctgca cctgatcacc     1320
tttgagaccg aggtgtatca ccaaggcctc aagattgacc tagagaccca ctccttgcca     1380
gttgtggtga tctccaacat ctgtcagatg ccaaatgcct gggcgtccat cctgtggtac     1440
aacatgctga ccaacaatcc caagaatgta aactttttta ccaagccccc aattggaacc     1500
tgggatcaag tggccgaggt cctgagctgg cagttctcct ccaccaccaa gcgaggactg     1560
agcatcgagc agctgactac actggcagag aaactcttgg acctggtgt gaattattca     1620
gggtgtcaga tcacatgggc taaattttgc aaagaaaaca tggctggcaa gggcttctcc     1680
ttctgggtct ggctggacaa tatcattgac cttgtgaaaa agtacatcct ggccctttgg     1740
aacgaagggt acatcatggg ctttatcagt aaggagcggg agcggccat cttgagcact     1800
aagcctccag gcaccttcct gctaagattc agtgaaagca gcaaagaagg aggcgtcact     1860
ttcacttggg tggagaagga catcagcggt aagacccaga tccagtccgt ggaaccatac     1920
acaaagcagc agctgaacaa catgtcattt gctgaaatca tcatgggcta taagatcatg     1980
gatgctacca atatcctggt gtctccactg gtctatctct atcctgacat tcccaaggag     2040
gaggcattcg gaaagtattg tcggccagag agccaggagc atcctgaagc tgacccaggt     2100
agcgctgccc catacctgaa gaccaagttt atctgtgtga caccaacgac ctgcagcaat     2160
accattgacc tgccgatgtc cccccgcact ttagattcat tgatgcagtt tggaaataat     2220
ggtgaaggtg ctgaaccctc agcaggaggg cagtttgagt ccctcacctt tgacatggag     2280
```

```
ttgacctcgg agtgcgctac ctcccccatg                                      2310
```

<210> SEQ ID NO 58
<211> LENGTH: 1575
<212> TYPE: DNA
<213> ORGANISM: Homo sapiens
<220> FEATURE:
<223> OTHER INFORMATION: lymphocyte-activation gene 3 (LAG3)

<400> SEQUENCE: 58

```
atgtgggagg ctcagttcct gggcttgctg tttctgcagc cgctttgggt ggctccagtg      60
aagcctctcc agccaggggc tgaggtcccg gtggtgtggg cccaggaggg ggctcctgcc     120
cagctcccct gcagccccac aatccccctc caggatctca gccttctgcg aagagcaggg     180
gtcacttggc agcatcagcc agacagtggc ccgcccgctg ccgcccccgg ccatcccctg     240
gcccccggcc ctcacccggc ggcgccctcc tcctgggggc ccaggccccg ccgctacacg     300
gtgctgagcg tgggtcccgg aggcctgcgc agcggggagc tgcccctgca gccccgcgtc     360
cagctggatg agcgcggccg gcagcgcggg gacttctcgc tatggctgcg cccagcccgg     420
cgcgcggacg ccgcgagta ccgcgccgcg gtgcacctca gggaccgcgc cctctcctgc     480
cgcctccgtc tgcgcctggg ccaggcctcg atgactgcca gcccccagg atctctcaga     540
gcctccgact gggtcatttt gaactgctcc ttcagccgcc tgaccgccc agcctctgtg     600
cattggttcc ggaaccgggg ccaggccga gtccctgtcc gggagtcccc ccatcaccac     660
ttagcggaaa gcttcctctt cctgcccaa gtcagccca tggactctgg gccctggggc     720
tgcatcctca cctacagaga tggcttcaac gtctccatca tgtataacct cactgttctg     780
ggtctggagc ccccaactcc cttgacagtg tacgctggag caggttccag ggtgggggctg    840
ccctgccgcc tgcctgctgg tgtggggacc cggtctttcc tcactgccaa gtggactcct     900
cctggggag gccctgacct cctggtgact ggagacaatg gcgactttac ccttcgacta     960
gaggatgtga gccaggccca ggctgggacc tacacctgcc atatccatct gcaggaacag    1020
cagctcaatg ccactgtcac attggcaatc atcacagtga ctcccaaatc ctttgggtca    1080
cctggatccc tggggaagct gctttgtgag gtgactccag tatctggaca agaacgcttt    1140
gtgtggagct ctctggacac cccatcccag aggagtttct caggaccttg gctggaggca    1200
caggaggccc agctccttc ccagccttgg caatgccagc tgtaccaggg ggagaggctt    1260
cttggagcag cagtgtactt cacagagctg tctagcccag gtgcccaacg ctctgggaga    1320
gccccaggtg ccctcccagc aggccacctc tgctgtttc tcatccttgg tgtcctttct    1380
ctgctccttt tggtgactgg agcctttggc tttcaccttt ggagaagaca gtggcgacca    1440
agacgatttt ctgccttaga gcaagggatt caccctccgc aggctcagag caagatagag    1500
gagctggagc aagaaccgga gccggagccg gagccggaac cggagcccga gcccgagccc    1560
gagccggagc agctc                                                    1575
```

<210> SEQ ID NO 59
<211> LENGTH: 903
<212> TYPE: DNA
<213> ORGANISM: Homo sapiens
<220> FEATURE:
<223> OTHER INFORMATION: T cell immunoglobulin and mucin-domain
      containing-3 (TIM-3)

<400> SEQUENCE: 59

```
atgttttcac atcttcccttt tgactgtgtc ctgctgctgc tgctgctact acttacaagg     60
```

```
tcctcagaag tggaatacag agcggaggtc ggtcagaatg cctatctgcc ctgcttctac    120
accccagccg ccccagggaa cctcgtgccc gtctgctggg gcaaaggagc ctgtcctgtg    180
tttgaatgtg caacgtggt gctcaggact gatgaaaggg atgtgaatta ttggacatcc     240
agatactggc taaatgggga tttccgcaaa ggagatgtgt ccctgaccat agagaatgtg    300
actctagcag acagtgggat ctactgctgc cggatccaaa tcccaggcat aatgaatgat    360
gaaaaattta acctgaagtt ggtcatcaaa ccagccaagg tcacccctgc accgactcgg    420
cagagagact tcactgcagc ctttccaagg atgcttacca ccaggggaca tggcccagca    480
gagacacaga cactggggag cctccctgat ataaatctaa cacaaatatc cacattggcc    540
aatgagttac gggactctag attggccaat gacttacggg actctggagc aaccatcaga    600
ataggcatct acatcggagc agggatctgt gctgggctgg ctctggctct tatcttcggc    660
gctttaattt tcaaatggta ttctcatagc aaagagaaga tacagaattt aagcctcatc    720
tctttggcca acctccctcc ctcaggattg caaatgcag tagcagaggg aattcgctca    780
gaagaaaaca tctataccat tgaagagaac gtatatgaag tggaggagcc caatgagtat    840
tattgctatg tcagcagcag gcagcaaccc tcacaacctt gggttgtcg ctttgcaatg     900 cca                                                                  903
```

<210> SEQ ID NO 60
<211> LENGTH: 732
<212> TYPE: DNA
<213> ORGANISM: Homo sapiens
<220> FEATURE:
<223> OTHER INFORMATION: T cell immunoreceptor with Ig and ITIM domains
      (TIGIT), isoform 1

<400> SEQUENCE: 60

```
atgcgctggt gtctcctcct gatctgggcc caggggctga ggcaggctcc cctcgcctca     60
ggaatgatga caggcacaat agaaacaacg gggaacattt ctgcagagaa aggtggctct    120
atcatcttac aatgtcacct ctcctccacc acggcacaag tgacccaggt caactgggag    180
cagcaggacc agcttctggc catttgtaat gctgacttgg ggtggcacat ctccccatcc    240
ttcaaggatc gagtggcccc aggtcccggc ctgggcctca ccctccagtc gctgaccgtg    300
aacgatacag gggagtactt ctgcatctat cacacctacc tgatgggac gtacactggg    360 agaatcttcc tggaggtcct agaaagctca gtggctgagc acggtgccag gttccagatt    420
ccattgcttg gagccatggc cgcgacgctg gtggtcatct gcacagcagt catcgtggtg    480
gtcgcgttga ctagaaagaa gaaagccctc agaatccatt ctgtggaagg tgacctcagg    540
agaaaatcag ctggacagga ggaatggagc cccagtgctc cctcaccccc aggaagctgt    600
gtccaggcag aagctgcacc tgctgggctc tgtggagagc agcggggaga ggactgtgcc    660
gagctgcatg actacttcaa tgtcctgagt tacagaagcc tgggtaactg cagcttcttc    720
acagagactg gt                                                        732
```

<210> SEQ ID NO 61
<211> LENGTH: 1065
<212> TYPE: DNA
<213> ORGANISM: Homo sapiens
<220> FEATURE:
<223> OTHER INFORMATION: GALECTIN-9/LGALS9, isoform 1

<400> SEQUENCE: 61

```
atggccttca gcggttccca ggctccctac ctgagtccag ctgtcccctt ttctggggact    60
```

| | |
|---|---|
| attcaaggag gtctccagga cggacttcag atcactgtca atgggaccgt tctcagctcc | 120 |
| agtggaacca ggtttgctgt gaactttcag actggcttca gtggaaatga cattgccttc | 180 |
| cacttcaacc ctcggtttga agatggaggg tacgtggtgt gcaacacgag cagaacgga | 240 |
| agctgggggc ccgaggagag gaagacacac atgcctttcc agaaggggat gccctttgac | 300 |
| ctctgcttcc tggtgcagag ctcagatttc aaggtgatgg tgaacgggat cctcttcgtg | 360 |
| cagtacttcc accgcgtgcc cttccaccgt gtggacacca tctccgtcaa tggctctgtg | 420 |
| cagctgtcct acatcagctt ccagaacccc cgcacagtcc ctgttcagcc tgccttctcc | 480 |
| acggtgccgt tctcccagcc tgtctgtttc cacccaggc ccaggggcg cagacaaaaa | 540 |
| cctcccggcg tgtggcctgc caacccggct cccattaccc agacagtcat ccacacagtg | 600 |
| cagagcgccc ctggacagat gttctctact cccgccatcc cacctatgat gtaccccca | 660 |
| cccgcctatc cgatgccttt catcaccacc attctgggag gctgtaccc atccaagtcc | 720 |
| atcctcctgt caggcactgt cctgccagt gctcagaggt tccacatcaa cctgtgctct | 780 |
| gggaaccaca tcgccttcca cctgaacccc cgttttgatg agaatgctgt ggtccgcaac | 840 |
| acccagatcg acaactcctg ggggtctgag gagcgaagtc tgccccgaaa aatgcccttc | 900 |
| gtccgtggcc agagcttctc agtgtggatc ttgtgtgaag ctcactgcct caaggtggcc | 960 |
| gtggatggtc agcacctgtt tgaatactac catcgcctga ggaacctgcc caccatcaac | 1020 |
| agactggaag tggggggcga catccagctg acccatgtgc agaca | 1065 |

<210> SEQ ID NO 62
<211> LENGTH: 720
<212> TYPE: DNA
<213> ORGANISM: Homo sapiens
<220> FEATURE:
<223> OTHER INFORMATION: LIGHT/TNSF14

<400> SEQUENCE: 62

| | |
|---|---|
| atggaggaga gtgtcgtacg gcccctcagtg tttgtggtgg atggacagac cgacatccca | 60 |
| ttcacgaggc tgggacgaag ccaccggaga cagtcgtgca gtgtggcccg ggtgggtctg | 120 |
| ggtctcttgc tgttgctgat ggggggccggg ctggccgtcc aaggctggtt cctcctgcag | 180 |
| ctgcactggc gtctaggaga gatggtcacc cgcctgcctg acggacctgc aggctcctgg | 240 |
| gagcagctga tacaagagcg aaggtctcac gaggtcaacc cagcagcgca tctcacaggg | 300 |
| gccaactcca gcttgaccgg cagcggggg ccgctgttat gggagactca gctgggcctg | 360 |
| gccttcctga ggggcctcag ctaccacgat ggggcccttg tggtcaccaa agctggctac | 420 |
| tactacatct actccaaggt gcagctgggc ggtgtgggct gcccgctggg cctggccagc | 480 |
| accatcaccc acgcctcta caagcgcaca cccgctacc ccgaggagct ggagctgttg | 540 |
| gtcagccagc agtcacccctg cggacgggcc accagcagct cccgggtctg tgggacagc | 600 |
| agcttcctgg gtggtgtggt acacctggag gctggggaga aggtggtcgt ccgtgtgctg | 660 |
| gatgaacgcc tggttcgact gcgtgatggt acccggtctt acttcggggc tttcatggtg | 720 |

<210> SEQ ID NO 63
<211> LENGTH: 849
<212> TYPE: DNA
<213> ORGANISM: Homo sapiens
<220> FEATURE:
<223> OTHER INFORMATION: HVEM/TNSFR14 (receptor for LIGHT ligand)

<400> SEQUENCE: 63

```
atggagcctc ctggagactg ggggcctcct ccctggagat ccaccccaa aaccgacgtc    60 ttgaggctgg tgctgtatct caccttcctg ggagccccct gctacgcccc agctctgccg   120
tcctgcaagg aggacgagta cccagtgggc tccgagtgct gccccaagtg cagtccaggt   180
tatcgtgtga aggaggcctg cggggagctg acgggcacag tgtgtgaacc ctgccctcca   240
ggcacctaca ttgcccacct caatggccta agcaagtgtc tgcagtgcca aatgtgtgac   300
ccagccatgg gcctgcgcgc gagccggaac tgctccagga cagagaacgc cgtgtgtggc   360
tgcagcccag gccacttctg catcgtccag gacggggacc actgcgccgc gtgccgcgct   420
tacgccacct ccagcccggg ccagagggtg cagaagggag gcaccgagag tcaggacacc   480
ctgtgtcaga actgcccccc ggggaccttc tctcccaatg ggaccctgga ggaatgtcag   540
caccagacca gtgcagctg gctggtgacg aaggccggag ctgggaccag cagctcccac   600
tgggtatggt ggtttctctc agggagcctc gtcatcgtca ttgtttgctc cacagttggc   660
ctaatcatat gtgtgaaaag aagaaagcca aggggtgatg tagtcaaggt gatcgtctcc   720
gtccagcgga aagacaggg ggcagaaggt gaggccacag tcattgaggc cctgcaggcc   780
cctccggacg tcaccacggt ggccgtggag gagacaatac cctcattcac ggggaggagc   840
ccaaaccac                                                           849

<210> SEQ ID NO 64
<211> LENGTH: 660
<212> TYPE: DNA
<213> ORGANISM: Homo sapiens
<220> FEATURE:
<223> OTHER INFORMATION: CD28

<400> SEQUENCE: 64
atgctcaggc tgctcttggc tctcaactta ttcccttcaa ttcaagtaac aggaaacaag    60
attttggtga agcagtcgcc catgcttgta gcgtacgaca tgcggtcaa ccttagctgc   120 aagtattcct acaatctctt ctcaagggag ttccgggcat cccttcacaa aggactggat   180
agtgctgtgg aagtctgtgt tgtatatggg aattactccc agcagcttca ggtttactca   240
aaaacggggt tcaactgtga tgggaaattg ggcaatgaat cagtgacatt ctacctccag   300
aatttgtatg ttaaccaaac agatatttac ttctgcaaaa ttgaagttat gtatcctcct   360
ccttacctag acaatgagaa gagcaatgga accattatcc atgtgaaagg aaacaccttt   420
tgtccaagtc ccctattttcc cggaccttct aagcccttt gggtgctggt ggtggttggt   480
ggagtcctgg cttgctatag cttgctagta acagtggcct ttattatttt ctgggtgagg   540
agtaagagga gcaggctcct gcacagtgac tacatgaaca tgactccccg ccgccccggg   600
cccacccgca agcattacca gccctatgcc ccaccacgcg acttcgcagc ctatcgctcc   660

<210> SEQ ID NO 65
<211> LENGTH: 1578
<212> TYPE: DNA
<213> ORGANISM: Homo sapiens
<220> FEATURE:
<223> OTHER INFORMATION: carcinoembryonic antigen-related cell adhesion
      molecule 1 (CEACAM1, or CD66a)

<400> SEQUENCE: 65
atggggcacc tctcagcccc acttcacaga gtgcgtgtac cctggcaggg gcttctgctc    60
acagcctcac ttctaacctt ctggaacccg ccaccactg cccagctcac tactgaatcc   120
atgccattca atgttgcaga ggggaaggag gttcttctcc ttgtccacaa tctgccccag   180
```

```
caacttttttg gctacagctg gtacaaaggg gaaagagtgg atggcaaccg tcaaattgta      240
ggatatgcaa taggaactca acaagctacc ccagggcccg caaacagcgg tcgagagaca      300 atataccca atgcatccct gctgatccag aacgtcaccc agaatgacac aggattctac       360
accctacaag tcataaagtc agatcttgtg aatgaagaag caactggaca gttccatgta      420
tacccggagc tgcccaagcc ctccatctcc agcaacaact ccaaccctgt ggaggacaag     480
gatgctgtgg ccttcacctg tgaacctgag actcaggaca caacctacct gtggtggata     540
aacaatcaga gcctcccggt cagtcccagg ctgcagctgt ccaatggcaa caggaccctc     600
actctactca gtgtcacaag gaatgacaca ggaccctatg agtgtgaaat acagaaccca     660
gtgagtgcga accgcagtga cccagtcacc ttgaatgtca cctatggccc ggacaccccc     720
accatttccc cttcagacac ctattaccgt ccaggggcaa acctcagcct ctcctgctat     780
gcagcctcta acccacctgc acagtactcc tggcttatca atggaacatt ccagcaaagc     840
acacaagagc tctttatccc taacatcact gtgaataata gtggatccta tacctgccac     900 gccataact cagtcactgg ctgcaacagg accacagtca gacgatcat agtcactgag      960 ctaagtccag tagtagcaaa gccccaaatc aaagccagca agaccacagt cacaggagat    1020
aaggactctg tgaacctgac ctgctccaca atgacactg gaatctccat ccgttggttc    1080
ttcaaaaacc agagtctccc gtcctcggag aggatgaagc tgtcccaggg caacaccacc    1140
ctcagcataa accctgtcaa gagggaggat gctgggacgt attggtgtga ggtcttcaac    1200
ccaatcagta agaaccaaag cgaccccatc atgctgaacg taaactataa tgctctacca    1260
caagaaaatg gcctctcacc tgggcccatt gctggcattg tgattggagt agtggccctg    1320
gttgctctga tagcagtagc cctggcatgt tttctgcatt tcgggaagac cggcagggca    1380
agcgaccagc gtgatctcac agagcacaaa ccctcagtct ccaaccacac tcaggaccac    1440
tccaatgacc cacctaacaa gatgaatgaa gttacttatt ctaccctgaa ctttgaagcc    1500
cagcaaccca cacaaccaac ttcagcctcc ccatccctaa cagccacaga aataattat     1560 tcagaagtaa aaaagcag                                                   1578
```

<210> SEQ ID NO 66
<211> LENGTH: 864
<212> TYPE: DNA
<213> ORGANISM: Homo sapiens
<220> FEATURE:
<223> OTHER INFORMATION: CD80/B7-1

<400> SEQUENCE: 66

```
atgggccaca cacggaggca gggaacatca ccatccaagt gtccatacct caatttcttt      60
cagctcttgg tgctggctgg tctttctcac ttctgttcag gtgttatcca cgtgaccaag     120
gaagtgaaag aagtggcaac gctgtcctgt ggtcacaatg tttctgttga agagctggca     180
caaactcgca tctactggca aaaggagaag aaaatggtgc tgactatgat gtctgggac      240 atgaatatat ggcccgagta caagaaccgg accatctttg atatcactaa taacctctcc     300
attgtgatcc tggctctgcg cccatctgac gagggcacat acgagtgtgt tgttctgaag     360
tatgaaaaag acgctttcaa gcgggaacac ctggctgaag tgacgttatc agtcaaagct     420
gacttcccta cacctagtat atctgacttt gaaattccaa cttctaatat tagaaggata     480
atttgctcaa cctctggagg ttttccagag cctcacctct cctggttgga aaatggagaa     540
gaattaaatg ccatcaacac aacagtttcc caagatcctg aaactgagct ctatgctgtt     600
agcagcaaac tggatttcaa tatgacaacc aaccacagct tcatgtgtct catcaagtat     660
```

```
ggacatttaa gagtgaatca gaccttcaac tggaatacaa ccaagcaaga gcattttcct    720
gataacctgc tcccatcctg ggccattacc ttaatctcag taaatggaat ttttgtgata    780
tgctgcctga cctactgctt tgccccaaga tgcagagaga aaggaggaa tgagagattg     840 agaagggaaa gtgtacgccc tgta                                           864
```

```
<210> SEQ ID NO 67
<211> LENGTH: 995
<212> TYPE: DNA
<213> ORGANISM: Homo sapiens
<220> FEATURE:
<223> OTHER INFORMATION: CD86/B7-2

<400> SEQUENCE: 67
cagccaaaat ggatcccag tgcactatgg gactgagtaa cattctcttt gtgatggcct      60
tcctgctctc tggtgctgct cctctgaaga ttcaagctta tttcaatgag actgcagacc    120
tgccatgcca atttgcaaac tctcaaaacc aaagcctgag tgagctagta gtattttggc    180
aggaccagga aaacttggtt ctgaatgagg tatacttagg caaagagaaa tttgacagtg    240
ttcattccaa gtatatgggc cgcacaagtt ttgattcgga cagttggacc ctgagacttc    300
acaatcttca gatcaaggac aagggcttgt atcaatgtat catccatcac aaaaagccca    360
caggaatgat tcgcatccac cagatgaatt ctgaactgtc agtgcttgct aacttcagtc    420
aacctgaaat agtaccaatt tctaatataa cagaaaatgt gtacataaat ttgacctgct    480
catctataca cggttaccca gaacctaaga agatgagtgt tttgctaaga accaagaatt    540
caactatcga gtatgatggt attatgcaga atctcaagga taatgtcaca gaactgtacg    600
acgtttccat cagcttgtct gtttcattcc ctgatgttac gagcaatatg accatcttct    660
gtattctgga aactgacaag acgcggcttt tatcttcacc tttctctata gagcttgagg    720
accctcagcc tcccccagac acattcctt ggattacagc tgtacttcca acagttatta     780
tatgtgtgat ggttttctgt ctaattctat ggaaatggaa gaagaagaag cggcctcgca    840
actcttataa atgtggaacc aacacaatgg agagggaaga gagtgaacag accaagaaaa    900
gagaaaaaat ccatatacct gaaagatctg atgaagccca gcgtgttttt aaaagttcga    960
agacatcttc atgcgacaaa agtgatacat gtttt                               995
```

```
<210> SEQ ID NO 68
<211> LENGTH: 1095
<212> TYPE: DNA
<213> ORGANISM: Homo sapiens
<220> FEATURE:
<223> OTHER INFORMATION: CD244/2B4

<400> SEQUENCE: 68
atgctggggc aagtggtcac cctcatactc ctcctgctcc tcaaggtgta tcagggcaaa     60
ggatgccagg atcagctga ccatgtggtt agcatctcgg gagtgcctct tcagttacaa     120
ccaaacagca tacagacgaa ggttgacagc attgcatgga gaagttgct gccctcacaa     180 aatggatttc atcacatatt gaagtgggag aatggctctt tgccttccaa tacttccaat    240
gatagattca gttttatagt caagaacttg agtcttctca tcaaggcagc tcagcagcag    300
gacagtggcc tctactgcct ggaggtcacc agtatatctg aaaagttca gacagccacg    360 ttccaggttt ttgtatttga taagttgag aaacccgcc tacaggggca ggggaagatc      420
ctggacagag ggagatgcca gtggctctg tcttgcttgg tctccaggga tggcaatgtg    480
```

```
tcctatgctt ggtacagagg gagcaagctg atccagacag cagggaacct cacctacctg    540
gacgaggagg ttgacattaa tggcactcac acatatacct gcaatgtcag caatcctgtt    600
agctgggaaa gccacaccct gaatctcact caggactgtc agaatgccca tcaggaattc    660
agattttggc cgttttttggt gatcatcgtg attctaagcg cactgttcct tggcacccctt   720 gcctgcttct gtgtgtggag gagaaagagg aaggagaagc agtcagagac cagtcccaag    780 gaattttttga caatttacga agatgtcaag gatctgaaaa ccaggagaaa tcacgagcag    840
gagcagactt ttcctggagg ggggagcacc atctactcta tgatccagtc ccagtcttct    900
gctcccacgt cacaagaacc tgcatataca ttatattcat taattcagcc ttccaggaag    960
tctggatcca ggaagaggaa ccacagccct tccttcaata gcactatcta tgaagtgatt   1020
ggaaagagtc aacctaaagc ccagaaccct gctcgattga ccgcaaaga gctggagaac    1080 tttgatgttt attcc                                                   1095

<210> SEQ ID NO 69
<211> LENGTH: 1251
<212> TYPE: DNA
<213> ORGANISM: Homo sapiens
<220> FEATURE:
<223> OTHER INFORMATION: CD155/PVR

<400> SEQUENCE: 69
atggcccgag ccatggccgc cgcgtggccg ctgctgctgg tggcgctact ggtgctgtcc     60
tggccacccc caggaaccgg ggacgtcgtc gtgcaggcgc ccacccaggt gcccggcttc    120
ttgggcgact ccgtgacgct gccctgctac ctacaggtgc ccaacatgga ggtgacgcat    180
gtgtcacagc tgacttgggc gcggcatggt gaatctggca gcatggccgt cttccaccaa    240
acgcagggcc ccagctattc ggagtccaaa cggctggaat cgtggcagc cagactgggc    300 gcggagctgc ggaatgcctc gctgaggatg ttcgggttgc gcgtagagga tgaaggcaac    360
tacacctgcc tgttcgtcac gttcccgcag ggcagcagga gcgtggatat ctggctccga    420
gtgcttgcca agccccagaa cacagctgag gttcagaagg tccagctcac tggagagcca    480
gtgcccatgg cccgctgcgt ctccacaggg ggtcgcccgc cagcccaaat cacctggcac    540
tcagacctgg gcgggatgcc caatacgagc caggtgccag ggttcctgtc tggcacagtc    600
actgtcacca gcctctggat attggtgccc tcaagccagg tggacggcaa gaatgtgacc    660
tgcaaggtgg agcacgagag cttgtgagaag cctcagctgc tgactgtgaa cctcaccgtg    720 tactacccccc cagaggtatc catctctggc tatgataaca actggtacct tggccagaat    780
gaggccaccc tgacctgcga tgctcgcagc aacccagagc ccacaggcta taattggagc    840
acgaccatgg gtcccctgcc acccttttgct gtggcccagg cgcccagct cctgatccgt    900 cctgtggaca aaccaatcaa cacaacttta atctgcaacg tcaccaatgc cctaggagct    960
cgccaggcag aactgaccgt ccaggtcaaa gagggacctc cagtgagca ctcaggcatg   1020 tcccgtaacg ccatcatctt cctggttctg ggaatcctgg ttttttctgat cctgctgggg    1080 atcgggattt atttctattg gtccaaatgt tcccgtgagg tcctttggca ctgtcatctg   1140
tgtccctcga gtacagagca tgccagcgcc tcagctaatg gcatgtctc ctattcagct   1200 gtgagcagag agaacagctc ttcccaggat ccacagacag agggcacaag g            1251

<210> SEQ ID NO 70
<211> LENGTH: 1614
<212> TYPE: DNA
<213> ORGANISM: Homo sapiens
```

```
<220> FEATURE:
<223> OTHER INFORMATION: CD122/nectin-2

<400> SEQUENCE: 70
atggcccggg ccgctgccct cctgccgtcg agatcgccgc cgacgccgct gctgtggccg      60
ctgctgctgc tgctgctcct ggaaaccgga gcccaggatg tgcgagttca agtgctaccc     120
gaggtgcgag ccagctcgg gggcaccgtg agctgccgt gccacctgct gccacctgtt      180
cctggactgt acatctccct ggtgacctgg cagcgcccag atgcacctgc gaaccaccag    240
aatgtggccg ccttccaccc taagatgggt cccagcttcc ccagcccgaa gcctggcagc    300
gagcggctgt ccttcgtctc tgccaagcag agcactgggc aagacacaga ggcagagctc    360
caggacgcca cgctggccct ccacgggctc acggtggagg acgagggcaa ctacacttgc    420
gagtttgcca ccttccccaa gggtccgtc cgagggatga cctggctcag agtcatagcc     480
aagcccaaga ccaagctga ggcccagaag gtcacgttca gccaggaccc tacgacagtg      540
gccctctgca tctccaaaga gggccgccca cctgcccgga tctcctggct ctcatccctg    600
gactgggaag ccaaagagac tcaggtgtca gggaccctgg ccggaactgt cactgtcacc    660
agccgcttca ccttggtgcc ctcgggccga gcagatggtg tcacggtcac ctgcaaagtg    720
gagcatgaga gcttcgagga accagccctg ataccctgtga ccctctctgt acgctaccct   780
cctgaagtgt ccatctccgg ctatgatgac aactggtacc tcggccgtac tgatgccacc    840
ctgagctgtg acgtccgcag caacccagag cccacgggct atgactggag cacgacctca    900
ggcaccttcc cgacctccgc agtggcccag ggctcccagc tggtcatcca cgcagtggac    960
agtctgttca ataccacctt cgtctgcaca gtcaccaatg ccgtgggcat gggccgcgct   1020
gagcaggtca tctttgtccg agagaccccc aacacagcag gcgcagggc cacaggcggc   1080 atcatcgggg gcatcatcgc cgccatcatt gctactgctg tggctgccac gggcatcctt   1140
atctgccggc agcagcggaa ggagcagacg ctgcaggggg cagaggagga cgaagacctg   1200
gagggacctc cctcctacaa gccaccgacc ccaaaagcga agctggaggc acaggagatg   1260
ccctcccagc tcttcactct ggggccctcg gagcacagcc cactcaagac ccctacttt     1320 gatgctggcg cctcatgcac tgagcaggaa atgcctcgat accatgagct gcccaccttg   1380
gaagaacggt caggacccttt gcaccctgga gccacaagcc tggggtcccc catcccggtg   1440
cctccagggc cacctgctgt ggaagacgtt tccctggatc tagaggatga ggaggggag    1500 gaggaggaag agtatctgga caagatcaac cccatctatg atgctctgtc ctatagcagc    1560
ccctctgatt cctaccaggg caaaggcttt gtcatgtccc gggccatgta tgtg          1614

<210> SEQ ID NO 71
<211> LENGTH: 1008
<212> TYPE: DNA
<213> ORGANISM: Homo sapiens
<220> FEATURE:
<223> OTHER INFORMATION: CD226 antigen

<400> SEQUENCE: 71
atggattatc ctactttact tttggctctt cttcatgtat acagagctct atgtgaagag      60
gtgctttggc atacatcagt tcccttttgcc gagaacatgt ctctagaatg tgtgtatcca   120
tcaatgggca tcttaacaca ggtggagtgg ttcaagatcg ggacccagca ggattccata    180
gccattttca gccctactca tggcatggtc ataaggaagc cctatgctga gagggtttac    240
tttttgaatt caacgatggc ttccaataac atgactcttt tctttcggaa tgcctctgaa    300
```

```
gatgatgttg gctactattc ctgctctctt tacacttacc cacagggaac ttggcagaag    360
gtgatacagg tggttcagtc agatagtttt gaggcagctg tgccatcaaa tagccacatt    420
gtttcggaac ctggaaagaa tgtcacactc acttgtcagc ctcagatgac gtggcctgtg    480
caggcagtga ggtgggaaaa gatccagccc cgtcagatcg acctcttaac ttactgcaac    540
ttggtccatg gcagaaattt cacctccaag ttcccaagac aaatagtgag caactgcagc    600
cacggaaggt ggagcgtcat cgtcatcccc gatgtcacag tctcagactc ggggctttac    660
cgctgctact tgcaggccag cgcaggagaa acgaaacct tcgtgatgag attgactgta     720
gccgagggta aaaccgataa ccaatatacc ctctttgtgg ctggagggac agttttattg    780
ttgttgtttg ttatctcaat taccaccatc attgtcattt tccttaacag aaggagaagg    840
agagagagaa gagatctatt tacagagtcc tgggatacac agaaggcacc caataactat    900
agaagtccca tctctaccag tcaacctacc aatcaatcca tggatgatac aagagaggat    960
atttatgtca actatccaac cttctctcgc agaccaaaga ctagagtt               1008

<210> SEQ ID NO 72
<211> LENGTH: 545
<212> TYPE: DNA
<213> ORGANISM: Homo sapiens
<220> FEATURE:
<223> OTHER INFORMATION: CD160 antigen

<400> SEQUENCE: 72
ggatgctgtt ggaacccggc agaggctgct gtgccctggc catcctgctg gcaattgtgg     60
acatccagtc tggtggatgc attaacatca ccagctcagc ttcccaggaa ggaacgcgac    120
taaacttaat ctgtactgta tggcataaga agaagagagc tgagggggttt gtagtgtttt    180 tgtgcaagga caggtctgga gactgttctc ctgagaccag tttaaaacag ctgagactta    240
aaagggatcc tgggatagat ggtgttggtg aaatatcatc tcagttgatg ttcaccataa    300
gccaagtcac accgttgcac agtgggacct accagtgttg tgccagaagc cagaagtcag    360
gtatccgcct tcagggccat ttttctcca ttctattcac agagacaggg aactacacag     420
tgacgggatt gaaacaaaga caacaccttg agttcagcca taatgaaggc actctcagtt    480
caggcttcct acaagaaaag gtctgggtaa tgctggtcac cagccttgtg gcccttcaag    540
ctttg                                                                545

<210> SEQ ID NO 73
<211> LENGTH: 264
<212> TYPE: DNA
<213> ORGANISM: Homo sapiens
<220> FEATURE:
<223> OTHER INFORMATION: human U6 RNA Pol III promoter

<400> SEQUENCE: 73
aaggtcgggc aggaagaggg cctatttccc atgattcctt catatttgca tatacgatac     60
aaggctgtta gagagataat tagaattaat ttgactgtaa acacaaagat attagtacaa    120
aatacgtgac gtagaaagta ataatttctt gggtagtttg cagttttaaa attatgtttt    180
aaaatggact atcatatgct taccgtaact tgaaagtatt tcgatttctt ggctttatat    240
atcttgtgga aggacgaaa ctag                                            264

<210> SEQ ID NO 74
<211> LENGTH: 99
<212> TYPE: DNA
<213> ORGANISM: Homo sapiens
```

```
<220> FEATURE:
<223> OTHER INFORMATION: human H1 RNA Pol III promoter

<400> SEQUENCE: 74
atatttgcat gtcgctatgt gttctgggaa atcaccataa acgtgaaatg tctttggatt    60
tgggaatctt ataagttctg tatgagacca ctccctagg                          99

<210> SEQ ID NO 75
<211> LENGTH: 58
<212> TYPE: DNA
<213> ORGANISM: Artificial Sequence
<220> FEATURE:
<223> OTHER INFORMATION: shRNA-encoding sequence targeting muPD-L1

<400> SEQUENCE: 75
ccggccgaaa tgatacacaa ttcgactcga gtcgaattgt gtatcatttc ggttttg      58

<210> SEQ ID NO 76
<211> LENGTH: 57
<212> TYPE: DNA
<213> ORGANISM: Artificial Sequence
<220> FEATURE:
<223> OTHER INFORMATION: shRNA-encoding sequence targeting muSIRPA

<400> SEQUENCE: 76
ccggccacaa ctggaatgtc ttcatctcga gatgaagaca ttccagttgt ggttttt      57

<210> SEQ ID NO 77
<211> LENGTH: 58
<212> TYPE: DNA
<213> ORGANISM: Artificial Sequence
<220> FEATURE:
<223> OTHER INFORMATION: shRNA-encoding sequence targeting muTREX1,
      clone 1

<400> SEQUENCE: 77
ccggacaacc aacctaaggc cacatctcga gatgtggcct taggttggtt gttttttg     58

<210> SEQ ID NO 78
<211> LENGTH: 58
<212> TYPE: DNA
<213> ORGANISM: Artificial Sequence
<220> FEATURE:
<223> OTHER INFORMATION: shRNA-encoding sequence targeting muTREX1,
      clone 2

<400> SEQUENCE: 78
ccggcctaga tggtaccttc tgtgtctcga gacacagaag gtaccatcta ggttttg      58

<210> SEQ ID NO 79
<211> LENGTH: 3966
<212> TYPE: DNA
<213> ORGANISM: Artificial Sequence
<220> FEATURE:
<223> OTHER INFORMATION: Vector1-human shTREX1-1_shPDL1-1

<400> SEQUENCE: 79
ctttcctgcg ttatccctg attctgtgga taaccgtatt accgcctttg agtgagctga    60
taccgctcgc cgcagccgaa cgaccgagcg cagcgagtca gtgagcgagg aagcggaaga  120
gcgcccaata cgcaaaccgc ctctccccgc gcgttggccg attcattaat gcagctggca  180
cgacaggttt cccgactgga aagcgggcag tgagcgcaac gcaattaata cgcgtaccgc  240
tagccaggaa gagtttgtag aaacgcaaaa aggccatccg tcaggatggc cttctgctta  300
```

```
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggccctt aaaggaacca attcagtcga gaattggtac    600
catatttgca tgtcgctatg tgttctggga aatcaccata aacgtgaaat gtctttggat    660
ttgggaatct tataagttct gtatgagacc actccctagg cagcgcatgg gcgtcaattc    720
tagagattga cgcccatgcg ctgctttttt cgacagatct ggcgcgccat agtggccagc    780
ggccgcaggt aagccagccc aggcctcgcc ctccagctca aggcgggaca ggtgccctag    840
agtagcctgc atccagggac aggccccagc cgggtgctga cacgtccacc tccatctctt    900
cctcaggtct gcccgggtgg catccctgtg accccctccc agtgcctctc ctggccctgg    960
aagttgccac tccagtgccc accagccttg tcctaataaa attaagttgc atcattttgt   1020
ctgactaggt gtccttctat aatattatgg ggtggagggg ggtggtatgg agcaaggggc   1080
ccaagttaac ttgtttattg cagcttataa tggttacaaa taaagcaata gcatcacaaa   1140
tttcacaaat aaagcatttt tttcactgca ttctagttgt ggtttgtcca aactcatcaa   1200
tgtatcttat catgtctgga tccaaggtcg gcaggaaga gggcctattt cccatgattc   1260
cttcatattt gcatatacga tacaaggctg ttagagagat aattagaatt aatttgactg   1320
taaacacaaa gatattagta caaaatacgt gacgtagaaa gtaataattt cttgggtagt   1380
ttgcagtttt aaaattatgt tttaaaatgg actatcatat gcttaccgta acttgaaagt   1440
atttcgattt cttggcttta tatatcttgt ggaaaggacg aaactaggta gagtatggta   1500
gcaatatcta gagtattgct accatactct acttttttcg agtagctaga gaattcatgg   1560
taatagcgat gactaatacg tagatgtact gccaagtagg aaagtcccat aaggtcatgt   1620
actgggcata atgccaggcg ggccatttac cgtcattgac gtcaataggg ggcgtacttg   1680
gcatatgata cacttgatgt actgccaagt gggcagttta ccgtaaatag tccacccatt   1740
gacgtcaatg gaaagtccct attggcgtta ctatgggaac atacgtcatt attgacgtca   1800
atgggcgggg gtcgttgggc ggtcagccag gcgggccatt taccgtaagt tatgtaacgc   1860
ggaactccat atatgggcta tgaactaatg acccgtaat tgattactat taataactag   1920
ccatccagct gatatcccat ggtcatagct gtttcctggc agctctggcc cgtgtctcaa   1980
aatctctgat gttacattgc acaagataaa aatatatcat catgaacaat aaaactgtct   2040
gcttacataa acagtaatac aagggtgtt atgaaaaatg ttggttttat cggctggcgc   2100
ggaatggtcg gctctgttct catgcaacgc atggtagagg agcgcgattt cgacgctatt   2160
cgccctgttt tcttttctac ctcccagttt ggacaggcgg cgcccacctt cggcgacacc   2220
tccaccggca cgctacagga cgcttttgat ctggatgcgc taaaagcgct cgatatcatc   2280
gtgacctgcc agggcggcga ttataccaac gaaatttatc aaagctgcg cgaaagcgga   2340 tggcagggtt actggattga tgcggcttct acgctgcgca tgaaagatga tgccattatt   2400
attctcgacc cggtcaacca ggacgtgatt accgacggcc tgaacaatgg cgtgaagacc   2460
tttgtgggcg gtaactgtac cgttagcctg atgttgatgt cgctgggcgg tctctttgcc   2520
cataatctcg ttgactgggt atccgtcgcg acctatcagg ccgcctccgg cggcggcgcg   2580
cgccatatgc gcgagctgtt aacccagatg ggtcagttgt atggccatgt cgccgatgaa   2640
ctggcgacgc cgtcttccgc aattcttgat attgaacgca aagttacggc attgacccgc   2700
```

```
agcggcgagc tgccggttga taactttggc gtaccgctgg cgggaagcct gatcccctgg    2760
atcgacaaac agctcgataa cggccagagc cgcgaagagt ggaaaggcca ggcggaaacc    2820
aacaagattc tcaatactgc ctctgtgatt ccggttgatg gtttgtgtgt gcgcgtcggc    2880
gcgctgcgct gtcacagcca ggcgttcacc atcaagctga aaaagaggt atccattccg     2940 acggtggaag aactgctggc ggcacataat ccgtgggcga agtggtgcc gaacgatcgt     3000 gatatcacta tgcgcgaatt aaccccggcg gcggtgaccg gcacgttgac tacgccggtt    3060
ggtcgtctgc gtaagctgaa catggggcca gagttcttgt cggcgtttac cgtaggcgac    3120
cagttgttat ggggcgccgc cgagccgctg cgtcgaatgc tgcgccagtt ggcgtagtca    3180
gaattggtta attggttgta acactggcag agcattacgc tgacttgacg gacggcgca    3240 agctcatgac caaatccct taacgtgagt tacgcgtcgt tccactgagc gtcagacccc    3300
gtagaaaaga tcaaggatc ttcttgagat ccttttttc tgcgcgtaat ctgctgcttg    3360
caaacaaaaa aaccaccgct accagcggtg gtttgtttgc cggatcaaga gctaccaact    3420 cttttccga aggtaactgg cttcagcaga gcgcagatac caaatactgt ccttctagtg     3480
tagccgtagt taggccacca cttcaagaac tctgtagcac cgcctacata cctcgctctg    3540
ctaatcctgt taccagtggc tgctgccagt ggcgataagt cgtgtcttac cgggttggac    3600
tcaagacgat agttaccgga taaggcgcag cggtcgggct gaacggggg ttcgtgcaca    3660 cagcccagct tggagcgaac gacctacacc gaactgagat acctacagcg tgagcattga    3720
gaaagcgcca cgcttcccga agggagaaag gcggacaggt atccggtaag cggcagggtc    3780
ggaacaggag agcgcacgag ggagcttcca gggggaaacg cctggtatct ttatagtcct    3840 gtcgggttc gccacctctg acttgagcgt cgatttttgt gatgctcgtc aggggggcgg    3900
agcctatgga aaaacgccag caacgcggcc tttttacggt tcctggcctt ttgctggcct    3960
tttgct                                                              3966
```

<210> SEQ ID NO 80
<211> LENGTH: 3972
<212> TYPE: DNA
<213> ORGANISM: Artificial Sequence
<220> FEATURE:
<223> OTHER INFORMATION: Vector2-mouse shTREX1-1_shPDL1-1

<400> SEQUENCE: 80

```
ctttcctgcg ttatcccctg attctgtgga taaccgtatt accgcctttg agtgagctga    60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta ggcgggcgt cctgcccgcc accctccggg ccgttgcttc    360
acaacgttca atccgctcc cggcggattt gtcctactca ggagagcgtt caccgacaaa    420
caacagataa aacgaaaggc ccagtcttcc gactgagcct tcgtttat ttgatgcctg     480 gcagttccct actctcgcgt taacgctagc atggatgttt cccagtcac gacgttgtaa    540 aacgacggcc agtcttaagc tcgggccctt aaaggaacca attcagtcga gaattggtac    600
catatttgca tgtcgctatg tgttctggga atcaccata acgtgaaat gtctttggat    660 ttgggaatct tataagttct gtatgagacc actccctaga caaccaacct aaggccacat    720
```

```
ctcgagatgt ggccttaggt tggttgtttt tttcgacaga tctggcgcgc catagtggcc    780
agcggccgca ggtaagccag cccaggcctc gccctccagc tcaaggcggg acaggtgccc    840
tagagtagcc tgcatccagg gacaggcccc agccgggtgc tgacacgtcc acctccatct    900
cttcctcagg tctgcccggg tggcatccct gtgacccctc cccagtgcct ctcctggccc    960
tggaagttgc cactccagtg cccaccagcc ttgtcctaat aaaattaagt tgcatcattt   1020
tgtctgacta ggtgtccttc tataatatta tggggtggag ggggtggta tggagcaagg    1080 ggcccaagtt aacttgttta ttgcagctta taatggttac aaataaagca atagcatcac   1140
aaatttcaca aataaagcat tttttcact gcattctagt tgtggtttgt ccaaactcat     1200
caatgtatct tatcatgtct ggatccaagg tcgggcagga agagggccta tttcccatga   1260
ttccttcata tttgcatata cgatacaagg ctgttagaga gataattaga attaatttga   1320
ctgtaaacac aaagatatta gtacaaaata cgtgacgtag aaagtaataa tttcttgggt   1380
agtttgcagt tttaaaatta tgttttaaaa tggactatca tatgcttacc gtaacttgaa   1440
agtatttcga tttcttggct ttatatatct tgtggaaagg acgaaactag ccgaaatgat   1500
acacaattcg actcgagtcg aattgtgtat catttcggtt ttttcgagta gctagagaat   1560
tcatggtaat agcgatgact aatacgtaga tgtactgcca gtaggaaag tcccataagg    1620 tcatgtactg gcataatgc caggcgggcc atttaccgtc attgacgtca ataggggcg     1680 tacttggcat atgatacact tgatgtactg ccaagtgggc agtttaccgt aaatagtcca   1740
cccattgacg tcaatggaaa gtccctattg gcgttactat gggaacatac gtcattattg   1800
acgtcaatgg gcggggtcg ttgggcggtc agccaggcgg ccatttacc gtaagttatg     1860 taacgcggaa ctccatatat gggctatgaa ctaatgaccc cgtaattgat tactattaat   1920
aactagccat ccagctgata tcccatggtc atagctgttt cctggcagct ctggcccgtg   1980
tctcaaaatc tctgatgtta cattgcacaa gataaaaata tatcatcatg aacaataaaa   2040
ctgtctgctt acataaacag taatacaagg ggtgttatga aaatgttgg ttttatcggc    2100 tggcgcggaa tggtcggctc tgttctcatg caacgcatgg tagaggagcg cgatttcgac   2160
gctattcgcc ctgttttctt ttctacctcc cagtttggac aggcggcgcc caccttcggc   2220
gacacctcca ccggcacgct acaggacgct tttgatctgg atgcgctaaa agcgctcgat   2280
atcatcgtga cctgccaggg cggcgattat accaacgaaa tttatccaaa gctgcgcgaa   2340
agcggatggc agggttactg gattgatgcg gcttctacgc tgcgcatgaa agatgatgcc   2400
attattattc tcgaccccgt caaccaggac gtgattaccg acggcctgaa caatggcgtg   2460
aagacctttg tgggcggtaa ctgtaccgtt agcctgatgt tgatgtcgct gggcggtctc   2520
tttgcccata atctcgttga ctgggtatcc gtcgcgacct atcaggccgc ctccggcggc   2580
ggcgcgcgcc atatgcgcga gctgttaacc cagatgggtc agttgtatgg ccatgtcgcc   2640
gatgaactgg cgacgccgtc ttccgcaatt cttgatattg aacgcaaagt tacggcattg   2700
acccgcagcg gcgagctgcc ggttgataac tttggcgtac cgctggcggg aagcctgatc   2760
ccctggatcg acaaacagct cgataacggc cagagccgcg aagagtggaa aggccaggcg   2820
gaaaccaaca agattctcaa tactgcctct gtgattccgg ttgatggttt gtgtgtgcgc   2880
gtcggcgcgc tgcgctgtca cagccaggcg ttcaccatca agctgaaaaa agaggtatcc   2940
attccgacgg tggaagaact gctgcggca cataatccgt gggcgaaagt ggtgccgaac   3000
gatcgtgata tcactatgcg cgaattaacc ccggcggcgg tgaccggcac gttgactacg   3060
ccggttggtc gtctgcgtaa gctgaacatg gggccagagt tcttgtcggc gtttaccgta   3120
```

```
ggcgaccagt tgttatgggg cgccgccgag ccgctgcgtc gaatgctgcg ccagttggcg   3180
tagtcagaat tggttaattg gttgtaacac tggcagagca ttacgctgac ttgacgggac   3240
ggcgcaagct catgaccaaa atcccttaac gtgagttacg cgtcgttcca ctgagcgtca   3300
gaccccgtag aaaagatcaa aggatcttct tgagatcctt ttttctgcg cgtaatctgc    3360 tgcttgcaaa caaaaaaacc accgctacca gcggtggttt gtttgccgga tcaagagcta   3420
ccaactcttt ttccgaaggt aactggcttc agcagagcgc agataccaaa tactgtcctt   3480
ctagtgtagc cgtagttagg ccaccacttc aagaactctg tagcaccgcc tacatacctc   3540
gctctgctaa tcctgttacc agtggctgct gccagtggcg ataagtcgtg tcttaccggg   3600
ttggactcaa gacgatagtt accggataag gcgcagcggt cgggctgaac ggggggttcg   3660
tgcacacagc ccagcttgga gcgaacgacc tacaccgaac tgagatacct acagcgtgag   3720
cattgagaaa gcgccacgct tcccgaaggg agaaaggcgg acaggtatcc ggtaagcggc   3780
agggtcggaa caggagagcg cacgaggag cttccagggg gaaacgcctg gtatctttat   3840
agtcctgtcg ggtttcgcca cctctgactt gagcgtcgat ttttgtgatg ctcgtcaggg   3900
gggcggagcc tatggaaaaa cgccagcaac gcggcctttt tacggttcct ggccttttgc   3960
tggccttttg ct                                                       3972

<210> SEQ ID NO 81
<211> LENGTH: 1281
<212> TYPE: DNA
<213> ORGANISM: Salmonella typhimurium
<220> FEATURE:
<223> OTHER INFORMATION: aroA

<400> SEQUENCE: 81
atggaatccc tgacgttaca acccatcgcg cgggtcgatg gcgccattaa tttacctggc     60
tccaaaagtg tttcaaaccg tgctttgctc ctggcggctt tagcttgtgg taaaaccgct    120
ctgacgaatc tgctggatag cgatgacgtc cgccatatgc tcaatgccct gagcgcgttg    180
gggatcaatt acacccttc tgccgatcgc accgctgtg atatcacggg taatggcggc    240
gcattacgtg cgccaggcgc tctggaactg tttctcggta tgccggaac cgcgatgcgt    300 ccgttagcgg cagcgctatg tctggggcaa aatgagatag tgttaaccgg cgaaccgcgt    360
atgaaagagc gtccgatagg ccatctggtc gattcgctgc gtcagggcgg ggcgaatatt    420
gattacctgg agcaggaaaa ctatccgccc ctgcgtctgc gcggcggttt taccggcggc    480
gacattgagg ttgatggtag cgtttccagc cagttcctga ccgctctgct gatgacggcg    540
ccgctggccc ctaaagacac aattattcgc gttaaaggcg aactggtatc aaaaccttac    600
atcgatatca cgctaaattt aatgaaaacc tttggcgtgg atagcgaa ccaccactac     660 caacaatttg tcgtgaaggg aggtcaacag tatcactctc aggtcgcta tctggtcgag    720 ggcgatgcct cgtcagcgtc ctattttctc gccgctgggg cgataaaagg cggcacggta    780
aaagtgaccg gaattggccg caaaagtatg caggcgata ttcgttttgc cgatgtgctg    840
gagaaaatgg cgcgaccat tacctggggc gatgattta ttgcctgcac gcgcggtgaa     900
ttgcacgcca tagatatgga tatgaaccat attccggatg cggcgatgac gattgccacc    960
acggcgctgt tgcgaaagg aaccacgacg ttgcgcaata tttataactg gcgagtgaaa   1020
gaaaccgatc gcctgttcgc gatggcgacc gagctacgta agtgggcgc tgaagtcgaa   1080 gaagggcacg actatattcg tatcacgccg ccggcgaagc tccaacacgc ggatattggc   1140
```

| | |
|---|---|
| acgtacaacg accaccgtat ggcgatgtgc ttctcactgg tcgcactgtc cgatacgcca | 1200 |
| gttacgatcc tggaccctaa atgtaccgca aaaacgttcc ctgattattt cgaacaactg | 1260 |
| gcgcgaatga gtacgcctgc c | 1281 |

<210> SEQ ID NO 82
<211> LENGTH: 1094
<212> TYPE: DNA
<213> ORGANISM: Salmonella typhimurium
<220> FEATURE:
<223> OTHER INFORMATION: aroC

<400> SEQUENCE: 82

| | |
|---|---|
| acggagccgt gatggcagga acacaattg gacaactctt tcgcgtaacc actttcggcg | 60 |
| aatcacacgg gctggcgctt gggtgtatcg tcgatggcgt gccgcccggc atcccgttga | 120 |
| cggaggccga tctgcaacac gatctcgaca gacgccgccc cggcacctcg cgctatacta | 180 |
| cccagcgccg cgaaccggac caggtaaaaa ttctctccgg cgtgtttgat ggcgtgacga | 240 |
| ccggcaccag cattggccta ctgattgaaa acaccgatca gcgctcgcag gactacagcg | 300 |
| cgattaaaga tgttttttcgt ccgggacacg cggattacac ctatgagcag aaatacggcc | 360 |
| tgcgcgatta ccgtggcggt ggacgttctt ccgcgcgtga aaccgcgatg cgcgtagcgg | 420 |
| caggggcgat cgccaagaaa tacctggcgg aaaagttcgg catcgaaatc gcggctgcc | 480 |
| tgacccagat gggcgacatt ccgctggaga ttaaagactg cgtcaggtt gagcttaatc | 540 |
| cgttcttttg tcccgatgcg gacaaacttg acgcgctgga cgaactgatg cgcgcgctga | 600 |
| aaaaagaggg tgactccatc ggcgcgaaag tgacggtgat ggcgagcggc gtgccggcag | 660 |
| ggcttggcga accggtattt gaccgactgg atgcggacat cgcccatgcg ctgatgagca | 720 |
| ttaatgcggt gaaaggcgtg gagatcgcg aaggatttaa cgtggtggcg ctgcgcggca | 780 |
| gccagaatcg cgatgaaatc acggcgcagg ttttcagag caaccacgct ggcggcatcc | 840 |
| tcggtggcat cagtagcggg caacacattg tggcgcatat ggcgctgaaa cctacctcca | 900 |
| gcattaccgt gccgggacgt acgatcaacc gggcaggtga agaagtcgaa atgatcacca | 960 |
| aagggcgcca cgatccgtgt gtggggattc gcgcagtgcc gatcgcagaa gccatgctgg | 1020 |
| cgatcgtgct gatggatcac ctgctgcgcc atcgggcaca gaatgcggat gtaaagacag | 1080 |
| agattccacg ctgg | 1094 |

<210> SEQ ID NO 83
<211> LENGTH: 767
<212> TYPE: DNA
<213> ORGANISM: Salmonella typhimurium
<220> FEATURE:
<223> OTHER INFORMATION: aroD

<400> SEQUENCE: 83

| | |
|---|---|
| aagggtacca aatgaaaacc gtaactgtaa gagatctcgt ggttggcgaa ggcgcgccaa | 60 |
| agatcattgt gtcgctaatg ggaaaaacca ttaccgatgt gaaatcggaa gcactcgcct | 120 |
| accgtgaagc ggatttcgat attctggagt ggcgcgttga ccattttgcc aacgtgacaa | 180 |
| cggcggaaag cgtacttgag gccgccggcg ccatccggga gattattacc gataaaccct | 240 |
| tgctatttac cttccgcagc gcgaaagaag gcggcgaaca ggcgctaacc accggacagt | 300 |
| atatcgatct gaatcgtgca gcggttgaca gcggtctggt cgatatgatc gatcttgagc | 360 |
| tttttaccgg cgacgatgag gtgaaagcca ccgtcggcta tgctcatcaa cacaatgttg | 420 |
| cggtgatcat gtctaaccat gattttcata aaacgcccgc agcggaagag attgttcagc | 480 |

| | |
|---|---|
| gtctgcgtaa aatgcaggaa ctgggcgctg atattccgaa gatcgccgtc atgccacaga | 540 |
| ctaaagccga tgtcctgacc ttacttaccg ccactgtaga aatgcaggag cgctatgcgg | 600 |
| atcgtccgat tattaccatg tcgatgtcga aaaccggggt aatatctcgt cttgccggcg | 660 |
| aagtgttcgg ttctgcggca acgttttggc cggtgaaaaa agcatctgcg ccgggacaaa | 720 |
| tatcggtagc cgatctgcgt accgtattaa ctatattgca ccaggcg | 767 |

<210> SEQ ID NO 84
<211> LENGTH: 684
<212> TYPE: DNA
<213> ORGANISM: Salmonella typhimurium
<220> FEATURE:
<223> OTHER INFORMATION: PhoP

<400> SEQUENCE: 84

| | |
|---|---|
| aagggagaag agatgatgcg cgtactggtt gtagaggata atgcattatt acgccaccac | 60 |
| ctgaaggttc agctccagga ttcaggtcac caggtcgatg ccgcagaaga tgccagggaa | 120 |
| gctgattact accttaatga acaccttccg gatatcgcta ttgtcgattt aggtctgccg | 180 |
| gatgaagacg gcctttcctt aatacgccgc tggcgcagca gtgatgtttc actgccggtt | 240 |
| ctggtgttaa ccgcgcgcga aggctggcag gataaagtcg aggttctcag ctccggggcc | 300 |
| gatgactacg tgacgaagcc attccacatc gaagaggtaa tggcgcgtat gcaggcgtta | 360 |
| atgcgccgta atagcggtct ggcctcccag gtgatcaaca tcccgccgtt ccaggtggat | 420 |
| ctctcacgcc gggaattatc cgtcaatgaa gaggtcatca aactcacggc gttcgaatac | 480 |
| accattatgg aaacgcttat ccgtaacaac ggtaaagtgg tcagcaaaga ttcgctgatg | 540 |
| cttcagctgt atccggatgc ggaactgcgg gaaagtcata ccattgatgt ctctcatgggg | 600 |
| cgtctgcgga aaaaaataca ggcccagtat ccgcacgatg tcattaccac cgtacgcgga | 660 |
| caaggatatc tttttgaatt gcgc | 684 |

<210> SEQ ID NO 85
<211> LENGTH: 1461
<212> TYPE: DNA
<213> ORGANISM: Salmonella typhimurium
<220> FEATURE:
<223> OTHER INFORMATION: PhoQ

<400> SEQUENCE: 85

| | |
|---|---|
| atgaataaat tgctcgcca ttttctgccg ctgtcgctgc gggttcgttt tttgctggcg | 60 |
| acagccggcg tcgtgctggt gctttctttg gcatatggca tagtggcgct ggtcggctat | 120 |
| agcgtaagtt ttgataaaac caccttcgt ttgctgcgcg gcgaaagcaa cctgttttat | 180 |
| accctcgcca aatgggaaaa taataaaatc agcgttgagc tgcctgaaaa tctggacatg | 240 |
| caaagcccga ccatgacgct gatttacgat gaaacgggca attattatg gacgcagcgc | 300 |
| aacattccct ggctgattaa aagcattcaa ccggaatggt aaaaacgaa cggcttccat | 360 |
| gaaattgaaa ccaacgtaga cgccaccagc acgctgttga gcgaagacca ttccgcgcag | 420 |
| gaaaaactca agaagtacg tgaagatgac gatgatgccg agatgaccca ctcggtagcg | 480 |
| gtaaatattt atcctgccac ggcgcggatg ccgcagttaa ccatcgtggt ggtcgatacc | 540 |
| attccgatag aactaaaacg ctcctatatg gtgtggagct ggttcgtata cgtgctggcc | 600 |
| gccaatttac tgttagtcat tcctttactg tggatcgccg cctggtggag cttacgccct | 660 |
| atcgaggcgc tggcgcggga agtccgcgag cttgaagatc atcaccgcga aatgctcaat | 720 |

| | |
|---|---|
| ccggagacga cgcgtgagct gaccagcctt gtgcgcaacc ttaatcaact gctcaaaagc | 780 |
| gagcgtgaac gttataacaa ataccgcacg accctgaccg acctgacgca cagtttaaaa | 840 |
| acgccgctcg cggttttgca gagtacgtta cgctctttac gcaacgaaaa gatgagcgtc | 900 |
| agcaaagctg aaccggtgat gctggaacag atcagccgga tttcccagca gatcggctat | 960 |
| tatctgcatc gcgccagtat gcgcggtagc ggcgtgttgt taagccgcga actgcatccc | 1020 |
| gtcgcgccgt tgttagataa cctgatttct gcgctaaata aagtttatca gcgtaaaggg | 1080 |
| gtgaatatca gtatggatat ttcaccagaa atcagttttg tcggcgagca aaacgacttt | 1140 |
| gtcgaagtga tgggcaacgt actggacaac gcttgtaaat attgtctgga gtttgtcgag | 1200 |
| atttcggctc gccagaccga cgatcatttg catattttcg tcgaagatga cggcccaggc | 1260 |
| attccccaca gcaaacgttc cctggtgttt gatcgcggtc agcgcgccga taccctacga | 1320 |
| ccaggacaag gcgtggggct ggctgtcgcg cgcgagatta cggaacaata cgccgggcag | 1380 |
| atcattgcca gcgacagtct gctcggtggc gcccgtatgg aggtcgtttt tggccgacag | 1440 |
| catcccacac agaaagagga a | 1461 |

<210> SEQ ID NO 86
<211> LENGTH: 2731
<212> TYPE: DNA
<213> ORGANISM: Salmonella typhimurium
<220> FEATURE:
<223> OTHER INFORMATION: Adenylate cyclase (cyaA)

<400> SEQUENCE: 86

| | |
|---|---|
| tctttcttta cggtcaatga gcaaggtgtt aaattgatca cgttttagac cattttttcg | 60 |
| tcggtattag ataaaaatat gcaggcgaga aagggtaacg gttattttttg acatacggtt | 120 |
| tatcccgaat ggcgacggtc aagtactgac ctgcaccatg acgggtagca acatcaggcg | 180 |
| atacgtcttg tacctctata ttgagactct gaaacagaga ctggatgcca taaatcaact | 240 |
| gcgtgtggat cgcgcgcttg ctgccatggg acccgctttt cagcaggttt acagtcttct | 300 |
| gccgacatta ttgcactatc accatccact gatgccgggt taccttgatg gtaacgttcc | 360 |
| cagcggtatt tgcttctaca cgcctgatga aacccaacgc cactatctga acgaacttga | 420 |
| gctgtaccgc ggtatgacgc gcaggaccc gccgaagggc gagctgccga ttaccggcgt | 480 |
| ttacaccatg ggcagcacct cctcggtcgg gcagagctgc tcgtccgacc tggatatctg | 540 |
| ggtgtgccat cagtcctggc tcgacggcga agagcgtcag ttgctgcaac gtaagtgtag | 600 |
| cctgctggaa agctgggccg cctcgcttgg cgttgaggtg agcttcttcc tgatcgacga | 660 |
| gaaccgtttc cgccataacg aaagcggcag tctgggcggg gaagactgtg gttctacgca | 720 |
| gcatatcctg ttgcttgatg agtttttatcg taccgctgtg cgcctggccg ggaagcgtat | 780 |
| cctgtggagt atggtgccgt gcgacgaaga agagcattac gacgactatg tcatgacgct | 840 |
| ctatgcgcag ggcgtattaa cgccaaacga atggctggat ctgggggggct taagctcgct | 900 |
| ctccgccgaa gagtactttg gcgccagcct gtggcagcta tacaagagca ttgactcgcc | 960 |
| gtacaaagcg gtgctgaaaa cgctgctgct ggaagcctat tcatgggaat atcctaaccc | 1020 |
| acgtctgctg gcgaaagata ttaaacaacg tctgcatgac ggtgaaatcg tatcgtttgg | 1080 |
| actcgatccc tactgcatga tgctggaacg ggtcactgaa tacctgacgg cgattgaaga | 1140 |
| tccgacgcgg ctggatttag tccgccgctg cttttacctg aaagtgtgcg agaaattaag | 1200 |
| tcgcgagcgt gcctgcgtag gctggcgtcg ggaagtatta agccagttag tcagcgagtg | 1260 |
| gggatgggac gacgcgcgtc tgaccatgct cgataatcgc gcaaactgga aaatcgatca | 1320 |

```
ggtgcgcgaa gcccacaacg aattgctcga cgccatgatg caaagctatc gtaatctgat    1380
tcgctttgcg cggcgcaaca acctcagcgt gagtgccagc ccgcaggata tcggcgtact    1440
gacgcgtaag ctgtacgcgg cttttgaagc gttgccgggt aaagtcacgc tggtgaaccc    1500
gcagatatcg ccggatctgt ccgagccgaa tttaaccttt atccatgtgc cgccgggacg    1560
cgccaaccgt tcaggctggt atctctacaa ccgcgcgccg aacatggatt ccatcatcag    1620
ccatcagccg ctggaatata accgttatct taataagctg gtcgcgtggg cgtggttcaa    1680
cggcctgctg acgtcgcgaa cgcatctgtt tattaagggc aacggtattg tcgacctgcc    1740
taagttacag gagatggtcg ccgatgtttc gcaccatttc ccgctgcgct tgcctgctcc    1800
gacgccgaaa gcgctctaca gccctgtga aattcgccat ctggcgatta tcgttaacct    1860
cgaatatgac ccgacggcgg cgtttcgcaa taaagtggtc cattttgact tccgtaagct    1920
ggacgttttc agctttggcg aagagcaaaa ctgtctgata ggcagtatcg acttgttata    1980
tcgcaactcg tggaacgaag tgcgtactct gcactttaac ggcgagcagg cgatgatcga    2040
agcgctgaaa acgattctgg ggaaaatgca ccaggatgcc gcgccgccgg atagcgtgga    2100
ggtgttctgc tacagtcagc atcttcgcgg cctgattcgc acccgtgtgc agcaactggt    2160
ctccgaatgt attgagctac gtcttccag cacccgtcag gagaccggtc gcttcaaggc    2220
gctgcgggtt tccgggcaga cgtgggggct attcttcgaa cgcttgaatg tctcggtgca    2280
gaagctggag aacgctatcg aattctacgg cgcgatttcg cataacaagc tgcacgggct    2340
gtcggtacag gtggaaacca accaggtgaa attgccgtca gtggtggatg gcttcgccag    2400
cgaagggatt atccagttct tctttgaaga acaggcgat gagaaaggct ttaacattta    2460
tattctggat gaaagtaacc gggcggaagt atatcaccac tgcgaaggta gcaaggaaga    2520
actggtgcgc gacgtcagtc gcttctattc gtcatcgcac gatcgcttca cgtatggctc    2580
cagttttatc aactttaacc tgccgcagtt ctaccagata gtgaaaaccg atggccgcgc    2640
gcaggtgatc ccattccgta cgcagcctat caacaccgtg ccgccagcaa accaggatca    2700
tgacgcgccg ctattgcagc agtattttc g                                    2731
```

<210> SEQ ID NO 87
<211> LENGTH: 826
<212> TYPE: DNA
<213> ORGANISM: Salmonella typhimurium
<220> FEATURE:
<223> OTHER INFORMATION: cAMP-activated global transcriptional regulator
      (crp)

<400> SEQUENCE: 87

```
aagctatgct aaaacagaca agatgctaca gtaatacatt gacgtactgc atgtatgcag      60
aggacatcac attacaggct acaatctatt ttcgtagccc ccttcccagg tagcgggaag     120 tatattttg caaccccaga gacagtgccg ttttctggct ctggagacag cttataacag     180
aggataaccg cgcatggtgc ttggcaaacc gcaaacagac ccgactcttg aatggttctt     240
gtctcattgc acattcata gtacccgtc aaagagcacg ctgattcacc agggtgaaaa     300
agcagaaacg ctgtactaca tcgttaaagg ctccgtggca gtgctgatca agatgaaga     360 agggaaagaa atgatccttt cttatctgaa tcagggtgat tttattggtg aactgggcct     420
gtttgaagaa ggccaggaac gcagcgcctg gtacgtgcg aaaaccgcat gtgaggtcgc     480
tgaaatttcc tacaaaaaat tcgccaatt aatccaggtc aacccggata ttctgatgcg     540
cctctcttcc cagatggctc gtcgcttaca agtcacctct gaaaaagtag gtaacctcgc     600
```

```
cttccttgac gtcaccgggc gtatcgctca gacgctgctg aatctggcga aacagcccga    660
tgccatgacg cacccggatg ggatgcagat caaaatcact cgtcaggaaa tcggccagat    720
cgtcggctgc tcccgcgaaa ccgttggtcg tattttgaaa atgctggaag atcaaaacct    780
gatctccgcg catggcaaga ccatcgtcgt ctacggcacc cgttaa                   826
```

<210> SEQ ID NO 88
<211> LENGTH: 1566
<212> TYPE: DNA
<213> ORGANISM: Homo sapiens
<220> FEATURE:
<223> OTHER INFORMATION: cyclic GMP-AMP (cGAMP) synthase (cGAS), isoform 1

<400> SEQUENCE: 88

```
atgcagcctt ggcacggaaa ggccatgcag agagcttccg aggccggagc cactgccccc     60
aaggcttccg cacggaatgc cagggggcgcc ccgatggatc ccaccgagtc tccggctgcc    120
cccgaggccg ccctgcctaa ggcgggaaag ttcggccccg ccaggaagtc gggatcccgg    180
cagaaaaaga gcgccccgga cacccaggag aggccgcccg tccgcgcaac tggggcccgc    240
gccaaaaagg cccctcagcg cgcccaggac acgcagccgt ctgacgccac cagcgccccc    300
ggggcagagg ggctggagcc tcctgcggct cgggagccgg ctctttccag ggctggttct    360
tgccgccaga ggggcgcgcg ctgctccacg aagccaagac ctccgcccgg gccctgggac    420
gtgcccagcc ccggcctgcc ggtctcggcc ccattctcg tacggaggga tgcggcgcct    480
ggggcctcga agctccgggc ggttttggag aagttgaagc tcagccgcga tgatatctcc    540
acggcggcgg ggatggtgaa aggggttgtg gaccacctgc tgctcagact gaagtgcgac    600
tccgcgttca gaggcgtcgg gctgctgaac accgggagct actatgagca cgtgaagatt    660
tctgcaccta atgaatttga tgtcatgttt aaactggaag tccccagaat tcaactagaa    720
gaatattcca acactcgtgc atattacttt gtgaaattta aagaaatcc gaaagaaat    780 cctctgagtc agttttttaga aggtgaaata ttatcagctt ctaagatgct gtcaaagttt    840
aggaaaatca ttaaggaaga aattaacgac attaaagata cagatgtcat catgaagagg    900 aaagaggag ggagccctgc tgtaacactt cttattagtg aaaaaaatatc tgtggatata    960 accctggctt tggaatcaaa aagtagctgg cctgctagca cccaagaagg cctgcgcatt   1020
caaaactggc tttcagcaaa agttaggaag caactacgac taaagccatt ttaccttgta   1080
cccaagcatg caaaggaagg aaatggtttc caagaagaaa catggcggct atccttctct   1140
cacatcgaaa aggaaatttt gaacaatcat ggaaaatcta aacgtgctg tgaaaacaaa   1200 gaagagaaat gttgcaggaa agattgttta aaactaatga ataccttttt agaacagctg   1260
aaagaaaggt ttaaagacaa aaaacatctg gataaattct cttcttatca tgtgaaaact   1320
gccttctttc acgtatgtac ccagaaccct caagacagtc agtgggaccg caaagacctg   1380
ggcctctgct ttgataactg cgtgacatac tttcttcagt gcctcaggac agaaaaactt   1440
gagaattatt ttattcctga attcaatcta ttctctagca acttaattga caaagaagt   1500 aaagaatttc tgacaaagca aattgaatat gaaagaaaca atgagtttcc agttttttgat   1560 gaattt                                                             1566
```

<210> SEQ ID NO 89
<211> LENGTH: 1137
<212> TYPE: DNA
<213> ORGANISM: Homo sapiens

```
<220> FEATURE:
<223> OTHER INFORMATION: Stimulator of Interferon Genes (STING)

<400> SEQUENCE: 89
atgccccact ccagcctgca tccatccatc ccgtgtccca ggggtcacgg ggcccagaag      60
gcagccttgg ttctgctgag tgcctgcctg gtgacccttt ggggggctagg agagccacca    120
gagcacactc tccggtacct ggtgctccac ctagcctccc tgcagctggg actgctgtta    180
aacgggtct gcagcctggc tgaggagctg cgccacatcc actccaggta ccggggcagc     240
tactggagga ctgtgcgggc ctgcctgggc tgcccctcc gccgtggggc cctgttgctg     300
ctgtccatct atttctacta ctccctccca aatgcggtcg gcccgccctt cacttggatg    360
cttgccctcc tgggcctctc gcaggcactg aacatcctcc tgggcctcaa gggcctggcc    420
ccagctgaga tctctgcagt gtgtgaaaaa gggaatttca acgtggccca tgggctggca    480
tggtcatatt acatcggata tctgcggctg atcctgccag agctccaggc ccggattcga    540
acttacaatc agcattacaa caacctgcta cggggtgcag tgagccagcg gctgtatatt    600
ctcctcccat ggactgtgg ggtgcctgat aacctgagta tggctgaccc caacattcgc     660
ttcctggata aactgcccca gcagaccggt gaccatgctg gcatcaagga tcgggtttac    720
agcaacagca tctatgagct tctggagaac gggcagcggg cgggcacctg tgtcctggag    780
tacgccaccc ccttgcagac tttgtttgcc atgtcacaat acagtcaagc tggctttagc    840
cgggaggata ggcttgagca ggccaaactc ttctgccgga cacttgagga catcctggca    900
gatgccctg agtctcagaa caactgccgc ctcattgcct accaggaacc tgcagatgac    960
agcagcttct cgctgtccca ggaggttctc cggcacctgc ggcaggagga aaaggaagag   1020
gttactgtgg gcagcttgaa gacctcagcg gtgcccagta cctccacgat gtcccaagag   1080
cctgagctcc tcatcagtgg aatggaaaag cccctccctc tccgcacgga tttctct    1137

<210> SEQ ID NO 90
<211> LENGTH: 972
<212> TYPE: DNA
<213> ORGANISM: Salmonella typhimurium
<220> FEATURE:
<223> OTHER INFORMATION: lipid A biosynthesis myristoyltransferase
      (msbB)

<400> SEQUENCE: 90
ttatttgatg ggataaagat ctttacgctt atacggctga atctcgcctg gcttgcgggt     60
tttgagcagc ttcaggatcc aggtgtactg ttccggatgc gggccgacaa aaatttcgac   120
ctcttcgttc atccgtctgg cgatagtgtg gtcgtcagcc gtgagcagat cgtccattgg   180
cgggcgaatc tggatagtca ggcgatgcgt tttaccatta tacaccggga aaagcggtat   240
cacgcgtgcg cggcacactt tcatcagccg accaattgca ggcagcgtcg ctttgtatgt   300
cgcaaagaaa tcaacgaatt cactatgctc cgggccgtga tcctggtccg gcaggtagta   360
acccccagtag ccctgacgaa cagactgaat aaagggttta tcccgtcat acgcgcatg    420
caaacgtccg ccgaaacgcc gacgcactgt gttccagata tagtcaaaaa ccggattacc   480
ctgattatga acatcgccg ccatttttg cccctgagag gccatcagca tggctggaat     540
gtcgacgccc cagccatgcg gtacgagaaa aatgactttt tcgtcgttac gacgcatctc   600
ctcgataatc tccagacctt cccagtcaac acgctgttga attttttcg gaccgcgcat    660
cgccaactca gccatcatcg ccattgcctg tggcgcggtg cgaacatct catcgacaat    720
cgcttcgcgc tcagcttcgc tacgctgcgg aaagcacaac gacagattaa ttagcgcccg   780
```

```
gcgacgagaa ctcttcccca gccgtccggc aaaacgcccc agcgtcgcca gcaaagggtc      840
gcggaatgat gccggtgtta atgcgatccc cgccattgcc gccgcgccca accaggcgcc      900
ccaatactgt ggatagcgaa aggattttc gaattcaggg atatactcac tattattttt      960
tttggtttcc at                                                          972
```

<210> SEQ ID NO 91
<211> LENGTH: 1038
<212> TYPE: DNA
<213> ORGANISM: Salmonella typhimurium
<220> FEATURE:
<223> OTHER INFORMATION: Phosphoribosylaminoimidazole synthetase (purI)

<400> SEQUENCE: 91

```
ttattcaata accacacgct gttcggaatc agaggctttg atgataccga ttttccatgc       60
gttttcacct ttctcgttta gcagagcaag cgctttgtcc gcttccggag cggagagcgc      120
aatcaccatg ccgacgccgc agttaaaggt acggtacatt tcatgtcggc tgacattacc      180
ggcggtttgc agccaggtaa agatggcggg ccactgccag gacgactcat taattaccgc      240
ctgggtattc tccggcagaa cgcgcggaat attttcccaa aagcccccgc cggtgaggtg      300
ggcgatagcg tgtacatcga cgttttcaat cagttccaga accgattta cgtagatacg      360 ggtcggttca agcagatgat cggccagcgg cttcccttcc agcagagtgg tttgtgggtc      420
gcagccgcta acgtcaataa ttttccgcac cagcgaatat ccattcgagt gcgggccgct      480
ggagccgagt gcaatcagca cgtcgccttc ggcaacccgg gagccgtcga tgattctga      540 tttttcgact acgccgacgc agaaacccgc cacatcgtaa tcttcgccgt gatacatgcc      600
cggcatttcc gccgtctcgc cgccgaccag cgcgcagccg gattgcaggc agccttcggc      660
aataccgttg atcacgctgg cggcggtatc gacatccagt ttacccgtgg catagtaatc      720
gaggaaaaac agcggttccg cgccctgaac gaccagatcg tttacgcaca ttgccaccag      780
atcaataccg atagcgtcgt gacgctttaa gtccatcgcc aggcgaagtt tggtacctac      840
gccgtcagtg ccggaaacca gtaccggttc acgatatttt tgcggcaacg cgcacagcgc      900
accgaaaccg cccagaccgc ccataacctc cgggcggcga gttttcttca ctacgccttt      960
gattcgatca accagagcgt tacccgcatc aatatcgacg ccggcatctt tatagctaag     1020
agaggtctta tcggtcac                                                   1038
```

<210> SEQ ID NO 92
<211> LENGTH: 426
<212> TYPE: DNA
<213> ORGANISM: Homo sapiens
<220> FEATURE:
<223> OTHER INFORMATION: Survivin (SVN)/BIRC5, isoform 1

<400> SEQUENCE: 92

```
atgggtgccc cgacgttgcc ccctgcctgg cagcccttc tcaaggacca ccgcatctct       60
acattcaaga actggccctt cttggagggc tgcgcctgca ccccggagcg gatggccgag      120
gctggcttca tccactgccc cactgagaac gagccagact ggcccagtg tttcttctgc      180 ttcaaggagc tggaaggctg ggagccagat gacgacccca tagaggaaca taaaaagcat      240
tcgtccggtt gcgctttcct ttctgtcaag aagcagtttg aagaattaac ccttggtgaa      300 ttttgaaac tggacagaga aagagccaag aacaaaattg caaaggaaac caacaataag      360
aagaaagaat tgaggaaac tgcggagaaa gtgcgccgtg ccatcgagca gctggctgcc      420
``` atggat                                                                                                      426

<210> SEQ ID NO 93
<211> LENGTH: 285
<212> TYPE: DNA
<213> ORGANISM: E. coli
<220> FEATURE:
<223> OTHER INFORMATION: araBAD promoter (pBAD)

<400> SEQUENCE: 93
aagaaaccaa ttgtccatat tgcatcagac attgccgtca ctgcgtcttt tactggctct     60
tctcgctaac caaaccggta accccgctta ttaaaagcat tctgtaacaa agcgggacca    120
aagccatgac aaaaacgcgt aacaaaagtg tctataatca cggcagaaaa gtccacattg    180
attatttgca cggcgtcaca ctttgctatg ccatagcatt tttatccata agattagcgg    240
atcttacctg acgcttttta tcgcaactct ctactgtttc tccat                    285

<210> SEQ ID NO 94
<211> LENGTH: 459
<212> TYPE: DNA
<213> ORGANISM: Homo sapiens
<220> FEATURE:
<223> OTHER INFORMATION: Interleukin 2 (IL-2)

<400> SEQUENCE: 94
atgtacagga tgcaactcct gtcttgcatt gcactaagtc ttgcacttgt cacaaacagt     60
gcacctactt caagttctac aaagaaaaca cagctacaac tggagcattt actgctggat    120
ttacagatga ttttgaatgg aattaataat tacaagaatc ccaaactcac caggatgctc    180
acatttaagt tttacatgcc caagaaggcc acagaactga acatcttca gtgtctagaa     240 gaagaactca aacctctgga ggaagtgcta aatttagctc aaagcaaaaa ctttcactta    300
agacccaggg acttaatcag caatatcaac gtaatagttc tggaactaaa gggatctgaa    360
acaacattca tgtgtgaata tgctgatgag acagcaacca ttgtagaatt tctgaacaga    420
tggattacct tttgtcaaag catcatctca acactgact                          459

<210> SEQ ID NO 95
<211> LENGTH: 567
<212> TYPE: DNA
<213> ORGANISM: Homo sapiens
<220> FEATURE:
<223> OTHER INFORMATION: Interferon (IFN) alpha

<400> SEQUENCE: 95
atggcctcgc cctttgcttt actgatggtc ctggtggtgc tcagctgcaa gtcaagctgc     60
tctctgggct gtgatctccc tgagacccac agcctggata acaggaggac cttgatgctc    120
ctggcacaaa tgagcagaat ctctcctttc tcctgtctga tggacagaca tgactttgga    180
tttccccagg aggagtttga tggcaaccag ttccagaagg ctccagccat ctctgtcctc    240
catgagctga tccagcagat cttcaacctc tttaccacaa aagattcatc tgctgcttgg    300
gatgaggacc tcctagacaa attctgcacc gaactctacc agcagctgaa tgacttggaa    360
gcctgtgtga tgcaggagga gggtgggaa gaaactcccc tgatgaatgc ggactccatc     420
ttggctgtga agaaatactt ccgaagaatc actctctatc tgacagagaa gaaatacagc    480
ccttgtgcct gggaggttgt cagagcagaa atcatgagat ccctctcttt atcaacaaac    540
ttgcaagaaa gattaaggag gaaggaa                                        567

```
<210> SEQ ID NO 96
<211> LENGTH: 729
<212> TYPE: DNA
<213> ORGANISM: Homo sapiens
<220> FEATURE:
<223> OTHER INFORMATION: CD48, isoform 1

<400> SEQUENCE: 96
atgtgctcca gaggttggga ttcgtgtctg ctctggaat tgctactgct gcctctgtca      60
ctcctggtga ccagcattca aggtcacttg gtacatatga ccgtggtctc cggcagcaac     120
gtgactctga acatctctga gagcctgcct gagaactaca acaactaac ctggttttat     180
actttcgacc agaagattgt agaatgggat tccagaaaat ctaagtactt tgaatccaaa     240
tttaaaggca gggtcagact tgatcctcag agtggcgcac tgtacatctc taaggtccag     300
aaagaggaca cagcaccta catcatgagg gtgttgaaaa agactgggaa tgagcaagaa     360
tggaagatca agctgcaagt gcttgaccct gtacccaagc ctgtcatcaa aattgagaag     420
atagaagaca tggatgacaa ctgttatctg aaactgtcat gtgtgatacc tggcgagtct     480
gtaaactaca cctggtatgg ggacaaaagg ccctcccaa aggagctcca gaacagtgtg     540
cttgaaacca cccttatgcc acataattac tccaggtgtt atacttgcca agtcagcaat     600
tctgtgagca gcaagaatgg cacggtctgc ctcagtccac cctgtaccct ggcccggtcc     660
tttggagtag aatggattgc aagttggcta gtggtcacgg tgcccaccat tcttggcctg     720
ttacttacc                                                              729

<210> SEQ ID NO 97
<211> LENGTH: 1602
<212> TYPE: DNA
<213> ORGANISM: Homo sapiens
<220> FEATURE:
<223> OTHER INFORMATION: CD276/B7-H3, isoform 1

<400> SEQUENCE: 97
atgctgcgtc ggcgggggcag ccctggcatg ggtgtgcatg tgggtgcagc cctgggagca      60
ctgtggttct gcctcacagg agccctggag gtccaggtcc ctgaagaccc agtggtggca     120
ctggtgggca ccgatgccac cctgtgctgc tccttctccc ctgagcctgg cttcagcctg     180
gcacagctca acctcatctg gcagctgaca gataccaaac agctggtgca cagctttgct     240
gagggccagg accagggcag cgcctatgcc aaccgcacgg ccctcttccc ggacctgctg     300
gcacagggca acgcatccct gaggctgcag cgcgtgcgtg tggcggacga gggcagcttc     360
acctgcttcg tgagcatccg ggatttcggc agcgctgccg tcagcctgca ggtggccgct     420
ccctactcga agcccagcat gaccctggag cccaacaagg acctgcggcc aggggacacg     480
gtgaccatca gtgctccag ctaccagggc taccctgagg ctgaggtgtt ctggcaggat     540
gggcagggtg tgcccctgac tggcaacgtg accacgtcgc agatggccaa cgagcagggc     600
ttgtttgatg tgcacagcat cctgcgggtg gtgctgggtg caaatggcac ctacagctgc     660
ctggtgcgca accccgtgct gcagcaggat gcgcacagct ctgtcaccat cacacccccag     720
agaagcccca caggagccgt ggaggtccag gtccctgagg accgtggtgg ggccctagtg     780
ggcaccgatg ccaccctgcg ctgctccttc tcccccgagc ctggcttcag cctggcacag     840
ctcaacctca tctggcagct gacagacacc aaacagctgg tgcacagttt caccgaaggc     900
cgggaccagg gcagcgccta tgccaaccgc acggccctct cccgacct gctgcacaa     960
ggcaatgcat ccctgaggct gcagcgcgtg cgtgtggcgg acgagggcag cttcacctgc    1020
```

```
ttcgtgagca tccgggattt cggcagcgct gccgtcagcc tgcaggtggc cgctccctac    1080
tcgaagccca gcatgaccct ggagcccaac aaggacctgc ggccagggga cacggtgacc    1140
atcacgtgct ccagctaccg gggctaccct gaggctgagg tgttctggca ggatgggcag    1200
ggtgtgcccc tgactggcaa cgtgaccacg tcgcagatgg ccaacgagca gggcttgttt    1260
gatgtgcaca gcgtcctgcg ggtggtgctg ggtgcgaatg cacctacag ctgcctggtg    1320 cgcaaccccg tgctgcagca ggatgcgcac ggctctgtca ccatcacagg gcagcctatg    1380
acattccccc cagaggccct gtgggtgacc gtggggctgt ctgtctgtct cattgcactg    1440
ctggtggccc tggctttcgt gtgctggaga aagatcaaac agagctgtga ggaggagaat    1500
gcaggagctg aggaccagga tggggaggga gaaggctcca agacagccct gcagcctctg    1560
aaacactctg acagcaaaga agatgatgga caagaaatag cc                      1602
```

<210> SEQ ID NO 98
<211> LENGTH: 846
<212> TYPE: DNA
<213> ORGANISM: Homo sapiens
<220> FEATURE:
<223> OTHER INFORMATION: B7-H4/VTCN1

<400> SEQUENCE: 98

```
atggcttccc tggggcagat cctcttctgg agcataatta gcatcatcat tattctggct    60
ggagcaattg cactcatcat tggctttggt atttcaggga cactccat cacagtcact    120 actgtcgcct cagctgggaa cattggggag gatgaatcc tgagctgcac ttttgaacct    180
gacatcaaac tttctgatat cgtgatacaa tggctgaagg aaggtgtttt aggcttggtc    240
catgagttca aagaaggcaa agatgagctg tcggagcagg atgaaatgtt cagaggccgg    300
acagcagtgt ttgctgatca agtgatagtt ggcaatgcct ctttgcggct gaaaaacgtg    360
caactcacag atgctggcac ctacaaatgt tatatcatca cttctaaagg caaggggaat    420
gctaaccttg agtataaaac tggagccttc agcatgccgg aagtgaatgt ggactataat    480
gccagctcag agaccttgcg tgtgaggct ccccgatggt tccccagcc cacagtggtc    540 tgggcatccc aagttgacca gggagccaac ttctcggaag tctccaatac cagctttgag    600
ctgaactctg agaatgtgac catgaaggtt gtgtctgtgc tctacaatgt tacgatcaac    660
aacacatact cctgtatgat tgaaaatgac attgccaaag caacagggga tatcaaagtg    720
acagaatcgg agatcaaaag gcggagtcac ctacagctgc taaactcaaa ggcttctctg    780
tgtgtctctt ctttctttgc catcagctgg gcacttctgc ctctcagccc ttacctgatg    840
ctaaaa                                                              846
```

<210> SEQ ID NO 99
<211> LENGTH: 867
<212> TYPE: DNA
<213> ORGANISM: Homo sapiens
<220> FEATURE:
<223> OTHER INFORMATION: BTLA/CD272, isoform 1

<400> SEQUENCE: 99

```
atgaagacat tgcctgccat gcttggaact gggaaattat tttgggtctt cttcttaatc    60
ccatatctgg acatctggaa catccatggg aaagaatcat gtgatgtaca gctttatata    120
aagagacaat ctgaacactc catcttagca ggagatccct ttgaactaga atgccctgtg    180
aaatactgtg ctaacaggcc tcatgtgact tggtgcaagc tcaatggaac aacatgtgta    240
aaacttgaag atagacaaac aagttggaag gaagagaaga acatttcatt tttcattcta    300
```

```
cattttgaac cagtgcttcc taatgacaat gggtcatacc gctgttctgc aaattttcag    360
tctaatctca ttgaaagcca ctcaacaact ctttatgtga cagatgtaaa aagtgcctca    420
gaacgaccct ccaaggacga aatggcaagc agaccctggc tcctgtatag tttacttcct    480 ttgggggat tgcctctact catcactacc tgtttctgcc tgttctgctg cctgagaagg    540
caccaaggaa agcaaaatga actctctgac acagcaggaa gggaaattaa cctggttgat    600
gctcacctta agagtgagca aacagaagca agcaccaggc aaaattccca agtactgcta    660
tcagaaactg gaatttatga taatgaccct gacctttgtt tcaggatgca ggaagggtct    720
gaagtttatt ctaatccatg cctggaagaa acaaaccag gcattgttta tgcttccctg    780
aaccattctg tcattggacc gaactcaaga ctggcaagaa atgtaaaaga agcaccaaca    840
gaatatgcat ccatatgtgt gaggagt                                       867
```

<210> SEQ ID NO 100
<211> LENGTH: 276
<212> TYPE: DNA
<213> ORGANISM: Homo sapiens
<220> FEATURE:
<223> OTHER INFORMATION: Chemokine (C-C motif) ligand 4 (CCL4)

<400> SEQUENCE: 100

```
atgaagctct gcgtgactgt cctgtctctc ctcatgctag tagctgcctt ctgctctcca     60
gcgctctcag caccaatggg ctcagaccct cccaccgcct gctgcttttc ttacaccgcg    120
aggaagcttc ctcgcaactt tgtggtagat tactatgaga ccagcagcct ctgctcccag    180
ccagctgtgg tattccaaac caaaagaagc aagcaagtct gtgctgatcc cagtgaatcc    240
tgggtccagg agtacgtgta tgacctggaa ctgaac                              276
```

<210> SEQ ID NO 101
<211> LENGTH: 3537
<212> TYPE: DNA
<213> ORGANISM: Homo sapiens
<220> FEATURE:
<223> OTHER INFORMATION: CD103/ITGAE

<400> SEQUENCE: 101

```
atgtggctct tccacactct gctctgcata gccagcctgg ccctgctggc cgctttcaat     60
gtggatgtgg cccggccctg gctcacgccc aagggaggtg ccccttttcgt gctcagctcc    120 cttctgcacc aagaccccag caccaaccag acctggctcc tggtcaccag ccccagaacc    180
aagaggacac cagggcccct ccatcgatgt tcccttgtcc aggatgaaat cctttgccat    240
cctgtagagc atgtccccat ccccaagggg aggcaccggg gagtgaccgt tgtccggagc    300
caccacggtg ttttgatatg cattcaagtg ctggtccggc ggcctcacag cctcagctca    360
gaactcacag gcacctgtag cctcctgggc cctgacctcc gtcccaggc tcaggccaac    420 ttcttcgacc ttgaaaatct cctggatcca gatgcacgtg tggacactgg agactgctac    480
agcaacaaag aaggcggtgg agaagacgat gtgaacacag ccaggcagcg ccgggctctg    540
gagaaggagg aggaggaaga caaggaggag gaggaagacg aggaggagga ggaagctggc    600
accgagattg ccatcatcct ggatggctca ggaagcattg atccccaga ctttcagaga    660 gccaaagact tcatctccaa catgatgagg aacttctatg aaaagtgttt tgagtgcaac    720
tttgccttgg tgcagtatgg aggagtgatc cagactgagt ttgaccttcg ggacagccag    780
gatgtgatgg cctccctcgc cagagtccag aacatcactc aagtgggag tgtcaccaag    840
```

```
actgcctcag ccatgcaaca cgtcttagac agcatcttca cctcaagcca cggctccagg      900
agaaaggcat ccaaggtcat ggtggtgctc accgatggtg gcatattcga ggacccctc       960
aaccttacga cagtcatcaa ctcccccaaa atgcaggatg ttgagcgctt tgccattggg     1020
gtgggagaag aatttaagag tgctaggact gcgagggaac tgaacctgat cgcctcagac     1080
ccggatgaga cccatgcttt caaggtgacc aactacatgg cgctggatgg gctgctgagc     1140
aaactgcggt acaacatcat cagcatgaaa ggcacggttg agacgcccct tcactaccag     1200
ctggcacaga ttggcttcag tgctcagatc ctggatgagc ggcaggtgct gctcggcgcc     1260
gtcggggcct ttgactggtc cggaggggcg ttgctctacg acacacgcag ccgccggggc     1320
cgcttcctga accagacagc ggcggcggcg gcagacgcgg aggctgcgca gtacagctac     1380
ctgggttacg ctgtggccgt gctgcacaag acctgcagcc tctcctacat cgcgggggct     1440
ccacggtaca aacatcatgg ggccgtgttt gagctccaga aggagggcag agaggccagc     1500
ttcctgccag tgctggaggg agagcagatg gggtcctatt ttggctctga gctgtgccct     1560
gtggacattg acatggatgg aagcacggac ttcttgctgg tggctgctcc atttaccac      1620
gttcatggag aagaaggcag agtctacgtg taccgtctca gcgagcagga tggttctttc     1680
tccttggcac gcatactgag tgggcacccc gggttcacca atgcccgctt tggctttgcc     1740
atggcggcta tgggggatct cagtcaggat aagctcacag atgtggccat cggggccccc     1800
ctggaaggtt ttggggcaga tgatggtgcc agcttcggca gtgtgtatat ctacaatgga     1860
cactgggacg gcctctccgc cagcccctcg cagcggatca gagcctccac ggtggcccca     1920
ggactccagt acttcggcat gtccatggct ggtggctttg atattagtgg cgacggcctt     1980
gccgacatca ccgtgggcac tctgggccag gcggttgtgt tccgctcccg gcctgtggtt     2040
cgcctgaagg tctccatggc cttcacccc agcgcactgc ccatcggctt caacggcgtc      2100
gtgaatgtcc gtttatgttt tgaaatcagc tctgtaacca cagcctctga gtcaggcctc     2160
cgcgaggcac ttctcaactt cacgctggat gtggatgtgg ggaagcagag gagacggctg     2220
cagtgttcag acgtaagaag ctgtctgggc tgcctgaggg agtggagcag cggatcccag     2280
cttttgtgagg acctcctgct catgcccaca gaggagagc tctgtgagga ggactgcttc      2340
tccaatgcca gtgtcaaagt cagctaccag ctccagaccc ctgagggaca gacggaccat     2400
ccccagccca tcctggaccg ctacactgag ccctttgcca tcttccagct gcccatgag      2460
aaggcctgca agaataagct gtttttgtgtc gcagaattac agttggccac caccgtctct    2520
cagcaggagt tggtggtggg tctcacaaag gagctgaccc tgaacattaa cctaactaac     2580
tccggggaag attcctacat gacaagcatg gccttgaatt accccagaaa cctgcagttg     2640
aagaggatgc aaaagcctcc ctctccaaac attcagtgtg atgaccctca gccggttgct     2700
tctgtcctga tcatgaactg caggattggt caccccgtcc tcaagaggtc atctgctcat     2760
gtttcagtcg tttggcagct agaggagaat gcctttccaa acaggacagc agacatcact     2820
gtgactgtca ccaattccaa tgaaagacgg tctttggcca acgagaccca cacccttcaa     2880
ttcaggcatg gcttcgttgc agttctgtcc aaaccatcca taatgtacgt gaacacaggc     2940
caggggcttt ctcaccacaa agaattcctc ttccatgtac atgggagaa cctcttttga      3000
gcagaatacc agttgcaaat ttgcgtccca accaaattac gaggtctcca ggttgtagca     3060
gtgaagaagc tgacgaggac tcaggcctcc acggtgtgca cctggagtca ggagcgcgct     3120
tgtgcgtaca gttcggttca gcatgtgaa gaatggcatt cagtgagctg tgtcatcgct      3180
tcagataaag aaaatgtcac cgtggctgca gagatctcct gggatcactc tgaggagtta     3240
```

```
ctaaaagatg taactgaact gcagatcctt ggtgaaatat ctttcaacaa atctctatat    3300
gagggactga atgcagagaa ccacagaact aagatcactg tcgtcttcct gaaagatgag    3360
aagtaccatt ctttgcctat catcattaaa ggcagcgttg gtggacttct ggtgttgatc    3420
gtgattctgg tcatcctgtt caagtgtggc ttttttaaaa gaaaatatca acaactgaac    3480
ttggagagca tcaggaaggc ccagctgaaa tcagagaatc tgctcgaaga agagaat       3537
```

<210> SEQ ID NO 102
<211> LENGTH: 1671
<212> TYPE: DNA
<213> ORGANISM: Homo sapiens
<220> FEATURE:
<223> OTHER INFORMATION: CD19, isoform 1

<400> SEQUENCE: 102

```
atgccacctc ctcgcctcct cttcttcctc ctcttcctca cccccatgga agtcaggccc      60
gaggaacctc tagtggtgaa ggtggaagag ggagataacg ctgtgctgca gtgcctcaag     120
gggacctcag atggccccac tcagcagctg acctggtctc gggagtcccc gcttaaaccc     180
ttcttaaaac tcagcctggg gctgccaggc tgggaatccc acatgaggcc cctggccatc     240
tggcttttca tcttcaacgt ctctcaacag atgggggggct ctacctgtg ccagccgggg     300 ccccctctg agaaggcctg gcagcctggc tggacagtca atgtggaggg cagcggggag     360
ctgttccggt ggaatgtttc ggacctaggt ggcctgggct gtggcctgaa gaacaggtcc     420
tcagagggcc ccagctcccc ttccgggaag ctcatgagcc caagctgta tgtgtgggcc     480 aaagaccgcc ctgagatctg ggagggagag cctccgtgtc tccaccgag ggacagcctg     540 aaccagagcc tcagccagga cctcaccatg gcccctggct ccacactctg gctgtcctgt     600
ggggtacccc ctgactctgt gtccagggc cccctctcct ggacccatgt gcaccccaag     660
gggcctaagt cattgctgag cctagagctg aaggacgatc gcccggccag agatatgtgg     720
gtaatggaga cgggtctgtt gttgcccggg gccacagctc aagacgctgg aaagtattat     780
tgtcaccgtg gcaacctgac catgtcattc cacctggaga tcactgctcg gccagtacta     840
tggcactggc tgctgaggac tggtggctgg aaggtctcag ctgtgacttt ggcttatctg     900
atcttctgcc tgtgttccct tgtgggcatt cttcatctc aaagagccct ggtcctgagg     960
aggaaaagaa agcgaatgac tgaccccacc aggagattct tcaaagtgac gcctcccca    1020 ggaagcgggc cccagaacca gtacgggaac gtgctgtctc tccccacacc cacctcaggc    1080
ctcggacgcg cccagcgttg gccgcaggc tggggggca ctgccccgtc ttatggaaac    1140
ccgagcagcg acgtccaggc ggatggagcc ttggggtccc ggagcccgcc gggagtgggc    1200
ccagaagaag aggaagggga gggctatgag gaacctgaca gtgaggagga ctccgagttc    1260
tatgagaacg actccaacct gggcaggac cagctctccc aggatggcag cggctacgag    1320
aaccctgagg atgagccccct gggtcctgag gatgaagact ccttctcaa cgctgagtct    1380 tatgagaacg aggatgaaga gctgacccag ccggtcgcca ggacaatgga cttcctgagc    1440
cctcatgggt cagcctggga ccccagccgg aagcaacct ccctggcagg gtccagtcc    1500 tatgaggata tgagaggaat cctgtatgca gccccccagc tccgctccat tcggggccag    1560
cctggaccca atcatgagga agatgcagac tcttatgaga acatggataa tccccgatggg    1620 ccagacccag cctggggagg aggggccgc atgggcacct ggagcaccag g              1671
```

<210> SEQ ID NO 103

```
<211> LENGTH: 579
<212> TYPE: DNA
<213> ORGANISM: Homo sapiens
<220> FEATURE:
<223> OTHER INFORMATION: Interleukin 18 (IL-18), isoform 1

<400> SEQUENCE: 103
atggctgctg aaccagtaga agacaattgc atcaactttg tggcaatgaa atttattgac        60
aatacgcttt actttatagc tgaagatgat gaaaacctgg aatcagatta ctttggcaag       120
cttgaatcta aattatcagt cataagaaat ttgaatgacc aagttctctt cattgaccaa       180
ggaaatcggc ctctatttga agatatgact gattctgact gtagagataa tgcaccccgg       240
accatattta ttataagtat gtataaagat agccagccta gaggtatggc tgtaactatc       300
tctgtgaagt gtgagaaaat ttcaactctc tcctgtgaga acaaaattat ttcctttaag       360
gaaatgaatc ctcctgataa catcaaggat acaaaaagtg acatcatatt ctttcagaga       420
agtgtcccag acatgataa taagatgcaa tttgaatctt catcatacga aggatacttt       480
ctagcttgtg aaaaagagag agaccttttt aaactcattt tgaaaaaaga ggatgaattg       540
ggggatagat ctataatgtt cactgttcaa aacgaagac                              579

<210> SEQ ID NO 104
<211> LENGTH: 1005
<212> TYPE: DNA
<213> ORGANISM: Homo sapiens
<220> FEATURE:
<223> OTHER INFORMATION: Fas ligand

<400> SEQUENCE: 104
atgctgggca tctggaccct cctacctctg gttcttacgt ctgttgctag attatcgtcc        60
aaaagtgtta atgcccaagt gactgacatc aactccaagg gattggaatt gaggaagact       120
gttactacag ttgagactca gaacttggaa ggcctgcatc atgatggcca attctgccat       180
aagccctgtc ctccaggtga aggaaagct agggactgca cagtcaatgg ggatgaacca       240
gactgcgtgc cctgccaaga agggaaggag tacacagaca agcccattt tcttccaaa        300 tgcagaagat gtagattgtg tgatgaagga catggcttag aagtgaaat aaactgcacc       360 cggacccaga ataccaagtg cagatgtaaa ccaaactttt tttgtaactc tactgtatgt       420
gaacactgtg acccttgcac caaatgtgaa catggaatca tcaaggaatg cacactcacc       480
agcaacacca gtgcaaaga ggaaggatcc agatctaact gggtggct ttgtcttctt        540 cttttgccaa ttccactaat tgtttgggtg aagagaaagg aagtacgaaa acatgcaga       600 aagcacagaa aggaaaacca aggttctcat gaatctccaa ctttaaatcc tgaaacagtg       660
gcaataaatt tatctgatgt tgacttgagt aaatatatca ccactattgc tggagtcatg       720
acactaagtc aagttaaagg cttttgttcga aagaatggtg tcaatgaagc caaaatagat       780
gagatcaaga tgacaatgt ccaagacaca gcagaacaga agttcaact gcttcgtaat        840 tggcatcaac ttcatggaaa gaagaagcg tatgacacat tgattaaaga tctcaaaaaa       900
gccaatcttt gtactcttgc agagaaaatt cagactatca tcctcaagga cattactagt       960
gactcagaaa attcaaactt cagaaatgaa atccaaagct tggtc                      1005

<210> SEQ ID NO 105
<211> LENGTH: 1023
<212> TYPE: DNA
<213> ORGANISM: Salmonella typhimurium
<220> FEATURE:
<223> OTHER INFORMATION: firA/SSC
```

<400> SEQUENCE: 105

```
atgccttcaa ttcgactggc tgacttagca gaacagttgg atgcagaatt acacggtgat      60
ggcgatatcg tcatcaccgg cgttgcgtcc atgcaatctg caacaacagg ccacattacg     120
tttatggtga atcctaagta ccgtgaacac ttaggtttat gccaggcttc tgcggttgtc     180
atgacgcagg acgatcttcc ttttgctaag agtgcggcgc tggtagttaa aaatccctac     240
ctgacctacg cgcgcatggc gcaaatttta gatactacgc cgcagcccgc gcagaatatc     300
gcgccaagcg ccgtgattga tgcgacggca acgctgggta gcaatgtttc agtcggcgcg     360
aatgcggtga ttgaatctgg cgtacaactg gcgataacg tggttatcgg cgcaggctgt     420
ttcgtcggaa aaatagcaa atcggggcg ggttcacgct tgtgggcgaa cgtaacgatt     480
taccacgaca ttcagatcgg tgagaattgc ctgatccagt ccagtacggt gatcggcgcg     540
gacggttttg ctacgctaa cgatcgtggc aactgggtga agatcccaca actgggccgg     600
gtcattattg gcgatcgtgt cgagatcggc gcttgtacca ccattgaccg tggcgcgttg     660
gatgatactg ttattggcaa tggcgtgatt attgataatc agtgccagat tgcacataac     720
gtcgtgattg gcgacaatac ggcagttgcc ggtggcgtca ttatggcggg tagcctgaag     780
attggccgtt actgcatgat tggcggcgcc agcgtgatca atgggcatat ggaaatatgc     840
gacaaagtca cggtaactgg catgggtatg gtgatgcgtc ccatcacgga accgggcgtc     900
tactcctcag gcattccgct gcaacccaac aaagtatggc gtaaaactgc tgcactggtg     960
atgaacattg atgatatgag caagcgtctc aaagcgattg agcgcaaggt taatcaacaa    1020
gac                                                                 1023
```

<210> SEQ ID NO 106
<211> LENGTH: 918
<212> TYPE: DNA
<213> ORGANISM: E. coli
<220> FEATURE:
<223> OTHER INFORMATION: htrB

<400> SEQUENCE: 106

```
atgacgaatc tacccaagtt ctccaccgca ctgcttcatc cgcgttattg gttaacctgg      60
ttgggtattg gcgtactttg gttagtcgtg caattgccct acccggttat ctaccgcctc     120
ggttgtggat taggaaaact ggcgttacgt tttatgaaac gacgcgcaaa aattgtgcat     180
cgcaacctgg aactgtgctt cccggaaatg agcgaacaag aacgccgtaa atggtggtg     240
aagaatttcg aatccgttgg catgggcctg atggaaccg gcatggcgtg gttctggccg     300
gaccgccgaa tcgcccgctg gacggaagtg atcggcatgg aacacattcg tgacgtgcag     360
gcgcaaaaac gcggcatcct gttagttggc atccattttc tgacactgga gctgggtgcg     420
cggcagtttg gtatgcagga accgggtatt ggcgtttatc gcccgaacga taatccactg     480
attgactggc tacaaacctg ggccgtttg cgctcaaata atcgatgct cgaccgcaaa     540
gatttaaaag gcatgattaa agccctgaaa aaaggcgaag tggtctggta cgcaccggat     600
catgattacg gcccgcgctc aagcgttttc gtcccgttgt ttgccgttga gcaggctgcg     660
accacgaccg gaacctggat gctggcacgg atgtccggcg catgtctggt gcccttcgtt     720
ccacgccgta agccagatgg caaagggtat caattgatta tgctgccgcc agagtgttct     780
ccgccactgg atgatgccga aactaccgcc gcgtggatga caaagtggt cgaaaaatgc     840
atcatgatgg caccagagca gtatatgtgg ttacaccgtc gctttaaaac acgcccggaa     900
```

```
ggcgttcctt cacgctat                                                918
```

<210> SEQ ID NO 107
<211> LENGTH: 717
<212> TYPE: DNA
<213> ORGANISM: Salmonella typhimurium
<220> FEATURE:
<223> OTHER INFORMATION: ompR

<400> SEQUENCE: 107

```
atgcaagaga attataagat tctggtggtt gatgacgata tgcgtctgcg ggcgctactg    60
gaacgttatc tgaccgagca gggcttccag gttcgaagcg tcgctaacgc tgagcagatg   120
gatcgtctgc tgacccgtga atctttccat ctcatggtac tggatttaat gctgccaggt   180
gaagatggtc tgtcgatttg tcgtcgcctg cgtagtcaaa gtaatccaat gccgatcatt   240
atggtcacgg cgaagggtga agaggttgac cgtatcgtcg ggctggaaat cggcgccgat   300
gactacattc ctaaaccgtt taacccgcgc gagctgttgg cgcgtattcg gcccgtgtta   360
cgtcgtcagg caaacgaact gcccggcgcg ccgtcgcagg aagaggccgt tatcgcgttc   420
ggtaagttta aactgaacct cggtacgcgc gagatgttcc gtgaagatga accgatgccg   480
ctgaccagcg gggagtttgc ggtactgaaa gcgttagtca gccatccgcg cgagccgctc   540
tctcgcgata gctgatgaa tctggcccgt ggccgcgagt attccgcgat ggaacgctcc   600
atcgacgtcc agatctcccg cctgcgccgt atggtggaag aagatccggc acatccgcgt   660
tatattcaga ccgtctgggg cctgggctac gtctttgtac cggacggttc taaagca      717
```

<210> SEQ ID NO 108
<211> LENGTH: 498
<212> TYPE: DNA
<213> ORGANISM: Homo sapiens
<220> FEATURE:
<223> OTHER INFORMATION: Inteferon (IFN) gamma

<400> SEQUENCE: 108

```
atgaaatata caagttatat cttggctttt cagctctgca tcgttttggg ttctcttggc    60
tgttactgcc aggacccata tgtaaaagaa gcagaaaacc ttaagaaata ttttaatgca   120
ggtcattcag atgtagcgga taatggaact cttttcttag cattttgaa gaattggaaa    180 gaggagagtg acagaaaaat aatgcagagc caaattgtct cctttttactt caaactttt    240 aaaaacttta agatgaccca gagcatccaa aagagtgtgg agaccatcaa ggaagacatg   300
aatgtcaagt ttttcaatag caacaaaaag aaacgagatg acttcgaaaa gctgactaat   360
tattcggtaa ctgacttgaa tgtccaacgc aaagcaatac atgaactcat ccaagtgatg   420
gctgaactgt cgccagcagc taaaacaggg aagcgaaaaa ggagtcagat gctgtttcga   480
ggtcgaagag catcccag                                                498
```

<210> SEQ ID NO 109
<211> LENGTH: 699
<212> TYPE: DNA
<213> ORGANISM: Homo sapiens
<220> FEATURE:
<223> OTHER INFORMATION: Tumor necrosis factor (TNF) alpha

<400> SEQUENCE: 109

```
atgagcactg aaagcatgat ccgggacgtg gagctggccg aggaggcgct ccccaagaag    60 acagggggc cccagggctc caggcggtgc ttgttcctca gcctcttctc cttcctgatc   120
gtggcaggcg ccaccacgct cttctgcctg ctgcactttg gagtgatcgg ccccagagg   180
```

```
gaagagttcc ccagggacct ctctctaatc agccctctgg cccaggcagt cagatcatct    240
tctcgaaccc cgagtgacaa gcctgtagcc catgttgtag caaaccctca agctgagggg    300
cagctccagt ggctgaaccg ccgggccaat gccctcctgg ccaatggcgt ggagctgaga    360
gataaccagc tggtggtgcc atcagagggc ctgtacctca tctactccca ggtcctcttc    420
aagggccaag gctgcccctc cacccatgtg ctcctcaccc acaccatcag ccgcatcgcc    480
gtctcctacc agaccaaggt caacctcctc tctgccatca gagccctg ccagagggag    540 accccagagg gggctgaggc caagccctgg tatgagccca tctatctggg aggggtcttc    600
cagctggaga agggtgaccg actcagcgct gagatcaatc ggcccgacta tctcgacttt    660
gccgagtctg ggcaggtcta ctttgggatc attgccctg                          699
```

<210> SEQ ID NO 110
<211> LENGTH: 825
<212> TYPE: DNA
<213> ORGANISM: Homo sapiens
<220> FEATURE:
<223> OTHER INFORMATION: Atg5 long isoform

<400> SEQUENCE: 110

```
atgacagatg acaaagatgt gcttcgagat gtgtggtttg gacgaattcc aacttgtttc    60
acgctatatc aggatgagat aactgaaagg gaagcagaac catactattt gcttttgcca    120
agagtaagtt atttgacgtt ggtaactgac aaagtgaaaa agcactttca gaaggttatg    180
agacaagaag acattagtga gatatggttt gaatatgaag gcacaccact gaaatggcat    240
tatccaattg gtttgctatt tgatcttctt gcatcaagtt cagctcttcc ttggaacatc    300
acagtacatt ttaagagttt tccagaaaaa gaccttctgc actgtccatc taaggatgca    360
attgaagctc attttatgtc atgtatgaaa gaagctgatg ctttaaaaca taaaagtcaa    420
gtaatcaatg aaatgcagaa aaagatcac aagcaactct ggatgggatt gcaaaatgac    480
agatttgacc agttttgggc catcaatcgg aaactcatgg aatatcctgc agaagaaaat    540
ggatttcgtt atatccccctt tagaatatat cagacaacga ctgaaagacc tttcattcag    600
aagctgtttc gtcctgtggc tgcagatgga cagttgcaca cactaggaga tctcctcaaa    660
gaagtttgtc cttctgctat tgatcctgaa gatggggaaa aaagaatca agtgatgatt    720 catggaattg agccaatgtt ggaaacacct ctgcagtggc tgagtgaaca tctgagctac    780
ccggataatt ttcttcatat tagtatcatc ccacagccaa cagat                   825
```

<210> SEQ ID NO 111
<211> LENGTH: 1350
<212> TYPE: DNA
<213> ORGANISM: Homo sapiens
<220> FEATURE:
<223> OTHER INFORMATION: Beclin1

<400> SEQUENCE: 111

```
atggaagggt ctaagacgtc caacaacagc accatgcagg tgagcttcgt gtgccagcgc    60
tgcagccagc ccctgaaact ggacacgagt ttcaagatcc tggaccgtgt caccatccag    120
gaactcacag ctccattact taccacagcc aggcgaaac aggagagac ccaggaggaa    180 gagactaact caggagagga gccatttatt gaaactcctc gccaggatgg tgtctctcgc    240
agattcatcc cccagccag gatgatgtcc acagaaagtg ccaacagctt cactctgatt    300
ggggaggcat ctgatggcgg caccatggag aacctcagcc gaagactgaa ggtcactggg    360
```

```
gaccttttg  acatcatgtc  gggccagaca  gatgtggatc  acccactctg  tgaggaatgc    420
acagatactc  ttttagacca  gctggacact  cagctcaacg  tcactgaaaa  tgagtgtcag    480
aactacaaac  gctgtttgga  gatcttagag  caaatgaatg  aggatgacag  tgaacagtta    540
cagatggagc  taaaggagct  ggcactagag  gaggagaggc  tgatccagga  gctggaagac    600
gtggaaaaga  accgcaagat  agtggcagaa  atctcgaga   aggtccaggc  tgaggctgag    660
agactggatc  aggaggaagc  tcagtatcag  agagaataca  gtgaatttaa  acgcagcag    720 ctggagctgg  atgatgagct  gaagagtgtt  gaaaaccaga  tgcgttatgc  ccagacgcag    780
ctggataagc  tgaagaaaac  caacgtcttt  aatgcaacct  tccacatctg  gcacagtgga    840
cagtttggca  caatcaataa  cttcaggctg  ggtcgcctgc  ccagtgttcc  cgtggaatgg    900
aatgagatta  atgctgcttg  gggccagact  gtgttgctgc  tccatgctct  ggccaataag    960
atgggtctga  aatttcagag  ataccgactt  gttccttacg  gaaaccattc  atatctggag   1020
tctctgacag  acaaatctaa  ggagctgccg  ttatactgtt  ctgggggggtt  gcggttttc   1080 tgggacaaca  agtttgacca  tgcaatggtg  gcttcctgg   actgtgtgca  gcagttcaaa   1140
gaagaggttg  agaaaggcga  gacacgtttt  tgtcttccct  acaggatgga  tgtggagaaa   1200
ggcaagattg  aagacacagg  aggcagtggc  ggctcctatt  ccatcaaaac  ccagtttaac   1260
tctgaggagc  agtggacaaa  agctctcaag  ttcatgctga  cgaatcttaa  gtggggtctt   1320
gcttgggtgt  cctcacaatt  ttataacaaa                                       1350

<210> SEQ ID NO 112
<211> LENGTH: 2352
<212> TYPE: DNA
<213> ORGANISM: Homo sapiens
<220> FEATURE:
<223> OTHER INFORMATION: Toll-like receptor 2 (TLR2)

<400> SEQUENCE: 112
atgccacata  ctttgtggat  ggtgtgggtc  ttgggggtca  tcatcagcct  ctccaaggaa     60
gaatcctcca  atcaggcttc  tctgtcttgt  gaccgcaatg  gtatctgcaa  gggcagctca    120
ggatctttaa  actccattcc  ctcagggctc  acagaagctg  taaaaagcct  tgacctgtcc    180
aacaacagga  tcacctacat  tagcaacagt  gacctacaga  ggtgtgtgaa  cctccaggct    240
ctggtgctga  catccaatgg  aattaacaca  atagaggaag  attcttttc   ttccctgggc    300 agtcttgaac  atttagactt  atcctataat  tacttatcta  atttatcgtc  ttcctggttc    360
aagccccttt  cttctttaac  attcttaaac  ttactgggaa  atccttacaa  accctaggg    420 gaaacatctc  ttttttctca  tctcacaaaa  ttgcaaatcc  tgagagtggg  aaatatggac    480
accttcacta  agattcaaag  aaaagatttt  gctggactta  ccttccttga  ggaacttgag    540
attgatgctt  cagatctaca  gagctatgag  ccaaaaagtt  tgaagtcaat  tcagaatgta    600
agtcatctga  tccttcatat  gaagcagcat  attttactgc  tggagatttt  tgtagatgtt    660
acaagttccg  tggaatgttt  ggaactgcga  gatactgatt  tggacacttt  ccatttttca    720
gaactatcca  ctggtgaaac  aaattcattg  attaaaaagt  ttacatttag  aaatgtgaaa    780
atcaccgatg  aaagtttgtt  tcaggttatg  aaacttttga  atcagatttc  tggattgtta    840
gaattagagt  ttgatgactg  tacccttaat  ggagttggta  attttagagc  atctgataat    900
gacagagtta  tagatccagg  taaagtggaa  acgttaacaa  tccggaggct  gcatattcca    960
aggttttact  tattttatga  tctgagcact  ttatattcac  ttacagaaag  agttaaaaga   1020
atcacagtag  aaaacagtaa  agtttttctg  gttccttgtt  tactttcaca  acatttaaaa   1080
```

```
tcattagaat acttggatct cagtgaaaat ttgatggttg aagaatactt gaaaaattca   1140
gcctgtgagg atgcctggcc ctctctacaa actttaattt taaggcaaaa tcatttggca   1200
tcattggaaa aaaccggaga gactttgctc actctgaaaa acttgactaa cattgatatc   1260
agtaagaata gttttcattc tatgcctgaa acttgtcagt ggccagaaaa gatgaaatat   1320
ttgaacttat ccagcacacg aatacacagt gtaacaggct gcattcccaa gacactggaa   1380
attttagatg ttagcaacaa caatctcaat ttatttttctt tgaatttgcc gcaactcaaa   1440
gaactttata tttccagaaa taagttgatg actctaccag atgcctccct cttacccatg   1500
ttactagtat tgaaaatcag taggaatgca ataactacgt tttctaagga gcaacttgac   1560
tcatttcaca cactgaagac tttggaagct ggtggcaata acttcatttg ctcctgtgaa   1620
ttcctctcct tcactcagga gcagcaagca ctggccaaag tcttgattga ttggccagca   1680
aattacctgt gtgactctcc atcccatgtg cgtggccagc aggttcagga tgtccgcctc   1740
tcggtgtcgg aatgtcacag acagcactg gtgtctggca tgtgctgtgc tctgttcctg   1800
ctgatcctgc tcacgggggt cctgtgccac cgtttccatg gcctgtggta tatgaaaatg   1860
atgtgggcct ggctccaggc caaaaggaag cccaggaaag ctcccagcag gaacatctgc   1920
tatgatgcat ttgtttctta cagtgagcgg gatgcctact gggtggagaa ccttatggtc   1980
caggagctgg agaacttcaa tccccccttc aagttgtgtc ttcataagcg ggacttcatt   2040
cctggcaagt ggatcattga caatatcatt gactccattg aaaagagcca caaaactgtc   2100
tttgtgcttt ctgaaaactt tgtgaagagt gagtggtgca agtatgaact ggacttctcc   2160
catttccgtc ttttgatga gaacaatgat gctgccattc tcattcttct ggagcccatt   2220
gagaaaaaag ccattccca gcgcttctgc aagctgcgga agataatgaa caccaagacc   2280
tacctggagt ggcccatgga cgaggctcag cgggaaggat tttgggtaaa tctgagagct   2340
gcgataaagt cc                                                      2352

<210> SEQ ID NO 113
<211> LENGTH: 2517
<212> TYPE: DNA
<213> ORGANISM: Homo sapiens
<220> FEATURE:
<223> OTHER INFORMATION: TLR4, isoform 1

<400> SEQUENCE: 113
atgatgtctg cctcgcgcct ggctgggact ctgatcccag ccatggcctt cctctcctgc    60
gtgagaccag aaagctggga gccctgcgtg gaggtggttc ctaatattac ttatcaatgc    120
atggagctga atttctacaa aatccccgac aacctcccct ctcaaccaa gaacctggac    180 ctgagcttta atcccctgag gcatttaggc agctatagct tcttcagttt cccagaactg    240
caggtgctgg atttatccag gtgtgaaatc cagacaattg aagatggggc atatcagagc    300
ctaagccacc tctctacctt aatattgaca ggaaacccca tccagagttt agccctggga    360
gccttttctg gactatcaag tttacagaag ctggtggctg tggagacaaa tctagcatct    420
ctagagaact tccccattgg acatctcaaa actttgaaag aacttaatgt ggctcacaat    480
cttatccaat ctttcaaatt acctgagtat ttttctaatc tgaccaatct agagcacttg    540
gacctttcca gcaacaagat tcaaagtatt tattgcacag acttgcgggt tctacatcaa    600
atgcccctac tcaatctctc tttagacctg tccctgaacc ctatgaactt tatccaacca    660 ggtgcatta aagaaattag gcttcataag ctgacttta gaaataattt tgatagttta    720
```

-continued

| | |
|---|---|
| aatgtaatga aaacttgtat tcaaggtctg gctggtttag aagtccatcg tttggttctg | 780 |
| ggagaattta gaaatgaagg aaacttggaa aagtttgaca aatctgctct agagggcctg | 840 |
| tgcaatttga ccattgaaga attccgatta gcatacttag actactacct cgatgatatt | 900 |
| attgacttat ttaattgttt gacaaatgtt tcttcatttt ccctggtgag tgtgactatt | 960 |
| gaaagggtaa aagacttttc ttataatttc ggatggcaac atttagaatt agttaactgt | 1020 |
| aaatttggac agtttcccac attgaaactc aaatctctca aaaggcttac tttcacttcc | 1080 |
| aacaaaggtg ggaatgcttt ttcagaagtt gatctaccaa gccttgagtt tctagatctc | 1140 |
| agtagaaatg gcttgagttt caaaggttgc tgttctcaaa gtgattttgg gacaaccagc | 1200 |
| ctaaagtatt tagatctgag cttcaatggt gttattacca tgagttcaaa cttcttgggc | 1260 |
| ttagaacaac tagaacatct ggatttccag cattccaatt tgaaacaaat gagtgagttt | 1320 |
| tcagtattcc tatcactcag aaacctcatt taccttgaca tttctcatac tcacaccaga | 1380 |
| gttgctttca atggcatctt caatggcttg tccagtctcg aagtcttgaa aatggctggc | 1440 |
| aattctttcc aggaaaactt ccttccagat atcttcacag agctgagaaa cttgaccttc | 1500 |
| ctggacctct ctcagtgtca actggagcag ttgtctccaa cagcatttaa ctcactctcc | 1560 |
| agtcttcagg tactaaatat gagccacaac aacttctttt cattggatac gtttccttat | 1620 |
| aagtgtctga actccctcca ggttcttgat tacagtctca atcacataat gacttccaaa | 1680 |
| aaacaggaac tacagcattt tccaagtagt ctagctttct taaatcttac tcagaatgac | 1740 |
| tttgcttgta cttgtgaaca ccagagtttc tgcaatggat caaggacca gaggcagctc | 1800 |
| ttggtggaag ttgaacgaat ggaatgtgca acaccttcag ataagcaggg catgcctgtg | 1860 |
| ctgagtttga atatcaccctg tcagatgaat aagaccatca ttggtgtgtc ggtcctcagt | 1920 |
| gtgcttgtag tatctgttgt agcagttctg gtctataagt tctattttca cctgatgctt | 1980 |
| cttgctggct gcataaagta tggtagaggt gaaaacatct atgatgcctt tgttatctac | 2040 |
| tcaagccagg atgaggactg ggtaaggaat gagctagtaa agaatttaga agaaggggtg | 2100 |
| cctccatttc agctctgcct tcactacaga gactttattc ccggtgtggc cattgctgcc | 2160 |
| aacatcatcc atgaaggttt ccataaaagc cgaaaggtga ttgttgtggt gtcccagcac | 2220 |
| ttcatccaga gccgctggtg tatctttgaa tatgagattg ctcagacctg cagtttctg | 2280 |
| agcagtcgtg ctggtatcat cttcattgtc ctgcagaagg tggagaagac cctgctcagg | 2340 |
| cagcaggtgg agctgtaccg ccttctcagc aggaacactt acctggagtg ggaggacagt | 2400 |
| gtcctggggc ggcacatctt ctggagacga ctcagaaaag ccctgctgga tggtaaatca | 2460 |
| tggaatccag aaggaacagt gggtacagga tgcaattggc aggaagcaac atctatc | 2517 |

<210> SEQ ID NO 114
<211> LENGTH: 2574
<212> TYPE: DNA
<213> ORGANISM: Homo sapiens
<220> FEATURE:
<223> OTHER INFORMATION: TLR5

<400> SEQUENCE: 114

| | |
|---|---|
| atgggagacc acctggacct tctcctagga gtggtgctca tggccggtcc tgtgtttgga | 60 |
| attccttcct gctcctttga tggccgaata gccttttatc gtttctgcaa cctcacccag | 120 |
| gtcccccagg tcctcaacac cactgagagg ctcctgctga gcttcaacta tatcaggaca | 180 |
| gtcactgctt catccttccc cttttctggaa cagctgcagc tgctggagct cgggagccag | 240 |
| tataccccct tgactattga caaggaggcc ttcagaaacc tgcccaacct tagaatcttg | 300 |

```
gacctgggaa gtagtaagat atacttcttg catccagatg cttttcaggg actgttccat    360
ctgtttgaac ttagactgta tttctgtggt ctctctgatg ctgtattgaa agatggttat    420
ttcagaaatt taaaggcttt aactcgcttg gatctatcca aaaatcagat tcgtagcctt    480
taccttcatc cttcatttgg gaagttgaat tccttaaagt ccatagattt ttcctccaac    540
caaatattcc ttgtatgtga acatgagctc gagcccctac aagggaaaac gctctccttt    600
tttagcctcg cagctaatag cttgtatagc agagtctcag tggactgggg aaaatgtatg    660
aacccattca gaaacatggt gctggagata ctagatgttt ctggaaatgg ctggacagtg    720
gacatcacag gaaactttag caatgccatc agcaaaagcc aggccttctc tttgattctt    780
gcccaccaca tcatgggtgc cgggtttggc ttccataaca tcaaagatcc tgaccagaac    840
acatttgctg gcctggccag aagttcagtg agacacctgg atctttcaca tgggtttgtc    900
ttctccctga actcacgagt ctttgagaca ctcaaggatt tgaaggttct gaaccttgcc    960
tacaacaaga taaataagat tgcagatgaa gcattttacg gacttgacaa cctccaagtt   1020
ctcaatttgt catataacct tctgggggaa ctttacagtt cgaatttcta tggactacct   1080
aaggtagcct acattgattt gcaaaagaat cacattgcaa taattcaaga ccaaacattc   1140
aaattcctgg aaaaattaca gaccttggat ctccgagaca atgctcttac aaccattcat   1200
tttattccaa gcatacccga tatcttcttg agtggcaata aactagtgac tttgccaaag   1260
atcaaccta cagcgaacct catccactta tcagaaaaca ggctagaaaa tctagatatt   1320
ctctactttc tcctacgggt acctcatctc cagattctca tttaaatca aaatcgcttc   1380
tcctcctgta gtggagatca aaccccttca gagaatccca gcttagaaca gcttttcctt   1440
ggagaaaata tgttgcaact tgcctgggaa actgagctct gttgggatgt ttttgaggga   1500
ctttctcatc ttcaagttct gtatttgaat cataactatc ttaattccct tccaccagga   1560
gtatttagcc atctgactgc attaagggga ctaagcctca actccaacag gctgacagtt   1620
ctttctcaca atgatttacc tgctaattta gagatcctgg acatatccag gaaccagctc   1680
ctagctccta atcctgatgt atttgtatca cttagtgtct tggatataac tcataacaag   1740
ttcatttgtg aatgtgaact tagcactttt atcaattggc ttaatcacac caatgtcact   1800
atagctgggc ctcctgcaga catatattgt gtgtaccctg actcgttctc tggggtttcc   1860
ctcttctctc tttccacgga aggttgtgat gaagaggaag tcttaaagtc cctaaagttc   1920
tccctttca ttgtatgcac tgtcactctg actctgttcc tcatgaccat cctcacagtc   1980
acaaagttcc ggggcttctg ttttatctgt tataagacag cccagagact ggtgttcaag   2040
gaccatcccc agggcacaga acctgatatg tacaaatatg atgcctattt gtgcttcagc   2100
agcaaagact tcacatgggt gcagaatgct ttgctcaaac acctggacac tcaatacagt   2160
gaccaaaaca gattcaacct gtgctttgaa gaaagagact ttgtcccagg agaaaaccgc   2220
attgccaata tccaggatgc catctggaac agtagaaaga tcgtttgtct tgtgagcaga   2280
cacttcctta gagatggctg gtgccttgaa gccttcagtt atgcccaggg caggtgctta   2340
tctgacctta cagtgctctc tcatcatggt gtggttgggt ccttgtccca gtaccagttg   2400
atgaaacatc aatccatcag aggctttgta cagaaacagc agtatttgag gtggcctgag   2460
gatctccagg atgttggctg gtttcttcat aaactctctc aacagatact aagaaagaa   2520
aaagaaaaga agaagacaa taacattccg ttgcaaactg tagcaaccat ctcc          2574
```

<210> SEQ ID NO 115

<211> LENGTH: 2712
<212> TYPE: DNA
<213> ORGANISM: Homo sapiens
<220> FEATURE:
<223> OTHER INFORMATION: TLR3, isoform 1

<400> SEQUENCE: 115

| | |
|---|---:|
| atgagacaga ctttgccttg tatctacttt tgggggggcc ttttgccctt tgggatgctg | 60 |
| tgtgcatcct ccaccaccaa gtgcactgtt agccatgaag ttgctgactg cagccacctg | 120 |
| aagttgactc aggtacccga tgatctaccc acaaacataa cagtgttgaa ccttacccat | 180 |
| aatcaactca gaagattacc agccgccaac ttcacaaggt atagccagct aactagcttg | 240 |
| gatgtaggat ttaacaccat ctcaaaactg gagccagaat tgtgccagaa acttcccatg | 300 |
| ttaaaagttt tgaacctcca gcacaatgag ctatctcaac tttctgataa aaccttttgcc | 360 |
| ttctgcacga atttgactga actccatctc atgtccaact caatccagaa aattaaaaat | 420 |
| aatcccttg tcaagcagaa gaatttaatc acattagatc tgtctcataa tggcttgtca | 480 |
| tctacaaaat taggaactca ggttcagctg gaaaatctcc aagagcttct attatcaaac | 540 |
| aataaaattc aagcgctaaa aagtgaagaa ctggatatct ttgccaattc atctttaaaa | 600 |
| aaattagagt tgtcatcgaa tcaaattaaa gagttttctc agggtgttt tcacgcaatt | 660 |
| ggaagattat ttggcctctt tctgaacaat gtccagctgg gtcccagcct tacagagaag | 720 |
| ctatgtttgg aattagcaaa cacaagcatt cggaatctgt ctctgagtaa cagccagctg | 780 |
| tccaccacca gcaatacaac tttcttggga ctaaagtgga caaatctcac tatgctcgat | 840 |
| cttttcctaca caacttaaa tgtggttggt aacgattcct ttgcttggct tccacaacta | 900 |
| gaatatttct tcctagagta taataatata cagcatttgt tttctcactc tttgcacggg | 960 |
| cttttcaatg tgaggtacct gaatttgaaa cggtctttta ctaaacaaag tatttccctt | 1020 |
| gcctcactcc ccaagattga tgatttttct tttcagtggc taaaatgttt ggagcacctt | 1080 |
| aacatggaag ataatgatat tccaggcata aaaagcaata tgttcacagg attgataaac | 1140 |
| ctgaaatact taagtctatc caactccttt acaagtttgc gaactttgac aaatgaaaca | 1200 |
| tttgtatcac ttgctcattc tcccttacac atactcaacc taaccaagaa taaaatctca | 1260 |
| aaaatagaga gtgatgcttt ctcttggttg ggccacctag aagtacttga cctgggcctt | 1320 |
| aatgaaattg gcaagaact cacaggccag gaatggagag gtctagaaaa tattttcgaa | 1380 |
| atctatcttt cctacaacaa gtacctgcag ctgactagga actccttgc cttggtccca | 1440 |
| agccttcaac gactgatgct ccgaagggtg gcccttaaaa atgtggatag ctctccttca | 1500 |
| ccattccagc tcttcgtaa cttgaccatt ctggatctaa gcaacaacaa catagccaac | 1560 |
| ataaatgatg acatgttgga gggtcttgag aaactagaaa ttctcgattt gcagcataac | 1620 |
| aacttagcac ggctctggaa acacgcaaac cctggtggtc ccatttattt cctaaagggt | 1680 |
| ctgtctcacc tccacatcct taacttggag tccaacggct tgacgagat cccagttgag | 1740 |
| gtcttcaagg atttatttga actaaagatc atcgatttag gattgaataa tttaaacaca | 1800 |
| cttccagcat ctgtctttaa taatcaggtg tctctaaagt cattgaacct tcagaagaat | 1860 |
| ctcataacat ccgttgagaa gaaggttttc gggccagctt tcaggaacct gactgagtta | 1920 |
| gatatgcgct ttaatccctt tgattgcacg tgtgaaagta ttgcctggtt tgttaattgg | 1980 |
| attaacgaga cccataccaa catccctgag ctgtcaagcc actacctttg caacactcca | 2040 |
| cctcactatc atgggttccc agtgagactt tttgatacat catcttgcaa agacagtgcc | 2100 |
| ccctttgaac tcttttcat gatcaatacc agtatcctgt tgattttat ctttattgta | 2160 |

| | |
|---|---|
| cttctcatcc actttgaggg ctggaggata tcttttattt ggaatgtttc agtacatcga | 2220 |
| gttcttggtt tcaaagaaat agacagacag acagaacagt ttgaatatgc agcatatata | 2280 |
| attcatgcct ataaagataa ggattgggtc tgggaacatt tctcttcaat ggaaaaggaa | 2340 |
| gaccaatctc tcaaattttg tctgaagaa agggactttg aggcgggtgt ttttgaacta | 2400 |
| gaagcaattg ttaacagcat caaaagaagc agaaaatta ttttgttat aacacaccat | 2460 |
| ctattaaaag acccattatg caaaagattc aaggtacatc atgcagttca acaagctatt | 2520 |
| gaacaaaatc tggattccat tatattggtt tccttgagg agattccaga ttataaactg | 2580 |
| aaccatgcac tctgtttgcg aagaggaatg tttaaatctc actgcatctt gaactggcca | 2640 |
| gttcagaaag aacggatagg tgcctttcgt cataaattgc aagtagcact tggatccaaa | 2700 |
| aactctgtac at | 2712 |

<210> SEQ ID NO 116
<211> LENGTH: 3096
<212> TYPE: DNA
<213> ORGANISM: Homo sapiens
<220> FEATURE:
<223> OTHER INFORMATION: TLR9

<400> SEQUENCE: 116

| | |
|---|---|
| atgggttct gccgcagcgc cctgcacccg ctgtctctcc tggtgcaggc catcatgctg | 60 |
| gccatgaccc tggccctggg taccttgcct gccttcctac cctgtgagct ccagccccac | 120 |
| ggcctggtga actgcaactg gctgttcctg aagtctgtgc cccacttctc catggcagca | 180 |
| ccccgtggca atgtcaccag cctttccttg tcctccaacc gcatccacca cctccatgat | 240 |
| tctgactttg cccacctgcc cagcctgcgg catctcaacc tcaagtggaa ctgcccgccg | 300 |
| gttggcctca gccccatgca cttccctgc cacatgacca tcgagcccag caccttcttg | 360 |
| gctgtgccca ccctggaaga gctaaacctg agctacaaca acatcatgac tgtgcctgcg | 420 |
| ctgcccaaat ccctcatatc cctgtccctc agccatacca acatcctgat gctagactct | 480 |
| gccagcctcg ccggcctgca tgccctgcgc ttcctattca tggacggcaa ctgttattac | 540 |
| aagaacccct gcaggcaggc actggaggtg gccccgggtg ccctccttgg cctgggcaac | 600 |
| ctcacccacc tgtcactcaa gtacaacaac ctcactgtgg tgccccgcaa cctgccttcc | 660 |
| agcctggagt atctgctgtt gtcctacaac cgcatcgtca actggccgcc tgaggacctg | 720 |
| gccaatctga ccgccctgcg tgtgctcgat gtgggcggaa attgccgccg ctgcgaccac | 780 |
| gctcccaacc cctgcatgga gtgccctcgt cacttccccc agctacatcc cgataccttc | 840 |
| agccacctga gccgtcttga aggcctggtg ttgaaggaca gttctctctc ctggctgaat | 900 |
| gccagttggt tccgtgggct gggaaacctc cgagtgctgg acctgagtga aacttcctc | 960 |
| tacaaatgca tcactaaaac caaggccttc agggcctaa cacagctgcg caagcttaac | 1020 |
| ctgtccttca attaccaaaa agggtgtcc tttgccacc tgtctctggc cccttccttc | 1080 |
| gggagcctgg tcgccctgaa ggagctggac atgcacggca tcttcttccg ctcactcgat | 1140 |
| gagaccacgc tccggccact ggcccgcctg cccatgctcc agactctgcg tctgcagatg | 1200 |
| aacttcatca accaggccca gctcggcatc ttcagggcct ccctggcct gcgctacgtg | 1260 |
| gacctgtcgg acaaccgcat cagcggagct tcggagctga cagccaccat ggggaggca | 1320 |
| gatgagggg agaaggtctg gctgcagcct ggggaccttg ctccggcccc agtgacact | 1380 |
| cccagctctg aagacttcag gcccaactgc agcaccctca acttcacctt ggatctgtca | 1440 |

| | |
|---|---|
| cggaacaacc tggtgaccgt gcagccggag atgtttgccc agctctcgca cctgcagtgc | 1500 |
| ctgcgcctga gccacaactg catctcgcag gcagtcaatg gctcccagtt cctgccgctg | 1560 |
| accggtctgc aggtgctaga cctgtcccac aataagctgg acctctacca cgagcactca | 1620 |
| ttcacggagc taccgcgact ggaggccctg gacctcagct acaacagcca gcccttggc | 1680 |
| atgcagggcg tgggccacaa cttcagcttc gtggctcacc tgcgcaccct cgccacctc | 1740 |
| agcctggccc acaacaacat ccacagccaa gtgtcccagc agctctgcag tacgtcgctg | 1800 |
| cgggccctgg acttcagcgg caatgcactg gccatatgt gggccgaggg agacctctat | 1860 |
| ctgcacttct ccaaggcct gagcggtttg atctggctgg acttgtccca gaaccgcctg | 1920 |
| cacaccctcc tgccccaaac cctgcgcaac ctccccaaga gcctacaggt gctgcgtctc | 1980 |
| cgtgacaatt acctggcctt ctttaagtgg tggagcctcc acttcctgcc caaactggaa | 2040 |
| gtcctcgacc tggcaggaaa ccagctgaag gccctgacca atggcagcct gctgctggc | 2100 |
| acccggctcc ggaggctgga tgtcagctgc aacagcatca gcttcgtggc ccccggcttc | 2160 |
| ttttccaagg ccaaggagct gcgagagctc aaccttagcg ccaacgccct caagacagtg | 2220 |
| gaccactcct ggtttgggcc ctggcgagt gccctgcaaa tactagatgt aagcgccaac | 2280 |
| cctctgcact gcgcctgtgg ggcggccttt atggacttcc tgctggaggt gcaggctgcc | 2340 |
| gtgcccggtc tgcccagccg ggtgaagtgt ggcagtccgg ccagctcca gggcctcagc | 2400 |
| atctttgcac aggacctgcg cctctgcctg gatgaggccc tctcctggga ctgtttcgcc | 2460 |
| ctctcgctgc tggctgtggc tctgggcctg ggtgtgccca tgctgcatca cctctgtggc | 2520 |
| tgggacctct ggtactgctt ccacctgtgc ctggcctggc ttccctggcg ggggcggcaa | 2580 |
| agtgggcgag atgaggatgc cctgccctac gatgccttcg tggtcttcga caaaacgcag | 2640 |
| agcgcagtgg cagactgggt gtacaacgag cttcgggggc agctggagga gtgccgtggg | 2700 |
| cgctgggcac tccgcctgtg cctggaggaa cgcgactggc tgcctggcaa accctctttt | 2760 |
| gagaacctgt gggcctcggt ctatggcagc cgcaagacgc tgtttgtgct ggcccacacg | 2820 |
| gaccgggtca gtggtctctt gcgcgccagc ttcctgctgg cccagcagcg cctgctggag | 2880 |
| gaccgcaagg acgtcgtggt gctggtgatc ctgagccctg acggccgccg ctcccgctac | 2940 |
| gtgcggctgc gccagcgcct ctgccgccag agtgtcctcc tctggcccca ccagcccagt | 3000 |
| ggtcagcgca gcttcgggc ccagctgggc atggccctga ccagggacaa ccaccacttc | 3060 |
| tataaccgga acttctgcca gggacccacg gccgaa | 3096 |

<210> SEQ ID NO 117
<211> LENGTH: 3147
<212> TYPE: DNA
<213> ORGANISM: Homo sapiens
<220> FEATURE:
<223> OTHER INFORMATION: TLR7

<400> SEQUENCE: 117

| | |
|---|---|
| atggtgtttc caatgtggac actgaagaga caaattctta ccttttttaa cataatccta | 60 |
| atttccaaac tccttgggc tagatggttt cctaaaactc tgccctgtga tgtcactctg | 120 |
| gatgttccaa agaaccatgt gatcgtggac tgcacagaca gcattgac agaaattcct | 180 |
| ggaggtattc ccacgaacac cacgaacctc accctcacca ttaaccacat accagacatc | 240 |
| tccccagcgt cctttcacag actggaccat ctggtagaga tcgatttcag atgcaactgt | 300 |
| gtacctattc cactggggtc aaaaaacaac atgtgcatca gaggctgca gattaaaccc | 360 |
| agaagcttta gtggactcac ttatttaaaa tcccttttacc tggatggaaa ccagctacta | 420 |

```
gagataccgc agggcctccc gcctagctta cagcttctca gccttgaggc caacaacatc    480
ttttccatca gaaagagaaa tctaacagaa ctggccaaca tagaaatact ctacctgggc    540
caaaactgtt attatcgaaa tccttgttat gtttcatatt caatagagaa agatgccttc    600
ctaaacttga caaagttaaa agtgctctcc ctgaaagata caatgtcac agccgtccct     660 actgttttgc catctacttt aacagaacta tatctctaca caacatgat tgcaaaaatc     720 caagaagatg attttaataa cctcaaccaa ttacaaattc ttgacctaag tggaaattgc    780
cctcgttgtt ataatgcccc atttccttgt gcgccgtgta aaataattc tcccctacag     840 atccctgtaa atgcttttga tgcgctgaca gaattaaaag ttttacgtct acacagtaac    900
tctcttcagc atgtgccccc aagatggttt aagaacatca acaaactcca ggaactggat    960
ctgtcccaaa acttcttggc caagaaaatt ggggatgcta aatttctgca ttttctcccc   1020
agcctcatcc aattggatct gtctttcaat tttgaacttc aggtctatcg tgcatctatg   1080
aatctatcac aagcattttc ttcactgaaa agcctgaaaa ttctgcggat cagaggatat   1140
gtctttaaag agttgaaaag ctttaacctc tcgccattac ataatcttca aaatcttgaa   1200
gttcttgatc ttggcactaa ctttataaaa attgctaacc tcagcatgtt taaacaattt   1260
aaaagactga agtcataga tctttcagtg aataaaatat caccttcagg agattcaagt    1320
gaagttggct tctgctcaaa tgccagaact tctgtagaaa gttatgaacc ccaggtcctg   1380
gaacaattac attatttcag atatgataag tatgcaagga gttgcagatt caaaaacaaa   1440
gaggcttctt tcatgtctgt taatgaaagc tgctacaagt atgggcagac cttggatcta   1500
agtaaaaata gtatatttt tgtcaagtcc tctgattttc agcatctttc tttcctcaaa    1560
tgcctgaatc tgtcaggaaa tctcattagc caaactctta atggcagtga attccaacct   1620
ttagcagagc tgagatattt ggacttctcc aacaaccggc ttgatttact ccattcaaca   1680
gcatttgaag agcttcacaa actgaagtt ctggatataa gcagtaatag ccattatttt    1740
caatcagaag gaattactca tatgctaaac tttaccaaga acctaaaggt tctgcagaaa   1800
ctgatgatga cgacaatga catctcttcc tccaccagca ggaccatgga gagtgagtct    1860
cttagaactc tggaattcag aggaaatcac ttagatgttt tatggagaga aggtgataac   1920
agatacttac aattattcaa gaatctgcta aaattagagg aattagacat ctctaaaaat   1980
tccctaagtt tcttgccttc tggagttttt gatggtatgc ctccaaatct aaagaatctc   2040
tctttggcca aaaatgggct caaatctttc agttggaaga actccagtg tctaaagaac    2100 ctggaaactt tggacctcag ccacaaccaa ctgaccactg tccctgagag attatccaac   2160
tgttccagaa gcctcaagaa tctgattctt aagaataatc aaatcaggag tctgacgaag   2220
tattttctac aagatgcctt ccagttgcga tatctggatc tcagctcaaa taaaatccag   2280
atgatccaaa agaccagctt cccagaaaat gtcctcaaca atctgaagat gttgcttttg   2340
catcataatc ggtttctgtg cacctgtgat gctgtgtggt ttgtctggtg ggttaaccat   2400
acggaggtga ctattcctta cctggccaca gatgtgactt gtgtggggcc aggagcacac   2460
aagggccaaa gtgtgatctc cctggatctg tacacctgtg agttagatct gactaacctg   2520
attctgttct cactttccat atctgtatct ctctttctca tggtgatgat gacagcaagt   2580 caccctctatt tctgggatgt gtggtatatt taccatttct gtaaggccaa gataaagggg   2640
tatcagcgtc taatatcacc agactgttgc tatgatgctt ttattgtgta tgacactaaa   2700
gacccagctg tgaccgagtg ggttttggct gagctggtgg ccaaactgga agacccaaga   2760
```

-continued

```
gagaaacatt ttaatttatg tctcgaggaa agggactggt taccagggca gccagttctg   2820
gaaaaccttt cccagagcat acagcttagc aaaaagacag tgtttgtgat gacagacaag   2880
tatgcaaaga ctgaaaattt taagatagca ttttacttgt cccatcagag gctcatggat   2940
gaaaaagttg atgtgattat cttgatattt cttgagaagc cctttcagaa gtccaagttc   3000
ctccagctcc ggaaaaggct ctgtgggagt tctgtccttg agtggccaac aaacccgcaa   3060
gctcacccat acttctggca gtgtctaaag aacgccctgg ccacagacaa tcatgtggcc   3120
tatagtcagg tgttcaagga aacggtc                                      3147

<210> SEQ ID NO 118
<211> LENGTH: 3177
<212> TYPE: DNA
<213> ORGANISM: Homo sapiens
<220> FEATURE:
<223> OTHER INFORMATION: TLR8, isoform 1

<400> SEQUENCE: 118
atgaaggagt catctttgca aaatagctcc tgcagcctgg gaaaggagac taaaaaggaa     60
aacatgttcc ttcagtcgtc aatgctgacc tgcattttcc tgctaatatc tggttcctgt    120
gagttatgcg ccgaagaaaa tttttctaga agctatcctt gtgatgagaa aaagcaaaat    180
gactcagtta ttgcagagtg cagcaatcgt cgactacagg aagttcccca acggtgggc     240 aaatatgtga cagaactaga cctgtctgat aatttcatca cacacataac gaatgaatca    300
tttcaagggc tgcaaaatct cactaaaata aatctaaacc acaaccccaa tgtacagcac    360
cagaacggaa atcccggtat acaatcaaat ggcttgaata tcacagacgg ggcattcctc    420
aacctaaaaa acctaaggga gttactgctt gaagacaacc agttacccca aatacctctc    480
ggtttgccag agtctttgac agaacttagt ctaattcaaa acaatatata caacataact    540
aaagagggca tttcaagact tataaacttg aaaaatctct atttggcctg aactgctat    600 tttaacaaag tttgcgagaa aactaacata gaagatggag tatttgaaac gctgacaaat    660
ttggagttgc tatcactatc tttcaattct cttttcacacg tgccacccaa actgccaagc    720
tccctacgca aacttttttct gagcaacacc cagatcaaat acattagtga agaagatttc    780
aagggattga taaatttaac attactagat ttaagcggga actgtccgag gtgcttcaat    840
gccccatttc catgcgtgcc ttgtgatggt ggtgcttcaa ttaatataga tcgttttgct    900
tttcaaaact tgacccaact tcgatacccta aacctctcta gcacttccct caggaagatt    960
aatgctgcct ggtttaaaaa tatgcctcat ctgaaggtgc tggatcttga attcaactat   1020
ttagtgggag aaatagcctc tgggcatttt ttaacgatgc tgccccgctt agaaatactt   1080
gacttgtctt ttaactatat aaaggggagt tatccacagc atattaatat tccagaaaac   1140
ttctctaaac ttttgtctct acgggcattg catttaagag gttatgtgtt ccaggaactc   1200
agagaagatg atttccagcc cctgatgcag cttccaaact tatcgactat caacttgggt   1260 attaattta ttaagcaaat cgatttcaaa cttttccaaa atttctccaa tctggaaatt   1320
atttacttgt cagaaaacag aatatcaccg ttggtaaaag atacccggca gagttatgca   1380
aatagttcct cttttcaacg tcatatccgg aaacgacgct caacagattt tgagtttgac   1440
ccacattcga actttttatca tttcacccgt cctttaataa agccacaatg tgctgcttat   1500
ggaaaagcct tagatttaag cctcaacagt attttcttca ttgggccaaa ccaatttgaa   1560
aatcttcctg acattgcctg tttaaatctg tctgcaaata gcaatgctca agtgttaagt   1620
ggaactgaat tttcagccat tcctcatgtc aaatatttgg atttgacaaa caatagacta   1680
```

```
gactttgata atgctagtgc tcttactgaa ttgtccgact tggaagttct agatctcagc    1740
tataattcac actatttcag aatagcaggc gtaacacatc atctagaatt tattcaaaat    1800
ttcacaaatc taaaagtttt aaacttgagc cacaacaaca tttatacttt aacagataag    1860
tataacctgg aaagcaagtc cctggtgaaa ttagttttca gtggcaatcg ccttgacatt    1920
ttgtggaatg atgatgacaa caggtatatc tccattttca aaggtctcaa gaatctgaca    1980
cgtctggatt tatcccttaa taggctgaag cacatcccaa tgaagcatt ccttaatttg     2040 ccagcgagtc tcactgaact acatataaat gataatatgt taaagttttt taactggaca    2100
ttactccagc agtttcctcg tctcgagttg cttgacttac gtggaaacaa actactcttt    2160
ttaactgata gcctatctga ctttacatct tcccttcgga cactgctgct gagtcataac    2220
aggatttccc acctaccctc tggctttctt tctgaagtca gtagtctgaa gcacctcgat    2280
ttaagttcca atctgctaaa acaatcaac aaatccgcac ttgaaactaa gaccaccacc     2340
aaattatcta tgttggaact acacggaaac cccttttgaat gcacctgtga cattggagat    2400
ttccgaagat ggatggatga acatctgaat gtcaaaattc ccagactggt agatgtcatt    2460
tgtgccagtc ctggggatca agagggaag agtattgtga gtctggagct aacaacttgt    2520
gtttcagatg tcactgcagt gatattattt ttcttcacgt tctttatcac caccatggtt    2580 atgtggctg ccctggctca ccatttgttt tactgggatg tttggtttat atataatgtg     2640
tgtttagcta aggtaaaagg ctacaggtct cttttccacat cccaaacttt ctatgatgct    2700
tacatttctt atgacaccaa agatgcctct gttactgact gggtgataaa tgagctgcgc    2760
taccaccttg aagagagccg agacaaaaac gttctccttt gtctagagga gagggattgg    2820
gacccgggat tggccatcat cgacaacctc atgcagagca tcaaccaaag caagaaaaca    2880
gtatttgttt taaccaaaaa atatgcaaaa agctggaact ttaaaacagc ttttttacttg   2940 gctttgcaga ggctaatgga tgagaacatg atgtgattta tatttatcct gctggagcca    3000
gtgttacagc attctcagta tttgaggcta cggcagcgga tctgtaagag ctccatcctc    3060
cagtggcctg acaacccgaa ggcagaaggc ttgttttggc aaactctgag aaatgtggtc    3120
ttgactgaaa atgattcacg gtataacaat atgtatgtcg attccattaa gcaatac       3177
```

<210> SEQ ID NO 119
<211> LENGTH: 636
<212> TYPE: DNA
<213> ORGANISM: Homo sapiens
<220> FEATURE:
<223> OTHER INFORMATION: Interleukin 6 (IL-6)

<400> SEQUENCE: 119

```
atgaactcct ctccacaag cgccttcggt ccagttgcct tctccctggg gctgctcctg       60
gtgttgcctg ctgccttccc tgccccagta cccccaggag aagattccaa agatgtagcc    120
gccccacaca gacagccact cacctcttca gaacgaattg acaaacaaat tcggtacatc    180
ctcgacggca tctcagccct gagaaaggag acatgtaaca agagtaacat gtgtgaaagc    240
agcaaagagg cactggcaga aaacaacctg aaccttccaa agatggctga aaagatgga    300 tgcttccaat ctggattcaa tgaggagact tgcctggtga aatcatcac tggtcttttg     360 gagtttgagg tatacctaga gtacctccag aacagatttg agtagtgag gaacaagcc      420 agagctgtgc agatgagtac aaaagtcctg atccagttcc tgcagaaaaa ggcaagaat    480 ctagatgcaa taaccacccc tgacccaacc acaaatgcca gcctgctgac gaagctgcag    540
```

```
gcacagaacc agtggctgca ggacatgaca actcatctca ttctgcgcag ctttaaggag      600
ttcctgcagt ccagcctgag ggctcttcgg caaatg                               636
```

<210> SEQ ID NO 120
<211> LENGTH: 951
<212> TYPE: DNA
<213> ORGANISM: Homo sapiens
<220> FEATURE:
<223> OTHER INFORMATION: MyD88, isoform 1

<400> SEQUENCE: 120

```
atgcgacccg accgcgctga ggctccagga ccgcccgcca tggctgcagg aggtcccggc       60
gcggggtctg cggccccggt ctcctccaca tcctcccttc ccctggctgc tctcaacatg      120
cgagtgcggc gccgcctgtc tctgttcttg aacgtgcgga cacaggtggc ggccgactgg      180
accgcgctgg cggaggagat ggactttgag tacttggaga tccggcaact ggagacacaa      240
gcggacccca ctggcaggct gctggacgcc tggcagggac gccctggcgc ctctgtaggc      300
cgactgctcg agctgcttac caagctgggc gcgcgacgacg tgctgctgga gctgggaccc      360
agcattgagg aggattgcca aaagtatatc ttgaagcagc agcaggagga ggctgagaag      420
cctttacagg tggccgctgt agacagcagt gtcccacgga cagcagagct ggcgggcatc      480
accacacttg atgacccccct ggggcatatg cctgagcgtt tcgatgcctt catctgctat      540
tgccccagcg acatccagtt tgtgcaggag atgatccggc aactgaaaca gacaaactat      600
cgactgaagt tgtgtgtgtc tgaccgcgat gtcctgcctg gcacctgtgt ctggtctatt      660
gctagtgagc tcatcgaaaa gaggttggct agaaggccac ggggtgggtg ccgccggatg      720
gtggtggttg tctctgatga ttacctgcag agcaaggaat gtgacttcca gaccaaattt      780
gcactcagcc tctctccagg tgcccatcag aagcgactga tccccatcaa gtacaaggca      840
atgaagaaag agttccccag catcctgagg ttcatcactg tctgcgacta caccaacccc      900
tgcaccaaat cttggttctg gactcgcctt gccaaggcct tgtccctgcc c              951
```

<210> SEQ ID NO 121
<211> LENGTH: 807
<212> TYPE: DNA
<213> ORGANISM: Homo sapiens
<220> FEATURE:
<223> OTHER INFORMATION: Interleukin 1-beta (IL-1beta)

<400> SEQUENCE: 121

```
atggcagaag tacctgagct cgccagtgaa atgatggctt attacagtgg caatgaggat       60
gacttgttct ttgaagctga tggccctaaa cagatgaagt gctccttcca ggacctggac      120
ctctgccctc tggatggcgg catccagcta cgaatctccg accaccacta cagcaagggc      180
ttcaggcagg ccgcgtcagt tgttgtggcc atggacaagc tgaggaagat gctggttccc      240
tgcccacaga ccttccagga gaatgacctg agcaccttct ttcccttcat ctttgaagaa      300
gaacctatct tcttcgacac atgggataac gaggcttatg tgcacgatgc acctgtacga      360
tcactgaact gcacgctccg ggactcacag caaaaaagct ggtgatgtc tggtccatat      420 gaactgaaag ctctccacct ccagggcag gatatggage acaagtggt gttctccatg      480 tcctttgtac aaggagaaga agtaatgac aaaatacctg tggccttggg cctcaaggaa      540 agaatctgt acctgtcctg cgtgttgaaa gatgataagc ccactctaca gctggagagt      600
gtagatccca aaaattaccc aaagaagaag atggaaaagc gatttgtctt caacaagata      660
gaaatcaata caagctgga atttgagtct gcccagttcc ccaactggta catcagcacc      720
```

| | |
|---|---:|
| tctcaagcag aaaacatgcc cgtcttcctg ggagggacca aaggcggcca ggatataact | 780 |
| gacttcacca tgcaatttgt gtcttcc | 807 |

<210> SEQ ID NO 122
<211> LENGTH: 3075
<212> TYPE: DNA
<213> ORGANISM: Homo sapiens
<220> FEATURE:
<223> OTHER INFORMATION: MDA5/IFIH1, isoform 1

<400> SEQUENCE: 122

| | |
|---|---:|
| atgtcgaatg ggtattccac agacgagaat ttccgctatc tcatctcgtg cttcagggcc | 60 |
| agggtgaaaa tgtacatcca ggtggagcct gtgctggact acctgacctt tctgcctgca | 120 |
| gaggtgaagg agcagattca gaggacagtc gccacctccg gaacatgca ggcagttgaa | 180 |
| ctgctgctga gcaccttgga aagggagtc tggcaccttg gttggactcg ggaattcgtg | 240 |
| gaggccctcc ggagaaccgg cagccctctg gccgcccgct acatgaaccc tgagctcacg | 300 |
| gacttgccct ctccatcgtt tgagaacgct catgatgaat atctccaact gctgaacctc | 360 |
| cttcagccca ctctggtgga caagcttcta gttagacg tcttggataa gtgcatggag | 420 |
| gaggaactgt tgacaattga agacagaaac cggattgctg ctgcagaaaa caatggaaat | 480 |
| gaatcaggtg taagagagct actaaaaagg attgtgcaga agaaaactg gttctctgca | 540 |
| tttctgaatg ttcttcgtca aacaggaaac aatgaacttg tccaagagtt aacaggctct | 600 |
| gattgctcag aaagcaatgc agagattgag aatttatcac aagttgatgg tcctcaagtg | 660 |
| gaagagcaac ttctttcaac cacagttcag ccaaatctgg agaaggaggt ctggggcatg | 720 |
| gagaataact catcagaatc atcttttgca gattcttctg tagtttcaga atcagacaca | 780 |
| agtttggcag aaggaagtgt cagctgctta gatgaaagtc ttggacataa cagcaacatg | 840 |
| ggcagtgatt caggcaccat gggaagtgat tcagatgaag agaatgtggc agcaagagca | 900 |
| tccccggagc cagaactcca gctcaggcct taccaaatgg aagttgccca gccagccttg | 960 |
| gaagggaaga atatcatcat ctgcctccct acagggagtg gaaaaaccag agtggctgtt | 1020 |
| tacattgcca aggatcactt agacaagaag aaaaaagcat ctgagcctgg aaaagttata | 1080 |
| gttcttgtca ataaggtact gctagttgaa cagctcttcc gcaaggagtt ccaaccattt | 1140 |
| ttgaagaaat ggtatcgtgt tattggatta agtggtgata cccaactgaa atatcattt | 1200 |
| ccagaagttg tcaagtcctg tgatattatt atcagtacag ctcaaatcct tgaaaactcc | 1260 |
| ctcttaaact tggaaaatgg agaagatgct ggtgttcaat gtcagactt ttccctcatt | 1320 |
| atcattgatg aatgtcatca caccaacaaa gaagcagtgt ataataacat catgaggcat | 1380 |
| tatttgatgc agaagttgaa aaacaataga ctcaagaaag aaaacaaacc agtgattccc | 1440 |
| cttcctcaga tactgggact aacagcttca cctggtgttg gaggggccac gaagcaagcc | 1500 |
| aaagctgaag aacacatttt aaaactatgt gccaatcttg atgcatttac tattaaaact | 1560 |
| gttaaagaaa accttgatca actgaaaaac caaatacagg agccatgcaa gaagtttgcc | 1620 |
| attgcagatg caaccagaga agatccattt aagagaaac ttctagaaat aatgacaagg | 1680 |
| attcaaactt attgtcaaat gagtccaatg tcagattttg aactcaacc ctatgaacaa | 1740 |
| tgggccattc aaatggaaaa aaagctgca aagaaggaa atcgcaaaga acgtgtttgt | 1800 |
| gcagaacatt tgaggaagta caatgaggcc tacaaaatta tgacacaat tcgaatgata | 1860 |
| gatgcgtata ctcatcttga aactttctat aatgaagaga agataagaa gtttgcagtc | 1920 |

-continued

| | |
|---|---|
| atagaagatg atagtgatga gggtggtgat gatgagtatt gtgatggtga tgaagatgag | 1980 |
| gatgatttaa agaaaccttt gaaactggat gaaacagata gatttctcat gactttattt | 2040 |
| tttgaaaaca ataaaatgtt gaaaaggctg gctgaaaacc cagaatatga aaatgaaaag | 2100 |
| ctgaccaaat taagaaatac cataatggag caatatacta ggactgagga atcagcacga | 2160 |
| ggataatct ttacaaaaac acgacagagt gcatatgcgc tttcccagtg gattactgaa | 2220 |
| aatgaaaaat ttgctgaagt aggagtcaaa gcccaccatc tgattggagc tggacacagc | 2280 |
| agtgagttca aacccatgac acagaatgaa caaaagaag tcattagtaa atttcgcact | 2340 |
| ggaaaaataa atctgcttat cgctaccaca gtggcagaag aaggtctgga tattaaagaa | 2400 |
| tgtaacattg ttatccgtta tggtctcgtc accaatgaaa tagccatggt ccaggcccgt | 2460 |
| ggtcgagcca gagctgatga gagcacctac gtcctggttg ctcacagtgg ttcaggagtt | 2520 |
| atcgaacatg agacagttaa tgatttccga gagaagatga tgtataaagc tatacattgt | 2580 |
| gttcaaaata tgaaaccaga ggagtatgct cataagattt tggaattaca gatgcaaagt | 2640 |
| ataatggaaa agaaaatgaa aaccaagaga aatattgcca agcattacaa gaataaccca | 2700 |
| tcactaataa ctttcctttg caaaaactgc agtgtgctag cctgttctgg ggaagatatc | 2760 |
| catgtaattg agaaaatgca tcacgtcaat atgaccccag aattcaagga actttacatt | 2820 |
| gtaagagaaa acaaagcact gcaaaagaag tgtgccgact atcaaataaa tggtgaaatc | 2880 |
| atctgcaaat gtggccaggc ttggggaaca atgatggtgc acaaaggctt agatttgcct | 2940 |
| tgtctcaaaa taaggaattt tgtagtggtt ttcaaaaata attcaacaaa gaaacaatac | 3000 |
| aaaaagtggg tagaattacc tatcacattt cccaatcttg actattcaga atgctgttta | 3060 |
| tttagtgatg aggat | 3075 |

<210> SEQ ID NO 123
<211> LENGTH: 1620
<212> TYPE: DNA
<213> ORGANISM: Homo sapiens
<220> FEATURE:
<223> OTHER INFORMATION: IPS-1/MAVS, isoform 1

<400> SEQUENCE: 123

| | |
|---|---|
| atgccgtttg ctgaagacaa gacctataag tatatctgcc gcaatttcag caattttgc | 60 |
| aatgtggatt tgtagagat tctgccttac ctgccctgcc tcacagcaag agaccaggat | 120 |
| cgactgcggg ccacctgcac actctcaggg aaccgggaca ccctctggca tctcttcaat | 180 |
| acccttcagc ggcggcccgg ctgggtggag tacttcattg cggcactgag gggctgtgag | 240 |
| ctagttgatc tcgcggacga agtggcctct gtctaccaga gctaccagcc tcggacctcg | 300 |
| gaccgtcccc cagacccact ggagccaccg tcacttcctg ctgagaggcc agggccccc | 360 |
| acacctgctg cggcccacag catccctac aacagctgca gagagaagga gccaagttac | 420 |
| cccatgcctg tccaggagac ccaggcgcca gagtccccag gagagaattc agagcaagcc | 480 |
| ctgcagacgc tcagccccag agccatccca aggaatccag atggtggccc ctggagtcc | 540 |
| tcctctgacc tggcagccct cagccctctg acctccagcg ggcatcagga gcaggacaca | 600 |
| gaactgggca gtaccacac agcaggtgcg acctccagcc tcacaccatc ccgtgggcct | 660 |
| gtgtctccat ctgtctcctt ccagcccctg gcccgttcca ccccaggggc aagccgcttg | 720 |
| cctggaccca gggtcagt tgtatctact ggcacctcct tctcctcctc atcccctggc | 780 |
| ttggcctctg caggggctgc agagggtaaa cagggtgcag agagtgacca ggccgagcct | 840 |
| atcatctgct ccagtggggc agaggcacct gccaactctc tgcctccaa agtgcctacc | 900 |

```
accttgatgc ctgtgaacac agtggccctg aaagtgcctg ccaacccagc atctgtcagc    960
acagtgccct ccaagttgcc aactagctca agcccctg gtgcagtgcc ttctaatgcg    1020
ctcaccaatc cagcaccatc caaattgccc atcaactcaa cccgtgctgg catggtgcca   1080
tccaaagtgc ctactagcat ggtgctcacc aaggtgtctg ccagcacagt ccccactgac   1140
gggagcagca gaaatgagga accccagca gctccaacac ccgccggcgc cactggaggc    1200
agctcagcct ggctagacag cagctctgag aataggggcc ttgggtcgga gctgagtaag   1260
cctggcgtgc tggcatccca ggtagacagc ccgttctcgg gctgcttcga ggatcttgcc   1320
atcagtgcca gcacctcctt gggcatgggg ccctgccatg cccagagga gaatgagtat    1380
aagtccgagg cacctttgg gatccacgtg gctgagaacc ccagcatcca gctcctggag    1440
ggcaaccctg gccacctgc ggacccggat ggcggcccca ggccacaagc cgaccggaag    1500
ttccaggaga gggaggtgcc atgccacagg ccctcacctg gggctctgtg gctccaggtg   1560
gctgtgacag gggtgctggt agtcacactc ctggtggtgc tgtaccggcg cgtctgcac    1620
```

<210> SEQ ID NO 124
<211> LENGTH: 2775
<212> TYPE: DNA
<213> ORGANISM: Homo sapiens
<220> FEATURE:
<223> OTHER INFORMATION: RIG-1/DDX58, isoform 1

<400> SEQUENCE: 124

```
atgaccaccg agcagcgacg cagcctgcaa gccttccagg attatatccg gaagaccctg     60
gaccctacct acatcctgag ctacatggcc cctggtttta gggaggaaga ggtgcagtat    120
attcaggctg agaaaaacaa caagggccca atggaggctg ccacacttt tctcaagttc    180
ctgttggagc tccaggagga aggctggttc cgtggctttt tggatgccct agaccatgca    240
ggttattctg gactttatga agccattgaa agttgggatt tcaaaaaaat tgaaaagttg    300
gaggagtata gattacttt aaaacgttta caaccagaat ttaaaaccag aattatccca    360
accgatatca tttctgatct gtctgaatgt taattaatc aggaatgtga agaaattcta    420
cagatttgct ctactaaggg gatgatgca ggtgcagaga aattggtgga atgccttctc    480
agatcagaca aggaaaactg gcccaaaact ttgaaacttg ctttggagaa agaaaggaac    540
aagttcagtg aactgtggat tgtagagaaa ggtataaaag atgttgaaac agaagatctt    600
gaggataaga tggaaacttc tgacatacag atttctacc aagaagatcc agaatgccag    660
aatcttagtg agaattcatg tccaccttca gaagtgtctg atacaaactt gtacagccca    720
tttaaaccaa gaaattacca attagagctt gctttgcctg ctatgaaagg aaaaacaca    780
ataatatgtg ctcctacagg ttgtggaaaa acctttgttt cactgcttat atgtgaacat    840
catcttaaaa aattcccaca aggacaaaag gggaagttg ttctttttgc gaatcagatc    900
ccagtgtatg aacagcagaa atctgtattc tcaaaatact ttgaaagaca tgggtataga    960
gttacaggca ttctggagc aacagctgag aatgtcccag tggaacagat tgttgagaac   1020
aatgacatca tcatttaac tccacagatt cttgtgaaca accttaaaaa gggaacgatt    1080
ccatcactat ccatctttac tttgatgata tttgatgaat gccacaacac tagtaaacaa    1140
cacccgtaca atatgatcat gtttaattat ctagatcaga aacttggagg atcttcaggc    1200
ccactgcccc aggtcattgg gctgactgcc tcggttggtg ttggggatgc caaaaacaca    1260
gatgaagcct tggattatat ctgcaagctg tgtgcttctc ttgatgcgtc agtgatagca    1320
```

| | |
|---|---|
| acagtcaaac acaatctgga ggaactggag caagttgttt ataagcccca gaagttttc | 1380 |
| aggaaagtgg aatcacggat tagcgacaaa tttaaataca tcatagctca gctgatgagg | 1440 |
| gacacagaga gtctggcaaa gagaatctgc aaagacctcg aaaacttatc tcaaattcaa | 1500 |
| aatagggaat ttggaacaca gaaatatgaa caatggattg ttacagttca gaaagcatgc | 1560 |
| atggtgttcc agatgccaga caaagatgaa gagagcagga tttgtaaagc cctgttttta | 1620 |
| tacacttcac atttgcggaa atataatgat gccctcatta tcagtgagca tgcacgaatg | 1680 |
| aaagatgctc tggattactt gaaagacttc ttcagcaatg tccgagcagc aggattcgat | 1740 |
| gagattgagc aagatcttac tcagagattt gaagaaaagc tgcaggaact agaaagtgtt | 1800 |
| tccagggatc ccagcaatga gaatcctaaa cttgaagacc tctgcttcat cttacaagaa | 1860 |
| gagtaccact taaacccaga gacaataaca attctctttg tgaaaaccag agcacttgtg | 1920 |
| gacgctttaa aaaattggat tgaaggaaat cctaaactca gttttctaaa acctggcata | 1980 |
| ttgactggac gtggcaaaac aaatcagaac acaggaatga ccctcccggc acagaagtgt | 2040 |
| atattggatg cattcaaagc cagtggagat cacaatattc tgattgccac ctcagttgct | 2100 |
| gatgaaggca ttgacattgc acagtgcaat cttgtcatcc tttatgagta tgtgggcaat | 2160 |
| gtcatcaaaa tgatccaaac cagaggcaga ggaagagcaa gaggtagcaa gtgcttcctt | 2220 |
| ctgactagta atgctggtgt aattgaaaaa gaacaaataa acatgtacaa agaaaaaatg | 2280 |
| atgaatgact ctattttacg ccttcagaca tgggacgaag cagtatttag ggaaaagatt | 2340 |
| ctgcatatac agactcatga aaaattcatc agagatagtc aagaaaaacc aaaacctgta | 2400 |
| cctgataagg aaaataaaaa actgctctgc agaaagtgca aagccttggc atgttacaca | 2460 |
| gctgacgtaa gagtgataga ggaatgccat tacactgtgc ttggagatgc ttttaaggaa | 2520 |
| tgctttgtga gtagaccaca tcccaagcca agcagttttt caagttttga aaaaagagca | 2580 |
| aagatattct gtgcccgaca gaactgcagc catgactggg gaatccatgt gaagtacaag | 2640 |
| acatttgaga ttccagttat aaaaattgaa agttttgtgg tggaggatat tgcaactgga | 2700 |
| gttcagacac tgtactcgaa gtggaaggac tttcattttg agaagatacc atttgatcca | 2760 |
| gcagaaatgt ccaaa | 2775 |

<210> SEQ ID NO 125
<211> LENGTH: 1494
<212> TYPE: DNA
<213> ORGANISM: Homo sapiens
<220> FEATURE:
<223> OTHER INFORMATION: IRF5, transcript variant 2

<400> SEQUENCE: 125

| | |
|---|---|
| atgaaccagt ccatcccagt ggctcccacc ccaccccgcc gcgtgcggct gaagccctgg | 60 |
| ctggtggccc aggtgaacag ctgccagtac ccagggcttc aatgggtcaa cggggaaaag | 120 |
| aaattattct gcatcccctg gaggcatgcc acaaggcatg gtcccagcca ggacggagat | 180 |
| aacaccatct tcaaggcctg gccaaggag acagggaaat acaccgaagg cgtggatgaa | 240 |
| gccgatccgg ccaagtggaa ggccaacctg cgctgtgccc ttaacaagag ccgggacttc | 300 |
| cgcctcatct acgacgggcc ccgggacatg ccacctcagc cctacaagat ctacgaggtc | 360 |
| tgctccaatg ccctgctcc acagactcc cagcccctg aggattactc ttttggtgca | 420 |
| ggagaggagg aggaagaaga ggaagagctg cagaggatgt tgccaagcct gagcctcaca | 480 |
| gaggatgtca gtggccgcc cactctgcag ccgcccactc tgcggccgcc tactctgcag | 540 |
| ccgcccactc tgcagccgcc cgtggtgctg ggtccccctg ctccagaccc cagccccctg | 600 |

```
gctcctcccc ctggcaaccc tgctggcttc agggagcttc tctctgaggt cctggagcct      660
gggcccctgc ctgccagcct gccccctgca ggcgaacagc tcctgccaga cctgctgatc      720 agccccaca tgctgcctct gaccgacctg gagatcaagt ttcagtaccg ggggcggcca       780
ccccgggccc tcaccatcag caaccccat ggctgccggc tcttctacag ccagctggag       840
gccacccagg agcaggtgga actcttcggc cccataagcc tggagcaagt gcgcttcccc     900
agccctgagg acatccccag tgacaagcag cgcttctaca cgaaccagct gctggatgtc     960
ctggaccgcg ggctcatcct ccagctacag ggccaggacc tttatgccat ccgcctgtgt    1020
cagtgcaagg tgttctggag cgggccttgt gcctcagccc atgactcatg ccccaacccc   1080
atccagcggg aggtcaagac caagcttttc agcctggagc attttctcaa tgagctcatc   1140
ctgttccaaa agggccagac caacaccca ccacccttcg agatcttctt ctgctttggg    1200
gaagaatggc ctgaccgcaa accccgagag aagaagctca ttactgtaca ggtggtgcct   1260
gtagcagctc gactgctgct ggagatgttc tcagggagc tatcttggtc agctgatagt     1320
atccggctac agatctcaaa cccagacctc aaagaccgca tggtggagca attcaaggag   1380
ctccatcaca tctggcagtc ccagcagcgg ttgcagcctg tggcccaggc ccctcctgga    1440
gcaggccttg gtgttggcca ggggccctgg cctatgcacc cagctggcat gcaa          1494
```

<210> SEQ ID NO 126
<211> LENGTH: 1284
<212> TYPE: DNA
<213> ORGANISM: Homo sapiens
<220> FEATURE:
<223> OTHER INFORMATION: IRF3/TBK1, isoform 1

<400> SEQUENCE: 126

```
accatgggaa ccccaaagcc acggatcctg ccctggctgg tgtcgcagct ggacctgggg       60
caactggagg gcgtggcctg ggtgaacaag agccgcacgc gcttccgcat cccttggaag      120
cacggcctac ggcaggatgc acagcaggag gatttcggaa tcttccaggc ctgggccgag     180
gccactggtg catatgttcc cgggagggat aagccagacc tgccaacctg gaagaggaat     240
ttccgctctg ccctcaaccg caaagaaggg ttgcgtttag cagaggaccg gagcaaggac     300
cctcacgacc cacataaaat ctacgagttt gtgaactcag gagttgggga cttttcccag     360
ccagacacct ctccggacac caatggtgga ggcagtactt ctgatacca ggaagacatt      420 ctggatgagt tactgggtaa catggtgttg gccccactcc cagatccggg acccccaagc    480
ctggctgtag cccctgagcc ctgccctcag ccctgcgga gccccagctt ggacaatccc     540
actcccttcc caaacctggg gccctctgag aacccactga gcggctgtt ggtgccgggg     600 gaagagtggg agttcgaggt gacagccttc taccggggcc gccaagtctt ccagcagacc    660
atctcctgcc cggagggcct gcggctggtg gggtccgaag tgggagacag gacgctgcct    720
ggatggccag tcacactgcc agaccctggc atgtccctga cagacagggg agtgatgagc    780
tacgtgaggc atgtgctgag ctgcctgggt gggggactgg ctctctggcg ggccgggcag    840
tggctctggg cccagcggct ggggcactgc cacacatact gggcagtgag cgaggagctg    900
ctccccaaca gcgggcatgg gcctgatggc gaggtcccca ggacaaggaa ggaggcgtg    960 tttgacctgg ggcccttcat tgtagatctg attaccttca cggaaggaag cggacgctca   1020
ccacgctatg ccctctggtt ctgtgtgggg gagtcatggc cccaggacca gccgtggacc   1080
aagaggctcg tgatggtcaa ggttgtgccc acgtgcctca gggccttggt agaaatggcc   1140
```

| | |
|---|---|
| cgggtaggggg gtgcctcctc cctggagaat actgtggacc tgcacatttc aacagccac | 1200 |
| ccactctccc tcacctccga ccagtacaag gcctacctgc aggacttggt ggagggcatg | 1260 |
| gatttccagg gccctgggga gagc | 1284 |

<210> SEQ ID NO 127
<211> LENGTH: 1275
<212> TYPE: DNA
<213> ORGANISM: Homo sapiens
<220> FEATURE:
<223> OTHER INFORMATION: TANK

<400> SEQUENCE: 127

| | |
|---|---|
| atggataaaa acattggcga gcaactcaat aaagcgtatg aagccttccg gcaggcatgc | 60 |
| atggatagag attctgcagt aaaagaatta cagcaaaaga ctgagaacta tgagcagaga | 120 |
| atacgtgaac aacaggaaca gctgtcactt caacagacta ttattgacaa gctaaaatct | 180 |
| cagttacttc ttgtgaattc cactcaagat aacaattatg ctgtgttcc tctgcttgaa | 240 |
| gacagtgaaa caagaaagaa taatttgact cttgatcagc acaagataa agtgatttca | 300 |
| ggaatagcaa gagaaaaact accaaaggta agaagacaag aggtttcttc tcctagaaaa | 360 |
| gaaacttcag caaggagtct tggcagtcct ttgctccatg aaagggggtaa tatagagaag | 420 |
| actttctggg atctgaaaga agaatttcat aaaatatgca tgctagcaaa agcacagaaa | 480 |
| gaccacttaa gcaaacttaa tataccagac actgcaactg aaacacagtg ctctgtgcct | 540 |
| atacagtgta cggataaaac agataaacaa gaagcgctgt ttaagcctca ggctaaagat | 600 |
| gatataaata gaggtgcacc atccatcaca tctgtcacac caagaggact gtgcagagat | 660 |
| gaggaagaca cctcttttga atcactttct aaattcaatg tcaagtttcc acctatggac | 720 |
| aatgactcaa ctttcttaca tagcactcca gagagacccg gcatccttag tcctgccacg | 780 |
| tctgaggcag tgtgccaaga gaaatttaat atggagttca gagacaaccc agggaacttt | 840 |
| gttaaaacag aagaaacttt atttgaaatt caggaattg accccatagc ttcagctata | 900 |
| caaaaccta aaacaactga caaaacaaag ccctcaaatc tcgtaaacac ttgtatcagg | 960 |
| acaactctgg atagagctgc gtgtttgcca cctggagacc ataatgcatt atatgtaaat | 1020 |
| agcttcccac ttctggaccc atctgatgca ccttttccct cactcgattc cccgggaaaa | 1080 |
| gcaatccgag gaccacagca gcccatttgg aagcccttc ctaatcaaga cagtgactcg | 1140 |
| gtggtactaa gtggcacaga ctcagaactg catataccctc gagtatgtga attctgtcaa | 1200 |
| gcagttttcc caccatccat tacatccagg ggggatttcc ttcggcatct taattcacac | 1260 |
| ttcaatggag agact | 1275 |

<210> SEQ ID NO 128
<211> LENGTH: 2136
<212> TYPE: DNA
<213> ORGANISM: Homo sapiens
<220> FEATURE:
<223> OTHER INFORMATION: TRIF/TICAM1

<400> SEQUENCE: 128

| | |
|---|---|
| atggcctgca caggcccatc acttcctagc gccttcgaca ttctaggtgc agcaggccag | 60 |
| gacaagctct tgtatctgaa gcacaaactg aagaccccac gcccaggctg ccaggggcag | 120 |
| gacctcctgc atgccatggt tctcctgaag ctgggccagg aaactgaggc caggatctct | 180 |
| ctagaggcat tgaaggccga tgcggtggcc cggctggtgg cccgccagtg ggctggcgtg | 240 |
| gacagcaccg aggacccaga ggagccccca gatgtgtcct gggctgtggc ccgcttgtac | 300 |

```
cacctgctgg ctgaggagaa gctgtgcccc gcctcgctgc gggacgtggc ctaccaggaa      360
gccgtccgca ccctcagctc cagggacgac caccggctgg gggaacttca ggatgaggcc      420
cgaaaccggt gtgggtggga cattgctggg gatccaggga gcatccggac gctccagtcc      480
aatctgggct gcctcccacc atcctcggct ttgccctctg ggaccaggag cctcccacgc      540
cccattgacg gtgtttcgga ctggagccaa gggtgctccc tgcgatccac tggcagccct      600
gcctccctgg ccagcaactt ggaaatcagc cagtcccta ccatgccctt cctcagcctg       660
caccgcagcc acatgggcc cagcaagctc tgtgacgacc cccaggccag cttggtgccc       720
gagcctgtcc ccgtggctg ccaggagcct gaggagatga gctggccgcc atcggggag        780 attgccagcc caccagagct gccaagcagc ccacctcctg ggcttcccga agtggcccca      840
gatgcaacct ccactggcct ccctgatacc cccgcagctc cagaaaccag caccaactac      900
ccagtggagt gcaccgaggg gtctgcaggc ccccagtctc tccccttgcc tattctggag      960
ccggtcaaaa accctgctc tgtcaaagac cagacgccac tccaactttc tgtagaagat      1020
accacctctc caaataccaa gccgtgccca cctactccca ccaccccaga aacatcccct     1080
cctcctcctc ctcctcctcc ttcatctact ccttgttcag ctcacctgac ccctcctcc     1140 ctgttccctt cctccctgga atcatcatcg gaacagaaat tctataactt tgtgatcctc    1200
cacgccaggg cagacgaaca catcgccctg cgggttcggg agaagctgga ggcccttggc    1260
gtgcccgacg gggccacctt ctgcgaggat ttccaggtgc cggggcgcgg ggagctgagc    1320
tgcctgcagg acgccataga ccactcagct ttcatcatcc tacttctcac ctccaacttc    1380
gactgtcgcc tgagcctgca ccaggtgaac caagccatga tgagcaacct cacgcgacag    1440
gggtcgccag actgtgtcat cccccttcctg cccctggaga gctccccggc ccagctcagc   1500
tccgacacgg ccagcctgct ctccgggctg gtgcggctgg acgaacactc ccagatcttc    1560
gccaggaagg tggccaacac cttcaagccc acaggcttc aggcccgaaa ggccatgtgg     1620
aggaaggaac aggacacccg agccctgcgg gaacagagcc aacacctgga cggtgagcgg    1680
atgcaggcgg cggcactgaa cgcagcctac tcagcctacc tccagagcta cttgtcctac    1740
caggcacaga tggagcagct ccaggtggct tttgggagca catgtcatt tgggactggg     1800 gcgccctatg gggctcgaat gccctttggg ggccaggtgc ccctgggagc ccgccaccc    1860 tttcccactt ggccggggtg cccgcagccg ccaccctgc acgcatggca ggctggcacc    1920
cccccaccgc cctccccaca gccagcagcc tttccacagt cactgcccctt cccgcagtcc  1980 ccagccttcc ctacggcctc acccgcaccc cctcagagcc cagggctgca accctcatt    2040 atccaccacg cacagatggt acagctgggg ctgaacaacc acatgtggaa ccagagaggg    2100
tcccaggcgc ccgaggacaa gacgcaggag gcagaa                              2136
```

<210> SEQ ID NO 129
<211> LENGTH: 381
<212> TYPE: DNA
<213> ORGANISM: Homo sapiens
<220> FEATURE:
<223> OTHER INFORMATION: Batf3

<400> SEQUENCE: 129

```
atgtcgcaag ggctcccggc cgccggcagc gtcctgcaga ggagcgtcgc ggcgcccggg       60
aaccagccgc agccgcagcc gcagcagcag agccctgagg atgatgacag gaaggtccga      120
aggagagaaa aaaccgagt tgctgctcag agaagtcgga agaagcagac ccagaaggct      180
```

```
gacaagctcc atgaggaata tgagagcctg agcaagaaa acaccatgct gcggagagag      240
atcgggaagc tgacagagga gctgaagcac ctgacagagg cactgaagga gcacgagaag      300
atgtgcccgc tgctgctctg ccctatgaac tttgtgccag tgcctccccg gccggaccct      360
gtggccggct gcttgccccg a                                                381

<210> SEQ ID NO 130
<211> LENGTH: 459
<212> TYPE: DNA
<213> ORGANISM: Homo sapiens
<220> FEATURE:
<223> OTHER INFORMATION: IL-4, isoform 1

<400> SEQUENCE: 130
atgggtctca cctcccaact gcttccccct ctgttcttcc tgctagcatg tgccggcaac       60
tttgtccacg acacaagtg cgatatcacc ttacaggaga tcatcaaaac tttgaacagc      120
ctcacagagc agaagactct gtgcaccgag ttgaccgtaa cagacatctt tgctgcctcc      180
aagaacacaa ctgagaagga aaccttctgc agggctgcga ctgtgctccg gcagttctac      240
agccaccatg agaaggacac tcgctgcctg ggtgcgactg cacagcagtt ccacaggcac      300
aagcagctga tccgattcct gaaacggctc gacaggaacc tctggggcct ggcgggcttg      360
aattcctgtc ctgtgaagga agccaaccag agtacgttgg aaaacttctt ggaaaggcta      420
aagacgatca tgagagagaa atattcaaag tgttcgagc                             459

<210> SEQ ID NO 131
<211> LENGTH: 534
<212> TYPE: DNA
<213> ORGANISM: Homo sapiens
<220> FEATURE:
<223> OTHER INFORMATION: IL-10

<400> SEQUENCE: 131
atgcacagct cagcactgct ctgttgcctg gtcctcctga ctggggtgag ggccagccca       60
ggccagggca cccagtctga aacagctgc acccacttcc caggcaacct gcctaacatg      120
cttcgagatc tccagagatgc cttcagcaga gtgaagactt tctttcaaat gaaggatcag      180
ctggacaact tgttgttaaa ggagtccttg ctggaggact taagggtta cctgggttgc      240 caagccttgt ctgagatgat ccagttttac ctggaggagg tgatgcccca agctgagaac      300
caagacccag acatcaaggc gcatgtgaac tccctggggg agaacctgaa gaccctcagg      360
ctgaggctac ggcgctgtca tcgatttctt ccctgtgaaa acaagagcaa ggccgtggag      420
caggtgaaga atgcctttaa taagctccaa gagaaaggca tctacaaagc catgagtgag      480
tttgacatct tcatcaacta catagaagcc tacatgacaa tgaagatacg aaac           534

<210> SEQ ID NO 132
<211> LENGTH: 759
<212> TYPE: DNA
<213> ORGANISM: Homo sapiens
<220> FEATURE:
<223> OTHER INFORMATION: IL-12 alpha

<400> SEQUENCE: 132
atgtggcccc tgggtcagc ctcccagcca ccgccctcac ctgccgcggc cacaggtctg        60
catccagcgg ctcgccctgt gtccctgcag tgcggctca gcatgtgtcc agcgcgcagc      120
ctcctccttg tggctaccct ggtcctcctg gaccacctca gtttggccag aaacctcccc      180
gtggccactc cagacccagg aatgttccca tgccttcacc actcccaaaa cctgctgagg      240
```

| | |
|---|---|
| gccgtcagca acatgctcca gaaggccaga caaactctag aattttaccc ttgcacttct | 300 |
| gaagagattg atcatgaaga tatcacaaaa gataaaacca gcacagtgga ggcctgttta | 360 |
| ccattggaat taaccaagaa tgagagttgc ctaaattcca gagagacctc tttcataact | 420 |
| aatgggagtt gcctggcctc cagaaagacc tcttttatga tggccctgtg ccttagtagt | 480 |
| atttatgaag acttgaagat gtaccaggtg gagttcaaga ccatgaatgc aaagcttctg | 540 |
| atggatccta agaggcagat ctttctagat caaaacatgc tggcagttat tgatgagctg | 600 |
| atgcaggccc tgaatttcaa cagtgagact gtgccacaaa atcctccct tgaagaaccg | 660 |
| gatttttata aaactaaaat caagctctgc atacttcttc atgctttcag aattcgggca | 720 |
| gtgactattg atagagtgat gagctatctg aatgcttcc | 759 |

<210> SEQ ID NO 133
<211> LENGTH: 986
<212> TYPE: DNA
<213> ORGANISM: Homo sapiens
<220> FEATURE:
<223> OTHER INFORMATION: IL-12 beta

<400> SEQUENCE: 133

| | |
|---|---|
| agatgtgtca ccagcagttg gtcatctctt ggttttccct ggttttctg gcatctcccc | 60 |
| tcgtggccat atgggaactg aagaaagatg tttatgtcgt agaattggat tggtatccgg | 120 |
| atgcccctgg agaaatggtg gtcctcacct gtgacacccc tgaagaagat ggtatcacct | 180 |
| ggaccttgga ccagagcagt gaggtcttag gctctggcaa aaccctgacc atccaagtca | 240 |
| aagagtttgg agatgctggc cagtacacct gtcacaaagg aggcgaggtt ctaagccatt | 300 |
| cgctcctgct gcttcacaaa aaggaagatg gaatttggtc cactgatatt ttaaaggacc | 360 |
| agaaagaacc caaaaataag acctttctaa gatgcgaggc caagaattat tctggacgtt | 420 |
| tcacctgctg gtggctgacg acaatcagta ctgatttgac attcagtgtc aaaagcagca | 480 |
| gaggctcttc tgacccccaa ggggtgacgt gcggagctgc tacactctct gcagagagag | 540 |
| tcagagggga caacaaggag tatgagtact cagtggagtg ccaggaggac agtgcctgcc | 600 |
| cagctgctga ggagagtctg cccattgagg tcatggtgga tgccgttcac aagctcaagt | 660 |
| atgaaaacta caccagcagc ttcttcatca gggacatcat caaacctgac ccacccaaga | 720 |
| acttgcagct gaagccatta aagaattctc ggcaggtgga ggtcagctgg gagtaccctg | 780 |
| acacctggag tactccacat tcctacttct ccctgacatt ctgcgttcag gtccagggca | 840 |
| agagcaagag agaaaagaaa gatagagtct tcacggacaa gacctcagcc acggtcatct | 900 |
| gccgcaaaaa tgccagcatt agcgtgcggg cccaggaccg ctactatagc tcatcttgga | 960 |
| gcgaatgggc atctgtgccc tgcagt | 986 |

<210> SEQ ID NO 134
<211> LENGTH: 276
<212> TYPE: DNA
<213> ORGANISM: Homo sapiens
<220> FEATURE:
<223> OTHER INFORMATION: MIP-1 alpha/ CCL3

<400> SEQUENCE: 134

| | |
|---|---|
| atgcaggtct ccactgctgc ccttgctgtc ctcctctgca ccatggctct ctgcaaccag | 60 |
| ttctctgcat cacttgctgc tgacacgccg accgcctgct gcttcagcta cacctcccgg | 120 |
| cagattccac agaatttcat agctgactac tttgagacga gcagccagtg ctccaagccc | 180 |

| | |
|---|---|
| ggtgtcatct tcctaaccaa gcgaagccgg caggtctgtg ctgaccccag tgaggagtgg | 240 |
| gtccagaaat atgtcagcga cctggagctg agtgcc | 276 |

<210> SEQ ID NO 135
<211> LENGTH: 1530
<212> TYPE: DNA
<213> ORGANISM: Homo sapiens
<220> FEATURE:
<223> OTHER INFORMATION: CD39/ENTPD1, isoform 1

<400> SEQUENCE: 135

| | |
|---|---|
| atggaagata caaaggagtc taacgtgaag acattttgct ccaagaatat cctagccatc | 60 |
| cttggcttct cctctatcat agctgtgata gctttgcttg ctgtggggtt gacccagaac | 120 |
| aaagcattgc cagaaaacgt taagtatggg attgtgctgg atgcgggttc ttctcacaca | 180 |
| agtttataca tctataagtg gccagcagaa aaggagaatg acacaggcgt ggtgcatcaa | 240 |
| gtagaagaat gcagggttaa aggtcctgga atctcaaaat tgttcagaa agtaaatgaa | 300 |
| ataggcattt acctgactga ttgcatggaa agagctaggg aagtgattcc aaggtcccag | 360 |
| caccaagaga cacccgttta cctgggagcc acggcaggca tgcggttgct caggatggaa | 420 |
| agtgaagagt tggcagacag ggttctggat gtggtgaga ggagcctcag caactacccc | 480 |
| tttgacttcc agggtgccag gatcattact ggccaagagg aaggtgccta tggctggatt | 540 |
| actatcaact atctgctggg caaattcagt cagaaaacaa ggtggttcag catagtccca | 600 |
| tatgaaacca ataatcagga aacctttgga gctttggacc ttggggagc ctctacacaa | 660 |
| gtcactttg tacccaaaa ccagactatc gagtccccag ataatgctct gcaatttcgc | 720 |
| ctctatggca aggactacaa tgtctacaca catagcttct tgtgctatgg aaggatcag | 780 |
| gcactctggc agaaactggc caaggacatt caggttgcaa gtaatgaaat tctcagggac | 840 |
| ccatgctttc atcctggata taagaaggta gtgaacgtaa gtgaccttta caagaccccc | 900 |
| tgcaccaaga gatttgagat gactcttcca ttccagcagt ttgaaatcca gggtattgga | 960 |
| aactatcaac aatgccatca agcatcctg gagctcttca acaccagtta ctgcccttac | 1020 |
| tcccagtgtg ccttcaatgg gattttcttg ccaccactcc agggggattt tgggcatttt | 1080 |
| tcagcttttt actttgtgat gaagttttta aacttgacat cagagaaagt ctctcaggaa | 1140 |
| aaggtgactg agatgatgaa aaagttctgt gctcagcctt ggaggagat aaaaacatct | 1200 |
| tacgctggag taaaggagaa gtacctgagt gaatactgct tttctggtac ctacattctc | 1260 |
| tccctccttc tgcaaggcta tcatttcaca gctgattcct gggagcacat ccatttcatt | 1320 |
| ggcaagatcc agggcagcga cgccggctgg actttgggct acatgctgaa cctgaccaac | 1380 |
| atgatcccag ctgagcaacc attgtccaca cctctctccc actccaccta tgtcttcctc | 1440 |
| atggttctat tctccctggt cctttcaca gtggccatca taggcttgct tatctttcac | 1500 |
| aagccttcat atttctggaa agatatggta | 1530 |

<210> SEQ ID NO 136
<211> LENGTH: 1722
<212> TYPE: DNA
<213> ORGANISM: Homo sapiens
<220> FEATURE:
<223> OTHER INFORMATION: CD73/NT5E, isoform 1

<400> SEQUENCE: 136

| | |
|---|---|
| atgtgtcccc gagccgcgcg ggcgcccgcg acgctactcc tcgccctggg cgcggtgctg | 60 |
| tggcctgcgg ctggcgcctg ggagcttacg attttgcaca ccaacgacgt gcacagccgg | 120 |

```
ctggagcaga ccagcgagga ctccagcaag tgcgtcaacg ccagccgctg catgggtggc      180
gtggctcggc tcttcaccaa ggttcagcag atccgccgcg ccgaacccaa cgtgctgctg      240
ctggacgccg gcgaccagta ccagggcact atctggttca ccgtgtacaa gggcgccgag      300
gtggcgcact tcatgaacgc cctgcgctac gatgccatgg cactgggaaa tcatgaattt      360
gataatggtg tggaaggact gatcgagcca ctcctcaaag aggccaaatt tccaattctg      420
agtgcaaaca ttaaagcaaa ggggccacta gcatctcaaa tatcaggact ttatttgcca      480 tataagttc ttcctgttgg tgatgaagtt gtgggaatcg ttggatacac ttccaaagaa       540
accccttttc tctcaaatcc agggacaaat ttagtgtttg aagatgaaat cactgcatta      600
caacctgaag tagataagtt aaaaactcta aatgtgaaca aaattattgc actgggacat      660
tcgggttttg aaatggataa actcatcgct cagaaagtga ggggtgtgga cgtcgtggtg      720
ggaggacact ccaacacatt tctttacaca ggcaatccac cttccaaaga ggtgcctgct      780
gggaagtacc cattcatagt cacttctgat gatgggcgga aggttcctgt agtccaggcc      840
tatgcttttg gcaaatacct aggctatctg aagatcgagt ttgatgaaag aggaaacgtc      900
atctcttccc atggaaatcc cattcttcta acagcagca ttcctgaaga tccaagcata       960
aaagcagaca ttaacaaatg gaggataaaa ttggataatt attctaccca ggaattaggg     1020
aaaacaattg tctatctgga tggctcctct caatcatgcc gctttagaga atgcaacatg     1080
ggcaacctga tttgtgatgc aatgattaac aacaacctga cacacgga tgaaatgttc       1140 tggaaccacg tatccatgtg catttttaaat ggaggtggta tccggtcgcc cattgatgaa    1200
cgcaacaatg gcacaattac ctgggagaac ctggctgctg tattgccctt ggaggcaca     1260 tttgacctag tccagttaaa aggttccacc ctgaagaagg cctttgagca tagcgtgcac    1320
cgctacggcc agtccactgg agagttcctg caggtgggcg aatccatgt ggtgtatgat     1380 ctttcccgaa aacctggaga cagagtagtc aaattagatg ttctttgcac caagtgtcga    1440
gtgcccagtt atgaccctct caaaatggac gaggtatata aggtgatcct cccaaacttc    1500
ctggccaatg gtggagatgg gttccagatg ataaaagatg aattattaag acatgactct    1560
ggtgaccaag atatcaacgt ggtttctaca tatatctcca aaatgaaagt aatttatcca    1620
gcagttgaag gtcggatcaa gttttccaca ggaagtcact gccatggaag cttttctta    1680 atatttcttt cactttgggc agtgatcttt gttttatacc aa                        1722
```

<210> SEQ ID NO 137
<211> LENGTH: 297
<212> TYPE: DNA
<213> ORGANISM: Homo sapiens
<220> FEATURE:
<223> OTHER INFORMATION: IL-8 (CXCL8)

<400> SEQUENCE: 137

```
atgacttcca agctggccgt ggctctcttg gcagccttcc tgatttctgc agctctgtgt       60
gaaggtgcag ttttgccaag gagtgctaaa gaacttagat gtcagtgcat aaagacatac      120
tccaaacctt tccaccccaa atttatcaaa gaactgagag tgattgagag tggaccacac      180
tgcgccaaca cagaaattat tgtaaagctt tctgatggaa gagagctctg tctggacccc      240
aaggaaaact gggtgcagag ggttgtggag aagttttga agagggctga gaattca         297
```

<210> SEQ ID NO 138
<211> LENGTH: 1596
<212> TYPE: DNA

<213> ORGANISM: Homo sapiens
<220> FEATURE:
<223> OTHER INFORMATION: ICAM1

<400> SEQUENCE: 138

```
atggctccca gcagccccg gcccgcgctg cccgcactcc tggtcctgct cggggctctg      60
ttcccaggac ctggcaatgc ccagacatct gtgtccccct caaaagtcat cctgccccgg    120
ggaggctccg tgctggtgac atgcagcacc tcctgtgacc agcccaagtt gttgggcata    180
gagacccgt tgcctaaaaa ggagttgctc ctgcctggga caaccggaa ggtgtatgaa      240
ctgagcaatg tgcaagaaga tagccaacca atgtgctatt caaactgccc tgatgggcag    300
tcaacagcta aaaccttcct caccgtgtac tggactccag aacgggtgga actggcaccc    360
ctccctctt ggcagccagt gggcaagaac cttaccctac gctgccaggt ggagggtggg     420
gcaccccggg ccaacctcac cgtggtgctg ctccgtgggg agaaggagct gaaacgggag    480
ccagctgtgg gggagcccgc tgaggtcacg accacggtgc tggtgaggag agatcaccat    540
ggagccaatt tctcgtgccg cactgaactg gacctgcggc ccaagggct ggagctgttt     600
gagaacacct cggcccccta ccagctccag acctttgtcc tgccagcgac tcccccacaa    660
cttgtcagcc cccgggtcct agaggtggac acgcagggga ccgtggtctg ttccctggac    720
gggctgttcc cagtctcgga ggcccaggtc cacctggcac tggggaccca gaggttgaac    780
cccacagtca cctatggcaa cgactccttc tcggccaagg cctcagtcag tgtgaccgca    840
gaggacgagg gcacccagcg gctgacgtgt gcagtaatac tggggaacca gagccaggag    900
acactgcaga cagtgaccat ctacagcttt ccggcgccca cgtgattct gacgaagcca     960
gaggtctcag aagggaccga ggtgacagtg aagtgtgagg cccaccctag agccaaggtg   1020
acgctgaatg gggttccagc ccagccactg gcccgagggg cccagctcct gctgaaggcc   1080
accccagagg acaacgggcg cagcttctcc tgctctgcaa ccctggaggt ggccggccag   1140
cttatacaca gaaccagac ccgggagctt cgtgtcctgt atggccccg actgacgag      1200
agggattgtc cgggaaactg gacgtggcca gaaaattccc agcagactcc aatgtgccag   1260
gcttggggga acccattgcc cgagctcaag tgtctaaagg atggcacttt cccactgccc   1320
atcggggaat cagtgactgt cactcgagat cttgagggca cctacctctg tcgggccagg   1380
agcactcaag gggaggtcac ccgcaaggtg accgtgaatg tgctctcccc ccggtatgag   1440
attgtcatca tcactgtggt agcagccgca gtcataatgg gcactgcagg cctcagcacg   1500
tacctctata accgccagcg gaagatcaag aaatacagac tacaacaggc ccaaaagggg   1560
accccccatga aaccgaacac acaagccacg cctccc                             1596
```

<210> SEQ ID NO 139
<211> LENGTH: 1488
<212> TYPE: DNA
<213> ORGANISM: Homo sapiens
<220> FEATURE:
<223> OTHER INFORMATION: angiopoietin 2, isoform 1

<400> SEQUENCE: 139

```
atgtggcaga ttgttttctt tactctgagc tgtgatcttg tcttggccgc agcctataac      60
aactttcgga gagcatgga cagcatagga agaagcaat atcaggtcca gcatgggtcc      120
tgcagctaca ctttcctcct gccagagatg gacaactgcc gctcttcctc cagcccctac    180
gtgtccaatg ctgtgcagag ggacgcgccg ctcgaatacg atgactcggt gcagaggctg    240
caagtgctgg agaacatcat ggaaaacaac actcagtggc taatgaagct tgagaattat    300
```

```
atccaggaca acatgaagaa agaaatggta gagatacagc agaatgcagt acagaaccag    360
acggctgtga tgatagaaat agggacaaac ctgttgaacc aaacagcgga gcaaacgcgg    420
aagttaactg atgtggaagc ccaagtatta aatcagacca cgagacttga acttcagctc    480
ttggaacact ccctctcgac aaacaaattg aaaaacaga ttttggacca gaccagtgaa    540
ataaacaaat tgcaagataa gaacagtttc ctagaaaaga aggtgctagc tatggaagac    600
aagcacatca tccaactaca gtcaataaaa gaagagaaaa tcagctaca ggtgttagta     660 tccaagcaaa attccatcat tgaagaacta gaaaaaaaa tagtgactgc cacggtgaat     720
aattcagttc ttcagaagca gcaacatgat ctcatggaga cagttaataa cttactgact    780
atgatgtcca catcaaactc agctaaggac cccactgttg ctaaagaaga acaaatcagc    840
ttcagagact gtgctgaagt attcaaatca ggacacacca cgaatggcat ctacacgtta    900
acattcccta attctacaga agagatcaag gcctactgtg acatggaagc tggaggaggc    960
gggtggacaa ttattcagcg acgtgaggat ggcagcgttg attttcagag gacttggaaa   1020
gaatataaag tgggatttgg taacccttca ggagaatatt ggctgggaaa tgagtttgtt   1080
tcgcaactga ctaatcagca acgctatgtg cttaaaatac accttaaaga ctgggaaggg   1140
aatgaggctt actcattgta tgaacatttc tatctctcaa gtgaagaact caattatagg   1200
attcacctta aaggacttac agggacagcc ggcaaaataa gcagcatcag ccaaccagga   1260
aatgatttta gcacaaagga tggagacaac gacaaatgta tttgcaaatg ttcacaaatg   1320
ctaacaggag gctggtggtt tgatgcatgt ggtccttcca acttgaacgg aatgtactat   1380
ccacagaggc agaacacaaa taagttcaac ggcattaaat ggtactactg gaaaggctca   1440
ggctattcgc tcaaggccac aaccatgatg atccgaccag cagatttc                1488
```

<210> SEQ ID NO 140  
<211> LENGTH: 2766  
<212> TYPE: DNA  
<213> ORGANISM: Homo sapiens  
<220> FEATURE:  
<223> OTHER INFORMATION: NLRP3, isoform 2

<400> SEQUENCE: 140

```
atgaagatgg caagcacccg ctgcaagctg gccaggtacc tggaggacct ggaggatgtg     60
gacttgaaga aatttaagat gcacttagag gactatcctc cccagaaggg ctgcatcccc    120
ctcccgaggg gtcagacaga gaaggcagac catgtggatc tagccacgct aatgatcgac    180
ttcaatgggg aggagaaggc gtgggccatg ccgtgtgga tcttcgctgc gatcaacagg     240
agagaccttt atgagaaagc aaaaagagat gagccgaagt ggggttcaga taatgcacgt    300
gtttcgaatc ccactgtgat atgccaggaa gacagcattg aagaggagtg gatgggttta    360
ctggagtacc tttcgagaat ctctatttgt aaaatgaaga agattaccg taagaagtac     420 agaaagtacg tgagaagcag attccagtgc attgaagaca ggaatgcccg tctgggtgag    480
agtgtgagcc tcaacaaacg ctacacacga ctgcgtctca tcaaggagca ccggagccag    540
caggagaggg agcaggagct tctggccatc ggcaagacca agacgtgtga gagccccgtg    600
agtcccatta gatggagtt gctgtttgac cccgatgatg agcattctga gcctgtgcac    660
accgtggtgt tccaggggc ggcagggatt gggaaaacaa tcctggccag aagatgatg      720 ttggactggg cgtcggggac actctaccaa gacaggtttg actatctgtt ctatatccac    780
tgtcgggagg tgagccttgt gacacagagg agcctggggg acctgatcat gagctgctgc    840
```

-continued

```
cccgacccaa acccacccat ccacaagatc gtgagaaaac cctccagaat cctcttcctc    900
atggacggct tcgatgagct gcaaggtgcc tttgacgagc acataggacc gctctgcact    960
gactggcaga aggccgagcg gggagacatt ctcctgagca gcctcatcag aaagaagctg   1020
cttcccgagg cctctctgct catcaccacg agacctgtgg ccctggagaa actgcagcac   1080
ttgctggacc atcctcggca tgtggagatc ctgggtttct ccgaggccaa aaggaaagag   1140
tacttcttca gtacttctc tgatgaggcc caagccaggg cagccttcag tctgattcag   1200
gagaacgagg tcctcttcac catgtgcttc atcccctgg tctgctggat cgtgtgcact    1260
ggactgaaac agcagatgga gagtggcaag agccttgccc agacatccaa gaccaccacc   1320
gcggtgtacg tcttcttcct ttccagtttg ctgcagcccc ggggagggag ccaggagcac   1380
ggcctctgcg cccacctctg ggggctctgc tctttggctg cagatggaat ctggaaccag   1440
aaaatcctgt ttgaggagtc cgacctcagg aatcatggac tgcagaaggc ggatgtgtct   1500
gctttcctga ggatgaacct gttccaaaag gaagtggact gcgagaagtt ctacagcttc   1560
atccacatga ctttccagga gttctttgcc gccatgtact acctgctgga agaggaaaag   1620
gaaggaagga cgaacgttcc agggagtcgt ttgaagcttc ccagccgaga cgtgacagtc   1680
cttctggaaa actatggcaa attcgaaaag gggtatttga tttttgttgt acgtttcctc   1740
tttggcctgg taaaccagga gaggacctcc tacttggaga agaaattaag ttgcaagatc   1800
tctcagcaaa tcaggctgga gctgctgaaa tggattgaag tgaaagccaa agctaaaaag   1860
ctgcagatcc agcccagcca gctggaattg ttctactgtt tgtacgagat gcaggaggag   1920
gacttcgtgc aaagggccat ggactatttc cccaagattg agatcaatct ctccaccaga   1980
atggaccaca tggtttcttc ctttttgcatt gagaactgtc atcgggtgga gtcactgtcc   2040
ctggggtttc tccataacat gcccaaggag gaagaggagg aggaaaagga aggccgacac   2100
cttgatatgg tgcagtgtgt cctcccaagc tcctctcatg ctgcctgttc tcatggttg    2160
gggcgctgtg gcctctcgca tgagtgctgc ttcgacatct ccttggtcct cagcagcaac   2220
cagaagctgg tggagctgga cctgagtgac aacgccctcg gtgacttcgg aatcagactt   2280
ctgtgtgtgg gactgaagca cctgttgtgc aatctgaaga agctctggtt ggtgaattct   2340
ggccttacgt cagtctgttg ttcagctttg tcctcggtac tcagcactaa tcagaatctc   2400
acgcaccttt acctgcgagg caacactctc ggagacaagg ggatcaaact actctgtgag   2460
ggactcttgc accccgactg caagcttcag gtgttggaat tagacaactg caacctcacg   2520
tcacactgct gctgggatct ttccacactt ctgacctcca gccagagcct gcgaaagctg   2580
agcctgggca caatgacct gggcgacctg ggggtcatga tgttctgtga agtgctgaaa   2640
cagcagagct gcctcctgca gaacctgggg ttgtctgaaa tgtatttcaa ttatgagaca   2700
aaaagtgcgt tagaaacact tcaagaagaa aagcctgagc tgaccgtcgt ctttgagcct   2760
tcttgg                                                             2766
```

<210> SEQ ID NO 141
<211> LENGTH: 831
<212> TYPE: DNA
<213> ORGANISM: Homo sapiens
<220> FEATURE:
<223> OTHER INFORMATION: CD40, isoform 1

<400> SEQUENCE: 141

```
atggttcgtc tgcctctgca gtgcgtcctc tggggctgct tgctgaccgc tgtccatcca     60
gaaccaccca ctgcatgcag agaaaaacag tacctaataa acagtcagtg ctgttctttg    120
```

```
tgccagccag dacagaaact ggtgagtgac tgcacagagt tcactgaaac ggaatgcctt      180
ccttgcggtg aaagcgaatt cctagacacc tggaacagag agacacactg ccaccagcac      240
aaatactgcg accccaacct agggcttcgg gtccagcaga agggcacctc agaaacagac      300
accatctgca cctgtgaaga aggctggcac tgtacgagtg aggcctgtga gagctgtgtc      360
ctgcaccgct catgctcgcc cggctttggg gtcaagcaga ttgctacagg ggtttctgat      420
accatctgcg agccctgccc agtcggcttc ttctccaatg tgtcatctgc tttcgaaaaa      480 tgtcacccctt ggacaagctg tgagaccaaa gacctggttg tgcaacaggc aggcacaaac     540
aagactgatg ttgtctgtgg tccccaggat cggctgagag ccctggtggt gatccccatc      600
atcttcggga tcctgtttgc catcctcttg gtgctggtct ttatcaaaaa ggtggccaag      660
aagccaacca taaggccccc caccccaagc aggaacccc aggagatcaa ttttcccgac       720
gatcttcctg gctccaacac tgctgctcca gtgcaggaga ctttacatgg atgccaaccg      780
gtcacccagg aggatggcaa agagagtcgc atctcagtgc aggagagaca g              831

<210> SEQ ID NO 142
<211> LENGTH: 783
<212> TYPE: DNA
<213> ORGANISM: Homo sapiens
<220> FEATURE:
<223> OTHER INFORMATION: CD40 ligand (CD40L)

<400> SEQUENCE: 142
atgatcgaaa catacaacca aacttctccc cgatctgcgg ccactggact gcccatcagc       60
atgaaaattt ttatgtattt acttactgtt tttcttatca cccagatgat tgggtcagca      120 cttttttgctg tgtatcttca tagaaggttg gacaagatag aagatgaaag gaatcttcat     180 gaagatttg tattcatgaa aacgatacag agatgcaaca caggagaaag atccttatcc       240
ttactgaact gtgaggagat taaaagccag tttgaaggct ttgtgaagga tataatgtta      300
aacaaagagg agacgaagaa agaaaacagc tttgaaatgc aaaaaggtga tcagaatcct      360
caaattgcgg cacatgtcat aagtgaggcc agcagtaaaa caacatctgt gttacagtgg      420
gctgaaaaag gatactacac catgagcaac aacttggtaa ccctggaaaa tgggaaacag      480
ctgaccgtta aaagacaagg actctattat atctatgccc aagtcacctt ctgttccaat      540
cgggaagctt cgagtcaagc tccatttata gccagcctct gcctaaagtc ccccggtaga     600
ttcgagagaa tcttactcag agctgcaaat acccacagtt ccgccaaacc ttgcgggcaa     660
caatccattc acttgggagg agtatttgaa ttgcaaccag gtgcttcggt gtttgtcaat     720
gtgactgatc caagccaagt gagccatggc actggcttca cgtcctttgg cttactcaaa     780
ctc                                                                   783

<210> SEQ ID NO 143
<211> LENGTH: 579
<212> TYPE: DNA
<213> ORGANISM: Homo sapiens
<220> FEATURE:
<223> OTHER INFORMATION: CD-70 antigen, isoform 1

<400> SEQUENCE: 143
atgccggagg agggttcggg ctgctcggtg cggcgcaggc cctatggggtg cgtcctgcgg      60 gctgctttgg tcccattggt cgcgggcttg gtgatctgcc tcgtggtgtg catccagcgc     120
ttcgcacagg ctcagcagca gctgccgctc gagtcacttg ggtgggacgt agctgagctg    180
```

```
cagctgaatc acacaggacc tcagcaggac cccaggctat actggcaggg gggcccagca      240
ctgggccgct ccttcctgca tggaccgag ctggacaagg ggcagctacg tatccatcgt       300
gatggcatct acatggtaca catccaggtg acgctggcca tctgctcctc cacgacggcc      360
tccaggcacc accccaccac cctggccgtg gaatctgct ctcccgcctc ccgtagcatc       420
agcctgctgc gtctcagctt ccaccaaggt tgtaccattg cctcccagcg cctgacgccc      480
ctggcccgag gggacacact ctgcaccaac ctcactggga cacttttgcc ttcccgaaac      540
actgatgaga ccttctttgg agtgcagtgg gtgcgcccc                            579
```

```
<210> SEQ ID NO 144
<211> LENGTH: 765
<212> TYPE: DNA
<213> ORGANISM: Homo sapiens
<220> FEATURE:
<223> OTHER INFORMATION: CD137 (TNFRSF9)

<400> SEQUENCE: 144
atgggaaaca gctgttacaa catagtagcc actctgttgc tggtcctcaa ctttgagagg      60
acaagatcat tgcaggatcc ttgtagtaac tgcccagctg gtacattctg tgataataac     120
aggaatcaga tttgcagtcc ctgtcctcca aatagtttct ccagcgcagg tggacaaagg     180
acctgtgaca tatgcaggca gtgtaaaggt gttttcagga ccaggaagga gtgttcctcc     240
accagcaatg cagagtgtga ctgcactcca gggtttcact gctgggggc aggatgcagc      300 atgtgtgaac aggattgtaa acaaggtcaa gaactgacaa aaaaaggttg taaagactgt     360
tgctttggga catttaacga tcagaaacgt ggcatctgtc gaccctggac aaactgttct     420
ttggatggaa agtctgtgct tgtgaatggg acgaaggaga gggacgtggt ctgtggacca     480
tctccagccg acctctctcc gggagcatcc tctgtgaccc cgcctgcccc tgcgagagag     540
ccaggacact ctccgcagat catctccttc tttcttgcgc tgacgtcgac tgcgttgctc     600
ttcctgctgt tcttcctcac gctccgtttc tctgttgtta acggggcag aaagaaactc     660 ctgtatatat tcaaacaacc atttatgaga ccagtacaaa ctactcaaga ggaagatggc     720
tgtagctgcc gatttccaga agaagaagaa ggaggatgtg aactg                     765
```

```
<210> SEQ ID NO 145
<211> LENGTH: 807
<212> TYPE: DNA
<213> ORGANISM: Homo sapiens
<220> FEATURE:
<223> OTHER INFORMATION: CD200, isoform 1

<400> SEQUENCE: 145
atggagaggc tggtgatcag gatgcccttc tctcatctgt ctacctacag cctggtttgg     60
gtcatggcag cagtggtgct gtgcacagca caagtgcaag tggtgaccca ggatgaaaga    120
gagcagctgt acacacctgc ttccttaaaa tgctctctgc aaaatgccca ggaagccctc    180
attgtgacat ggcagaaaaa gaaagctgta agcccagaaa acatggtcac cttcagcgag    240
aaccatgggg tggtgatcca gcctgcctat aaggacaaga taaacattac ccagctggga    300
ctccaaaact caaccatcac cttctggaat atcacccctg gaggatgaagg gtgttacatg    360 tgtctcttca ataccttgg ttttgggaag atctcaggaa cggcctgcct caccgtctat     420
gtacagccca gtatccct tcactacaaa ttctctgaag accacctaaa tatcacttgc     480
tctgccactg cccgcccagc ccccatggtc ttctggaagg tccctcggtc agggattgaa    540
aatagtacag tgactctgtc tcacccaaat gggaccacgt ctgttaccag catcctccat    600
```

```
atcaaagacc ctaagaatca ggtggggaag gaggtgatct gccaggtgct gcacctgggg    660
actgtgaccg actttaagca aaccgtcaac aaaggctatt ggttttcagt tccgctattg    720
ctaagcattg tttccctggt aattcttctc gtcctaatct caatcttact gtactggaaa    780
cgtcaccgga atcaggaccg agagccc                                        807
```

<210> SEQ ID NO 146
<211> LENGTH: 1236
<212> TYPE: DNA
<213> ORGANISM: Homo sapiens
<220> FEATURE:
<223> OTHER INFORMATION: A2aR (ADORA2A)

<400> SEQUENCE: 146

```
atgcccatca tgggctcctc ggtgtacatc acggtggagc tggccattgc tgtgctggcc     60
atcctgggca atgtgctggt gtgctgggcc gtgtggctca acagcaacct gcagaacgtc    120
accaactact ttgtggtgtc actggcggcg gccgacatcg cagtgggtgt gctcgccatc    180
ccctttgcca tcaccatcag caccgggttc tgcgctgcct gccacggctg cctcttcatt    240
gcctgcttcg tcctggtcct cacgcagagc tccatcttca gtctcctggc catcgccatt    300
gaccgctaca ttgccatccg catcccgctc cggtacaatg gcttggtgac cggcacgagg    360
gctaagggca tcattgccat ctgctgggtg ctgtcgtttg ccatcggcct gactcccatg    420
ctaggttgga caaactgcgg tcagccaaag gagggcaaga accactccca gggctgcggg    480
gagggccaag tggcctgtct ctttgaggat gtggtcccca tgaactacat ggtgtacttc    540
aacttctttg cctgtgtgct ggtgcccctg ctgctcatgc tgggtgtcta tttgcggatc    600
ttcctggcgg cgcgacgaca gctgaagcag atggagagcc agcctctgcc ggggagcgg    660 gcacggtcca cactgcagaa ggaggtccat gctgccaagt cactggccat cattgtgggg    720
ctctttgccc tctgctggct gccccctaca atcatcaact gcttcacttt cttctgcccc    780
gactgcagcc acgcccctct ctggctcatg tacctggcca tcgtcctctc ccacaccaat    840
tcggttgtga atcccttcat ctacgcctac cgtatccgcg agttccgcca gaccttccgc    900
aagatcattc gcagccacgt cctgaggcag caagaacctt tcaaggcagc tggcaccagt    960
gcccgggtct tggcagctca tggcagtgac ggagagcagg tcagcctccg tctcaacggc   1020
cacccgccag gagtgtgggc caacggcagt gctccccacc tgagcggag gcccaatggc   1080 tatgccctgg gctggtgag tggagggagt gcccaagagt cccagggga cacgggcctc   1140 ccagacgtgg agctccttag ccatgagctc aagggagtgt gcccagagcc ccctggccta   1200
gatgaccccc tggcccagga tggagcagga gtgtcc                             1236
```

<210> SEQ ID NO 147
<211> LENGTH: 723
<212> TYPE: DNA
<213> ORGANISM: Homo sapiens
<220> FEATURE:
<223> OTHER INFORMATION: GITR/TNFRSF18, isoform 1

<400> SEQUENCE: 147

```
atggcacagc acggggcgat gggcgcgttt cggccctgt gcggcctggc gctgctgtgc     60
gcgctcagcc tgggtcagcg ccccaccggg gtcccgggt gcggccctgg gcgcctcctg    120
cttgggacgg gaacgacagc gcgctgctgc cgggttcaca cgacgcgctg ctgccgcgat    180
taccggggcg aggagtgctg ttccgagtgg gactgcatgt gtgtccagcc tgaattccac    240
```

| | |
|---|---|
| tgcggagacc cttgctgcac gacctgccgg caccacccett gtcccccagg ccagggggta | 300 |
| cagtcccagg ggaaattcag ttttggcttc cagtgtatcg actgtgcctc ggggaccttc | 360 |
| tccgggggcc acgaaggcca ctgcaaacct tggacagact gcacccagtt cgggtttctc | 420 |
| actgtgttcc ctgggaacaa gacccacaac gctgtgtgcg tcccagggtc cccgccggca | 480 |
| gagccgcttg ggtggctgac cgtcgtcctc ctggccgtgg ccgcctgcgt cctcctcctg | 540 |
| acctcggccc agcttggact gcacatctgg cagctgagga gtcagtgcat gtggcccga | 600 |
| gagacccagc tgctgctgga ggtgccgccg tcgaccgaag acgccagaag ctgccagttc | 660 |
| cccgaggaag agcggggcga gcgatcggca gaggagaagg ggcggctggg agacctgtgg | 720 |
| gtg | 723 |

<210> SEQ ID NO 148
<211> LENGTH: 1362
<212> TYPE: DNA
<213> ORGANISM: Homo sapiens
<220> FEATURE:
<223> OTHER INFORMATION: B7-H6 (NCR3LG1)

<400> SEQUENCE: 148

| | |
|---|---|
| atgacgtgga gggctgccgc ctccacgtgc gcggcgctcc tgattctgct gtgggcgctg | 60 |
| acgaccgaag gtgatctgaa agtagagatg atggcagggg ggactcagat cacacccctg | 120 |
| aatgacaatg tcaccatatt ctgcaatatc ttttattccc aacccctcaa catcacgtct | 180 |
| atgggtatca cctggttttg gaagagtctg acgtttgaca agaagtcaa agtctttgaa | 240 |
| ttttttggag atcaccaaga ggcattccga cctggagcca ttgtgtctcc atggaggctg | 300 |
| aagagtgggg acgcctcact gcggctgcct ggaatccagc tggaggaagc aggagagtac | 360 |
| cgatgtgagg tggtggtcac ccctctgaag gcacagggaa cagtccagct tgaagttgtg | 420 |
| gcttccccag ccagcagatt gttgctggat caagtgggca tgaaagagaa tgaagacaaa | 480 |
| tatatgtgtg agtcaagtgg gttctaccca gaggctatta atataacatg ggagaagcag | 540 |
| acccagaagt ttcccatcc catagagatt tctgaggatg tcatcactgg tcccaccatc | 600 |
| aagaatatgg atgcacatt taatgtcact agctgcttga agctgaactc ctctcaggaa | 660 |
| gaccctggga ctgtctacca gtgtgtggta cggcatgcgt ccttgcatac cccttgagg | 720 |
| agcaacttta ccctgactgc tgctcggcac agtctttctg aaactgagaa gacagataat | 780 |
| ttttccattc attggtggcc tatttcattc attggtgttg gactggtttt attaattgtt | 840 |
| ttgattcctt ggaaaaagat atgtaacaaa tcatcttcag cctatactcc tctcaagtgc | 900 |
| attctgaaac actggaactc cttttgacact cagactctga agaaagagca cctcatattc | 960 |
| ttttgcactc gggcatggcc gtcttaccag ctgcaggatg gggaggcttg gcctcctgag | 1020 |
| ggaagtgtta atattaatac tattcaacaa ctagatgttt tctgcagaca ggagggcaaa | 1080 |
| tggtccgagg ttcettatgt gcaagccttc tttgccttgc gagacaaccc agatctttgt | 1140 |
| cagtgttgta gaattgaccc tgctctccta acagttacat caggcaagtc catagatgat | 1200 |
| aattccacaa agtctgagaa acaaaccect agggaacact cggatgcagt tccggatgcc | 1260 |
| ccaatccttc ctgtctcccc tatctgggaa cctcctccag ccacaacatc aacaactcca | 1320 |
| gttctatcct cccaaccccc aactttactg ttaccectac ag | 1362 |

<210> SEQ ID NO 149
<211> LENGTH: 597
<212> TYPE: DNA
<213> ORGANISM: Homo sapiens
<220> FEATURE:
<223> OTHER INFORMATION: ICOS, isoform 1

<400> SEQUENCE: 149

```
atgaagtcag gcctctggta tttctttctc ttctgcttgc gcattaaagt tttaacagga      60
gaaatcaatg ttctgccaa ttatgagatg tttatatttc acaacggagg tgtacaaatt     120
ttatgcaaat atcctgacat tgtccagcaa tttaaaatgc agttgctgaa agggggcaa     180 atactctgcg atctcactaa gacaaaagga agtggaaaca cagtgtccat taagagtctg     240
aaattctgcc attctcagtt atccaacaac agtgtctctt ttttctata caacttggac     300 cattctcatg ccaactatta cttctgcaac ctatcaattt ttgatcctcc tccttttaaa     360
gtaactctta caggaggata tttgcatatt tatgaatcac aactttgttg ccagctgaag     420
ttctggttac ccataggatg tgcagccttt gttgtagtct gcattttggg atgcatactt     480
atttgttggc ttacaaaaaa gaagtattca tccagtgtgc acgaccctaa cggtgaatac     540
atgttcatga gcagtgaa cacagccaaa aaatctagac tcacagatgt gaccta         597
```

<210> SEQ ID NO 150
<211> LENGTH: 906
<212> TYPE: DNA
<213> ORGANISM: Homo sapiens
<220> FEATURE:
<223> OTHER INFORMATION: ICOS ligand, isoform 1

<400> SEQUENCE: 150

```
atgcggctgg gcagtcctgg actgctcttc ctgctcttca gcagccttcg agctgatact      60
caggagaagg aagtcagagc gatggtaggc agcgacgtgg agctcagctg cgcttgccct     120
gaaggaagcc gttttgattt aaatgatgtt tacgtatatt ggcaaaccag tgagtcgaaa     180
accgtggtga cctaccacat cccacagaac agctccttgg aaaacgtgga cagccgctac     240
cggaaccgag ccctgatgtc accggccggc atgctgcggg gcgacttctc cctgcgcttg     300
ttcaacgtca cccccagga cgagcagaag tttcactgcc tggtgttgag ccaatccctg     360
ggattccagg aggttttgag cgttgaggtt acactgcatg tggcagcaaa cttcagcgtg     420
cccgtcgtca gcgccccca cagcccctcc caggatgagc tcaccttcac gtgtacatcc     480
ataaacggct accccaggcc caacgtgtac tggatcaata agacggacaa cagcctgctg     540
gaccaggctc tgcagaatga caccgtcttc ttgaacatgc ggggcttgta tgacgtggtc     600
agcgtgctga ggatcgcacg gacccccagc gtgaacattg ctgctgcat agagaacgtg     660 cttctgcaga gaacctgac tgtcggcagc agacaggaa atgacatcgg agagagagac     720
aagatcacag agaatccagt cagtaccggc gagaaaacg cggccacgtg gagcatcctg     780
gctgtcctgt cctgcttgt ggtcgtgcg gtggccatag ctgggtgtg cagggaccga     840 tgcctccaac acagctatgc aggtgcctgg gctgtgagtc cggagacaga gctcactggc     900
cacgtt                                                              906
```

<210> SEQ ID NO 151
<211> LENGTH: 1344
<212> TYPE: DNA
<213> ORGANISM: Homo sapiens
<220> FEATURE:
<223> OTHER INFORMATION: gp49B/LILRB4, isoform 1

<400> SEQUENCE: 151

```
atgatcccca ccttcacggc tctgctctgc ctcgggctga gtctgggccc caggacccac      60
```

-continued

| | |
|---|---|
| atgcaggcag ggcccctccc caaacccacc ctctgggctg agccaggctc tgtgatcagc | 120 |
| tgggggaact ctgtgaccat ctggtgtcag gggaccctgg aggctcggga gtaccgtctg | 180 |
| gataaagagg aaagcccagc accctgggac agacagaacc cactggagcc caagaacaag | 240 |
| gccagattct ccatcccatc catgacagag gactatgcag ggagataccg ctgttactat | 300 |
| cgcagccctg taggctggtc acagcccagt gaccccctgg agctggtgat gacaggagcc | 360 |
| tacagtaaac ccacccttc agccctgccg agtcctcttg tgacctcagg aaagagcgtg | 420 |
| accctgctgt gtcagtcacg gagcccaatg gacactttc ttctgatcaa ggagcgggca | 480 |
| gcccatcccc tactgcatct gagatcagag acggagctc agcagcacca ggctgaattc | 540 |
| cccatgagtc ctgtgacctc agtgcacggg gggacctaca ggtgcttcag ctcacacggc | 600 |
| ttctcccact acctgctgtc acaccccagt gaccccctgg agctcatagt ctcaggatcc | 660 |
| ttggagggtc ccaggccctc acccacaagg tccgtctcaa cagctgcagg ccctgaggac | 720 |
| cagcccctca tgcctacagg gtcagtcccc cacagtggtc tgagaaggca ctgggaggta | 780 |
| ctgatcgggg tcttggtggt ctccatcctg cttctctccc tcctcctctt cctcctcctc | 840 |
| caacactggc gtcagggaaa acacaggaca ttggcccaga gacaggctga tttccaacgt | 900 |
| cctccagggg ctgccgagcc agagcccaag gacgggggcc tacagaggag gtccagccca | 960 |
| gctgctgacg tccagggaga aaacttctgt gctgccgtga agaacacaca gcctgaggac | 1020 |
| ggggtggaaa tggacactcg gcagagccca cacgatgaag accccaggc agtgacgtat | 1080 |
| gccaaggtga acactccag acctaggaga gaaatggcct ctcctccctc cccactgtct | 1140 |
| ggggaattcc tggacacaaa ggacagacag gcagaagagg acagacagat ggacactgag | 1200 |
| gctgctgcat ctgaagcccc ccaggatgtg acctacgccc ggctgcacag cttaccctc | 1260 |
| agacagaagg caactgagcc tcctccatcc caggaagggg cctctccagc tgagcccagt | 1320 |
| gtctatgcca ctctggccat ccac | 1344 |

<210> SEQ ID NO 152
<211> LENGTH: 1896
<212> TYPE: DNA
<213> ORGANISM: Homo sapiens
<220> FEATURE:
<223> OTHER INFORMATION: PIR-B/LILRB3, isoform 1

<400> SEQUENCE: 152

| | |
|---|---|
| atgacgcccg ccctcacagc cctgctctgc cttgggctga gtctgggccc caggacccgc | 60 |
| atgcaggcag ggcccttccc caaacccacc ctctgggctg agccaggctc tgtgatcagc | 120 |
| tgggggagcc ccgtgaccat ctggtgtcag gggagcctgg aggcccagga gtaccaactg | 180 |
| gataaagagg gaagcccaga gccctgggac agaaataacc cactggaacc caagaacaag | 240 |
| gccagattct ccatcccatc catgacacag caccatgcag ggagataccg ctgccactat | 300 |
| tacagctctg caggctggtc agagcccagc gacccctgg agctggtgat gacaggattc | 360 |
| tacaacaaac ccacctctc agccctgccc agccctgtgg tggcctcagg ggaatatgg | 420 |
| accctccgat gtggctcaca gaagggatat accatttg ttctgatgaa ggaaggagaa | 480 |
| caccagctcc cccggaccct ggactcacag cagctccaca gtggggggtt ccaggccctg | 540 |
| ttccctgtgg gccccgtgac cccagccac aggtggaggt tcacatgcta ttactattat | 600 |
| acaaacaccc cctgggtgtg gtcccacccc agtgaccccc tggagattct gccctcaggc | 660 |
| gtgtctagga agccctccct cctgacccctg cagggccctg tcctggcccc tgggcagagc | 720 |
| ctgacccctcc agtgtggctc tgatgtcggc tacgacagat tgttctgta taaggagggg | 780 |

-continued

```
gaacgtgact tcctccagcg ccctggccag cagccccagg ctgggctctc ccaggccaac    840
ttcaccctgg gccctgtgag ccgctcctac gggggccagt acaggtgcta tggtgcacac    900
aacctctcct ccgagtggtc ggcccccagt gaccccctgg acatcctgat cacaggacag    960
atctatgaca ccgtctccct gtcagcacag ccgggcccca cagtggcctc aggagagaac   1020
atgaccctgc tgtgtcagtc acgggggtat tttgacactt tccttctgac caaagaaggg   1080
gcagcccatc ccccactgcg tctgagatca atgtacggag ctcataagta ccaggctgaa   1140
ttccccatga gtcctgtgac ctcagcccac gcggggacct acaggtgcta cggctcacgc   1200
agctccaacc cccacctgct gtctttcccc agtgagcccc tggaactcat ggtctcagga   1260
cactctggag gctccagcct cccacccaca gggccgccct ccacacctgg tctgggaaga   1320
tacctggagg ttttgattgg ggtctcggtg gccttcgtcc tgctgctctt cctcctcctc   1380
ttcctcctcc tcctccgtca gcgtcacagc aaacacagga catctgacca gagaaagact   1440
gatttccagc gtcctgcagg ggctgcggag acagagccca aggacagggg cctgctgagg   1500
aggtccagcc cagctgctga cgtccaggaa gaaaacctct atgctgctgt gaaggacaca   1560
cagtctgagg acagggtgga gctggacagt cagcagagcc cacacgatga agaccccag    1620 gcagtgacgt atgccccggt gaaacactcc agtcctagga gagaaatggc ctctcctccc   1680
tcctcactgt ctggggaatt cctggacaca aaggacagac aggtggaaga ggacaggcag   1740
atggacactg aggctgctgc atctgaagcc tcccaggatg tgacctacgc cagctgcac    1800 agcttgaccc ttagacggaa ggcaactgag cctcctccat cccaggaagg ggaacctcca   1860
gctgagccca gcatctacgc cactctggcc atccac                             1896
```

<210> SEQ ID NO 153
<211> LENGTH: 1014
<212> TYPE: DNA
<213> ORGANISM: Homo sapiens
<220> FEATURE:
<223> OTHER INFORMATION: HLA-G alpha chain

<400> SEQUENCE: 153

```
atggtggtca tggcgccccg aaccctcttc ctgctgctct cggggggccct gaccctgacc     60 gagacctggg cggcctccca ctccatgagg tatttcagcg ccgccgtgtc ccggcccggc    120
cgcggggagc cccgcttcat cgccatgggc tacgtggacg acacgcagtt cgtgcggttc    180
gacagcgact cggcgtgtcc gaggatggag ccgcgggcgc cgtgggtgga gcaggagggg    240
ccggagtatt gggaagagga gacacggaac accaaggccc acgcacagac tgacagaatg    300
aacctgcaga ccctgcgcgg ctactacaac cagagcgagg ccagttctca caccctccag    360
tggatgattg gctgcgacct ggggtccgac ggacgcctcc tccgcgggta tgaacagtat    420
gcctacgatg gcaaggatta cctcgccctg aacgaggacc tgcgctcctg gaccgcagcg    480
gacactgcgg ctcagatctc caagcgcaag tgtgaggcgg ccaatgtggc tgaacaaagg    540
agagcctacc tggagggcac gtgcgtggag tggctccaca gatacctgga gaacgggaag    600
gagatgctgc agcgcgcgga ccccccaag acacacgtga cccaccaccc tgtctttgac    660
tatgaggcca ccctgaggtg ctgggccctg gcttctacc ctgcggagat catactgacc    720
tggcagcggg atggggagga ccagacccag gacgtggagc tcgtggagac caggcctgca    780
ggggatggaa ccttccagaa gtgggcagct gtggtggtgc cttctggaga ggagcagaga    840
tacacgtgcc atgtgcagca tgaggggctg ccggagcccc tcatgctgag atggaagcag    900
```

| | | |
|---|---|---|
| tcttccctgc ccaccatccc catcatgggt atcgttgctg gcctggttgt ccttgcagct | 960 | |
| gtagtcactg gagctgcggt cgctgctgtg ctgtggagaa agaagagctc agat | 1014 | |

<210> SEQ ID NO 154
<211> LENGTH: 1092
<212> TYPE: DNA
<213> ORGANISM: Homo sapiens
<220> FEATURE:
<223> OTHER INFORMATION: TIM1/HAVCR1

<400> SEQUENCE: 154

| | |
|---|---|
| atgcatcctc aagtggtcat cttaagcctc atcctacatc tggcagattc tgtagctggt | 60 |
| tctgtaaagg ttggtggaga ggcaggtcca tctgtcacac taccctgcca ctacagtgga | 120 |
| gctgtcacat ccatgtgctg gaatagaggc tcatgttctc tattcacatg ccaaaatggc | 180 |
| attgtctgga ccaatggaac ccacgtcacc tatcggaagg acacacgcta taagctattg | 240 |
| ggggaccttt caagaaggga tgtctctttg accatagaaa atacagctgt gtctgacagt | 300 |
| ggcgtatatt gttgccgtgt tgagcaccgt gggtggttca atgacatgaa atcaccgta | 360 |
| tcattggaga ttgtgccacc caaggtcacg actactccaa ttgtcacaac tgttccaacc | 420 |
| gtcacgactg ttcgaacgag caccactgtt ccaacgacaa cgactgttcc aatgacgact | 480 |
| gttccaacga caactgttcc aacaacaatg agcattccaa cgacaacgac tgttctgacg | 540 |
| acaatgactg tttcaacgac aacgagcgtt ccaacgacaa cgagcattcc aacaacaaca | 600 |
| agtgttccag tgacaacaac tgtctctacc tttgttcctc caatgccttt gcccaggcag | 660 |
| aaccatgaac cagtagccac ttcaccatct tcacctcagc cagcagaaac ccaccctacg | 720 |
| acactgcagg gagcaataag gagagaaccc accagctcac cattgtactc ttacacaaca | 780 |
| gatgggaatg acaccgtgac agagtcttca gatggccttt ggaataacaa tcaaactcaa | 840 |
| ctgttcctag aacatagtct actgacggcc aataccacta aggaatcta tgctggagtc | 900 |
| tgtatttctg tcttggtgct tcttgctctt ttgggtgtca tcattgccaa aaagtatttc | 960 |
| ttcaaaaagg aggttcaaca actaagtgtt tcatttagca gccttcaaat taaagctttg | 1020 |
| caaaatgcag ttgaaaagga agtccaagca gaagacaata tctacattga gaatagtctt | 1080 |
| tatgccacgg ac | 1092 |

<210> SEQ ID NO 155
<211> LENGTH: 1134
<212> TYPE: DNA
<213> ORGANISM: Homo sapiens
<220> FEATURE:
<223> OTHER INFORMATION: TIM4/TIMD4, isoform 1

<400> SEQUENCE: 155

| | |
|---|---|
| atgtccaaag aacctctcat tctctggctg atgattgagt tttggtggct ttacctgaca | 60 |
| ccagtcactt cagagactgt tgtgacggag gttttgggtc accgggtgac tttgccctgt | 120 |
| ctgtactcat cctggtctca aacagcaac agcatgtgct gggggaaaga ccagtgcccc | 180 |
| tactccggtt gcaaggaggc gctcatccgc actgatggaa tgagggtgac ctcaagaaag | 240 |
| tcagcaaaat atagacttca ggggactatc ccgagaggtg atgtctcctt gaccatctta | 300 |
| aaccccagtg aaagtgacag cggtgtgtac tgctgccgca taagtgcc tggctggttc | 360 |
| aacgatgtaa agataaacgt gcgcctgaat ctacagagag cctcaacaac cacgcacaga | 420 |
| acagcaacca ccaccacacg cagaacaaca acaacaagcc ccaccaccac ccgacaaatg | 480 |
| acaacaaccc cagctgcact tccaacaaca gtcgtgacca cacccgatct cacaaccgga | 540 |

```
acaccactcc agatgacaac cattgccgtc ttcacaacag caaacacgtg cctttcacta      600
accccaagca cccttccgga ggaagccaca ggtcttctga ctcccgagcc ttctaaggaa      660
gggcccatcc tcactgcaga atcagaaact gtcctcccca gtgattcctg gagtagtgtt      720
gagtctactt ctgctgacac tgtcctgctg acatccaaag agtccaaagt ttgggatctc      780
ccatcaacat cccacgtgtc aatgtggaaa acgagtgatt ctgtgtcttc cctcagcct       840 ggagcatctg atacagcagt tcctgagcag aacaaaacaa caaaaacagg acagatggat      900 ggaatacccca tgtcaatgaa gaatgaaatg cccatctccc aactactgat gatcatcgcc     960
ccctccttgg gatttgtgct cttcgcattg tttgtggcgt ttctcctgag agggaaactc     1020
atggaaacct attgttcgca gaaacacaca aggctagact acattggaga tagtaaaaat    1080
gtcctcaatg acgtgcagca tggaagggaa gacgaagacg gccttttac cctc           1134
```

<210> SEQ ID NO 156
<211> LENGTH: 831
<212> TYPE: DNA
<213> ORGANISM: Homo sapiens
<220> FEATURE:
<223> OTHER INFORMATION: OX-40/CD134/TNFRSF4

<400> SEQUENCE: 156

```
atgtgcgtgg gggctcggcg gctgggccgc gggccgtgtg cggctctgct cctcctgggc        60
ctggggctga gcaccgtgac ggggctccac tgtgtcgggg acacctaccc cagcaacgac       120
cggtgctgcc acgagtgcag gccaggcaac ggggatggtga ccgctgcag ccgctcccag       180 aacacggtgt gccgtccgtg cgggccgggc ttctacaacg acgtggtcag ctccaagccg       240
tgcaagccct gcacgtggtg taacctcaga agtgggagtg agcggaagca gctgtgcacg       300
gccacacagg acacagtctg ccgctgccgg gcgggcaccc agccctggga cagctacaag       360
cctggagttg actgtgcccc ctgccctcca gggcacttct ccccaggcga caaccaggcc       420
tgcaagccct ggaccaactg caccttggct gggaagcaca ccctgcagcc ggccagcaat       480
agctcggacg caatctgtga ggacaggggac cccccagcca cgcagcccca ggagacccag       540 ggcccccgg ccaggcccat cactgtccag cccactgaag cctggcccag aacctcacag       600
ggaccctcca cccggcccgt ggaggtcccc ggggccgtg cggttgccgc atcctgggc        660 ctgggcctgg tgctggggct gctgggcccc ctggccatcc tgctggccct gtacctgctc      720
cggagggacc agaggctgcc cccgatgcc cacaagcccc tggggggagg cagtttccgg       780
acccccatcc aagaggagca ggccgacgcc cactccaccc tggccaagat c               831
```

<210> SEQ ID NO 157
<211> LENGTH: 549
<212> TYPE: DNA
<213> ORGANISM: Homo sapiens
<220> FEATURE:
<223> OTHER INFORMATION: OX-40L/CD252/TNFSF4, isoform 1

<400> SEQUENCE: 157

```
atggaaaggg tccaaccccct ggaagagaat gtgggaaatg cagccaggcc aagattcgag        60
aggaacaagc tattgctggt ggcctctgta attcaggac tggggctgct cctgtgcttc         120
acctacatct gcctgcactt ctctgctctt caggtatcac atcggtatcc tcgaattcaa        180
agtatcaaag tacaatttac cgaatataag aaggagaaag gtttcatcct cacttcccaa        240
aaggaggatg aaatcatgaa ggtgcagaac aactcagtca tcatcaactg tgatgggttt        300
```

| tatctcatct ccctgaaggg ctacttctcc caggaagtca acattagcct tcattaccag | 360 |
| aaggatgagg agcccctctt ccaactgaag aaggtcaggt ctgtcaactc cttgatggtg | 420 |
| gcctctctga cttacaaaga caaagtctac ttgaatgtga ccactgacaa tacctccctg | 480 |
| gatgacttcc atgtgaatgg cggagaactg attcttatcc atcaaaatcc tggtgaattc | 540 |
| tgtgtccctt | 549 |

<210> SEQ ID NO 158
<211> LENGTH: 1950
<212> TYPE: DNA
<213> ORGANISM: Homo sapiens
<220> FEATURE:
<223> OTHER INFORMATION: ILT-2/LILRB1, isoform 1

<400> SEQUENCE: 158

| atgacccca tcctcacggt cctgatctgt ctcgggctga gtctgggccc ccggacccac | 60 |
| gtgcaggcag ggcacctccc caagcccacc ctctgggctg aaccaggctc tgtgatcacc | 120 |
| caggggagtc ctgtgaccct caggtgtcag ggggccagg agacccagga gtaccgtcta | 180 |
| tatagagaaa agaaaacagc accctggatt acacggatcc acaggagct tgtgaagaag | 240 |
| ggccagttcc ccatcccatc catcacctgg gaacacacag gcggtatcg ctgttactat | 300 |
| ggtagcgaca ctgcaggccg ctcagagagc agtgaccccc tggagctggt ggtgacagga | 360 |
| gcctacatca aacccaccct ctcagcccag cccagccccg tggtgaactc aggagggaat | 420 |
| gtaaccctcc agtgtgactc acaggtggca tttgatggct tcattctgtg taaggaagga | 480 |
| gaagatgaac acccacaatg cctgaactcc agccccatg cccgtgggtc gtcccgcgcc | 540 |
| atcttctccg tgggccccgt gagcccgagt cgcaggtggt ggtacaggtg ctatgcttat | 600 |
| gactcgaact ctccctatga gtggtctcta cccagtgatc tcctggagct cctggtccta | 660 |
| ggtgtttcta agaagccatc actctcagtg cagccaggtc ctatcgtggc ccctgaggag | 720 |
| accctgactc tgcagtgtgg ctctgatgct ggctacaaca gatttgttct gtataaggac | 780 |
| ggggaacgtg acttccttca gctcgctggc gcacagcccc aggctgggct ctcccaggcc | 840 |
| aacttcaccc tgggccctgt gagccgctcc tacgggggcc agtacagatg ctacggtgca | 900 |
| cacaacctct cctccgagtg gtcggccccc agcgaccccc tggacatcct gatcgcagga | 960 |
| cagttctatg acagagtctc cctctcggtg cagccgggcc ccacggtggc ctcaggagag | 1020 |
| aacgtgaccc tgctgtgtca gtcacaggga tggatgcaaa ctttccttct gaccaaggag | 1080 |
| ggggcagctg atgacccatg gcgtctaaga tcaacgtacc aatctcaaaa ataccaggct | 1140 |
| gaattcccca tgggtcctgt gacctcagcc catgcgggga cctacaggtg ctacggctca | 1200 |
| cagagctcca acccttacct gctgactcac cccagtgacc cctggagct cgtggtctca | 1260 |
| ggaccgtctg ggggccccag ctccccgaca acaggcccca cctccacatc tggccctgag | 1320 |
| gaccagcccc tcacccccac cgggtcggat ccccagagtg gtctgggaag gcacctgggg | 1380 |
| gttgtgatcg gcatcttggt ggccgtcatc ctactgctcc tcctcctcct cctcctcttc | 1440 |
| ctcatcctcc gacatcgacg tcagggcaaa cactggacat cgacccagag aaaggctgat | 1500 |
| ttccaacatc ctgcaggggc tgtgggccca gagcccacag acagaggcct gcagtggagg | 1560 |
| tccagcccag ctgccgatgc ccaggaagaa aacctctatg ctgccgtgaa gcacacacag | 1620 |
| cctgaggatg gggtggagat ggacactcgg agcccacacg atgaagaccc ccaggcagtg | 1680 |
| acgtatgccg aggtgaaaca ctccagacct aggagagaaa tggcctctcc tccttcccca | 1740 |
| ctgtctgggg aattcctgga cacaaaggac agacaggcg aagaggacag gcagatggac | 1800 |

```
actgaggctg ctgcatctga agcccccag gatgtgacct acgcccagct gcacagcttg    1860
accctcagac gggaggcaac tgagcctcct ccatcccagg aagggccctc tccagctgtg    1920
cccagcatct acgccactct ggccatccac                                     1950
```

<210> SEQ ID NO 159
<211> LENGTH: 1794
<212> TYPE: DNA
<213> ORGANISM: Homo sapiens
<220> FEATURE:
<223> OTHER INFORMATION: ILT-4/LILRB2, isoform 1

<400> SEQUENCE: 159

```
atgacccca tcgtcacagt cctgatctgt ctcgggctga gtctgggccc caggacccgc      60
gtgcagacag ggaccatccc caagcccacc ctgtgggctg agccagactc tgtgatcacc    120
caggggagtc ccgtcaccct cagttgtcag gggagccttg aagcccagga gtaccgtcta    180
tatagggaga aaaaatcagc atcttggatt acacggatac gaccagagct tgtgaagaac    240
ggccagttcc acatcccatc catcacctgg gaacacacag gcgatatgg ctgtcagtat    300
tacagccgcg ctcggtggtc tgagctcagt gacccctgg tgctggtgat gacaggagcc    360
tacccaaaac ccaccctctc agcccagccc agccctgtgg tgacctcagg aggaagggtg    420
accctccagt gtgagtcaca ggtggcattt ggcggcttca ttctgtgtaa ggaaggagaa    480
gatgaacacc cacaatgcct gaactcccag ccccatgccc gtgggtcgtc ccgcgccatc    540
ttctccgtgg gccccgtgag cccgaatcgc aggtggtcgc acaggtgcta tggttatgac    600
ttgaactctc cctatgtgtg gtcttcaccc agtgatctcc tggagctcct ggtcccaggt    660
gtttctaaga gccatcact ctcagtgcag ccgggtcctg tcatggcccc tggggaaagc    720
ctgacccctcc agtgtgtctc tgatgtcggc tatgacagat ttgttctgta caaggagggg    780
gaacgtgacc ttcgccagct ccctggccgg cagcccagg ctgggctctc ccaggccaac    840
ttcaccctgg gccctgtgag ccgctcctac ggggccagt acagatgcta cggtgcacac    900
aacctctcct ctgagtgctc ggcccccagc gaccccctgg acatcctgat cacaggacag    960
atccgtggca caccttcat ctcagtgcag ccaggcccca cagtggccc aggagagaac   1020
gtgaccctgc tgtgtcagtc atggcggcag ttccacactt ccttctgac caaggcggga   1080
gcagctgatg ccccactccg tctaagatca atacacgaat atcctaagta ccaggctgaa   1140
ttccccatga gtcctgtgac ctcagcccac gcggggacct acaggtgcta cggctcactc   1200
aactccgacc cctacctgct gtctcacccc agtgagcccc tggagctcgt ggtctcagga   1260
ccctccatgg gttccagccc cccacccacc ggtcccatct ccacacctgc aggccctgag   1320
gaccagcccc tcacccccac tgggtcgat cccaaagtg gtctgggaag cacctgggg   1380
gttgtgatcg gcatcttggt ggccgtcgtc ctactgctcc tcctcctcct cctcctcttc   1440
ctcatcctcc gacatcgacg tcagggcaaa cactggacat cgaccagag aaaggctgat   1500
ttccaacatc ctgcagggc tgtggggcca gagcccacag acagaggcct gcagtggagg   1560
tccagcccag ctgccgacgc ccaggaagaa aacctctatg ctgccgtgaa ggacacacag   1620
cctgaagatg gggtggagat ggacactcgg gctgctgcat ctgaagcccc caggatgtgt   1680
acctacgccc agctgcacag cttgaccctc agacggaagg caactgagcc tcctccatcc   1740
caggaaaggg aacctccagc tgagcccagc atctacgcca cctggccat ccac          1794
```

<210> SEQ ID NO 160

```
<211> LENGTH: 717
<212> TYPE: DNA
<213> ORGANISM: Homo sapiens
<220> FEATURE:
<223> OTHER INFORMATION: BCL-2 isoform alpha

<400> SEQUENCE: 160
atggcgcacg ctgggagaac agggtacgat aaccgggaga tagtgatgaa gtacatccat      60
tataagctgt cgcagagggg ctacgagtgg gatgcgggag atgtgggcgc cgcgcccccg     120
ggggccgccc ccgcaccggg catcttctcc tcccagcccg gcacacgcc ccatccagcc      180
gcatcccggg accggtcgc caggacctcg ccgctgcaga ccccggctgc ccccggcgcc     240
gccgcgggc ctgcgctcag cccggtgcca cctgtggtcc acctgaccct ccgccaggcc     300
ggcgacgact tctcccgccg ctaccgccgc gacttcgccg agatgtccag ccagctgcac     360
ctgacgccct tcaccgcgcg gggacgcttt gccacggtgg tggaggagct cttcagggac     420
ggggtgaact gggggaggat tgtggccttc tttgagttcg gtggggtcat gtgtgtggag     480
agcgtcaacc gggagatgtc gccctggtg acaacatcg ccctgtggat gactgagtac       540
ctgaaccggc acctgcacac ctggatccag gataacggag ctgggatgc ctttgtggaa      600
ctgtacggcc ccagcatgcg gcctctgttt gatttctcct ggctgtctct gaagactctg     660
ctcagtttgg ccctggtggg agcttgcatc accctgggtg cctatctggg ccacaag        717

<210> SEQ ID NO 161
<211> LENGTH: 4050
<212> TYPE: DNA
<213> ORGANISM: Homo sapiens
<220> FEATURE:
<223> OTHER INFORMATION: MDR1/ABCB1, isoform 1

<400> SEQUENCE: 161
atgagtgtca acttgcaagg ggaccagaga ggtgcaacgg aagccagaac attcctcctg      60
gaaattcaac tgtttcgca gtttctcgag gaatcagcat tcagtcaatc cgggccggga     120
gcagtcatct gtggtctttc cactaaagtc ggagtatctt cttccaaaat ttcacgtctt     180
ggtggccgtt ccaaggagcg cgaggtcgga atggatcttg aaggggaccg caatggagga     240
gcaaagaaga agaactttt taaactgaac aataaaagtg aaaagataa gaggaaaag       300
aaaccaactg tcagtgtatt ttcaatgttt cgctattcaa attggcttga caagttgtat     360
atggtggtgg aactttggc tgccatcatc catgggctg acttcctct catgatgctg       420
gtgtttggag aaatgacaga tatctttgca aatgcaggaa atttagaaga tctgatgtca     480
aacatcacta atagaagtga tatcaatgat acagggttct tcatgaatct ggaggaagac     540
atgaccaggt atgcctatta ttacagtgga attggtgctg gggtgctggt tgctgcttac     600
attcaggttt cattttggtg cctggcagct ggaagacaaa tacacaaaat tagaaaacag     660
ttttttcatg ctataatgcg acaggagata ggctggtttg atgtgcacga tgttggggag     720
cttaacaccc gacttacaga tgatgtctcc aagattaatg aaggaattgg tgacaaaatt     780
ggaatgttct ttcagtcaat ggcaacattt ttcactgggt ttatagtagg atttacacgt     840
ggttggaagc taacccttgt gattttggcc atcagtcctg tcttggact gtcagctgct     900
gtctgggcaa agatactatc ttcatttact gataaagaac tcttagcgta tgcaaaagct     960
ggagcagtag ctgaagaggt cttggcagca attagaactg tgattgcatt tggaggacaa    1020
aagaaagaac ttgaaggta caacaaaaat ttagaagaag ctaaagaat gggataaag       1080
aaagctatta cagccaatat ttctataggt gctgctttcc tgctgatcta tgcatcttat    1140
```

```
gctctggcct tctggtatgg gaccaccttg gtcctctcag gggaatattc tattggacaa   1200
gtactcactg tattcttttc tgtattaatt ggggctttta gtgttggaca ggcatctcca   1260
agcattgaag catttgcaaa tgcaagagga gcagcttatg aaatcttcaa gataattgat   1320
aataagccaa gtattgacag ctattcgaag agtgggcaca aaccagataa tattaaggga   1380
aatttggaat tcagaaatgt tcacttcagt tacccatctc gaaagaagt  taagatcttg   1440 aagggtctga acctgaaggt gcagagtggg cagacggtgg ccctggttgg aaacagtggc   1500
tgtgggaaga gcacaacagt ccagctgatg cagaggctct atgaccccac agaggggatg   1560
gtcagtgttg atggacagga tattaggacc ataaatgtaa ggtttctacg ggaaatcatt   1620
ggtgtggtga gtcaggaacc tgtattgttt gccaccacga tagctgaaaa cattcgctat   1680
ggccgtgaaa atgtcaccat ggatgagatt gagaaagctg tcaaggaagc caatgcctat   1740
gactttatca tgaaactgcc tcataaattt gacaccctgg ttggagagag aggggcccag   1800
ttgagtggtg ggcagaagca gaggatcgcc attgcacgtg ccctggttcg caaccccaag   1860
atcctcctgc tggatgaggc cacgtcagcc ttggacacag aaagcgaagc agtggttcag   1920
gtggctctgg ataaggccag aaaaggtcgg accaccattg tgatagctca tcgtttgtct   1980
acagttcgta atgctgacgt catcgctggt ttcgatgatg gagtcattgt ggagaaagga   2040
aatcatgatg aactcatgaa agagaaaggc atttacttca aacttgtcac aatgcagaca   2100
gcaggaaatg aagttgaatt agaaaatgca gctgatgaat ccaaaagtga aattgatgcc   2160
ttggaaatgt cttcaaatga ttcaagatcc agtctaataa gaaaaagatc aactcgtagg   2220
agtgtccgtg gatcacaagc ccaagacaga aagcttagta ccaaagaggc tctggatgaa   2280
agtataccct cagtttcctt ttggaggatt atgaagctaa atttaactga atggccttat   2340
tttgttgttg gtgtattttg tgccattata aatggaggcc tgcaaccagc atttgcaata   2400
atattttcaa agattatagg ggttttttaca agaattgatg atcctgaaac aaaacgacag   2460
aatagtaact tgttttcact attgtttcta gcccttggaa ttatttcttt tattacatttt   2520 ttccttcagg gtttcacatt tggcaaagct ggagagatcc tcaccaagcg gctccgatac   2580
atggttttcc gatccatgct cagacaggat gtgagttggt ttgatgaccc taaaaacacc   2640
actggagcat tgactaccag gctcgccaat gatgctgctc aagttaaagg ggctataggt   2700
tccaggcttg ctgtaattac ccagaatata gcaaatcttg gacaggaat  aattatatcc   2760 ttcatctatg gttggcaact aacactgtta ctcttagcaa ttgtaccat  cattgcaata   2820 gcaggagttg ttgaaatgaa aatgttgtct ggacaagcac tgaaagataa gaagaacta   2880 gaaggttctg ggaagatcgc tactgaagca atagaaaact tccgaaccgt tgtttctttg   2940
actcaggagc agaagtttga acatatgtat gctcagagtt tgcaggtacc atacagaaac   3000 tcttttgagga aagcacacat ctttggaatt acatttttcct tcacccaggc aatgatgtat   3060
ttttcctatg ctggatgttt ccggtttgga gcctacttgg tggcacataa actcatgagc   3120
tttgaggatg ttctgttagt attttcagct gttgtctttg gtgccatggc cgtggggcaa   3180
gtcagttcat tgctcctga  ctatgccaaa gccaaaatat cagcagccca catcatcatg   3240
atcattgaaa aaccccttt  gattgacagc tacagcacgg aaggcctaat gccgaacaca   3300
ttggaaggaa atgtcacatt tggtgaagtt gtattcaact atcccacccg accggacatc   3360
ccagtgcttc agggactgag cctggaggtg aagaagggcc agacgctggc tctggtgggc   3420
agcagtggct gtgggaagag cacagtggtc cagctcctgg agcggttcta cgacccttg   3480
```

| | |
|---|---|
| gcagggaaag tgctgcttga tggcaaagaa ataaagcgac tgaatgttca gtggctccga | 3540 |
| gcacacctgg gcatcgtgtc ccaggagccc atcctgtttg actgcagcat tgctgagaac | 3600 |
| attgcctatg agacaacag ccgggtggtg tcacaggaag agattgtgag ggcagcaaag | 3660 |
| gaggccaaca tacatgcctt catcgagtca ctgcctaata aatatagcac taaagtagga | 3720 |
| gacaaaggaa ctcagctctc tggtggccag aaacaacgca ttgccatagc tcgtgccctt | 3780 |
| gttagacagc ctcatatttt gcttttggat gaagccacgt cagctctgga tacagaaagt | 3840 |
| gaaaaggttg tccaagaagc cctggacaaa gccagagaag ccgcacctg cattgtgatt | 3900 |
| gctcaccgcc tgtccaccat ccagaatgca gacttaatag tggtgtttca gaatggcaga | 3960 |
| gtcaaggagc atggcacgca tcagcagctg ctggcacaga aaggcatcta tttttcaatg | 4020 |
| gtcagtgtcc aggctggaac aaagcgccag | 4050 |

```
<210> SEQ ID NO 162
<211> LENGTH: 990
<212> TYPE: DNA
<213> ORGANISM: Homo sapiens
<220> FEATURE:
<223> OTHER INFORMATION: Arginase1, isoform 1

<400> SEQUENCE: 162
```

| | |
|---|---|
| atgagcgcca agtccagaac catagggatt attggagctc ctttctcaaa gggacagcca | 60 |
| cgaggagggg tggaagaagg ccctacagta ttgagaaagg ctggtctgct tgagaaactt | 120 |
| aaagaacaag taactcaaaa cttttttaatt ttagagtgtg atgtgaagga ttatggggac | 180 |
| ctgcccttg ctgacatccc taatgacagt cccttcaaa ttgtgaagaa tccaaggtct | 240 |
| gtgggaaaag caagcgagca gctggctggc aaggtggcag aagtcaagaa gaacggaaga | 300 |
| atcagcctgg tgctgggcgg agaccacagt ttggcaattg aagcatctc tggccatgcc | 360 |
| agggtccacc ctgatcttgg agtcatctgg gtggatgctc acactgatat caacactcca | 420 |
| ctgacaacca caagtggaaa cttgcatgga caacctgtat cttcctcct gaaggaacta | 480 |
| aaaggaaaga ttcccgatgt gccaggattc tcctgggtga ctccctgtat atctgccaag | 540 |
| gatattgtgt atattggctt gagagacgtg gacccgtgggg aacactacat tttgaaaact | 600 |
| ctaggcatta aatactttc aatgactgaa gtggacagac taggaattgg caaggtgatg | 660 |
| gaagaaacac tcagctatct actaggaaga aagaaaggc caattcatct aagttttgat | 720 |
| gttgacggac tggaccatc tttcacacca gctactggca caccagtcgt gggaggtctg | 780 |
| acatacagag aaggtctcta catcacagaa gaaatctaca aaacagggct actctcagga | 840 |
| ttagatataa tggaagtgaa cccatccctg ggaagacac cagaagaagt aactcgaaca | 900 |
| gtgaacacag cagttgcaat aaccttggct tgtttcggac ttgctcggga gggtaatcac | 960 |
| aagcctattg actaccttaa cccacctaag | 990 |

```
<210> SEQ ID NO 163
<211> LENGTH: 3459
<212> TYPE: DNA
<213> ORGANISM: Homo sapiens
<220> FEATURE:
<223> OTHER INFORMATION: nitric oxide synthase, inducible (iNOS/NOS2),
      isoform 1

<400> SEQUENCE: 163
```

| | |
|---|---|
| atggcctgtc cttggaaatt tctgttcaag accaaattcc accagtatgc aatgaatggg | 60 |
| gaaaaagaca tcaacaacaa tgtggagaaa gccccctgtg ccacctccag tccagtgaca | 120 |

```
caggatgacc ttcagtatca caacctcagc aagcagcaga atgagtcccc gcagcccctc    180
gtggagacgg gaaagaagtc tccagaatct ctggtcaagc tggatgcaac cccattgtcc    240
tccccacggc atgtgaggat caaaaactgg ggcagcggga tgactttcca agacacactt    300
caccataagg ccaaagggat tttaacttgc aggtccaaat cttgcctggg gtccattatg    360
actcccaaaa gtttgaccag aggacccagg acaagccta cccctccaga tgagcttcta    420
cctcaagcta tcgaatttgt caaccaatat acggctcct tcaaagaggc aaaaatagag    480
gaacatctgg ccagggtgga agcggtaaca aaggagatag aaacaacagg aacctaccaa    540
ctgacgggag atgagctcat cttcgccacc aagcaggcct ggcgcaatgc cccacgctgc    600
attgggagga tccagtggtc caacctgcag gtcttcgatg cccgcagctg ttccactgcc    660
cgggaaatgt ttgaacacat ctgcagacac gtgcgttact ccaccaacaa tggcaacatc    720
aggtcggcca tcaccgtgtt cccccagcgg agtgatggca agcacgactt ccgggtgtgg    780
aatgctcagc tcatccgcta tgctggctac cagatgccag atggcagcat cagaggggac    840
cctgccaacg tggaattcac tcagctgtgc atcgacctgg gctggaagcc caagtacggc    900
cgcttcgatg tggtccccct ggtcctgcag gccaatggcc gtgaccctga gctcttcgaa    960
atcccacctg accttgtgct tgaggtggcc atggaacatc ccaaatacga gtggtttcgg   1020
gaactggagc taaagtggta cgccctgcct gcagtggcca acatgctgct tgaggtgggc   1080
ggcctggagt tcccagggtg ccccttcaat ggctggtaca tgggcacaga gatcggagtc   1140
cgggacttct gtgacgtcca gcgctacaac atcctggagg aagtgggcag gagaatgggc   1200
ctggaaacgc acaagctggc ctcgctctgg aaagaccagg ctgtcgttga gatcaacatt   1260
gctgtgctcc atagtttcca gaagcagaat gtgaccatca tggaccacca ctcggctgca   1320
gaatccttca tgaagtacat gcagaatgaa taccggtccc gtggggctg cccggcagac   1380 tggattggc tggtccctcc catgtctggg agcatcaccc ccgtgtttca ccaggagatg   1440
ctgaactacg tcctgtcccc tttctactac tatcaggtag aggcctggaa aacccatgtc   1500
tggcaggacg agaagcggag acccaagaga agagagattc cattgaaagt cttggtcaaa   1560
gctgtgctct ttgcctgtat gctgatgcgc aagacaatgg cgtcccgagt cagagtcacc   1620
atcctctttg cgacagagac aggaaaatca gaggcgctgg cctgggacct ggggccctta   1680
ttcagctgtg ccttcaaccc caaggttgtc tgcatggata agtacaggct gagctgcctg   1740
gaggaggaac ggctgctgtt ggtggtgacc agtacgtttg gcaatggaga ctgccctggc   1800
aatggagaga aactgaagaa atcgctcttc atgctgaaag agctcaacaa caaattcagg   1860
tacgctgtgt ttggcctcgg ctccagcatg taccctcggt tctgcgcctt tgctcatgac   1920
attgatcaga agctgtccca cctgggggcc tctcagctca ccccgatggg agaagggat   1980 gagctcagtg ggcaggagga cgccttccgc agctgggccg tgcaaacctt caaggcagcc   2040
tgtgagacgt ttgatgtccg aggcaaacag cacattcaga tccccaagct ctacacctcc   2100
aatgtgacct gggacccgca ccactacagg ctcgtgcagg actcacagcc tttggacctc   2160
agcaaagccc tcagcagcat gcatgccaag aacgtgttca ccatgaggct caaatctcgg   2220
cagaatctac aaagtccgac atccagccgt gccaccatcc tggtggaact ctcctgtgag   2280
gatggccaag gcctgaacta cctgccgggg gagcaccttg ggtttgccc aggcaaccag   2340 ccggccctgg tccaaggtat cctggagcga gtggtggatg ccccacacc ccaccagaca   2400 gtgcgcctga aggccctgga tgagagtggc agctactggg tcagtgacaa gaggctgccc   2460
ccctgctcac tcagccaggc cctcacctac ttcctggaca tcaccacacc cccaaccag   2520
```

```
ctgctgctcc aaaagctggc ccaggtggcc acagaagagc ctgagagaca gaggctggag   2580
gccctgtgcc agccctcaga gtacagcaag tggaagttca ccaacagccc cacattcctg   2640
gaggtgctag aggagttccc gtccctgcgg gtgtctgctg gcttcctgct ttcccagctc   2700
cccattctga agcccaggtt ctactccatc agctcctccc gggatcacac gcccacagag   2760
atccacctga ctgtggccgt ggtcacctac cacacccgag atggccaggg tcccctgcac   2820
cacggcgtct gcagcacatg gctcaacagc ctgaagcccc aagacccagt gccctgcttt   2880

gtgcggaatg ccagcggctt ccacctcccc gaggatccct cccatccttg catcctcatc   2940
gggcctggca caggcatcgc gcccttccgc agtttctggc agcaacggct ccatgactcc   3000
cagcacaagg gagtgcgggg aggccgcatg accttggtgt ttgggtgccg ccgcccagat   3060
gaggaccaca tctaccagga ggagatgctg gagatggccc agaagggggt gctgcatgcg   3120
gtgcacacag cctattcccg cctgcctggc aagcccaagg tctatgttca ggacatcctg   3180
cggcagcagc tggccagcga ggtgctccgt gtgctccaca aggagccagg ccacctctat   3240
gtttgcgggg atgtgcgcat ggcccgggac gtggcccaca ccctgaagca gctggtggct   3300
gccaagctga aattgaatga ggagcaggtc gaggactatt tctttcagct caagagccag   3360
aagcgctatc acgaagatat ctttggtgct gtatttcctt acgaggcgaa gaaggacagg   3420
gtggcggtgc agcccagcag cctggagatg tcagcgctc                          3459
```

<210> SEQ ID NO 164
<211> LENGTH: 3765
<212> TYPE: DNA
<213> ORGANISM: Homo sapiens
<220> FEATURE:
<223> OTHER INFORMATION: Her2

<400> SEQUENCE: 164

```
atggagctgg cggccttgtg ccgctggggg ctcctcctcg ccctcttgcc ccccggagcc     60
gcgagcaccc aagtgtgcac cggcacagac atgaagctgc ggctccctgc cagtcccgag    120
acccacctgg acatgctccg ccacctctac cagggctgcc aggtggtgca gggaaacctg    180
gaactcacct acctgcccac caatgccagc ctgtccttcc tgcaggatat ccaggaggtg    240
cagggctacg tgctcatcgc tcacaaccaa gtgaggcagg tcccactgca gaggctgcgg    300
attgtgcgag gcacccagct ctttgaggac aactatgccc tggccgtgct agacaatgga    360
gacccgctga acaataccac ccctgtcaca ggggcctccc caggaggcct gcgggagctg    420
cagcttcgaa gcctcacaga gatcttgaaa ggaggggtct tgatccagcg gaacccccag    480
ctctgctacc aggacacgat tttgtggaag gacatcttcc acaagaacaa ccagctggct    540

ctcacactga tagacaccaa ccgctctcgg gcctgccacc cctgttctcc gatgtgtaag    600
ggctcccgct gctggggaga gagttctgag gattgtcaga gcctgacgcg cactgtctgt    660
gccggtggct gtgcccgctg caaggggcca ctgcccactg actgctgcca tgagcagtgt    720
gctgccggct gcacgggccc caagcactct gactgcctgg cctgcctcca cttcaaccac    780
agtggcatct gtgagctgca ctgcccagcc ctggtcacct acaacacaga cacgtttgag    840
tccatgccca atcccgaggg ccggtataca ttcggcgcca gctgtgtgac tgcctgtccc    900
tacaactacc tttctacgga cgtgggatcc tgcaccctcg tctgccccct gcacaaccaa    960

gaggtgacag cagaggatgg aacacagcgg tgtgagaagt gcagcaagcc ctgtgcccga   1020
gtgtgctatg gtctgggcat ggagcacttg cgagaggtga gggcagttac cagtgccaat   1080
```

-continued

```
atccaggagt tgctggctg caagaagatc tttgggagcc tggcatttct gccggagagc   1140
tttgatgggg acccagcctc caacactgcc ccgctccagc cagagcagct ccaagtgttt   1200
gagactctgg aagagatcac aggttaccta tacatctcag catggccgga cagcctgcct   1260
gacctcagcg tcttccagaa cctgcaagta atccggggac gaattctgca caatggcgcc   1320
tactcgctga ccctgcaagg gctgggcatc agctggctgg ggctgcgctc actgagggaa   1380
ctgggcagtg gactggccct catccaccat aacacccacc tctgcttcgt gcacacggtg   1440
ccctgggacc agctctttcg gaacccgcac caagctctgc tccacactgc caaccggcca   1500
gaggacgagt gtgtgggcga gggcctggcc tgccaccagc tgtgcgcccg agggcactgc   1560
tggggtccag ggcccaccca gtgtgtcaac tgcagccagt tccttcgggg ccaggagtgc   1620
gtggaggaat gccgagtact gcaggggctc cccaggagt atgtgaatgc caggcactgt   1680
ttgccgtgcc accctgagtg tcagcccag aatggctcag tgacctgttt tggaccggag   1740
gctgaccagt gtgtggcctg tgcccactat aaggaccctc ccttctgcgt ggcccgctgc   1800
cccagcggtg tgaaacctga cctctcctac atgcccatct ggaagtttcc agatgaggag   1860
ggcgcatgcc agccttgccc catcaactgc acccactcct gtgtggacct ggatgacaag   1920
ggctgccccg ccgagcagag agccagccct ctgacgtcca tcatctctgc ggtggttggc   1980
attctgctgg tcgtggtctt gggggtggtc tttgggatcc tcatcaagcg acggcagcag   2040
aagatccgga agtacacgat gcggagactg ctgcaggaaa cggagctggt ggagccgctg   2100
acacctagcg gagcgatgcc caaccaggcg cagatgcgga tcctgaaaga cggagctg   2160 aggaaggtga aggtgcttgg atctggcgct tttggcacag tctacaaggg catctggatc   2220
cctgatgggg agaatgtgaa aattccagtg gccatcaaag tgttgaggga aaacacatcc   2280
cccaaagcca caaagaaat cttagacgaa gcatacgtga tggctggtgt gggctcccca   2340
tatgtctccc gccttctggg catctgcctg acatccacgg tgcagctggt gacacagctt   2400 atgcccatg gctgcctctt agaccatgtc cgggaaaacc gcggacgcct gggctcccag   2460
gacctgctga actggtgtat gcagattgcc aaggggatga gctacctgga ggatgtgcgg   2520
ctcgtacaca gggacttggc cgctcggaac gtgctggtca agagtcccaa ccatgtcaaa   2580
attacagact cgggctggc tcggctgctg acattgacg agacagagta ccatgcagat   2640
gggggcaagg tgcccatcaa gtggatgcg ctggagtcca ttctccgccg gcggttcacc   2700
caccagagtg atgtgtggag ttatggtgtg actgtgtggg agctgatgac ttttggggcc   2760
aaaccttacg atgggatccc agcccggag atccctgacc tgctggaaaa gggggagcgg   2820
ctgccccagc ccccatctg caccattgat gtctacatga tcatggtcaa atgttggatg   2880
attgactctg aatgtcggcc aagattccgg gagttggtgt ctgaattctc ccgcatggcc   2940
agggaccccc agcgctttgt ggtcatccag aatgaggact tgggcccagc cagtcccttg   3000
gacagcacct tctaccgctc actgctggag gacgatgaca tggggacct ggtggatgct   3060 gaggagtatc tggtacccca gcagggcttc ttctgtccag accctgcccc gggcgctggg   3120
ggcatggtcc accacaggca ccgcagctca tctaccagga gtggcggtgg ggacctgaca   3180
ctagggctgg agccctctga agaggaggcc cccaggtctc cactggcacc ctccgaaggg   3240
gctggctccg atgtatttga tggtgacctg ggaatggggg cagccaaggg gctgcaaagc   3300
ctccccacac atgaccccag ccctctacag cggtacagtg aggacccac agtaccctg   3360 ccctctgaga ctgatggcta cgttgccccc ctgacctgca gccccagcc tgaatatgtg   3420 aaccagccag atgttcggcc ccagccccct tcgccccgag agggccctct gcctgctgcc   3480
```

```
cgacctgctg gtgccactct ggaaaggccc aagactctct ccccagggaa gaatggggtc    3540
gtcaaagacg ttttgcctt tgggggtgcc gtggagaacc ccgagtactt gacaccccag    3600
ggaggagctg cccctcagcc ccaccctcct cctgccttca gcccagcctt cgacaacctc    3660
tattactggg accaggaccc accagagcgg ggggctccac ccagcacctt caaagggaca    3720
cctacggcag agaacccaga gtacctgggt ctggacgtgc cagtg                   3765
```

```
<210> SEQ ID NO 165
<211> LENGTH: 567
<212> TYPE: DNA
<213> ORGANISM: Homo sapiens
<220> FEATURE:
<223> OTHER INFORMATION: KRAS

<400> SEQUENCE: 165
atgactgaat ataaacttgt ggtagttgga gctggtggcg taggcaagag tgccttgacg     60
atacagctaa ttcagaatca tttgtggac gaatatgatc caacaataga ggattcctac    120
aggaagcaag tagtaattga tggagaaacc tgtctcttgg atattctcga cacagcaggt   180
caagaggagt acagtgcaat gagggaccag tacatgagga ctggggaggg ctttctttgt   240
gtatttgcca taaataatac taaatcattt gaagatattc accattatag agaacaaatt   300
aaaagagtta aggactctga agatgtacct atggtcctag taggaaataa atgtgatttg   360
ccttctagaa cagtagacac aaaacaggct caggacttag caagaagtta tggaattcct   420
tttattgaaa catcagcaaa gacaagacag agagtggagg atgcttttta tacattggtg   480
agggagatcc gacaatacag attgaaaaaa atcagcaaag aagaaaagac tcctggctgt   540
gtgaaaatta aaaatgcat tataatg                                        567
```

```
<210> SEQ ID NO 166
<211> LENGTH: 1809
<212> TYPE: DNA
<213> ORGANISM: Homo sapiens
<220> FEATURE:
<223> OTHER INFORMATION: PLK1

<400> SEQUENCE: 166
atgagtgctg cagtgactgc agggaagctg gcacgggcac cggccgaccc tgggaaagcc     60
ggggtccccg gagttgcagc tcccggagct ccggcggcgg ctccaccggc gaaagagatc    120
ccggaggtcc tagtggaccc acgcagccgg cggcgctatg tgcggggccg cttttttggc    180
aagggcggct ttgccaagtg cttcgagatc tcggacgcgg acaccaagga ggtgttcgcg    240
ggcaagattg tgcctaagtc tctgctgctc aagccgcacc agagggagaa gatgtccatg    300
gaaatatcca ttcaccgcag cctcgcccac agcacgtcg taggattcca cggctttttc    360
gaggacaacg acttcgtgtt cgtggtgttg gagctctgcc gccggaggtc tctcctggag    420
ctgcacaaga ggaggaaagc cctgactgag cctgaggccc gatactacct acggcaaatt   480
gtgcttggct gccagtacct gcaccgaaac cgagttattc atcgagacct caagctgggc    540 aacctttcc tgaatgaaga tctggaggtg aaaataggg attttggact ggcaaccaaa    600
gtcgaatatg acgggagag gaagaagacc ctgtgtggga ctcctaatta catagctccc    660
gaggtgctga gcaagaaagg gcacagtttc gaggtggatg tgtggtccat gggtgtatc    720 atgtataact tgttagtggg caaaccacct ttgagactt cttgcctaaa agagacctac    780
ctccggatca agaagaatga atacagtatt cccaagcaca tcaaccccgt ggccgcctcc    840
```

| | |
|---|---|
| ctcatccaga agatgcttca gacagatccc actgcccgcc caaccattaa cgagctgctt | 900 |
| aatgacgagt tctttacttc tggctatatc cctgcccgtc tccccatcac ctgcctgacc | 960 |
| attccaccaa ggttttcgat tgctcccagc agcctggacc ccagcaaccg gaagcccctc | 1020 |
| acagtcctca ataaaggctt ggagaacccc ctgcctgagc gtccccggga aaaagaagaa | 1080 |
| ccagtggttc gagagacagg tgaggtggtc gactgccacc tcagtgacat gctgcagcag | 1140 |
| ctgcacagtg tcaatgcctc caagcccctcg gagcgtgggc tggtcaggca agaggaggct | 1200 |
| gaggatcctg cctgcatccc catcttctgg gtcagcaagt gggtggacta ttcggacaag | 1260 |
| tacggccttg ggtatcagct ctgtgataac agcgtggggg tgctcttcaa tgactcaaca | 1320 |
| cgcctcatcc tctacaatga tggtgacagc ctgcagtaca tagagcgtga cggcactgag | 1380 |
| tcctacctca ccgtgagttc ccatcccaac tccttgatga agaagatcac cctccttaaa | 1440 |
| tatttccgca attacatgag cgagcacttg ctgaaggcag gtgccaacat cacgccgcgc | 1500 |
| gaaggtgatg agctcgcccg gctgccctac ctacggacct ggttccgcac ccgcagcgcc | 1560 |
| atcatcctgc acctcagcaa cggcagcgtg cagatcaact tcttccagga tcacaccaag | 1620 |
| ctcatcttgt gcccactgat ggcagccgtg acctacatcg acgagaagcg ggacttccgc | 1680 |
| acataccgcc tgagtctcct ggaggagtac ggctgctgca aggagctggc cagccggctc | 1740 |
| cgctacgccc gcactatggt ggacaagctg ctgagctcac gctcggccag caaccgtctc | 1800 |
| aaggcctcc | 1809 |

<210> SEQ ID NO 167
<211> LENGTH: 876
<212> TYPE: DNA
<213> ORGANISM: Salmonella typhimurium
<220> FEATURE:
<223> OTHER INFORMATION: dapA, strain LT2

<400> SEQUENCE: 167

| | |
|---|---|
| atgttcacgg gaagtattgt cgcgcttgtt acgccgatgg atgagaaagg taacgtcagt | 60 |
| aggtcttgcc tgaaaaaact cattgattat catgtcgcca acggtacctc ggcgattgtt | 120 |
| tcggttggca ctaccggcga gtctgccacg ctaagccatg atgaacatgg cgatgtcgtg | 180 |
| atgatgacgc tggaactggc tgacggacgt attccggtta tcgccggcac gggcgcaaac | 240 |
| gcgaccgcgg aagcgattag cctgacgcag cgttttaacg atagcggtat tgtaggctgc | 300 |
| ctgacggtaa cgccgtacta caatcgcccc acgcaggaag gtttgttcca gcatttcaaa | 360 |
| gccatcgcgg aacacactga cttgccgcaa attctgtata atgtgccgtc ccgtaccggt | 420 |
| tgcgatatgt tgccggaaac cgtgggtcgt ctggcggaaa taaaaaatat tatcgctatc | 480 |
| aaagaggcga cagggaactt aacccgcgtt caccagatca aagagctggt ttcagacgat | 540 |
| tttattctgc ttagcggcga tgacgcgtct gcgctggact ttatgcaact gggtggtcat | 600 |
| ggcgtgattt ccgttacggc taacgtagcg gcgcgcgaga tggctgacat gtgcaaactg | 660 |
| gcggcggaag gcaatttgc cgaggcgcgc gctatcaacc agcgtctgat gccgttacac | 720 |
| aacaaactat ttgtcgaacc caatcctatc ccggtgaaat gggcatgtaa ggcattgggt | 780 |
| cttgtggcga ccgacacgct gcgcctgcca atgacgccta tcacggacca tggtcgtgac | 840 |
| atcgtcaaag cagcgcttca gcatgctggc ctgctg | 876 |

<210> SEQ ID NO 168
<211> LENGTH: 819
<212> TYPE: DNA
<213> ORGANISM: Salmonella typhimurium
<220> FEATURE:
<223> OTHER INFORMATION: dapB, strain LT2

<400> SEQUENCE: 168

| | |
|---|---|
| atgcatgaag cacaaatccg cgtcgccatt gccggcgccg gtggccgcat gggacggcag | 60 |
| ttaatccagg ccgccatggc gatggaaggt gttcagctgg gtgccgcgct ggagcgcgaa | 120 |
| ggctcttcct tgctgggcag cgatgctggc gaactggcag gggcgggaaa gtccggcgtg | 180 |
| atcgttcaaa gcagccttga ggcggtaaaa gatgattttg acgttttcat cgattttacc | 240 |
| cgtccggaag gcacgttgac gcatctggcg ttttgccgcc agcatggtaa agggatggtg | 300 |
| attggtacta ccggctttga cgacgccggt aaacaagcca ttcgcgaggc gtcacaagag | 360 |
| attgcgatcg ttttcgccgc aaactttagc gtcggcgtta acgtcatgct caagctgctg | 420 |
| gagaaagccg cgaaggtaat gggcgactat agcgatattg aaattattga agcgcaccac | 480 |
| cgccataaag tggatgcacc gtcgggtacg gcgctggcaa tgggcgaggc aatcgccggg | 540 |
| gcgctggata aaaatctgaa ggactgcgcg gtctactcgc gtgaaggtta taccggcgag | 600 |
| cgcgtagcgg gcacgattgg ctttgcgacc gttcgggcgg cgacatcgt cggcgaacat | 660 |
| accgcgatgt ttgccgatat tggcgagcgc gtagagatta cgcataaagc ttccagccgc | 720 |
| atgacgtttg caaatggcgc gttgcgatcg gcgttatggc taaaaacgaa gaaaaatggg | 780 |
| ctatttgaca tgcgggatgt gctggggctg gatgtatta | 819 |

<210> SEQ ID NO 169
<211> LENGTH: 876
<212> TYPE: DNA
<213> ORGANISM: E. coli
<220> FEATURE:
<223> OTHER INFORMATION: dapA

<400> SEQUENCE: 169

| | |
|---|---|
| atgttcacgg gaagtattgt cgcgattgtt actccgatgg atgaaaaagg taatgtctgt | 60 |
| cgggctagct tgaaaaaact gattgattat catgtcgcca gcggtacttc ggcgatcgtt | 120 |
| tctgttggca ccactggcga gtccgctacc ttaaatcatg acgaacatgc tgatgtggtg | 180 |
| atgatgacgc tggatctggc tgatgggcgc attccggtaa ttgccgggac cggcgctaac | 240 |
| gctactgcgg aagccattag cctgacgcag cgcttcaatg acagtggtat cgtcggctgc | 300 |
| ctgacggtaa ccccttacta caatcgtccg tcgcaagaag gttttgtatca gcatttcaaa | 360 |
| gccatcgctg agcatactga cctgccgcaa attctgtata atgtgccgtc ccgtactggc | 420 |
| tgcgatctgc tcccggaaac ggtgggccgt ctggcgaaag taaaaaatat tatcggaatc | 480 |
| aaagaggcaa cagggaactt aacgcgtgta aaccagatca agagctggtt tcagatgat | 540 |
| tttgttctgc tgagcggcga tgatgcgagc gcgctggact tcatgcaatt gggcggtcat | 600 |
| ggggttattt ccgttacgac taacgtcgca gcgcgtgata tggcccagat gtgcaaactg | 660 |
| gcagcagaag aacattttgc cgaggcacgc gttattaatc agcgtctgat gccattacac | 720 |
| aacaaactat tgtcgaacc caatccaatc ccggtgaaat gggcatgtaa ggaactgggt | 780 |
| cttgtggcga ccgatacgct gcgcctgcca atgacaccaa tcaccgacag tggtcgtgag | 840 |
| acggtcagag cggcgcttaa gcatgccggt ttgctg | 876 |

<210> SEQ ID NO 170
<211> LENGTH: 819
<212> TYPE: DNA
<213> ORGANISM: E. coli
<220> FEATURE:

<223> OTHER INFORMATION: dapB

<400> SEQUENCE: 170

| | | | | | |
|---|---|---|---|---|---|
| atgcatgatg | caaacatccg | cgttgccatc | gcgggagccg | ggggggcgtat | gggccgccag | 60 |
| ttgattcagg | cggcgctggc | attagagggc | gtgcagttgg | gcgctgcgct | ggagcgtgaa | 120 |
| ggatcttctt | tactgggcag | cgacgccggt | gagctggccg | gagccgggaa | aacaggcgtt | 180 |
| accgtgcaaa | gcagcctcga | tgcggtaaaa | gatgattttg | atgtgtttat | cgattttacc | 240 |
| cgtccggaag | gtacgctgaa | ccatctcgct | ttttgtcgcc | agcatggcaa | agggatggtg | 300 |
| atcggcacta | cggggtttga | cgaagccggt | aaacaagcaa | ttcgtgacgc | cgctgccgat | 360 |
| attgcgattg | tctttgcggc | caattttagc | gttggcgtta | acgtcatgct | taagctgctg | 420 |
| gagaaagcag | ccaaagtgat | gggtgactac | accgatatcg | aaattattga | agcacatcat | 480 |
| agacataaag | ttgatgcgcc | gtcaggcacc | gcactggcaa | tgggagaggc | gatcgcccac | 540 |
| gcccttgata | aagatctgaa | agattgcgcg | gtctacagtc | gtgaaggcca | caccggtgaa | 600 |
| cgtgtgcctg | gcaccattgg | ttttgccacc | gtgcgtgcag | gtgacatcgt | tggtgaacat | 660 |
| accgcgatgt | tgccgatat | tggcgagcgt | ctggagatca | cccataaggc | gtccagccgt | 720 |
| atgacatttg | ctaacggcgc | ggtaagatcg | gctttgtggt | tgagtggtaa | ggaaagcggt | 780 |
| cttttttgata | tgcgagatgt | acttgatctc | aataatttg | | | 819 |

<210> SEQ ID NO 171
<211> LENGTH: 1218
<212> TYPE: DNA
<213> ORGANISM: E. coli
<220> FEATURE:
<223> OTHER INFORMATION: dapC

<400> SEQUENCE: 171

| | | | | | |
|---|---|---|---|---|---|
| atggcaattg | aacaaacagc | aattacacgc | gcgactttcg | atgaagtgat | cctgccgatt | 60 |
| tatgctccgg | cagagtttat | tccggtaaaa | ggtcagggca | gccgaatctg | ggatcagcaa | 120 |
| ggcaaggagt | atgtcgattt | cgcgggtggc | attgcagtta | cggcgttggg | ccattgccat | 180 |
| cctgcgctgg | tgaacgcgtt | aaaaacccag | ggcgaaactc | tgtggcatat | cagtaacgtt | 240 |
| tcaccaatg | aaccggcgct | gcgtcttggg | cgtaaactga | ttgaggcaac | gtttgccgaa | 300 |
| cgcgtggtgt | ttatgaactc | cggcacggaa | gctaacgaaa | ccgcctttaa | actggcacgc | 360 |
| cattacgcct | gtgtgcgtca | tagcccgttc | aaaaccaaaa | ttattgcctt | ccataacgct | 420 |
| tttcatggtc | gctcgctgtt | taccgtttcg | gtgggtgggc | agccaaaata | ttccgacggc | 480 |
| tttgggccga | aaccggcaga | catcatccac | gttcccttta | acgatctcca | tgcagtgaaa | 540 |
| gcggtgatgg | atgatcacac | ctgtgcggtg | gtggttgagc | cgatccaggg | cgagggcggt | 600 |
| gtgacggcag | cgacgccaga | gttttttgcag | ggcttgcgcg | agctgtgcga | tcaacatcag | 660 |
| gcattattgg | tgtttgatga | agtgcagtgc | gggatgggc | ggaccggcga | tttgtttgct | 720 |
| tacatgcact | acgcgttagc | gccggatatt | ctgacctctg | cgaaagcgtt | aggcggcggc | 780 |
| ttcccgatta | gcgccatgct | gaccacggcg | gaaattgctt | ctgcgtttca | tcctggttct | 840 |
| cacggttcca | cctacggcgg | taatcctctg | gcctgtgcag | tagcggggc | ggcgtttgat | 900 |
| atcatcaata | cccctgaagt | gctggaaggc | attcaggcga | acgccagcg | ttttgttgac | 960 |
| catctgcaga | agatcgatca | gcagtacgat | gtatttagcg | atattcgcgg | tatgggctg | 1020 |
| ttgattggcg | cagagctgaa | accacagtac | aaaggtcggg | cgcgtgattt | cctgtatgcg | 1080 |
| ggcgcagagg | ctggcgtaat | ggtgctgaat | gccggaccgg | atgtgatgcg | ttttgcaccg | 1140 |

```
tcgctggtgg tggaagatgc ggatatcgat gaagggatgc aacgtttcgc ccacgcggtg    1200
gcgaaggtgg ttggggcg                                                  1218

<210> SEQ ID NO 172
<211> LENGTH: 822
<212> TYPE: DNA
<213> ORGANISM: E. coli
<220> FEATURE:
<223> OTHER INFORMATION: dapD

<400> SEQUENCE: 172
atgcagcagt tacagaacat tattgaaacc gcttttgaac gccgtgccga gatcacgcca      60
gccaatgcag acaccgttac ccgcgaagcg gataatcagg tgatcgccct gctggattcc     120
ggcgcactgc gtgtagcgga aaaaattgac ggtcagtggg tgacgcatca gtggttgaaa     180
aaagcggtgc tgctctcttt ccgtattaat gataatcagg tgatcgaagg ggcagaaagc     240
cgctacttcg acaaagtgcc gatgaaattc gccgactacg acgaagcacg tttccagaaa     300
gaaggcttcc gcgttgtgcc accagcggcg gtacgtcagg gtgcgtttat tgcccgtaac     360
accgtgctga tgccgtctta cgtcaacatc ggcgcatatg ttgatgaagg caccatggtt     420
gatacctggg cgaccgtcgg ttcttgtgcg cagattggta aaaacgttca cctttccggt     480
ggcgtgcgca tcggcggcgt gctggaaccg ctgcaggcta acccaaccat gattgaagat     540
aattgcttca tcggcgcgcg ctctgaactg gttgaagggg tgattgtcga agaaggttcc     600
gtcatttcca tggcgtata cattggtcag agcacccgta tttacgaccg tgaaaccggc     660
gaaatccact acgtcgcgt tccggcgggg tctgtggttg tttcaggtaa tctgccgtca     720
aaagatggca atacagcct ctactgtgcg gttatcgtta agaaagttga cgcgaaaact     780
cgcggcaaag tcggcattaa cgaactgctg cgtaccatcg ac                        822

<210> SEQ ID NO 173
<211> LENGTH: 1125
<212> TYPE: DNA
<213> ORGANISM: E. coli
<220> FEATURE:
<223> OTHER INFORMATION: dapE

<400> SEQUENCE: 173
atgtcgtgcc cggttattga gctgacacaa cagcttattc gccgcccttc cctgagtcct     60
gatgatgcag gatgccaggc tttgttgatt gaacgtttgc aggcgatcgg ttttaccgtt     120
gaacgcatgg actttgccga tacgcagaat ttttgggcat ggcgtgggca gggtgaaacg     180
ttagcctttg ccgggcatac cgacgtggtg ccgcctggcg acgccgatcg ttggatcaat     240
cccccgtttg aacccaccat tcgtgacggc atgttattcg ggcgcggtgc ggcagatatg     300
aaaggctcgc tggcggcgat ggtggtggcg gcagaacgtt tgtcgcaca acatcccaac     360 catacggggc gactggcatt tctgatcacc tctgatgaag aagccagtgc ccacaacggt     420
acggtaaaag tcgtcgaagc gttaatggca cgtaatgagc gtctcgatta ctgcctggtt     480
ggcgaaccgt cgagtatcga agtggtaggt gatgtggtga aaatggtcg tcgcggatca     540 ttaacctgca accttaccat tcatggcgtt caggggcatg ttgcctaccc acatctggct     600
gacaatccgg tacatcgcgc agcacctttc cttaatgaat tagtggctat tgagtgggat     660
cagggcaatg aattcttccc ggcgaccagt atgcagattg ccaatattca ggcgggaacg     720
ggcagtaaca acgttattcc gggtgaactg tttgtgcagt ttaacttccg cttcagcacc     780
```

-continued

```
gaactgactg atgagatgat caaagcgcag gtgcttgccc tgcttgaaaa acatcaactg      840
cgctatacgg tggattggtg gctttccggg cagccatttt tgaccgcgcg cggtaaactg      900
gtggatgcgg tcgttaacgc ggttgagcac tataatgaaa ttaaaccgca gctactgacc     960
acaggcggaa cgtccgacgg gcgctttatt gcccgcatgg gggcgcaggt ggtggaactc     1020
gggccggtca atgccactat tcataaaatt aatgaatgtg tgaacgctgc cgacctgcag     1080
ctacttgccc gtatgtatca acgtatcatg aacagctcg tcgcc                      1125
```

<210> SEQ ID NO 174
<211> LENGTH: 1179
<212> TYPE: DNA
<213> ORGANISM: Homo sapiens
<220> FEATURE:
<223> OTHER INFORMATION: p53

<400> SEQUENCE: 174

```
atggaggagc cgcagtcaga tcctagcgtc gagccccctc tgagtcagga aacattttca      60
gacctatgga aactacttcc tgaaaacaac gttctgtccc ccttgccgtc ccaagcaatg     120
gatgatttga tgctgtcccc ggacgatatt gaacaatggt tcactgaaga cccaggtcca     180
gatgaagctc ccagaatgcc agaggctgct ccccgcgtgg cccctgcacc agcagctcct     240
acaccggcgg cccctgcacc agccccctcc tggcccctgt catcttctgt cccttcccag     300
aaaacctacc agggcagcta cggtttccgt ctgggcttct tgcattctgg gacagccaag     360
tctgtgactt gcacgtactc ccctgccctc aacaagatgt ttgccaact ggccaagacc      420 tgccctgtgc agctgtgggt tgattccaca ccccgcccg caccgcgt ccgcgccatg         480 gccatctaca gcagtcaca gcacatgacg gaggttgtga ggcgctgccc ccaccatgag      540
cgctgctcag atagcgatgg tctggcccct cctcagcatc ttatccgagt ggaaggaaat     600
ttgcgtgtgg agtatttgga tgacagaaac acttttcgac atagtgtggt ggtgccctat    660
gagccgcctg aggttggctc tgactgtacc accatccact acaactacat gtgtaacagt    720
tcctgcatgg gcggcatgaa ccggaggccc atcctcacca tcatcacact ggaagactcc    780
agtggtaatc tactgggacg gaacagcttt gaggtgcatg tttgtgcctg tcctgggaga    840
gaccggcgca cagaggaaga gaatctccgc aagaaagggg agcctcacca cgagctgccc    900
ccagggagca ctaagcgagc actgtccaac aacaccagct cctctcccca gccaaagaag    960
aaaccactgg atgagaata tttcaccctt cagatccgtg ggcgtgagcg cttcgagatg    1020
ttccgagagc tgaatgaggc cttggaactc aaggatgccc aggctgggaa ggagccaggg    1080
gggagcaggg ctcactccag ccacctgaag tccaaaaagg gtcagtctac ctcccgccat    1140
aaaaaactca tgttcaagac agaagggcct gactcagac                           1179
```

<210> SEQ ID NO 175
<211> LENGTH: 1470
<212> TYPE: DNA
<213> ORGANISM: Homo sapiens
<220> FEATURE:
<223> OTHER INFORMATION: ERBA

<400> SEQUENCE: 175

```
atggaacaga agccaagcaa ggtggagtgt gggtcagacc cagaggagaa cagtgccagg     60
tcaccagatg aaagcgaaa aagaaagaac ggccaatgtt ccctgaaaac cagcatgtca    120
gggtatatcc ctagttacct ggacaaagac gagcagtgtg tcgtgtgtgg ggacaaggca    180
actggttatc actaccgctg tatcacttgt gagggctgca aggctttctt cgccgcaca    240
```

-continued

| | |
|---|---|
| atccagaaga acctccatcc cacctattcc tgcaaatatg acagctgctg tgtcattgac | 300 |
| aagatcaccc gcaatcagtg ccagctgtgc cgcttcaaga agtgcatcgc cgtgggcatg | 360 |
| gccatggact tggttctaga tgactcgaag cgggtggcca agcgtaagct gattgagcag | 420 |
| aaccgggagc ggcggcggaa ggaggagatg atccgatcac tgcagcagcg accagagccc | 480 |
| actcctgaag agtgggatct gatccacatt gccacagagg cccatcgcag caccaatgcc | 540 |
| cagggcagcc attggaaaca gaggcggaaa ttcctgcccg atgacattgg ccagtcaccc | 600 |
| attgtctcca tgccggacgg agacaaggtg gacctggaag ccttcagcga gtttaccaag | 660 |
| atcatcaccc cggccatcac ccgtgtggtg gactttgcca aaaaactgcc catgttctcc | 720 |
| gagctgcctt gcgaagacca gatcatcctc ctgaaggggt gctgcatgga gatcatgtcc | 780 |
| ctgcgggcgg ctgtccgcta cgaccctgag agcgacaccc tgacgctgag tgggagatg | 840 |
| gctgtcaagc gggagcagct caagaatggc ggcctgggcg tagtctccga cgccatcttt | 900 |
| gaactgggca gtcactctc tgcctttaac ctggatgaca cggaagtggc tctgctgcag | 960 |
| gctgtgctgc taatgtcaac agaccgctcg ggcctgctgt gtgtggacaa gatcgagaag | 1020 |
| agtcaggagg cgtacctgct ggcgttcgag cactacgtca accaccgcaa acacaacatt | 1080 |
| ccgcacttct ggcccaagct gctgatgaag gagagagaag tgcagagttc gattctgtac | 1140 |
| aaggggcag cggcagaagg ccggccgggc gggtcactgg gcgtccaccc ggaaggacag | 1200 |
| cagcttctcg gaatgcatgt tgttcagggt ccgcaggtcc ggcagcttga gcagcagctt | 1260 |
| ggtgaagcgg gaagtctcca agggccggtt cttcagcacc agagcccgaa gagcccgcag | 1320 |
| cagcgtctcc tggagctgct ccaccgaagc ggaattctcc atgcccgagc ggtctgtggg | 1380 |
| gaagacgaca gcagtgaggc ggactccccg agctcctctg aggaggaacc ggaggtctgc | 1440 |
| gaggacctgg caggcaatgc agcctctccc | 1470 |

<210> SEQ ID NO 176
<211> LENGTH: 1317
<212> TYPE: DNA
<213> ORGANISM: Homo sapiens
<220> FEATURE:
<223> OTHER INFORMATION: myc

<400> SEQUENCE: 176

| | |
|---|---|
| atgcccctca acgttagctt caccaacagg aactatgacc tcgactacga ctcggtgcag | 60 |
| ccgtatttct actgcgacga ggaggagaac ttctaccagc agcagcagca gagcgagctg | 120 |
| cagccccgc gcccagcga ggatatctgg aagaaattcg agctgctgcc caccccgccc | 180 |
| ctgtccccta gccgccgctc cgggctctgc tcgccctcct acgttgcggt cacacccttc | 240 |
| tcccttcggg gagacaacga cggcggtggc gggagcttct ccacggccga ccagctggag | 300 |
| atggtgaccg agctgctggg aggagacatg gtgaaccaga gtttcatctg cgacccggac | 360 |
| gacgagacct tcatcaaaaa catcatcatc caggactgta tgtggagcgg cttctcggcc | 420 |
| gccgccaagc tcgtctcaga aagctggcc tcctaccagg ctgcgcgcaa agacagcggc | 480 |
| agcccgaacc ccgccgcgg ccacagcgtc tgctccacct ccagcttgta cctgcaggat | 540 |
| ctgagcgccg ccgcctcaga gtgcatcgac cctcgtgg tcttccccta ccctctcaac | 600 |
| gacagcagct cgcccaagtc ctgcgcctcg caagactcca gcgccttctc tccgtcctcg | 660 |
| gattctctgc tctcctcgac ggagtcctcc ccgcagggca gccccgagcc cctggtgctc | 720 |
| catgaggaga caccgcccac caccagcagc gactctgagg aggaacaaga agatgaggaa | 780 |

-continued

```
gaaatcgatg ttgtttctgt ggaaaagagg caggctcctg gcaaaaggtc agagtctgga    840
tcaccttctg ctggaggcca cagcaaacct cctcacagcc cactggtcct caagaggtgc    900
cacgtctcca cacatcagca caactacgca gcgcctccct ccactcggaa ggactatcct    960
gctgccaaga gggtcaagtt ggacagtgtc agagtcctga cacagatcag caacaaccga   1020
aaatgcacca gccccaggtc ctcggacacc gaggagaatg tcaagaggcg aacacacaac   1080
gtcttggagc gccagaggag gaacgagcta aaacggagct tttttgccct gcgtgaccag   1140
atcccggagt tggaaaacaa tgaaaaggcc cccaaggtag ttatccttaa aaaagccaca   1200
gcatacatcc tgtccgtcca agcagaggag caaaagctca tttctgaaga ggacttgttg   1260
cggaaacgac gagaacagtt gaaacacaaa cttgaacagc tacggaactc ttgtgcg      1317
```

<210> SEQ ID NO 177
<211> LENGTH: 2283
<212> TYPE: DNA
<213> ORGANISM: Homo sapiens
<220> FEATURE:
<223> OTHER INFORMATION: MYB

<400> SEQUENCE: 177

```
atggcccgaa gaccccggca cagcatatat agcagtgacg aggatgatga ggactttgag     60
atgtgtgacc atgactatga tgggctgctt cccaagtctg gaaagcgtca cttggggaaa    120
acaaggtgga cccgggaaga ggatgaaaaa ctgaagaagc tggtggaaca aatggaaca    180 gatgactgga agttattgc caattatctc ccgaatcgaa cagatgtgca gtgccagcac    240
cgatggcaga agtactaaa ccctgagctc atcaagggtc cttggaccaa agaagaagat    300
cagagagtga tagagcttgt acagaaatac ggtccgaaac gttggtctgt tattgccaag    360
cacttaaagg ggagaattgg aaaacaatgt agggagaggt ggcataacca cttgaatcca    420
gaagttaaga aaacctcctg gacagaagag gaagacagaa ttatttacca ggcacacaag    480
agactgggga cagatgggc agaaatcgca aagctactgc ctggacgaac tgataatgct    540
atcaagaacc actggaattc tacaatgcgt cggaaggtcg aacaggaagg ttatctgcag    600
gagtcttcaa aagccagcca gccagcagtg gccacaagct tccagaagaa cagtcatttg    660
atgggttttg ctcaggctcc gcctacagct caactccctg ccactggcca gcccactgtt    720
aacaacgact attcctatta ccacatttct gaagcacaaa atgtctccag tcatgttcca    780 tacctgtag cgttacatgt aaatatagtc aatgtccctc agccagctgc cgcagccatt    840
cagagacact ataatgatga agaccctgag aaggaaaagc gaataaagga attagaattg    900
ctcctaatgt caaccgagaa tgagctaaaa ggacagcagg tgctaccaac acagaaccac    960
acatgcagct accccgggtg gcacagcacc accattgccg accacaccag acctcatgga   1020
gacagtgcac ctgtttcctg tttgggagaa caccactcca ctccatctct gccagcggat   1080
cctggctccc tacctgaaga aagcgcctcg ccagcaaggt gcatgatcgt ccaccagggc   1140
accattctgg ataatgttaa gaacctctta gaatttgcag aaacactcca atttatagat   1200
tctgattctt catcatggtg tgatctcagc agttttgaat ctttgaagag agcagatttt   1260
tcacctagcc aacatcacac aggcaaagcc ctacagcttc agcaaagaga gggcaatggg   1320
actaaacctg caggagaacc tagcccaagg gtgaacaaac gtatgttgag tgagagttca   1380
cttgacccac ccaaggtctt acctcctgca aggcacagca caattccact ggtcatcctt   1440
cgaaaaaaac ggggccaggc cagcccctta gccactggag actgtagctc cttcatattt   1500
gctgacgtca gcagttcaac tcccaagcgt tcccctgtca aaagcctacc cttctctccc   1560
```

-continued

```
tcgcagttct taaacacttc cagtaaccat gaaaactcag acttggaaat gccttcttta    1620
acttccaccc ccctcattgg tcacaaattg actgttacaa caccatttca tagagaccag    1680
actgtgaaaa ctcaaaagga aaatactgtt tttagaaccc cagctatcaa aaggtcaatc    1740
ttagaaagct ctccaagaac tcctacacca ttcaaacatg cacttgcagc tcaagaaatt    1800
aaatacggtc ccctgaagat gctacctcag acaccctctc atctagtaga agatctgcag    1860
gatgtgatca acaggaatc  tgatgaatct ggaattgttg ctgagtttca agaaaatgga    1920
ccacccttac tgaagaaaat caaacaagag gtggaatctc aactgataa  atcaggaaac    1980 ttcttctgct cacaccactg ggaaggggac agtctgaata cccaactgtt cacgcagacc    2040
tcgcctgtgg cagatgcacc gaatattctt acaagctccg ttttaatggc accagcatca    2100
gaagatgaag acaatgttct caaagcattt acagtaccta aaaacaggtc cctggcgagc    2160
cccttgcagc cttgtagcag tacctgggaa cctgcatcct gtggaaagat ggaggagcag    2220
atgacatctt ccagtcaagc tcgtaaatac gtgaatgcat tctcagcccg gacgctggtc    2280
atg                                                                  2283
```

<210> SEQ ID NO 178
<211> LENGTH: 993
<212> TYPE: DNA
<213> ORGANISM: Homo sapiens
<220> FEATURE:
<223> OTHER INFORMATION: JUN

<400> SEQUENCE: 178

```
atgactgcaa agatggaaac gaccttctat gacgatgccc tcaacgcctc gttcctcccg    60
tccgagagcg gaccttatgg ctacagtaac cccaagatcc tgaaacagag catgaccctg    120
aacctggccg acccagtggg gagcctgaag ccgcacctcc gcgccaagaa ctcggacctc    180
ctcacctcgc ccgacgtggg gctgctcaag ctggcgtcgc ccgagctgga gcgcctgata    240
atccagtcca gcaacgggca catcaccacc acgccgaccc ccacccagtt cctgtgcccc    300
aagaacgtga cagatgagca gggggcttc  gccgagggct tcgtgcgcgc cctggccgaa    360
ctgcacagcc agaacacgct gcccagcgtc acgtcggcgg cgcagccggt caacggggca    420
ggcatggtgg ctcccgcggt agcctcggtg gcagggggca gcggcagcgg cggcttcagc    480
gccagcctgc acagcgagcc gccggtctac gcaaacctca gcaacttcaa cccaggcgcg    540
ctgagcagcg gcggcgggc  gccctcctac ggcgcggccg gcctggcctt tcccgcgcaa    600
ccccagcagc agcagcagcc gccgcaccac ctgccccagc agatgcccgt gcagcacccg    660
cggctgcagg ccctgaagga ggagcctcag acagtgcccg agatgcccgg cgagacaccg    720
cccctgtccc ccatcgacat ggagtcccag gagcggatca aggcggagag gaagcgcatg    780
aggaaccgca tcgctgcctc caagtgccga aaaaggaagc tggagagaat cgcccggctg    840
gaggaaaaag tgaaaacctt gaaagctcag aactcggagt ggcgtccac  ggccaacatg    900 ctcagggaac aggtggcaca gcttaaacag aaagtcatga ccacgttaa  cagtgggtgc    960 caactcatgc taacgcagca gttgcaaaca ttt                                 993
```

<210> SEQ ID NO 179
<211> LENGTH: 3633
<212> TYPE: DNA
<213> ORGANISM: Homo sapiens
<220> FEATURE:
<223> OTHER INFORMATION: ERBB

<400> SEQUENCE: 179

```
atgcgaccct ccgggacggc cggggcagcg ctcctggcgc tgctggctgc gctctgcccg      60
gcgagtcggg ctctggagga aaagaaagtt tgccaaggca cgagtaacaa gctcacgcag     120
ttgggcactt tgaagatca ttttctcagc ctccagagga tgttcaataa ctgtgaggtg     180
gtccttggga atttggaaat tacctatgtg cagaggaatt atgatctttc cttcttaaag     240
accatccagg aggtggctgg ttatgtcctc attgccctca acacagtgga gcgaattcct     300
ttggaaaacc tgcagatcat cagaggaaat atgtactacg aaaattccta tgccttagca     360
gtcttatcta actatgatgc aaataaaacc ggactgaagg agctgcccat gagaaattta     420
caggaaatcc tgcatggcgc cgtgcggttc agcaacaacc ctgccctgtg caacgtggag     480
agcatccagt ggcgggacat agtcagcagt gactttctca gcaacatgtc gatggacttc     540
cagaaccacc tgggcagctg ccaaaagtgt gatccaagct gtcccaatgg agctgctgg     600
ggtgcaggag aggagaactg ccagaaactg accaaaatca tctgtgccca gcagtgctcc     660
gggcgctgcc gtggcaagtc ccccagtgac tgctgccaca accagtgtgc tgcaggctgc     720
acaggccccc gggagagcga ctgcctggtc tgccgcaaat ccgagacga agccacgtgc     780
aaggacacct gccccccact catgctctac aaccccacca cgtaccagat ggatgtgaac     840
cccgagggca aatacagctt tggtgccacc tgcgtgaaga agtgtcccg taattatgtg     900
gtgacagatc acggctcgtg cgtccgagcc tgtggggccg acagctatga gatggaggaa     960
gacggcgtcc gcaagtgtaa gaagtgcgaa gggccttgcc gcaaagtgtg taacggaata    1020
ggtattggtg aatttaaaga ctcactctcc ataaatgcta cgaatattaa acacttcaaa    1080
aactgcacct ccatcagtgg cgatctccac atcctgccgg tggcatttag gggtgactcc    1140
ttcacacata ctcctcctct ggatccacag gaactggata ttctgaaaac cgtaaaggaa    1200
atcacagggt ttttgctgat tcaggcttgg cctgaaaaca ggacggacct ccatgccttt    1260
gagaacctag aaatcatacg cggcaggacc aagcaacatg gtcagttttc tcttgcagtc    1320
gtcagcctga acataacatc cttgggatta cgctccctca aggagataag tgatggagat    1380
gtgataattt caggaaacaa aaatttgtgc tatgcaaata caataaactg aaaaaactg    1440
tttgggacct ccggtcagaa aaccaaaatt ataagcaaca gaggtgaaaa cagctgcaag    1500
gccacaggcc aggtctgcca tgccttgtgc tcccccgagg ctgctgggg cccggagccc    1560
agggactgcg tctcttgccg gaatgtcagc cgaggcaggg aatgcgtgga caagtgcaac    1620
cttctggagg gtgagccaag ggagtttgtg gagaactctg agtgcataca gtgccaccca    1680
gagtgcctgc ctcaggccat gaacatcacc tgcacaggac ggggaccaga caactgtatc    1740
cagtgtgccc actacattga cggccccac tgcgtcaaga cctgcccggc aggagtcatg    1800
ggagaaaaca cacccctggt ctggaagtac gcagacgccg ccatgtgtg ccacctgtgc    1860
catccaaact gcacctacgg atgcactggg ccaggtcttg aaggctgtcc aacgaatggg    1920
cctaagatcc cgtccatcgc cactgggatg gtgggggccc tcctcttgct gctggtggtg    1980
gccctgggga tcggcctctt catgcgaagg cgccacatcg ttcggaagcg cacgctgcgg    2040
aggctgctgc aggagaggga gcttgtgagg cctcttacac ccagtggaga agctcccaac    2100
caagctctct tgaggatctt gaaggaaact gaattcaaaa agatcaaagt gctgggctcc    2160
ggtgcgttcg gcacggtgta taagggactc tggatcccag aaggtgagaa agttaaaatt    2220
cccgtcgcta tcaaggaatt aagagaagca acatctccga aagccaacaa ggaaatcctc    2280
gatgaagcct acgtgatggc cagcgtggac aaccccccacg tgtgccgcct gctgggcatc    2340
```

-continued

```
tgcctcacct ccaccgtgca gctcatcacg cagctcatgc ccttcggctg cctcctggac    2400
tatgtccggg aacacaaaga caatattggc tcccagtacc tgctcaactg gtgtgtgcag    2460
atcgcaaagg gcatgaacta cttggaggac cgtcgcttgg tgcaccgcga cctggcagcc    2520
aggaacgtac tggtgaaaac accgcagcat gtcaagatca cagattttgg gctggccaaa    2580
ctgctgggtg cggaagagaa agaataccat gcagaaggag gcaaagtgcc tatcaagtgg    2640
atggcattgg aatcaattt acacagaatc tatcccacc agagtgatgt ctggagctac    2700
ggggtgactg tttgggagtt gatgaccttt ggatccaagc catatgacgg aatccctgcc    2760
agcgagatct cctccatcct ggagaaagga gaacgcctcc ctcagccacc catatgtacc    2820
atcgatgtct acatgatcat ggtcaagtgc tggatgatag acgcagatag tcgcccaaag    2880
ttccgtgagt tgatcatcga attctccaaa atggcccgag accccagcg ctaccttgtc    2940 attcagggggg atgaaagaat gcatttgcca agtcctacag actccaactt ctaccgtgcc    3000
ctgatggatg aagaagacat ggacgacgtg gtggatgccg acgagtacct catcccacag    3060
cagggcttct tcagcagccc ctccacgtca cggactcccc tcctgagctc tctgagtgca    3120
accagcaaca attccaccgt ggcttgcatt gatagaaatg gctgcaaag ctgtcccatc    3180 aaggaagaca gcttcttgca gcgatacagc tcagaccca caggcgcctt gactgaggac    3240
agcatagacg acaccttcct cccagtgcct gaatacataa accagtccgt tcccaaaagg    3300
cccgctggct ctgtgcagaa tcctgtctat cacaatcagc ctctgaaccc cgcgcccagc    3360
agagacccac actaccagga cccccacagc actgcagtgg gcaaccccga gtatctcaac    3420
actgtccagc ccacctgtgt caacagcaca ttcgacagcc ctgcccactg ggcccagaaa    3480
ggcagccacc aaattagcct ggacaaccct gactaccagc aggacttctt tcccaaggaa    3540
gccaagccaa atggcatctt taagggctcc acagctgaaa atgcagaata cctaagggtc    3600
gcgccacaaa gcagtgaatt tattggagca tga                                 3633
```

<210> SEQ ID NO 180
<211> LENGTH: 5589
<212> TYPE: DNA
<213> ORGANISM: Homo sapiens
<220> FEATURE:
<223> OTHER INFORMATION: BRCA1

<400> SEQUENCE: 180

```
atggattat ctgctcttcg cgttgaagaa gtacaaaatg tcattaatgc tatgcagaaa      60
atcttagagt gtcccatctg tctggagttg atcaaggaac ctgtctccac aaagtgtgac    120
cacatatttt gcaaattttg catgctgaaa cttctcaacc agaagaaagg gccttcacag    180
tgtcctttat gtaagaatga tataaccaaa aggagcctac aagaaagtac gagatttagt    240
caacttgttg aagagctatt gaaaatcatt tgtgcttttc agcttgacac aggtttggag    300
tatgcaaaca gctataattt tgcaaaaaag gaaaataact ctcctgaaca tctaaaagat    360
gaagtttcta tcatccaaag tatgggctac agaaaccgtg ccaaaagact tctacagagt    420
gaacccgaaa atccttcctt gcaggaaacc agtctcagtg tccaactctc taaccttgga    480
actgtgagaa ctctgaggac aaagcagcgg atacaacctc aaaagacgtc tgtctacatt    540
gaattgggat ctgattcttc tgaagatacc gttaataagg caacttattg cagtgtggga    600
gatcaagaat tgttacaaat cacccctcaa ggaaccaggg atgaaatcag tttggattct    660
gcaaaaaagg ctgcttgtga attttctgag acggatgtaa caaatactga acatcatcaa    720
```

-continued

```
cccagtaata atgatttgaa caccactgag aagcgtgcag ctgagaggca tccagaaaag    780
tatcagggta gttctgtttc aaacttgcat gtggagccat gtggcacaaa tactcatgcc    840
agctcattac agcatgagaa cagcagttta ttactcacta aagacagaat gaatgtagaa    900
aaggctgaat tctgtaataa aagcaaacag cctggcttag caaggagcca acataacaga    960
tgggctggaa gtaaggaaac atgtaatgat aggcggactc ccagcacaga aaaaaggta   1020 gatctgaatg ctgatcccct gtgtgagaga aagaatgga ataagcagaa actgccatgc   1080
tcagagaatc ctagagatac tgaagatgtt ccttggataa cactaaatag cagcattcag   1140
aaagttaatg agtggttttc cagaagtgat gaactgttag gttctgatga ctcacatgat   1200
ggggagtctg aatcaaatgc caaagtagct gatgtattgg acgttctaaa tgaggtagat   1260
gaatattctg gttcttcaga gaaaatagac ttactggcca gtgatcctca tgaggcttta   1320
atatgtaaaa gtgaaagagt tcactccaaa tcagtagaga gtaatattga agacaaaata   1380
tttgggaaaa cctatcggaa gaaggcaagc ctccccaact taagccatgt aactgaaaat   1440
ctaattatag gagcatttgt tactgagcca cagataatac aagagcgtcc cctcacaaat   1500
aaattaaagc gtaaaaggag acctacatca ggccttcatc ctgaggattt tatcaagaaa   1560
gcagatttgg cagttcaaaa gactcctgaa atgataaatc agggaactaa ccaaacggag   1620
cagaatggtc aagtgatgaa tattactaat agtggtcatg agaataaaac aaaaggtgat   1680
tctattcaga atgagaaaaa tcctaaccca atagaatcac tcgaaaaaga atctgctttc   1740
aaaacgaaag ctgaacctat aagcagcagt ataagcaata tggaactcga attaaatatc   1800
cacaattcaa aagcacctaa aaagaatagg ctgaggagga agtcttctac caggcatatt   1860
catgcgcttg aactagtagt cagtagaaat ctaagcccac ctaattgtac tgaattgcaa   1920
attgatagtt gttctagcag tgaagagata agaaaaaaa agtacaacca aatgccagtc   1980
aggcacagca gaaacctaca actcatggaa ggtaaagaac ctgcaactgg agccaagaag   2040
agtaacaagc caaatgaaca gacaagtaaa agacatgaca gcgatacttt cccagagctg   2100
aagttaacaa atgcacctgg ttcttttact aagtgttcaa ataccagtga acttaaagaa   2160
tttgtcaatc ctagccttcc aagagaagaa aagaagagaa aactagaaac agttaaagtg   2220
tctaataatg ctgaagaccc caaagatctc atgttaagtg gagaaagggt tttgcaaact   2280
gaaagatctg tagagagtag cagtatttca ttggtacctg gtactgatta tggcactcag   2340
gaaagtatct cgttactgga agttagcact ctagggaagg caaaaacaga accaaataaa   2400
tgtgtgagtc agtgtgcagc atttgaaaac cccaagggac taattcatgg ttgttccaaa   2460
gataatagaa atgacacaga aggctttaag tatccattgg acatgaagt taaccacagt   2520 cgggaaacaa gcatagaaat ggaagaaagt gaacttgatg ctcagtattt gcagaataca   2580
ttcaaggttt caaagcgcca gtcatttgct ccgttttcaa atccaggaaa tgcagaagag   2640
gaatgtgcaa cattctctgc ccactctggg tccttaaaga acaaagtcc aaaagtcact   2700 tttgaatgtg aacaaaagga agaaaatcaa ggaaagaatg agtctaatat caagcctgta   2760
cagacagtta atatcactgc aggctttcct gtggttggtc agaaagataa gccagttgat   2820
aatgccaaat gtagtatcaa aggaggctct aggttttgtc tatcatctca gttcagaggc   2880
aacgaaactg gactcattac tccaaataaa catggacttt tacaaaaccc atatcgtata   2940
ccaccacttt ttcccatcaa gtcatttgtt aaaactaaat gtaagaaaaa tctgctagag   3000
gaaaactttg aggaacattc aatgtcacct gaaagagaaa tggaaatga aacattcca   3060 agtacagtga gcacaattag ccgtaataac attagagaaa atgttttaa agaagccagc   3120
```

```
tcaagcaata ttaatgaagt aggttccagt actaatgaag tgggctccag tattaatgaa   3180
ataggttcca gtgatgaaaa cattcaagca gaactaggta gaaacagagg gccaaaattg   3240
aatgctatgc ttagattagg ggttttgcaa cctgaggtct ataaacaaag tcttcctgga   3300
agtaattgta agcatcctga aataaaaaag caagaatatg aagaagtagt tcagactgtt   3360
aatacagatt tctctccata tctgatttca gataacttag aacagcctat gggaagtagt   3420
catgcatctc aggtttgttc tgagacacct gatgacctgt tagatgatgg tgaaataaag   3480
gaagatacta gttttgctga aaatgacatt aaggaaagtt ctgctgtttt tagcaaaagc   3540
gtccagaaag gagagcttag caggagtcct agccctttca cccatacaca tttggctcag   3600
ggttaccgaa gaggggccaa gaaattagag tcctcagaag agaacttatc tagtgaggat   3660
gaagagcttc cctgcttcca cacttgtta tttggtaaag taaacaatat accttctcag    3720
tctactaggc atagcaccgt tgctaccgag tgtctgtcta agaacacaga ggagaattta   3780
ttatcattga agaatagctt aaatgactgc agtaaccagg taatattggc aaaggcatct   3840
caggaacatc accttagtga ggaaacaaaa tgttctgcta gcttgttttc ttcacagtgc   3900
agtgaattgg aagacttgac tgcaaataca aacacccagg atcctttctt gattggttct   3960
tccaaacaaa tgaggcatca gtctgaaagc cagggagttg gtctgagtga caaggaattg   4020
gtttcagatg atgaagaaag aggaacgggc ttggaagaaa ataatcaaga agagcaaagc   4080
atggattcaa acttaggtga agcagcatct gggtgtgaga gtgaaacaag cgtctctgaa   4140
gactgctcag ggctatcctc tcagagtgac attttaacca ctcagcagag ggataccatg   4200
caacataacc tgataaagct ccagcaggaa atggctgaac tagaagctgt gttagaacag   4260
catgggagcc agccttctaa cagctaccct tccatcataa gtgactcttc tgcccttgag   4320
gacctgcgaa atccagaaca aagcacatca gaaaaagcag tattaacttc acagaaaagt   4380
agtgaatacc ctataagcca gaatccagaa ggcctttctg ctgacaagtt tgaggtgtct   4440
gcagatagtt ctaccagtaa aaataaagaa ccaggagtgg aaaggtcatc cccttctaaa   4500
tgcccatcat tagatgatag gtggtacatg cacagttgct ctgggagtct tcagaataga   4560
aactacccat ctcaagagga gctcattaag gttgttgatg tggaggagca acagctggaa   4620
gagtctgggc cacacgattt gacgaaaaca tcttacttgc caaggcaaga tctagaggga   4680
accccttacc tggaatctgg aatcagcctc ttctctgatg accctgaatc tgatccttct   4740
gaagacagag ccccagagtc agctcgtgtt ggcaacatac catcttcaac ctctgcattg   4800
aaagttcccc aattgaaagt tgcagaatct gcccagagtc cagctgctgc tcatactact   4860
gatactgctg ggtataatgc aatggaagaa agtgtgagca gggagaagcc agaattgaca   4920
gcttcaacag aaagggtcaa caaaagaatg tccatggtgg tgtctggcct gaccccagaa   4980
gaatttatgc tcgtgtacaa gtttgccaga aaacaccaca tcactttaac taatctaatt   5040
actgaagaga ctactcatgt tgttatgaaa acagatgctg agtttgtgtg tgaacggaca   5100
ctgaaatatt ttctaggaat tgcgggagga aaatgggtag ttagctattt ctgggtgacc   5160
cagtctatta agaaagaaa aatgctgaat gagcatgatt ttgaagtcag aggagatgtg   5220
gtcaatggaa gaaaccacca aggtccaaag cgagcaagag aatcccagga cagaaagatc   5280 ttcaggggc tagaaatctg ttgctatggg cccttcacca acatgcccac agatcaactg   5340
gaatggatgg tacagctgtg tggtgcttct gtggtgaagg agctttcatc attcacccett  5400 ggcacaggtg tccacccaat tgtggttgtg cagccagatg cctggacaga ggacaatggc   5460
```

| | |
|---|---:|
| ttccatgcaa ttgggcagat gtgtgaggca cctgtggtga cccgagagtg ggtgttggac | 5520 |
| agtgtagcac tctaccagtg ccaggagctg acacctacc tgatacccca gatcccccac | 5580 |
| agccactac | 5589 |

<210> SEQ ID NO 181
<211> LENGTH: 10254
<212> TYPE: DNA
<213> ORGANISM: Homo sapiens
<220> FEATURE:
<223> OTHER INFORMATION: BRCA2

<400> SEQUENCE: 181

| | |
|---|---:|
| atgcctattg gatccaaaga gaggccaaca ttttttgaaa ttttaagac acgctgcaac | 60 |
| aaagcagatt taggaccaat aagtcttaat tggtttgaag aactttcttc agaagctcca | 120 |
| ccctataatt ctgaacctgc agaagaatct gaacataaaa acaacaatta cgaaccaaac | 180 |
| ctatttaaaa ctccacaaag gaaaccatct tataatcagc tggcttcaac tccaataata | 240 |
| ttcaaagagc aagggctgac tctgccgctg taccaatctc ctgtaaaaga attagataaa | 300 |
| ttcaaattag acttaggaag gaatgttccc aatagtagac ataaaagtct tcgcacagtg | 360 |
| aaaactaaaa tggatcaagc agatgatgtt tcctgtccac ttctaaattc ttgtcttagt | 420 |
| gaaagtcctg ttgttctaca atgtacacat gtaacaccac aaagagataa gtcagtggta | 480 |
| tgtgggagtt tgtttcatac accaaagttt gtgaagggtc gtcagacacc aaaacatatt | 540 |
| tctgaaagtc taggagctga ggtggatcct gatatgtctt ggtcaagttc tttagctaca | 600 |
| ccacccaccc ttagttctac tgtgctcata gtcagaaatg aagaagcatc tgaaactgta | 660 |
| tttcctcatg atactactgc taatgtgaaa agctatttt ccaatcatga tgaaagtctg | 720 |
| aagaaaaatg atagatttat cgcttctgtg acagacagtg aaaacacaaa tcaaagagaa | 780 |
| gctgcaagtc atggatttgg aaaaacatca gggaattcat ttaaagtaaa tagctgcaaa | 840 |
| gaccacattg gaaagtcaat gccaaatgtc ctagaagatg aagtatatga acagttgta | 900 |
| gatacctctg aagaagatag tttttcatta tgttttccta atgtagaac aaaaaatcta | 960 |
| caaaagtaa gaactagcaa gactaggaaa aaaattttcc atgaagcaaa cgctgatgaa | 1020 |
| tgtgaaaaat ctaaaaacca gtgaaagaa aaatactcat ttgtatctga gtggaacca | 1080 |
| aatgatactg atccattaga ttcaaatgta gcaaatcaga gcccttga gagtggaagt | 1140 |
| gacaaaatct ccaaggaagt tgtaccgtct ttggcctgtg aatggtctca actaacccctt | 1200 |
| tcaggtctaa atgagccca gatggagaaa atacccctat tgcatatttc ttcatgtgac | 1260 |
| caaaatattt cagaaaaaga cctattagac acagagaaca aagaagaa agattttctt | 1320 |
| acttcagaga attctttgcc acgtatttct agcctaccaa atcagaaa gccattaaat | 1380 |
| gaggaaacag tggtaaataa gagagatgaa gagcagcatc ttgaatctca tacagactgc | 1440 |
| attcttgcag taaagcaggc aatatctgga acttctccag tggcttcttc atttcagggt | 1500 |
| atcaaaaagt ctatattcag aataagagaa tcacctaaag gactttcaa tgcaagttt | 1560 |
| tcaggtcata tgactgatcc aaactttaaa aagaaactg aagcctctga agtggactg | 1620 |
| gaaatacata ctgtttgctc acagaaggag gactccttat gtccaaattt aattgataat | 1680 |
| ggaagctggc cagccaccac cacacagaat tctgtagctt tgaagaatgc aggtttaata | 1740 |
| tccacttga aaagaaaac aaataagttt atttatgcta acatgatga acatcttat | 1800 |
| aaaggaaaaa aaataccgaa agaccaaaaa tcagaactaa ttaactgttc agcccagttt | 1860 |
| gaagcaaatg cttttgaagc accacttaca tttgcaaatg ctgattcagg tttattgcat | 1920 |

```
tcttctgtga aaagaagctg ttcacagaat gattctgaag aaccaacttt gtccttaact    1980
agctcttttg ggacaattct gaggaaatgt tctagaaatg aaacatgttc taataataca    2040
gtaatctctc aggatcttga ttataaagaa gcaaaatgta ataaggaaaa actacagtta    2100
tttattaccc cagaagctga ttctctgtca tgcctgcagg aaggacagtg tgaaaatgat    2160
ccaaaaagca aaaagttttc agatataaaa gaagaggtct tggctgcagc atgtcaccca    2220
gtacaacatt caaagtggaa atacagtgat actgactttc aatcccagaa aagtctttta    2280
tatgatcatg aaaatgccag cactcttatt ttaactccta cttccaagga tgttctgtca    2340
aacctagtca tgatttctag aggcaaagaa tcatacaaaa tgtcagacaa gctcaaaggt    2400
aacaattatg aatctgatgt tgaattaacc aaaaatattc ccatggaaaa gaatcaagat    2460
gtatgtgctt taaatgaaaa ttataaaaac gttgagctgt tgccacctga aaatacatg     2520
agagtagcat caccttcaag aaaggtacaa ttcaaccaaa acacaaatct aagagtaatc    2580
caaaaaatc aagaagaaac tacttcaatt tcaaaaataa ctgtcaatcc agactctgaa     2640
gaacttttct cagacaatga gaataatttt gtcttccaag tagctaatga aaggaataat    2700
cttgctttag gaaatactaa ggaacttcat gaaacagact tgacttgtgt aaacgaaccc    2760
attttcaaga actctaccat ggttttatat ggagacacag gtgataaaca agcaacccaa    2820
gtgtcaatta aaaagatttt ggtttatgtt cttgcagagg agaacaaaaa tagtgtaaag    2880
cagcatataa aaatgactct aggtcaagat ttaaaatcgg acatctcctt gaatatagat    2940
aaaataccag aaaaaaataa tgattacatg aacaaatggg caggactctt aggtccaatt    3000
tcaaatcaca gttttggagg tagcttcaga acagcttcaa ataaggaaat caagctctct    3060
gaacataaca ttaagaagag caaaatgttc ttcaaagata ttgaagaaca atatcctact    3120
agtttagctt gtgttgaaat tgtaaatacc ttggcattag ataatcaaaa gaaactgagc    3180
aagcctcagt caattaatac tgtatctgca catttacaga gtagtgtagt tgtttctgat    3240
tgtaaaaata gtcatataac ccctcagatg ttattttcca agcaggattt taattcaaac    3300
cataatttaa cacctagcca aaaggcagaa attacagaac tttctactat attagaagaa    3360
tcaggaagtc agtttgaatt tactcagttt agaaaaccaa gctacatatt gcagaagagt    3420
acatttgaag tgcctgaaaa ccagatgact atcttaaaga ccacttctga ggaatgcaga    3480
gatgctgatc ttcatgtcat aatgaatgcc ccatcgattg gtcaggtaga cagcagcaag    3540
caatttgaag gtacagttga aattaaacgg aagtttgctg gcctgttgaa aaatgactgt    3600
aacaaaagtg cttctggtta tttaacagat gaaaatgaag tggggtttag gggcttttat    3660
tctgctcatg gcacaaaact gaatgtttct actgaagctc tgcaaaaagc tgtgaaactg    3720
tttagtgata ttgagaatat tagtgaggaa acttctgcag aggtacatcc aataagttta    3780
tcttcaagta aatgtcatga ttctgttgtt tcaatgttta agatagaaaa tcataatgat    3840
aaaactgtaa gtgaaaaaaa taataaatgc caactgatat tacaaaataa tattgaaatg    3900
actactggca cttttgttga agaaattact gaaaattaca agagaaatac tgaaaatgaa    3960
gataacaaat atactgctgc cagtagaaat tctcataact tagaatttga tggcagtgat    4020
tcaagtaaaa atgatactgt ttgtattcat aaagatgaaa cggacttgct atttactgat    4080
cagcacaaca tatgtcttaa attatctggc cagtttatga aggagggaaa cactcagatt    4140
aaagaagatt tgtcagattt aactttttg gaagttgcga aagctcaaga agcatgtcat    4200
ggtaatactt caaataaaga acagttaact gctactaaaa cggagcaaaa tataaaagat    4260
```

-continued

```
tttgagactt ctgatacatt ttttcagact gcaagtggga aaaatattag tgtcgccaaa    4320
gagtcattta ataaaattgt aaatttcttt gatcagaaac cagaagaatt gcataacttt    4380
tccttaaatt ctgaattaca ttctgacata agaaagaaca aaatggacat tctaagttat    4440
gaggaaacag acatagttaa acacaaaata ctgaaagaaa gtgtcccagt tggtactgga    4500
aatcaactag tgaccttcca gggacaaccc gaacgtgatg aaaagatcaa agaacctact    4560
ctattgggtt ttcatacagc tagcgggaaa aagttaaaa ttgcaaagga atctttggac    4620
aaagtgaaaa accttttga tgaaaagag caaggtacta gtgaaatcac cagttttagc    4680
catcaatggg caaagaccct aaagtacaga gaggcctgta aagaccttga attagcatgt    4740
gagaccattg agatcacagc tgccccaaag tgtaaagaaa tgcagaattc tctcaataat    4800
gataaaaacc ttgttctat tgagactgtg gtgccaccta agctcttaag tgataattta    4860
tgtagacaaa ctgaaaatct caaaacatca aaaagtatct ttttgaaagt taaagtacat    4920
gaaaatgtag aaaagaaac agcaaaaagt cctgcaactt gttacacaaa tcagtcccct    4980
tattcagtca ttgaaaattc agccttagct ttttacacaa gttgtagtag aaaaacttct    5040
gtgagtcaga cttcattact tgaagcaaaa aaatggctta gagaaggaat atttgatggt    5100
caaccagaaa gaataaatac tgcagattat gtaggaaatt atttgtatga aaataattca    5160
aacagtacta tagctgaaaa tgacaaaaat catctctccg aaaaacaaga tacttattta    5220
agtaacagta gcatgtctaa cagctattcc taccattctg atgaggtata taatgattca    5280
ggatatctct caaaaaataa acttgattct ggtattgagc cagtattgaa gaatgttgaa    5340
gatcaaaaaa acactagttt ttccaaagta atatccaatg taaaagatgc aaatgcatac    5400
ccacaaactg taaatgaaga tatttgcgtt gaggaacttg tgactagctc ttcaccctgc    5460
aaaaataaaa atgcagccat taaattgtcc atatctaata gtaataattt tgaggtaggg    5520
ccacctgcat ttaggatagc cagtggtaaa atcgtttgtg tttcacatga aacaattaaa    5580
aaagtgaaag acatatttac agacagtttc agtaaagtaa ttaaggaaaa caacgagaat    5640
aaatcaaaaa tttgccaaac gaaaattatg gcaggttgtt acgaggcatt ggatgattca    5700
gaggatattc ttcataactc tctagataat gatgaatgta gcacgcattc acataaggtt    5760
tttgctgaca ttcagagtga agaaattta caacataacc aaaatatgtc tggattggag    5820
aaagtttcta aatatcacc ttgtgatgtt agtttggaaa cttcagatat atgtaaatgt    5880
agtataggga agcttcataa gtcagtctca tctgcaaata cttgtgggat ttttagcaca    5940
gcaagtggaa aatctgtcca ggtatcagat gcttcattac aaaacgcaag acaagtgttt    6000
tctgaaatag aagatagtac caagcaagtc ttttccaaag tattgtttaa agtaacgaa    6060 cattcagacc agctcacaag agaagaaaat actgctatac gtactccaga acatttaata    6120
tcccaaaaag ctttttcata taatgtggta aattcatctg ctttctctgg atttagtaca    6180
gcaagtggaa agcaagtttc cattttagaa agttccttac acaaagttaa gggagtgtta    6240
gaggaatttg atttaatcag aactgagcat agtcttcact attcacctac gtctagacaa    6300
aatgtatcaa aatacttcc tcgtgttgat aagagaaacc cagagcactg tgtaaactca    6360 gaaatgaaa aaacctgcag taagaaattt aaattatcaa ataacttaaa tgttgaaggt    6420
ggttcttcag aaaataatca ctctattaaa gtttctccat atctctctca atttcaacaa    6480
gacaaacaac agttggtatt aggaaccaaa gtgtcacttg ttgagaacat tcatgttttg    6540 ggaaagaac aggcttcacc taaaaacgta aaaatggaaa ttggtaaaac tgaaactttt    6600
tctgatgttc ctgtgaaaac aaatatagaa gtttgttcta cttactccaa agattcagaa    6660
```

```
aactactttg aaacagaagc agtagaaatt gctaaagctt ttatggaaga tgatgaactg    6720
acagattcta aactgccaag tcatgccaca cattctcttt ttacatgtcc cgaaaatgag    6780
gaaatggttt tgtcaaattc aagaattgga aaaagaagag gagagcccct tatcttagtg    6840
ggagaaccct caatcaaaag aaacttatta aatgaatttg acaggataat agaaaatcaa    6900
gaaaaatcct taaaggcttc aaaaagcact ccagatggca aataaaaga tcgaagattg     6960 tttatgcatc atgtttcttt agagccgatt acctgtgtac cctttcgcac aactaaggaa    7020
cgtcaagaga tacagaatcc aaattttacc gcacctggtc aagaatttct gtctaaatct    7080
catttgtatg aacatctgac tttgaaaaaa tcttcaagca atttagcagt ttcaggacat    7140
ccattttatc aagttctgc tacaagaaat gaaaaaatga cacttgat tactacaggc       7200 agaccaacca aagtctttgt tccacctttt aaaactaaat cacattttca cagagttgaa    7260
cagtgtgtta ggaatattaa cttggaggaa aacagacaaa agcaaaacat tgatggacat    7320
ggctctgatg atagtaaaaa taagattaat gacaatgaga ttcatcagtt taacaaaaac    7380
aactccaatc aagcagcagc tgtaactttc acaaagtgtg aagaagaacc tttagattta    7440
attacaagtc ttcagaatgc cagagatata caggatatgc gaattaagaa gaaacaaagg    7500
caacgcgtct ttccacagcc aggcagtctg tatcttgcaa aacatccac tctgcctcga     7560 atctctctga aagcagcagt aggaggccaa gttccctctg cgtgttctca taaacagctg    7620
tatacgtatg gcgtttctaa acattgcata aaaattaaca gcaaaaatgc agagtctttt    7680
cagtttcaca ctgaagatta ttttggtaag gaaagtttat ggactggaaa aggaatacag    7740
ttggctgatg gtggatggct catacccctcc aatgatggaa aggctggaaa agaagaattt   7800
tatagggctc tgtgtgacac tccaggtgtg gatccaaagc ttatttctag aatttgggtt    7860
tataatcact atagatggat catatggaaa ctggcagcta tggaatgtgc ctttcctaag    7920
gaatttgcta atagatgcct aagcccagaa agggtgcttc ttcaactaaa atacagatat    7980
gatacggaaa ttgatagaag cagaagatcg gctataaaaa agataatgga aagggatgac    8040
acagctgcaa aaacacttgt tctctgtgtt tctgacataa tttcattgag cgcaaatata    8100
tctgaaactt ctagcaataa aactagtagt gcagataccc aaaaagtggc cattattgaa    8160
cttacagatg ggtggtatgc tgttaaggcc cagttagatc ctccccctctt agctgtctta   8220 aagaatggca gactgacagt tggtcagaag attattcttc atggagcaga actggtgggc    8280
tctcctgatg cctgtacacc tcttgaagcc ccagaatctc ttatgttaaa gatttctgct    8340
aacagtactc ggcctgctcg ctggtatacc aaacttggat tctttcctga ccctagacct    8400
tttcctctgc ccttatcatc gcttttcagt gatggaggaa atgttggttg tgttgatgta    8460
attattcaaa gagcataccc tatacagtgg atggagaaga catcatctgg attatacata    8520
tttcgcaatg aaagagagga agaaaaggaa gcagcaaaat atgtggaggc ccaacaaaag    8580
agactagaag cctattcac taaaattcag gaggaatttg aagaacatga agaaacaca      8640 acaaaaccat atttaccatc acgtgcacta acaagacagc aagttcgtgc tttgcaagat    8700
ggtgcagagc tttatgaagc agtgaagaat gcagcagacc cagcttacct tgagggttat    8760
ttcagtgaag agcagttaag agccttgaat aatcacagga aatgttgaa tgataagaaa     8820 caagctcaga tccagttgga aattaggaag gccatggaat ctgctgaaca aaaggaacaa    8880
ggtttatcaa gggatgtcac aaccgtgtgg aagttgcgta ttgtaagcta ttcaaaaaaa    8940
gaaaaagatt cagttatact gagtatttgg cgtccatcat cagatttata ttctctgtta    9000
```

```
acagaaggaa agagatacag aatttatcat cttgcaactt caaaatctaa aagtaaatct    9060
gaaagagcta acatacagtt agcagcgaca aaaaaaactc agtatcaaca actaccggtt    9120
tcagatgaaa ttttatttca gatttaccag ccacgggagc cccttcactt cagcaaattt    9180
ttagatccag actttcagcc atcttgttct gaggtggacc taataggatt tgtcgtttct    9240
gttgtgaaaa aaacaggact tgccccttc gtctatttgt cagacgaatg ttacaattta    9300
ctggcaataa agttttggat agaccttaat gaggacatta ttaagcctca tatgttaatt    9360
gctgcaagca acctccagtg gcgaccagaa tccaaatcag gccttcttac tttatttgct    9420
ggagattttt ctgtgttttc tgctagtcca aaagagggcc actttcaaga gacattcaac    9480
aaaatgaaaa atactgttga gaatattgac atactttgca atgaagcaga aaacaagctt    9540
atgcatatac tgcatgcaaa tgatcccaag tggtccaccc caactaaaga ctgtacttca    9600
gggccgtaca ctgctcaaat cattcctggt acaggaaaca agcttctgat gtcttctcct    9660
aattgtgaga tatattatca aagtcccttta tcactttgta tggccaaaag gaagtctgtt    9720
tccacacctg tctcagccca gatgacttca aagtcttgta aaggggagaa agagattgat    9780
gaccaaaaga actgcaaaaa gagaagagcc ttggatttct tgagtagact gcctttacct    9840
ccacctgtta gtcccatttg tacatttgtt tctccggctg cacagaaggc atttcagcca    9900
ccaaggagtt gtggcaccaa atacgaaaca cccataaaga aaaagaact gaattctcct    9960 cagatgactc catttaaaaa attcaatgaa atttctcttt tggaaagtaa ttcaatagct    10020
gacgaagaac ttgcattgat aaatacccaa gctctttgt ctggttcaac aggagaaaaa    10080
caatttatat ctgtcagtga atccactagg actgctccca ccagttcaga agattatctc    10140
agactgaaac gacgttgtac tacatctctg atcaaagaac aggagagttc ccaggccagt    10200
acggaagaat gtgagaaaaa taagcaggac acaattacaa ctaaaaaata tatc          10254
```

<210> SEQ ID NO 182
<211> LENGTH: 2487
<212> TYPE: DNA
<213> ORGANISM: Homo sapiens
<220> FEATURE:
<223> OTHER INFORMATION: MCC

<400> SEQUENCE: 182

```
atgaattccg gagttgccat gaaatatgga aacgactcct cggccgagct gagtgagctc     60
cattcagcag ccctggcatc actaaaggga gatatagtgg aacttaataa acgtctccag    120
caaacagaga gggaacggga ccttctggaa aagaaattgg ccaaggcaca gtgcgagcag    180
tcccacctca tgagagagca tgaggatgtc caggagcgaa cgacgcttcg ctatgaggaa    240
cgcatcacag agctccacag cgtcattgcg gagctcaaca agaagataga ccgtctgcaa    300
ggcaccacca tcagggagga agatgagtac tcagaactgc gatcagaact cagccagagc    360
caacacgagg tcaacgagga ctctcgaagc atggaccaag accagacctc tgtctctatc    420
cccgaaaacc agtctaccat ggttactgct gacatggaca actgcagtga cctgaactca    480
gaactgcaga gggtgctgac agggctggag aatgttgtct gcggcaggaa gaagagcagc    540
tgcagcctct ccgtggccga ggtggacagg cacattgagc agctcaccac agccagcgag    600
cactgtgacc tggctattaa gacagtcgag gagattgagg gggtgcttgg ccgggacctg    660
tatcccaacc tggctgaaga gaggtctcgg tgggagaagg agctggctgg gctgagggaa    720
gagaatgaga gcctgactgc catgctgtgc agcaaagagg aagaactgaa ccggactaag    780
gccaccatga atgccatccg ggaagagcgg gaccggctcc ggaggcgggt cagagagctt    840
```

```
caaactcgac tacagagcgt gcaggccaca ggtccctcca gccctggccg cctcacttcc    900
accaaccgcc cgattaaccc cagcactggg gagctgagca caagcagcag cagcaatgac    960
attcccatcg ccaagattgc tgagagggtg aagctatcaa agacaaggtc cgaatcgtca   1020
tcatctgatc ggccagtcct gggctcagaa atcagtagca tagggtatc cagcagtgtg    1080
gctgaacacc tggcccactc acttcaggac tgctccaata ccaagagat tttccaaaca    1140
ctctactcac acggatctgc catctcagaa agcaagatta gagagtttga ggtgaaaaca   1200
gaacggctga atagccggat tgagcacctc aaatcccaaa atgacctcct gaccataacc   1260
ttggaggaat gtaaaagcaa tgctgagagg atgagcatgc tggtgggaaa atacgaatcc   1320
aatgccacag cgctgaggct ggccttgcag tacagcgagc agtgcatcga agcctacgaa   1380
ctcctcctgg cgctggcaga gagtgagcag agcctcatcc tggggcagtt ccgagcggcg   1440
ggcgtggggt cctcccctgg agaccagtcg ggggatgaaa acatcactca gatgctcaag   1500
cgagctcatg actgccggaa gacagctgag aacgctgcca aggccctgct catgaagctg   1560
gacggcagct gtggggagc cttgcccgtg ccggctgca gcgtgcagcc ctgggagagc      1620
ctttcctcca acagccacac cagcacaacc agctccacag ccagtagttg cgacaccgag   1680
ttcactaaag aagacgagca gaggctgaag gattatatcc agcagctcaa gaatgacagg   1740
gctgcggtca gctgaccat gctggagctg gaaagcatcc acatcgatcc tctcagctat    1800
gacgtcaagc ctcggggaga cagccagagg ctggatctgg aaaacgcagt gcttatgcag   1860
gagctcatgg ccatgaagga ggagatggcc gagttgaagg cccagctcta cctactggag   1920
aaagagaaga aggccctgga gctgaagctg agcacgcggg aggcccagga gcaggcctac   1980
ctggtgcaca ttgagcacct gaagtccgag gtggaggagc agaaggagca gcggatgcga   2040
tccctcagct ccaccagcag cggcagcaaa gataaacctg gcaaggagtg tgctgatgct   2100
gcctccccag ctctgtccct agctgaactc aggacaacgt gcagcgagaa tgagctggct   2160
gcggagttca ccaacgccat cgtcgagaa aagaagttga aggccagagt tcaagagctg    2220
gtgagtgcct tggagagact caccaagagc agtgaaatcc gacatcagca atctgcagag   2280
ttcgtgaatg atctaaagcg ggccaacagc aacctggtgg ctgcctatga aaagcaaag    2340
aaaaagcatc aaaacaaact gaagaagtta gagtcgcaga tgatggccat ggtggagaga   2400
catgagaccc aagtgaggat gctcaagcaa agaatagctc tgctagagga ggagaactcc   2460
aggcccacaca ccaatgaaac ttcgctt                                     2487
```

<210> SEQ ID NO 183
<211> LENGTH: 2253
<212> TYPE: DNA
<213> ORGANISM: Homo sapiens
<220> FEATURE:
<223> OTHER INFORMATION: EZH2, isoform 1

<400> SEQUENCE: 183

```
atgggccaga ctgggaagaa atctgagaag ggaccagttt gttggcggaa gcgtgtaaaa     60
tcagagtaca tgcgactgag acagctcaag aggttcagac gagctgatga agtaaagagt    120
atgtttagtt ccaatcgtca gaaaatttg gaaagaacgg aaatcttaaa ccaagaatgg    180
aaacagcgaa ggatacagcc tgtgcacatc ctgacttctg tgagctcatt gcgcgggact    240
agggagtgtt cggtgaccag tgacttggat tttccaacac aagtcatccc attaaagact   300
ctgaatgcag ttgcttcagt acccataatg tattcttggt ctcccctaca gcagaatttt   360
```

```
atggtggaag atgaaactgt tttacataac attccttata tgggagatga agttttagat        420
caggatggta ctttcattga agaactaata aaaattatg atgggaaagt acacggggat         480
agagaatgtg ggtttataaa tgatgaaatt tttgtggagt tggtgaatgc ccttggtcaa        540
tataatgatg atgacgatga tgatgatgga gacgatcctg aagaaagaga agaaaagcag        600
aaagatctgg aggatcaccg agatgataaa gaaagccgcc cacctcggaa atttccttct        660
gataaaattt ttgaagccat ttcctcaatg tttccagata agggcacagc agaagaacta        720
aaggaaaaat ataagaact caccgaacag cagctcccag gcgcacttcc tcctgaatgt         780 accccccaaca tagatggacc aaatgctaaa tctgttcaga gagagcaaag cttacactcc       840
tttcatacgc ttttctgtag gcgatgtttt aaatatgact gcttcctaca tcgtaagtgc       900
aattattctt ttcatgcaac acccaacact tataagcgga agaacacaga aacagctcta       960
gacaacaaac cttgtggacc acagtgttac cagcatttgg agggagcaaa ggagtttgct      1020
gctgctctca ccgctgagcg gataaagacc ccaccaaaac gtccaggagg ccgcagaaga      1080
ggacggcttc ccaataacag tagcaggccc agcaccccca ccattaatgt gctggaatca      1140
aaggatacag acagtgatag ggaagcaggg actgaaacgg ggggagagaa caatgataaa      1200
gaagaagaag agaagaaaga tgaaacttcg agctcctctg aagcaaattc tcggtgtcaa      1260
acaccaataa agatgaagcc aaatattgaa cctcctgaga atgtggagtg gagtggtgct      1320
gaagcctcaa tgtttagagt cctcattggc acttactatg acaatttctg tgccattgct      1380
aggttaattg ggaccaaaac atgtagacag gtgtatgagt ttagagtcaa agaatctagc      1440
atcatagctc cagctcccgc tgaggatgtg gatactcctc aaggaaaaa gaagaggaaa       1500 caccggttgt gggctgcaca ctgcagaaag atacagctga aaaggacgg ctcctctaac       1560 catgtttaca actatcaacc ctgtgatcat ccacggcagc cttgtgacag ttcgtgccct      1620
tgtgtgatag cacaaaattt tgtgaaaag ttttgtcaat gtagttcaga gtgtcaaaac       1680 cgcttccgg gatgccgctg caaagcacag tgcaacacca agcagtgccc gtgctacctg      1740
gctgtccgag agtgtgaccc tgacctctgt cttacttgtg gagccgctga ccattgggac      1800
agtaaaaatg tgtcctgcaa gaactgcagt attcagcggg gctccaaaaa gcatctattg      1860
ctggcaccat ctgacgtggc aggctggggg atttttatca agatcctgt gcagaaaaat      1920 gaattcatct cagaatactg tggagagatt atttctcaag atgaagctga cagaagaggg      1980
aaagtgtatg ataaatacat gtgcagcttt ctgttcaact tgaacaatga ttttgtggtg      2040
gatgcaaccc gcaagggtaa caaaattcgt tttgcaaatc attcggtaaa tccaaactgc      2100
tatgcaaaag ttatgatggt taacggtgat cacaggatag gtattttgc caagagagcc      2160 atccagactg gcgaagagct gttttttgat tacagataca gccaggctga tgccctgaag      2220
tatgtcggca tcgaaagaga aatggaaatc cct                                   2253
```

<210> SEQ ID NO 184
<211> LENGTH: 1053
<212> TYPE: DNA
<213> ORGANISM: Homo sapiens
<220> FEATURE:
<223> OTHER INFORMATION: NIPP1/PPP1R8, isoform alpha

<400> SEQUENCE: 184

```
atggcggcag ccgcgaactc cggctctagc ctcccgctgt cgactgccc aacctgggca          60 ggtaagcccc ctcccggttt acatctggat gtagtcaaag agacaaaact aattgagaaa        120
ctgattattg atgagaagaa gtattactta tttgggagaa accctgattt gtgtgacttt       180
```

```
accattgacc accagtcttg ctctcgggtc catgctgcac ttgtctacca caagcatctg      240
aagagagttt tcctgataga tctcaacagt cacacacggca ctttcttggg tcacattcgg     300
ttggaacctc acaagcctca gcaaattccc atcgattcca cggtctcatt tggcgcatcc     360
acaagggcat acactctgcg cgagaagcct cagacattgc catcggctgt gaaaggagat     420
gagaagatgg gtggagagga tgatgaactc aagggcttac tggggcttcc agaggaggaa     480
actgagcttg ataacctgac agagttcaac actgcccaca caagcggat ttctacccctt     540 accattgagg agggaaatct ggacattcaa agaccaaaga ggaagaggaa gaactcacgg     600
gtgacattca gtgaggatga tgagatcatc aacccagagg atgtggatcc ctcagttggt     660
cgattcagga acatggtgca aactgcagtg gtcccagtca agaagaagcg tgtggagggc     720
cctggctccc tgggcctgga ggaatcaggg agcaggcgca tgcagaactt tgccttcagc     780
ggaggactct acggggggcct gccccccaca cacagtgaag caggctccca gccacatggc     840
atccatggga cagcactcat cggtggcttg cccatgccat acccaaacct tgcccctgat     900
gtggacttga ctcctgttgt gccgtcagca gtgaacatga accctgcacc aaaccctgca     960
gtctataacc ctgaagctgt aaatgaaccc aagaagaaga aatatgcaaa agaggcttgg    1020
ccaggcaaga agcccacacc ttccttgctg att                                  1053

<210> SEQ ID NO 185
<211> LENGTH: 990
<212> TYPE: DNA
<213> ORGANISM: Homo sapiens
<220> FEATURE:
<223> OTHER INFORMATION: PPP1CA, isoform 1

<400> SEQUENCE: 185
atgtccgaca gcgagaagct caacctggac tcgatcatcg ggcgcctgct ggaagtgcag       60
ggctcgcggc ctggcaagaa tgtacagctg acagagaacg agatccgcgg tctgtgcctg      120
aaatcccggg agattttttct gagccagccc attcttctgg agctggaggc acccctcaag     180
atctgcggtg acatacacgg ccagtactac gaccttctgc gactatttga gtatggcggt      240
ttccctcccg agagcaacta cctctttctg ggggactatg tggacagggg caagcagtcc      300
ttggagacca tctgcctgct gctggcctat aagatcaagt accccgagaa cttcttcctg      360
ctccgtggga ccacgagtg tgccagcatc aaccgcatct atggtttcta cgatgagtgc       420
aagagacgct acaacatcaa actgtggaaa accttcactg actgcttcaa ctgcctgccc      480
atcgcggcca tagtggacga aaagatcttc tgctgccacg gaggcctgtc cccggacctg      540
cagtctatgg agcagattcg gcggatcatg cggcccacag atgtgcctga ccagggcctg      600
ctgtgtgacc tgctgtggtc tgaccctgac aaggacgtgc agggctgggg cgagaacgac      660
cgtggcgtct cttttaccctt tggagccgag gtggtggcca agttcctcca caagcacgac      720
ttggacctca tctgccgagc acaccaggtg gtagaagacg gctacgagtt ctttgccaag      780
cggcagctgg tgacactttt ctcagctccc aactactgtg gcgagtttga caatgctggc      840
gccatgatga gtgtggacga gacccctcatg tgctctttcc agatcctcaa gccccgccgac     900 aagaacaagg ggaagtacgg gcagttcagt ggcctgaacc ctggaggccg acccatcacc      960
ccaccccgca attccgccaa agccaagaaa                                       990

<210> SEQ ID NO 186
<211> LENGTH: 1818
<212> TYPE: DNA
```

<213> ORGANISM: Homo sapiens
<220> FEATURE:
<223> OTHER INFORMATION: TAK1/MAP3K7, isoform 1B

<400> SEQUENCE: 186

```
atgtctacag cctctgccgc ctcctcctcc tcctcgtctt cggccggtga gatgatcgaa      60
gccccttccc aggtcctcaa cttttgaagag atcgactaca aggagatcga ggtggaagag    120
gttgttggaa gaggagcctt tggagttgtt tgcaaagcta agtggagagc aaaagatgtt    180
gctattaaac aaatagaaag tgaatctgag aggaaagcgt ttattgtaga gcttcggcag    240
ttatcccgtg tgaaccatcc taatattgta aagctttatg agcctgctt gaatccagtg    300
tgtcttgtga tggaatatgc tgaaggggc tctttatata atgtgctgca tggtgctgaa    360
ccattgccat attatactgc tgcccacgca atgagttggt gtttacagtg ttcccaagga    420
gtggcttatc ttcacagcat gcaacccaaa gcgctaattc acagggacct gaaaccacca    480
aacttactgc tggttgcagg ggggacagtt ctaaaaattt gtgattttgg tacagcctgt    540
gacattcaga cacacatgac caataacaag gggagtgctg cttggatggc acctgaagtt    600
tttgaaggta gtaattacag tgaaaaatgt gacgtcttca gctggggtat tattctttgg    660
gaagtgataa cgcgtcggaa acccttttgat gagattggtg gcccagcttt ccgaatcatg    720
tgggctgttc ataatggtac tcgaccacca ctgataaaaa atttacctaa gcccattgag    780
agcctgatga ctcgttgttg gtctaaagat ccttcccagc gcccttcaat ggaggaaatt    840
gtgaaaataa tgactcactt gatgcggtac tttccaggag cagatgagcc attacagtat    900
ccttgtcagt attcagatga aggacagagc aactctgcca ccagtacagg ctcattcatg    960
gacattgctt ctacaaatac gagtaacaaa agtgacacta tatggagca agttcctgcc   1020
acaaatgata ctattaagcg cttagaatca aaattgttga aaaatcaggc aaagcaacag   1080
agtgaatctg gacgtttaag cttgggagcc tcccgtggga gcagtgtgga gagcttgccc   1140
ccaacctctg agggcaagag gatgagtgct gacatgtctg aaatagaagc taggatcgcc   1200
gcaaccacag cctattccaa gcctaaacgg ggccaccgta aaactgcttc atttggcaac   1260
attctggatg tccctgagat cgtcatatca ggcaacggac agccaagacg tagatccatc   1320
caagacttga ctgtaactgg aacagaacct ggtcaggtga gcagtaggtc atccagtccc   1380
agtgtcagaa tgattactac ctcaggacca acctcagaaa agccaactcg aagtcatcca   1440
tggacccctg atgattccac agataccaat ggatcagata actccatccc aatggcttat   1500
cttacactgg atcaccaact acagcctcta gcaccgtgcc caaactccaa agaatctatg   1560
gcagtgtttg aacagcattg taaaatggca caagaatata tgaaagttca acagaaatt   1620
gcattgttat acagagaaa gcaagaacta gttgcagaac tggaccagga tgaaaaggac   1680
cagcaaaata catctcgcct ggtacaggaa cataaaaagc ttttagatga aaacaaagc   1740
ctttctactt actaccagca atgcaaaaaa caactagagg tcatcagaag tcagcagcag   1800
aaacgacaag gcacttca                                                  1818
```

<210> SEQ ID NO 187
<211> LENGTH: 204
<212> TYPE: DNA
<213> ORGANISM: Unknown
<220> FEATURE:
<223> OTHER INFORMATION: CMV promoter

<400> SEQUENCE: 187

```
gtgatgcggt tttggcagta catcaatggg cgtggatagc ggtttgactc acggggattt      60
```

```
ccaagtctcc accccattga cgtcaatggg agtttgtttt ggcaccaaaa tcaacgggac      120
tttccaaaat gtcgtaacaa ctccgcccca ttgacgcaaa tgggcggtag gcgtgtacgg      180
tgggaggtct atataagcag agct                                              204
```

```
<210> SEQ ID NO 188
<211> LENGTH: 1212
<212> TYPE: DNA
<213> ORGANISM: Homo sapiens
<220> FEATURE:
<223> OTHER INFORMATION: Caspase-1, isoform alpha

<400> SEQUENCE: 188
atggccgaca aggtcctgaa ggagaagaga aagctgtttt tccgttccat gggtgaaggt       60
acaataaatg gcttactgga tgaattatta cagacaaggg tgctgaacaa ggaagagatg      120
gagaaagtaa aacgtgaaaa tgctacagtt atggataaga cccgagcttt gattgactcc      180
gttattccga aggggcaca ggcatgccaa atttgcatca catacatttg tgaagaagac       240
agttacctgg cagggacgct gggactctca gcagatcaaa catctggaaa ttaccttaat      300
atgcaagact ctcaaggagt actttcttcc tttccagctc ctcaggcagt gcaggacaac      360
ccagctatgc ccacatcctc aggctcagaa gggaatgtca agctttgctc cctagaagaa      420
gctcaaagga tatggaaaca aaagtcggca gagatttatc caataatgga caagtcaagc      480
cgcacacgtc ttgctctcat tatctgcaat gaagaatttg acagtattcc tagaagaact      540
ggagctgagg ttgacatcac aggcatgaca atgctgctac aaaatctggg gtacagcgta      600
gatgtgaaaa aaaatctcac tgcttcggac atgactacag agctggaggc atttgcacac      660
cgcccagagc acaagacctc tgacagcacg ttcctggtgt tcatgtctca tggtattcgg      720
gaaggcattt gtgggaagaa acactctgag caagtcccag atatactaca actcaatgca      780
atctttaaca tgttgaatac caagaactgc ccaagtttga aggacaaacc gaaggtgatc      840
atcatccagg cctgccgtgg tgacagccct ggtgtggtgt ggtttaaaga ttcagtagga      900
gtttctggaa accatatcttt accaactaca gaagagtttg aggatgatgc tattaagaaa      960
gcccacatag agaaggattt tatcgctttc tgctcttcca ccagataaa tgtttcttgg     1020 agacatccca caatgggctc tgttttttatt ggaagactca ttgaacatat gcaagaatat      1080
gcctgttcct gtgatgtgga ggaaattttc cgcaaggttc gatttttcatt tgagcagcca      1140 gatggtagag cgcagatgcc caccactgaa agagtgactt tgacaagatg tttctacctc      1200
ttcccaggac at                                                          1212
```

```
<210> SEQ ID NO 189
<211> LENGTH: 885
<212> TYPE: DNA
<213> ORGANISM: Homo sapiens
<220> FEATURE:
<223> OTHER INFORMATION: cyclin-D1/CCND1

<400> SEQUENCE: 189
atggaacacc agctcctgtg ctgcgaagtg gaaaccatcc gccgcgcgta ccccgatgcc       60
aacctcctca cgaccgggt gctgcgggcc atgctgaagg cggaggagac ctgcgcgccc      120
tcggtgtcct acttcaaatg tgtgcagaag gaggtcctgc cgtccatgcg gaagatcgtc      180
gccacctgga tgctggaggt ctgcgaggaa cagaagtgcg aggaggaggt cttcccgctg      240
gccatgaact acctggaccg cttcctgtcg ctggagcccg tgaaaaagag ccgcctgcag      300
```

```
ctgctggggg ccacttgcat gttcgtggcc tctaagatga aggagaccat cccctgacg      360 gccgagaagc tgtgcatcta caccgacaac tccatccggc ccgaggagct gctgcaaatg      420
gagctgctcc tggtgaacaa gctcaagtgg aacctggccg caatgacccc gcacgatttc      480
attgaacact tcctctccaa aatgccagag gcggaggaga caaacagat catccgcaaa      540 cacgcgcaga ccttcgttgc cctctgtgcc acagatgtga agttcatttc caatccgccc      600
tccatggtgg cagcggggag cgtggtggcc gcagtgcaag gcctgaacct gaggagcccc      660
aacaacttcc tgtcctacta ccgcctcaca cgcttcctct ccagagtgat caagtgtgac      720
ccggactgcc tccgggcctg ccaggagcag atcgaagccc tgctggagtc aagcctgcgc      780
caggcccagc agaacatgga ccccaaggcc gccgaggagg aggaagagga ggaggaggag      840
gtggacctgg cttgcacacc caccgacgtg cgggacgtgg acatc                     885
```

```
<210> SEQ ID NO 190
<211> LENGTH: 996
<212> TYPE: DNA
<213> ORGANISM: Homo sapiens
<220> FEATURE:
<223> OTHER INFORMATION: A2b receptor (ADORA2B)

<400> SEQUENCE: 190
atgctgctgg agacacagga cgcgctgtac gtggcgctgg agctggtcat cgccgcgctt      60
tcggtggcgg gcaacgtgct ggtgtgcgcc gcggtgggca cggcgaacac tctgcagacg      120
cccaccaact acttcctggt gtccctggct gcggccgacg tggccgtggg gctcttcgcc      180 atccccttg ccatcaccat cagcctgggc ttctgcactg acttctacgg ctgcctcttc      240
ctcgcctgct tcgtgctggt gctcacgcag agctccatct tcagccttct ggccgtggca      300
gtcgacagat acctggccat ctgtgtcccg ctcaggtata aaagtttggt cacggggacc      360
cgagcaagag gggtcattgc tgtcctctgg gtccttgcct ttggcatcgg attgactcca      420
ttcctggggt ggaacagtaa agacagtgcc accaacaact gcacagaacc ctgggatgga      480
accacgaatg aaagctgctg ccttgtgaag tgtctctttg agaatgtggt ccccatgagc      540
tacatggtat atttcaattt ctttgggtgt gttctgccc cactgcttat aatgctggtg      600
atctacatta agatcttcct ggtggcctgc aggcagcttc agcgcactga gctgatggac      660
cactcgagga ccaccctcca gcgggagatc catgcagcca gtcactggc catgattgtg      720 gggattttg ccctgtgctg gttacctgtg catgctgtta actgtgtcac tcttttccag      780
ccagctcagg gtaaaaataa gcccaagtgg gcaatgaata tggccattct tctgtcacat      840
gccaattcag ttgtcaatcc cattgtctat gcttaccgga accgagactt ccgctacact      900
tttcacaaaa ttatctccag gtatcttctc tgccaagcag atgtcaagag tgggaatggt      960
caggctgggg tacagcctgc tctcggtgtg ggccta                               996
```

```
<210> SEQ ID NO 191
<211> LENGTH: 1242
<212> TYPE: DNA
<213> ORGANISM: Homo sapiens
<220> FEATURE:
<223> OTHER INFORMATION: HHLA2, isoform 1

<400> SEQUENCE: 191
atgaaggcac agacagcact gtctttcttc ctcattctca taacatctct gagtggatct      60
caaggcatat tcccctttggc tttcttcatt tatgttccta tgaatgaaca aatcgtcatt      120
ggaagacttg atgaagatat aattctccct tcttcatttg agagggggatc cgaagtcgta      180
```

```
atacactgga agtatcaaga tagctataag gttcacagtt actacaaagg cagtgaccat    240
ttggaaagcc aagatcccag atatgcaaac aggacatccc ttttctataa tgagattcaa    300
aatgggaatg cgtcgctatt tttcagaaga gtaagccttc tggacgaagg aatttacacc    360
tgctatgtag aacagcaat tcaagtgatt acaaacaaag tggtgctaaa ggtgggagtt    420
tttctcacac ccgtgatgaa gtatgaaaag aggaacacaa acagcttctt aatatgcagc    480
gtgttaagtg tttatcctcg tccaattatc acgtggaaaa tggacaacac acctatctct    540
gaaaacaaca tggaagaaac agggtctttg gattcttttt ctattaacag cccactgaat    600
attacaggat caaattcatc ttatgaatgt acaattgaaa attcactgct gaagcaaaca    660
tggacagggc gctggacgat gaaagatggc cttcataaaa tgcaaagtga acacgtttca    720
ctctcatgtc aacctgtaaa tgattatttt tcaccaaacc aagacttcaa agttacttgg    780
tccagaatga aaagtgggac tttctctgtc ctggcttact atctgagctc ctcacaaaat    840
acaattatca atgaatcccg attctcatgg aacaaagagc tgataaacca gagtgacttc    900
tctatgaatt tgatggatct taatctttca gacagtgggg aatatttatg caatatttct    960
tcggatgaat atactttact taccatccac acagtgcatg tagaaccgag ccaagaaaca   1020
gcttcccata caaaggctt atggattttg tgccctctg cgattttggc agcttttctg   1080
ctgatttgga gcgtaaaatg ttgcagagcc cagctagaag ccaggaggag cagacaccct   1140
gctgatggag cccaacaaga aagatgttgt gtccctcctg gtgagcgctg tcccagtgca   1200
cccgataatg gcgaagaaaa tgtgcctctt tcaggaaaag ta                      1242
```

<210> SEQ ID NO 192
<211> LENGTH: 1128
<212> TYPE: DNA
<213> ORGANISM: Herpes simplex
<220> FEATURE:
<223> OTHER INFORMATION: herpes simplex virus thymidine kinase (HSV TK)

<400> SEQUENCE: 192

```
atggcttcgt accctgcca tcaacacgcg tctgcgttcg accaggctgc gcgttctcgc     60
ggccatagca accgacgtac ggcgttgcgc cctcgccggc agcaagaagc cacggaagtc    120
cgcctggagc agaaaatgcc cacgctactg cgggtttata tagacggtcc tcacgggatg    180
ggaaaaccca ccaccacgca actgctggtg cccctgggtt cgcgcgacga tatcgtctac    240
gtacccgagc cgatgactta ctggcaggtg ctgggggctt ccgagacaat cgcgaacatc    300
tacaccacac aacaccgcct cgaccagggt gagatatcgg ccggggacgc ggcggtggta    360
atgacaagcg cccagataac aatgggcatg ccttatgccg tgaccgacgc cgttctggct    420
cctcatgtcg gggggaggc tgggagttca catgccccgc cccgccct caccctcatc    480 ttcgaccgcc atcccatcgc cgccctcctg tgctacccgg ccgcgcgata ccttatgggc    540
agcatgaccc ccaggccgt gctggcgttc gtggccctca tcccgccgac cttgcccggc    600
acaaacatcg tgttggggc ccttccggag acagacaca tcgaccgcct ggccaaacgc    660 cagcgcccg cgagcggct tgacctggct atgctggccg cgattcgccg cgtttacggg    720
ctgcttgcca atacggtgcg gtatctgcag gcggcgggt cgtggtggga ggattgggga    780
cagctttcgg gacggccgt gccgcccag ggtgccgagc cccagagcaa cgcgggccca    840
cgaccccata tcggggacac gttatttacc ctgtttcggg ccccgagtt gctgccccc    900 aacggcgacc tgtataacgt gtttgcctgg gccttggacg tcttggccaa acgcctccgt    960
```

```
cccatgcacg tctttatcct ggattacgac caatcgcccg ccggctgccg ggacgccctg    1020
ctgcaactta cctccgggat ggtccagacc cacgtcacca ccccaggctc ataccgacg     1080 atctgcgacc tggcgcgcac gtttgcccgg gagatggggg aggctaac                1128
```

<210> SEQ ID NO 193
<211> LENGTH: 1173
<212> TYPE: DNA
<213> ORGANISM: Homo sapiens
<220> FEATURE:
<223> OTHER INFORMATION: Human TGF-beta isoform 1

<400> SEQUENCE: 193

```
atgccgccct ccgggctgcg gctgctgccg ctgctgctac cgctgctgtg gctactggtg     60
ctgacgcctg gccggccggc cgcgggacta ccacctgca agactatcga catggagctg     120
gtgaagcgga agcgcatcga ggccatccgc ggccagatcc tgtccaagct gcggctcgcc    180
agccccccga ccaggggga ggtgccgccc ggcccgctgc ccgaggccgt gctcgccctg     240
tacaacagca cccgcgaccg ggtggccggg gagagtgcag aaccggagcc cgagcctgag    300
gccgactact acgccaagga ggtcacccgc gtgctaatgg tggaaaccca acgaaaatc     360 tatgacaagt tcaagcagag tacacacagc atatatatgt tcttcaacac atcagagctc    420
cgagaagcgg tacctgaacc cgtgttgctc tcccgggcag agctgcgtct gctgaggctc    480 aagttaaaaag tggagcagca cgtggagctg taccagaaat acagcaacaa ttcctggcga    540
tacctcagca accggctgct ggcacccagc gactcgccag agtggttatc ttttgatgtc    600 accgagttg tgcggcagtg gttgagccgt ggagggggaaa ttgagggctt tcgccttagc    660
gcccactgct cctgtgacag cagggataac acactgcaag tggacatcaa cgggttcact    720
accggccgcc gaggtgaccct ggccaccatt catggcatga accggccttt cctgcttctc    780
atggccaccc cgctggagag ggcccagcat ctgcaaagct cccggcaccg ccgagccctg    840
gacaccaact attgcttcag ctccacggag aagaactgct gcgtgcggca gctgtacatt    900
gacttccgca aggacctcgg ctggaagtgg atccacgagc ccaagggcta ccatgccaac    960
ttctgcctcg ggccctgccc ctacatttgg agcctggaca cgcagtacag caaggtcctg    1020
gccctgtaca accagcataa cccgggcgcc tcggcggcgc cgtgctgcgt gccgcaggcg    1080
ctggagccgc tgcccatcgt gtactacgtg ggccgcaagc ccaaggtgga gcagctgtcc    1140
aacatgatcg tgcgctcctg caagtgcagc tga                                 1173
```

<210> SEQ ID NO 194
<211> LENGTH: 699
<212> TYPE: DNA
<213> ORGANISM: Homo sapiens
<220> FEATURE:
<223> OTHER INFORMATION: Human VEGF

<400> SEQUENCE: 194

```
atgaactttc tgctgtcttg ggtgcattgg agccttgcct tgctgctcta cctccaccat     60
gccaagtggt cccaggctgc acccatggca gaaggaggag ggcagaatca tcacgaagtg    120
gtgaagttca tggatgtcta tcagcgcagc tactgccatc caatcgagac cctggtggac    180
atcttccagg agtaccctga tgagatcgag tacatcttca agccatcctg tgtgcccctg    240
atgcgatgcg ggggctgctg caatgacgag ggcctggagt gtgtgccac tgaggagtcc    300 aacatcacca tgcagattat gcggatcaaa cctcaccaag ccagcacat aggagagatg    360 agcttcctac agcacaacaa atgtgaatgc agaccaaaga aagatagagc aagacaagaa    420
```

-continued

```
aaaaaatcag ttcgaggaaa gggaaagggg caaaaacgaa agcgcaagaa atcccggtat    480
aagtcctgga gcgtgtacgt tggtgcccgc tgctgtctaa tgccctggag cctccctggc    540
ccccatccct gtgggccttg ctcagagcgg agaaagcatt tgtttgtaca agatccgcag    600
acgtgtaaat gttcctgcaa aaacacagac tcgcgttgca aggcgaggca gcttgagtta    660
aacgaacgta cttgcagatg tgacaagccg aggcggtga                           699

<210> SEQ ID NO 195
<211> LENGTH: 19
<212> TYPE: DNA
<213> ORGANISM: Homo sapiens
<220> FEATURE:
<223> OTHER INFORMATION: Human TGF-beta isoform 1 shRNA target 1

<400> SEQUENCE: 195
gaaacccaca acgaaatct                                                  19

<210> SEQ ID NO 196
<211> LENGTH: 19
<212> TYPE: DNA
<213> ORGANISM: Homo sapiens
<220> FEATURE:
<223> OTHER INFORMATION: Human TGF-beta isoform1 shRNA target 2

<400> SEQUENCE: 196
gtacacacag catatatat                                                  19

<210> SEQ ID NO 197
<211> LENGTH: 19
<212> TYPE: DNA
<213> ORGANISM: Homo sapiens
<220> FEATURE:
<223> OTHER INFORMATION: Human TGF-beta isoform1 shRNA target 3

<400> SEQUENCE: 197
ctgctgaggc tcaagttaa                                                  19

<210> SEQ ID NO 198
<211> LENGTH: 19
<212> TYPE: DNA
<213> ORGANISM: Homo sapiens
<220> FEATURE:
<223> OTHER INFORMATION: Human TGF-beta isoform1 shRNA target 4

<400> SEQUENCE: 198
gtggagctgt accagaaat                                                  19

<210> SEQ ID NO 199
<211> LENGTH: 19
<212> TYPE: DNA
<213> ORGANISM: Homo sapiens
<220> FEATURE:
<223> OTHER INFORMATION: Human TGF-beta isoform1 shRNA target 5

<400> SEQUENCE: 199
gactcgccag agtggttat                                                  19

<210> SEQ ID NO 200
<211> LENGTH: 19
<212> TYPE: DNA
<213> ORGANISM: Homo sapiens
<220> FEATURE:
<223> OTHER INFORMATION: Human TGF-beta isoform1 shRNA target 6
```

```
<400> SEQUENCE: 200
gagccgtgga ggggaaatt                                                  19

<210> SEQ ID NO 201
<211> LENGTH: 19
<212> TYPE: DNA
<213> ORGANISM: Homo sapiens
<220> FEATURE:
<223> OTHER INFORMATION: Human TGF-beta isoform1 shRNA target 7

<400> SEQUENCE: 201
cctgtgacag cagggataa                                                  19

<210> SEQ ID NO 202
<211> LENGTH: 19
<212> TYPE: DNA
<213> ORGANISM: Homo sapiens
<220> FEATURE:
<223> OTHER INFORMATION: Human TGF-beta isoform1 shRNA target 8

<400> SEQUENCE: 202
gccctggaca ccaactatt                                                  19

<210> SEQ ID NO 203
<211> LENGTH: 19
<212> TYPE: DNA
<213> ORGANISM: Homo sapiens
<220> FEATURE:
<223> OTHER INFORMATION: Human TGF-beta isoform1 shRNA target 9

<400> SEQUENCE: 203
ccctgtacaa ccagcataa                                                  19

<210> SEQ ID NO 204
<211> LENGTH: 19
<212> TYPE: DNA
<213> ORGANISM: Homo sapiens
<220> FEATURE:
<223> OTHER INFORMATION: Human VEGF shRNA target 1

<400> SEQUENCE: 204
gagatcgagt acatcttca                                                  19

<210> SEQ ID NO 205
<211> LENGTH: 19
<212> TYPE: DNA
<213> ORGANISM: Homo sapiens
<220> FEATURE:
<223> OTHER INFORMATION: Human VEGF shRNA target 2

<400> SEQUENCE: 205
gcagattatg cggatcaaa                                                  19

<210> SEQ ID NO 206
<211> LENGTH: 19
<212> TYPE: DNA
<213> ORGANISM: Homo sapiens
<220> FEATURE:
<223> OTHER INFORMATION: Human VEGF shRNA target 3

<400> SEQUENCE: 206
gatagagcaa gacaagaaa                                                  19

<210> SEQ ID NO 207
<211> LENGTH: 19
```

```
<212> TYPE: DNA
<213> ORGANISM: Homo sapiens
<220> FEATURE:
<223> OTHER INFORMATION: Human VEGF shRNA target 4

<400> SEQUENCE: 207
ggagaaagca tttgtttgt                                                      19

<210> SEQ ID NO 208
<211> LENGTH: 19
<212> TYPE: DNA
<213> ORGANISM: Homo sapiens
<220> FEATURE:
<223> OTHER INFORMATION: Human VEGF shRNA target 5

<400> SEQUENCE: 208
gatccgcaga cgtgtaaat                                                      19

<210> SEQ ID NO 209
<211> LENGTH: 19
<212> TYPE: DNA
<213> ORGANISM: Homo sapiens
<220> FEATURE:
<223> OTHER INFORMATION: Human VEGF shRNA target 6

<400> SEQUENCE: 209
gcgaggcagc ttgagttaa                                                      19

<210> SEQ ID NO 210
<211> LENGTH: 3888
<212> TYPE: DNA
<213> ORGANISM: Artificial Sequence
<220> FEATURE:
<223> OTHER INFORMATION: ARI-134

<400> SEQUENCE: 210
ctttcctgcg ttatccctg attctgtgga taaccgtatt accgcctttg agtgagctga        60
taccgctcgc cgcagccgaa cgaccgagcg cagcgagtca gtgagcgagg aagcggaaga      120
gcgcccaata cgcaaaccgc ctctccccgc gcgttggccg attcattaat gcagctggca      180
cgacaggttt cccgactgga aagcgggcag tgagcgcaac gcaattaata cgcgtaccgc      240
tagccaggaa gagtttgtag aaacgcaaaa aggccatccg tcaggatggc cttctgctta      300
gtttgatgcc tggcagttta tggcgggcgt cctgcccgcc accctccggg ccgttgcttc      360
acaacgttca aatccgctcc cggcggattt gtcctactca ggagagcgtt caccgacaaa      420
caacagataa aacgaaaggc ccagtcttcc gactgagcct ttcgttttat ttgatgcctg      480
gcagttccct actctcgcgt taacgctagc atggatgttt tcccagtcac gacgttgtaa      540
aacgacggcc agtcttaagc tcgggcccca aataatgatt ttattttgac tgatagtgac      600
ctgttcgttg caacaaattg atgagcaatg cttttttata atgccaactt tgtacaaaaa      660
agcaggcttt aaaggaacca attcagtcga gaattggtac catatttgca tgtcgctatg      720
tgttctggga aatcaccata aacgtgaaat gtctttggat ttgggaatct tataagttct      780
gtatgagacc actccctagg ccacactgta tggactattc tagagatagt ccatacagtg      840
tggctttttt cgacagatct ggcgcgccat agtggccagc ggccgcaggt aagccagccc      900
aggcctcgcc ctccagctca aggcgggaca ggtgccctag agtagcctgc atccagggac      960
aggccccagc cgggtgctga cacgtccacc tccatctctt cctcaggtct gcccgggtga     1020
catccctgtg acccctcccc agtgcctctc ctggccctga aagttgccac tccagtgccc     1080
```

```
accagccttg tcctaataaa attaagttgc atcattttgt ctgactaggt gtccttctat    1140
aatattatgg ggtggagggg ggtggtatgg agcaagggc ccaagttaac ttgtttattg    1200
cagcttataa tggttacaaa taaagcaata gcatcacaaa tttcacaaat aaagcatttt    1260
tttcactgca ttctagttgt ggtttgtcca aactcatcaa tgtatcttat catgtctgga    1320
tccaaggtcg ggcaggaaga gggcctattt cccatgattc cttcatattt gcatatacga    1380
tacaaggctg ttagagagat aattagaatt aatttgactg taaacacaaa gatattagta    1440
caaaatacgt gacgtagaaa gtaataattt cttgggtagt ttgcagtttt aaaattatgt    1500
tttaaaatgg actatcatat gcttaccgta acttgaaagt atttcgattt cttggcttta    1560
tatatcttgt ggaaaggacg aaactaggcc gactacaagc gaattatcta gagtaattcg    1620
cttgtagtcg gctttttcg agtagctaga gaattcatgg taatagcgat gactaatacg    1680
tagatgtact gccaagtagg aaagtcccat aaggtcatgt actgggcata atgccaggcg    1740
ggccatttac cgtcattgac gtcaataggg ggcgtacttg gcatatgata cacttgatgt    1800
actgccaagt gggcagttta ccgtaaatag tccaccccatt gacgtcaatg gaaagtccct    1860
attggcgtta ctatgggaac atacgtcatt attgacgtca atgggcgggg gtcgttgggc    1920
ggtcagccag gcgggccatt taccgtaagt tatgtaacgc ggaactccat atatgggcta    1980
tgaactaatg accccgtaat tgattactat taataactag acccagcttt cttgtacaaa    2040
gttggcatta taagaaagca ttgcttatca atttgttgca acgaacaggt cactatcagt    2100
caaaataaaa tcattatttg ccatccagct gatatcccct atagtgagtc gtattacatg    2160
gtcatagctg tttcctggca gctctggccc gtgtctcaaa atctctgatg ttacattgca    2220
caagataaaa atatatcatc atgaacaata aaactgtctg cttacataaa cagtaataca    2280
aggggtgtta tgagccatat tcaacgggaa acgtcgaggc cgcgattaaa ttccaacatg    2340
gatgctgatt tatatgggta taaatgggct cgcgataatg tcgggcaatc aggtgcgaca    2400
atctatcgct tgtatgggaa gcccgatgcg ccagagttgt ttctgaaaca tggcaaaggt    2460
agcgttgcca atgatgttac agatgagatg gtcagactaa actggctgac ggaatttatg    2520
cctcttccga ccatcaagca ttttatccgt actcctgatg atgcatggtt actcaccact    2580
gcgatccccg gaaaacagc attccaggta ttagaagaat atcctgattc aggtgaaaat    2640
attgttgatg cgctggcagt gttcctgcgc cggttgcatt cgattcctgt ttgtaattgt    2700
ccttttaaca gcgatcgcgt atttcgtctc gctcaggcgc aatcacgaat gaataacggt    2760
ttggttgatg cgagtgattt tgatgacgag cgtaatggct ggcctgttga acaagtctgg    2820
aaagaaatgc ataaactttt gccattctca ccggattcag tcgtcactca tggtgatttc    2880
tcacttgata accttatttt tgacgagggg aaattaatag gttgtattga tgttggacga    2940
gtcggaatcg cagaccgata ccaggatctt gccatcctat ggaactgcct cggtgagttt    3000
tctccttcat tacagaaacg ctttttcaa aaatatggta ttgataatcc tgatatgaat    3060
aaattgcagt ttcatttgat gctcgatgag ttttttctaat cagaattggt taattggttg    3120
taacactggc agagcattac gctgacttga cgggacggcg caagctcatg accaaaatcc    3180
cttaacgtga ttacgcgtc gttccactga gcgtcagacc ccgtagaaaa gatcaaagga    3240
tcttcttgag atccttttt tctgcgcgta atctgctgct tgcaaacaaa aaaaccaccg    3300
ctaccagcgg tggtttgttt gccggatcaa gagctaccaa ctcttttttcc gaaggtaact    3360 ggcttcagca gagcgcagat accaaatact gtccttctag tgtagccgta gttaggccac    3420
cacttcaaga actctgtagc accgcctaca tacctcgctc tgctaatcct gttaccagtg    3480
```

```
gctgctgcca gtggcgataa gtcgtgtctt accgggttgg actcaagacg atagttaccg    3540
gataaggcgc agcggtcggg ctgaacgggg ggttcgtgca cacagcccag cttggagcga    3600
acgacctaca ccgaactgag atacctacag cgtgagcatt gagaaagcgc cacgcttccc    3660
gaagggagaa aggcggacag gtatccggta agcggcaggg tcggaacagg agagcgcacg    3720
agggagcttc caggggggaaa cgcctggtat ctttatagtc ctgtcgggtt tcgccacctc    3780
tgacttgagc gtcgattttt gtgatgctcg tcagggggggc ggagcctatg gaaaaacgcc    3840
agcaacgcgg ccttttttacg gttcctggcc ttttgctggc cttttgct    3888
```

<210> SEQ ID NO 211
<211> LENGTH: 3888
<212> TYPE: DNA
<213> ORGANISM: Artificial Sequence
<220> FEATURE:
<223> OTHER INFORMATION: ARI-135

<400> SEQUENCE: 211

```
ctttcctgcg ttatcccctg attctgtgga taaccgtatt accgcctttg agtgagctga      60
taccgctcgc cgcagccgaa cgaccgagcg cagcgagtca gtgagcgagg aagcggaaga     120
gcgcccaata cgcaaaccgc ctctccccgc gcgttggccg attcattaat gcagctggca     180
cgacaggttt cccgactgga aagcgggcag tgagcgcaac gcaattaata cgcgtaccgc     240
tagccaggaa gagtttgtag aaacgcaaaa aggccatccg tcaggatggc cttctgctta     300
gtttgatgcc tggcagttta tggcgggcgt cctgcccgcc accctccggg ccgttgcttc     360
acaacgttca aatccgctcc cggcggattt gtcctactca ggagagcgtt caccgacaaa     420
caacagataa aacgaaaggc ccagtcttcc gactgagcct ttcgttttat ttgatgcctg     480
gcagttccct actctcgcgt taacgctagc atggatgttt cccagtcac gacgttgtaa     540 aacgacggcc agtcttaagc tcgggcccca ataatgatt ttattttgac tgatagtgac     600
ctgttcgttg caacaaattg atgagcaatg cttttttata atgccaactt tgtacaaaaa     660
agcaggcttt aaaggaacca attcagtcga gaattggtac catatttgca tgtcgctatg     720
tgttctggga aatcaccata aacgtgaaat gtctttggat ttgggaatct tataagttct     780
gtatgagacc actccctagg agctggctcc tggtgaattc tagagattca ccaggagcca     840 gctcttttttt cgacagatct ggcgcgccat agtggccagc ggccgcaggt aagccagccc     900
aggcctcgcc ctccagctca aggcgggaca ggtgccctag agtagcctgc atccagggac     960
aggccccagc cgggtgctga cacgtccacc tccatctctt cctcaggtct gcccgggtgg    1020
catccctgtg accctccccc agtgcctctc ctggccctgg aagttgccac tccagtgccc    1080
accagccttg tcctaataaa attaagttgc atcattttgt ctgactaggt gtccttctat    1140
aatattatgg ggtggagggg ggtggtatgg agcaaggggc caagttaac ttgtttattg    1200 cagcttataa tggttacaaa taaagcaata gcatcacaaa tttcacaaat aaagcatttt    1260
tttcactgca ttctagttgt ggtttgtcca aactcatcaa tgtatcttat catgtctgga    1320
tccaaggtcg gcaggaaga gggcctattt cccatgattc cttcatattt gcatatacga    1380
tacaaggctt ttagagagat aattagaatt aatttgactt aaacacaaa gatattagta    1440 caaaatacgt gacgtagaaa gtaataattt cttgggtagt ttgcagtttt aaaattatgt    1500
tttaaaatgg actatcatat gcttaccgta acttgaaagt atttcgattt cttggcttta    1560
tatatcttgt ggaaaggacg aaactaggcc gactacaagc gaattatcta gagtaattcg    1620
```

|  |  |  |  |  |  |
|---|---|---|---|---|---|
| cttgtagtcg | gcttttttcg | agtagctaga | gaattcatgg | taatagcgat | gactaatacg | 1680 |
| tagatgtact | gccaagtagg | aaagtcccat | aaggtcatgt | actgggcata | atgccaggcg | 1740 |
| ggccatttac | cgtcattgac | gtcaataggg | ggcgtacttg | gcatatgata | cacttgatgt | 1800 |
| actgccaagt | gggcagttta | ccgtaaatag | tccacccatt | gacgtcaatg | gaaagtccct | 1860 |
| attggcgtta | ctatgggaac | atacgtcatt | attgacgtca | atgggcgggg | gtcgttgggc | 1920 |
| ggtcagccag | gcgggccatt | taccgtaagt | tatgtaacgc | ggaactccat | atatgggcta | 1980 |
| tgaactaatg | acccgtaat | tgattactat | taataactag | acccagcttt | cttgtacaaa | 2040 |
| gttggcatta | taagaaagca | ttgcttatca | atttgttgca | acgaacaggt | cactatcagt | 2100 |
| caaaataaaa | tcattatttg | ccatccagct | gatatcccct | atagtgagtc | gtattacatg | 2160 |
| gtcatagctg | tttcctggca | gctctggccc | gtgtctcaaa | atctctgatg | ttacattgca | 2220 |
| caagataaaa | atatatcatc | atgaacaata | aaactgtctg | cttacataaa | cagtaataca | 2280 |
| aggggtgtta | tgagccatat | tcaacgggaa | acgtcgaggc | cgcgattaaa | ttccaacatg | 2340 |
| gatgctgatt | tatatgggta | taaatgggct | cgcgataatg | tcgggcaatc | aggtgcgaca | 2400 |
| atctatcgct | tgtatgggaa | gcccgatgcg | ccagagttgt | ttctgaaaca | tggcaaaggt | 2460 |
| agcgttgcca | atgatgttac | agatgagatg | gtcagactaa | actggctgac | ggaatttatg | 2520 |
| cctcttccga | ccatcaagca | ttttatccgt | actcctgatg | atgcatggtt | actcaccact | 2580 |
| gcgatccccg | gaaaaacagc | attccaggta | ttagaagaat | atcctgattc | aggtgaaaat | 2640 |
| attgttgatg | cgctggcagt | gttcctgcgc | cggttgcatt | cgattcctgt | ttgtaattgt | 2700 |
| ccttttaaca | gcgatcgcgt | atttcgtctc | gctcaggcgc | aatcacgaat | gaataacggt | 2760 |
| ttggttgatg | cgagtgattt | tgatgacgag | cgtaatggct | ggcctgttga | acaagtctgg | 2820 |
| aaagaaatgc | ataaactttt | gccattctca | ccggattcag | tcgtcactca | tggtgatttc | 2880 |
| tcacttgata | accttatttt | tgacgagggg | aaattaatag | gttgtattga | tgttggacga | 2940 |
| gtcggaatcg | cagaccgata | ccaggatctt | gccatcctat | ggaactgcct | cggtgagttt | 3000 |
| tctccttcat | tacagaaacg | gctttttcaa | aaatatggta | ttgataatcc | tgatatgaat | 3060 |
| aaattgcagt | ttcatttgat | gctcgatgag | ttttttctaat | cagaattggt | taattggttg | 3120 |
| taacactggc | agagcattac | gctgacttga | cgggacggcg | caagctcatg | accaaaatcc | 3180 |
| cttaacgtga | gttacgcgtc | gttccactga | gcgtcagacc | ccgtagaaaa | gatcaaagga | 3240 |
| tcttcttgag | atcctttttt | tctgcgcgta | atctgctgct | tgcaaacaaa | aaaaccaccg | 3300 |
| ctaccagcgg | tggtttgttt | gccggatcaa | gagctaccaa | ctcttttttcc | gaaggtaact | 3360 |
| ggcttcagca | gagcgcagat | accaaatact | gtccttctag | tgtagccgta | gttaggccac | 3420 |
| cacttcaaga | actctgtagc | accgcctaca | tacctcgctc | tgctaatcct | gttaccagtg | 3480 |
| gctgctgcca | gtggcgataa | gtcgtgtctt | accgggttgg | actcaagacg | atagttaccg | 3540 |
| gataaggcgc | agcggtcggg | ctgaacgggg | ggttcgtgca | cacagcccag | cttggagcga | 3600 |
| acgacctaca | ccgaactgag | atacctacag | cgtgagcatt | gagaaagcgc | cacgcttccc | 3660 |
| gaagggagaa | aggcggacag | gtatccggta | agcggcaggg | tcggaacagg | agagcgcacg | 3720 |
| agggagcttc | caggggggaaa | cgcctggtat | ctttatagtc | ctgtcgggtt | tcgccacctc | 3780 |
| tgacttgagc | gtcgattttt | gtgatgctcg | tcagggggc | ggagcctatg | gaaaaacgcc | 3840 |
| agcaacgcgg | ccttttacg | gttcctggcc | ttttgctggc | cttttgct |  | 3888 |

<210> SEQ ID NO 212
<211> LENGTH: 3888

<212> TYPE: DNA
<213> ORGANISM: Artificial Sequence
<220> FEATURE:
<223> OTHER INFORMATION: ARI-136

<400> SEQUENCE: 212

```
ctttcctgcg ttatcccctg attctgtgga taaccgtatt accgcctttg agtgagctga      60
taccgctcgc cgcagccgaa cgaccgagcg cagcgagtca gtgagcgagg aagcggaaga     120
gcgcccaata cgcaaaccgc ctctccccgc gcgttggccg attcattaat gcagctggca     180
cgacaggttt cccgactgga agcgggcag tgagcgcaac gcaattaata cgcgtaccgc      240
tagccaggaa gagtttgtag aaacgcaaaa aggccatccg tcaggatggc cttctgctta     300
gtttgatgcc tggcagttta tggcgggcgt cctgcccgcc accctccggg ccgttgcttc     360
acaacgttca aatccgctcc cggcggattt gtcctactca ggagagcgtt caccgacaaa     420
caacagataa aacgaaaggc ccagtcttcc gactgagcct ttcgttttat ttgatgcctg     480
gcagttccct actctcgcgt taacgctagc atggatgttt cccagtcac gacgttgtaa      540
aacgacggcc agtcttaagc tcgggcccca ataatgatt ttattttgac tgatagtgac      600
ctgttcgttg caacaaattg atgagcaatg ctttttata atgccaactt tgtacaaaaa      660
agcaggcttt aaaggaacca attcagtcga gaattggtac catatttgca tgtcgctatg     720
tgttctggga atcaccata aacgtgaaat gtctttggat ttgggaatct tataagttct      780
gtatgagacc actccctagg cagctggaat tctttctatc tagagtagaa agaattccag     840
ctgctttttt cgacagatct ggcgcgccat agtggccagc ggccgcaggt aagccagccc     900
aggcctcgcc ctccagctca aggcgggaca ggtgccctag agtagcctgc atccagggac     960
aggcccagc cggtgctga cacgtccacc tccatctctt cctcaggtct gcccgggtgg      1020
catccctgtg acccctcccc agtgcctctc ctggccctgg aagttgccac tccagtgccc    1080
accagccttg tcctaataaa attaagttgc atcattttgt ctgactaggt gtccttctat    1140
aatattatgg ggtggagggg ggtggtatgg agcaagggc ccaagttaac ttgtttattg     1200
cagcttataa tggttacaaa taaagcaata gcatcacaaa tttcacaaat aaagcatttt    1260
tttcactgca ttctagttgt ggtttgtcca aactcatcaa tgtatcttat catgtctgga    1320
tccaaggtcg ggcaggaaga gggcctattt cccatgattc cttcatattt gcatatacga    1380
tacaaggctg ttagagagat aattagaatt aatttgactg taaacacaaa gatattagta    1440
caaaatacgt gacgtagaaa gtaataattt cttgggtagt ttgcagtttt aaaattatgt    1500
tttaaaatgg actatcatat gcttaccgta acttgaaagt atttcgattt cttggcttta    1560
tatatcttgt ggaaaggacg aaactaggcc gactacaagc gaattatcta gagtaattcg    1620
cttgtagtcg gcttttttcg agtagctaga gaattcatgg taatagcgat gactaatacg    1680
tagatgtact gccaagtagg aaagtcccat aaggtcatgt actgggcata atgccaggcg    1740
ggccatttac cgtcattgac gtcaataggg gcgtacttg gcatatgata cacttgatgt     1800
actgccaagt gggcagttta ccgtaaatag tccacccatt gacgtcaatg gaaagtccct    1860
attggcgtta ctatgggaac atacgtcatt attgacgtca atgggcgggg tcgttgggc    1920
ggtcagccag gcgggccatt taccgtaagt tatgtaacgc ggaactccat atatgggcta    1980
tgaactaatg accccgtaat tgattactat taataactag acccagcttt cttgtacaaa    2040
gttggcatta taagaaagca ttgcttatca atttgttgca acgaacaggt cactatcagt    2100
caaaataaaa tcattatttg ccatccagct gatatcccct atagtgagtc gtattacatg    2160
```

| | |
|---|---|
| gtcatagctg tttcctggca gctctggccc gtgtctcaaa atctctgatg ttacattgca | 2220 |
| caagataaaa atatatcatc atgaacaata aaactgtctg cttacataaa cagtaataca | 2280 |
| aggggtgtta tgagccatat tcaacgggaa acgtcgaggc cgcgattaaa ttccaacatg | 2340 |
| gatgctgatt tatatgggta taaatgggct cgcgataatg tcgggcaatc aggtgcgaca | 2400 |
| atctatcgct tgtatgggaa gcccgatgcg ccagagttgt ttctgaaaca tggcaaaggt | 2460 |
| agcgttgcca atgatgttac agatgagatg gtcagactaa actggctgac ggaatttatg | 2520 |
| cctcttccga ccatcaagca ttttatccgt actcctgatg atgcatggtt actcaccact | 2580 |
| gcgatcccg gaaaaacagc attccaggta ttagaagaat atcctgattc aggtgaaaat | 2640 |
| attgttgatg cgctggcagt gttcctgcgc cggttgcatt cgattcctgt ttgtaattgt | 2700 |
| ccttttaaca cgatcgcgt atttcgtctc gctcaggcgc aatcacgaat gaataacggt | 2760 |
| ttggttgatg cgagtgattt tgatgacgag cgtaatggct ggcctgttga acaagtctgg | 2820 |
| aaagaaatgc ataaactttt gccattctca ccggattcag tcgtcactca tggtgatttc | 2880 |
| tcacttgata accttatttt tgacgagggg aaattaatag gttgtattga tgttggacga | 2940 |
| gtcggaatcg cagaccgata ccaggatctt gccatcctat ggaactgcct cggtgagttt | 3000 |
| tctccttcat tacagaaacg gcttttcaa aaatatggta ttgataatcc tgatatgaat | 3060 |
| aaattgcagt ttcatttgat gctcgatgag ttttctaat cagaattggt taattggttg | 3120 |
| taacactggc agagcattac gctgacttga cgggacggcg caagctcatg accaaaatcc | 3180 |
| cttaacgtga gttacgcgtc gttccactga gcgtcagacc ccgtagaaaa gatcaaagga | 3240 |
| tcttcttgag atcctttttt tctgcgcgta atctgctgct tgcaaacaaa aaaaccaccg | 3300 |
| ctaccagcgg tggtttgttt gccggatcaa gagctaccaa ctcttttcc gaaggtaact | 3360 |
| ggcttcagca gagcgcagat accaaatact gtccttctag tgtagccgta gttaggccac | 3420 |
| cacttcaaga actctgtagc accgcctaca tacctcgctc tgctaatcct gttaccagtg | 3480 |
| gctgctgcca gtggcgataa gtcgtgtctt accgggttgg actcaagacg atagttaccg | 3540 |
| gataaggcgc agcggtcggg ctgaacgggg ggttcgtgca cacagcccag cttggagcga | 3600 |
| acgacctaca ccgaactgag atacctacag cgtgagcatt gagaaagcgc cacgcttccc | 3660 |
| gaagggagaa aggcggacag gtatccggta agcggcaggg tcggaacagg agagcgcacg | 3720 |
| agggagcttc caggggggaaa cgcctggtat ctttatagtc ctgtcgggtt tcgccacctc | 3780 |
| tgacttgagc gtcgattttt gtgatgctcg tcagggggggc ggagcctatg gaaaaacgcc | 3840 |
| agcaacgcgg ccttttacg gttcctggcc ttttgctggc cttttgct | 3888 |

<210> SEQ ID NO 213
<211> LENGTH: 3890
<212> TYPE: DNA
<213> ORGANISM: Artificial Sequence
<220> FEATURE:
<223> OTHER INFORMATION: ARI-137

<400> SEQUENCE: 213

| | |
|---|---|
| ctttcctgcg ttatcccctg attctgtgga taaccgtatt accgcctttg agtgagctga | 60 |
| taccgctcgc cgcagccgaa cgaccgagcg cagcgagtca gtgagcgagg aagcggaaga | 120 |
| gcgcccaata cgcaaaccgc ctctccccgc gcgttggccg attcattaat gcagctggca | 180 |
| cgacaggttt cccgactgga aagcgggcag tgagcgcaac gcaattaata cgcgtaccgc | 240 |
| tagccaggaa gagtttgtag aaacgcaaaa aggccatccg tcaggatggc cttctgctta | 300 |
| gtttgatgcc tggcagttta tggcgggcgt cctgcccgcc accctccggg ccgttgcttc | 360 |

```
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt cccagtcac gacgttgtaa     540 aacgacggcc agtcttaagc tcgggcccca ataatgatt ttattttgac tgatagtgac     600
ctgttcgttg caacaaattg atgagcaatg cttttttata atgccaactt tgtacaaaaa    660
agcaggcttt aaaggaacca attcagtcga aattggtac catatttgca tgtcgctatg     720
tgttctggga aatcaccata aacgtgaaat gtctttggat ttgggaatct tataagttct    780
gtatgagacc actccctagg atgtgacctt ctacaagatt ctagagatct tgtagaaggt    840
cacatctttt ttcgacagat ctggcgcgcc atagtggcca gcggccgcag gtaagccagc    900
ccaggcctcg ccctccagct caaggcggga caggtgccct agagtagcct gcatccaggg    960
acaggcccca gccgggtgct gacacgtcca cctccatctc ttcctcaggt ctgcccgggt   1020
ggcatccctg tgaccctcc ccagtgcctc tcctggccct ggaagttgcc actccagtgc    1080
ccaccagcct tgtcctaata aaattaagtt gcatcatttt gtctgactag gtgtccttct   1140
ataatattat ggggtggagg ggggtggtat ggagcaaggg gcccaagtta acttgtttat   1200
tgcagcttat aatggttaca aataaagcaa tagcatcaca aatttcacaa ataaagcatt   1260
tttttcactg cattctagtt gtggtttgtc caaactcatc aatgtatctt atcatgtctg   1320
gatccaaggt cgggcaggaa gagggcctat ttcccatgat tccttcatat ttgcatatac   1380
gatacaaggc tgttagagag ataattagaa ttaatttgac tgtaaacaca agatattag    1440 tacaaaatac gtgacgtaga aagtaataat ttcttgggta gtttgcagtt ttaaaattat   1500
gttttaaaat ggactatcat atgcttaccg taacttgaaa gtatttcgat ttcttggctt   1560
tatatatctt gtggaaagga cgaaactagg ccgactacaa gcgaattatc tagagtaatt   1620
cgcttgtagt cggcttttttt cgagtagcta gagaattcat ggtaatagcg atgactaata   1680
cgtagatgta ctgccaagta ggaaagtccc ataaggtcat gtactgggca taatgccagg   1740
cgggccattt accgtcattg acgtcaatag ggggcgtact tggcatatga tacacttgat   1800
gtactgccaa gtgggcagtt taccgtaaat agtccaccca ttgacgtcaa tggaaagtcc   1860
ctattggcgt tactatggga acatacgtca ttattgacgt caatgggcgg gggtcgttgg   1920
gcggtcagcc aggcgggcca tttaccgtaa gttatgtaac gcggaactcc atatatgggc   1980
tatgaactaa tgaccccgta attgattact attaataact agaccagct ttcttgtaca    2040 aagttggcat tataagaaag cattgcttat caatttgttg caacgaacag gtcactatca   2100
gtcaaaataa aatcattatt tgccatccag ctgatatccc ctatagtgag tcgtattaca   2160
tggtcatagc tgtttcctgg cagctctggc ccgtgtctca aaatctctga tgttacattg   2220
cacaagataa aaatatatca tcatgaacaa taaaactgtc tgcttacata aacagtaata   2280
caaggggtgt tatgagccat attcaacggg aaacgtcgag gccgcgatta aattccaaca   2340
tggatgctga tttatatggg tataaatggg ctcgcgataa tgtcgggcaa tcaggtgcga   2400
caatctatcg cttgtatggg aagcccgatg cgccagagtt gtttctgaaa catggcaaag   2460
gtagcgttgc caatgatgtt acagatgaga tggtcagact aaactggctg acggaattta   2520
tgcctcttcc gaccatcaag cattttatcc gtactcctga tgatgcatgg ttactcacca   2580
ctgcgatccc cggaaaaaca gcattccagg tattagaaga atatcctgat tcaggtgaaa   2640
atattgttga tgcgctggca gtgttcctgc gccggttgca ttcgattcct gtttgtaatt   2700
```

-continued

| | |
|---|---|
| gtccttttaa cagcgatcgc gtatttcgtc tcgctcaggc gcaatcacga atgaataacg | 2760 |
| gtttggttga tgcgagtgat tttgatgacg agcgtaatgg ctggcctgtt gaacaagtct | 2820 |
| ggaaagaaat gcataaactt tgccattct caccggattc agtcgtcact catggtgatt | 2880 |
| tctcacttga taaccttatt tttgacgagg ggaaattaat aggttgtatt gatgttggac | 2940 |
| gagtcggaat cgcagaccga taccaggatc ttgccatcct atggaactgc ctcggtgagt | 3000 |
| tttctccttc attacagaaa cggcttttc aaaaatatgg tattgataat cctgatatga | 3060 |
| ataaattgca gtttcattttg atgctcgatg agttttcta atcagaattg gttaattggt | 3120 |
| tgtaacactg gcagagcatt acgctgactt gacgggacgg cgcaagctca tgaccaaaat | 3180 |
| cccttaacgt gagttacgcg tcgttccact gagcgtcaga ccccgtagaa aagatcaaag | 3240 |
| gatcttcttg agatcctttt tttctgcgcg taatctgctg cttgcaaaca aaaaaaccac | 3300 |
| cgctaccagc ggtggtttgt ttgccggatc aagagctacc aactcttttt ccgaaggtaa | 3360 |
| ctggcttcag cagagcgcag ataccaaata ctgtccttct agtgtagccg tagttaggcc | 3420 |
| accacttcaa gaactctgta gcaccgccta catacctcgc tctgctaatc ctgttaccag | 3480 |
| tggctgctgc cagtggcgat aagtcgtgtc ttaccgggtt ggactcaaga cgatagttac | 3540 |
| cggataaggc gcagcggtcg ggctgaacgg ggggttcgtg cacacagccc agcttggagc | 3600 |
| gaacgaccta caccgaactg agatacctac agcgtgagca ttgagaaagc gccacgcttc | 3660 |
| ccgaagggag aaaggcggac aggtatccgg taagcggcag ggtcggaaca ggagagcgca | 3720 |
| cgagggagct ccaggggga aacgcctggt atctttatag tcctgtcggg tttcgccacc | 3780 |
| tctgacttga gcgtcgattt ttgtgatgct cgtcaggggg gcggagccta tggaaaaacg | 3840 |
| ccagcaacgc ggccttttta cggttcctgg ccttttgctg gcctttgct | 3890 |

<210> SEQ ID NO 214
<211> LENGTH: 3379
<212> TYPE: DNA
<213> ORGANISM: Artificial Sequence
<220> FEATURE:
<221> NAME/KEY: misc_feature
<222> LOCATION: (1018)...(1038)
<223> OTHER INFORMATION: n may be any nucleotide
<220> FEATURE:
<221> NAME/KEY: misc_feature
<222> LOCATION: (1060)...(1080)
<223> OTHER INFORMATION: n may be any nucleotide
<220> FEATURE:
<221> NAME/KEY: source
<222> LOCATION: (1)...(3379)
<223> OTHER INFORMATION: ARI-205

<400> SEQUENCE: 214

| | |
|---|---|
| ctttcctgcg ttatccctg attctgtgga taaccgtatt accgcctttg agtgagctga | 60 |
| taccgctcgc cgcagccgaa cgaccgagcg cagcgagtca gtgagcgagg aagcggaaga | 120 |
| gcgcccaata cgcaaaccgc ctctccccgc gcgttggccg attcattaat gcagctggca | 180 |
| cgacaggttt cccgactgga aagcgggcag tgagcgcaac gcaattaata cgcgtaccgc | 240 |
| tagccaggaa gagtttgtag aaacgcaaaa aggccatccg tcaggatggc cttctgctta | 300 |
| gtttgatgcc tggcagttta tggcgggcgt cctgcccgcc accctccggg ccgttgcttc | 360 |
| acaacgttca aatccgctcc cggcggattt gtcctactca ggagagcgtt caccgacaaa | 420 |
| caacagataa aacgaaaggc ccagtcttcc gactgagcct ttcgttttat ttgatgcctg | 480 |
| gcagttccct actctcgcgt taacgctagc atggatgttt tcccagtcac gacgttgtaa | 540 |
| aacgacggcc agtcttaagc tcgggcccca ataatgatt ttattttgac tgatagtgac | 600 |

```
ctgttcgttg caacaaattg atgagcaatg cttttttata atgccaactt tgtacaaaaa    660
agcaggcttt aaaggaacca attcagtcga ctggatccaa ggtcgggcag gaagagggcc    720
tatttcccat gattccttca tatttgcata tacgatacaa ggctgttaga gagataatta    780
gaattaattt gactgtaaac acaaagatat tagtacaaaa tacgtgacgt agaaagtaat    840
aatttcttgg gtagtttgca gttttaaaat tatgttttaa aatggactat catatgctta    900
ccgtaacttg aaagtatttc gatttcttgg ctttatatat cttgtggaaa ggacgaaact    960
agtccggatc aacgccctag gtttatgttt ggatgaactg acatacgcgt atccgtcnnn   1020
nnnnnnnnnn nnnnnnnngt agtgaaatat atattaaacn nnnnnnnnnn nnnnnnnnnn   1080
tacggtaacg cggaattcgc aactatttta tcaattttt gcgtcgactc gagtagctag   1140
agaattcatg gtaatagcga tgactaatac gtagatgtac tgccaagtag gaaagtccca   1200
taaggtcatg tactgggcat aatgccaggc gggccattta ccgtcattga cgtcaatagg   1260
gggcgtactt ggcatatgat acacttgatg tactgccaag tgggcagttt accgtaaata   1320
gtccacccat tgacgtcaat ggaaagtccc tattggcgtt actatgggaa catacgtcat   1380
tattgacgtc aatgggcggg ggtcgttggg cggtcagcca ggcgggccat ttaccgtaag   1440
ttatgtaacg cggaactcca tatatgggct atgaactaat gaccccgtaa ttgattacta   1500
ttaataacta gacccagctt tcttgtacaa agttggcatt ataagaaagc attgcttatc   1560
aatttgttgc aacgaacagg tcactatcag tcaaaataaa atcattattt gccatccagc   1620
tgatatcccc tatagtgagt cgtattacat ggtcatagct gtttcctggc agctctggcc   1680
cgtgtctcaa aatctctgat gttacattgc acaagataaa aatatatcat catgaacaat   1740
aaaactgtct gcttacataa acagtaatac aaggggtgtt atgagccata ttcaacggga   1800
aacgtcgagg ccgcgattaa attccaacat ggatgctgat ttatatgggt ataaatgggc   1860
tcgcgataat gtcgggcaat caggtgcgac aatctatcgc ttgtatggga agcccgatgc   1920
gccagagttg tttctgaaac atggcaaagg tagcgttgcc aatgatgtta cagatgagat   1980
ggtcagacta aactggctga cggaatttat gcctcttccg accatcaagc atttatccg   2040 tactcctgat gatgcatggt tactcaccac tgcgatcccc ggaaaaacag cattccaggt   2100
attagaagaa tatcctgatt caggtgaaaa tattgttgat gcgctggcag tgttcctgcg   2160
ccggttgcat tcgattcctg tttgtaattg tccttttaac agcgatcgcg tatttcgtct   2220
cgctcaggcg caatcacgaa tgaataacgg tttggttgat gcgagtgatt ttgatgacga   2280
gcgtaatggc tggcctgttg aacaagtctg gaaagaaatg cataaacttt tgccattctc   2340
accggattca gtcgtcactc atggtgattt ctcacttgat aaccttattt ttgacgaggg   2400
gaaattaata ggttgtattg atgttggacg agtcggaatc gcagaccgat accaggatct   2460
tgccatccta tggaactgcc tcggtgagtt ttctccttca ttacagaaac ggctttttca   2520
aaaatatggt attgataatc ctgatatgaa taaattgcag tttcatttga tgctcgatga   2580 gttttttctaa tcagaattgg ttaattggtt gtaacactgg cagagcatta cgctgacttg   2640
acgggacggc gcaagctcat gaccaaaatc ccttaacgtg agttacgcgt cgttccactg   2700
agcgtcagac cccgtagaaa agatcaaagg atcttcttga gatccttttt ttctgcgcgt   2760
aatctgctgc ttgcaaacaa aaaaaccacc gctaccagcg gtggtttgtt tgccggatca   2820
agagctacca actcttttc cgaaggtaac tggcttcagc agagcgcaga taccaaatac   2880
tgtccttcta gtgtagccgt agttaggcca ccacttcaag aactctgtag caccgcctac   2940
```

```
atacctcgct ctgctaatcc tgttaccagt ggctgctgcc agtggcgata agtcgtgtct    3000 taccggggttg gactcaagac gatagttacc ggataaggcg cagcggtcgg gctgaacggg    3060
gggttcgtgc acacagccca gcttggagcg aacgacctac accgaactga gatacctaca    3120
gcgtgagcat tgagaaagcg ccacgcttcc gaagggaga aaggcggaca ggtatccggt     3180
aagcggcagg gtcggaacag gagagcgcac gagggagctt ccagggggaa acgcctggta    3240
tctttatagt cctgtcgggt ttcgccacct ctgacttgag cgtcgatttt tgtgatgctc    3300
gtcagggggg cggagcctat ggaaaaacgc cagcaacgcg gccttttttac ggttcctggc    3360 cttttgctgg cctttttgct                                                3379

<210> SEQ ID NO 215
<211> LENGTH: 4744
<212> TYPE: DNA
<213> ORGANISM: Artificial Sequence
<220> FEATURE:
<221> NAME/KEY: misc_feature
<222> LOCATION: (3377)...(3398)
<223> OTHER INFORMATION: n may be any nucleotide
<220> FEATURE:
<221> NAME/KEY: misc_feature
<222> LOCATION: (3418)...(3439)
<223> OTHER INFORMATION: n may be any nucleotide
<220> FEATURE:
<221> NAME/KEY: source
<222> LOCATION: (1)...(4744)
<223> OTHER INFORMATION: ARI-206

<400> SEQUENCE: 215
aacatgtgag caaaaggcca gcaaaaggcc aggaaccgta aaaaggccgc gttgctggcg     60
tttttccata ggctccgccc ccctgacgag catcacaaaa atcgacgctc aagtcagagg    120
tggcgaaacc cgacaggact ataaagatac caggcgtttc ccctggaag ctccctcgtg     180 cgctctcctg ttccgaccct gccgcttacc ggatacctgt ccgcctttct cccttcggga    240
agcgtggcgc tttctcaatg ctcacgctgt aggtatctca gttcggtgta ggtcgttcgc    300
tccaagctgg gctgtgtgca cgaaccccccc gttcagcccg accgctgcgc cttatccggt     360
aactatcgtc ttgagtccaa cccggtaaga cacgacttat cgccactggc agcagccact    420
ggtaacagga ttagcagagc gaggtatgta ggcggtgcta cagagttctt gaagtggtgg    480
cctaactacg gctacactag aaggacagta tttggtatct gcgctctgct gaagccagtt    540
accttcggaa aaagagttgg tagctcttga tccggcaaac aaaccaccgc tggtagcggt    600
ggtttttttg tttgcaagca gcagattacg cgcagaaaaa aaggatctca agaagatcct    660
ttgatctttt ctacggggtc tgacgctcag tggaacgacg cgtaactcac gttaagggat    720
tttggtcatg agcttgcgcc gtcccgtcaa gtcagcgtaa tgctctgcca gtgttacaac    780
caattaacca attctgatta gaaaaactca tcgagcatca atgaaactg caatttattc     840 atatcaggat tatcaatacc atattttga aaaagccgtt tctgtaatga aggagaaaac    900
tcaccgaggc agttccatag gatggcaaga tcctggtatc ggtctgcgat tccgactcgt    960
ccaacatcaa tacaacctat taatttcccc tcgtcaaaaa taaggttatc aagtgagaaa    1020
tcaccatgag tgacgactga atccggtgag aatggcaaaa gtttatgcat ttctttccag    1080
acttgttcaa caggccagcc attacgctcg tcatcaaaat cactcgcatc aaccaaaccg    1140
ttattcattc gtgattgcgc ctgagcgaga cgaaatacgc gatcgctgtt aaaaggacaa    1200
ttacaaacag gaatcgaatg caaccggcgc aggaacactg ccagcgcatc aacaatattt    1260
tcacctgaat caggatattc ttctaatacc tggaatgctg ttttccggg gatcgcagtg    1320
```

```
gtgagtaacc atgcatcatc aggagtacgg ataaaatgct tgatggtcgg aagaggcata   1380
aattccgtca gccagtttag tctgaccatc tcatctgtaa catcattggc aacgctacct   1440
ttgccatgtt tcagaaacaa ctctggcgca tcgggcttcc catacaagcg atagattgtc   1500
gcacctgatt gcccgacatt atcgcgagcc catttatacc catataaatc agcatccatg   1560
ttggaattta atcgcggcct cgacgtttcc cgttgaatat ggctcataac accccttgta   1620
ttactgttta tgtaagcaga cagttttatt gttcatgatg atatatttt atcttgtgca    1680 atgtaacatc agagattttg agacacgggc cagagctgcc aggaaacagc tatgaccatg   1740
taatacgact cactataggg gatatcagct ggatggcaaa taatgatttt attttgactg   1800
atagtgacct gttcgttgca acaaattgat aagcaatgct ttcttataat gccaactttg   1860
tacaagaaag ctgggtctag ttattaatag taatcaatta cggggtcatt agttcatagc   1920
ccatatatgg agttccgcgt tacataactt acggtaaatg gcccgcctgg ctgaccgccc   1980
aacgaccccc gcccattgac gtcaataatg acgtatgttc ccatagtaac gccaataggg   2040
actttccatt gacgtcaatg ggtggactat ttacggtaaa ctgcccactt ggcagtacat   2100
caagtgtatc atatgccaag tacgccccct attgacgtca atgacggtaa atggcccgcc   2160
tggcattatg cccagtacat gaccttatgg gactttccta cttggcagta catctacgta   2220
ttagtcatcg ctattaccat ggtgatgcgg ttttggcagt acatcaatgg gcgtggatag   2280
cggtttgact cacggggatt tccaagtctc cacccccattg acgtcaatgg gagtttgttt   2340
tggcaccaaa atcaacggga ctttccaaaa tgtcgtaaca actccgcccc attgacgcaa   2400
atgggcggta ggcgtgtacg gtgggaggtc tatataagca gagctctctg gctaactaga   2460
gaacccactg cttactggct tatcgaaatt aatacgactc actataggga cccaagct    2520 tagatctgtt tccggtcgcc accatgagcg agctgatcaa ggagaacatg cacatgaagc   2580
tgtacatgga gggcaccgtg aacaaccacc acttcaagtg cacatccgag ggcgaaggca   2640
agccctacga gggcacccag accatgaaga tcaaggtggt cgagggcggc cctctcccct   2700
tcgccttcga catcctggct accagcttca tgtacggcag caaagccttc atcaaccaca   2760
cccagggcat ccccgacttc tttaagcagt ccttccctga gggcttcaca tgggagagaa   2820
tcaccacata cgaagacggg ggcgtgctga ccgctaccca ggacaccagc ttccagaacg   2880
gctgcatcat ctacaacgtc aagatcaacg gggtgaactt cccatccaac ggccctgtga   2940
tgcagaagaa aacacgcggc tgggaggcca acaccgagat gctgtacccc gctgacggcg   3000
gcctgagagg ccacagccag atgggccctga agctcgtggg cggggggctac ctgcactgct   3060 ccttcaagac cacatacaga tccaagaaac ccgctaagaa cctcaagatg cccggcttcc   3120
acttcgtgga ccacagactg gaaagaatca aggaggccga caaagagacc tacgtcgagc   3180
agcacgagat ggctgtggcc aagtactgcg acctccctag caaactgggg cacagataat   3240
cgatagtttg tttgaatgag gcttcagtac tttacagaat cgttgcctgc acatcttgga   3300
aacacttgct gggattactt cttcaggtta acccaacaga aggctcgaga aggtatattg   3360
ctgttgacag tgagcgnnnn nnnnnnnnnn nnnnnnnnnta gtgaagccac agatgtannn   3420
nnnnnnnnnn nnnnnnnnnt gcctactgcc tcggaattca aggggctact ttaggagcaa   3480
ttatcttgtt tactaaaact gaataccttg ctatctcttt gatacatttt tacaaagctg   3540
aattaaaatg gtataaatta aatcactttt tcaattctc tagaggtacc gcatgcgtac    3600
gtggccagcg gccgcaggta agccagccca ggcctcgccc tccagctcaa ggcgggacag   3660
```

| | |
|---|---|
| gtgccctaga gtagcctgca tccagggaca ggccccagcc gggtgctgac acgtccacct | 3720 |
| ccatctcttc ctcaggtctg cccgggtggc atccctgtga cccctcccca gtgcctctcc | 3780 |
| tggccctgga agttgccact ccagtgccca ccagccttgt cctaataaaa ttaagttgca | 3840 |
| tcattttgtc tgactaggtg tccttctata atattatggg gtggagggg gtggtatgga | 3900 |
| gcaaggggcc caagttaact tgtttattgc agcttataat ggttacaaat aaagcaatag | 3960 |
| catcacaaat ttcacaaata aagcattttt ttcactgcat tctagttgtg gtttgtccaa | 4020 |
| actcatcaat gtatcttatc atgtctggat ccagtcgact gaattggttc ctttaaagcc | 4080 |
| tgcttttttg tacaaagttg gcattataaa aaagcattgc tcatcaattt gttgcaacga | 4140 |
| acaggtcact atcagtcaaa ataaaatcat tatttgggc ccgagcttaa gactggccgt | 4200 |
| cgttttacaa cgtcgtgact gggaaaacat ccatgctagc gttaacgcga gagtagggaa | 4260 |
| ctgccaggca tcaaataaaa cgaaaggctc agtcggaaga ctgggccttt cgttttatct | 4320 |
| gttgtttgtc ggtgaacgct ctcctgagta ggacaaatcc gccggagcg gatttgaacg | 4380 |
| ttgtgaagca acggcccgga gggtggcggg caggacgccc gccataaact gccaggcatc | 4440 |
| aaactaagca gaaggccatc ctgacggatg ccttttttgc gtttctacaa actcttcctg | 4500 |
| gctagcggta cgcgtattaa ttgcgttgcg ctcactgccc gctttccagt cgggaaacct | 4560 |
| gtcgtgccag ctgcattaat gaatcggcca acgcgcgggg agaggcggtt tgcgtattgg | 4620 |
| gcgctcttcc gcttcctcgc tcactgactc gctgcgctcg gtcgttcggc tgcggcgagc | 4680 |
| ggtatcagct cactcaaagg cggtaatacg gttatccaca gaatcagggg ataacgcagg | 4740 |
| aaag | 4744 |

<210> SEQ ID NO 216
<211> LENGTH: 3377
<212> TYPE: DNA
<213> ORGANISM: Artificial Sequence
<220> FEATURE:
<221> NAME/KEY: misc_feature
<222> LOCATION: (1018)...(1036)
<223> OTHER INFORMATION: n may be any nucleotide
<220> FEATURE:
<221> NAME/KEY: misc_feature
<222> LOCATION: (1058)...(1078)
<223> OTHER INFORMATION: n may be any nucleotide
<220> FEATURE:
<221> NAME/KEY: source
<222> LOCATION: (1)...(3377)
<223> OTHER INFORMATION: ARI-207

<400> SEQUENCE: 216

| | |
|---|---|
| ctttcctgcg ttatcccctg attctgtgga taaccgtatt accgcctttg agtgagctga | 60 |
| taccgctcgc cgcagccgaa cgaccgagcg cagcgagtca gtgagcgagg aagcggaaga | 120 |
| gcgcccaata cgcaaaccgc ctctccccgc gcgttggccg attcattaat gcagctggca | 180 |
| cgacaggttt cccgactgga aagcgggcag tgagcgcaac gcaattaata cgcgtaccgc | 240 |
| tagccaggaa gagtttgtag aaacgcaaaa aggccatccg tcaggatggc cttctgctta | 300 |
| gtttgatgcc tggcagttta tggcgggcgt cctgcccgcc accctccggg ccgttgcttc | 360 |
| acaacgttca aatccgctcc cggcggattt gtcctactca ggagagcgtt caccgacaaa | 420 |
| caacagataa aacgaaaggc ccagtcttcc gactgagcct ttcgttttat ttgatgcctg | 480 |
| gcagttccct actctcgcgt taacgctagc atggatgttt tcccagtcac gacgttgtaa | 540 |
| aacgacggcc agtcttaagc tcgggcccca ataatgatt ttattttgac tgatagtgac | 600 |
| ctgttcgttg caacaaattg atgagcaatg ctttttttata atgccaactt tgtacaaaaa | 660 |

```
agcaggcttt aaaggaacca attcagtcga ctggatccaa ggtcgggcag gaagagggcc    720
tatttcccat gattccttca tatttgcata tacgatacaa ggctgttaga gagataatta    780
gaattaattt gactgtaaac acaaagatat tagtacaaaa tacgtgacgt agaaagtaat    840
aatttcttgg gtagtttgca gttttaaaat tatgttttaa aatggactat catatgctta    900
ccgtaacttg aaagtatttc gatttcttgg ctttatatat cttgtggaaa ggacgaaact    960
agtccggatc aacgccctag gtttatgttt ggatgaactg acatacgcgt atccgtcnnn   1020
nnnnnnnnnn nnnnngtag tgaaatatat attaaacnnn nnnnnnnnn nnnnnnnta      1080 cggtaacgcg gaattcgcaa ctattttatc aattttttgc gtcgactcga gtagctagag   1140
aattcatggt aatagcgatg actaatacgt agatgtactg ccaagtagga aagtcccata   1200
aggtcatgta ctgggcataa tgccaggcgg gccatttacc gtcattgacg tcaataggg    1260 gcgtacttgg catatgatac acttgatgta ctgccaagtg ggcagtttac cgtaaatagt   1320
ccacccattg acgtcaatgg aaagtcccta ttggcgttac tatgggaaca tacgtcatta   1380
ttgacgtcaa tgggcggggg tcgttgggcg gtcagccagg cgggccattt accgtaagtt   1440
atgtaacgcg gaactccata tatgggctat gaactaatga ccccgtaatt gattactatt   1500
aataactaga cccagctttc ttgtacaaag ttggcattat aagaaagcat tgcttatcaa   1560
tttgttgcaa cgaacaggtc actatcagtc aaaataaaat cattatttgc catccagctg   1620 atatcccccta tagtgagtcg tattacatgg tcatagctgt ttcctggcag ctctggcccg   1680
tgtctcaaaa tctctgatgt tacattgcac aagataaaaa tatatcatca tgaacaataa   1740
aactgtctgc ttacataaac agtaatacaa ggggtgttat gagccatatt caacgggaaa   1800
cgtcgaggcc gcgattaaat tccaacatgg atgctgattt atatgggtat aaatgggctc   1860
gcgataatgt cgggcaatca ggtgcgacaa tctatcgctt gtatgggaag cccgatgcgc   1920
cagagttgtt tctgaaacat ggcaaaggta gcgttgccaa tgatgttaca gatgagatgg   1980
tcagactaaa ctggctgacg gaatttatgc ctcttccgac catcaagcat tttatccgta   2040
ctcctgatga tgcatggtta ctcaccactg cgatccccgg aaaaacagca ttccaggtat   2100
tagaagaata tcctgattca ggtgaaaata ttgttgatgc gctggcagtg ttcctgcgcc   2160
ggttgcattc gattcctgtt tgtaattgtc cttttaacag cgatcgcgta tttcgtctcg   2220
ctcaggcgca atcacgaatg aataacggtt tggttgatgc gagtgatttt gatgacgagc   2280
gtaatggctg gcctgttgaa caagtctgga agaaatgca taaacttttg ccattctcac    2340
cggattcagt cgtcactcat ggtgatttct cacttgataa ccttattttt gacgagggga   2400
aattaatagg ttgtattgat gttggacgag tcggaatcgc agaccgatac caggatcttg   2460
ccatcctatg gaactgcctc ggtgagtttt ctccttcatt acagaaacgg ctttttcaaa   2520
aatatggtat tgataatcct gatatgaata aattgcagtt tcatttgatg ctcgatgagt   2580
ttttctaatc agaattggtt aattggttgt aacactggca gagcattacg ctgacttgac   2640
gggacggcgc aagctcatga ccaaaatccc ttaacgtgag ttacgcgtcg ttccactgag   2700
cgtcagaccc cgtagaaaag atcaaaggat cttcttgaga tcctttttt ctgcgcgtaa    2760 tctgctgctt gcaaacaaaa aaaccaccgc taccagcggt ggtttgtttg ccggatcaag   2820
agctaccaac tctttttccg aaggtaactg gcttcagcag agcgcagata ccaaatactg   2880
tccttctagt gtagccgtag ttaggccacc acttcaagaa ctctgtagca ccgcctacat   2940
acctcgctct gctaatcctg ttaccagtgg ctgctgccag tggcgataag tcgtgtctta   3000
```

```
ccgggttgga ctcaagacga tagttaccgg ataaggcgca gcggtcgggc tgaacggggg    3060
gttcgtgcac acagcccagc ttggagcgaa cgacctacac cgaactgaga tacctacagc    3120
gtgagcattg agaaagcgcc acgcttcccg aagggagaaa ggcggacagg tatccggtaa    3180
gcggcagggt cggaacagga gagcgcacga gggagcttcc aggggggaaac gcctggtatc    3240 tttatagtcc tgtcgggttt cgccacctct gacttgagcg tcgattttg tgatgctcgt    3300 cagggggggcg gagcctatgg aaaaacgcca gcaacgcggc cttttacgg ttcctggcct    3360 tttgctggcc ttttgct                                                   3377

<210> SEQ ID NO 217
<211> LENGTH: 4738
<212> TYPE: DNA
<213> ORGANISM: Artificial Sequence
<220> FEATURE:
<221> NAME/KEY: misc_feature
<222> LOCATION: (3377)...(3395)
<223> OTHER INFORMATION: n may be any nucleotide
<220> FEATURE:
<221> NAME/KEY: misc_feature
<222> LOCATION: (3415)...(3433)
<223> OTHER INFORMATION: n may be any nucleotide
<220> FEATURE:
<221> NAME/KEY: source
<222> LOCATION: (1)...(4738)
<223> OTHER INFORMATION: ARI-208

<400> SEQUENCE: 217
aacatgtgag caaaaggcca gcaaaaggcc aggaaccgta aaaaggccgc gttgctggcg     60 ttttccata ggctccgccc ccctgacgag catcacaaaa atcgacgctc aagtcagagg    120
tggcgaaacc cgacaggact ataaagatac caggcgtttc ccctggaag ctccctcgtg    180 cgctctcctg ttccgaccct gccgcttacc ggatacctgt ccgcctttct cccttcggga    240
agcgtggcgc tttctcaatg ctcacgctgt aggtatctca gttcggtgta ggtcgttcgc    300
tccaagctgg gctgtgtgca cgaacccccc gttcagcccg accgctgcgc cttatccggt    360
aactatcgtc ttgagtccaa cccggtaaga cacgacttat cgccactggc agcagccact    420
ggtaacagga ttagcagagc gaggtatgta ggcggtgcta cagagttctt gaagtggtgg    480
cctaactacg gctacactag aaggacagta tttggtatct gcgctctgct gaagccagtt    540
accttcggaa aaagagttgg tagctcttga tccggcaaac aaaccaccgc tggtagcggt    600
ggtttttttg tttgcaagca gcagattacg cgcagaaaaa aaggatctca agaagatcct    660
ttgatctttt ctacggggtc tgacgctcag tggaacgacg cgtaactcac gttaagggat    720
tttggtcatg agcttgcgcc gtcccgtcaa gtcagcgtaa tgctctgcca gtgttacaac    780
caattaacca attctgatta gaaaaactca tcgagcatca aatgaaactg caatttattc    840
atatcaggat tatcaatacc atattttga aaaagccgtt tctgtaatga aggagaaaac    900
tcaccgaggc agttccatag gatggcaaga tcctggtatc ggtctgcgat tccgactcgt    960
ccaacatcaa tacaacctat taatttcccc tcgtcaaaaa taaggttatc aagtgagaaa    1020
tcaccatgag tgacgactga atccggtgag aatggcaaaa gtttatgcat ttctttccag    1080
acttgttcaa caggccagcc attacgctcg tcatcaaaat cactcgcatc aaccaaaccg    1140
ttattcattc gtgattgcgc ctgagcgaga cgaaatacgc gatcgctgtt aaaaggacaa    1200
ttacaaacag gaatcgaatg caaccggcgc aggaacactg ccagcgcatc aacaatattt    1260
tcacctgaat caggatattc ttctaatacc tggaatgctg ttttccggg gatcgcagtg    1320 gtgagtaacc atgcatcatc aggagtacgg ataaaatgct tgatggtcgg aagaggcata    1380
```

```
aattccgtca gccagtttag tctgaccatc tcatctgtaa catcattggc aacgctacct    1440
ttgccatgtt tcagaaacaa ctctggcgca tcgggcttcc catacaagcg atagattgtc    1500
gcacctgatt gcccgacatt atcgcgagcc catttatacc catataaatc agcatccatg    1560
ttggaattta atcgcggcct cgacgtttcc cgttgaatat ggctcataac accccttgta    1620
ttactgttta tgtaagcaga cagtttatt gttcatgatg atatatttt atcttgtgca    1680 atgtaacatc agagattttg agacacgggc cagagctgcc aggaaacagc tatgaccatg    1740
taatacgact cactataggg gatatcagct ggatggcaaa taatgatttt attttgactg    1800
atagtgacct gttcgttgca acaaattgat aagcaatgct ttcttataat gccaactttg    1860
tacaagaaag ctgggtctag ttattaatag taatcaatta cggggtcatt agttcatagc    1920
ccatatatgg agttccgcgt tacataactt acggtaaatg gcccgcctgg ctgaccgccc    1980
aacgaccccc gcccattgac gtcaataatg acgtatgttc ccatagtaac gccaataggg    2040
actttccatt gacgtcaatg ggtggactat ttacggtaaa ctgcccactt ggcagtacat    2100
caagtgtatc atatgccaag tacgccccct attgacgtca atgacggtaa atggcccgcc    2160
tggcattatg cccagtacat gaccttatgg actttcctta cttggcagta catctacgta    2220
ttagtcatcg ctattaccat ggtgatgcgg ttttggcagt acatcaatgg gcgtggatag    2280
cggtttgact cacggggatt tccaagtctc cacccattg acgtcaatgg gagtttgttt    2340
tggcaccaaa atcaacggga ctttccaaaa tgtcgtaaca actccgcccc attgacgcaa    2400
atgggcggta ggcgtgtacg gtgggaggtc tatataagca gagctctctg gctaactaga    2460
gaacccactg cttactggct tatcgaaatt aatacgactc actataggga cccaagct    2520 tagatctgtt tccggtcgcc accatgagcg agctgatcaa ggagaacatg cacatgaagc    2580
tgtacatgga gggcaccgtg aacaaccacc acttcaagtg cacatccgag ggcgaaggca    2640
agccctacga gggcacccag accatgaaga tcaaggtggt cgagggcggc cctctcccct    2700
tcgccttcga catcctggct accagcttca gtacggcag caaagccttc atcaaccaca    2760
cccagggcat ccccgacttc tttaagcagt ccttccctga gggcttcaca tgggagagaa    2820
tcaccacata cgaagacggg ggcgtgctga ccgctaccca ggacaccagc ttccagaacg    2880
gctgcatcat ctacaacgtc aagatcaacg gggtgaactt cccatccaac ggccctgtga    2940
tgcagaagaa aacacgcggc tgggaggcca acaccgagat gctgtacccc gctgacggcg    3000
gcctgagagg ccacagccag atggccctga gctcgtgggg cggggctac ctgcactgct    3060 ccttcaagac cacatacaga tccaagaaac ccgctaagaa cctcaagatg cccggcttcc    3120
acttcgtgga ccacagactg gaaagaatca aggaggccga caaagagacc tacgtcgagc    3180
agcacgagat ggctgtggcc aagtactgcg acctccctag caaactgggg cacagataat    3240
cgatagtttg tttgaatgag gcttcagtac tttacagaat cgttgcctgc acatcttgga    3300
aacacttgct gggattactt cttcaggtta acccaacaga aggctcgaga aggtatattg    3360
ctgttgacag tgagcgnnnn nnnnnnnnn nnnntagtg aagccacaga tgtannnnnn    3420
nnnnnnnnnn nnntgcctac tgcctcggaa ttcaaggggc tactttagga gcaattatct    3480
tgtttactaa aactgaatac cttgctatct ctttgataca ttttacaaa gctgaattaa    3540 aatggtataa attaaatcac tttttttcaat tctctagagg taccgcatgc gtacgtggcc    3600
agcggccgca ggtaagccag cccaggcctc gccctccagc tcaaggcggg acaggtgccc    3660
tagagtagcc tgcatccagg gacaggcccc agccgggtgc tgacacgtcc acctccatct    3720
```

```
cttcctcagg tctgcccggg tggcatccct gtgacccctc ccagtgcct ctcctggccc      3780 tggaagttgc cactccagtg cccaccagcc ttgtcctaat aaaattaagt tgcatcattt      3840
tgtctgacta ggtgtccttc tataatatta tggggtggag gggggtggta tggagcaagg      3900
ggcccaagtt aacttgttta ttgcagctta taatggttac aaataaagca atagcatcac      3960
aaatttcaca aataaagcat ttttttcact gcattctagt tgtggtttgt ccaaactcat      4020
caatgtatct tatcatgtct ggatccagtc gactgaattg gttcctttaa agcctgcttt      4080
tttgtacaaa gttggcatta taaaaaagca ttgctcatca atttgttgca acgaacaggt      4140
cactatcagt caaaataaaa tcattatttg ggcccgagc ttaagactgg ccgtcgtttt      4200
acaacgtcgt gactgggaaa acatccatgc tagcgttaac gcgagagtag ggaactgcca      4260
ggcatcaaat aaaacgaaag gctcagtcgg aagactgggc ctttcgtttt atctgttgtt      4320
tgtcggtgaa cgctctcctg agtaggacaa atccgccggg agcggatttg aacgttgtga      4380
agcaacggcc cggagggtgg cgggcaggac gcccgccata aactgccagg catcaaacta      4440
agcagaaggc catcctgacg gatggccttt ttgcgtttct acaaactctt cctgctagc      4500 ggtacgcgta ttaattgcgt tgcgctcact gcccgctttc cagtcgggaa acctgtcgtg      4560
ccagctgcat taatgaatcg gccaacgcgc ggggagaggc ggtttgcgta ttgggcgctc      4620
ttccgcttcc tcgctcactg actcgctgcg ctcggtcgtt cggctgcggc gagcggtatc      4680
agctcactca aaggcggtaa tacggttatc cacagaatca ggggataacg caggaaag      4738
```

<210> SEQ ID NO 218
<211> LENGTH: 6329
<212> TYPE: DNA
<213> ORGANISM: Artificial Sequence
<220> FEATURE:
<223> OTHER INFORMATION: pKD46

<400> SEQUENCE: 218

```
catcgattta ttatgacaac ttgacggcta tcatcattcac ttttcttca caaccggcac        60 ggaactcgct cgggctggcc ccggtgcatt ttttaaatac ccgcgagaaa tagagttgat       120
cgtcaaaacc aacattgcga ccgacggtgg cgataggcat ccgggtggtg ctcaaaagca       180
gcttcgcctg gctgatacgt tggtcctcgc gccagcttaa gacgctaatc cctaactgct       240
ggcggaaaag atgtgacaga cgcgacggcg acaagcaaac atgctgtgcg acgctggcga       300
tatcaaaatt gctgtctgcc aggtgatcgc tgatgtactg acaagcctcg cgtacccgat       360
tatccatcgg tggatggagc gactcgttaa tcgcttccat gcgccgcagt aacaattgct       420
caagcagatt tatcgccagc agctccgaat agcgcccttc cccttgcccg gcgttaatga       480
tttgcccaaa caggtcgctg aaatgcggct ggtgcgcttc atccgggcga agaaccccg       540 tattggcaaa tattgacggc cagttaagcc attcatgcca gtaggcgcgc ggacgaaagt       600
aaacccactg gtgataccat tcgcgagcct ccggatgacg accgtagtga tgaatctctc       660
ctggcgggaa cagcaaaata tcacccggtc ggcaaacaaa ttctcgtccc tgattttca       720 ccaccccctg accgcgaatg gtgagattga gaatataacc tttcattccc agcggtcggt       780
cgataaaaaa atcgagataa ccgttggcct caatcggcgt taaacccgcc accagatggg       840
cattaaacga gtatcccggc agcaggggat cattttgcgc ttcagccata cttttcatac       900
tcccgccatt cagagaagaa accaattgtc catattgcat cagacattgc cgtcactgcg       960
tcttttactg gctcttctcg ctaaccaaac cggtaacccc gcttattaaa agcattctgt      1020
aacaaagcgg gaccaaagcc atgacaaaaa cgcgtaacaa aagtgtctat aatcacggca      1080
```

```
gaaaagtcca cattgattat ttgcacggcg tcacactttg ctatgccata gcatttttat    1140
ccataagatt agcggatcct acctgacgct ttttatcgca actctctact gtttctccat    1200
acccgttttt ttgggaattc gagctctaag gaggttataa aaatggata ttaatactga    1260 aactgagatc aagcaaaagc attcactaac cccctttcct gttttcctaa tcagcccggc    1320
atttcgcggg cgatattttc acagctattt caggagttca gccatgaacg cttattacat    1380
tcaggatcgt cttgaggctc agagctgggc gcgtcactac cagcagctcg cccgtgaaga    1440
gaaagaggca gaactggcag acgacatgga aaaaggcctg ccccagcacc tgtttgaatc    1500
gctatgcatc gatcatttgc aacgccacgg ggccagcaaa aaatccatta cccgtgcgtt    1560
tgatgacgat gttgagtttc aggagcgcat ggcagaacac atccggtaca tggttgaaac    1620
cattgctcac caccaggttg atattgattc agaggtataa aacgaatgag tactgcactc    1680
gcaacgctgg ctgggaagct ggctgaacgt gtcggcatgg attctgtcga cccacaggaa    1740
ctgatcacca ctcttcgcca gacgcatttt aaaggtgatg ccagcgatgc gcagttcatc    1800
gcattactga tcgttgccaa ccagtacggc cttaatccgt ggacgaaaga aatttacgcc    1860
tttcctgata gcagaatgg catcgttccg gtggtgggcg ttgatggctg gtcccgcatc    1920
atcaatgaaa accagcagtt tgatggcatg gactttgagc aggacaatga atcctgtaca    1980
tgccggattt accgcaagga ccgtaatcat ccgatctgcg ttaccgaatg gatggatgaa    2040
tgccgccgcg aaccattcaa aactcgcgaa ggcagagaaa tcacggggcc gtggcagtcg    2100
catcccaaac ggatgttacg tcataaagcc atgattcagt gtgcccgtct ggccttcgga    2160
tttgctggta tctatgacaa ggatgaagcc gagcgcattg tcgaaaatac tgcatacact    2220
gcagaacgtc agccggaacg cgacatcact ccggttaacg atgaaaccat gcaggagatt    2280
aacactctgc tgatcgccct ggataaaaca tgggatgacg acttattgcc gctctgttcc    2340
cagatatttc gccgcgacat tcgtgcatcg tcagaactga cacaggccga agcagtaaaa    2400
gctcttggat tcctgaaaca gaaagccgca gagcagaagg tggcagcatg acaccggaca    2460
ttatcctgca gcgtaccggg atcgatgtga gagctgtcga acaggggat gatgcgtggc    2520 acaaattacg gctcggcgtc atcaccgctt cagaagttca aacgtgata gcaaaacccc    2580 gctccggaaa gaagtggcct gacatgaaaa tgtcctactt ccacaccctg cttgctgagg    2640
tttgcaccgg tgtggctccg gaagttaacg ctaaagcact ggcctgggga aaacagtacg    2700
agaacgacgc cagaaccctg tttgaattca cttccggcgt gaatgttact gaatccccga    2760
tcatctatcg cgacgaaagt atgcgtaccg cctgctctcc cgatggttta tgcagtgacg    2820
gcaacggcct tgaactgaaa tgcccgttta cctcccggga tttcatgaag ttccggctcg    2880
gtggtttcga ggccataaag tcagcttaca tggcccaggt gcagtacagc atgtgggtga    2940
cgcgaaaaaa tgcctggtac tttgccaact atgacccgcg tatgaagcgt gaaggcctgc    3000
attatgtcgt gattgagcgg gatgaaaagt acatggcgag ttttgacgag atcgtgccgg    3060
agttcatcga aaaaatggac gaggcactgg ctgaaattgg ttttgtattt ggggagcaat    3120
ggcgatgacg catcctcacg ataatatccg ggtaggcgca atcactttcg tctactccgt    3180
tacaaagcga ggctgggtat ttcccggcct ttctgttatc cgaaatccac tgaaagcaca    3240
gcggctggct gaggagataa ataataaacg aggggctgta tgcacaaagc atcttctgtt    3300
gagttaagaa cgagtatcga gatggcacat agccttgctc aaattggaat caggtttgtg    3360
ccaataccag tagaaacaga cgaagaatcc atgggtatgg acagttttcc ctttgatatg    3420
```

```
taacggtgaa cagttgttct actttttgttt gttagtcttg atgcttcact gatagataca    3480
agagccataa gaacctcaga tccttccgta tttagccagt atgttctcta gtgtggttcg    3540
ttgtttttgc gtgagccatg agaacgaacc attgagatca tacttacttt gcatgtcact    3600
caaaaatttt gcctcaaaac tggtgagctg aattttttgca gttaaagcat cgtgtagtgt    3660
ttttcttagt ccgttacgta ggtaggaatc tgatgtaatg gttgttggta ttttgtcacc    3720 attcatttttt atctggttgt tctcaagttc ggttacgaga tccatttgtc tatctagttc    3780
aacttggaaa atcaacgtat cagtcgggcg gcctcgctta tcaaccacca atttcatatt    3840
gctgtaagtg tttaaatctt tacttattgg tttcaaaacc cattggttaa gccttttaaa    3900
ctcatggtag ttattttcaa gcattaacat gaacttaaat tcatcaaggc taatctctat    3960
atttgccttg tgagttttct tttgtgttag ttctttttaat aaccactcat aaatcctcat    4020
agagtatttg ttttcaaaag acttaacatg ttccagatta tattttatga attttttttaa    4080 ctggaaaaga taaggcaata tctcttcact aaaaactaat tctaattttt cgcttgagaa    4140
cttggcatag tttgtccact ggaaaatctc aaagcccttta accaaggat tcctgatttc    4200 cacagttctc gtcatcagct ctctggttgc tttagctaat acaccataag cattttccct    4260
actgatgttc atcatctgag cgtattggtt ataagtgaac gataccgtcc gttctttcct    4320
tgtagggttt tcaatcgtgg ggttgagtag tgccacacag cataaaatta gcttggtttc    4380
atgctccgtt aagtcatagc gactaatcgc tagttcattt gctttgaaaa caactaattc    4440
agacatacat ctcaattggt ctaggtgatt ttaatcacta taccaattga gatgggctag    4500
tcaatgataa ttactagtcc ttttcctttg agttgtgggt atctgtaaat tctgctagac    4560
ctttgctgga aaacttgtaa attctgctag accctctgta aattccgcta gacctttgtg    4620
tgtttttttt gtttatattc aagtggttat aatttataga ataagaaag aataaaaaaa    4680 gataaaaaga atagatccca gccctgtgta taactcacta ctttagtcag ttccgcagta    4740
ttacaaaagg atgtcgcaaa cgctgtttgc tcctctacaa aacagacctt aaaaccctaa    4800
aggcttaagt agcaccctcg caagctcggt tgcggccgca atcgggcaaa tcgctgaata    4860
ttccttttgt ctccgaccat caggcacctg agtcgctgtc ttttttcgtga cattcagttc    4920 gctgcgctca cggctctggc agtgaatggg ggtaaatggc actacaggcg cctttttatgg    4980 attcatgcaa ggaaactacc cataatacaa gaaaagcccg tcacgggctt ctcagggcgt    5040
tttatggcgg gtctgctatg tggtgctatc tgactttttg ctgttcagca gttcctgccc    5100
tctgattttc cagtctgacc acttcggatt atcccgtgac aggtcattca gactggctaa    5160
tgcacccagt aaggcagcgg tatcatcaac ggggtctgac gctcagtgga acgaaaactc    5220
acgttaaggg attttggtca tgagattatc aaaaaggatc ttcacctaga tccttttaaa    5280
ttaaaaatga agttttaaat caatctaaag tatatatgag taaacttggt ctgacagtta    5340
ccaatgctta atcagtgagg cacctatctc agcgatctgt ctatttcgtt catccatagt    5400
tgcctgactc cccgtcgtgt agataactac gatacgggag ggcttaccat ctggccccag    5460
tgctgcaatg ataccgcgag acccacgctc accggctcca gatttatcag caataaacca    5520
gccagccgga agggccgagc gcagaagtgg tcctgcaact ttatccgcct ccatccagtc    5580
tattaattgt tgccgggaag ctagagtaag tagttcgcca gttaatagtt tgcgcaacgt    5640
tgttgccatt gctacaggca tcgtggtgtc acgctcgtcg tttggtatgg cttcattcag    5700
ctccggttcc caacgatcaa ggcgagttac atgatccccc atgttgtgca aaaaagcggt    5760
tagctccttc ggtcctccga tcgttgtcag aagtaagttg gccgcagtgt tatcactcat    5820
```

-continued

```
ggttatggca gcactgcata attctcttac tgtcatgcca tccgtaagat gcttttctgt    5880
gactggtgag tactcaacca agtcattctg agaatagtgt atgcggcgac cgagttgctc    5940
ttgcccggcg tcaatacggg ataataccgc gccacatagc agaactttaa aagtgctcat    6000
cattggaaaa cgttcttcgg ggcgaaaact ctcaaggatc ttaccgctgt tgagatccag    6060
ttcgatgtaa cccactcgtg cacccaactg atcttcagca tctttactt tcaccagcgt     6120 ttctgggtga gcaaaaacag gaaggcaaaa tgccgcaaaa aagggaataa gggcgacacg    6180
gaaatgttga atactcatac tcttcctttt tcaatattat tgaagcattt atcagggtta    6240
ttgtctcatg agcggataca tatttgaatg tatttagaaa aataaacaaa tagggggttcc    6300 gcgcacattt ccccgaaaag tgccacctg                                      6329
```

<210> SEQ ID NO 219
<211> LENGTH: 22
<212> TYPE: DNA
<213> ORGANISM: Artificial Sequence
<220> FEATURE:
<223> OTHER INFORMATION: asd-1 primer

<400> SEQUENCE: 219
ccttcctaac gcaaattccc tg                                              22

<210> SEQ ID NO 220
<211> LENGTH: 22
<212> TYPE: DNA
<213> ORGANISM: Artificial Sequence
<220> FEATURE:
<223> OTHER INFORMATION: asd-2 primer

<400> SEQUENCE: 220
ccaatgctct gcttaactcc tg                                              22

<210> SEQ ID NO 221
<211> LENGTH: 21
<212> TYPE: DNA
<213> ORGANISM: Artificial Sequence
<220> FEATURE:
<223> OTHER INFORMATION: asd-3 primer

<400> SEQUENCE: 221
gcctcgccat gtttcagtac g                                               21

<210> SEQ ID NO 222
<211> LENGTH: 21
<212> TYPE: DNA
<213> ORGANISM: Artificial Sequence
<220> FEATURE:
<223> OTHER INFORMATION: asd-4 primer

<400> SEQUENCE: 222
ggtctggtgc attccgagta c                                               21

<210> SEQ ID NO 223
<211> LENGTH: 23
<212> TYPE: DNA
<213> ORGANISM: Artificial Sequence
<220> FEATURE:
<223> OTHER INFORMATION: scFv-3 primer

<400> SEQUENCE: 223
cataatctgg gtccttggtc tgc                                             23

<210> SEQ ID NO 224
<211> LENGTH: 5728
<212> TYPE: DNA
<213> ORGANISM: Artificial Sequence
<220> FEATURE:
<223> OTHER INFORMATION: pJW168 plasmid

<400> SEQUENCE: 224

| | | | | | |
|---|---|---|---|---|---|
| ttactaatcg | ccatcttcca | gcaggcgcac | cattgcccct | gtttcactat | ccaggttacg | 60 |
| gatatagttc | atgacaatat | ttacattggt | ccagccacca | gcttgcatga | tctccggtat | 120 |
| tgaaactcca | gcgcgggcca | tatctcgcgc | ggctccgaca | cgggcactgt | gtccagacca | 180 |
| ggccaggtat | ctctgaccag | agtcatcctt | agcgccgtaa | atcaatcgat | gagttgcttc | 240 |
| aaaaatccct | tccagggcgc | gagttgatag | ctggctggtg | gcagatgcg | cggcaacacc | 300 |
| atttttctg | acccggcaaa | acaggtagtt | attcggatca | tcagctacac | cagagacgga | 360 |
| aatccatcgc | tcgaccagtt | tagttacccc | caggctaagt | gccttctcta | cacctgcggt | 420 |
| gctaaccagc | gttttcgttc | tgccaatatg | gattaacatt | ctcccaccgt | cagtacgtga | 480 |
| gatatcttta | accctgatcc | tggcaatttc | ggctatacgt | aacagggtgt | tataagcaat | 540 |
| ccccagaaat | gccagattac | gtatatcctg | gcagcgatcg | ctattttcca | tgagtgaacg | 600 |
| aacctggtcg | aaatcagtgc | gttcgaacgc | tagagcctgt | tttgcacgtt | caccggcatc | 660 |
| aacgttttct | tttcggatcc | gccgcataac | cagtgaaaca | gcattgctgt | cacttggtcg | 720 |
| tggcagcccg | gaccgacgat | gaagcatgtt | tagctggccc | aaatgttgct | ggatagtttt | 780 |
| tactgccaga | ccgcgcgcct | gaagatatag | aagataatcg | cgaacatctt | caggttctgc | 840 |
| gggaaaccat | ttccggttat | tcaacttgca | ccatgccgcc | cacgaccggc | aaacggacag | 900 |
| aagcattttc | caggtatgct | cagaaaacgc | ctggcgatcc | ctgaacatgt | ccatcaggtt | 960 |
| cttgcgaacc | tcatcactcg | ttgcatcgac | cggtaatgca | ggcaaatttt | ggtgtacggg | 1020 |
| cagtaaattg | gacatgtcaa | cggtacctgc | agtctagagt | cgaggcctgt | ttcctgtgtg | 1080 |
| aaattgttat | ccgctcacaa | ttccacacat | tatacgagcc | ggaagcataa | agtgtaaagc | 1140 |
| ctggggtgcc | taatgagtga | gctgtttcct | gtgtgaaatt | gttatccgct | cacaattcca | 1200 |
| cacattatac | gagccggaag | cataaagtgt | aaagcctggg | gtgcctaatg | agtgagctgc | 1260 |
| ctcgcgcgtt | tcggtgatga | cggtgaaaac | ctctgacaca | tgcagctccc | ggagacggtc | 1320 |
| acagcttgtc | tgtaagcgga | tgccgggagc | agacaagccc | gtcagggcgc | gtcagcgggt | 1380 |
| gttggcgggt | gtcggggcgc | agccatgacc | cagtcacgta | gcgatagcg | gagtgtatcc | 1440 |
| gacaccatcg | aatggtgcaa | aacctttcgc | ggtatggcat | gatagcgccc | ggaagagagt | 1500 |
| caattcaggg | tggtgaatgt | gaaaccagta | acgttatacg | atgtcgcaga | gtatgccggt | 1560 |
| gtctcttatc | agaccgtttc | ccgcgtggtg | aaccaggcca | gccacgtttc | tgcgaaaacg | 1620 |
| cgggaaaaag | tggaagcggc | gatggcggag | ctgaattaca | ttcccaaccg | cgtggcacaa | 1680 |
| caactggcgg | gcaaacagtc | gttgctgatt | ggcgttgcca | cctccagtct | ggccctgcac | 1740 |
| gcgccgtcgc | aaattgtcgc | ggcgattaaa | tctcgcgccg | atcaactggg | tgccagcgtg | 1800 |
| gtggtgtcga | tggtagaacg | aagcggcgtc | gaagcctgta | aagcggcggt | gcacaatctt | 1860 |
| ctcgcgcaac | gcgtcagtgg | gctgatcatt | aactatccgc | tggatgacca | ggatgccatt | 1920 |
| gctgtggaag | ctgcctgcac | taatgttccg | gcgttatttc | ttgatgtctc | tgaccagaca | 1980 |
| cccatcaaca | gtattatttt | ctcccatgaa | gacggtacgc | gactgggcgt | ggagcatctg | 2040 |
| gtcgcattgg | gtcaccagca | aatcgcgctg | ttagcgggcc | cattaagttc | tgtctcggcg | 2100 |

```
cgtctgcgtc tggctggctg gcataaatat ctcactcgca atcaaattca gccgatagcg   2160
gaacgggaag gcgactggag tgccatgtcc ggttttcaac aaaccatgca aatgctgaat   2220
gagggcatcg ttcccactgc gatgctggtt gccaacgatc agatggcgct gggcgcaatg   2280
cgcgccatta ccgagtccgg gctgcgcgtt ggtgcggata tctcggtagt gggatacgac   2340
gataccgaag acagctcatg ttatatcccg ccgttaacca ccatcaaaca ggattttcgc   2400
ctgctggggc aaaccagcgt ggaccgcttg ctgcaactct ctcagggcca ggcggtgaag   2460
ggcaatcagc tgttgcccgt ctcactggtg aaaagaaaaa ccaccctggc gcccaatacg   2520
caaaccgcct ctccccgcgc gttggccgat tcattaatgc agctggcacg acaggtttcc   2580
cgactggaaa gcgggcagtg agcgcaacgc aatcaatgtg agttagctca ctcattaggc   2640
accccaggct ttacacttta tgcttccgac catactggct taactatgcg gcatcagagc   2700
agattgtact gagagtgcac catcgatgca ggtggcactt ttcggggaaa tgtgcgcgga   2760
accctatttt gtttattttt ctaaatacat tcaaatatgt atccgctcat gagacaataa   2820
ccctgataaa tgcttcaata atattgaaaa aggaagagta tgagtattca acatttccgt   2880
gtcgccctta ttcccttttt tgcggcattt tgccttcctg tttttgctca cccagaaacg   2940
ctggtgaaag taaaagatgc tgaagatcag ttgggtgcac gagtgggtta catcgaactg   3000
gatctcaaca gcggtaagat ccttgagagt tttcgccccg aagaacgttt tccaatgatg   3060
agcacttttta aagttctgct atgtggcgcg gtattatccc gtattgacgc cgggcaagag   3120
caactcggtc gccgcataca ctattctcag aatgacttgg ttgagtactc accagtcaca   3180
gaaaagcatc ttacggatgg catgacagta agagaattat gcagtgctgc cataaccatg   3240
agtgataaca ctgcggccaa cttacttctg acaacgatcg gaggaccgaa ggagctaacc   3300
gcttttttgc acaacatggg ggatcatgta actcgccttg atcgttggga accggagctg   3360
aatgaagcca taccaaacga cgagcgtgac accacgatgc ctgtagcaat ggcaacaacg   3420
ttgcgcaaac tattaactgg cgaactactt actctagctt cccggcaaca attaatagac   3480
tggatggagg cggataaagt tgcaggacca cttctgcgct cggcccttcc ggctggctgg   3540
tttattgctg ataaatctgg agccggtgag cgtgggtctc gcggtatcat tgcagcactg   3600
gggccagatg gtaagccctc ccgtatcgta gttatctaca cgacggggag tcaggcaact   3660
atggatgaac gaaatagaca gatcgctgag ataggtgcct cactgattaa gcattggtaa   3720
ctgtcagacc aagtttactc atatatactt tagattgatt taaaacttca ttttttaattt   3780
aaaaggatct aggtgaagat cctttttgat aatctcatga ccaaaatccc ttaacgtgag   3840
ttttcgttcc actgagcgtc agaccccgtt gatgataccg ctgccttact gggtgcatta   3900
gccagtctga tgacctgtc acgggataat ccgaagtggt cagactggaa aatcagaggg   3960
caggaactgc tgaacagcaa aaagtcagat agcaccacat agcagacccg ccataaaacg   4020
ccctgagaag cccgtgacgg gcttttcttg tattatgggt agtttccttg catgaatcca   4080
taaaaggcgc ctgtagtgcc atttaccccc attcactgcc agagccgtga gcgcagcgaa   4140
ctgaatgtca cgaaaaagac agcgactcag gtgcctgatg tcggagacaa aaggaatat   4200
tcagcgattt gcccgattgc ggccgcaacc gagcttgcga gggtgctact taagccttta   4260
gggttttaag gtctgttttg tagaggagca aacagcgttt gcgacatcct tttgtaatac   4320
tgcggaactg actaaagtag tgagttatac acagggctgg gatctattct ttttatcttt   4380
ttttattctt tctttattct ataaattata accacttgaa tataaacaaa aaaaacacac   4440
```

| | |
|---|---|
| aaaggtctag cggaatttac agagggtcta gcagaattta caagttttcc agcaaaggtc | 4500 |
| tagcagaatt tacagatacc cacaactcaa aggaaaagga ctagtaatta tcattgacta | 4560 |
| gcccatctca attggtatag tgattaaaat cacctagacc aattgagatg tatgtctgaa | 4620 |
| ttagttgttt tcaaagcaaa tgaactagcg attagtcgct atgacttaac ggagcatgaa | 4680 |
| accaagctaa ttttatgctg tgtggcacta ctcaacccca cgattgaaaa ccctacaagg | 4740 |
| aaagaacgga cggtatcgtt cacttataac caatacgttc agatgatgaa catcagtagg | 4800 |
| gaaaatgctt atggtgtatt agctaaagca accagagagc tgatgacgag aactgtggaa | 4860 |
| atcaggaatc ctttggttaa aggctttgag attttccagt ggacaaacta tgccaagttc | 4920 |
| tcaagcgaaa aattagaatt agttttагt gaagagatat tgccttatct tttccagtta | 4980 |
| aaaaaattca taaatataa tctggaacat gttaagtctt ttgaaaacaa atactctatg | 5040 |
| aggatttatg agtggttatt aaaagaacta acacaaaaga aaactcacaa ggcaaatata | 5100 |
| gagattagcc ttgatgaatt taagttcatg ttaatgcttg aaaataacta ccatgagttt | 5160 |
| aaaaggctta accaatgggt tttgaaacca ataagtaaag atttaaacac ttacagcaat | 5220 |
| atgaaattgg tggttgataa gcgaggccgc ccgactgata cgttgatttt ccaagttgaa | 5280 |
| ctagatagac aaatggatct cgtaaccgaa cttgagaaca accagataaa atgaatggt | 5340 |
| gacaaaatac caacaaccat tacatcagat tcctacctac ataacggact aagaaaaaca | 5400 |
| ctacacgatg ctttaactgc aaaaattcag ctcaccagtt ttgaggcaaa аттттгgagт | 5460 |
| gacatgcaaa gtaagyatga tctcaatggt tcgttctcat ggctcacgca aaaacaacga | 5520 |
| accacactag agaacatact ggctaaatac ggaaggatct gaggttctta tggctcttgt | 5580 |
| atctatcagt gaagcatcaa gactaacaaa caaaagtaga acaactgttc accgttacat | 5640 |
| atcaagggga aaactgtcca tacccatggg ctagctgatc agccagtgcc aagcttgctc | 5700 |
| aatcaatcac cggatccccc gggaattc | 5728 |

<210> SEQ ID NO 225
<211> LENGTH: 3736
<212> TYPE: DNA
<213> ORGANISM: Artificial Sequence
<220> FEATURE:
<223> OTHER INFORMATION: pATIU6 plasmid

<400> SEQUENCE: 225

| | |
|---|---|
| gcgcccaata cgcaaaccgc ctctccccgc gcgttggccg attcattaat gcagctggca | 60 |
| cgacaggttt cccgactgga aagcgggcag tgagcgcaac gcaatggatc caaggtcggg | 120 |
| caggaagagg gcctatttcc catgattcct tcatatttgc atatacgata caaggctgtt | 180 |
| agagagataa ttagaattaa tttgactgta aacacaaaga tattagtaca aaatacgtga | 240 |
| cgtagaaagt aataatttct tgggtagttt gcagttttaa attatgttt taaatggac | 300 |
| tatcatatgc ttaccgtaac ttgaaagtat ttcgatttct tggctttata tattgtgg | 360 |
| aaaggacgaa actagtttt tctcgagtag ctagagaatt cttaagccag ccccgacacc | 420 |
| cgccaacacc cgctgacgcg ccctgacggg cttgtctgct cccggcatcc gcttacagac | 480 |
| aagctgtgac cgtctccggg agctgcatgt gtcagaggtt tcaccgtca tcaccgaaac | 540 |
| gcgcgagacg aaagggcctc gtgatacgcc tatttttata ggttaatgtc atgataataa | 600 |
| tggtttctta gacgtcaggt ggcactttt ggggaaatgt gaagcttcgc ggaaccccta | 660 |
| tttgtttatt ttctaaata cattcaaata tgtatccgct catgagacaa таасссгаt | 720 |
| aaatgcttca ataatattga aaaggaaga gtatgagtat tcaacatttc cgtgtcgccc | 780 |

```
ttattccctt ttttgcggca ttttgccttc ctgttttgc tcacccagaa acgctggtga    840
aagtaaaaga tgctgaagat cagttgggtg cacgagtggg ttacatcgaa ctggatctca    900
acagcggtaa gatccttgag agttttcgcc ccgaagaacg ttttccaatg atgagcactt    960
ttaaagttct gctatgtggc gcggtattat cccgtattga cgccgggcaa gagcaactcg   1020
gtcgccgcat acactattct cagaatgact tggttgagta ctcaccagtc acagaaaagc   1080
atcttacgga tggcatgaca gtaagagaat tatgcagtgc tgccataacc atgagtgata   1140
acactgcggc caacttactt ctgacaacga tcggaggacc gaaggagcta accgcttttt   1200
tgcacaacat gggggatcat gtaactcgcc ttgatcgttg ggaaccggag ctgaatgaag   1260
ccataccaaa cgacgagcgt gacaccacga tgcctgtagc aatggcaaca cgttgcgca    1320 aactattaac tggcgaacta cttactctag cttcccggca acaattaata gactggatgg   1380
aggcggataa agttgcagga ccacttctgc gctcggccct tccggctggc tggtttattg   1440
ctgataaatc tggagccggt gagcgtgggt ctcgcggtat cattgcagca ctggggccag   1500
atggtaagcc ctcccgtatc gtagttatct acacgacggg gagtcaggca actatggatg   1560
aacgaaatag acagatcgct gagataggtg cctcactgat taagcattgg taaaagcttc   1620
tgtcagacca agtttactca tatatacttt agattgattt aaaacttcat ttttaattta   1680
aaaggatcta ggtgaagatc ctttatggtg aaggatgcgc cacaggatac tggcgcgcat   1740
acacagcaca tctctttgca ggaaaaaaac gctatgaaaa atgttggttt tatcggctgg   1800
cgcggaatgg tcggctctgt tctcatgcaa cgcatggtag aggagcgcga tttcgacgct   1860
attcgccctg ttttcttttc tacctcccag tttggacagg cggcgccac cttcggcgac   1920 acctccaccg gcacgctaca ggacgctttt gatctggatg cgctaaaagc gctcgatatc   1980
atcgtgacct gccagggcgg cgattatacc aacgaaattt atccaaagct gcgcgaaagc   2040
ggatggcagg gttactggat tgatgcggct tctacgctgc gcatgaaaga tgatgccatt   2100
attattctcg acccggtcaa ccaggacgtg attaccgacg gcctgaacaa tggcgtgaag   2160
acctttgtgg gcggtaactg taccgttagc ctgatgttga tgtcgctggg cggtctcttt   2220
gcccataatc tcgttgactg ggtatccgtc gcgacctatc aggccgcctc cggcggcggc   2280
gcgcgccata tgcgcgagct gttaacccag atgggtcagt tgtatggcca tgtcgccgat   2340
gaactggcga cgccgtcttc cgcaattctt gatattgaac gcaaagttac ggcattgacc   2400
cgcagcggcg agctgccggt tgataacttt ggcgtaccgc tggcgggaag cctgatcccc   2460
tggatcgaca aacagctcga taacggccag agccgcgaag agtggaaagg ccaggcggaa   2520
accaacaaga ttctcaatac tgcctctgtg attccggttg atggtttgtg tgtgcgcgtc   2580
ggcgcgctgc gctgtcacag ccaggcgttc accatcaagc tgaaaaaaga ggtatccatt   2640
ccgacggtgg aagaactgct ggcggcacat aatccgtggg cgaaagtggt gccgaacgat   2700
cgtgatatca ctatgcgcga attaaccccg cggcggtga ccggcacgtt gactacgccg   2760
gttggtcgtc tgcgtaagct gaacatgggg ccagagttct tgtcggcgtt taccgtaggc   2820
gaccagttgt tatggggcgc cgccgagccg ctggtcgaa tgctgcgcca gttggcgtag   2880
ttgataatct catgaccaaa atcccttaac gtgagttttc gttccactga gcgtcagacc   2940
ccgtagaaaa gatcaaagga tcttcttgag atcctttttt tctgcgcgta atctgctgct   3000
tgcaaacaaa aaaccaccg ctaccagcgg tggtttgttt gccggatcaa gagctaccaa   3060 ctcttttttcc gaaggtaact ggcttcagca gagcgcagat accaaatact gttcttctag   3120
```

| | | |
|---|---|---|
| tgtagccgta gttaggccac cacttcaaga actctgtagc accgcctaca tacctcgctc | 3180 | |
| tgctaatcct gttaccagtg gctgctgcca gtggcgataa gtcgtgtctt accgggttgg | 3240 | |
| actcaagacg atagttaccg gataaggcgc agcggtcggg ctgaacgggg ggttcgtgca | 3300 | |
| cacagcccag cttggagcga acgacctaca ccgaactgag atacctacag cgtgagctat | 3360 | |
| gagaaagcgc cacgcttccc gaagggagaa aggcggacag gtatccggta agcggcaggg | 3420 | |
| tcggaacagg agagcgcacg agggagcttc caggggggaaa cgcctggtat ctttatagtc | 3480 | |
| ctgtcgggtt tcgccacctc tgacttgagc gtcgattttt gtgatgctcg tcagggggc | 3540 | |
| ggagcctatg gaaaaacgcc agcaacgcgg ccttttttacg gttcctggcc ttttgctggc | 3600 | |
| cttttgctca catgttcttt cctgcgttat cccctgattc tgtggataac cgtattaccg | 3660 | |
| cctttgagtg agctgatacc gctcgccgca gccgaacgac cgagcgcagc gagtcagtga | 3720 | |
| gcgaggaagc ggaaga | 3736 | |

<210> SEQ ID NO 226
<211> LENGTH: 26
<212> TYPE: DNA
<213> ORGANISM: Artificial Sequence
<220> FEATURE:
<223> OTHER INFORMATION: APR-001 Kan PrimerF

<400> SEQUENCE: 226

| | |
|---|---|
| aaaaaagctt gcagctctgg cccgtg | 26 |

<210> SEQ ID NO 227
<211> LENGTH: 38
<212> TYPE: DNA
<213> ORGANISM: Artificial Sequence
<220> FEATURE:
<223> OTHER INFORMATION: APR-002 Kan PrimerR

<400> SEQUENCE: 227

| | |
|---|---|
| aaaaaagctt ttagaaaaac tcatcgagca tcaaatga | 38 |

<210> SEQ ID NO 228
<211> LENGTH: 28
<212> TYPE: DNA
<213> ORGANISM: Artificial Sequence
<220> FEATURE:
<223> OTHER INFORMATION: APR-003 pATI ori T148CF

<400> SEQUENCE: 228

| | |
|---|---|
| acactagaag gacagtattt ggtatctg | 28 |

<210> SEQ ID NO 229
<211> LENGTH: 18
<212> TYPE: DNA
<213> ORGANISM: Artificial Sequence
<220> FEATURE:
<223> OTHER INFORMATION: APR-004 pATI ori T148CR

<400> SEQUENCE: 229

| | |
|---|---|
| agccgtagtt aggccacc | 18 |

<210> SEQ ID NO 230
<211> LENGTH: 3203
<212> TYPE: DNA
<213> ORGANISM: Artificial Sequence
<220> FEATURE:
<223> OTHER INFORMATION: pSL0147 plasmid

<400> SEQUENCE: 230

-continued

```
gacgaaaggg cctcgtgata cgcctatttt tataggttaa tgtcatgata ataatggttt    60
cttagacgtc aggtggcact tttcggggaa atgtgcgcgg aaccccctatt tgtttatttt   120 tctaaataca ttcaaatatg tatccgctca tgagacaata accctgataa atgcttcaat   180
aatattgaaa aaggaagagt atgagtattc aacatttccg tgtcgccctt attccctttt   240
ttgcggcatt ttgccttcct gttttttgctc acccagaaac gctggtgaaa gtaaaagatg   300
ctgaagatca gttgggtgca cgagtgggtt acatcgaact ggatctcaac agcggtaaga   360
tccttgagag ttttcgcccc gaagaacgtt ttccaatgat gagcactttt aaagttctgc   420
tatgtggcgc ggtattatcc cgtattgacg ccgggcaaga gcaactcggt cgccgcatac   480
actattctca gaatgacttg gttgagtact caccagtcac agaaaagcat cttacggatg   540
gcatgacagt aagagaatta tgcagtgctg ccataaccat gagtgataac actgcggcca   600
acttacttct gacaacgatc ggaggaccga aggagctaac cgcttttttg cacaacatgg   660
gggatcatgt aactcgcctt gatcgttggg aaccggagct gaatgaagcc ataccaaacg   720
acgagcgtga caccacgatg cctgtagcaa tggcaacaac gttgcgcaaa ctattaactg   780
gcgaactact tactctagct tcccggcaac aattaataga ctggatggag gcggataaag   840
ttgcaggacc acttctgcgc tcggcccttc cggctggctg gtttattgct gataaatctg   900
gagccggtga gcgtgggtct cgcggtatca ttgcagcact ggggccagat ggtaagccct   960
cccgtatcgt agttatctac acgacgggga gtcaggcaac tatggatgaa cgaaatagac  1020
agatcgctga gataggtgcc tcactgatta agcattggta actgtcagac caagtttact  1080
catatatact ttagattgat ttaaaacttc atttttaatt taaaaggatc taggtgaaga  1140
tcctttttga taatctcatg accaaaatcc cttaacgtga gttttcgttc cactgagcgt  1200 cagacccccgt agaaaagatc aaaggatctt cttgagatcc ttttttttctg cgcgtaatct  1260 gctgcttgca acaaaaaaaa ccaccgctac cagcggtggt ttgtttgccg gatcaagagc  1320
taccaactct ttttccgaag gtaactggct tcagcagagc gcagatacca aatactgttc  1380
ttctagtgta gccgtagtta ggccaccact tcaagaactc tgtagcaccg cctacatacc  1440
tcgctctgct aatcctgtta ccagtggctg ctgccagtgg cgataagtcg tgtcttaccg  1500
ggttggactc aagacgatag ttaccggata aggcgcagcg gtcgggctga acggggggtt  1560
cgtgcacaca gcccagcttg gagcgaacga cctacaccga actgagatac ctacagcgtg  1620
agctatgaga aagcgccacg cttcccgaag ggagaaaggc ggacaggtat ccggtaagcg  1680
gcagggtcgg aacaggagag cgcacgaggg agcttccagg gggaaacgcc tggtatcttt  1740
atagtcctgt cgggtttcgc cacctctgac ttgagcgtcg atttttgtga tgctcgtcag  1800
gggggcggag cctatggaaa aacgccagca acgcggcctt tttacggttc ctggccttt   1860 gctggccttt tgctcacatg ttctttcctg cgttatcccc tgattctgtg ataaccgta   1920 ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc  2040
cgattcatta atgcagctgg cacgacaggt ttcccgactg gaaagcgggc agtgagcgca  2100
acgcaattaa tgtgagttag ctcactcatt aggcacccca ggctttacac tttatgcttc  2160
cggctcgtat gttgtgtgga attgtgagcg gataacaatt tcacacagga aacagctatg  2220
accatgatta cgccaagctc ggcgcgccat gggatggaa cgcgttatcg gcaatctgga  2280
ggcaaagttt aatgataatt ttgcaaaaat aatgcgcgga ataatgatgc ataaagcggc  2340
```

| | |
|---|---|
| tatttcgccg cctaagaaaa agatcggggg aagtgaaaaa ttttctaaag ttcgaaattc | 2400 |
| aggtgccgat acaagggtta cggtgagaaa ccgtgggcaa cagcccaata acatcaagtt | 2460 |
| gtaattgata aggaaaagat catgggctag cctcaataag cttcttgcct ttctgcagac | 2520 |
| caaggaccca gattatgttg cagcaggccg gtacctccgt tctggcgcag gcgaaccagg | 2580 |
| ttccgcaaaa cgtcctctct ttactgcgtt aatccggcga ttgattcacc gacacgtggt | 2640 |
| acacaatcaa ggcagcgaaa gctgcctttt ttaattccgg agcctgtgta atgaaagaaa | 2700 |
| tcaccgtcac tgaacctgcc tttgtcaccc gcttttcctg ttctggctcg gcctgtcgcg | 2760 |
| accactgttg taagggctgg aaagttccat cccaatacgc gtcaattcac tggccgtcgt | 2820 |
| tttacaacgt cgtgactggg aaaaccctgg cgttacccaa cttaatcgcc ttgcagcaca | 2880 |
| tcccccttc gccagctggc gtaatagcga agaggcccgc accgatcgcc cttcccaaca | 2940 |
| gttgcgcagc ctgaatggcg aatggcgcct gatgcggtat tttctcctta cgcatctgtg | 3000 |
| cggtatttca caccgcatat ggtgcactct cagtacaatc tgctctgatg ccgcatagtt | 3060 |
| aagccagccc cgacacccgc caacacccgc tgacgcgccc tgacgggctt gtctgctccc | 3120 |
| ggcatccgct tacagacaag ctgtgaccgt ctccgggagc tgcatgtgtc agaggttttc | 3180 |
| accgtcatca ccgaaacgcg cga | 3203 |

<210> SEQ ID NO 231
<211> LENGTH: 3196
<212> TYPE: DNA
<213> ORGANISM: Artificial Sequence
<220> FEATURE:
<223> OTHER INFORMATION: pSL0148 plasmid

<400> SEQUENCE: 231

| | |
|---|---|
| gacgaaaggg cctcgtgata cgcctatttt tataggttaa tgtcatgata ataatggttt | 60 |
| cttagacgtc aggtggcact tttcggggaa atgtgcgcgg aacccctatt tgtttatttt | 120 |
| tctaaataca ttcaaatatg tatccgctca tgagacaata accctgataa atgcttcaat | 180 |
| aatattgaaa aaggaagagt atgagtattc aacatttccg tgtcgccctt attcccttt | 240 |
| ttgcggcatt ttgccttcct gttttgctc acccagaaac gctggtgaaa gtaaaagatg | 300 |
| ctgaagatca gttgggtgca cgagtgggtt acatcgaact ggatctcaac agcggtaaga | 360 |
| tccttgagag ttttcgcccc gaagaacgtt ttccaatgat gagcactttt aaagttctgc | 420 |
| tatgtggcgc ggtattatcc cgtattgacg ccgggcaaga gcaactcggt cgccgcatac | 480 |
| actattctca gaatgacttg gttgagtact caccagtcac agaaaagcat cttacggatg | 540 |
| gcatgacagt aagagaatta tgcagtgctg ccataaccat gagtgataac actgcggcca | 600 |
| acttacttct gacaacgatc ggaggaccga aggagctaac cgcttttttg cacaacatgg | 660 |
| gggatcatgt aactcgcctt gatcgttggg aaccggagct gaatgaagcc ataccaaacg | 720 |
| acgagcgtga ccacacgatg cctgtagcaa tggcaacaac gttgcgcaaa ctattaactg | 780 |
| gcgaactact tactctagct tcccggcaac aattaataga ctggatggag gcggataaag | 840 |
| ttgcaggacc acttctgcgc tcggcccttc cggctggctg gtttattgct gataaatctg | 900 |
| gagccggtga gcgtgggtct cgcggtatca ttgcagcact ggggccagat ggtaagccct | 960 |
| cccgtatcgt agttatctac acgacgggga gtcaggcaac tatggatgaa cgaaatagac | 1020 |
| agatcgctga gataggtgcc tcactgatta agcattggta actgtcagac caagtttact | 1080 |
| catatatact ttagattgat ttaaaacttc atttttaatt taaaaggatc taggtgaaga | 1140 |
| tcctttttga taatctcatg accaaaatcc cttaacgtga gttttcgttc cactgagcgt | 1200 |

```
cagaccccgt agaaaagatc aaaggatctt cttgagatcc ttttttttctg cgcgtaatct   1260 gctgcttgca aacaaaaaaa ccaccgctac cagcggtggt ttgtttgccg gatcaagagc   1320
taccaactct ttttccgaag gtaactggct tcagcagagc gcagatacca aatactgttc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggccttt   1860 gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagctc ggcgcgccat tgggatggaa cttccagacg acaagagtat   2280
cgcctttatt tacatacttt aacgctcgtt tcaggccggg gcggtttgca atcttgccac   2340
tgatacggtc ctcaaaaatg cggtcacaat ttgcactagt aagcgcatta cgctgtaaat   2400
cgatattttg gtcaattgtt gacacccgaa tatacccaat agtagccatg atttctcct   2460 ttacatcaga taaggaagaa ttttagtcgc ttttctcatg gaggattgct gctagcctca   2520
ataagcttct tgcctttctg cagaccaagg acccagatta tgtatggaat gtatggctgt   2580
aaatgatatt tcctacgggc gagaagctga aatatggccg cgggattatt ctatgcttgc   2640
tcgtcgagtt caatttctac gttttaatga tatccctgtt cgattggtga gtaataatgc   2700
ccggataatc acaggctaca ttgcgaagtt taatccgaag gaaaatttga ttctggcttc   2760
ggataaacct aaaggagttc catcccaata cgcgtcaatt cactggccgt cgttttacaa   2820
cgtcgtgact gggaaaaccc tggcgttacc caacttaatc gccttgcagc acatcccct   2880 ttcgccagct ggcgtaatag cgaagaggcc cgcaccgatc gcccttccca acagttgcgc   2940
agcctgaatg gcgaatggcg cctgatgcgg tattttctcc ttacgcatct gtgcggtatt   3000
tcacaccgca tatggtgcac tctcagtaca atctgctctg atgccgcata gttaagccag   3060
ccccgacacc cgccaacacc cgctgacgcg ccctgacggg cttgtctgct cccggcatcc   3120
gcttacagac aagctgtgac cgtctccggg agctgcatgt gtcagaggtt ttcaccgtca   3180
tcaccgaaac gcgcga                                                  3196
```

<210> SEQ ID NO 232
<211> LENGTH: 21
<212> TYPE: DNA
<213> ORGANISM: Artificial Sequence
<220> FEATURE:
<223> OTHER INFORMATION: flic-1 primer

<400> SEQUENCE: 232
cgttatcggc aatctggagg c                                            21

<210> SEQ ID NO 233
<211> LENGTH: 21
<212> TYPE: DNA
<213> ORGANISM: Artificial Sequence
<220> FEATURE:
<223> OTHER INFORMATION: flic-2 primer

<400> SEQUENCE: 233 ccagcccttta caacagtggt c                                           21

<210> SEQ ID NO 234
<211> LENGTH: 24
<212> TYPE: DNA
<213> ORGANISM: Artificial Sequence
<220> FEATURE:
<223> OTHER INFORMATION: flic-3 primer

<400> SEQUENCE: 234
gtctgtcaac aactggtcta acgg                                         24

<210> SEQ ID NO 235
<211> LENGTH: 23
<212> TYPE: DNA
<213> ORGANISM: Artificial Sequence
<220> FEATURE:
<223> OTHER INFORMATION: flic-4 primer

<400> SEQUENCE: 235
agacggtcct catccagata agg                                          23

<210> SEQ ID NO 236
<211> LENGTH: 22
<212> TYPE: DNA
<213> ORGANISM: Artificial Sequence
<220> FEATURE:
<223> OTHER INFORMATION: fljb-1 primer sequence

<400> SEQUENCE: 236
ttccagacga caagagtatc gc                                           22

<210> SEQ ID NO 237
<211> LENGTH: 27
<212> TYPE: DNA
<213> ORGANISM: Artificial Sequence
<220> FEATURE:
<223> OTHER INFORMATION: fljb-2 primer

<400> SEQUENCE: 237
cctttaggtt tatccgaagc cagaatc                                      27

<210> SEQ ID NO 238
<211> LENGTH: 20
<212> TYPE: DNA
<213> ORGANISM: Artificial Sequence
<220> FEATURE:
<223> OTHER INFORMATION: fljb-3 primer

<400> SEQUENCE: 238
caccaggttt ttcacgctgc                                              20

<210> SEQ ID NO 239
<211> LENGTH: 20
<212> TYPE: DNA
<213> ORGANISM: Artificial Sequence

```
<220> FEATURE:
<223> OTHER INFORMATION: fljb-4 primer

<400> SEQUENCE: 239
acacgcattt acgcctgtcg                                              20

<210> SEQ ID NO 240
<211> LENGTH: 1518
<212> TYPE: DNA
<213> ORGANISM: Artificial Sequence
<220> FEATURE:
<223> OTHER INFORMATION: cytoLLO ORF

<400> SEQUENCE: 240
atgaaagacg cctccgcgtt taacaaggag aactccatca gctccatggc ccgcccgct    60 tccccgccgg cgagccctaa aaccccgatc gagaaaaagc acgccgacga gattgacaaa  120
tatattcaag gtttagacta caataagaac aacgtgctgg tgtatcacgg cgatgcggtg  180
accaatgttc cgccgcgcaa gggctacaaa gatggtaacg aatatatcgt ggttgagaaa  240
aagaaaaaaa gcatcaacca gaacaacgcc gatatccaag ttgtgaacgc catcagctct  300
ttaacctatc cgggcgcgct ggtgaaagcc aacagcgaac tggtggaaaa ccagcccgat  360
gtgctgccgg tgaaacgcga ttcttttaacg ctgagcattg atttaccggg catgacgaac  420
caagataaca aaatcgtggt gaagaacgcg accaagtcca acgtgaacaa cgcggtgaac  480
acgctggtgg aacgctggaa cgaaaaatac gcccaagctt acccgaacgt gagcgcgaag  540
attgactacg acgacgaaat ggcctacagc gagagccagc tgatcgcgaa attcggcacc  600
gcgttcaaag cggtgaacaa ctcttttaaac gtgaactttg cgcgatcag cgaaggcaaa  660 atgcaagaag aggtgatcag ctttaaacaa atctattata cgtgaatgt taacgagccg  720 acgcgtccga gccgcttttt cggcaaagcg gtgacgaagg aacagctgca agcgcttggc  780
gtgaacgcgg aaaaccctcc ggcctatatt tccagcgtgg cgtatggccg ccaagtttat  840
ctgaagctga gcacgaacag ccacagcacc aaagttaagg cggcctttga tgcggcggtg  900
agcggcaaaa gcgttagcgg cgacgttgag ctgacgaaca tcatcaagaa cagctccttt  960
aaagcggtga tctatggcgg tagcgcgaaa gacgaagtgc agatcatcga cggcaatttta 1020 ggtgatctgc gcgatatttt aaaaaagggc gccaccttca accgtgagac gcccggtgtg 1080
ccgatcgcct acaccaccaa cttttttaaag gataacgagc tggccgtgat caaaaacaat 1140
tccgaatata tcgaaaccac gagcaaggcg tataccgatg caagatcaa cattgaccac 1200 agcggtggct atgtggcgca gttcaacatc agctgggatg aagtgaacta tgatccggag 1260
ggcaacgaga tcgtgcagca caagaactgg tccgagaaca caaatccaa gctggcgcat 1320 ttcaccagca gcatctatct gccgggcaac gcgcgcaaca ttaatgtgta cgcgaaagag 1380
tgcacgggtc ttgcgtggga atggtggcgc accgtgatcg atgatcgcaa tttaccgctg 1440
gtgaaaaacc gcaacatctc catctggggc accactttat acccgaaata ttccaacaaa 1500
gttgataacc ctattgag                                              1518

<210> SEQ ID NO 241
<211> LENGTH: 45
<212> TYPE: DNA
<213> ORGANISM: Artificial Sequence
<220> FEATURE:
<223> OTHER INFORMATION: LLO promoter

<400> SEQUENCE: 241
```

```
attatgtctt gacatgtagt gagtgggctg gtataatgca gcaag              45
```

<210> SEQ ID NO 242
<211> LENGTH: 1176
<212> TYPE: DNA
<213> ORGANISM: Artificial Sequence
<220> FEATURE:
<223> OTHER INFORMATION: Asd Gene ORF

<400> SEQUENCE: 242

```
ctacgccaac tggcgcagca ttcgacgcag cggctcggcg gcgccccata caactggtc    60
gcctacggta acgccgaca agaactctgg ccccatgttc agcttacgca gacgaccaac   120
cggcgtagtc aacgtgccgg tcaccgccgc cggggttaat tcgcgcatag tgatatcacg   180
atcgttcggc accactttcg cccacggatt atgtgccgcc agcagttctt ccaccgtcgg   240
aatggatacc tcttttttca gcttgatggt gaacgcctgg ctgtgacagc gcagcgcgcc   300
gacgcgcaca cacaaaccat caaccggaat cacagaggca gtattgagaa tcttgttggt   360
ttccgcctgg cctttccact cttcgcggct ctggccgtta tcgagctgtt tgtcgatcca   420
ggggatcagg cttcccgcca gcggtacgcc aaagttatca accggcagct cgccgctgcg   480
ggtcaatgcc gtaactttgc gttcaatatc aagaattgcg gaagacggcg tcgccagttc   540
atcggcgaca tggccataca actgacccat ctgggttaac agctcgcgca tatggcgcgc   600
gccgccgccg gaggcggcct gataggtcgc gacggatacc cagtcaacga gattatgggc   660
aaagagaccg cccagcgaca tcaacatcag gctaacggta cagttaccgc ccacaaaggt   720
cttcacgcca ttgttcaggc cgtcggtaat cacgtcctgg ttgaccgggt cgagaataat   780
aatggcatca tctttcatgc gcagcgtaga agccgcatca atccagtaac cctgccatcc   840
gctttcgcgc agctttggat aaatttcgtt ggtataatcg ccgccctggc aggtcacgat   900
gatatcgagc gcttttagcg catccagatc aaaagcgtcc tgtagcgtgc cggtggaggt   960
gtcgccgaag gtgggcgccg cctgtccaaa ctgggaggta gaaagaaaa cagggcgaat  1020
agcgtcgaaa tcgcgctcct ctaccatgcg ttgcatgaga acagagccga ccattccgcg  1080
ccagccgata aaaccaacat ttttcatagc gttttttcc tgcaaagaga tgtgctgtgt  1140
atgcgcgcca gtatcctgtg gcgcatcctt caccat                           1176
```

<210> SEQ ID NO 243
<211> LENGTH: 589
<212> TYPE: DNA
<213> ORGANISM: Artificial Sequence
<220> FEATURE:
<223> OTHER INFORMATION: pBR322 Origin

<400> SEQUENCE: 243

```
ttgagatcct ttttttctgc gcgtaatctg ctgcttgcaa acaaaaaaac caccgctacc    60
agcggtggtt tgtttgccgg atcaagagct accaactctt tttccgaagg taactggctt   120
cagcagagcg cagataccaa atactgtcct tctagtgtag ccgtagttag gccaccactt   180
caagaactct gtagcaccgc ctacatacct cgctctgcta atcctgttac cagtggctgc   240
tgccagtggc gataagtcgt gtcttaccgg gttggactca agacgatagt taccggataa   300
ggcgcagcgg tcgggctgaa cggggggttc gtgcacacag cccagcttgg agcgaacgac   360
ctacaccgaa ctgagatacc tacagcgtga gctatgagaa agcgccacgc ttcccgaagg   420
gagaaaggcg gacaggtatc cggtaagcgg cagggtcgga acaggagagc gcacgaggga   480
gcttccaggg ggaaacgcct ggtatcttta tagtcctgtc gggtttcgcc acctctgact   540
```

```
tgagcgtcga tttttgtgat gctcgtcagg ggggcggagc ctatggaaa         589
```

<210> SEQ ID NO 244
<211> LENGTH: 3269
<212> TYPE: DNA
<213> ORGANISM: Artificial Sequence
<220> FEATURE:
<223> OTHER INFORMATION: pEQU6 shSCR

<400> SEQUENCE: 244

```
ctttcctgcg ttatcccctg attctgtgga taaccgtatt accgcctttg agtgagctga    60
taccgctcgc cgcagccgaa cgaccgagcg cagcgagtca gtgagcgagg aagcggaaga   120
gcgcccaata cgcaaaccgc ctctccccgc gcgttggccg attcattaat gcagctggca   180
cgacaggttt cccgactgga aagcgggcag tgagcgcaac gcaattaata cgcgtaccgc   240
tagccaggaa gagtttgtag aaacgcaaaa aggccatccg tcaggatggc cttctgctta   300
gtttgatgcc tggcagttta tggcgggcgt cctgcccgcc accctccggg ccgttgcttc   360
acaacgttca atccgctcc cggcggattt gtcctactca ggagagcgtt caccgacaaa   420
caacagataa acgaaaggc ccagtcttcc gactgagcct ttcgttttat ttgatgcctg   480
gcagttccct actctcgcgt taacgctagc atggatgttt tcccagtcac gacgttgtaa   540
aacgacggcc agtcttaagc tcgggcccca ataatgatt ttattttgac tgatagtgac   600
ctgttcgttg caacaaattg atgagcaatg ctttttata atgccaactt tgtacaaaaa   660
agcaggcttt aaaggaacca attcagtcga ctggatccaa ggtcgggcag gaagagggcc   720
tatttcccat gattccttca tatttgcata tacgatacaa ggctgttaga gagataatta   780
gaattaattt gactgtaaac acaaagatat tagtacaaaa tacgtgacgt agaaagtaat   840
aatttcttgg gtagtttgca gttttaaaat tatgttttaa aatggactat catatgctta   900
ccgtaacttg aaagtatttc gatttcttgg ctttatatat cttgtggaaa ggacgaaact   960
agcaacaaga tgaagagcac caattctaga gattggtgct cttcatcttg ttgttttttc  1020
gagtagctag agaattcatg gtaatagcga tgactaatac gtagatgtac tgccaagtag  1080
gaaagtccca taaggtcatg tactgggcat aatgccaggc gggccattta ccgtcattga  1140
cgtcaatagg gggcgtactt ggcatatgat acacttgatg tactgccaag tgggcagttt  1200
accgtaaata gtccacccat tgacgtcaat ggaaagtccc tattggcgtt actatgggaa  1260
catacgtcat tattgacgtc aatgggcggg ggtcgttggg cggtcagcca ggcgggccat  1320
ttaccgtaag ttatgtaacg cggaactcca tatatgggct atgaactaat gaccccgtaa  1380
ttgattacta ttaataacta gacccagctt tcttgtacaa agttggcatt ataagaaagc  1440
attgcttatc aatttgttgc aacgaacagg tcactatcag tcaaaataaa atcattattt  1500
gccatccagc tgatatcccc tatagtgagt cgtattacat ggtcatagct gtttcctggc  1560
agctctggcc cgtgtctcaa aatctctgat gttacattgc acaagataaa aatatatcat  1620
catgaacaat aaaactgtct gcttacataa acagtaatac aaggggtgtt atgagccata  1680
ttcaacggga aacgtcgagg ccgcgattaa attccaacat ggatgctgat ttatatgggt  1740
ataaatgggc tcgcgataat gtcgggcaat caggtgcgac aatctatcgc ttgtatggga  1800
agcccgatgc gccagagttg tttctgaaac atggcaaagg tagcgttgcc aatgatgtta  1860
cagatgagat ggtcagacta aactggctga cggaatttat gcctcttccg accatcaagc  1920
attttatccg tactcctgat gatgcatggt tactcaccac tgcgatcccc ggaaaaacag  1980
```

-continued

| | |
|---|---:|
| cattccaggt attagaagaa tatcctgatt caggtgaaaa tattgttgat gcgctggcag | 2040 |
| tgttcctgcg ccggttgcat tcgattcctg tttgtaattg tccttttaac agcgatcgcg | 2100 |
| tatttcgtct cgctcaggcg caatcacgaa tgaataacgg tttggttgat gcgagtgatt | 2160 |
| ttgatgacga gcgtaatggc tggcctgttg aacaagtctg gaaagaaatg cataaacttt | 2220 |
| tgccattctc accggattca gtcgtcactc atggtgattt ctcacttgat aaccttattt | 2280 |
| ttgacgaggg gaaattaata ggttgtattg atgttggacg agtcggaatc gcagaccgat | 2340 |
| accaggatct tgccatccta tggaactgcc tcggtgagtt ttctccttca ttacagaaac | 2400 |
| ggctttttca aaaatatggt attgataatc ctgatatgaa taaattgcag tttcatttga | 2460 |
| tgctcgatga gttttctaa tcagaattgg ttaattggtt gtaacactgg cagagcatta | 2520 |
| cgctgacttg acgggacggc gcaagctcat gaccaaaatc ccttaacgtg agttacgcgt | 2580 |
| cgttccactg agcgtcagac cccgtagaaa agatcaaagg atcttcttga tccttttt | 2640 |
| ttctgcgcgt aatctgctgc ttgcaaacaa aaaaaccacc gctaccgcg gtggtttgtt | 2700 |
| tgccggatca agagctacca actctttttc cgaaggtaac tggcttcagc agagcgcaga | 2760 |
| taccaaatac tgtccttcta gtgtagccgt agttaggcca ccacttcaag aactctgtag | 2820 |
| caccgcctac atacctcgct ctgctaatcc tgttaccagt ggctgctgcc agtggcgata | 2880 |
| agtcgtgtct taccgggttg gactcaagac gatagttacc ggataaggcg cagcggtcgg | 2940 |
| gctgaacggg gggttcgtgc acacagccca gcttggagcg aacgacctac accgaactga | 3000 |
| gatacctaca gcgtgagcat tgagaaagcg ccacgcttcc cgaagggaga aaggcggaca | 3060 |
| ggtatccggt aagcggcagg gtcggaacag gagagcgcac gagggagctt ccaggggga | 3120 |
| acgcctggta tctttatagt cctgtcgggt ttcgccacct ctgacttgag cgtcgatttt | 3180 |
| tgtgatgctc gtcaggggg cggagcctat ggaaaaacgc cagcaacgcg gcctttttac | 3240 |
| ggttcctggc cttttgctgg ccttttgct | 3269 |

<210> SEQ ID NO 245
<211> LENGTH: 4642
<212> TYPE: DNA
<213> ORGANISM: Artificial Sequence
<220> FEATURE:
<223> OTHER INFORMATION: pATI2.0 U6-H1 Plasmid

<400> SEQUENCE: 245

| | |
|---|---:|
| accggtctgt ggaatgtgtg tcagttaggg tgtggaaagt ccccaggctc cccagcaggc | 60 |
| agaagtatgc aaagcatgca tctcaattag tcagcaacca accggtcttg cacctcagca | 120 |
| aaaggccatc cgtcaggatg gccttctgct tagtttgatg cctggcagtt tatggcgggc | 180 |
| gtcctgcccg ccacctccg ggccgttgct tcacaacgtt caaatccgct cccggcggat | 240 |
| ttgtcctact caggagagcg ttcaccgaca acaacagat aaaacgaaag gcccagtctt | 300 |
| ccgactgagc ctttcgtttt atttgggcgc gccatgcctg gcagttccct actctcgcgt | 360 |
| taacgctagc atggatgttt tcccagtcac gacgttctta agctcgggcc cttaaggaa | 420 |
| ccaattcagt cgagaattac tagtggtacc atatttgcat gtcgctatgt gttctgggaa | 480 |
| atcaccataa acgtgaaatg tctttggatt tgggaatctt ataagttctg tatgagacca | 540 |
| ctccctaggt ttttgtcgac agatctggcg cgccgactac caaaatgact tcggatatga | 600 |
| ccattatggt gccgacttc gtaatttacg cgtacccatt tggatgacgg tgcgtccatg | 660 |
| tttgttctgc atgcctgaga tagtaaggcc gaccccaac aatccacaag gccacgattg | 720 |
| acacatgagg ttcctttttt aaacctgaac ctttagttca cacaggtggc tgcgccgccg | 780 |

```
tgaatggtgg cagtagttac ttctaatcaa gctcaatccc tcggctctga agaggacata      840
gtagacctca tctggtcttt cgactacggg gggtaacaga tgtcggtggt ataacaatcc      900
tccacgagat catttcacgt aagcatgact tttacaccta tcggaatcat ataactgtta      960
ggcaatggtt tatgattggg cgacagacgt cagatcggcg aacctttacg tagcccccg     1020 ttcatctaga caggaagagg gcctatttcc catgattcct tcatatttgc atatacgata     1080
caaggctgtt agagagataa ttagaattaa tttgactgta aacacaaaga tattagtaca     1140
aaatacgtga cgtagaaagt aataatttct tgggtagttt gcagttttaa aattatgttt     1200
taaaatggac tatcatatgc ttaccgtaac ttgaaagtat ttcgatttct tggctttata     1260
tatcttgtgg aaaggacgaa acttgttttt tctcgagtag ctagagaatt cgtcgacgga     1320
actccatata tgggctatga actaatgacc ccgtaattga ttactattaa taactagcca     1380
tccagctgat atccgccggc gctgcagcta cgccaactgg cgcagcattc gacgcagcgg     1440
ctcggcggcg ccccataaca actggtcgcc tacggtaaac gccgacaaga actctggccc     1500
catgttcagc ttacgcagac gaccaaccgg cgtagtcaac gtgccggtca ccgccgccgg     1560
ggttaattcg cgcatagtga tatcacgatc gttcggcacc actttcgccc acggattatg     1620
tgccgccagc agttcttcca ccgtcggaat ggatacctct ttttcagct tgatggtgaa     1680 cgcctggctg tgacagcgca gcgcgccgac gcgcacacac aaaccatcaa ccggaatcac     1740
agaggcagta ttgagaatct tgttggtttc cgcctggcct ttccactctt cgcggctctg     1800
gccgttatcg agctgtttgt cgatccaggg gatcaggctt cccgccagcg gtacgccaaa     1860
gttatcaacc ggcagctcgc cgctgcgggt caatgccgta actttgcgtt caatatcaag     1920
aattgcggaa gacggcgtcg ccagttcatc ggcgacatgg ccatacaact gacccatctg     1980
ggttaacagc tcgcgcatat ggcgcgcgcc gccgccggag gcggcctgat aggtcgcgac     2040
ggatacccag tcaacgagat tatgggcaaa gagaccgccc agcgacatca acatcaggct     2100
aacggtacag ttaccgccca caaaggtctt cacgccattg ttcaggccgt cggtaatcac     2160
gtcctggttg accgggtcga gaataataat ggcatcatct ttcatgcgca gcgtagaagc     2220
cgcatcaatc cagtaaccct gccatccgct ttcgcgcagc tttggataaa tttcgttggt     2280
ataatcgccg ccctggcagg tcacgatgat atcgagcgct tttagcgcat ccagatcaaa     2340
agcgtcctgt agcgtgccgg tggaggtgtc gccgaaggtg ggcgccgcct gtccaaactg     2400
ggaggtagaa aagaaaacag ggcgaatagc gtcgaaatcg cgctcctcta ccatgcgttg     2460
catgagaaca gagccgacca ttccgcgcca gccgataaaa ccaacatttt tcatagcgtt     2520 ttttcctgc aaagagatgt gctgtgtatg cgcgccagta tcctgtggcg catccttcac     2580
cataaaggat cttcacctag atcctttaa attaaaaatg aagttttaaa tcaatctaaa     2640
gtatatatga gtaaacttgg tctgacagtc tgcaggatat cccatgggca ttggcgcaga     2700
aaaaaatgcc tgatgcgacg ctgcgcgtct tatactccca catatgccag attcagcaac     2760
ggatacggct tccccaactt gcccacttcc atacgtgtcc tccttaccag aaatttatcc     2820
ttaaccatgg aagctttgca gctctggccc gtgtctcaaa atctctgatg ttacattgca     2880
caagataaaa atatatcatc atgaacaata aaactgtctg cttacataaa cagtaataca     2940 agggggtgtta tgagccatat tcaacgggaa acgtcgaggc cgcgattaaa ttccaacatg     3000
gatgctgatt tatatgggta taatgggct cgcgataatg tcgggcaatc aggtgcgaca     3060
atctatcgct tgtatgggaa gcccgatgcg ccagagttgt ttctgaaaca tggcaaaggt     3120
```

```
agcgttgcca atgatgttac agatgagatg gtcagactaa actggctgac ggaatttatg    3180
cctcttccga ccatcaagca ttttatccgt actcctgatg atgcatggtt actcaccact    3240
gcgatccccg gaaaaacagc attccaggta ttagaagaat atcctgattc aggtgaaaat    3300
attgttgatg cgctggcagt gttcctgcgc cggttgcatt cgattcctgt ttgtaattgt    3360
ccttttaaca gcgatcgcgt atttcgtctc gctcaggcgc aatcacgaat gaataacggt    3420
ttggttgatg cgagtgattt tgatgacgag cgtaatggct ggcctgttga acaagtctgg    3480
aaagaaatgc ataaactttt gccattctca ccggattcag tcgtcactca tggtgatttc    3540
tcacttgata accttatttt tgacgagggg aaattaatag gttgtattga tgttggacga    3600
gtcggaatcg cagaccgata ccaggatctt gccatcctat ggaactgcct cggtgagttt    3660
tctccttcat tacagaaacg cttttttcaa aaatatggta ttgataatcc tgatatgaat    3720
aaattgcagt ttcatttgat gctcgatgag ttttttctaaa gctttcagaa ttggttaatt    3780
ggttgtaaca ctggcagagc attacgctga cttgacggga cggcgcaagc tcatggatcc    3840
caattggcgg ccgcttaatt aaacatgtga gctcgatgta cattcgaagg accccaaaat    3900
cccttaacgt gagttacgcg tcgttccact gagcgtcaga ccccgtagaa aagatcaaag    3960
gatcttcatc gatttgagat ccttttttttc tgcgcgtaat ctgctgcttg caaacaaaaa    4020
aaccaccgct accagcggtg gtttgtttgc cggatcaaga gctaccaact ctttttccga    4080
aggtaactgg cttcagcaga gcgcagatac caaatactgt ccttctagtg tagccgtagt    4140
taggccacca cttcaagaac tctgtagcac cgcctacata cctcgctctg ctaatcctgt    4200
taccagtggc tgctgccagt ggcgataagt cgtgtcttac cgggttggac tcaagacgat    4260
agttaccgga taaggcgcag cggtcgggct gaacggggggg ttcgtgcaca gcccagct    4320 tggagcgaac gacctacacc gaactgagat acctacagcg tgagctatga aaagcgcca    4380 cgcttcccga agggagaaag gcggacaggt atccggtaag cggcagggtc ggaacaggag    4440
agcgcacgag ggagcttcca gggggaaacg cctggtatct ttatagtcct gtcgggtttc    4500
gccacctctg acttgagcgt cgatttttgt gatgctcgtc aggggggcgg agcctatgga    4560
aaatcgattc cggaaacgcc aggctcttcc aacgcggcct ttttacggtt gaagagccct    4620
ggccttttgc tggccttttg ct                                             4642
```

<210> SEQ ID NO 246
<211> LENGTH: 1261
<212> TYPE: DNA
<213> ORGANISM: Artificial Sequence
<220> FEATURE:
<223> OTHER INFORMATION: ASD gene orf + 85 bp upstream

<400> SEQUENCE: 246

```
ctgtcagacc aagtttactc atatatactt tagattgatt taaaacttca ttttttaattt     60 aaaaggatct aggtgaagat cctttatggt gaaggatgcg ccacaggata ctggcgcgca    120
tacacagcac atctctttgc aggaaaaaaa cgctatgaaa aatgttggtt ttatcggctg    180
gcgcggaatg gtcggctctg ttctcatgca acgcatggta gaggagcgcg atttcgacgc    240
tattcgccct gttttctttt ctacctccca gtttggacag gcggcgccca ccttcggcga    300
cacctccacc ggcacgctac aggacgcttt tgatctggat gcgctaaaag cgctcgatat    360
catcgtgacc tgccagggcg gcgattatac caacgaaatt tatccaaagc tgcgcgaaag    420
cggatggcag ggttactgga ttgatgcggc ttctacgctg cgcatgaaag atgatgccat    480
tattattctc gacccggtca accaggacgt gattaccgac ggcctgaaca atggcgtgaa    540
```

```
gacctttgtg ggcggtaact gtaccgttag cctgatgttg atgtcgctgg gcggtctctt    600
tgcccataat ctcgttgact gggtatccgt cgcgacctat caggccgcct ccggcggcgg    660
cgcgcgccat atgcgcgagc tgttaaccca gatgggtcag ttgtatggcc atgtcgccga    720
tgaactggcg acgccgtctt ccgcaattct tgatattgaa cgcaaagtta cggcattgac    780
ccgcagcggc gagctgccgg ttgataactt tggcgtaccg ctggcgggaa gcctgatccc    840
ctggatcgac aaacagctcg ataacggcca gagccgcgaa gagtggaaag gccaggcgga    900
aaccaacaag attctcaata ctgcctctgt gattccggtt gatggtttgt gtgtgcgcgt    960
cggcgcgctg cgctgtcaca gccaggcgtt caccatcaag ctgaaaaaag aggtatccat   1020
tccgacggtg aagaactgc tggcggcaca taatccgtgg gcgaaagtgg tgccgaacga   1080
tcgtgatatc actatgcgcg aattaacccc ggcggcggtg accggcacgt tgactacgcc   1140
ggttggtcgt ctgcgtaagc tgaacatggg gccagagttc ttgtcggcgt ttaccgtagg   1200
cgaccagttg ttatggggcg ccgccgagcc gctgcgtcga atgctgcgcc agttggcgta   1260
g                                                                  1261
```

<210> SEQ ID NO 247
<211> LENGTH: 4112
<212> TYPE: DNA
<213> ORGANISM: Artificial Sequence
<220> FEATURE:
<223> OTHER INFORMATION: pATI2.0 synthetic v26 scramble pBR322ori.dna

<400> SEQUENCE: 247

```
accggtctgt ggaatgtgtg tcagttaggg tgtggaaagt ccccaggctc cccagcaggc     60
agaagtatgc aaagcatgca tctcaattag tcagcaacca accggtcttg cacctcagca    120
aaaggccatc cgtcaggatg gccttctgct tagtttgatg cctggcagtt tatggcgggc    180
gtcctgcccg ccaccctccg ggccgttgct tcacaacgtt caaatccgct cccggcggat    240
ttgtcctact caggagagcg ttcaccgaca acaacagat aaaacgaaag gcccagtctt    300
ccgactgagc ctttcgtttt atttgggccg ccatgcctg gcagttccct actctcgcgt    360
taacgctagc atggatgttt tcccagtcac gacgttctta agctcgggcc cttaaaggaa    420
ccaattcagt cgagaattac tagtggtacc caggaagagg gcctatttcc catgattcct    480
tcatatttgc atatacgata caaggctgtt agagagataa ttagaattaa tttgactgta    540
aacacaaaga tattagtaca aaatacgtga cgtagaaagt aataatttct tgggtagttt    600
gcagttttaa aattatgttt taaaatggac tatcatatgc ttaccgtaac ttgaaagtat    660
ttcgatttct tggctttata tatcttgtgg aaaggacgaa actagcaaca agatgaagag    720
caccaattct agagattggt gctcttcatc ttgttgtttt tctcgagtag ctagagaatt    780
cgtcgacgga actccatata tgggctatga actaatgacc ccgtaattga ttactattaa    840
taactagcca tccagctgat atccgccggc gctgcagcta cgccaactgg cgcagcattc    900
gacgcagcgg ctcggcggcg ccccataaca actggtcgcc tacggtaaac gccgacaaga    960
actctggccc catgttcagc ttacgcagac gaccaaccgg cgtagtcaac gtgccggtca   1020
ccgccgccgg ggttaattcg cgcatagtga tatcacgatc gttcggcacc actttcgccc   1080
acggattatg tgccgccagc agttcttcca ccgtcggaat ggatacctct ttttcagct   1140
tgatggtgaa cgcctggctg tgacagcgca gcgcgcgac gcgcacacac aaaccatcaa   1200
ccggaatcac agaggcagta ttgagaatct tgttggtttc cgcctggcct ttccactctt   1260
```

```
cgcggctctg gccgttatcg agctgtttgt cgatccaggg gatcaggctt cccgccagcg   1320
gtacgccaaa gttatcaacc ggcagctcgc cgctgcgggt caatgccgta actttgcgtt   1380
caatatcaag aattgcggaa gacggcgtcg ccagttcatc ggcgacatgg ccatacaact   1440
gacccatctg ggttaacagc tcgcgcatat ggcgcgcgcc gccgccggag gcggcctgat   1500
aggtcgcgac ggatacccag tcaacgagat tatgggcaaa gagaccgccc agcgacatca   1560
acatcaggct aacggtacag ttaccgccca caaaggtctt cacgccattg ttcaggccgt   1620
cggtaatcac gtcctggttg accgggtcga gaataataat ggcatcatct ttcatgcgca   1680
gcgtagaagc cgcatcaatc cagtaaccct gccatccgct ttcgcgcagc tttggataaa   1740
tttcgttggt ataatcgccg ccctggcagg tcacgatgat atcgagcgct tttagcgcat   1800
ccagatcaaa agcgtcctgt agcgtgccgg tggaggtgtc gccgaaggtg ggcgccgcct   1860
gtccaaactg ggaggtagaa agaaaaacag ggcgaatagc gtcgaaatcg cgctcctcta   1920
ccatgcgttg catgagaaca gagccgacca ttccgcgcca gccgataaaa ccaacatttt   1980
tcatagcgtt ttttcctgc aaagagatgt gctgtgtatg cgcgccagta tcctgtggcg   2040
catccttcac cataaaggat cttcacctag atcctttaa attaaaaatg aagttttaaa   2100
tcaatctaaa gtatatatga gtaaacttgg tctgacagtc tgcaggatat cccatgggca   2160
ttggcgcaga aaaaaatgcc tgatgcgacg ctgcgcgtct tatactccca catatgccag   2220
attcagcaac ggatacggct tccccaactt gcccacttcc atacgtgtcc tccttaccag   2280
aaatttatcc ttaaccatgg aagctttgca gctctggccc gtgtctcaaa atctctgatg   2340
ttacattgca caagataaaa atatatcatc atgaacaata aaactgtctg cttacataaa   2400
cagtaataca agggtgtta tgagccatat tcaacgggaa acgtcgaggc cgcgattaaa   2460
ttccaacatg gatgctgatt tatatgggta taaatgggct cgcgataatg tcgggcaatc   2520
aggtgcgaca atctatcgct tgtatgggaa gcccgatgcg ccagagttgt ttctgaaaca   2580
tggcaaaggt agcgttgcca atgatgttac agatgagatg gtcagactaa actggctgac   2640
ggaatttatg cctcttccga ccatcaagca ttttatccgt actcctgatg atgcatggtt   2700
actcaccact gcgatccccg gaaaacagc attccaggta ttagaagaat atcctgattc   2760
aggtgaaaat attgttgatg cgctggcagt gttcctgcgc cggttgcatt cgattcctgt   2820
ttgtaattgt cctttaaca gcgatcgcgt atttcgtctc gctcaggcgc aatcacgaat   2880
gaataacggt ttggttgatg cgagtgattt tgatgacgag cgtaatggct ggcctgttga   2940
acaagtctgg aaagaaatgc ataaactttt gccattctca ccggattcag tcgtcactca   3000
tggtgatttc tcacttgata accttatttt tgacgagggg aaattaatag gttgtattga   3060
tgttggacga gtcggaatcg cagaccgata ccaggatctt gccatcctat ggaactgcct   3120
cggtgagttt tctccttcat tacagaaacg gcttttcaa aaatatggta ttgataatcc   3180
tgatatgaat aaattgcagt ttcatttgat gctcgatgag ttttctaaa gctttcagaa   3240
ttggttaatt ggttgtaaca ctggcagagc attacgctga cttgacggga cggcgcaagc   3300
tcatggatcc caattggcgg ccgcttaatt aaacatgtga gctcgatgta cattcgaagg   3360
accccaaaat cccttaacgt gagttacgcg tcgttccact gagcgtcaga ccccgtagaa   3420
aagatcaaag gatcttcatc gatttgagat cctttttttc tgcgcgtaat ctgctgcttg   3480
caaacaaaaa aaccaccgct accagcggtg gtttgtttgc cggatcaaga gctaccaact   3540
cttttttccga aggtaactgg cttcagcaga gcgcagatac caaatactgt ccttctagtg   3600
tagccgtagt taggccacca cttcaagaac tctgtagcac cgcctacata cctcgctctg   3660
```

```
ctaatcctgt taccagtggc tgctgccagt ggcgataagt cgtgtcttac cgggttggac    3720
tcaagacgat agttaccgga taaggcgcag cggtcgggct gaacgggggg ttcgtgcaca    3780
cagcccagct tggagcgaac gacctacacc gaactgagat acctacagcg tgagctatga    3840
gaaagcgcca cgcttcccga agggagaaag gcggacaggt atccggtaag cggcagggtc    3900
ggaacaggag agcgcacgag ggagcttcca gggggaaacg cctggtatct ttatagtcct    3960
gtcgggtttc gccacctctg acttgagcgt cgatttttgt gatgctcgtc aggggggcgg    4020
agcctatgga aaatcgattc cggaaacgcc aggctcttcc aacgcggcct ttttacggtt    4080
gaagagccct ggccttttgc tggccttttg ct                                  4112

<210> SEQ ID NO 248
<211> LENGTH: 165
<212> TYPE: DNA
<213> ORGANISM: Artificial Sequence
<220> FEATURE:
<223> OTHER INFORMATION: miR-16-2

<400> SEQUENCE: 248
ccggatcaac gccctaggtt tatgtttgga tgaactgaca tacttgttcc actctagcag     60
cacgtaaata ttggcgtagt gaaatatata ttaaacacca atattactgt gctgctttag    120
tgtgacaggg atacagcaac tattttatca attgtttgcg tcgac                    165

<210> SEQ ID NO 249
<211> LENGTH: 165
<212> TYPE: DNA
<213> ORGANISM: Artificial Sequence
<220> FEATURE:
<221> NAME/KEY: misc_feature
<222> LOCATION: (55)...(75)
<223> OTHER INFORMATION: n may be any nucleotide
<220> FEATURE:
<221> NAME/KEY: misc_feature
<222> LOCATION: (97)...(117)
<223> OTHER INFORMATION: n may be any nucleotide
<220> FEATURE:
<221> NAME/KEY: source
<222> LOCATION: (1)...(165)
<223> OTHER INFORMATION: microRNA backbone where Ns represent inserted
      anti-sense and sense microRNAs

<400> SEQUENCE: 249
ccggatcaac gccctaggtt tatgtttgga tgaactgaca tacgcgtatc cgtcnnnnnn     60
nnnnnnnnnn nnnnngtagt gaaatatata ttaaacnnnn nnnnnnnnnn nnnnnnntac    120
ggtaacgcgg aattcgcaac tattttatca attttttgcg tcgac                    165

<210> SEQ ID NO 250
<211> LENGTH: 708
<212> TYPE: DNA
<213> ORGANISM: Salmonella typhimurium
<220> FEATURE:
<223> OTHER INFORMATION: endA

<400> SEQUENCE: 250
atgtaccgta atttctcttt tgccgctgtg ttgctggccg cagcgttttc aggccaggcc     60
ctggccgatg gcattaacaa tttttctcag gccaaagcgg cgagcgtcaa agtcaatgct    120
gacgcgcccg gcagctttta ctgcgggtgc caaatccgct ggcagggtaa aaaaggcgtc    180
gtagacctgg agtcctgcgg ctataaggtg cgtaaaaacg agaatcgcgc cagacgcatt    240
gagtgggagc acgttgtccc cgcctggcaa ttcggtcatc agcgccagtg ctggcaggac    300
```

```
ggcgggcgaa aaaactgcgc taaagacccg gtctaccgca aaatggaaag cgatatgcat    360
aacctgcaac ccgcgattgg cgaagtgaat ggcgatcgcg gcaactttat gtatagccag    420
tggaacggcg gcgaaggtca gtacgggcag tgcgccatga aagtagattt caaagcgaag    480
ctcgccgagc cgcccgcccg cgccgtggc gcaatcgccc gcacttattt ttatatgcgc    540
gaccaatacc aactgaaact ttcccgccaa caaacgcagc tttttaacgt ctgggataag    600
cagtaccccg ttaccgcctg ggagtgcgag cgcgatgcgc gtatcgcgaa ggtccagggt    660
aatcataatc cctatgtgca acgcgcttgc caggcgcgaa agagctaa                708
```

<210> SEQ ID NO 251
<211> LENGTH: 235
<212> TYPE: PRT
<213> ORGANISM: Salmonella typhimurium
<220> FEATURE:
<223> OTHER INFORMATION: endonuclease I

<400> SEQUENCE: 251

```
Met Tyr Arg Asn Phe Ser Phe Ala Ala Ala Leu Leu Ala Ala Ala Phe
1               5                   10                  15

Ser Gly Gln Ala Leu Ala Asp Gly Ile Asn Asn Phe Ser Gln Ala Lys
            20                  25                  30

Ala Ala Ser Val Lys Val Asn Ala Asp Ala Pro Gly Ser Phe Tyr Cys
        35                  40                  45

Gly Cys Gln Ile Arg Trp Gln Gly Lys Lys Gly Val Val Asp Leu Glu
    50                  55                  60

Ser Cys Gly Tyr Lys Val Arg Lys Asn Glu Asn Arg Ala Arg Arg Ile
65                  70                  75                  80

Glu Trp Glu His Val Val Pro Ala Trp Gln Phe Gly His Gln Arg Gln
                85                  90                  95

Cys Trp Gln Asp Gly Gly Arg Lys Asn Cys Ala Lys Asp Pro Val Tyr
            100                 105                 110

Arg Lys Met Glu Ser Asp Met His Asn Leu Gln Pro Ala Ile Gly Glu
        115                 120                 125

Val Asn Gly Asp Arg Gly Asn Phe Met Tyr Ser Gln Trp Asn Gly Gly
    130                 135                 140

Glu Gly Gln Tyr Gly Gln Cys Ala Met Lys Val Asp Phe Lys Ala Lys
145                 150                 155                 160

Ile Ala Glu Pro Pro Ala Arg Ala Arg Gly Ala Ile Ala Arg Ile Tyr
                165                 170                 175

Phe Tyr Met Arg Asp Gln Tyr Gln Leu Lys Leu Ser Arg Gln Gln Thr
            180                 185                 190

Gln Leu Phe Asn Val Trp Asp Lys Gln Tyr Pro Val Thr Ala Trp Glu
        195                 200                 205

Cys Glu Arg Asp Ala Arg Ile Ala Lys Val Gln Gly Asn His Asn Pro
    210                 215                 220

Tyr Val Gln Arg Ala Cys Gln Ala Arg Lys Ser
225                 230                 235
```

<210> SEQ ID NO 252
<211> LENGTH: 78
<212> TYPE: DNA
<213> ORGANISM: Homo sapiens
<220> FEATURE:
<223> OTHER INFORMATION: microRNA-103a1 (miR-103a1)

<400> SEQUENCE: 252

```
tactgccctc ggcttcttta cagtgctgcc ttgttgcata tggatcaagc agcattgtac    60
agggctatga aggcattg                                                  78

<210> SEQ ID NO 253
<211> LENGTH: 71
<212> TYPE: DNA
<213> ORGANISM: Homo sapiens
<220> FEATURE:
<223> OTHER INFORMATION: microRNA-30a (miR-30a)

<400> SEQUENCE: 253
gcgactgtaa acatcctcga ctggaagctg tgaagccaca gatgggcttt cagtcggatg    60
tttgcagctg c                                                         71

<210> SEQ ID NO 254
<211> LENGTH: 615
<212> TYPE: DNA
<213> ORGANISM: Artificial Sequence
<220> FEATURE:
<223> OTHER INFORMATION: pMB1 origin of replication

<400> SEQUENCE: 254
aaaggatctt cttgagatcc ttttttttctg cgcgtaatct gctgcttgca aacaaaaaaa    60
ccaccgctac cagcggtggt ttgtttgccg gatcaagagc taccaactct ttttccgaag   120
gtaactggct tcagcagagc gcagatacca aatactgttc ttctagtgta gccgtagtta   180
ggccaccact tcaagaactc tgtagcaccg cctacatacc tcgctctgct aatcctgtta   240
ccagtggctg ctgccagtgg cgataagtcg tgtcttaccg ggttggactc aagacgatag   300
ttaccggata aggcgcagcg gtcgggctga acggggggtt cgtgcacaca gcccagcttg   360
gagcgaacga cctacaccga actgagatac ctacagcgtg agctatgaga aagcgccacg   420
cttcccgaag ggagaaaggc ggacaggtat ccggtaagcg gcagggtcgg aacaggagag   480
cgcacgaggg agcttccagg gggaaacgcc tggtatcttt atagtcctgt cgggtttcgc   540
cacctctgac ttgagcgtcg atttttgtga tgctcgtcag ggggcggag cctatggaaa   600 aacgccagca acgcg                                                    615

<210> SEQ ID NO 255
<211> LENGTH: 913
<212> TYPE: DNA
<213> ORGANISM: Artificial Sequence
<220> FEATURE:
<223> OTHER INFORMATION: p15A origin of replication

<400> SEQUENCE: 255
gcgctagcgg agtgtatact ggcttactat gttggcactg atgagggtgt cagtgaagtg    60
cttcatgtgg caggagaaaa aaggctgcac cggtgcgtca gcagaatatg tgatacagga   120
tatattccgc ttcctcgctc actgactcgc tacgctcggt cgttcgactg cggcgagcgg   180
aaatggctta cgaacggggc ggagatttcc tggaagatgc caggaagata cttaacaggg   240
aagtgagagg gccgcggcaa agccgttttt ccataggctc cgcccccctg acaagcatca   300
cgaaatctga cgctcaaatc agtggtggcg aaacccgaca ggactataaa gataccaggc   360
gtttccccct ggcggctccc tcgtgcgctc tcctgttcct gcctttcggt ttaccggtgt   420
cattccgctg ttatggccgc gtttgtctca ttccacgcct gacactcagt tccgggtagg   480
cagttcgctc caagctggac tgtatgcacg aaccccccgt tcagtccgac cgctgcgcct   540
```

```
tatccggtaa ctatcgtctt gagtccaacc cggaaagaca tgcaaaagca ccactggcag    600
cagccactgg taattgattt agaggagtta gtcttgaagt catgcgccgg ttaaggctaa    660
actgaaagga caagttttgg tgactgcgct cctccaagcc agttacctcg gttcaaagag    720
ttggtagctc agagaacctt cgaaaaaccg ccctgcaagg cggttttttc gttttcagag    780
caagagatta cgcgcagacc aaaacgatct caagaagatc atcttattaa tcagataaaa    840
tatttctaga tttcgtgcaa atttatctct tcaaatgtag cacctgaagt cagccccata    900
cgatataagt tgt                                                        913

<210> SEQ ID NO 256
<211> LENGTH: 223
<212> TYPE: DNA
<213> ORGANISM: Artificial Sequence
<220> FEATURE:
<223> OTHER INFORMATION: pSC101 origin of replication

<400> SEQUENCE: 256
gagttataca cagggctggg atctattctt tttatctttt tttattcttt ctttattcta     60
taaattataa ccacttgaat ataaacaaaa aaaacacaca aaggtctagc ggaatttaca   120
gagggtctag cagaatttac aagttttcca gcaaaggtct agcagaattt acagataccc   180
acaactcaaa ggaaaaggac tagtaattat cattgactag ccc                     223

<210> SEQ ID NO 257
<211> LENGTH: 602
<212> TYPE: DNA
<213> ORGANISM: E. coli
<220> FEATURE:
<223> OTHER INFORMATION: ColE1 origin of replication

<400> SEQUENCE: 257
aggatcttct tgagatcctt tttttctgcg cgtaatctgc tgcttgcaaa caaaaaaacc     60
accgctacca acggtggttt gtttgccgga tcaagagcta ccaactcttt ttccgaaggt   120
aactggcttc agcagagcgc agataccaaa tactgtcctt ctagtgtagc cgtagtcggg   180
ccactacttc aagaactctg tagcaccgtt gtgccatca tcgctctgct aatccggtta   240
ccagtggctg ctgccagtgg cgttaaggcg tgccttaccg ggttggactc aagacgatag   300
ttaccggata aggcgcagcg tcgggctga acgggggggtt cgtgcacaca gcccagcttg   360
gagcgaacga cctacaccga actgagatac caacagcgtg agctatgaga aagcgccacg   420
cttcccgaag ggagaaaggc ggacaggtat ccggtaagcg gcagggtcgg aacaggagag   480
cgcacgaggg agcttccagg gggaaacgcc tggtatcttt atagtcctgt cgggtttcgc   540
cacctctgac ttgagcgtct atttttgtga tgctcgtcag ggggcggag cctatggaaa    600 aa                                                                   602

<210> SEQ ID NO 258
<211> LENGTH: 201
<212> TYPE: DNA
<213> ORGANISM: Pseudomonas syringae
<220> FEATURE:
<223> OTHER INFORMATION: pPS10 origin of replication

<400> SEQUENCE: 258
acctgaccgg cgcggaagcg ctcttgatct ttttttcttg ttttacttg ttgttccttg      60 ttttcgtaat tttaactata tgattataa gaaaaaaag ggtttaaagg ggacagattc    120
agggtttaaa ggggacagat tcagggttta aggggacag attcagggtt taagggggac   180
```
agattcaggc tgatatccac a                                            201

<210> SEQ ID NO 259
<211> LENGTH: 617
<212> TYPE: DNA
<213> ORGANISM: E. coli
<220> FEATURE:
<223> OTHER INFORMATION: RK2 origin of replication

<400> SEQUENCE: 259
ccgggctggt tgccctcgcc gctgggctgg cggccgtcta tggccctgca acgcgccag    60
aaacgccgtc gaagccgtgt gcgagacacc gcggccgccg gcgttgtgga taccacgcgg  120
aaaacttggc cctcactgac agatgagggg cggacgttga cacttgaggg gccgactcac  180
ccggcgcggc gttgacagat gaggggcagg ctcgatttcg gccggcgacg tggagctggc  240
cagcctcgca aatcggcgaa aacgcctgat tttacgcgag tttcccacag atgatgtgga  300
caagcctggg gataagtgcc ctgcggtatt gacacttgag gggcgcgact actgacagat  360
gaggggcgcg atccttgaca cttgaggggc agagtgatga cagatgaggg gcgcacctat  420
tgacatttga ggggctgtcc acaggcagaa aatccagcat ttgcaagggt ttccgcccgt  480
ttttcggcca ccgctaacct gtcttttaac ctgcttttaa accaatattt ataaaccttg  540
tttttaacca gggctgcgcc ctggcgcgtg accgcgcacg ccgaaggggg gtgccccccc  600
ttctcgaacc ctcccgg                                                 617

<210> SEQ ID NO 260
<211> LENGTH: 639
<212> TYPE: DNA
<213> ORGANISM: E. coli
<220> FEATURE:
<223> OTHER INFORMATION: R6K alpha origin of replication

<400> SEQUENCE: 260
tcttacttct ttgcgtagct gttaaataca gcgttgtttt gataaaatca tcattatcat    60
cgataatgct ttcttcaatt tttttatcct tactctttaa taaagcactt gctaataact  120
tcatacctttt tgcaactgtc aaatttggtt catcagggta aatgctttta aggcatacta  180
acaaataatc atggtcttca tcttcaactc taaactgaat ttttttcatc ataactccca  240
acaagaaccg actgtaggtc accgggcaaa cgctgaaaaa taacgtcgaa tgacgtcatt  300
ttgcggcgtt tgccctatcc tgcatcgcag tagaaaatgc cacaactgaa attgtgcttc  360
agtatgtaca gaaatgcaaa atctgaggga tttcgtagct gaaagatcgc cagtcttcga  420
ccgtaaggat aggagttgct gtaagacctg tgcgggcgt tcgcttcgcg aacgggtctg   480
gcagggggca caagcgctgt gctgtgatat atgcaaaaga agccaccac gaacgggagg    540
gcttcggcga atcgactata gtgatctatt taccccggctg attgtcgcct tctagccctc  600
gcgggcatca tgcaaccagt gcctgaattt agttatatg                          639

<210> SEQ ID NO 261
<211> LENGTH: 1027
<212> TYPE: DNA
<213> ORGANISM: E. coli
<220> FEATURE:
<223> OTHER INFORMATION: R6K beta origin of replication

<400> SEQUENCE: 261
tgaagctttt tttatgaatt tatctgaagc tgatgcagct tttctcaagg tatttgatga    60

```
aaccgtacct cccaaaaaag ctaaggggtg atatatggct aaaatttacg atttccctca    120
aggagccgaa cgccgcagga tgcaccgcaa atccagtgg aacaacgctg taaaattatc     180
taaaaatggc tggagtaagc cagaggttaa acgctggtct tttttagcat tcatctcaac    240
tggctggtat tactttcgcc tttcggtagc agtcattttc catatcatta ctatttgtgg    300
tttagctgtg ctcgcggcgt taagcaatac gatattctgg attggtggcg cgatatgtct    360
tgtaacctgg tatacaaatg accatcaaat ttggagtact aacaatctta ctatccctat    420
tgttttcgga ctttgggtgt taagtttagt agctgcacca ctcatagatt ttttcagtca    480
aaaattgccc ttttatcgtc ttcttgtgcc tgatgcgaag cgtgaggaag tgggcgaaga    540
tgattcttaa agccctgccc tgtacggctt taacgccttc tcgcggtaga tctatggatg    600
ttgagaatgt agtatggtta tactgcgatg caggataggg caaacgccgt aaaatgacgt    660
ctttgacgtt atttttcagc gcttgcccgg tgacctacag tcggtgcttg ttgggagatt    720
ttatgaagtt tactagtaaa ggattttatc agtgataaat atgcaaaggc tattaacatt    780
ttaaatgata accttaaaga aaactactat gttttttatg gtgtaaggtt aagtgaaatt    840
ctttttcctg caagtgatta tggtacagat gattttttta aggagtttga ggaaataaac    900
aacgttacct tgcctttagt tgttttttgaa ataaatgaac gtgaacctgt gattgtaatt    960
ggttttgatg aaataaatcc tgcgattctt atagagaaat ccggtataaa ggttttagta   1020
atcggac                                                             1027

<210> SEQ ID NO 262
<211> LENGTH: 442
<212> TYPE: DNA
<213> ORGANISM: E. coli
<220> FEATURE:
<223> OTHER INFORMATION: R6K gamma origin of replication

<400> SEQUENCE: 262
gatcgctagt ttgttttgac tccatccatt agggcttcta aaacgccttc taaggccatg     60
tcagccgtta agtgttcctg tgtcactgaa aattgctttg agaggctcta agggcttctc    120
agtgcgttac atccctggct tgttgtccac aaccgttaaa ccttaaaagc tttaaaagcc    180
ttatatattc tttttttttct tataaaactt aaaaccttag aggctattta agttgctgat    240
ttatattaat tttattgttc aaacatgaga gcttagtacg tgaaacatga gcttagta     300 cgttagccat gagagcttag tacgttagcc atgagggttt agttcgttaa acatgagagc    360
ttagtacgtt aaacatgaga gcttagtacg tgaaacatga gcttagta cgtactatca      420 acaggttgaa ctgctgatct tc                                             442

<210> SEQ ID NO 263
<211> LENGTH: 242
<212> TYPE: DNA
<213> ORGANISM: Enterobacteria phage P1
<220> FEATURE:
<223> OTHER INFORMATION: P1 origin of plasmid replication oriR

<400> SEQUENCE: 263
tttcccgtca acacacatcc tatatcccgc cagcacacat tagcaacccg tcagcacaca     60
tttttatccc tccagcacac atcgttttcc ctccagcaca catcgcgata cacttctaag    120
ccagacgtgg cgcggcctgc aacgatcagg gatctatatg gatctaattg ggatctgtat    180
ggacctgatt attggatcta tccagtggat aatgtggata agtgaaaaac cggccaacgt    240
ag                                                                   242
```

<210> SEQ ID NO 264
<211> LENGTH: 792
<212> TYPE: DNA
<213> ORGANISM: Artificial Sequence
<220> FEATURE:
<223> OTHER INFORMATION: R1 origin of replication

<400> SEQUENCE: 264

```
ttatccacat ttaactgcaa gggacttccc cataaggtta caaccgttca tgtcataaag      60
cgccagccgc cagtcttaca gggtgcaatg tatcttttaa acacctgttt atatctcctt     120
taaactactt aattacattc atttaaaaag aaaacctatt cactgcctgt cctgtggaca     180
gacagatatg cacctcccac cgcaagcggg gggccccgac cggagccact ttagttacaa     240
cacacaaaaa caacctccag aaaaaccccg gtccagcgca gaaccgaaac cacaaagccc     300
ctccctcata actgaaaagc ggccccgccc cggcccaaag ggccggaaca gagtcgcttt     360
taattatgaa tgttgtaact acatcttcat cgctgtcagt cttctcgctg gaagttctca     420
gtacacgctc gtaagcggcc ctcacggccc gctaacgcgg agatacgccc cgacttcggg     480
taaaccctcg tcgggaccac tccgaccgcg cacagaagct ctctcatggc tgaaagcggg     540
tatggtctgg cagggctggg gatgggtaag gtgaaatcta tcaatcagta ccggcttacg     600
ccgggcttcg gcggttttac tcctgtatca tatgaaacaa cagagtgccg ccttccatgc     660
cgctgatgcg gcatatcctg gtaacgatat ctgaattgtt atacatgtgt atatacgtgg     720
taatgacaaa aataggacaa gttaaaaatt tacaggcgat gcaatgattc aaacacgtaa     780
tcaatatctg ca                                                        792
```

<210> SEQ ID NO 265
<211> LENGTH: 2920
<212> TYPE: DNA
<213> ORGANISM: Artificial Sequence
<220> FEATURE:
<223> OTHER INFORMATION: pWSK origin of replication

<400> SEQUENCE: 265

```
ccgatgccct tgagagcctt caacccagtc agctccttcc ggtgggcgcg gggcatgact      60
atcgtcgccg cacttatgac tgtcttcttt atcatgcaac tcgtaggaca gggtgccggc     120
agcgctctgg tcatttttcg gcgaggaccg ctttcgctgg agcgcgacga tgatcggcct     180
gtcgcttgcg gtattcggaa tcttgcacgc cctcgctcaa gccttcgtca ctggtcccgc     240
caccaaacgt ttcggcgaga agcaggccat tatcgccggc atggcggccg acgcgctggg     300
ctacgtcttg ctggcgttcg cgacgcgagg ctggatggcc ttccccatta tgattcttct     360
cgcttccggc ggcatcggga tgcccgcgtt gcaggccatg ctgtccaggc aggtagatga     420
cgaccatcag ggacagcttc aaggatcgct cgcggctctt accagcctaa cttcgatcat     480
tggaccgctg atcgtcacgg cgatttatgc cgcctcggcg agcacatgga acgggttggc     540
atggattgta ggcgccgccc tataccttgt ctgcctcccc gcgttgcgtc gcggtgcatg     600
gagccgggcc acctcgacct gaatggaagc cggcggcacc tcgctaacgg attcaccact     660
ccgcagaccc gccataaaac gccctgagaa gcccgtgacg gcttttcttg tattatgggt     720
agtttccttg catgaatcc ataaaaggcg cctgtagtgc catttacccc cattcactgc      780
cagagccgtg agcgcagcga actgaatgtc acgaaaaaga cagcgactca ggtgcctgat     840
ggtcggagac aaaaggaata ttcagcgatt tgcccgagct tgcgagggtg ctacttaagc     900
```

-continued

```
ctttagggtt ttaaggtctg ttttgtagag gagcaaacag cgtttgcgac atccttttgt    960
aatactgcgg aactgactaa agtagtgagt tatacacagg gctgggatct attcttttta   1020
tcttttttta ttctttcttt attctataaa ttataaccac ttgaatataa acaaaaaaaa   1080
cacacaaagg tctagcggaa tttacagagg gtctagcaga atttacaagt tttccagcaa   1140
aggtctagca gaatttacag atacccacaa ctcaaaggaa aaggactagt aattatcatt   1200
gactagccca tctcaattgg tatagtgatt aaaatcacct agaccaattg agatgtatgt   1260
ctgaattagt tgttttcaaa gcaaatgaac tagcgattag tcgctatgac ttaacggagc   1320
atgaaaccaa gctaatttta tgctgtgtgg cactactcaa ccccacgatt gaaaaccta    1380
caaggaaaga acggacggta tcgttcactt ataaccaata cgctcagatg atgaacatca   1440
gtagggaaaa tgcttatggt gtattagcta aagcaaccag agagctgatg acgagaactg   1500
tggaaatcag gaatcctttg gttaaaggct ttgagatttt ccagtggaca aactatgcca   1560
agttctcaag cgaaaaatta gaattagttt ttagtgaaga gatattgcct tatcttttcc   1620
agttaaaaaa attcataaaa tataatctgg aacatgttaa gtcttttgaa aacaaatact   1680
ctatgaggat ttatgagtgg ttattaaaag aactaacaca aaagaaaact cacaaggcaa   1740
atatagagat tagccttgat gaatttaagt tcatgttaat gcttgaaaat aactaccatg   1800
agtttaaaag gcttaaccaa tgggttttga aaccaataag taaagattta aacacttaca   1860
gcaatatgaa attggtggtt gataagcgag gccgcccgac tgatacgttg attttccaag   1920
ttgaactaga tagacaaatg gatctcgtaa ccgaacttga gaacaaccag ataaaaatga   1980
atggtgacaa aataccaaca accattacat cagattccta cctacataac ggactaagaa   2040
aaacactaca cgatgcttta actgcaaaaa ttcagctcac cagttttgag gcaaaatttt   2100
tgagtgacat gcaaagtaag tatgatctca atggttcgtt ctcatggctc acgcaaaaac   2160
aacgaaccac actagagaac atactggcta aatacggaag gatctgaggt tcttatggct   2220
cttgtatcta tcagtgaagc atcaagacta acaaacaaaa gtagaacaac tgttcaccgt   2280
tacatatcaa agggaaaact gtccatatgc acagatgaaa acggtgtaaa aagatagat    2340
acatcagagc ttttacgagt ttttggtgca ttcaaagctg ttcaccatga acagatcgac   2400
aatgtaacag atgaacagca tgtaacacct aatagaacag gtgaaaccag taaaacaaag   2460
caactagaac atgaaattga acacctgaga caacttgtta cagctcaaca gtcacacata   2520
gacagcctga acaggcgat gctgcttatc gaatcaaagc tgccgacaac acgggagcca   2580
gtgacgcctc ccgtggggaa aaaatcatgg caattctgga agaaatagcg ctttcagccg   2640
gcaaaccggc tgaagccgga tctgcgattc tgataacaaa ctagcaacac cagaacagcc   2700
cgtttgcggg cagcaaaacc cgtacttttg gacgttccgg cggttttttg tggcgagtgg   2760
tgttcgggcg gtgcgcgcaa gatccattat gttaaacggg cgagtttaca tctcaaaacc   2820
gcccgcttaa caccatcaga aatcctcagc gcgattttaa gcaccaaccc ccccccgtaa   2880
cacccaaatc catactgaaa gtggctttgt tgaataaatc                        2920
```

<210> SEQ ID NO 266
<211> LENGTH: 37
<212> TYPE: DNA
<213> ORGANISM: E. coli
<220> FEATURE:
<223> OTHER INFORMATION: ColE2 origin of replication

<400> SEQUENCE: 266
aaaatgagac cagataagcc ttatcagata acagcgc    37

<210> SEQ ID NO 267
<211> LENGTH: 668
<212> TYPE: DNA
<213> ORGANISM: Artificial Sequence
<220> FEATURE:
<223> OTHER INFORMATION: pUC origin of replication

<400> SEQUENCE: 267

```
tgagcaaaag gccagcaaaa ggccaggaac cgtaaaaagg ccgcgttgct ggcgtttttc      60
cataggctcc gcccccctga cgagcatcac aaaaatcgac gctcaagtca gaggtggcga     120
aacccgacag gactataaag ataccaggcg tttccccctg gaagctccct cgtgcgctct     180
cctgttccga cccgccgct  taccggatac ctgtccgcct ttctcccttc gggaagcgtg     240
gcgctttctc atagctcacg ctgtaggtat ctcagttcgg tgtaggtcgt tcgctccaag     300
ctgggctgtg tgcacgaacc ccccgttcag cccgaccgct gcgccttatc cggtaactat     360
cgtcttgagt ccaacccggt aagacacgac ttatcgccac tggcagcagc cactggtaac     420
aggattagca gagcgaggta tgtaggcggt gctacagagt tcttgaagtg gtggcctaac     480
tacggctaca ctagaagaac agtatttggt atctgcgctc tgctgaagcc agttaccttc     540
ggaaaaagag ttggtagctc ttgatccggc aaacaaacca ccgctggtag cggtggtttt     600
tttgtttgca agcagcagat tacgcgcaga aaaaaaggat ctcaagaaga tcctttgatc     660
ttttctac                                                              668
```

<210> SEQ ID NO 268
<211> LENGTH: 457
<212> TYPE: DNA
<213> ORGANISM: Bacteriophage F1
<220> FEATURE:
<223> OTHER INFORMATION: F1 origin of replication

<400> SEQUENCE: 268

```
gacgcgccct gtagcggcgc attaagcgcg gcgggtgtgg tggttacgcg cagcgtgacc      60
gctacacttg ccagcgccct agcgcccgct cctttcgctt tcttcccttc ctttctcgcc     120
acgttcgccg gctttccccg tcaagctcta aatcgggggc tccctttagg gttccgattt     180
agtgctttac ggcacctcga ccccaaaaaa cttgattagg gtgatggttc acgtagtggg     240
ccatcgccct gatagacggt ttttcgccct ttgacgttgg agtccacgtt ctttaatagt     300
ggactcttgt tccaaactgg aacaacactc aaccctatct cggtctattc ttttgattta     360
taagggattt tgccgatttc ggcctattgg ttaaaaaatg agctgattta acaaaaattt     420
aacgcgaatt ttaacaaaat attaacgctt acaattt                              457
```